US012338199B2

(12) United States Patent
Han et al.

(10) Patent No.: US 12,338,199 B2
(45) Date of Patent: *Jun. 24, 2025

(54) BIS-OCTAHYDROPHENANTHRENE CARBOXAMIDES AND PROTEIN CONJUGATES THEREOF

(71) Applicant: REGENERON PHARMACEUTICALS, INC., Tarrytown, NY (US)

(72) Inventors: Amy Han, Hockessin, DE (US); Andrew J. Murphy, Croton-on-Hudson, NY (US); William Olson, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 344 days.

This patent is subject to a terminal disclaimer.

(21) Appl. No.: 17/494,762

(22) Filed: Oct. 5, 2021

(65) Prior Publication Data

US 2022/0112158 A1 Apr. 14, 2022

Related U.S. Application Data

(63) Continuation of application No. 15/975,654, filed on May 9, 2018, now abandoned.

(60) Provisional application No. 62/508,327, filed on May 18, 2017.

(51) Int. Cl.
| | |
|---|---|
| *C07C 237/52* | (2006.01) |
| *A61K 47/64* | (2017.01) |
| *A61K 47/68* | (2017.01) |
| *A61P 25/28* | (2006.01) |
| *A61P 29/00* | (2006.01) |
| *C07C 233/90* | (2006.01) |

(52) U.S. Cl.
CPC ............ *C07C 233/90* (2013.01); *A61K 47/64* (2017.08); *A61K 47/6803* (2017.08); *A61P 25/28* (2018.01); *A61P 29/00* (2018.01); *C07C 237/52* (2013.01)

(58) Field of Classification Search
CPC ............... A61K 47/64; A61K 47/6803; H01L 25/0753; H01L 27/1214; H01L 27/156; H01L 33/382; H01L 33/42; A61P 25/28; A61P 29/00; A61P 3/06
See application file for complete search history.

(56) References Cited

U.S. PATENT DOCUMENTS

| | | |
|---|---|---|
| 6,908,934 B2 | 6/2005 | Adams et al. |
| 11,377,502 B2 | 7/2022 | Gromada et al. |
| 2003/0125357 A1 | 7/2003 | Adams et al. |
| 2009/0030082 A1 | 1/2009 | Forman |
| 2016/0324981 A1 | 11/2016 | Pinkerton et al. |
| 2017/0189549 A1 | 7/2017 | Helin et al. |
| 2018/0333504 A1 | 11/2018 | Han et al. |
| 2018/0334426 A1 | 11/2018 | Han et al. |
| 2019/0367631 A1 | 12/2019 | Gromada et al. |

FOREIGN PATENT DOCUMENTS

| | | |
|---|---|---|
| CN | 101679297 A | 3/2010 |
| EP | 1398032 A1 | 3/2004 |
| WO | WO 01/41704 A1 | 6/2001 |
| WO | WO 2006/000577 A1 | 1/2006 |
| WO | WO 2018/213082 A1 | 11/2018 |
| WO | WO-2019217591 A1 * | 11/2019 .......... A61K 31/165 |

OTHER PUBLICATIONS

Chin et al., "Miniaturization of Cell-Based β-Lactamase-Dependent FRET Assays to Ultra-High Throughput Formats to Identify Agonists of Human Liver X Receptors", Assay and Drug Development Technologies, vol. 1, No. 6, 2003, pp. 777-787.

Bardyshev, "Diterpenoid Carboxylic Acid Anhydrides of the Abietane, Pimarane, and Isopimarane Series", Russian Journal of Organic Chemistry (Translation of Zhurnal Organicheskoi Khimii), 1999, 35(1), pp. 41-55.

Database Registry [online] Chemical Abstract Service, US; Retrieved from STN, Nov. 16, 1984, RN 53404-26-5, 1,2,3,4,4a,9,10,10a-Octahydro-1,4a-dimethyl-7-(1-methylethyl)-N-[[1,2,3,4,4a,9,10,10a-octahydro-1,4a-dimethyl-7-(1-methylethyl)-1-phenanthrenyl]methyl]-1-phenanthrene methaneamine; 1 page.

International Search Report and Written Opinion of PCT/US2019/062302 date of mailing Mar. 30, 2020; 11 pages.

Bischoff et al., "Non-redundant roles for LXRα and LXRβ in atherosclerosis susceptibility in low density lipoprotein receptor knockout mice", Journal of Lipid Research, 2010, vol. 51, pp. 900-906.

Bogan et al., "Liver X Receptor Modulation of Gene Expression Leading to Pro-luteolytic Effects in Primate Luteal Cells", Biology of Reproduction, 2012, 86(3):89, pp. 1-9.

Calkinn and Tontonoz, "Transcriptional integration of metabolism by the nuclear sterol-activated receptors LXR and FXR", Molecular Cell Biology, Apr. 2012, vol. 13, No. 4, pp. 213-224.

CAS No. 1221277-90-2, "2,4,6-Trimethyl-N-[3'-(methylsulfonyl)[1,1'-biphenyl]-4-yl]methyl]-N-[[5-(trifluoromethyl)-2-furanyl]methyl]benzenesulfonamide", printed Mar. 2, 2016; 2 pages.

Castrillo et al., "Crosstalk between LXR and Toll-like Receptor Signaling Mediates Bacterial and Viral Antagonism of Cholesterol Metabolism", Molecular Cell, Oct. 2003, vol. 12, pp. 805-816.

(Continued)

*Primary Examiner* — Jean P Cornet
(74) *Attorney, Agent, or Firm* — Squire Patton Boggs (US) LLP

(57) ABSTRACT

Provided herein are compounds, compositions and methods for the treatment of diseases and disorders associated with the liver X receptor, including bis-octahydrophenanthrene carboxamides and protein (e.g., antibody) drug conjugates thereof.

23 Claims, 27 Drawing Sheets

Specification includes a Sequence Listing.

(56) References Cited

OTHER PUBLICATIONS

Fukuchi et al., "Antiproliferative Effect of Liver X Receptor Agonists on LNCaP Human Prostate Cancer Cells", Cancer Research 64, Nov. 1, 2004, pp. 7686-7689.
Groot et al., "Synthetic LXR agonists increase LDL in CETP species", Journal of Lipid Research, 2005, vol. 46, pp. 2182-2191.
Honzumi et al., "LXRα regulates human CETP expression in vitro and in transgenic mice", Atherosclerosis 212, 2010, pp. 139-145.
Honzumi et al., "Synthetic LXR agonist inhibits the development of atherosclerosis in New Zealand White rabbits", Biochimica et Biophysica Acta 1811, 2011, pp. 1136-1145.
Joseph et al., "Synthetic LXR ligand inhibits the development of atherosclerosis in mice", PNAS, May 28, 2002, vol. 99, No. 11, pp. 7604-7609.
Koldamova et al., "The Liver X Receptor Ligand T0901317 Decreases Amyloid β Production in Vitro and in a Mouse Model of Alzheimer's Disease", Journal of Biological Chemistry, Feb. 11, 2005, vol. 280, No. 6, pp. 4079-4088.
Laffitte et al., "Activation of liver X receptor improves glucose tolerance through coordinate regulation of glucose metabolism in liver and adipose tissue", PNAS, Apr. 29, 2003, vol. 100, No. 9, pp. 5419-5424.
Lakomy et al., "Liver X Receptor-Mediated Induction of Cholesteryl Ester Transfer Protein Expression Is Selectively Impaired in Inflammatory Macrophages", Arterioscler Thromb Vasc Biol., Nov. 2009, vol. 29, pp. 1923-1929, DOI: 10.1161/ATVBAHA.109.193201.
Leik et al., "GW3965, a synthetic liver X receptor (LXR) agonist, reduces angiotensin II-mediated pressor responses in Sprague-Dawley rats", British Journal of Pharmacology, 2007, vol. 151, pp. 450-456.
Levin et al., "Macrophage Liver X Receptor Is Required for Antiatherogenic Activity of LXR Agonists", Arterioscler Thromb Vasc Biol., Jan. 2005, pp. 135-142, DOI: 10.1161/01.ATV.0000150044.84012.68.
Lim et al., "Targeted Delivery of LXR Agonist Using a Site-Specific Antibody-Drug Conjugate", Bioconjugate Chemistry, May 6, 2015, DOI: 10.1021/acs.bioconjchem.5b00203, 9 pages.
Lim et al., "Targeted Delivery of LXR Agonist Using a Site-Specific Antibody-Drug Conjugate", Bioconjugate Chem., 2015, vol. 26, No. 11, pp. 2216-2222.
Lima et al., "Bioisosterism: A Useful Strategy for Molecular Modification and Drug Design", Current Medicinal Chemistry, 2005, vol. 12, pp. 23-49.
Liu et al., "Design, synthesis, and structure-activity relationship of podocarpic acid amides as liver X receptor agonists for potential treatment of atherosclerosis", Bioorganic & Medicinal Chemistry Letters 15, 2005, pp. 4574-4578.
Patani et al., "Bioisosterism: A Rational Approach in Drug Design", Chemical Reviews, 1996, vol. 96, No. 8, pp. 3147-3176.
R.H. Bible, "The Conversion of Podocarpic Acid to Nimbiol", Tetrahedron, vol. 11, No. 1-2, Jan. 1, 1960, pp. 22-29, XP055494835.
Samal et al., "The First Synthesis of Water-Soluble Cyclodextrinazafullerenes", Synthetic Communications, 2002, vol. 32, No. 21, pp. 3367-3372.
Severson et al., "Hot-Tube Reactions of Dehydroabietic Acid with Ketene-Producing Reagents. Pyrolysis of the Acid Chloride and Symmetrical and Mixed Anhydride Derivatives of Dehydroabietic Acid", Canadian Journal of Chemistry, 1973, vol. 51 (19), pp. 3236-3241, corresponds to Severson et al., "ChemInform Abstract: Hot-Tube Reactions of Dehydroabietic Acid with Ketene-Producing Reagents. Pyrolysis of the Acid Chloride and Symmetrical and Mixed Anhydride Derivatives of Dehydroabietic Acid", Chemischer Informationsdienst, Jan. 22, 1974, pp. no-no, XP055494848. Weinheim DOI: 10.1002/chin.197403396 Retrieved from the Internet: URL:http://www.nrcresearchpress.com/doi/pdf/10.1139/v73-484 [retrieved on Jul. 26, 2018].
Sherwood and Short, "Podocarpic Acid. Part I", J. Chemical Society, 1938, pp. 1006-1013.
Singh et al., "Discovery and development of dimeric podocarpic acid leads as potent agonists of liver X receptor with HDL cholesterol raising activity in mice and hamsters", Bioorganic & Medicinal Chemistry Letters, 2005, vol. 15, pp. 2824-2828.
Solt et al., "LXR-Mediated Inhibition of CD4$^+$ T Helper Cells", PLOS One, Sep. 2012, vol. 7, issue 9, e46615; 11 pages.
Staveness et al., "Providing a New Aniline Bioisostere through the Photochemical Production of 1-Aminonorbornanes", Chem, vol. 5, Jan. 10, 2019, pp. 215-226.
Su et al., "Liver X receptor α induces 17β-hydroxysteroid dehydrogenase-13 expression through SREBP-1c", Am J Physiol Endocrinol Metab., Mar. 7, 2017, doi:10.1152/ajpendo.00310.2016, 33 pages.
Su et al., "Liver X receptor a induces 17β-hydroxysteroid dehydrogenase-13 expression through SREBP-1c", Am J Physiol Endocrinol Metab., Apr. 1, 2017;312(4), pp. E357-E367.
Tangirala et al., "Identification of macrophage liver X receptors as inhibitors of atherosclerosis", PNAS, Sep. 3, 2002, vo. 99, No. 18, pp. 11896-11901.
Terasaka et al., "T-0901317, a synthetic liver X receptor ligand, inhibits development of atherosclerosis in LDL receptor-deficient mice", FEBS Letters, 2003, vol. 536, pp. 6-11.
Tice et al., "The Medicinal Chemistry of Liver X Receptor (LXR) Modulators", Journal of Medicinal Chemistry, vol. 57, No. 17, Sep. 11, 2014, pp. 7182-7205, XP055494920.
Van Der Hoorn et al., "Low dose of the liver X receptor agonist, AZ876, reduces atherosclerosis in APOE*3Leiden mice without affecting liver or plasma triglyceride levels", British Journal of Pharmacology, 2011, vol. 162, pp. 1553-1563.
Verschuren et al., "LXR agonist suppresses atherosclerotic lesion growth and promotes lesion regression in apoE*3Leiden mice: time course and mechanisms", Journal of Lipid Research, 2009, vol. 50, pp. 301-311.
Wen et al., "Drug Delivery Approaches in Addressing Clinical Pharmacology-Related Issues: Opportunities and Challenges", The AAPS Journal, vol. 17, No. 6, Nov. 2015, pp. 1327-1340; DOI: 10.1208/s12248-015-9814-9.
Zuercher et al., "Discovery of Tertiary Sulfonamides as Potent Liver X Receptor Antagonists", J. Med. Chem., 2010, vol. 53, pp. 3412-3416.
Zeiss et al., "Synthesis and Stereochemistry of the 3-Keto-A4-steroidal System from Diterpenic Acids", Journal of the American Chemical Society, vol. 75, Dec. 5, 1953, pp. 5935-5940.
Zhou et al., "Tyrosine kinase inhibitory activity of dehydroabietylamine derivatives tested by homogeneous time-resolved fluorescence based high throughput screening model", Chinese Journal of Natural Medicines 2013, 11(5), pp. 506-513.

* cited by examiner

FIG. 1 Synthesis of 9a-9p
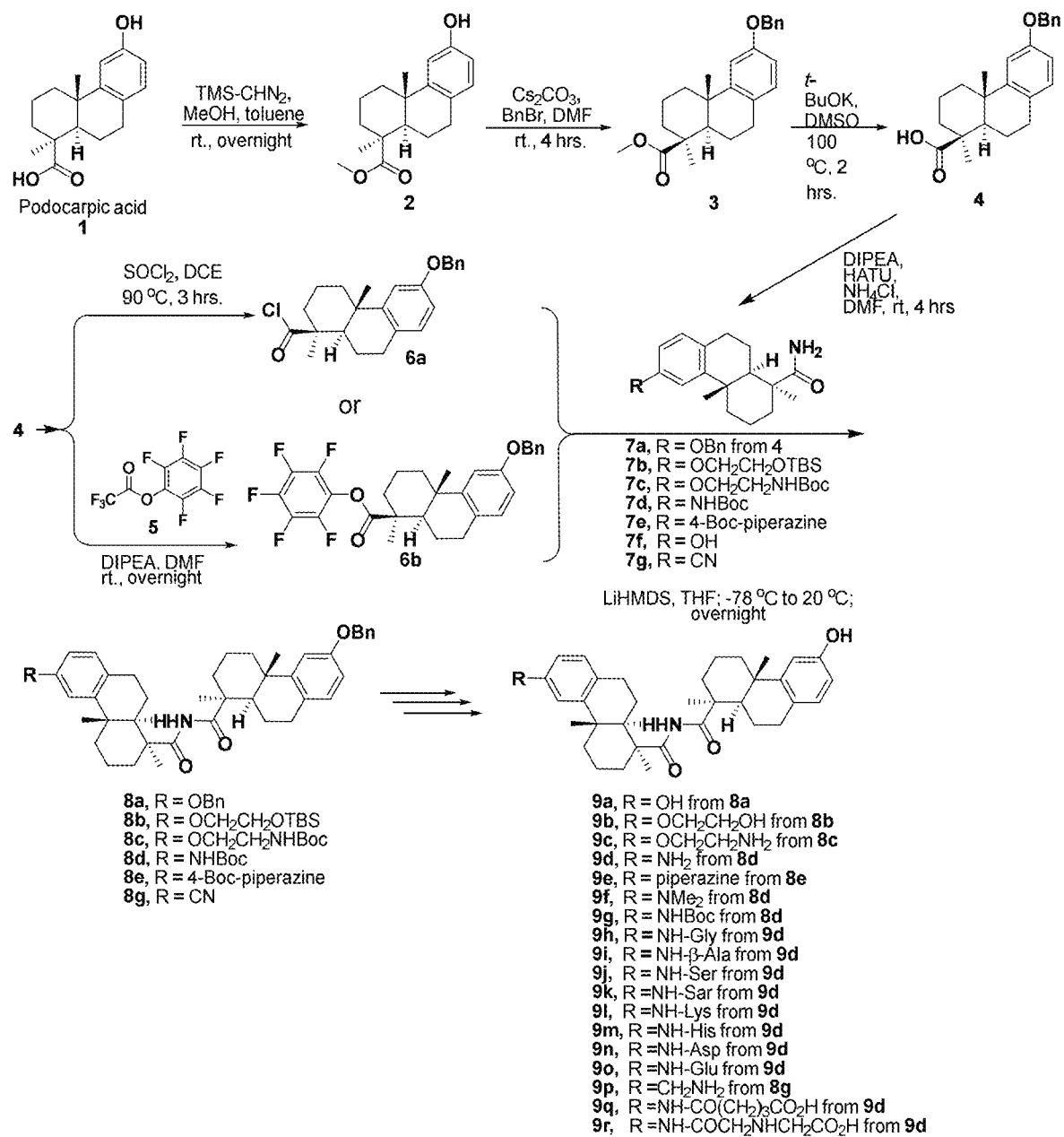

FIG. 1a Synthesis of 9d
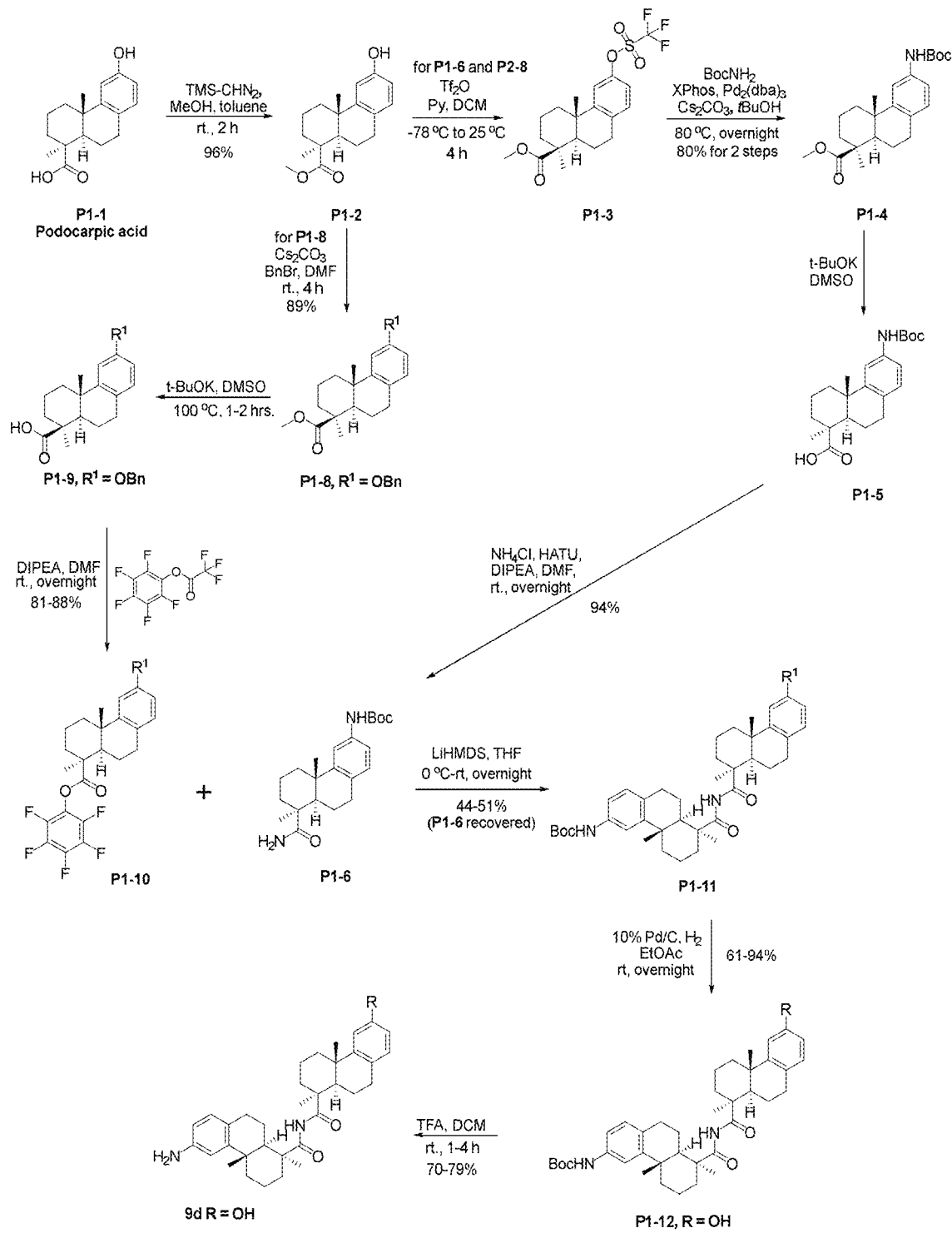

Figure 1b Synthesis of LP8
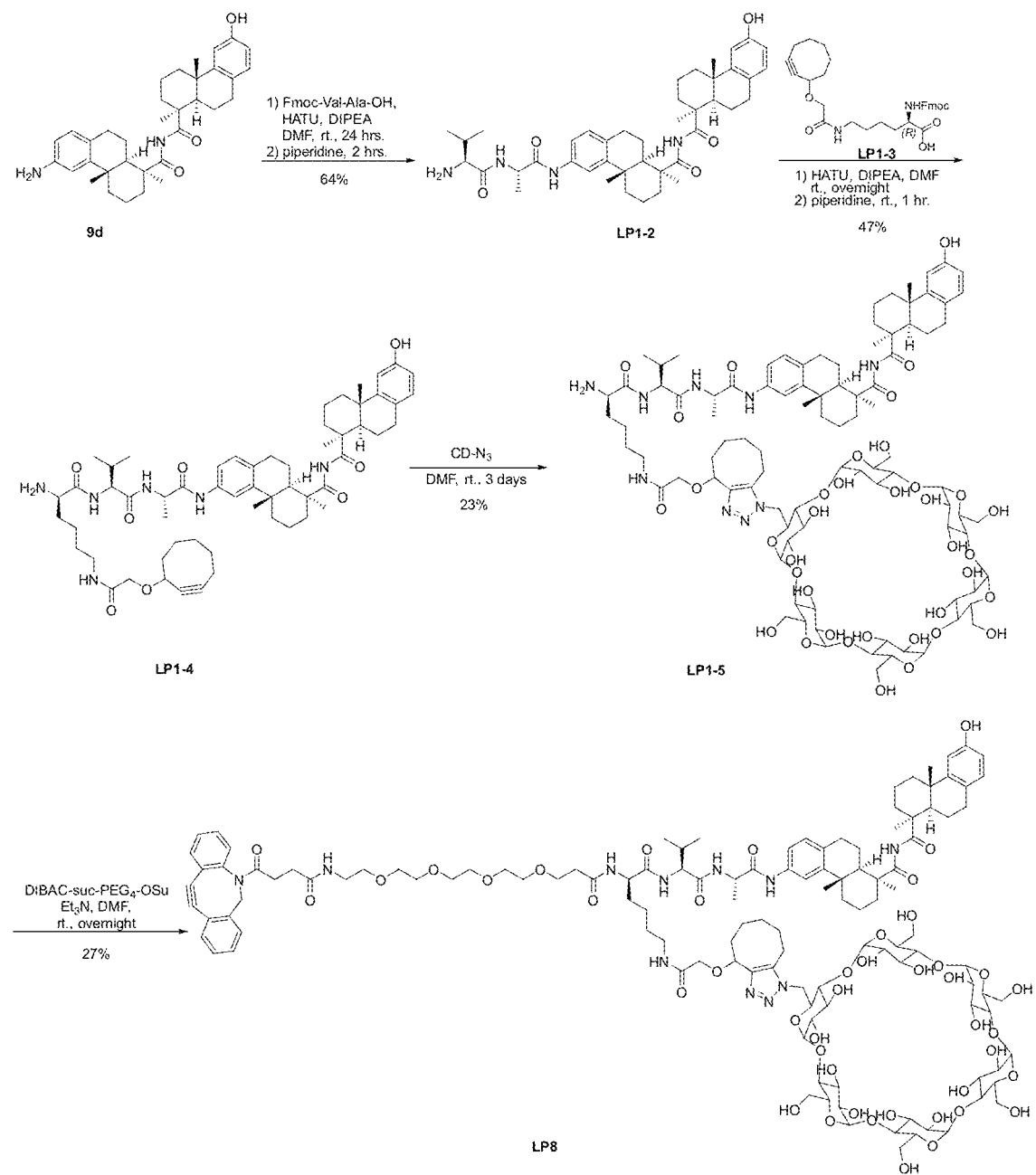

Figure 1c Synthesis of LP32

Figure 1d Synthesis of LP13
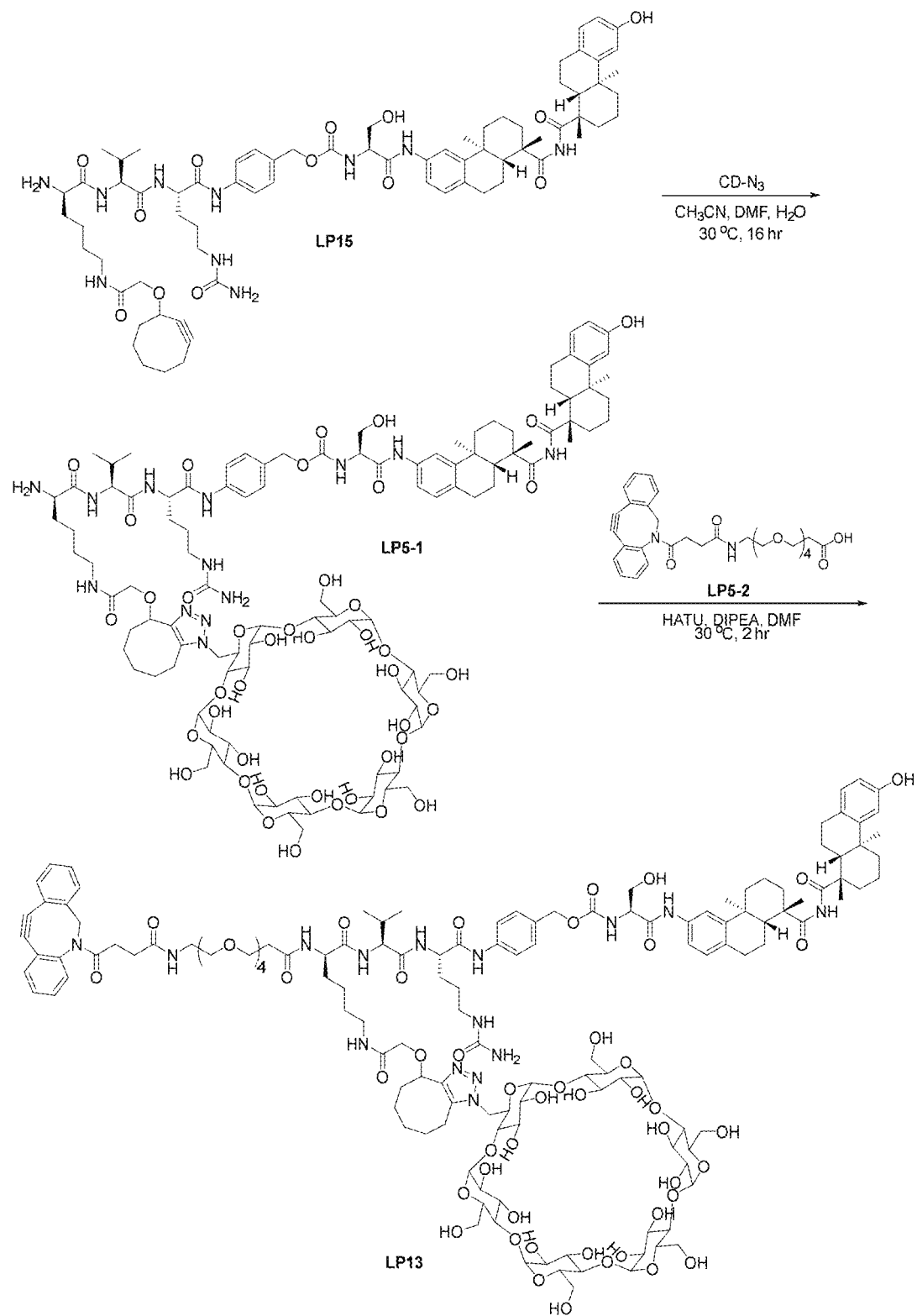

Figure 1e Synthesis of LP36
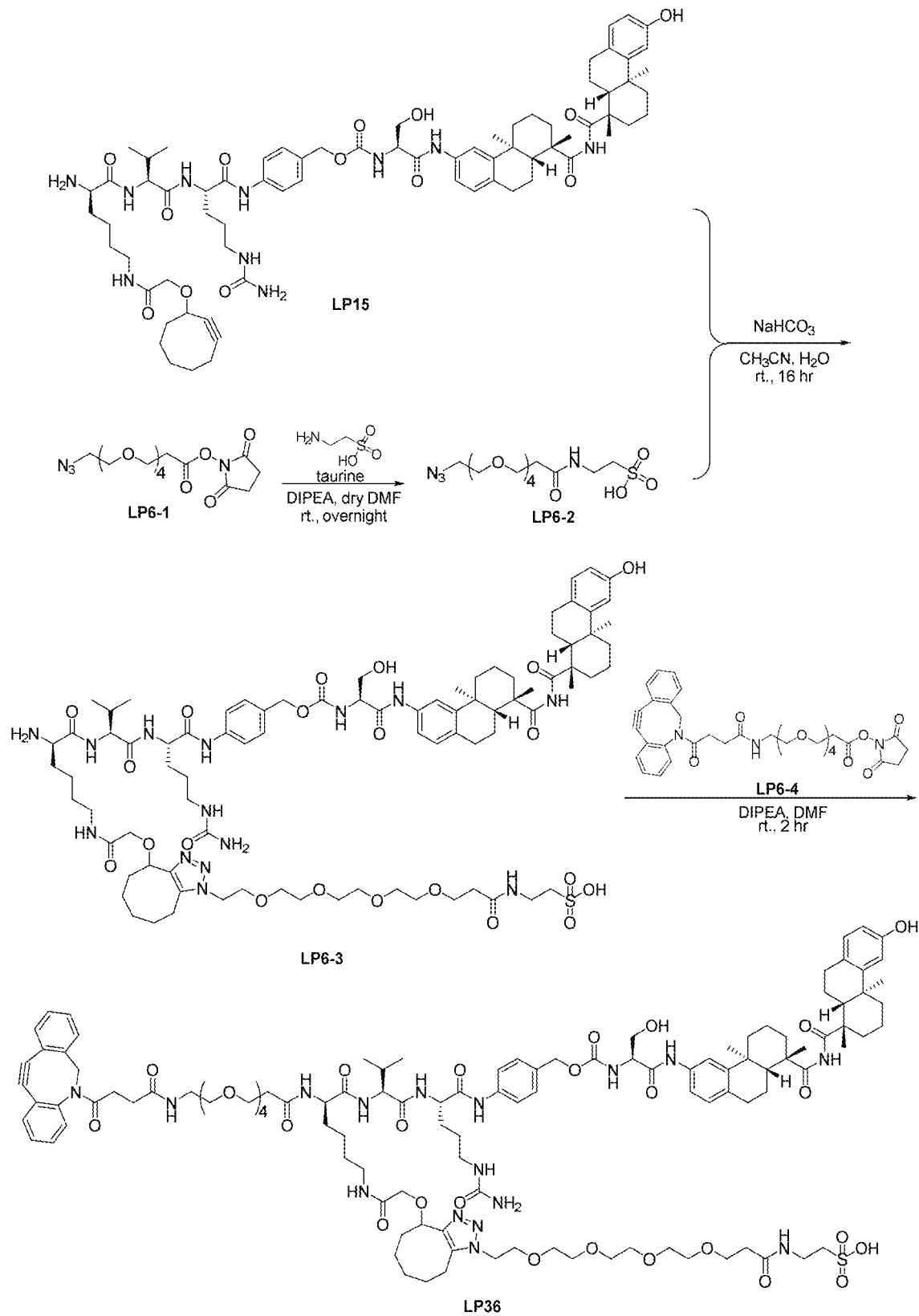

Figure 1f Synthesis of LP18
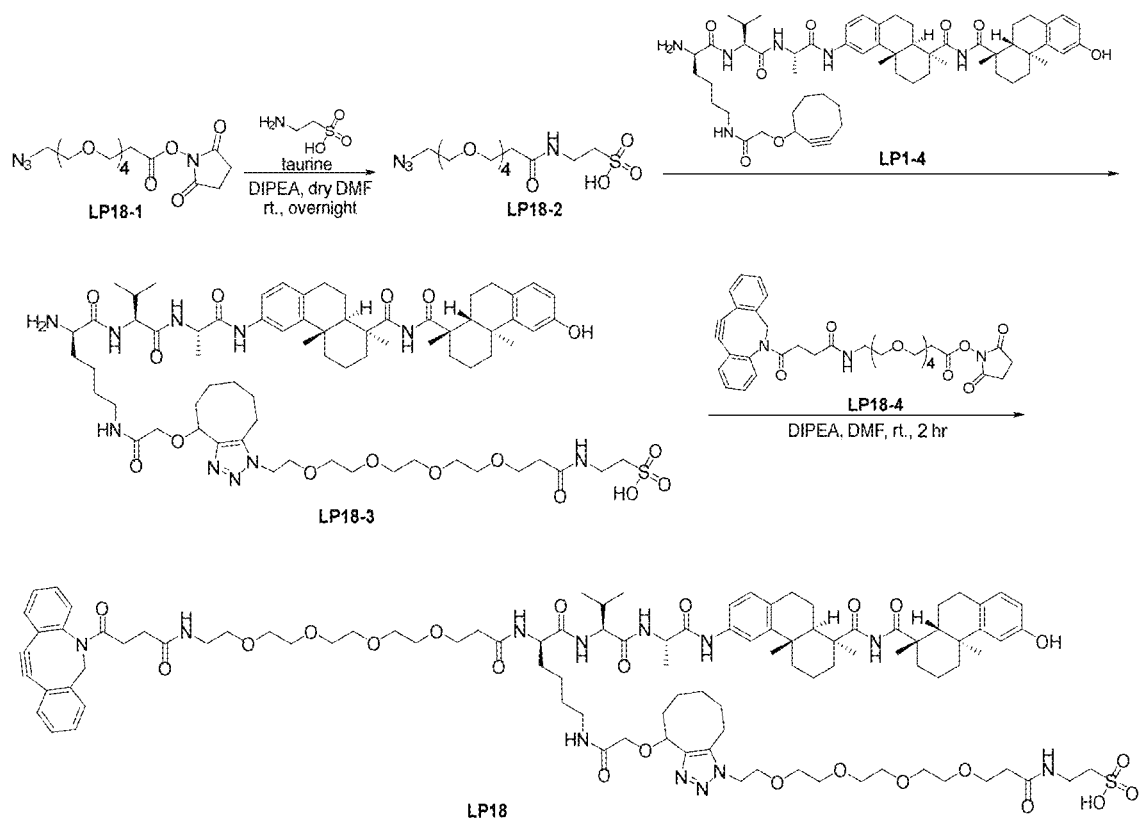

Figure 1g Synthesis of LP15
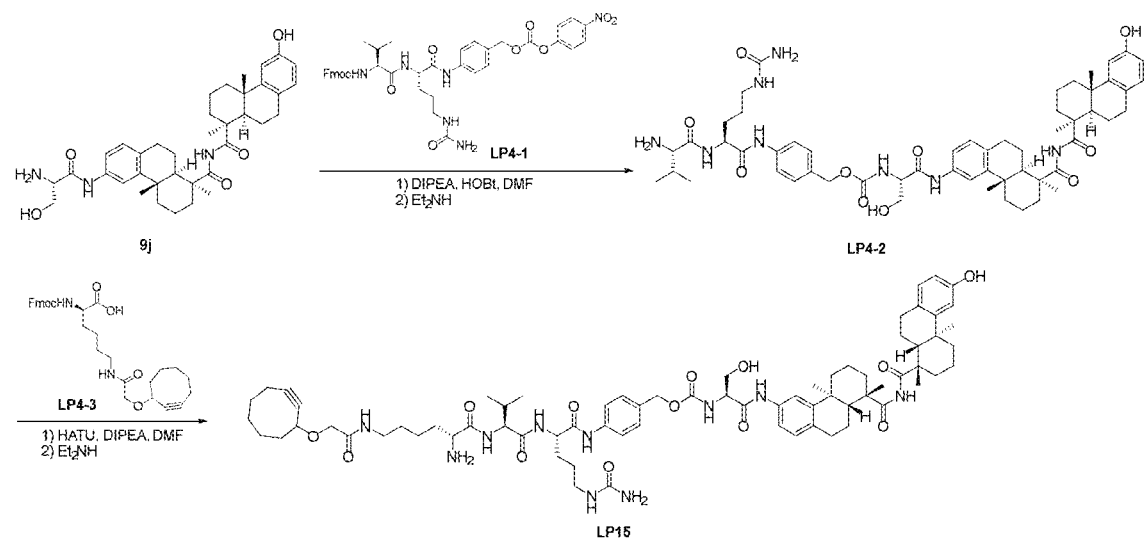

Figure 1h Synthesis of LP311
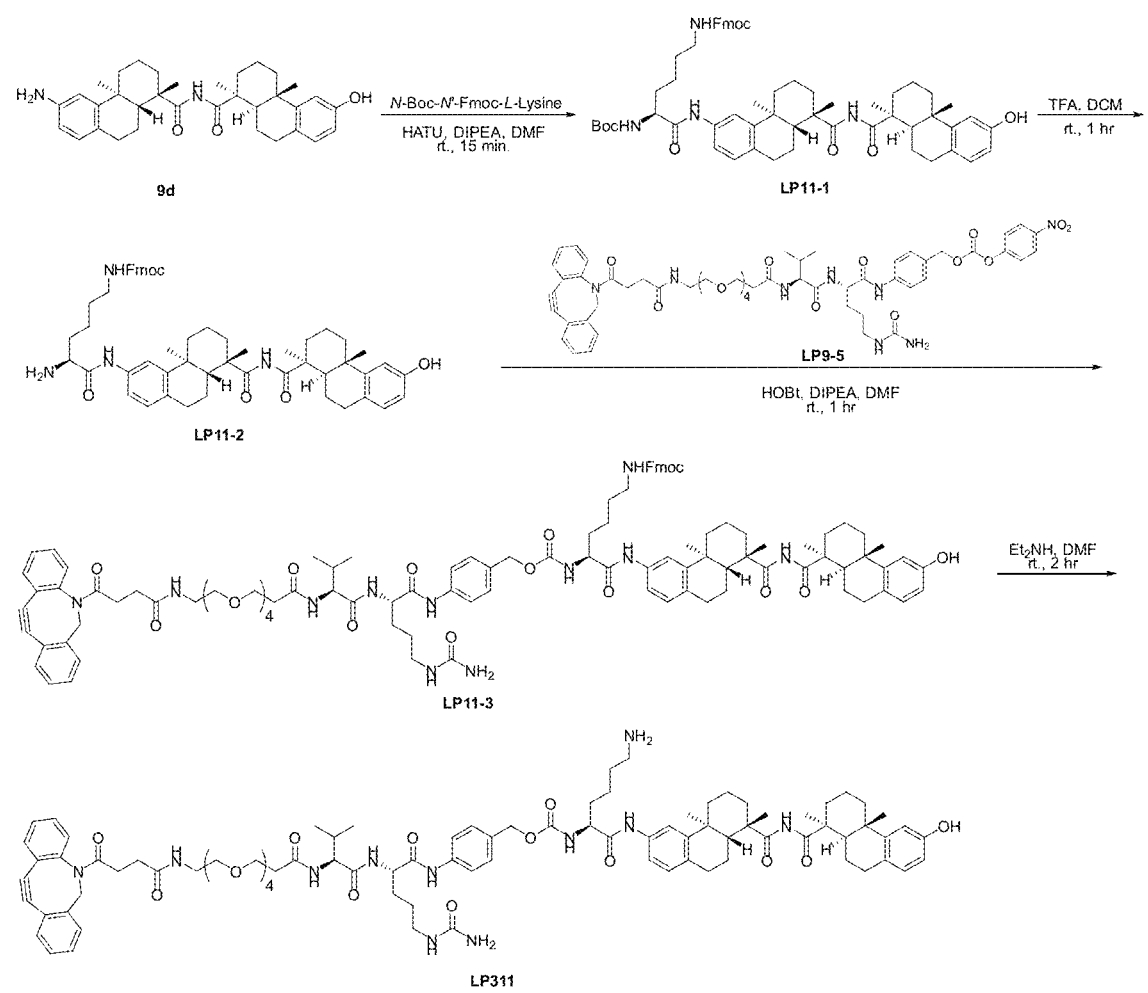

Figure 1i Synthesis of LP39
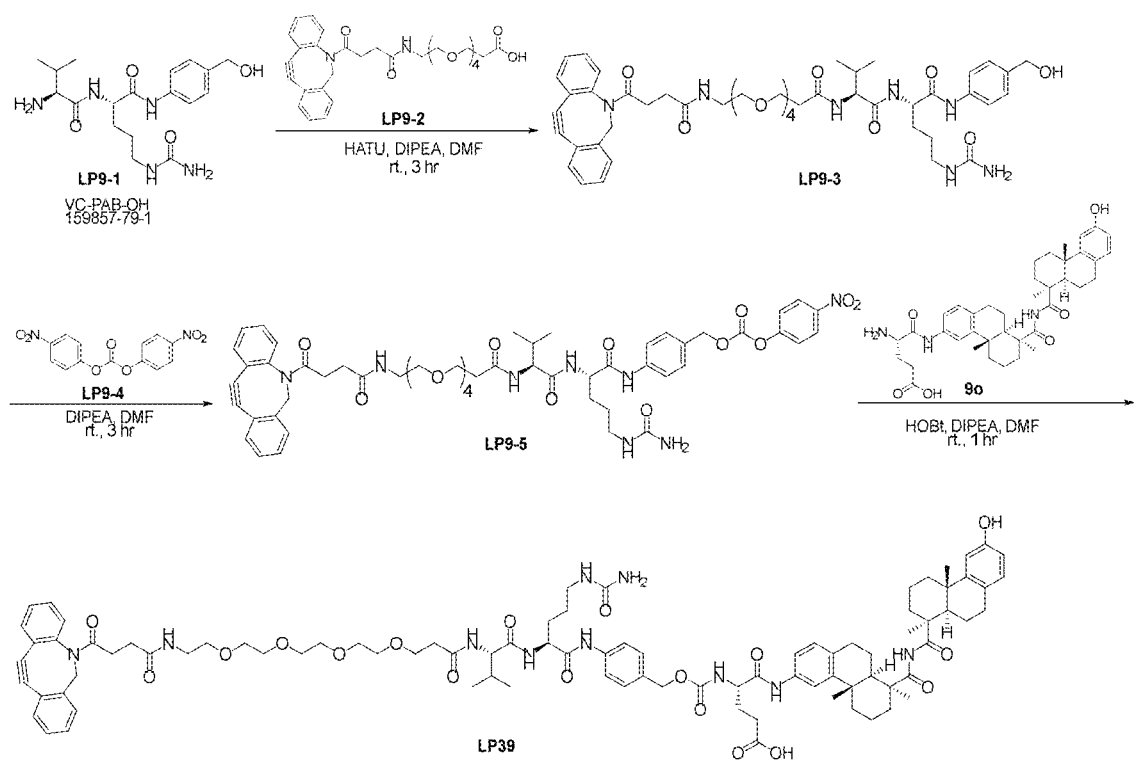

FIG. 2 Synthesis of Intermediates 7
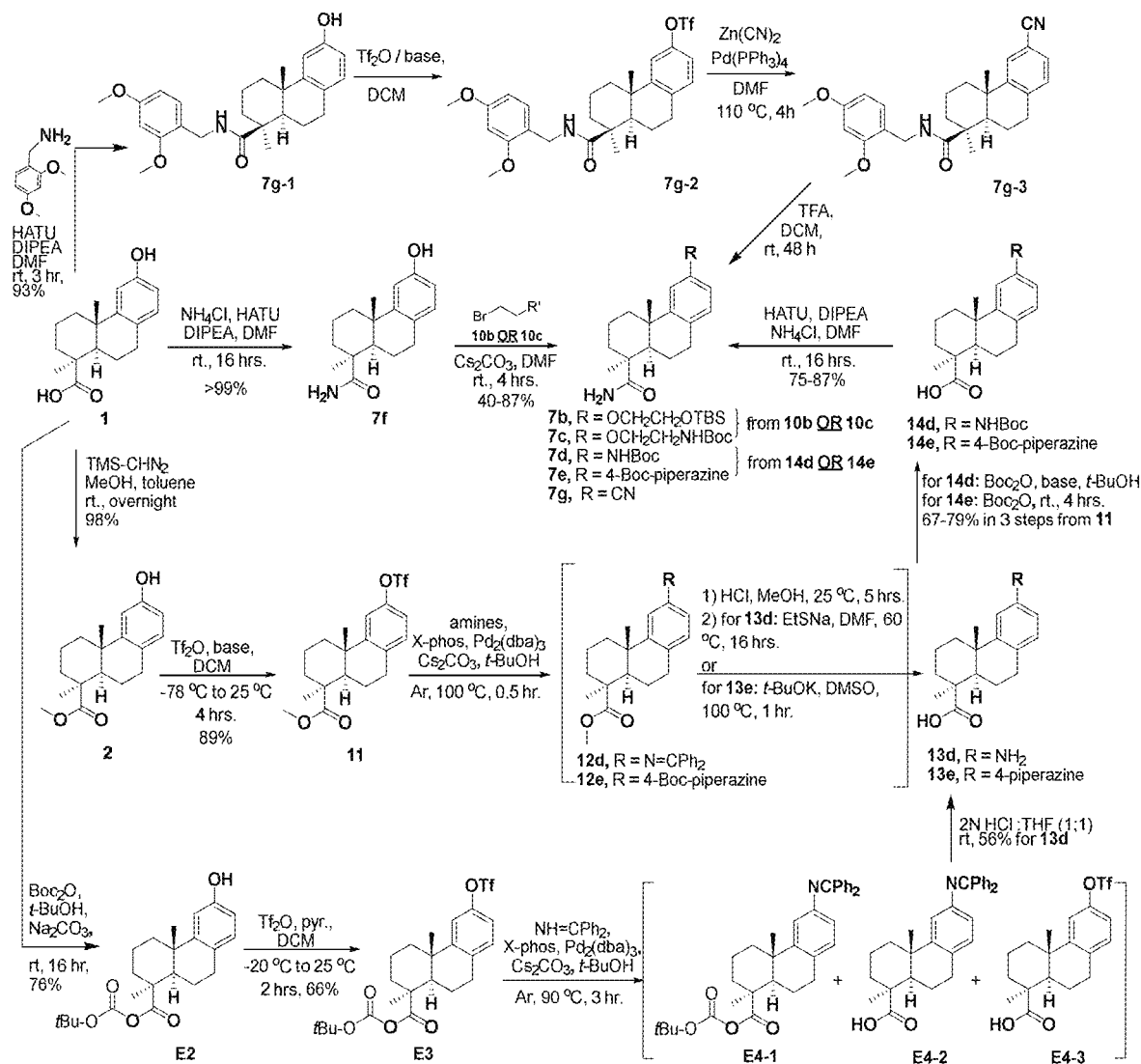

| Compound | ABCA1 induction EC$_{50}$ (M) | ABCG1 induction EC$_{50}$ (M) |
|---|---|---|
| 9d | 4.9E-14 | 6.6E-14 |
| 9c | 1.5E-08 | 1.5E-08 |
| 31 | 4.6E-08 | 4.8E-08 |
| 9h | 4.3E-15 | 8.0E-16 |
| TO91317 | 3.8E-08 | 1.0E-07 |

Statistical comparison by Welch's t-test, *p<0.05

SEQUENCE LISTING

```
<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Oxygen group replaces the nitrogen at the
      N-terminus

<400> SEQUENCE: 1

Ala Ala Ala Ala
1

<210> SEQ ID NO 2
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Hydroxyl group replaces the nitrogen at the
      N-terminus

<400> SEQUENCE: 2

Ala Ala Ala Ala
1

<210> SEQ ID NO 3
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 3

Ala Ala Ala Ala
1

<210> SEQ ID NO 4
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Linker site
<220> FEATURE:
<221> NAME/KEY: misc_feature
<222> LOCATION: (5)..(6)
<223> OTHER INFORMATION: Linker site

<400> SEQUENCE: 4

Glu Glu Gln Tyr Gln Ser Thr Tyr Arg
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
ctgaccaatg tgaacagctc cagc                                         24

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
acatgcgaca ggaggtgatg                                              20

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
atgcccgcag acaatacga                                               19

<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
agataataac ctcacggaag cccagcg                                      27

<210> SEQ ID NO 9
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 9
ggacctgctg aatggacatc                                              20

<210> SEQ ID NO 10
<211> LENGTH: 18
<212> TYPE: DNA
<213> ORGANISM: Artificial Sequence
<220> FEATURE:
<223> OTHER INFORMATION: Synthetic

<400> SEQUENCE: 10
ccgaggcaag gaggagaa                                                18

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
tcaacagcga cacccactcc tc                                           22

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ccaggtggtc tcctctgact                                              20

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
gcttgacaaa gtggtcgttg a                                            21
```

BIS-OCTAHYDROPHENANTHRENE CARBOXAMIDES AND PROTEIN CONJUGATES THEREOF

CROSS-REFERENCE TO RELATED APPLICATION

This application claims the benefit under 35 U.S.C. § 119 of U.S. provisional application No. 62/508,327, filed May 18, 2017, the content of which is hereby incorporated by reference in its entirety.

SEQUENCE LISTING

This application incorporates by reference the computer readable sequence listing in the file "10286WO01 Sequence Listing.txt," created Nov. 3, 2021, having 2.84 KB.

FIELD

Provided herein are novel, bis-octahydrophenanthrene carboxamides and protein conjugates thereof, and methods for treating a variety of diseases, disorders, and conditions including administering the bis-octahydrophenanthrene carboxamides, and protein conjugates thereof.

BACKGROUND

Antibody-drug conjugates (ADCs) are antibodies that are attached to biologically active small molecule drugs, thus combining the targeting specificity of antibodies with the mode-of-action and potency of small molecule drugs. The therapeutic utility of ADCs has been validated in cancer treatment and is a major ongoing focus of study. ADCE-TRIS® (bentruximab vedotin) and KADCYLA® (ado-trastuzumab emtansine) are two ADCs approved for the treatment of certain cancer types, and at least forty ADCs are currently in clinical development.

Liver X Receptor (LXR) includes LXRα and LXRβ which are ligand-dependent transcription factors that control the expression of genes involved in cholesterol, lipid and glucose homeostasis, inflammation, and innate immunity. LXRα is highly expressed in liver, intestine, adipose tissue, and differentiated macrophages; and LXRβ is ubiquitously expressed. LXRs have various biological functions including (i) stimulating the expression of cholesterol transporters, for example, ABCA1 and ABCG1, both of which mediate cellular cholesterol efflux; and (ii) negatively regulating macrophage inflammatory gene expression via repression of NF-kB activation. LXRs have also been implicated in atherosclerosis, proliferative disorders, neurodegenerative disorders, and inflammation. Proliferative disorders include melanomas, lung cancer, oral squamous carcinoma, and prostate cancer. (Pencheva et al. 2004; Wu et al. 2015; Kaneko et al. 2015; Chuu et al. 2006) Neurodegenerative disorders include Alzheimer's disease and myelin gene expression. (Terwel et al. 2011; Sandoval-Hernandez et al. 2016; Meffre et al. 2014) Inflammation includes inflammatory bowel disease, ulcerative colitis, Crohn's disease, and arthritis. (Anderson et al. 2011; Huang et al. 2015; Cui et al. 2012). Macrophage LXRs are known to include anti-atherogenic activity. LXR agonists are believed to be capable of (i) inhibiting the initiation and delay the progression of atherosclerosis; (ii) mitigating atherosclerosis and stabilizing established atherosclerotic lesions; and (iii) reducing lesion macrophage content by apoptosis.

The therapeutic potential of small molecule LXR modulators is limited by, for example, undesired modulation of LXR at non-target cells and/or low bioavailability. Modulation of LXR at non-target cells can lead to undesirable side effects, and low bioavailability may manifest for myriad reasons including, without limitation, low solubility that further exacerbates poor therapeutic windows for treatment. The development of ADCs comprising LXR modulators would allow for target-specific modulation of LXR, thereby avoiding side-effects caused by off-target modulation of LXR. Furthermore, such ADCs would provide improved modulation of biological targets, improved bioavailability, and improved therapeutic window. Therefore, there is a continuing need for effective treatments of, for example, metabolic diseases using small molecule ADCs of LXR modulators.

SUMMARY

Provided herein are compounds useful, for example, for the treatment of metabolic diseases including, without limitation, dyslipidemia. Also provided herein are compounds useful, for example, for the treatment of inflammation or a neurodegenerative disease. The compounds provided herein are according to Formula I.

In one embodiment, provided herein are compounds according to Formula I.

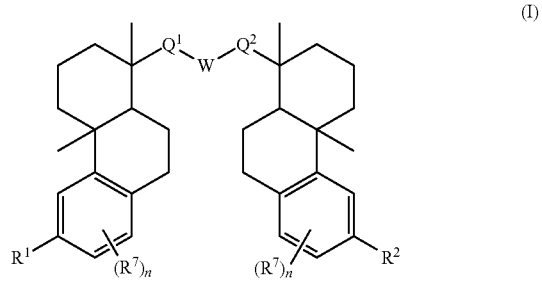

or a pharmaceutically acceptable salt, solvate, or stereoisomeric form thereof, wherein
each of $Q^1$ and $Q^2$ includes, independently, —$CH_2$—, —C(O)—, —C(H)(OH)—, —C(OH)$_2$—, —$SO_2$—, —SO—, —PO(O$R^{11}$)—, —PO(N$R^{11}$N$R^{12}$)—, —N$R^{11}$—, or —N=;
W includes —$CH_2$—, —N(H)—, or —O—;
$R^1$ includes —H, —O$R^6$, —OH, —$NH_2$, alkyl, or —OP(O)(O$R^6$)$_2$;
$R^2$ includes —H, —OH, —O$R^1$, halide, —$SO_2NR^{11}R^{12}$, —CON$R^{11}R^{12}$, —$CH_2NH_2$, $R^3$, $R^4$, $R^5$, or —O—$R^5$, wherein $R^1$ and $R^2$ are not simultaneously —H;
$R^3$ includes —N($R^6$)$_2$;
$R^4$ includes —X—Y—Z;
X includes the group consisting of —O— and —N(H)—;
Y includes the group consisting of alkylene, substituted alkylene (including oxo, i.e., =O), heteroalkylene, and substituted heteroalkylene (including oxo, i.e., =O);
Z includes the group consisting of —OH and —$NH_2$;
$R^5$ includes alkyl, heterocycloalkyl, or substituted heterocycloalkyl, wherein each heterocycloalkyl or substituted heterocycloalkyl comprises one, two, or three heteroatoms selected from nitrogen and oxygen, and includes at least one —OH or —$CH_2OH$, or at least one primary or secondary nitrogen;

each R⁶ includes, independently in each instance, —H, an amino acid residue, an N-alkyl amino acid residue, a peptide, a biodegradable moiety, or alkyl;

each R⁷ independently includes halo, $C_{1-6}$ alkyl, $C_{1-6}$ alkoxy, —CN, O-glucose, O-amino acid residue, and O-PEG$_n$, wherein each n is an integer from 0-3; and each R¹¹ and R¹² are independently selected from —H, alkyl, and aryl.

In one embodiment, provided herein are compounds according to Formula I.

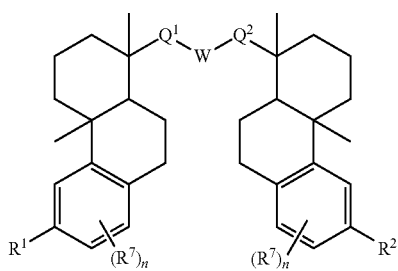

(I)

or a pharmaceutically acceptable salt, solvate, or stereoisomeric form thereof, wherein each of Q¹ and Q² includes, independently, —CH₂—, —C(O)—, —C(H)(OH)—, or —C(OH)₂—;

W includes —CH₂—, —N(H)—, or —O—;

R¹ includes —H, —OH, —NH₂, alkyl, or —OP(O)(OR⁶)₂;

R² includes —H, —OH, —CH₂NH₂, R³, R⁴, R⁵, or —O—R⁵, wherein R¹ and R² are not simultaneously —H;

R³ includes —N(R⁶)₂;

R⁴ includes —X—Y—Z;

X includes the group consisting of —O— and —N(H)—;

Y includes the group consisting of alkylene, substituted alkylene (including, without limitation, oxo substitution (i.e., =O)), heteroalkylene, and substituted heteroalkylene (including, without limitation, oxo substitution (i.e., =O));

Z includes the group consisting of —OH and —NH₂;

R⁵ includes alkyl, heterocycloalkyl, or substituted heterocycloalkyl, wherein each heterocycloalkyl or substituted heterocycloalkyl includes one, two, or three heteroatoms selected from nitrogen and oxygen, and includes at least one —OH or —CH₂OH substituent, or at least one primary or secondary nitrogen, for instance, O-glucose;

each R⁶ includes, independently in each instance, —H, an amino acid residue, an N-alkyl amino acid residue, a peptide, or alkyl; and each R⁷ independently includes halo, C1-6 alkyl, C1-6 alkoxy, —CN, O-glucose, O-amino acid residue, and O-PEG$_n$, wherein each n is an integer from 0-3.

In another embodiment, set forth herein is a linker-payload having a compound according to Formula I, above.

In another embodiment, set forth herein is an antibody-drug conjugate having a compound of Formula I or linker-payload, above, bonded to an antibody or an antigen binding fragment thereof.

In another embodiment, set forth herein are compounds according to Formula A:

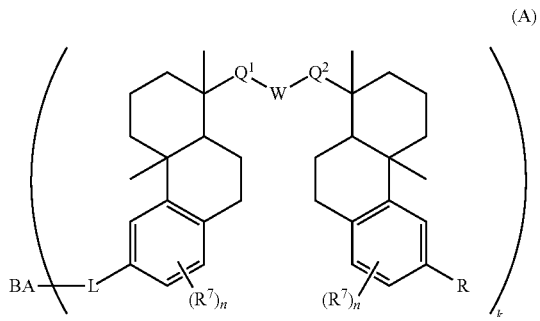

(A)

or a pharmaceutically acceptable salt, or stereoisomeric form thereof, wherein

L is a linker;

BA is a binding agent;

k is an integer from 1 to 30;

each of Q¹ and Q² is independently —CH₂—, —C(O)—, —C(H)(OH)—, or —C(OH)₂—;

W is —CH₂—, —N(H)—, or —O—;

R is independently —H, —OH, or —OP(O)(OR⁶)₂; and each R⁶ is, independently in each instance, —H, an amino acid residue, an N-alkyl amino acid residue, a peptide, or alkyl; and each R⁷ is independently halo, $C_{1-6}$ alkyl, $C_{1-6}$ alkoxy, —CN, O-glucose, O-amino acid residue, and O-PEG$_n$, wherein each n is an integer from 0-3.

In another embodiment, set forth herein is a pharmaceutical composition, including a compound, linker-payload, or antibody-drug conjugate described herein and a pharmaceutically acceptable excipient, carrier, or diluent.

In another embodiment, set forth herein is a method for the treatment of dyslipidemia, a metabolic disease, inflammation, or a neurodegenerative disease in a subject including the administration to the subject of an effective treatment amount of a compound, linker-payload, or antibody-drug conjugate, or pharmaceutical composition described herein.

In another embodiment, set forth herein are methods for making the compounds, linker-payloads, or antibody-drug conjugates, and compositions described herein.

BRIEF DESCRIPTIONS OF THE DRAWING

FIGS. 1, 1a-1i, 2, 3a-3e, and 4-10 show synthetic chemistry schemes for bis-octahydrophenanthrene carboxamides, cyclodextrin-based linker-payloads, and protein conjugates thereof.

Figure 16:
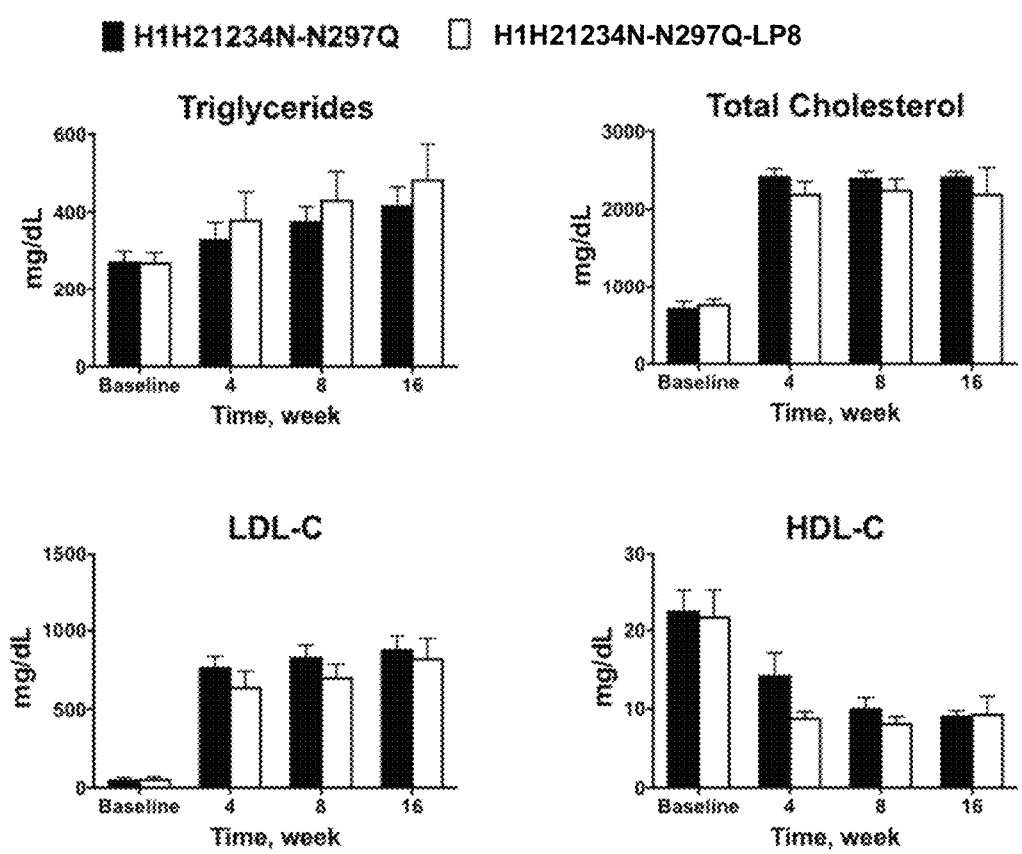

FIG. 16 provides a series of bar graphs illustrating the effect of an exemplary MSR1 antibody-LXR agonist conjugate and its unconjugated counterpart on serum lipid levels in a mouse model of atherosclerosis.

Figure 17:
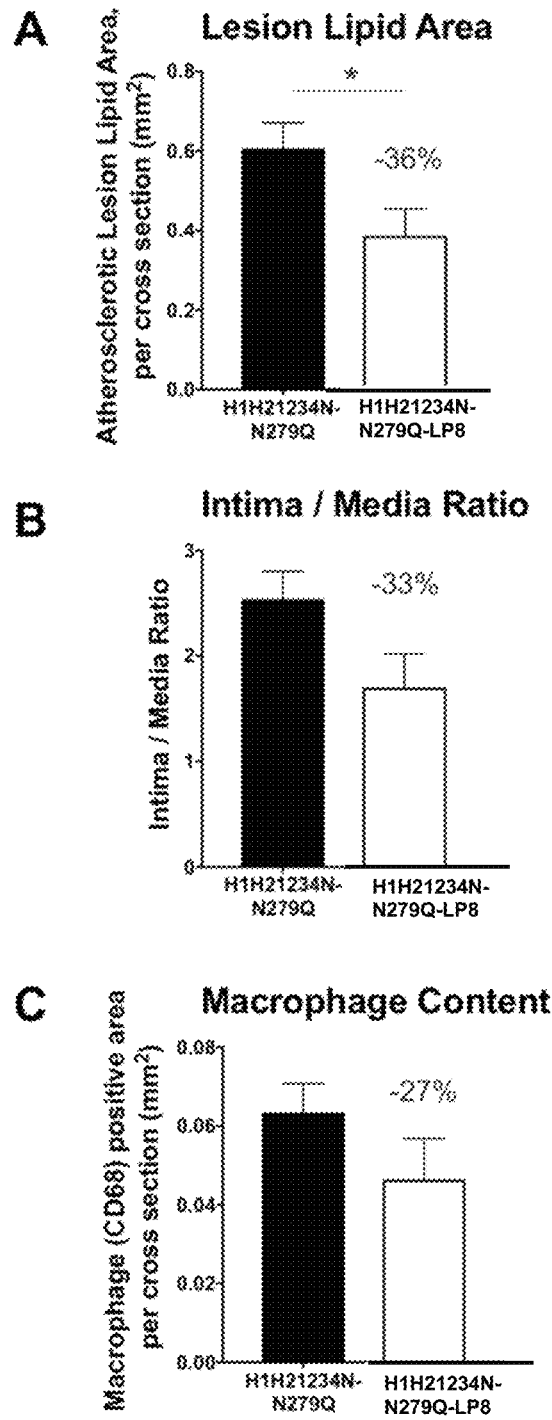

FIG. 17 provides a series of bar graphs illustrating the effect of an exemplary MSR1 antibody-LXR agonist conjugate and its unconjugated counterpart on lesion lipid area and macropphage (CD68) content in a mouse model of atherosclerosis.

Figure 18:
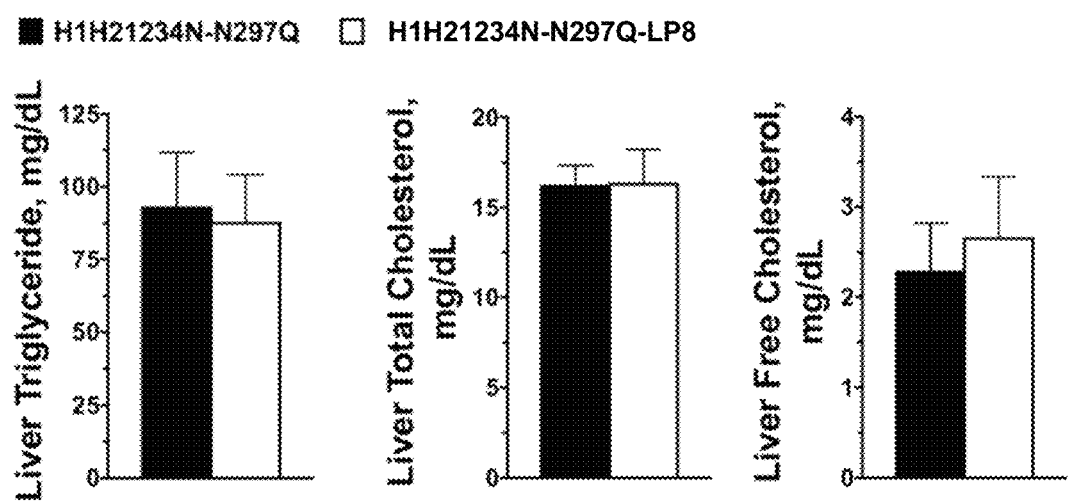

FIG. 18 provides a series of bar graphs illustrating the effect of an exemplary MSR1 antibody-LXR agonist conjugate and its unconjugated counterpart on hepatic triglyceride and cholesterol levels in a mouse model of atherosclerosis.

Figure 19:
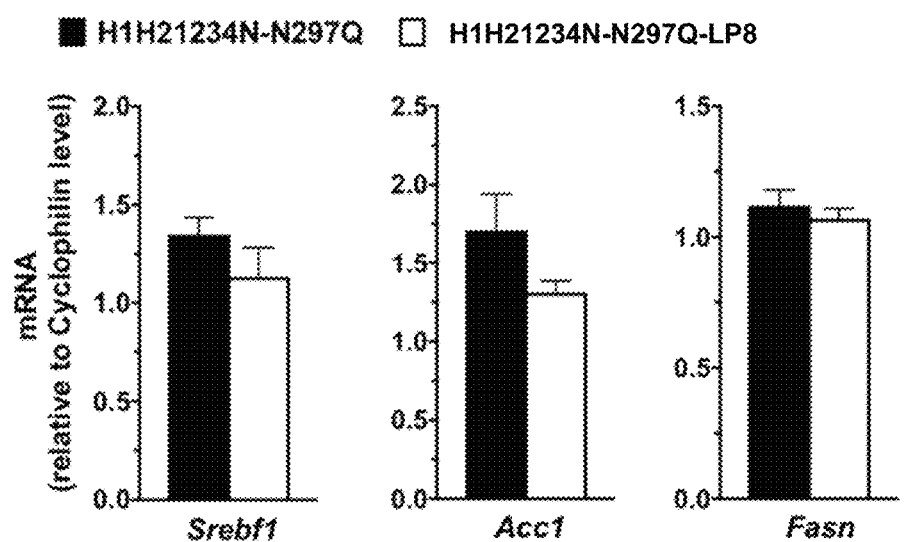

FIG. 19 provides a series of bar graphs illustrating the effect of an exemplary MSR1 antibody-LXR agonist conjugate and its unconjugated counterpart on de novo lipogenesis in a mouse model of atherosclerosis.

DESCRIPTION OF EXEMPLARY EMBODIMENTS

Provided herein are compounds, compositions, and methods useful for treating, for example, dyslipidemia, a metabolic disease, inflammation, or a neurodegenerative disease, in a subject.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term provided herein, these Definitions prevail unless stated otherwise.

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those radicals having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl. A pentyl moiety includes, but is not limited to, n-pentyl and i-pentyl. A hexyl moiety includes, but is not limited to, n-hexyl.

As used herein, "alkylene" refers to a divalent alkyl group. Unless specified otherwise, alkylene includes, but is not limited to, 1-20 carbon atoms. The alkylene group is optionally substituted as described herein for alkyl. In some embodiments, alkylene is unsubstituted.

As used herein, the term "O-amino acid" or "HO-amino acid" designates an amino acid wherein the native amino group at the N-terminus of an amino acid or an amino acid sequence has been replaced with an oxygen or hydroxyl group, respectively. For example, "O-AAAA" or "HO-AAAA" is intended to designate an amino acid sequence (AAAA) wherein the native amino group at the N-terminus has been replaced with an oxygen or hydroxyl group, respectively (e.g.,

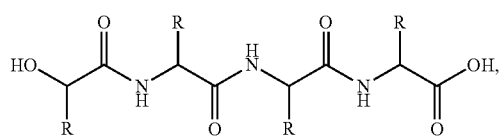

where each R is an amino acid side chain). Similarly, the terms "O-amino acid residue" or "HO-amino acid residue" refers to the chemical moiety within a compound that remains after a chemical reaction. For example, "O-amino acid residue" or "HO-amino acid residue" refers to the product of an amide coupling or peptide coupling of an O-amino acid or a HO-amino acid to a suitable coupling partner; wherein, for example, a water molecule is expelled after the amide or peptide coupling of the O-amino acid or a HO-amino acid, resulting in the product having the O-amino acid residue or a HO-amino acid residue incorporated therein.

Designation of an amino acid or amino acid residue without specifying its stereochemistry is intended to encompass the L form of the amino acid, the D form of the amino acid, or a racemic mixture thereof.

As used herein, "haloalkyl" refers to alkyl, as defined above, wherein the alkyl includes at least one substituent selected from a halogen, for example, fluorine (F), chlorine (Cl), bromine (Br), or iodine (I). Examples of haloalkyl include, but are not limited to, —$CF_3$, —$CH_2CF_3$, —$CCl_2F$, and —$CCl_3$.

As used herein, "alkenyl" refers to a monovalent hydrocarbon radical moiety containing at least two carbon atoms and one or more non-aromatic carbon-carbon double bonds. Alkenyl is optionally substituted and can be linear, branched, or cyclic. Alkenyl includes, but is not limited to, those radicals having 2-20 carbon atoms, i.e., $C_{2-20}$ alkenyl; 2-12 carbon atoms, i.e., $C_{2-12}$ alkenyl; 2-8 carbon atoms, i.e., $C_{2-8}$ alkenyl; 2-6 carbon atoms, i.e., $C_{2-6}$ alkenyl; and 2-4 carbon atoms, i.e., $C_{2-4}$ alkenyl. Examples of alkenyl moieties include, but are not limited to vinyl, propenyl, butenyl, and cyclohexenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those radicals having 2-20 carbon atoms, i.e., $C_{2-20}$ alkynyl; 2-12 carbon atoms, i.e., $C_{2-12}$ alkynyl; 2-8 carbon atoms, i.e., $C_{2-8}$ alkynyl; 2-6 carbon atoms, i.e., $C_{2-6}$ alkynyl; and 2-4 carbon atoms, i.e., $C_{2-4}$ alkynyl. Examples of alkynyl moieties include, but are not limited to ethynyl, propynyl, and butynyl.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2$—O for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to methoxy, ethoxy, n-propoxy, i-propoxy, n-butoxy, s-butoxy, t-butoxy, i-butoxy, a pentoxy moiety, and a hexoxy moiety, cyclopropoxy, cyclobutoxy, cyclopentoxy, and cyclohexoxy (i.e.,

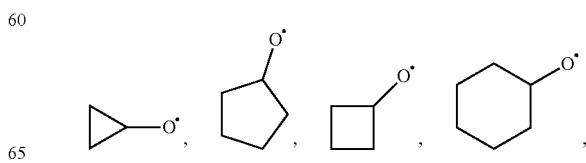

respectively).

As used herein, "haloalkoxy" refers to alkoxy, as defined above, wherein the alkoxy includes at least one substituent selected from a halogen, e.g., F, Cl, Br, or I.

As used herein, "aryl" refers to a monovalent moiety that is a radical of an aromatic compound wherein the ring atoms are carbon atoms. Aryl is optionally substituted and can be monocyclic or polycyclic, e.g., bicyclic or tricyclic. Examples of aryl moieties include, but are not limited to, those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are not limited to phenyl, naphthyl, fluorenyl, azulenyl, anthryl, phenanthryl, and pyrenyl.

As used herein, "arylalkyl" refers to a monovalent moiety that is a radical of an alkyl compound, wherein the alkyl compound is substituted with an aromatic substituent, i.e., the aromatic compound includes a single bond to an alkyl group and wherein the radical is localized on the alkyl group. An arylalkyl group bonds to the illustrated chemical structure via the alkyl group. An arylalkyl can be represented by the structure, e.g.,

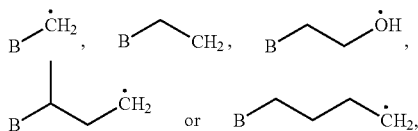

wherein B is an aromatic moiety, e.g., phenyl. Arylalkyl is optionally substituted, i.e., the aryl group and/or the alkyl group, can be substituted as disclosed herein. Examples of arylalkyl include, but are not limited to, benzyl.

As used herein, "alkylaryl" refers to a monovalent moiety that is a radical of an aryl compound, wherein the aryl compound is substituted with an alkyl substituent, i.e., the aryl compound includes a single bond to an alkyl group and wherein the radical is localized on the aryl group. An alkylaryl group bonds to the illustrated chemical structure via the aryl group. An alkylaryl can be represented by the structure, e.g.,

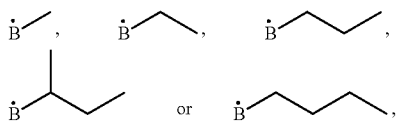

wherein B is an aromatic moiety, e.g., phenyl. Alkylaryl is optionally substituted, i.e., the aryl group and/or the alkyl group, can be substituted as disclosed herein. Examples of alkylaryl include, but are not limited to, toluyl.

As used herein, "aryloxy" refers to a monovalent moiety that is a radical of an aromatic compound wherein the ring atoms are carbon atoms and wherein the ring is substituted with an oxygen radical, i.e., the aromatic compound includes a single bond to an oxygen atom and wherein the radical is localized on the oxygen atom, e.g.,

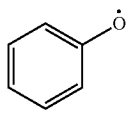

for phenoxy. Aryloxy substituents bond to the compound which they substitute through this oxygen atom. Aryloxy is optionally substituted. Aryloxy includes, but is not limited to, those radicals having 6 to 20 ring carbon atoms, i.e., $C_{6-20}$ aryloxy; 6 to 15 ring carbon atoms, i.e., $C_{6-15}$ aryloxy, and 6 to 10 ring carbon atoms, i.e., $C_{6-10}$ aryloxy. Examples of aryloxy moieties include, but are not limited to phenoxy, naphthoxy, and anthroxy.

As used herein, "$R^aR^bN$-aryloxy" refers to a monovalent moiety that is a radical of an aromatic compound wherein the ring atoms are carbon atoms and wherein the ring is substituted with at least one $R^aR^bN$— substituent and at least one oxygen radical, i.e., the aromatic compound includes a single bond to an $R^aR^bN$— substituent and a single bond to an oxygen atom and wherein the radical is localized on the oxygen atom, e.g.,

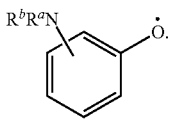

$R^aR^bN$-aryloxy substituents bond to the compound which they substitute through this oxygen atom. $R^aR^bN$-aryloxy is optionally substituted. $R^aR^bN$-aryloxy includes, but is not limited to, those having 6 to 20 ring carbon atoms, for example, $C_{6-20}$ $(R^aR^bN)_n$-aryloxy, 6 to 15 ring carbon atoms, for example, $C_{6-15}$ $(R^aR^bN)_n$-aryloxy, and 6 to 10 ring carbon atoms, for example, $C_{6-10}$ $(R^aR^bN)_n$-aryloxy, wherein n represents the number of $R^aR^bN$— substituents. An example of an $R^aR^bN$-aryloxy moiety includes, but is not limited to 4-(dimethylamino)-phenoxy,

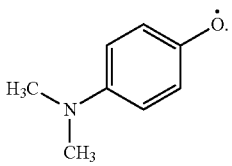

As used herein, "arylene" refers to a divalent moiety of an aromatic compound wherein the ring atoms are only carbon atoms. Arylene is optionally substituted and can be monocyclic or polycyclic, e.g., bicyclic or tricyclic. Examples of arylene moieties include, but are not limited to those having 6 to 20 ring carbon atoms, i.e., $C_{6-20}$ arylene; 6 to 15 ring carbon atoms, i.e., $C_{6-15}$ arylene, and 6 to 10 ring carbon atoms, i.e., $C_{6-10}$ arylene.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkynyl in which one or more carbon atoms are replaced by heteroatoms. Suitable heteroatoms include, but are not limited to, nitrogen, oxygen, and sulfur atoms. Heteroalkyl is optionally substituted. Examples of heteroalkyl moieties include, but are not limited to, aminoalkyl, sulfonylalkyl, and sulfinylalkyl. Examples of heteroalkyl moieties also include, but are not limited to, methylamino, methylsulfonyl, and methylsulfinyl.

As used herein, "heteroaryl" refers to a monovalent moiety that is a radical of an aromatic compound wherein the ring atoms contain carbon atoms and at least one oxygen, sulfur, nitrogen, or phosphorus atom. Examples of heteroaryl moieties include, but are not limited to those having 5 to 20 ring atoms; 5 to 15 ring atoms; and 5 to 10 ring atoms. Heteroaryl is optionally substituted.

As used herein, "heteroarylene" refers to an arylene in which one or more ring atoms of the aromatic ring are replaced with an oxygen, sulfur, nitrogen, or phosphorus atom. Heteroarylene is optionally substituted.

As used herein, "heterocycloalkyl" refers to a cycloalkyl in which one or more carbon atoms are replaced by heteroatoms. Suitable heteroatoms include, but are not limited to, nitrogen, oxygen, and sulfur atoms. Heterocycloalkyl is optionally substituted. Examples of heterocycloalkyl moieties include, but are not limited to, morpholinyl, piperidinyl, tetrahydropyranyl, pyrrolidinyl, imidazolidinyl, oxazolidinyl, thiazolidinyl, dioxolanyl, dithiolanyl, oxanyl, or thianyl.

As used herein, "Lewis acid" refers to a molecule or ion that accepts an electron lone pair. The Lewis acids used in the methods described herein are those other than protons. Lewis acids include, but are not limited to, non-metal acids, metal acids, hard Lewis acids, and soft Lewis acids. Lewis acids include, but are not limited to, Lewis acids of aluminum, boron, iron, tin, titanium, magnesium, copper, antimony, phosphorus, silver, ytterbium, scandium, nickel, and zinc. Illustrative Lewis acids include, but are not limited to, $AlBr_3$, $AlCl_3$, $BCl_3$, boron trichloride methyl sulfide, $BF_3$, boron trifluoride methyl etherate, boron trifluoride methyl sulfide, boron trifluoride tetrahydrofuran, dicyclohexylboron trifluoromethanesulfonate, iron (III) bromide, iron (III) chloride, tin (IV) chloride, titanium (IV) chloride, titanium (IV) isopropoxide, $Cu(OTf)_2$, $CuCl_2$, $CuBr_2$, zinc chloride, alkylaluminum halides ($R_nAlX_{3-n}$, wherein R is hydrocarbyl), $Zn(OTf)_2$, $ZnCl_2$, $Yb(OTf)_3$, $Sc(OTf)_3$, $MgBr_2$, $NiCl_2$, $Sn(OTf)_2$, $Ni(OTf)_2$, and $Mg(OTf)_2$.

As used herein, "N-containing heterocycloalkyl," refers to a cycloalkyl in which one or more carbon atoms are replaced by heteroatoms and wherein at least one heteroatom is a nitrogen atom. Suitable heteroatoms in addition to nitrogen, include, but are not limited to oxygen and sulfur atoms. N-containing heterocycloalkyl is optionally substituted. Examples of N-containing heterocycloalkyl moieties include, but are not limited to, morpholinyl, piperidinyl, pyrrolidinyl, imidazolidinyl, oxazolidinyl, or thiazolidinyl.

As used herein, "optionally substituted," when used to describe a radical moiety, for example, optionally substituted alkyl, means that such moiety is optionally bonded to one or more substituents. Examples of such substituents include, but are not limited to, halo, cyano, nitro, optionally substituted haloalkyl, azido, epoxy, optionally substituted heteroaryl, optionally substituted heterocycloalkyl,

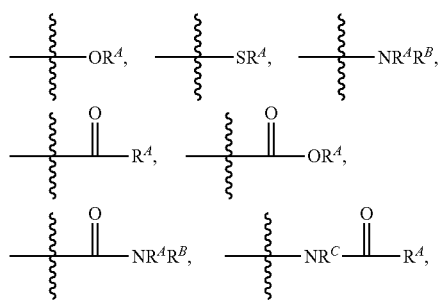

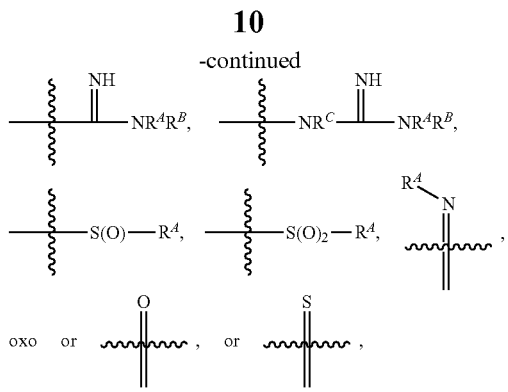

wherein $R^A$, $R^B$, and $R^C$ are, independently at each occurrence, a hydrogen atom, alkyl, alkenyl, alkynyl, aryl, alkylaryl, arylalkyl, heteroalkyl, heteroaryl, or heterocycloalkyl, or $R^A$ and $R^B$ together with the atoms to which they are bonded, form a saturated or unsaturated carbocyclic ring, wherein the ring is optionally substituted, and wherein one or more ring atoms is optionally replaced with a heteroatom. In certain embodiments, when a radical moiety is optionally substituted with an optionally substituted heteroaryl, optionally substituted heterocycloalkyl, or optionally substituted saturated or unsaturated carbocyclic ring, the substituents on the optionally substituted heteroaryl, optionally substituted heterocycloalkyl, or optionally substituted saturated or unsaturated carbocyclic ring, if they are substituted, are not substituted with substituents which are further optionally substituted with additional substituents. In some embodiments, when a group described herein is optionally substituted, the substituent bonded to the group is unsubstituted unless otherwise specified.

As used herein, "binding agent" refers to any molecule, e.g., protein, capable of binding with specificity to a given binding partner, e.g., antigen.

As used herein, "linker" refers to a divalent, trivalent, or multivalent moiety that covalently links the binding agent to one or more compounds described herein, for instance payload compounds and enhancement agents.

As used herein, "amide synthesis conditions" refers to reaction conditions suitable to effect the formation of an amide, e.g., by the reaction of a carboxylic acid, activated carboxylic acid, or acyl halide with an amine. In some examples, amide synthesis conditions refers to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid and an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy)tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b]pyridinium 3-oxid hexafluorophosphate (HATU), N-ethoxycarbonyl-2-ethoxy-1,2-dihydroquinoline (EEDQ), N-ethyl-N'-(3-dimethylaminopropyl)carbodiimide (EDC), 2-chloro-1,3-dimethylimidazolidinium hexafluorophosphate (CIP), 2-chloro-4,6-dimethoxy-1,3,5-triazine (CDMT), and carbonyldiimidazole (CDI). In some examples, a carboxylic acid is first converted to an activated carboxylic ester before treating the activated carboxylic ester with an amine to form an amide bond. In certain embodiments, the carboxylic acid is treated with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. The activated carboxylic esters for certain carboxylic acids are subsequently more susceptible to nucleophilic attack by an amine than the carboxylic acid is before it is activated. This results in amide bond formation. As such, the carboxylic acid is described as activated. Exemplary reagents include DCC and DIC.

As used herein, "regioisomer," "regioisomers," or "mixture of regioisomers" refers to the product(s) of 1,3-cycloadditions or strain-promoted alkyne-azide cycloadditions (SPAACs)—otherwise known as click reactions—that derive from suitable azides (e.g., —N$_3$, or PEG-N$_3$ derivatized antibodies) treated with suitable alkynes. In certain embodiments, for example, regioisomers and mixtures of regioisomers are characterized by the click reaction products shown below:

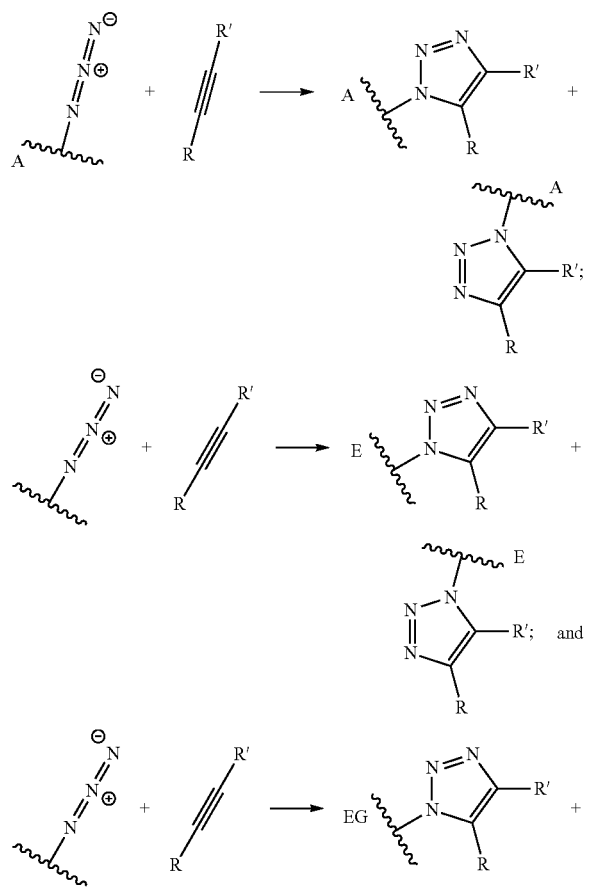

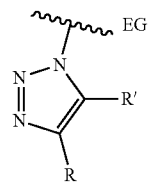

In certain embodiments, more than one suitable azide and more than one suitable alkyne can be utilized within a synthetic scheme en route to a product, where each pair of azide-alkyne can participate in one or more independent click reactions to generate a mixture of regioisomeric click reaction products. For example, a person of skill will recognize that a first suitable azide may independently react with a first suitable alkyne, and a second suitable azide may independently react with a second suitable alkyne, en route to a product, resulting in the generation of four possible click reaction regioisomers or a mixture of the four possible click reaction regioisomers in a sample of an ADC described herein. By way of further example, a person of skill will recognize that a first suitable azide may independently react with a first suitable alkyne, and a second suitable azide may independently react with a second suitable alkyne, en route to a product, resulting in the generation of four possible click reaction regioisomers or a mixture of the four possible click reaction regioisomers in a sample of an LP described herein.

As used herein, the term "residue" refers to the chemical moiety within a compound that remains after a chemical reaction. For example, the term "amino acid residue" or "N-alkyl amino acid residue" refers to the product of an amide coupling or peptide coupling of an amino acid or a N-alkyl amino acid to a suitable coupling partner; wherein, for example, a water molecule is expelled after the amide or peptide coupling of the amino acid or the N-alkylamino acid, resulting in the product having the amino acid residue or N-alkyl amino acid residue incorporated therein.

As used herein, "therapeutically effective amount" refers to an amount (e.g., of a compound) that is sufficient to provide a therapeutic benefit to a patient in the treatment or management of a disease or disorder, or to delay or minimize one or more symptoms associated with the disease or disorder.

Certain groups, moieties, substituents, and atoms are depicted with a wiggly line that intersects a bond or bonds to indicate the atom through which the groups, moieties, substituents, atoms are bonded. For example, a phenyl group that is substituted with a propyl group depicted as:

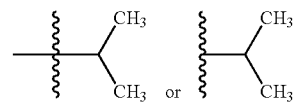

has the following structure:

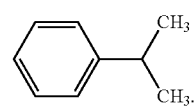

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group,

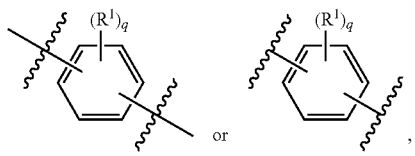

wherein subscript q is an integer from 0 to 4 and in which the positions of substituent $R^1$ are described generically, i.e., not directly attached to any vertex of the bond line structure, i.e., specific ring carbon atom, includes the following, non-limiting examples of groups in which the substituent $R^1$ is bonded to a specific ring carbon atom:

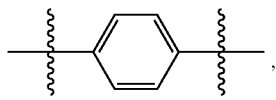

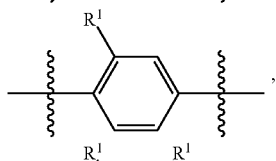

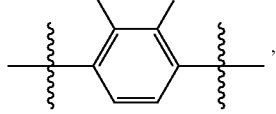

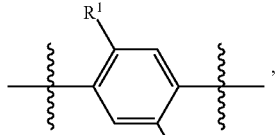

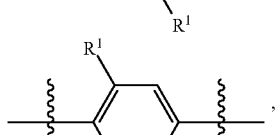

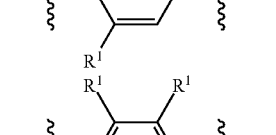

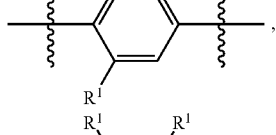

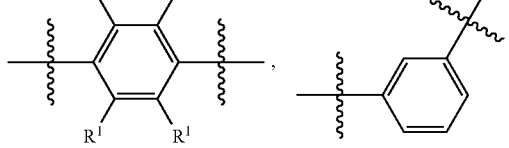

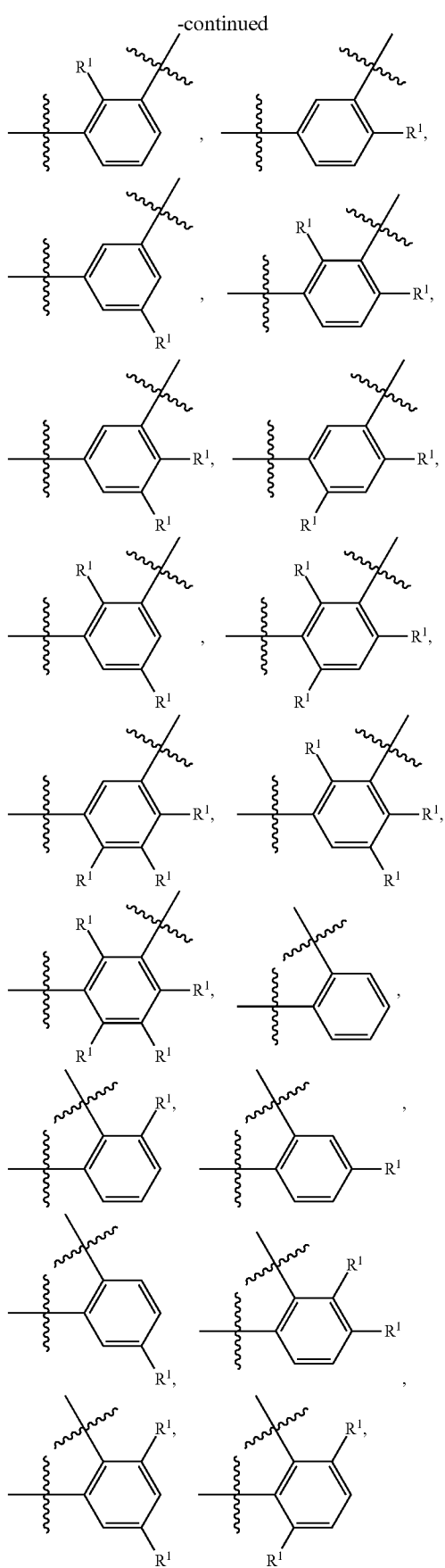

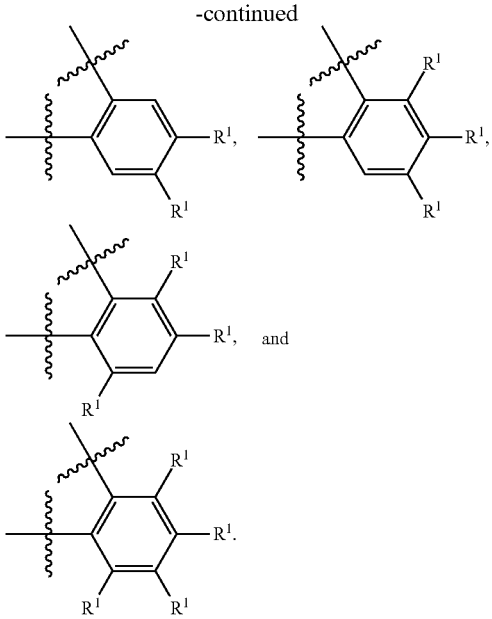

As used herein, the phrase "reactive linker," or the abbreviation "RL" refers to a monovalent group that includes a reactive group and spacer group, depicted for example, as

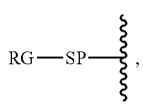

wherein RG is the reactive group and SP is the spacer group. As described herein, a reactive linker may include more than one reactive group and more than one spacer group. The spacer group is any divalent moiety that bridges the reactive group to another group, such as a payload. The reactive linkers (RL), together with the payloads to which they are bonded, provide intermediates ("linker-payloads") useful as synthetic precursors for the preparation of the antibody conjugates described herein. The reactive linker includes a reactive group ("RG"), which is a functional group or moiety that is capable of reacting with a reactive portion of another group, for instance, an antibody, modified antibody, or antigen binding fragment thereof, or an enhancement group. The moiety resulting from the reaction of the reactive group with the antibody, modified antibody, or antigen binding fragment thereof, together with the linking group, include the "binding agent linker" ("BL") portion of the conjugate, described herein. In certain embodiments, the "reactive group" is a functional group or moiety (e.g., maleimide or N-hydroxysuccinimide (NHS) ester) that reacts with a cysteine or lysine residue of an antibody or antigen-binding fragment thereof. In certain embodiments, the "reactive group" is a functional group or moiety that is capable of undergoing a click chemistry reaction (see, e.g., click chemistry, Huisgen *Proc. Chem. Soc.* 1961, Wang et al. *J. Am. Chem. Soc.* 2003, and Agard et al. *J. Am. Chem. Soc.* 2004). In some embodiments of said click chemistry reaction, the reactive group is an alkyne that is capable of undergoing a 1,3-cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3-cycloaddition reactions with alkynes in the absence of copper catalysts. Suitable alkynes also include, but are not limited to, dibenzoazacyclooctyne or

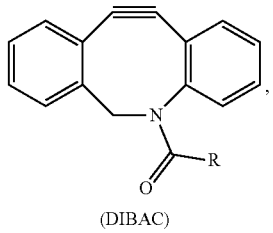
(DIBAC)

dibenzocyclooctyne or

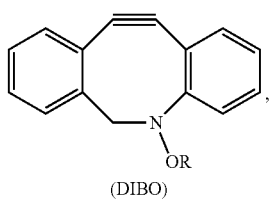
(DIBO)

biarylazacyclooctynone or

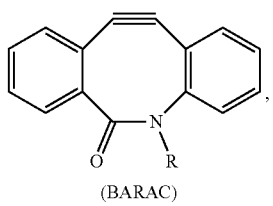
(BARAC)

difluorinated cyclooctyne or

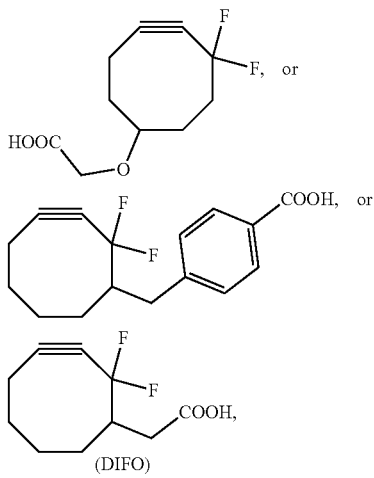
(DIFO)

substituted, e.g., fluorinated alkynes, aza-cycloalkynes, bicycle[6.1.0]nonyne or

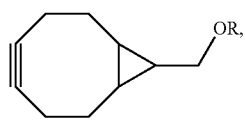

(BCN, where R is alkyl, alkoxy, or acyl)

and derivatives thereof. Particularly useful alkynes include and

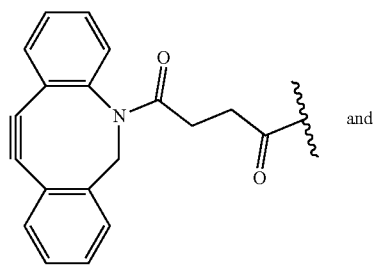 and

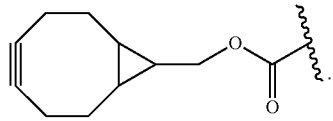

Linker-payloads including such reactive groups are useful for conjugating antibodies that have been functionalized with azido groups. Such functionalized antibodies include antibodies functionalized with azido-polyethylene glycol groups. In certain embodiments, such a functionalized antibody is derived by treating an antibody having at least one glutamine residue, e.g., heavy chain Gln295, with a compound bearing an an amino a group and an azide group, in the presence of the enzyme transglutaminase.

In some examples, the reactive group is an alkyne, e.g.,

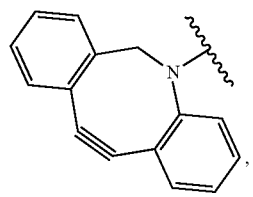 [SMILES: *N1Cc2ccccc2C#Cc2ccccc21]

which can react via click chemistry with an azide, e.g.,

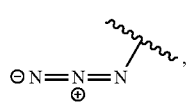

to form a click chemistry product, e.g.,

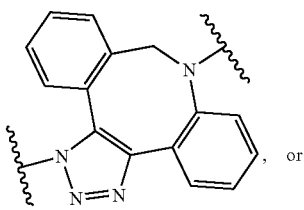, or

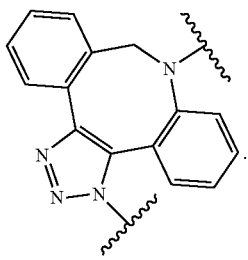.

In some examples, the group reacts with an azide on a modified antibody or antigen binding fragment thereof. In some examples, the reactive group is an alkyne, e.g.,

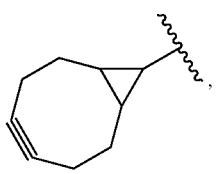 [SMILES: *C1C2CCC#CCCC12]

which can react via click chemistry with an azide, e.g.,

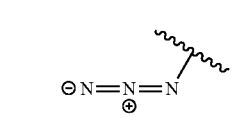 [SMILES: *N=[N+]=[N-]]

to form a click chemistry product, e.g.,

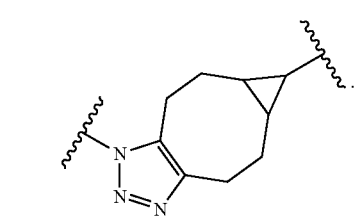 [SMILES: *C1C2CCc3nnn(*)c3CCC12].

In some examples, the reactive group is an alkyne, e.g.,

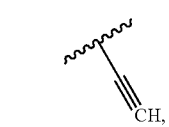

which can react via click chemistry with an azide, e.g.,

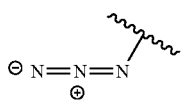

to form a click chemistry product, e.g.,

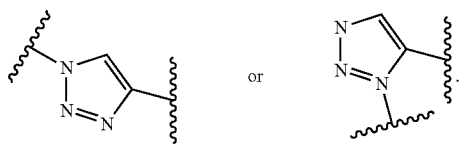

In some examples, the reactive group is a functional group, e.g.,

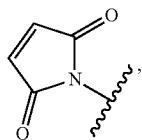

which reacts with a cysteine residue on an antibody or antigen-binding fragment thereof, to form a bond thereto, e.g.,

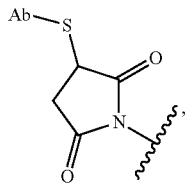

wherein Ab refers to an antibody or antigen-binding fragment thereof and S refers to the S atom on a cysteine residue through which the functional group bonds to the Ab. In some examples, the reactive group is a functional group, e.g.,

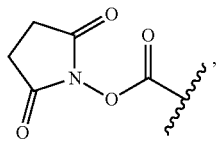 [SMILES: *C(=O)ON1C(=O)CCC1=O]

which reacts with a lysine residue on an antibody or antigen-binding fragment thereof, to form a bond thereto, e.g.,

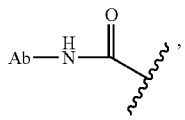

wherein Ab refers to an antibody or antigen-binding fragment thereof and NH refers to the NH atom on a lysine side chain residue through which the functional group bonds to the Ab.

As used herein, the phrase "biodegradable moiety" refers to a moiety that degrades in vivo to non-toxic, biocompatible components which can be cleared from the body by ordinary biological processes. In some embodiments, a biodegradable moiety completely or substantially degrades in vivo over the course of about 90 days or less, about 60 days or less, or about 30 days or less, where the extent of degradation is based on percent mass loss of the biodegradable moiety, and wherein complete degradation corresponds to 100% mass loss. Exemplary biodegradable moieties include, without limitation, aliphatic polyesters such as poly(s-caprolactone) (PCL), poly(3-hydroxybutyrate) (PHB), poly(glycolic acid) (PGA), poly(lactic acid) (PLA) and its copolymers with glycolic acid (i.e., poly(D,L-lactide-coglycolide) (PLGA) (Vert M, Schwach G, Engel R and Coudane J (1998) J Control Release 53(1-3):85-92; Jain R A (2000) Biomaterials 21(23):2475-2490; Uhrich K E, Cannizzaro S M, Langer R S and Shakesheff K M (1999) Chemical Reviews 99(11): 3181-3198; and Park T G (1995) Biomaterials 16(15):1123-1130, each of which are incorporated herein by reference in their entirety).

As used herein, the phrases "effective amount," "physiolocally effective amount," or "prophylactically effective amount" refer to that amount of compound that is sufficient to effect treatment, when administered to a subject in need of such treatment. A "physiologically effective amount" of an active substance indicates an efficacious amount of the active substances to have a significant, externally observable effect on the patient. Thus, a physiologically effective amount affects one or more of the characteristics (e.g., phenotype) in the patient without the need for special equipment to determine the effect. For example, a physiologically effective amount of a compound disclosed herein has a significant, externally observable effect on the behavior of the patient by reducing one or more of the symptoms of the condition to be treated. Accordingly, one can determine whether an efficacious amount of the active substance has been administered by observing the patient and observing whether changes have occurred in the patient due to the active substance.

As used herein, the phrase "binding agent linker," or "BL" refers to any divalent, trivalent, or multi-valent group or moiety that links, connects, or bonds a binding agent (e.g., an antibody or an antigen-binding fragment thereof) with a payload compound set forth herein (e.g., bis-octahydrophenanthrene carboxamides) and, optionally, with one or more side chain compounds. Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyl (PAB) units. In some embodiments, the binding agent linker (BL) includes a moiety that is formed by the reaction of the reactive group (RG) of a reactive linker (RL) and reactive portion of the binding agent, e.g., antibody, modified antibody, or antigen binding fragment thereof.

In some examples, the BL includes the following moiety:

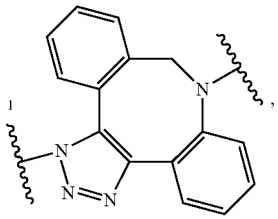 [SMILES: *N1Cc2ccccc2-c2c(nnn2*)-c2ccccc21]

or the triazolyl regioisomer, wherein $\xi^1$ is the bond to the binding agent. In some examples, the BL includes the following moiety:

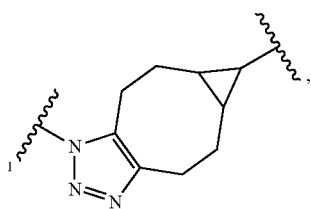 [SMILES: *C1C2CCc3nnn(*)c3CCC12]

wherein $\xi^1$ is the bond to the binding agent. In some examples, the BL includes the following moiety:

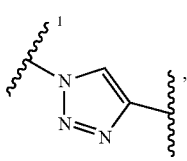

or the triazolyl regioisomer, wherein $\xi^1$ is the bond to the binding agent. In some examples, the BL includes the following moiety:

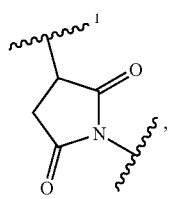 [SMILES: *C1CC(=O)N(*)C1=O]

wherein $\xi^1$ is the bond to the cysteine of the antibody or antigen-binding fragment thereof. In some examples, the BL includes the following moiety:

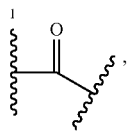

wherein $\xi^1$ is the bond to the lysine of the antibody or antigen-binding fragment thereof.

Compounds and Payloads

In some examples, set forth herein is a compound having the structure of Formula (I):

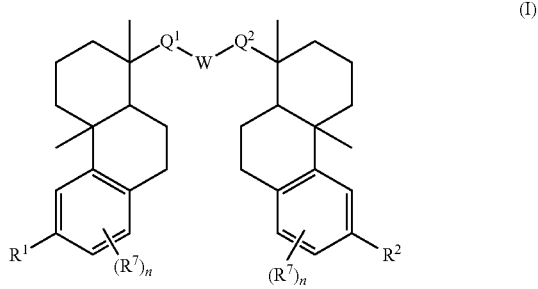

(I)

or a pharmaceutically acceptable salt, solvate, or stereoisomeric form wherein
each of $Q^1$ and $Q^2$ is, independently, —$CH_2$—, —C(O)—, —C(H)(OH)—, or —C(OH)$_2$—;
W is —$CH_2$—, —N(H)—, or —O—;
$R^1$ is —H, —OH, —$NH_2$, alkyl, or —OP(O)(OR$^6$)$_2$;
$R^2$ is —H, —OH, —$CH_2NH_2$, $R^3$, $R^4$, $R^5$, or —O—$R^5$, wherein $R^1$ and $R^2$ are not simultaneously —H;
$R^3$ is —N(R$^6$)$_2$;
$R^4$ is —X—Y—Z;
X is selected from the group consisting of —O— and —N(H)—;
Y is selected from the group consisting of alkylene, substituted alkylene (including, without limitation, oxo substitution, i.e., =O), heteroalkylene, and substituted heteroalkylene (including without limitation, oxo substitution (i.e., =O));
Z is selected from the group consisting of —OH and —$NH_2$;
$R^5$ is alkyl, heterocycloalkyl or substituted heterocycloalkyl, wherein each heterocycloalkyl or substituted heterocycloalkyl includes one, two, or three heteroatoms selected from nitrogen and oxygen, and includes at least one —OH and —$CH_2OH$ substituent, or at least one primary or secondary nitrogen, for instance, O-glucose;
each $R^6$ is in each instance, —H, an amino acid residue, an N-alkyl amino acid residue, a peptide, or alkyl; and
each $R^7$ is, independently, halo, $C_{1-6}$ alkyl, $C_{1-6}$ alkoxy, —CN, O-glucose, O-amino acid residue, and O-PEG$_n$, wherein each n is an integer from 0-3.

In Formula I, in certain embodiments, $R^5$ is heterocycloalkyl or substituted heterocycloalkyl. Useful heterocycloalkyl groups include tetrahydropyranyl, glycosidyl, and piperazinyl. These groups can be substituted or unsubstituted. In certain embodiments, they are unsubstituted. In certain embodiments, they are substituted. Exemplary substituents include at least one hydroxyl, at least one primary nitrogen, or at least one secondary nitrogen.

In certain embodiments of Formula I, $R^6$ is independently in each instance an amino acid residue, an N-alkyl amino acid residue, or a peptide. Those of skill in the art will recognize that the amino acid residue may be achiral or chiral, for example, L-amino acid or D-amino acid. The amino acids generally include an amino acid side chain. The side chain can be the side chain of any amino acids known to those of skill. In certain embodiments, the side chain is the side chain of histidine, alanine, isoleucine, arginine, leucine, asparagine, lysine, aspartic acid, methionine, cysteine, phenylalanine, glutamic acid, threonine, glutamine, tryptophan, valine, ornithine, selenocysteine, serine, glycine, homoglycine (e.g., β-homoglycine), or tyrosine. Those of skill in the art will recognize that the peptide may be achiral or chiral, for example, including racemic DL-amino acids or non-racemic D- or L-amino acids and diastereomeric mixtures thereof. The side chains of the peptides are as described in the context of amino acids, above. Those of skill in the art will recognize that the N-alkyl amino acid residue includes an alkyl substituent, as defined herein, at the terminal amino group of the amino acid residue or the terminal amino group of the peptide. Examples include N-methyl amino acids and N-ethyl amino acids.

In Formula I, in certain embodiments, each $R^7$ is halo, $C_{1-6}$ alkyl, $C_{1-6}$ alkoxy, —CN, O-glucose, O-amino acid residue, or O-PEG$_n$, wherein each n is an integer from 0-3. In certain embodiments, O-amino acid residue includes HO-amino acid residue as defined above. In one embodiment, O-PEG$_n$ is where n=0. In another embodiment, O-PEG$_n$ is where n=1. In another embodiment, O-PEG$_n$ is where n=2. In another embodiment, O-PEG$_n$ is where n=3.

In some examples, set forth herein is a compound having the structure of Formula (Ia):

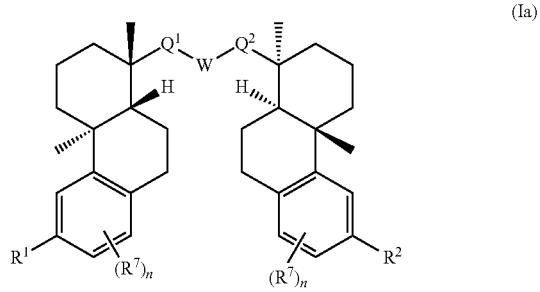

(Ia)

or a pharmaceutically acceptable salt, solvate, or stereoisomeric form, wherein
each of $Q^1$ and $Q^2$ is, independently, —CH$_2$—, —C(O)—, —C(H)(OH)—, or —C(OH)$_2$—;
W is —CH$_2$—, —N(H)—, or —O—;
$R^1$ is —H, —OH, —NH$_2$, alkyl, or —OP(O)(OR$^6$)(OH)—OP(O)(OR$^6$)$_2$;
$R^2$ is —H, —OH, —CH$_2$NH$_2$, $R^3$, $R^4$, $R^5$, or —O—R$^5$, wherein $R^1$ and $R^2$ are not simultaneously —H;
$R^3$ is —N(R$^6$)$_2$;
$R^4$ is —X—Y—Z;
X is selected from the group consisting of —O— and —N(H)—;
Y is selected from the group consisting of alkylene, substituted alkylene (including, without limitation, oxo substitution, i.e., =O), heteroalkylene, and substituted heteroalkylene (including, without limitation, oxo substitution (i.e., =O));

Z is selected from the group consisting of —OH and —NH$_2$;
$R^5$ is alkyl, heterocycloalkyl, or substituted heterocycloalkyl, wherein each heterocycloalkyl or substituted heterocycloalkyl includes one, two, or three heteroatoms selected from nitrogen and oxygen, and includes at least one —OH and —CH$_2$OH substituent, or at least one primary or secondary nitrogen, for instance, O-glucose;
each $R^6$ is in each instance, —H, an amino acid residue, an N-alkyl amino acid residue, a peptide, or alkyl; and
each $R^7$ is, independently, halo, $C_{1-6}$ alkyl, $C_{1-6}$ alkoxy, —CN, O-glucose, O-amino acid residue, and O-PEG$_n$, wherein each n is an integer from 0-3.

In Formula Ia, in certain embodiments, $R^5$ is heterocycloalkyl or substituted heterocycloalkyl. Useful heterocycloalkyl groups include tetrahydropyranyl, glycosidyl, and piperazinyl. These groups can be substituted or unsubstituted. In certain embodiments, they are unsubstituted. In certain embodiments, they are substituted. Exemplary substituents include at least one hydroxyl, at least one primary nitrogen, or at least one secondary nitrogen.

In certain embodiments of Formula Ia, $R^6$ is independently in each instance an amino acid residue, N-alkyl amino acid residue, or a peptide. Those of skill in the art will recognize that the amino acid residue may be achiral or chiral, for example, L-amino acid or D-amino acid. The amino acids generally include an amino acid side chain. The side chain can be the side chain of any amino acids known to those of skill. In certain embodiments, the side chain is the side chain of histidine, alanine, isoleucine, arginine, leucine, asparagine, lysine, aspartic acid, methionine, cysteine, phenylalanine, glutamic acid, threonine, glutamine, tryptophan, valine, ornithine, selenocysteine, serine, glycine, homoglycine (e.g., β-homoglycine), or tyrosine. Those of skill in the art will recognize that the peptide may be achiral or chiral, for example, including racemic DL-amino acids or non-racemic D- or L-amino acids and diastereomeric mixtures thereof. The side chains of the peptides are as described in the context of amino acids, above. Those of skill in the art will recognize that the N-alkyl amino acid residue includes an alkyl substituent, as defined herein, at the terminal amino group of the amino acid or the terminal amino group of the peptide.

In Formula Ia, in certain embodiments, $R^7$ is halo, $C_{1-6}$ alkyl, $C_{1-6}$ alkoxy, —CN, O-glucose, O-amino acid residue, or O-PEG$_n$, wherein each n is an integer from 0-3. In certain embodiments, O-amino acid residue includes HO-amino acid residue as defined above. In one embodiment, O-PEG$_n$ is where n=0. In another embodiment, O-PEG$_n$ is where n=1. In another embodiment, O-PEG$_n$ is where n=2. In yet another embodiment, O-PEG$_n$ is where n=3.

In one embodiment of Formula I or Ia, $Q^1$ is —CH$_2$— and $Q^2$ is —C(O)—. In another embodiment, $Q^1$ is —C(H)(OH)— and $Q^2$ is —C(O)—. In another embodiment, $Q^1$ is —C(O)— and $Q^2$ is —C(O)—. In yet another embodiment, $Q^1$ is —C(O)— and $Q^2$ is —CH$_2$—. In still yet another embodiment, $Q^1$ is —C(O)— and $Q^2$ is —C(H)(OH)—.

In one embodiment of Formula I or Ia, $Q^1$ is —CH$_2$—, $Q^2$ is —C(O)—, and W is —CH$_2$—. In another embodiment, $Q^1$ is —CH$_2$—, $Q^2$ is —C(O)—, W is —CH$_2$—, and $R^1$ is —H and $R^2$ is —OH, —CH$_2$NH$_2$, $R^3$, $R^4$, $R^5$, or —O—R$^5$. In another embodiment, $Q^1$ is —CH$_2$—, $Q^2$ is —C(O)—, W is —CH$_2$—, and $R^1$ is —H and $R^2$ is —OH. In another embodiment, $Q^1$ is —CH$_2$—, $Q^2$ is —C(O)—, W is —CH$_2$—, and $R^1$ is —H and $R^2$ is —CH$_2$NH$_2$. In another embodiment, $Q^1$ is —CH$_2$—, $Q^2$ is —C(O)—, W is —CH$_2$—, and R$^1$ is —H and R$^2$ is R$^3$. In another embodiment, Q$^1$ is —CH$_2$—, Q$^2$ is —C(O)—, W is —CH$_2$—, and R$^1$ is —H and R$^2$ is R$^4$. In another embodiment, Q$^1$ is —CH$_2$—, Q$^2$ is —C(O)—, W is —CH$_2$—, and R$^1$ is —H and R$^2$ is R$^5$. In another embodiment, Q$^1$ is —CH$_2$—, Q$^2$ is —C(O)—, W is —CH$_2$—, and R$^1$ is —H and R$^2$ is —O—R$^5$. In another embodiment, Q$^1$ is —CH$_2$—, Q$^2$ is —C(O)—, W is —CH$_2$—, and R$^1$ is —H and R$^2$ is selected from the group consisting of amino, dimethylamino, hydroxyl,

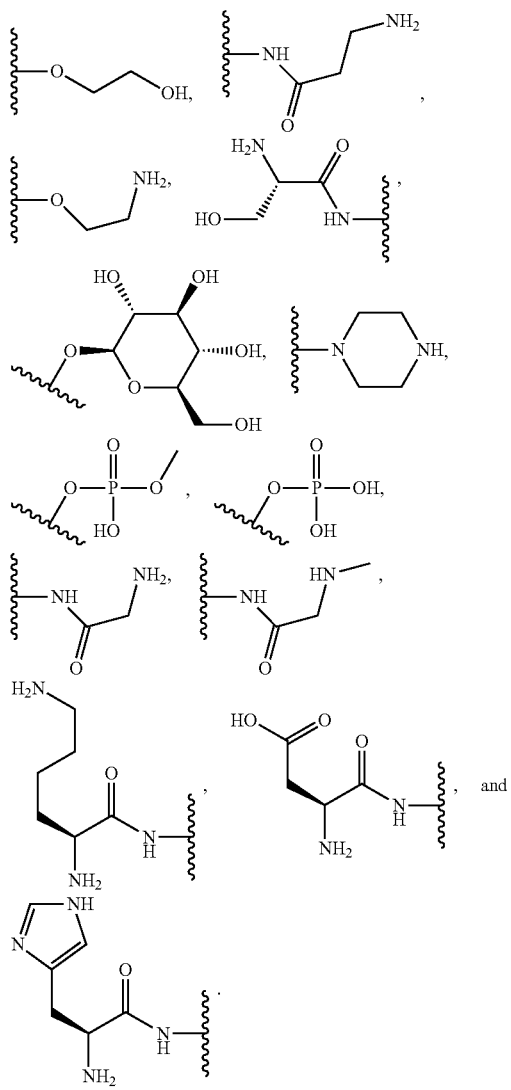

In another embodiment, Q$^1$ is —CH$_2$—, Q$^2$ is —C(O)—, W is —CH$_2$—, and R$^1$ is —OH and R$^2$ is —OH, —CH$_2$NH$_2$, R$^3$, R$^4$, R$^5$, or —O—R$^5$. In another embodiment, Q$^1$ is —CH$_2$—, Q$^2$ is —C(O)—, W is —CH$_2$—, and R$^1$ is —OH and R$^2$ is —OH. In another embodiment, Q$^1$ is —CH$_2$—, Q$^2$ is —C(O)—, W is —CH$_2$—, and R$^1$ is —OH and R$^2$ is —CH$_2$NH$_2$. In another embodiment, Q$^1$ is —CH$_2$—, Q$^2$ is —C(O)—, W is —CH$_2$—, and R$^1$ is —OH and R$^2$ is R$^3$. In another embodiment, Q$^1$ is —CH$_2$—, Q$^2$ is —C(O)—, W is —CH$_2$—, and R$^1$ is —OH and R$^2$ is R$^4$. In another embodiment, Q$^1$ is —CH$_2$—, Q$^2$ is —C(O)—, W is —CH$_2$—, and R$^1$ is —OH and R$^2$ is R$^5$. In another embodiment, Q$^1$ is —CH$_2$—, Q$^2$ is —C(O)—, W is —CH$_2$—, and R$^1$ is —OH and R$^2$ is —O—R$^5$. In another embodiment, Q$^1$ is —CH$_2$—, Q$^2$ is —C(O)—, W is —CH$_2$—, and R$^1$ is —OH and R$^2$ is selected from the group consisting of amino, dimethylamino, hydroxyl,

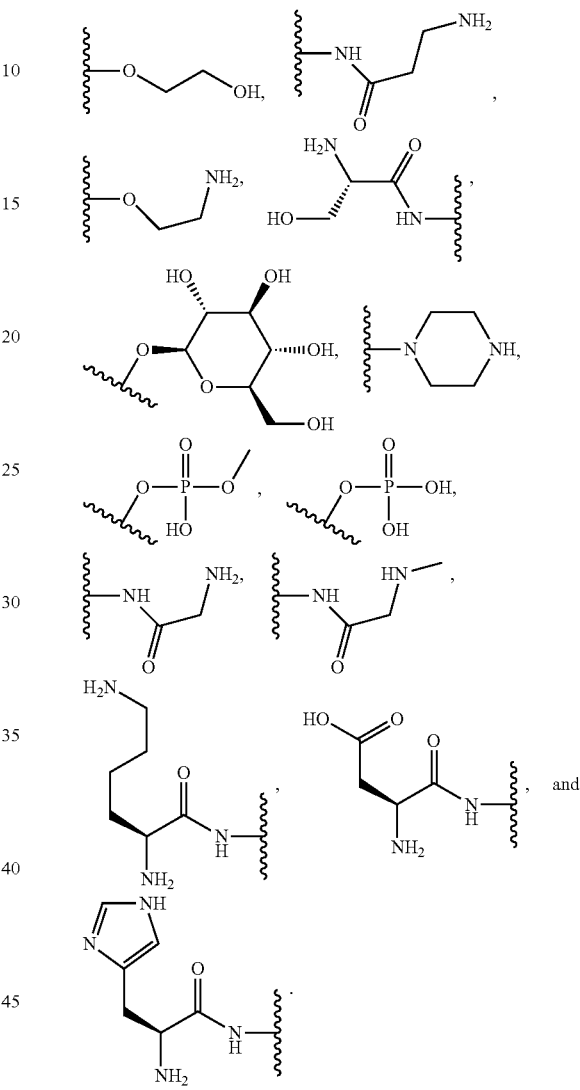

In another embodiment, Q$^1$ is —CH$_2$—, Q$^2$ is —C(O)—, W is —CH$_2$—, and R$^1$ is —NH$_2$ and R$^2$ is —OH, —CH$_2$NH$_2$, R$^3$, R$^4$, R$^5$, or —O—R$^5$. In another embodiment, Q$^1$ is —CH$_2$—, Q$^2$ is —C(O)—, W is —CH$_2$—, and R$^1$ is —NH$_2$ and R$^2$ is —OH. In another embodiment, Q$^1$ is —CH$_2$—, Q$^2$ is —C(O)—, W is —CH$_2$—, and R$^1$ is —NH$_2$ and R$^2$ is —CH$_2$NH$_2$. In another embodiment, Q$^1$ is —CH$_2$—, Q$^2$ is —C(O)—, W is —CH$_2$—, and R$^1$ is —NH$_2$ and R$^2$ is R$^3$. In another embodiment, Q$^1$ is —CH$_2$—, Q$^2$ is —C(O)—, W is —CH$_2$—, and R$^1$ is —NH$_2$ and R$^2$ is R$^4$. In another embodiment, Q$^1$ is —CH$_2$—, Q$^2$ is —C(O)—, W is —CH$_2$—, and R$^1$ is —NH$_2$ and R$^2$ is R$^5$. In another embodiment, Q$^1$ is —CH$_2$—, Q$^2$ is —C(O)—, W is —CH$_2$—, and R$^1$ is —NH$_2$ and R$^2$ is —O—R$^5$. In another embodiment, Q$^1$ is —CH$_2$—, Q$^2$ is —C(O)—, W is —CH$_2$—, and R$^1$ is —NH$_2$ and R$^2$ is selected from the group consisting of amino, dimethylamino, hydroxyl,

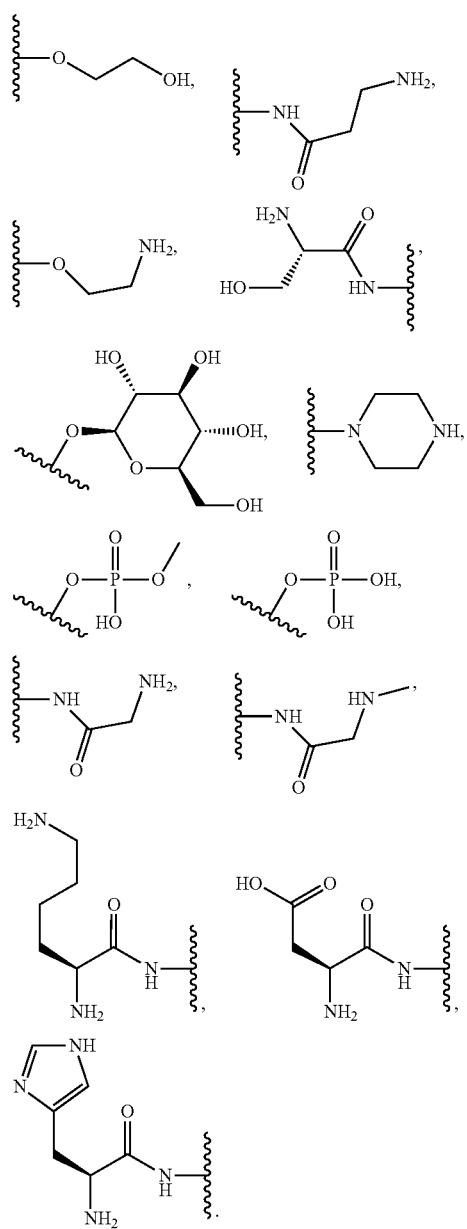
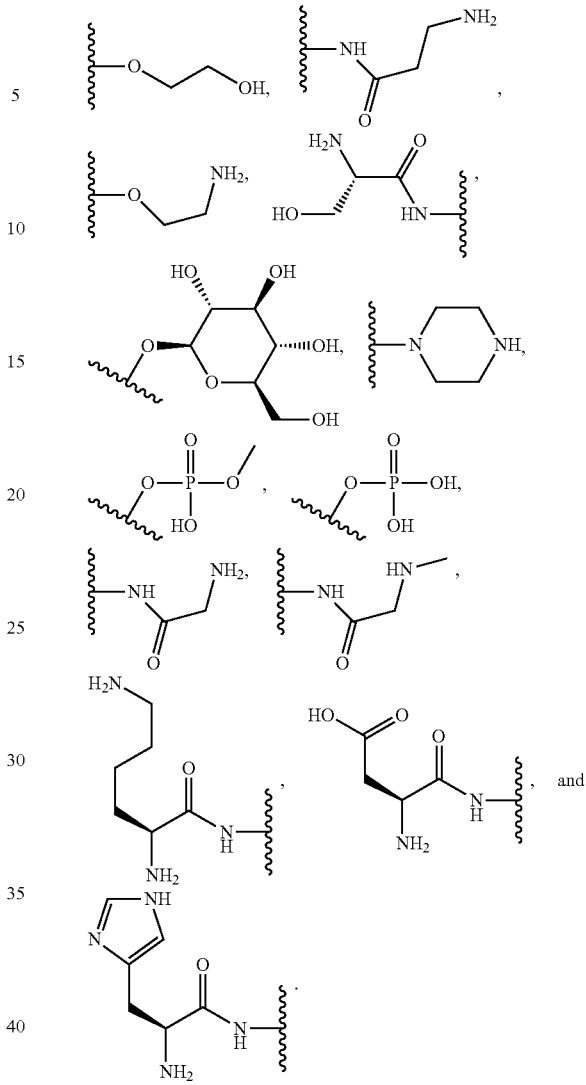

In another embodiment, $Q^1$ is —$CH_2$—, $Q^2$ is —C(O)—, W is —$CH_2$—, and $R^1$ is alkyl and $R^2$ is —OH, —$CH_2NH_2$, $R^3$, $R^4$, $R^5$, or —O—$R^5$. In another embodiment, $Q^1$ is —$CH_2$—, $Q^2$ is —C(O)—, W is —$CH_2$—, and $R^1$ is alkyl and $R^2$ is —OH. In another embodiment, $Q^1$ is —$CH_2$—, $Q^2$ is —C(O)—, W is —$CH_2$—, and $R^1$ is alkyl and $R^2$ is —$CH_2NH_2$. In another embodiment, $Q^1$ is —$CH_2$—, $Q^2$ is —C(O)—, W is —$CH_2$—, and $R^1$ is alkyl and $R^2$ is $R^3$. In another embodiment, $Q^1$ is —$CH_2$—, $Q^2$ is —C(O)—, W is —$CH_2$—, and $R^1$ is alkyl and $R^2$ is $R^4$. In another embodiment, $Q^1$ is —$CH_2$—, $Q^2$ is —C(O)—, W is —$CH_2$—, and $R^1$ is alkyl and $R^2$ is $R^5$. In another embodiment, $Q^1$ is —$CH_2$—, $Q^2$ is —C(O)—, W is —$CH_2$—, and $R^1$ is alkyl and $R^2$ is —O—$R^5$. In another embodiment, $Q^1$ is —$CH_2$—, $Q^2$ is —C(O)—, W is —$CH_2$—, and $R^1$ is alkyl and $R^2$ is selected from the group consisting of amino, dimethylamino, hydroxyl, In another embodiment of Formula I or Ia, $Q^1$ is —$CH_2$—, $Q^2$ is —C(O)—, W is —$CH_2$—, and $R^1$ is —OH or —OP(O)(OR$^6$)(OH) and $R^2$ is —H. In another embodiment, $Q^1$ is —$CH_2$—, $Q^2$ is —C(O)—, W is —$CH_2$—, and $R^1$ is —OH and $R^2$ is —H. In another embodiment, $Q^1$ is —$CH_2$—, $Q^2$ is —C(O)—, W is —$CH_2$—, and $R^1$ is —OP(O)(OR$^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —$CH_2$—, $Q^2$ is —C(O)—, and W is —O—. In another embodiment, $Q^1$ is —$CH_2$—, $Q^2$ is —C(O)—, W is —O—, and $R^1$ is —H and $R^2$ is —OH, —$CH_2NH_2$, $R^3$, $R^4$, $R^5$, or —O—$R^5$. In another embodiment, $Q^1$ is —$CH_2$—, $Q^2$ is —C(O)—, W is —O—, and $R^1$ is —H and $R^2$ is —OH. In another embodiment, $Q^1$ is —$CH_2$—, $Q^2$ is —C(O)—, W is —O—, and $R^1$ is —H and $R^2$ is —$CH_2NH_2$. In another embodiment, $Q^1$ is —$CH_2$—, $Q^2$ is —C(O)—, W is —O—, and $R^1$ is —H and $R^2$ is $R^3$. In another embodiment, $Q^1$ is —$CH_2$—, $Q^2$ is —C(O)—, W is —O—, and $R^1$ is —H and $R^2$ is $R^4$. In another embodiment, $Q^1$ is —$CH_2$—, $Q^2$ is —C(O)—, W is —O—, and $R^1$ is —H and $R^2$ is $R^5$. In another embodiment, $Q^1$ is —$CH_2$—, $Q^2$ is —C(O)—, W is —O—, and $R^1$ is —H and $R^2$ is —O—R⁵. In another embodiment, Q¹ is —CH₂—, Q² is —C(O)—, W is —CH₂—, and R¹ is —H and R² is selected from the group consisting of amino, dimethylamino, hydroxyl,

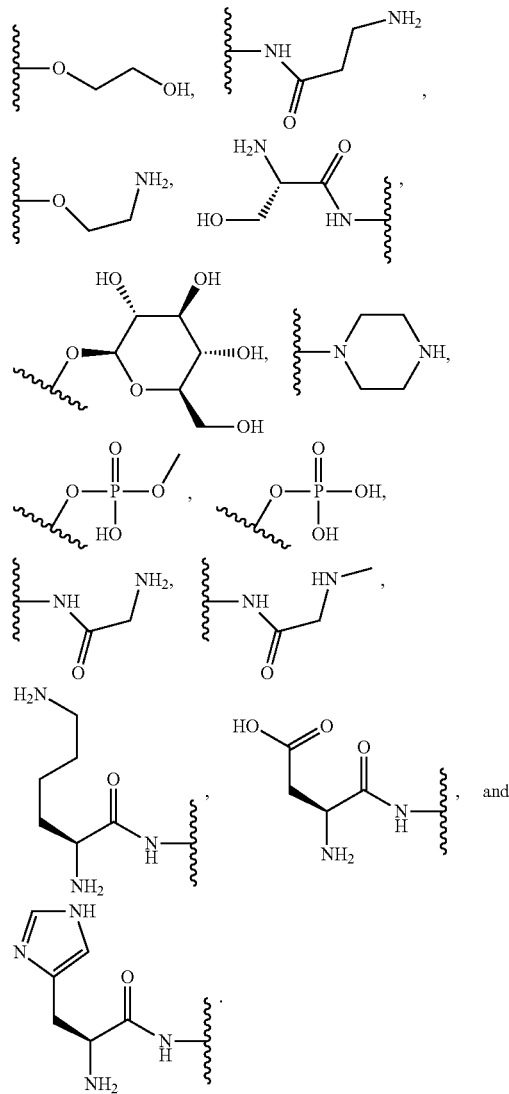

In another embodiment, Q¹ is —CH₂—, Q² is —C(O)—, W is —O—, and R¹ is —OH and R² is —OH, —CH₂NH₂, R³, R⁴, R⁵, or —O—R⁵. In another embodiment, Q¹ is —CH₂—, Q² is —C(O)—, W is —O—, and R¹ is —OH and R² is —OH. In another embodiment, Q¹ is —CH₂—, Q² is —C(O)—, W is —O—, and R¹ is —OH and R² is —CH₂NH₂. In another embodiment, Q¹ is —CH₂—, Q² is —C(O)—, W is —O—, and R¹ is —OH and R² is R³. In another embodiment, Q¹ is —CH₂—, Q² is —C(O)—, W is —O—, and R¹ is —OH and R² is R⁴. In another embodiment, Q¹ is —CH₂—, Q² is —C(O)—, W is —O—, and R¹ is —OH and R² is R⁵. In another embodiment, Q¹ is —CH₂—, Q² is —C(O)—, W is —O—, and R¹ is —OH and R² is —O—R⁵. In another embodiment, Q¹ is —CH₂—, Q² is —C(O)—, W is —CH₂—, and R¹ is —OH and R² is selected from the group consisting of amino, dimethylamino, hydroxyl,

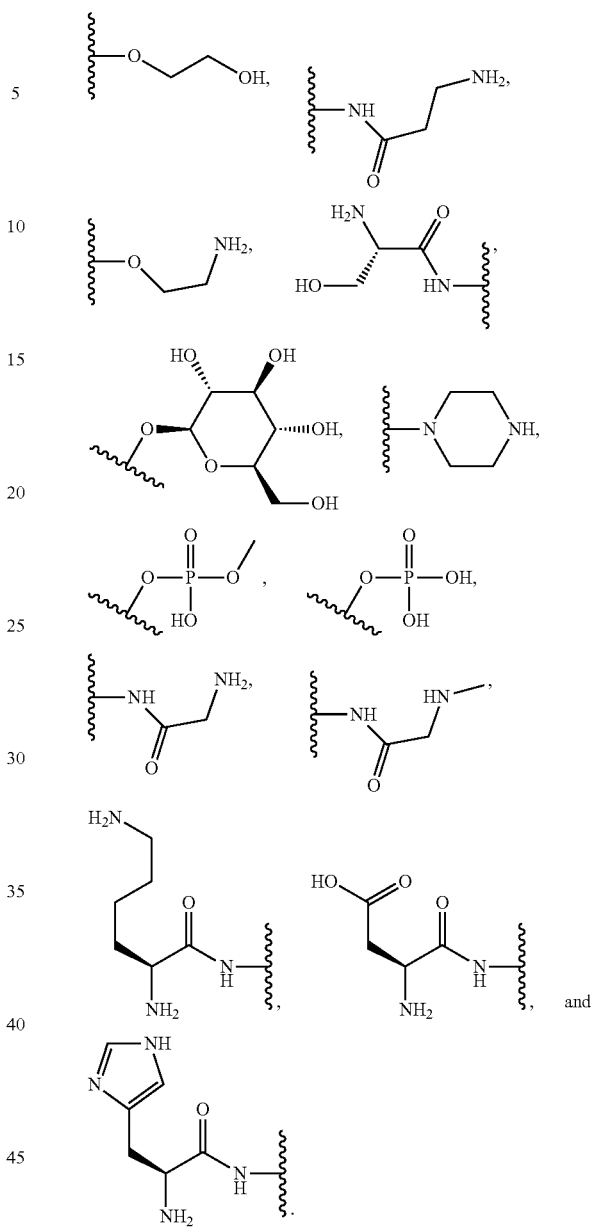

In another embodiment, Q¹ is —CH₂—, Q² is —C(O)—, W is —O—, and R¹ is —NH₂ and R² is —OH, —CH₂NH₂, R³, R⁴, R⁵, or —O—RS. In another embodiment, Q¹ is —CH₂—, Q² is —C(O)—, W is —O—, and R¹ is —NH₂ and R² is —OH. In another embodiment, Q¹ is —CH₂—, Q² is —C(O)—, W is —O—, and R¹ is —NH₂ and R² is —CH₂NH₂. In another embodiment, Q¹ is —CH₂—, Q² is —C(O)—, W is —O—, and R¹ is —NH₂ and R² is R³. In another embodiment, Q¹ is —CH₂—, Q² is —C(O)—, W is —O—, and R¹ is —NH₂ and R² is R⁴. In another embodiment, Q¹ is —CH₂—, Q² is —C(O)—, W is —O—, and R¹ is —NH₂ and R² is R⁵. In another embodiment, Q¹ is —CH₂—, Q² is —C(O)—, W is —O—, and R¹ is —NH₂ and R² is —O—R⁵. In another embodiment, Q¹ is —CH₂—, Q² is —C(O)—, W is —CH₂—, and R¹ is —NH₂ and R² is selected from the group consisting of amino, dimethylamino, hydroxyl,

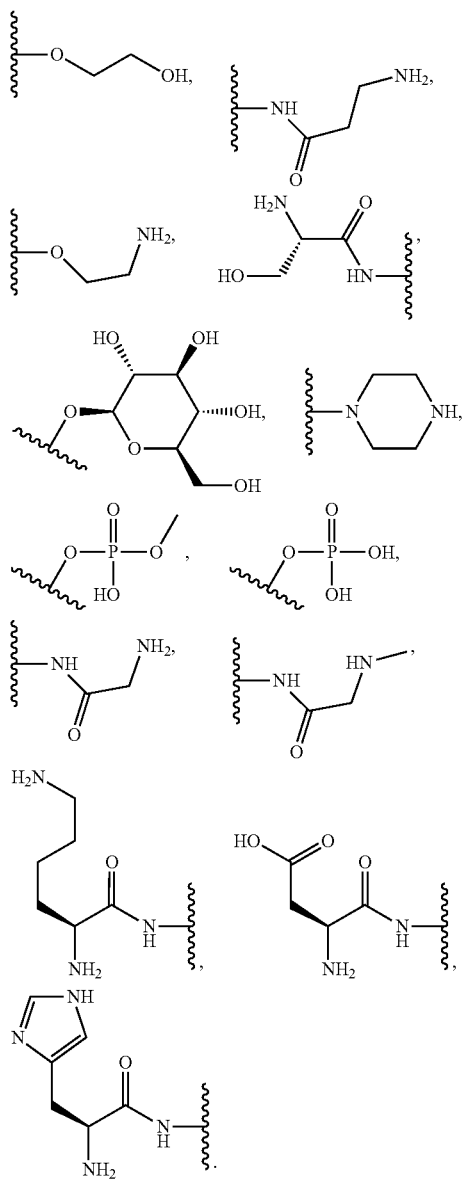

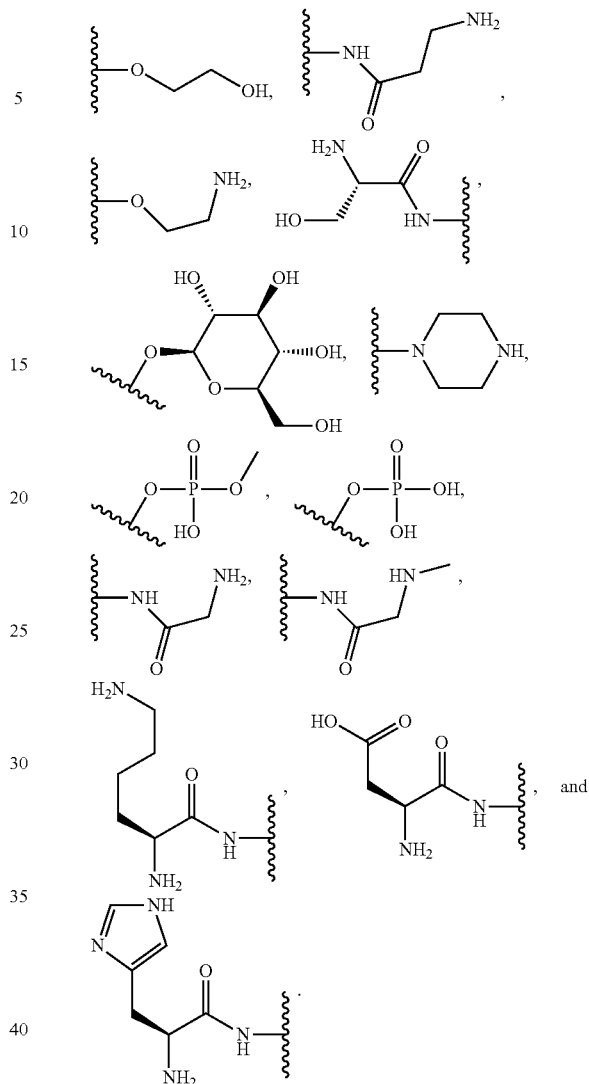

In another embodiment, $Q^1$ is —$CH_2$—, $Q^2$ is —C(O)—, W is —O—, and $R^1$ is alkyl and $R^2$ is —OH, —$CH_2NH_2$, $R^3$, $R^4$, $R^5$, or —O—$R^5$. In another embodiment, $Q^1$ is —$CH_2$—, $Q^2$ is —C(O)—, W is —O—, and $R^1$ is alkyl and $R^2$ is —OH. In another embodiment, $Q^1$ is —$CH_2$—, $Q^2$ is —C(O)—, W is —O—, and $R^1$ is alkyl and $R^2$ is —$CH_2NH_2$. In another embodiment, $Q^1$ is —$CH_2$—, $Q^2$ is —C(O)—, W is —O—, and $R^1$ is alkyl and $R^2$ is $R^3$. In another embodiment, $Q^1$ is —$CH_2$—, $Q^2$ is —C(O)—, W is —O—, and $R^1$ is alkyl and $R^2$ is $R^4$. In another embodiment, $Q^1$ is —$CH_2$—, $Q^2$ is —C(O)—, W is —O—, and $R^1$ is alkyl and $R^2$ is $R^5$. In another embodiment, $Q^1$ is —$CH_2$—, $Q^2$ is —C(O)—, W is —O—, and $R^1$ is alkyl and $R^2$ is —O—$R^5$. In another embodiment, $Q^1$ is —$CH_2$—, $Q^2$ is —C(O)—, W is —$CH_2$—, and $R^1$ is alkyl and $R^2$ is selected from the group consisting of amino, dimethylamino, hydroxyl, In another embodiment of Formula I or Ia, $Q^1$ is —$CH_2$—, $Q^2$ is —C(O)—, W is —O—, and $R^1$ is —OH or —OP(O)(OR$^6$)(OH) and $R^2$ is —H. In another embodiment, $Q^1$ is —$CH_2$—, $Q^2$ is —C(O)—, W is —O—, and $R^1$ is —OH and $R^2$ is —H. In another embodiment, $Q^1$ is —$CH_2$—, $Q^2$ is —C(O)—, W is —O—, and $R^1$ is —OP(O)(OR$^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —$CH_2$—, $Q^2$ is —C(O)—, and W is —NH—. In another embodiment, $Q^1$ is —$CH_2$—, $Q^2$ is —C(O)—, W is —NH—, and $R^1$ is —H and $R^2$ is —OH, —$CH_2NH_2$, $R^3$, $R^4$, $R^5$, or —O—$R^5$. In another embodiment, $Q^1$ is —$CH_2$—, $Q^2$ is —C(O)—W is —NH—, and $R^1$ is —H and $R^2$ is —OH. In another embodiment, $Q^1$ is —$CH_2$—, $Q^2$ is —C(O)—, W is —NH—, and $R^1$ is —H and $R^2$ is —$CH_2NH_2$. In another embodiment, $Q^1$ is —$CH_2$—, $Q^2$ is —C(O)—, W is —NH—, and $R^1$ is —H and $R^2$ is $R^3$. In another embodiment, $Q^1$ is —$CH_2$—, $Q^2$ is —C(O)—, W is —NH—, and $R^1$ is —H and $R^2$ is $R^4$. In another embodiment, $Q^1$ is —$CH_2$—, $Q^2$ is —C(O)—, W is —NH—, and $R^1$ is —H and $R^2$ is $R^5$. In another embodiment, $Q^1$ is —$CH_2$—, $Q^2$ is —C(O)—, W is —NH—, and $R^1$ is —H and $R^2$ is —O—$R^5$. In another embodiment, $Q^1$ is —CH$_2$—, $Q^2$ is —C(O)—, W is —CH$_2$—, and $R^1$ is —H and $R^2$ is selected from the group consisting of amino, dimethylamino, hydroxyl,

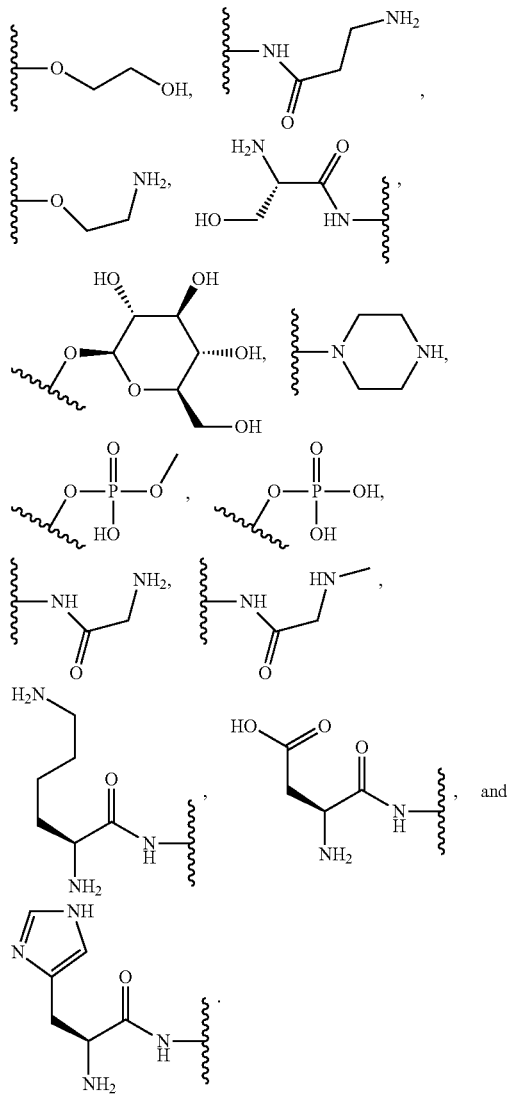

In another embodiment, $Q^1$ is —CH$_2$—, $Q^2$ is —C(O)—, W is —NH—, and $R^1$ is —OH and $R^2$ is —OH, —CH$_2$NH$_2$, $R^3$, $R^4$, $R^5$, or —O—$R^5$. In another embodiment, $Q^1$ is —CH$_2$—, $Q^2$ is —C(O)—, W is —NH—, and $R^1$ is —OH and $R^2$ is —OH. In another embodiment, $Q^1$ is —CH$_2$—, $Q^2$ is —C(O)—, W is —NH—, and $R^1$ is —OH and $R^2$ is —CH$_2$NH$_2$. In another embodiment, $Q^1$ is —CH$_2$—, $Q^2$ is —C(O)—, W is —NH—, and $R^1$ is —OH and $R^2$ is $R^3$. In another embodiment, $Q^1$ is —CH$_2$—, $Q^2$ is —C(O)—, W is —NH—, and $R^1$ is —OH and $R^2$ is $R^4$. In another embodiment, $Q^1$ is —CH$_2$—, $Q^2$ is —C(O)—, W is —NH—, and $R^1$ is —OH and $R^2$ is $R^5$. In another embodiment, $Q^1$ is —CH$_2$—, $Q^2$ is —C(O)—, W is —NH—, and $R^1$ is —OH and $R^2$ is —O—$R^5$. In another embodiment, $Q^1$ is —CH$_2$—, $Q^2$ is —C(O)—, W is —CH$_2$—, and $R^1$ is —OH and $R^2$ is selected from the group consisting of amino, dimethylamino, hydroxyl,

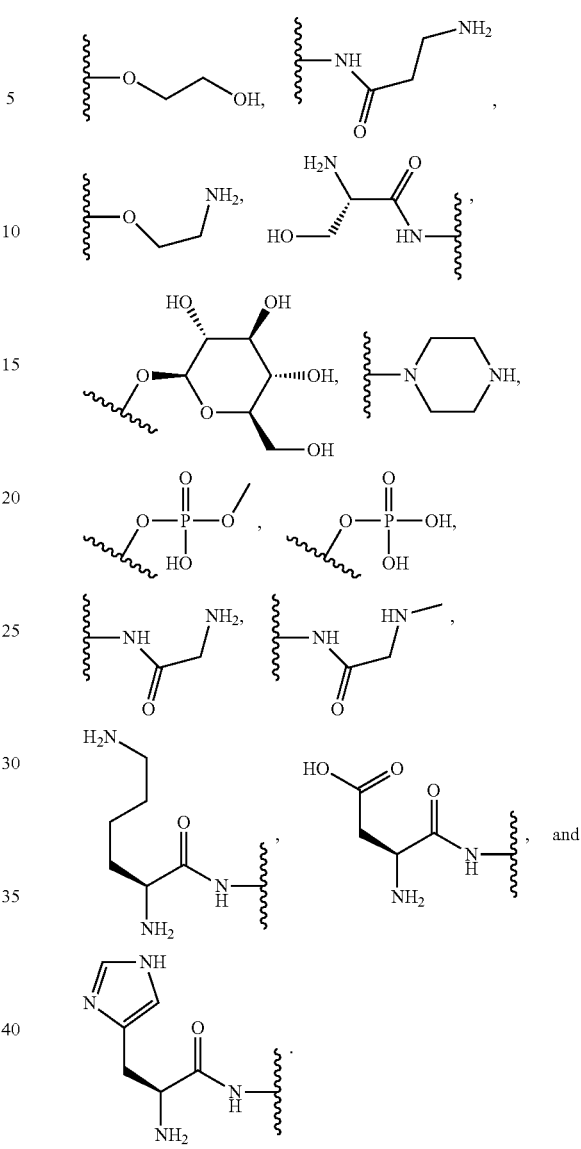

In another embodiment, $Q^1$ is —CH$_2$—, $Q^2$ is —C(O)—, W is —NH—, and $R^1$ is —NH$_2$ and $R^2$ is —OH, —CH$_2$NH$_2$, $R^3$, $R^4$, $R^5$, or —O—$R^5$. In another embodiment, $Q^1$ is —CH$_2$—, $Q^2$ is —C(O)—, W is —NH—, and $R^1$ is —NH$_2$ and $R^2$ is —OH. In another embodiment, $Q^1$ is —CH$_2$—, $Q^2$ is —C(O)—, W is —NH—, and $R^1$ is —NH$_2$ and $R^2$ is —CH$_2$NH$_2$. In another embodiment, $Q^1$ is —CH$_2$—, $Q^2$ is —C(O)—, W is —NH—, and $R^1$ is —NH$_2$ and $R^2$ is $R^3$. In another embodiment, $Q^1$ is —CH$_2$—, $Q^2$ is —C(O)—, W is —NH—, and $R^1$ is —NH$_2$ and $R^2$ is $R^4$. In another embodiment, $Q^1$ is —CH$_2$—, $Q^2$ is —C(O)—, W is —NH—, and $R^1$ is —NH$_2$ and $R^2$ is $R^5$. In another embodiment, $Q^1$ is —CH$_2$—, $Q^2$ is —C(O)—, W is —NH—, and $R^1$ is —NH$_2$ and $R^2$ is —O—$R^5$. In another embodiment, $Q^1$ is —CH$_2$—, $Q^2$ is —C(O)—, W is —CH$_2$—, and $R^1$ is —NH$_2$ and $R^2$ is selected from the group consisting of amino, dimethylamino, hydroxyl,

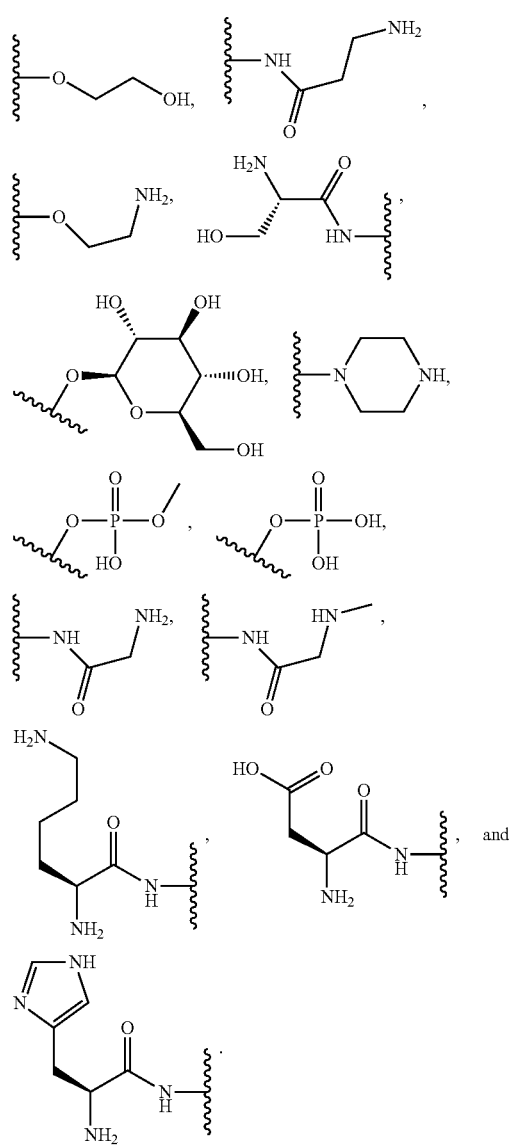
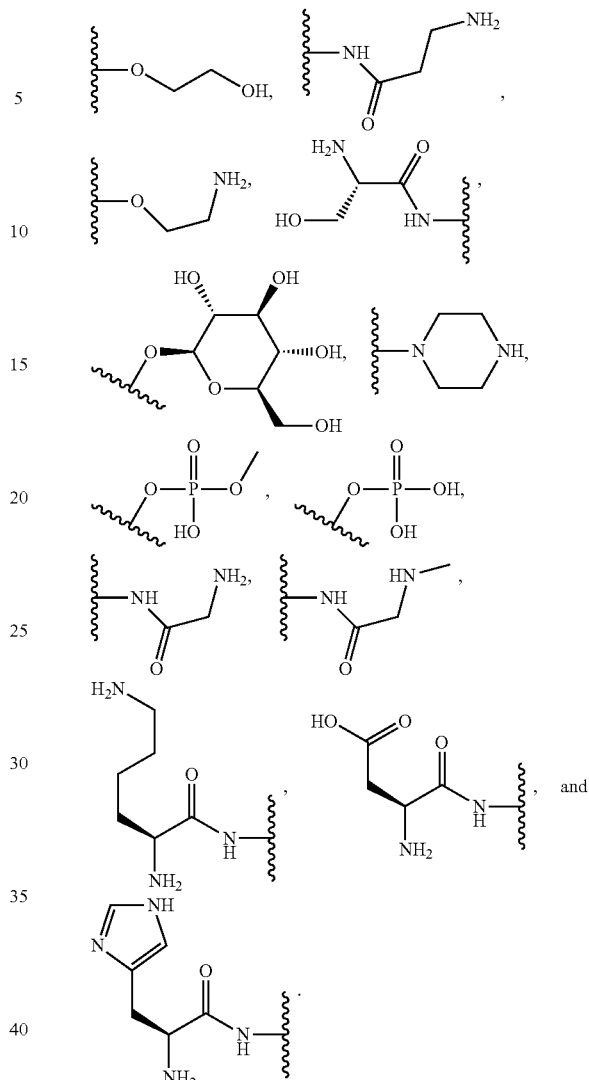

In another embodiment, $Q^1$ is —$CH_2$—, $Q^2$ is —C(O)—, W is —NH—, and $R^1$ is alkyl and $R^2$ is —OH, —$CH_2NH_2$, $R^3$, $R^4$, $R^1$, or —O—RS. In another embodiment, $Q^1$ is —$CH_2$—, $Q^2$ is —C(O)—, W is —NH—, and $R^1$ is alkyl and $R^2$ is —OH. In another embodiment, $Q^1$ is —$CH_2$—, $Q^2$ is —C(O)—, W is —NH—, and $R^1$ is alkyl and $R^2$ is —$CH_2NH_2$. In another embodiment, $Q^1$ is —$CH_2$—, $Q^2$ is —C(O)—, W is —NH—, and $R^1$ is alkyl and $R^2$ is $R^3$. In another embodiment, $Q^1$ is —$CH_2$—, $Q^2$ is —C(O)—, W is —NH—, and $R^1$ is alkyl and $R^2$ is $R^4$. In another embodiment, $Q^1$ is —$CH_2$—, $Q^2$ is —C(O)—, W is —NH—, and $R^1$ is alkyl and $R^2$ is $R^5$. In another embodiment, $Q^1$ is —$CH_2$—, $Q^2$ is —C(O)—, W is —NH—, and $R^1$ is alkyl and $R^2$ is —O—$R^5$. In another embodiment, $Q^1$ is —$CH_2$—, $Q^2$ is —C(O)—, W is —$CH_2$—, and $R^1$ is alkyl and $R^2$ is selected from the group consisting of amino, dimethylamino, hydroxyl, In another embodiment of Formula I or Ia, $Q^1$ is —$CH_2$—, $Q^2$ is —C(O)—, W is —NH—, and $R^1$ is —OH or —OP(O)($OR^6$)(OH) and $R^2$ is —H. In another embodiment, $Q^1$ is —$CH_2$—, $Q^2$ is —C(O)—, W is —NH—, and $R^1$ is —OH and $R^2$ is —H. In another embodiment, $Q^1$ is —$CH_2$—, $Q^2$ is —C(O)—, W is —NH—, and $R^1$ is —OP(O)($OR^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(H)(OH)—, $Q^2$ is —C(O)—, and W is —$CH_2$—. In another embodiment, $Q^1$ is —C(H)(OH)—, $Q^2$ is —C(O)—, W is —$CH_2$—, and $R^1$ is —H and $R^2$ is —OH, —$CH_2NH_2$, $R^3$, $R^4$, $R^5$, or —O—$R^5$. In another embodiment, $Q^1$ is —C(H)(OH)—, $Q^2$ is —C(O)—, W is —$CH_2$—, and $R^1$ is —H and $R^2$ is —OH. In another embodiment, $Q^1$ is —C(H)(OH)—, $Q^2$ is —C(O)—, W is —$CH_2$—, and $R^1$ is —H and $R^2$ is —$CH_2NH_2$. In another embodiment, $Q^1$ is —C(H)(OH)—, $Q^2$ is —C(O)—, W is —$CH_2$—, and $R^1$ is —H and $R^2$ is $R^3$. In another embodiment, $Q^1$ is —C(H)(OH)—, $Q^2$ is —C(O)—, W is —$CH_2$—, and $R^1$ is —H and $R^2$ is $R^4$. In another embodiment, $Q^1$ is —C(H)(OH)—, $Q^2$ is —C(O)—, W is —$CH_2$—, and $R^1$ is —H and $R^2$ is $R^5$. In another embodiment, $Q^1$ is —C(H)(OH)—, $Q^2$ is —C(O)—, W is —CH$_2$—, and $R^1$ is —H and $R^2$ is —O—$R^5$. In another embodiment, $Q^1$ is —C(H)(OH)—, $Q^2$ is —C(O)—, W is —CH$_2$—, and $R^1$ is —H and $R^2$ is selected from the group consisting of amino, dimethylamino, hydroxyl,

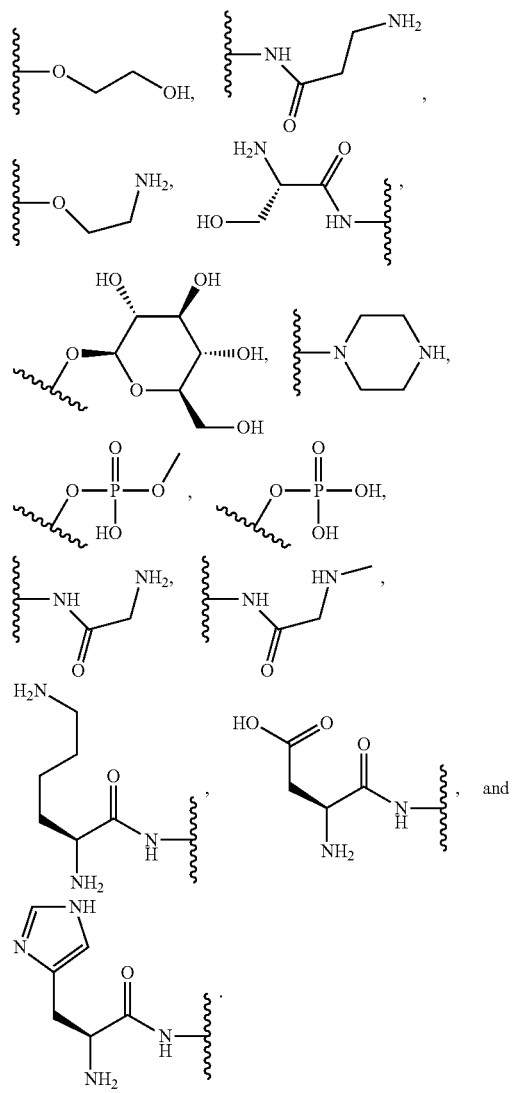

In another embodiment, $Q^1$ is —C(H)(OH)—, $Q^2$ is —C(O)—, W is —CH$_2$—, and $R^1$ is —OH and $R^2$ is —OH, —CH$_2$NH$_2$, $R^3$, $R^4$, $R^5$, or —O—$R^5$. In another embodiment, $Q^1$ is —C(H)(OH)—, $Q^2$ is —C(O)—, W is —CH$_2$—, and $R^1$ is —OH and $R^2$ is —OH. In another embodiment, $Q^1$ is —C(H)(OH)—, $Q^2$ is —C(O)—, W is —CH$_2$—, and $R^1$ is —OH and $R^2$ is —CH$_2$NH$_2$. In another embodiment, $Q^1$ is —C(H)(OH)—, $Q^2$ is —C(O)—, W is —CH$_2$—, and $R^1$ is —OH and $R^2$ is $R^3$. In another embodiment, $Q^1$ is —C(H)(OH)—, $Q^2$ is —C(O)—, W is —CH$_2$—, and $R^1$ is —OH and $R^2$ is $R^4$. In another embodiment, $Q^1$ is —C(H)(OH)—, $Q^2$ is —C(O)—, W is —CH$_2$—, and $R^1$ is —OH and $R^2$ is $R^5$. In another embodiment, $Q^1$ is —C(H)(OH)—, $Q^2$ is —C(O)—, W is —CH$_2$—, and $R^1$ is —OH and $R^2$ is —O—$R^5$. In another embodiment, $Q^1$ is —C(H)(OH)—, $Q^2$ is —C(O)—, W is —CH$_2$—, and $R^1$ is —OH and $R^2$ is selected from the group consisting of amino, dimethylamino, hydroxyl,

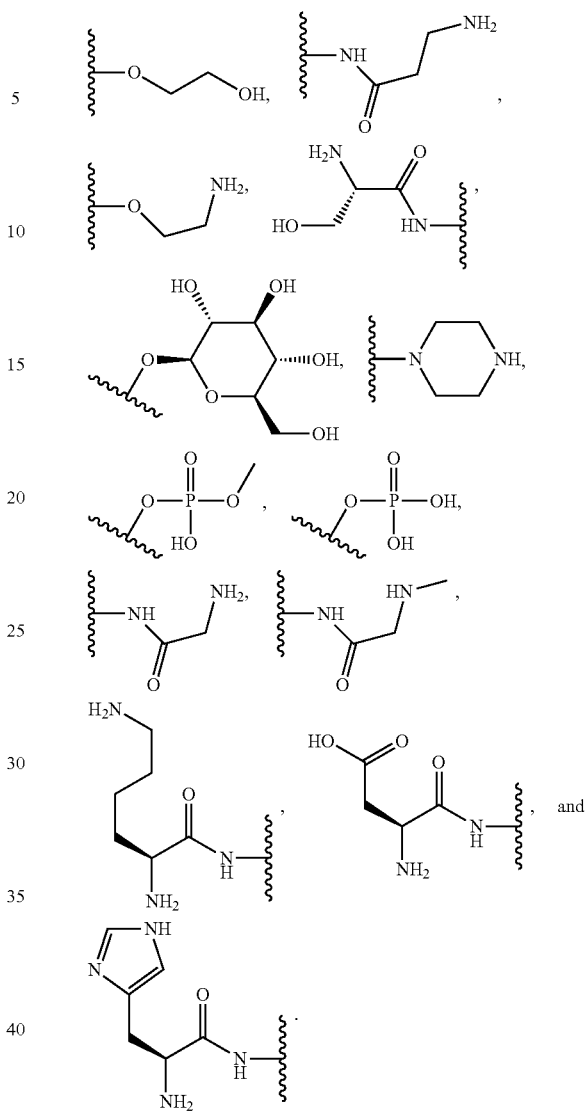

In another embodiment, $Q^1$ is —C(H)(OH)—, $Q^2$ is —C(O)—, W is —CH$_2$—, and $R^1$ is —NH$_2$ and $R^2$ is —OH, —CH$_2$NH$_2$, $R^3$, $R^4$, $R^5$, or —O—$R^5$. In another embodiment, $Q^1$ is —C(H)(OH)—, $Q^2$ is —C(O)—, W is —CH$_2$—, and $R^1$ is —NH$_2$ and $R^2$ is —OH. In another embodiment, $Q^1$ is —C(H)(OH)—, $Q^2$ is —C(O)—, W is —CH$_2$—, and $R^1$ is —NH$_2$ and $R^2$ is —CH$_2$NH$_2$. In another embodiment, $Q^1$ is —C(H)(OH)—, $Q^2$ is —C(O)—, W is —CH$_2$—, and $R^1$ is —NH$_2$ and $R^2$ is $R^3$. In another embodiment, $Q^1$ is —C(H)(OH)—, $Q^2$ is —C(O)—, W is —CH$_2$—, and $R^1$ is —NH$_2$ and $R^2$ is $R^4$. In another embodiment, $Q^1$ is —C(H)(OH)—, $Q^2$ is —C(O)—, W is —CH$_2$—, and $R^1$ is —NH$_2$ and $R^2$ is $R^5$. In another embodiment, $Q^1$ is —C(H)(OH)—, $Q^2$ is —C(O)—, W is —CH$_2$—, and $R^1$ is —NH$_2$ and $R^2$ is —O—$R^5$. In another embodiment, $Q^1$ is —C(H)(OH)—, $Q^2$ is —C(O)—, W is —CH$_2$—, and $R^1$ is —NH$_2$ and $R^2$ is selected from the group consisting of amino, dimethylamino, hydroxyl,

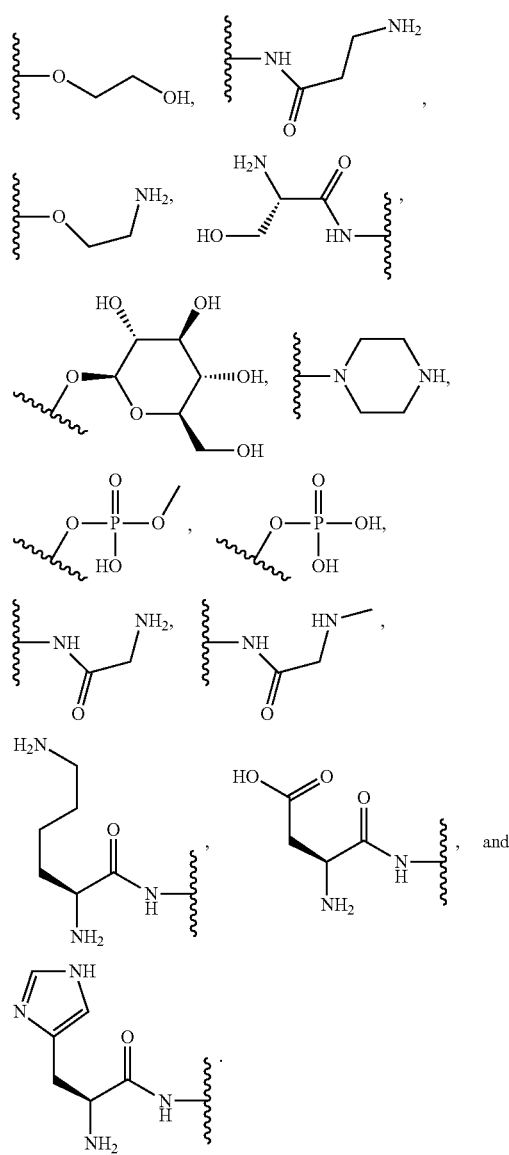

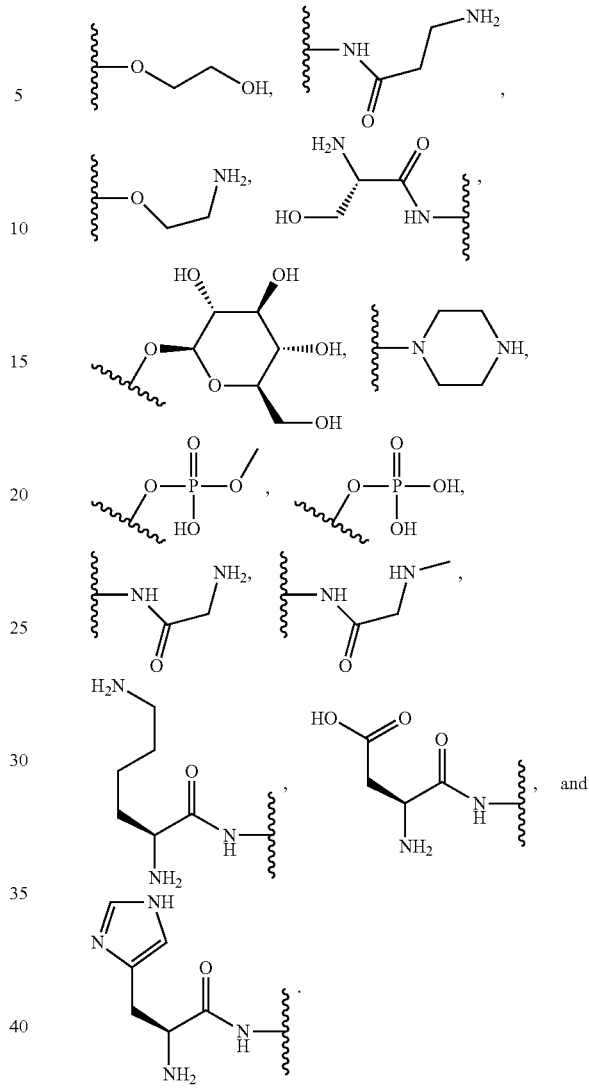

In another embodiment, $Q^1$ is —C(H)(OH)—, $Q^2$ is —C(O)—, W is —CH$_2$—, and $R^1$ is alkyl and $R^2$ is —OH, —CH$_2$NH$_2$, $R^3$, $R^4$, $R^5$, or —O—$R^5$. In another embodiment, $Q^1$ is —C(H)(OH)—, $Q^2$ is —C(O)—, W is —CH$_2$—, and $R^1$ is alkyl and $R^2$ is —OH. In another embodiment, $Q^1$ is —C(H)(OH)—, $Q^2$ is —C(O)—, W is —CH$_2$—, and $R^1$ is alkyl and $R^2$ is —CH$_2$NH$_2$. In another embodiment, $Q^1$ is —C(H)(OH)—, $Q^2$ is —C(O)—, W is —CH$_2$—, and $R^1$ is alkyl and $R^2$ is $R^3$. In another embodiment, $Q^1$ is —C(H)(OH)—, $Q^2$ is —C(O)—W is —CH$_2$—, and $R^1$ is alkyl and $R^2$ is $R^4$. In another embodiment, $Q^1$ is —C(H)(OH)—, $Q^2$ is —C(O)—, W is —CH$_2$—, and $R^1$ is alkyl and $R^2$ is $R^5$. In another embodiment, $Q^1$ is —C(H)(OH)—, $Q^2$ is —C(O)—, W is —CH$_2$—, and $R^1$ is alkyl and $R^2$ is —O—$R^5$. In another embodiment, $Q^1$ is —C(H)(OH)—, $Q^2$ is —C(O)—, W is —CH$_2$—, and $R^1$ is alkyl and $R^2$ is selected from the group consisting of amino, dimethylamino, hydroxyl, In another embodiment of Formula I or Ia, $Q^1$ is —C(H)(OH)—, $Q^2$ is —C(O)—, W is —CH$_2$—, and $R^1$ is —OH or —OP(O)(OR$^6$)(OH) and $R^2$ is —H. In another embodiment, $Q^1$ is —C(H)(OH)—, $Q^2$ is —C(O)—, W is —CH$_2$—, and $R^1$ is —OH and $R^2$ is —H. In another embodiment, $Q^1$ is —C(H)(OH)—, $Q^2$ is —C(O)—, W is —CH$_2$—, and $R^1$ is —OP(O)(OR$^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(H)(OH)—, $Q^2$ is —C(O)—, and W is —O—. In another embodiment, $Q^1$ is —C(H)(OH)—, $Q^2$ is —C(O)—, W is —O—, and $R^1$ is —H and $R^2$ is —OH, —CH$_2$NH$_2$, $R^3$, $R^4$, $R^5$, or —O—$R^5$. In another embodiment, $Q^1$ is —C(H,OH)—, $Q^2$ is —C(O)—, W is —O—, and $R^1$ is —H and $R^2$ is —OH. In another embodiment, $Q^1$ is —C(H,OH)—, $Q^2$ is —C(O)—, W is —O—, and $R^1$ is —H and $R^2$ is —CH$_2$NH$_2$. In another embodiment, $Q^1$ is —C(H,OH)—, $Q^2$ is —C(O)—, W is —O—, and $R^1$ is —H and $R^2$ is $R^3$. In another embodiment, $Q^1$ is —C(H,OH)—, $Q^2$ is —C(O)—, W is —O—, and $R^1$ is —H and $R^2$ is $R^4$. In another embodiment, $Q^1$ is —C(H,OH)—, $Q^2$ is —C(O)—, W is —O—, and $R^1$ is —H and $R^2$ is $R^5$. In another embodiment, $Q^1$ is —C(H,OH)—, $Q^2$ is —C(O)—, W is —O—, and $R^1$ is —H and $R^2$ is —O—$R^5$. In another embodiment, $Q^1$ is —CH$_2$—, $Q^2$ is —C(O)—, W is —CH$_2$—, and $R^1$ is —H and $R^2$ is selected from the group consisting of amino, dimethylamino, hydroxyl,

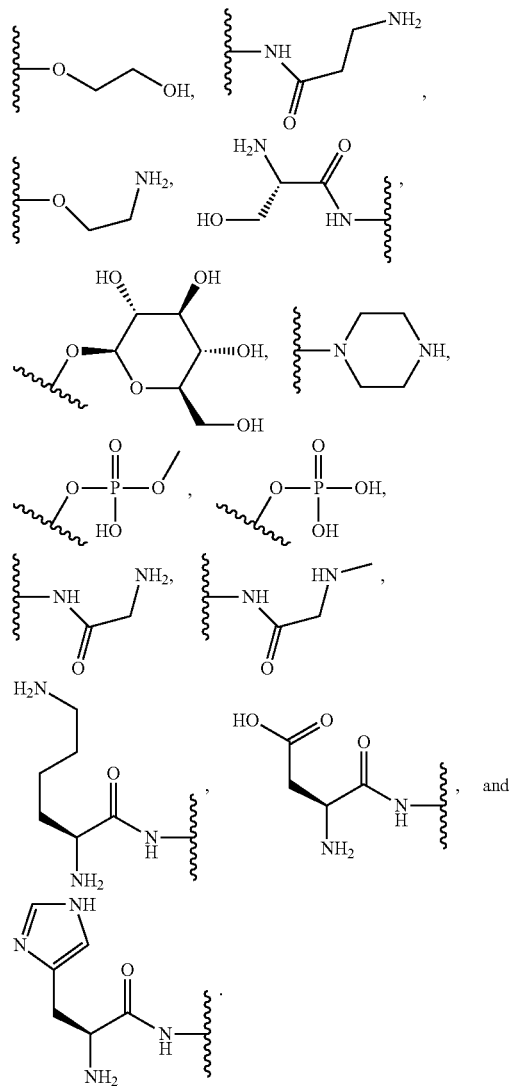

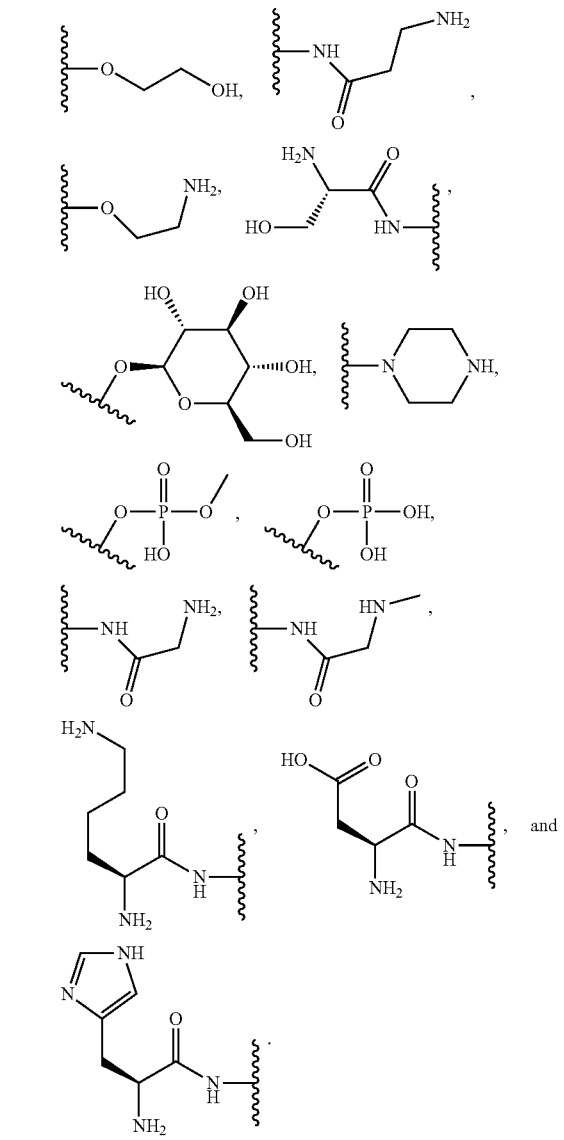

In another embodiment, $Q^1$ is —C(H)(OH)—, $Q^2$ is —C(O)—, W is —O—, and $R^1$ is —OH and $R^2$ is —OH, —CH$_2$NH$_2$, $R^3$, $R^4$, $R^5$, or —O—$R^5$. In another embodiment, $Q^1$ is —C(H)(OH)—, $Q^2$ is —C(O)—, W is —O—, and $R^1$ is —OH and $R^2$ is —OH. In another embodiment, $Q^1$ is —C(H)(OH)—, $Q^2$ is —C(O)—, W is —O—, and $R^1$ is —OH and $R^2$ is —CH$_2$NH$_2$. In another embodiment, $Q^1$ is —C(H)(OH)—, $Q^2$ is —C(O)—, W is —O—, and $R^1$ is —OH and $R^2$ is $R^3$. In another embodiment, $Q^1$ is —C(H)(OH)—, $Q^2$ is —C(O)—, W is —O—, and $R^1$ is —OH and $R^2$ is $R^4$. In another embodiment, $Q^1$ is —C(H)(OH)—, $Q^2$ is —C(O)—, W is —O—, and $R^1$ is —OH and $R^2$ is $R^5$. In another embodiment, $Q^1$ is —C(H)(OH)—, $Q^2$ is —C(O)—, W is —O—, and $R^1$ is —OH and $R^2$ is —O—$R^5$. In another embodiment, $Q^1$ is —C(H)(OH)—, $Q^2$ is —C(O)—, W is —O—, and $R^1$ is —OH and $R^2$ is selected from the group consisting of amino, dimethylamino, hydroxyl, In another embodiment, $Q^1$ is —C(H)(OH)—, $Q^2$ is —C(O)—, W is —O—, and $R^1$ is —NH$_2$ and $R^2$ is —OH, —CH$_2$NH$_2$, $R^3$, $R^4$, $R^5$, or —O—$R^5$. In another embodiment, $Q^1$ is —C(H)(OH)—, $Q^2$ is —C(O)—, W is —O—, and $R^1$ is —NH$_2$ and $R^2$ is —OH. In another embodiment, $Q^1$ is —C(H)(OH)—, $Q^2$ is —C(O)—, W is —O—, and $R^1$ is —NH$_2$ and $R^2$ is —CH$_2$NH$_2$. In another embodiment, $Q^1$ is —C(H)(OH)—, $Q^2$ is —C(O)—, W is —O—, and $R^1$ is —NH$_2$ and $R^2$ is $R^3$. In another embodiment, $Q^1$ is —C(H)(OH)—, $Q^2$ is —C(O)—, W is —O—, and $R^1$ is —NH$_2$ and $R^2$ is $R^4$. In another embodiment, $Q^1$ is —C(H)(OH)—, $Q^2$ is —C(O)—, W is —O—, and $R^1$ is —NH$_2$ and $R^2$ is $R^5$. In another embodiment, $Q^1$ is —C(H)(OH)—, $Q^2$ is —C(O)—, W is —O—, and $R^1$ is —NH$_2$ and $R^2$ is —O—$R^5$. In another embodiment, $Q^1$ is —C(H)(OH)—, $Q^2$ is —C(O)—, W is —O—, and $R^1$ is —NH$_2$ and $R^2$ is selected from the group consisting of amino, dimethylamino, hydroxyl,

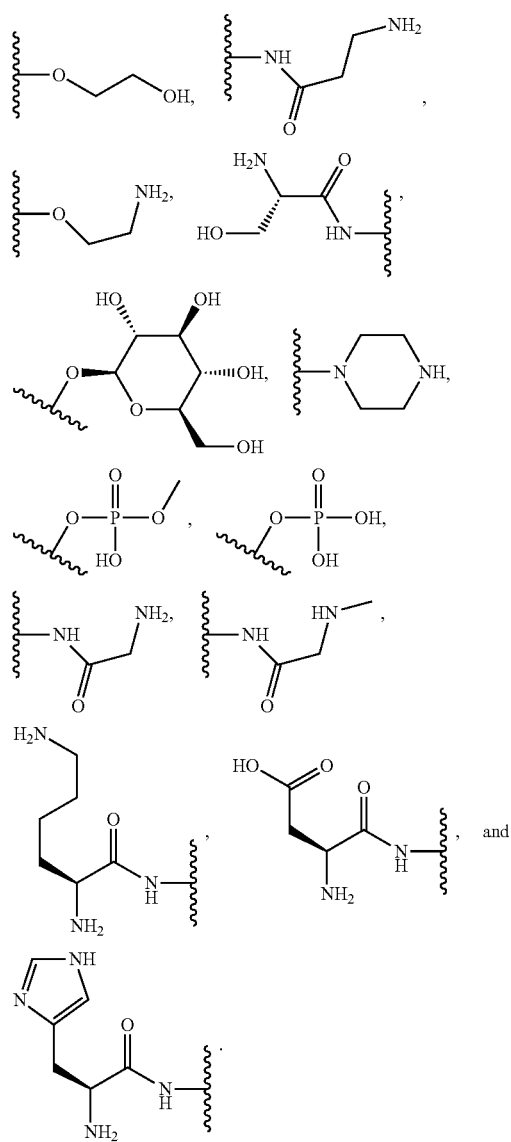
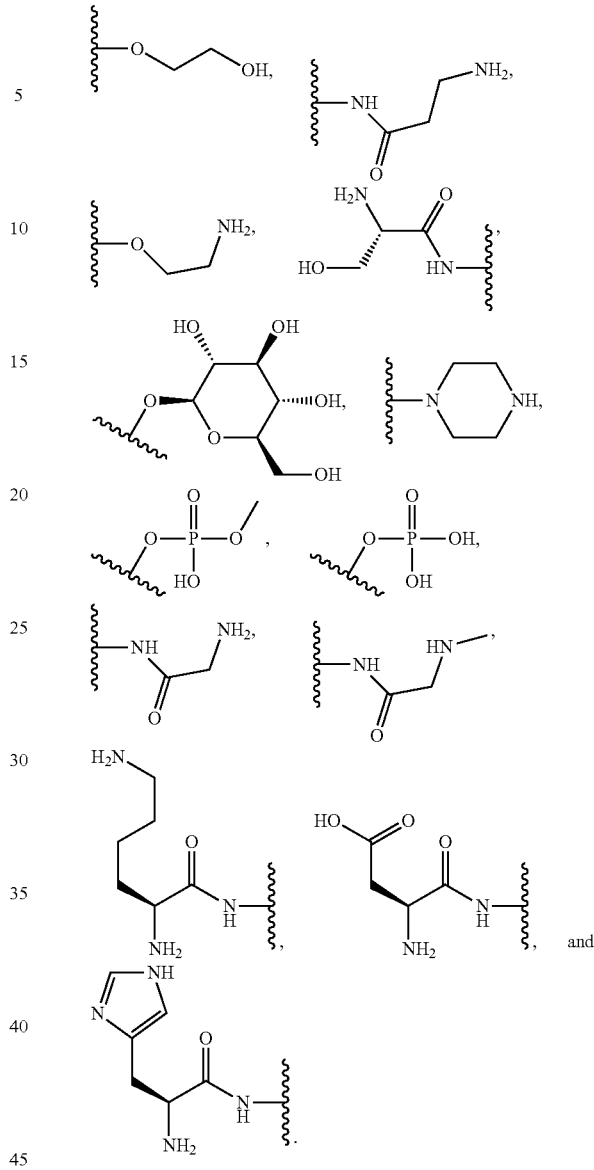

In another embodiment, $Q^1$ is —C(H)(OH)—, $Q^2$ is —C(O)—, W is —O—, and $R^1$ is alkyl and $R^2$ is —OH, —CH$_2$NH$_2$, $R^3$, $R^4$, $R^5$, or —O—$R^5$. In another embodiment, $Q^1$ is —C(H)(OH)—, $Q^2$ is —C(O)—, W is —O—, and $R^1$ is alkyl and $R^2$ is —OH. In another embodiment, $Q^1$ is —C(H)(OH)—, $Q^2$ is —C(O)—, W is —O—, and $R^1$ is alkyl and $R^2$ is —CH$_2$NH$_2$. In another embodiment, $Q^1$ is —C(H)(OH)—, $Q^2$ is —C(O)—, W is —O—, and $R^1$ is alkyl and $R^2$ is $R^3$. In another embodiment, $Q^1$ is —C(H)(OH)—, $Q^2$ is —C(O)—, W is —O—, and $R^1$ is alkyl and $R^2$ is $R^4$. In another embodiment, $Q^1$ is —C(H)(OH)—, $Q^2$ is —C(O)—, W is —O— and $R^1$ is alkyl and $R^2$ is $R^5$. In another embodiment, $Q^1$ is —C(H)(OH)—, $Q^2$ is —C(O)—, W is —O—, and $R^1$ is alkyl and $R^2$ is —O—$R^5$. In another embodiment, $Q^1$ is —C(H)(OH)—, $Q^2$ is —C(O)—, W is —O—, and $R^1$ is alkyl and $R^2$ is selected from the group consisting of amino, dimethylamino, hydroxyl, In another embodiment of Formula I or Ia, $Q^1$ is —C(H)(OH)—, $Q^2$ is —C(O)—, W is —O—, and $R^1$ is —OH or —OP(O)(OR$^6$)(OH) and $R^2$ is —H. In another embodiment, $Q^1$ is —C(H)(OH)—, $Q^2$ is —C(O)—, W is —O—, and $R^1$ is —OH and $R^2$ is —H. In another embodiment, $Q^1$ is —C(H)(OH)—, $Q^2$ is —C(O)—, W is —O—, and $R^1$ is —OP(O)(OR$^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(H)(OH)—, $Q^2$ is —C(O)—, and W is —NH—. In another embodiment, $Q^1$ is —C(H)(OH)—, $Q^2$ is —C(O)—, W is —NH—, and $R^1$ is —H and $R^2$ is —OH, —CH$_2$NH$_2$, $R^3$, $R^4$, $R^5$, or —O—$R^5$. In another embodiment, $Q^1$ is —C(H)(OH)—, $Q^2$ is —C(O)—, W is —NH—, and $R^1$ is —H and $R^2$ is —OH. In another embodiment, $Q^1$ is —C(H)(OH)—, $Q^2$ is —C(O)—, W is —NH—, and $R^1$ is —H and $R^2$ is —CH$_2$NH$_2$. In another embodiment, $Q^1$ is —C(H)(OH)—, $Q^2$ is —C(O)—, W is —NH—, and $R^1$ is —H and $R^2$ is $R^3$. In another embodiment, $Q^1$ is —C(H)(OH)—, $Q^2$ is —C(O)—, W is —NH—, and $R^1$ is —H and $R^2$ is $R^4$. In another embodiment, $Q^1$ is —C(H)(OH)—, $Q^2$ is —C(O)—, W is —NH—, and $R^1$ is —H and $R^2$ is $R^5$. In another embodiment, $Q^1$ is —C(H)(OH)—, $Q^2$ is —C(O)—, W is —NH—, and $R^1$ is —H and $R^2$ is —O—$R^5$. In another embodiment, $Q^1$ is —C(H)(OH)—, $Q^2$ is —C(O)—, W is —NH—, and $R^1$ is —H and $R^2$ is selected from the group consisting of amino, dimethylamino, hydroxyl,

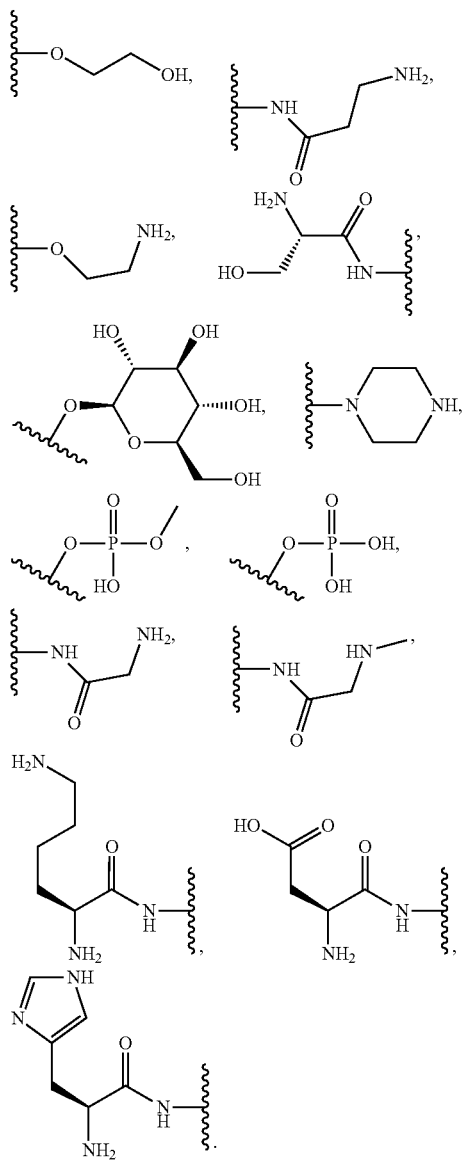

In another embodiment, $Q^1$ is —C(H)(OH)—, $Q^2$ is —C(O)—, W is —NH—, and $R^1$ is —OH and $R^2$ is —O—$R^5$. In another embodiment, $Q^1$ is —C(H)(OH)—, $Q^2$ is —C(O)—, W is —NH— and $R^1$ is —OH and $R^2$ is selected from the group consisting of amino, dimethylamino, hydroxyl,

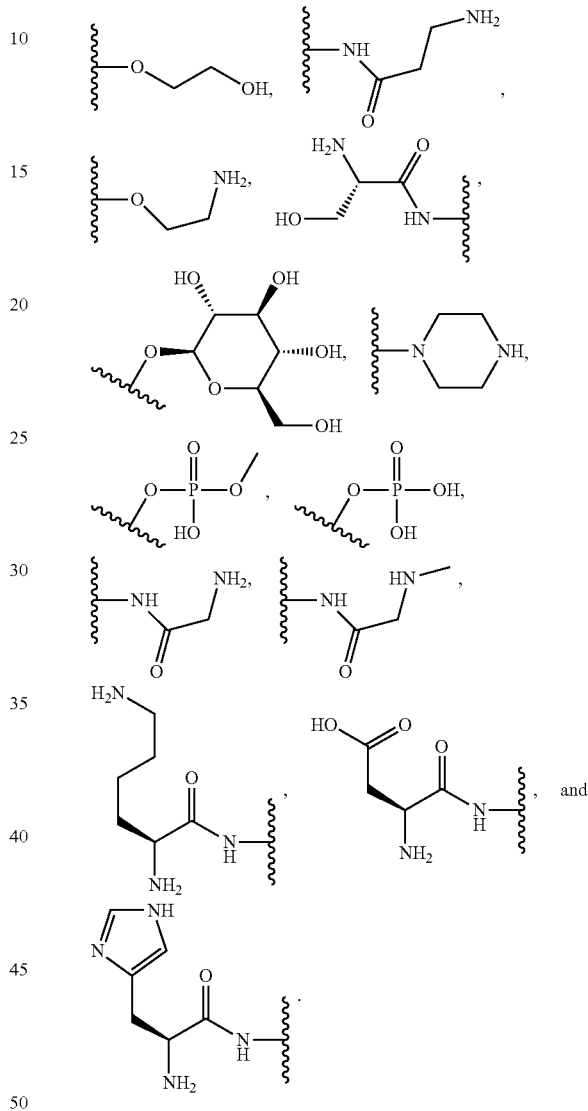

In another embodiment, $Q^1$ is —C(H)(OH)—, $Q^2$ is —C(O)—, W is —NH—, and $R^1$ is —OH and $R^2$ is —OH, —CH$_2$NH$_2$, $R^3$, $R^4$, $R^5$, or —O—RS. In another embodiment, $Q^1$ is —C(H)(OH)—, $Q^2$ is —C(O)—, W is —NH—, and $R^1$ is —OH and $R^2$ is —OH. In another embodiment, $Q^1$ is —C(H)(OH)—, $Q^2$ is —C(O)—, W is —NH—, and $R^1$ is —OH and $R^2$ is —CH$_2$NH$_2$. In another embodiment, $Q^1$ is —C(H)(OH)—, $Q^2$ is —C(O)—, W is —NH—, and $R^1$ is —OH and $R^2$ is $R^3$. In another embodiment, $Q^1$ is —C(H)(OH)—, $Q^2$ is —C(O)—, W is —NH—, and $R^1$ is —OH and $R^2$ is $R^4$. In another embodiment, $Q^1$ is —C(H)(OH)—, $Q^2$ is —C(O)—, W is —NH—, and $R^1$ is —OH and $R^2$ is $R^5$.

In another embodiment, $Q^1$ is —C(H)(OH)—, $Q^2$ is —C(O)—, W is —NH—, and $R^1$ is —NH$_2$ and $R^2$ is —OH, —CH$_2$NH$_2$, $R^3$, $R^4$, $R^5$, or —O—$R^5$. In another embodiment, $Q^1$ is —C(H)(OH)—, $Q^2$ is —C(O)—, W is —NH—, and $R^1$ is —NH$_2$ and $R^2$ is —OH. In another embodiment, $Q^1$ is —C(H)(OH)—, $Q^2$ is —C(O)—, W is —NH—, and $R^1$ is —NH$_2$ and $R^2$ is —CH$_2$NH$_2$. In another embodiment, $Q^1$ is —C(H)(OH)—, $Q^2$ is —C(O)—, W is —NH—, and $R^1$ is —NH$_2$ and $R^2$ is $R^3$. In another embodiment, $Q^1$ is —C(H)(OH)—, $Q^2$ is —C(O)—, W is —NH—, and $R^1$ is —NH$_2$ and $R^2$ is $R^4$. In another embodiment, $Q^1$ is —C(H)(OH)—, $Q^2$ is —C(O)—, W is —NH—, and $R^1$ is —NH$_2$ and $R^2$ is $R^5$. In another embodiment, $Q^1$ is —C(H)(OH)—, $Q^2$ is —C(O)—, W is —NH—, and $R^1$ is —NH$_2$ and $R^2$ is —O—$R^5$. In another embodiment, $Q^1$ is —C(H)(OH)—, $Q^2$ is is —C(O)—, W is —NH—, and R$^1$ is —NH$_2$ and R$^2$ is selected from the group consisting of amino, dimethylamino, hydroxyl,

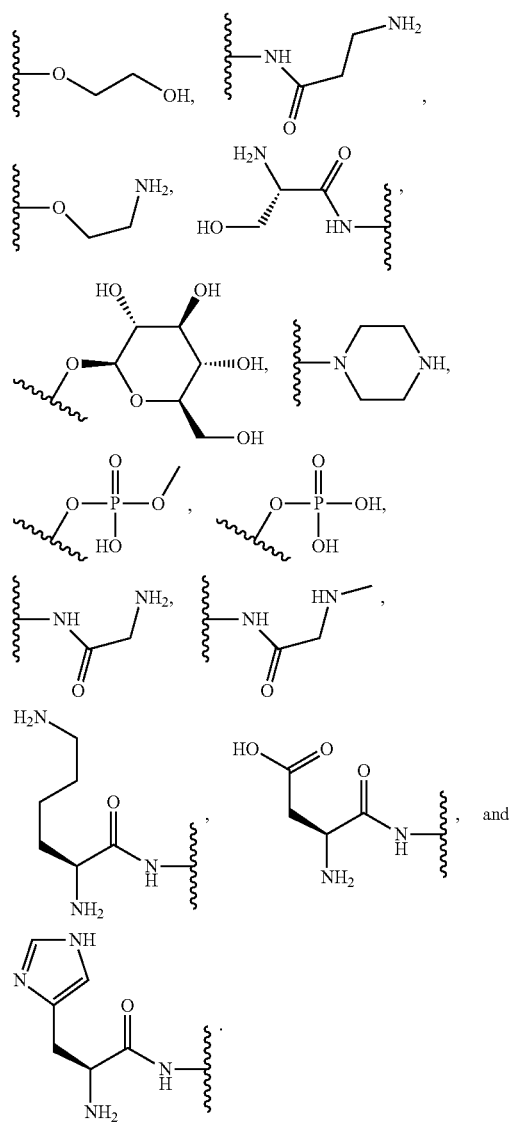

In another embodiment, Q$^1$ is —C(H)(OH)—, Q$^2$ is —C(O)—, W is —NH—, and R$^1$ is alkyl and R$^2$ is —OH, —CH$_2$NH$_2$, R$^3$, R$^4$, R$^5$, or —O—R$^5$. In another embodiment, Q$^1$ is —C(H)(OH)—, Q$^2$ is —C(O)—, W is —NH—, and R$^1$ is alkyl and R$^2$ is —OH. In another embodiment, Q$^1$ is —C(H)(OH)—, Q$^2$ is —C(O)—, W is —NH—, and R$^1$ is alkyl and R$^2$ is —CH$_2$NH$_2$. In another embodiment, Q$^1$ is —C(H)(OH)—, Q$^2$ is —C(O)—, W is —NH—, and R$^1$ is alkyl and R$^2$ is R$^3$. In another embodiment, Q$^1$ is —C(H)(OH)—, Q$^2$ is —C(O)—, W is —NH—, and R$^1$ is alkyl and R$^2$ is R$^4$. In another embodiment, Q$^1$ is —C(H)(OH)—, Q$^2$ is —C(O)—, W is —NH—, and R$^1$ is alkyl and R$^2$ is R$^5$. In another embodiment, Q$^1$ is —C(H)(OH)—, Q$^2$ is —C(O)—, W is —NH—, and R$^1$ is alkyl and R$^2$ is —O—R$^5$. In another embodiment, Q$^1$ is —C(H)(OH)—, Q$^2$ is —C(O)—, W is —NH—, and R$^1$ is alkyl and R$^2$ is selected from the group consisting of amino, dimethylamino, hydroxyl,

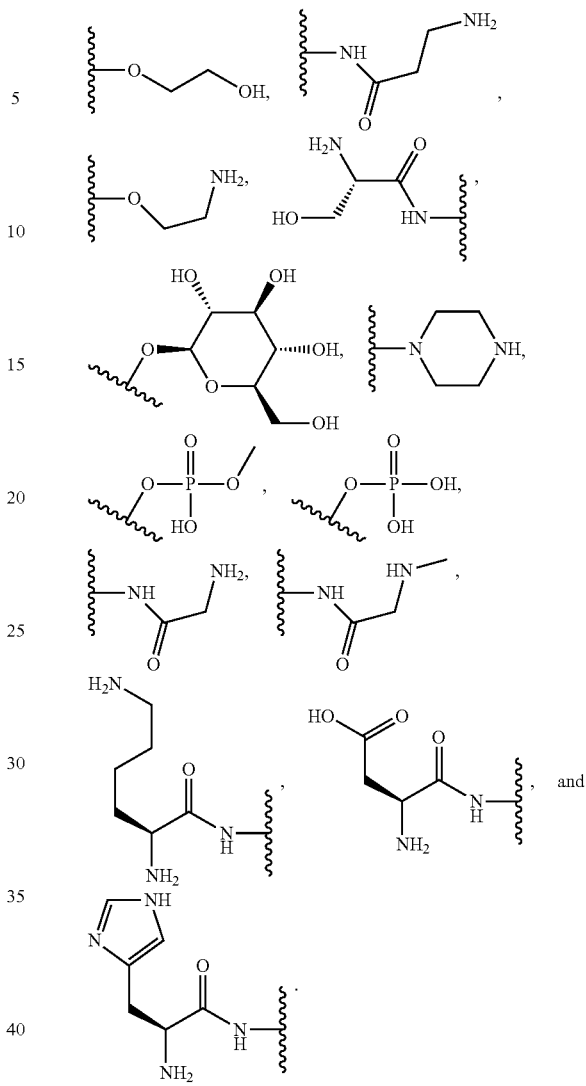

In another embodiment of Formula I or Ia, Q$^1$ is —C(H)(OH)—, Q$^2$ is —C(O)—, W is —NH—, and R$^1$ is —OH or —OP(O)(OR$^6$)(OH) and R$^2$ is —H. In another embodiment, Q$^1$ is —C(H)(OH)—, Q$^2$ is —C(O)—, W is —NH—, and R$^1$ is —OH and R$^2$ is —H. In another embodiment, Q$^1$ is —C(H)(OH)—, Q$^2$ is —C(O)—, W is —NH—, and R$^1$ is —OP(O)(OR$^6$)(OH) and R$^2$ is —H. In any one of the foregoing embodiments in this paragraph, R$^6$ may be selected from the group consisting of hydroxyl and methyl.

In one embodiment of Formula I or Ia, Q$^1$ is —C(O)—, Q$^2$ is —C(O)—, and W is —CH$_2$—. In another embodiment, Q$^1$ is —C(O)—, Q$^2$ is —C(O)—, W is —CH$_2$—, and R$^1$ is —H and R$^2$ is —OH, —CH$_2$NH$_2$, R$^3$, R$^4$, R$^5$, or —O—R$^5$. In another embodiment, Q$^1$ is —C(O)—, Q$^2$ is —C(O)—, W is —CH$_2$—, and R$^1$ is —H and R$^2$ is —OH. In another embodiment, Q$^1$ is —C(O)—, Q$^2$ is —C(O)—, W is —CH$_2$—, and R$^1$ is —H and R$^2$ is —CH$_2$NH$_2$. In another embodiment, Q$^1$ is —C(O)—, Q$^2$ is —C(O)—, W is —CH$_2$—, and R$^1$ is —H and R$^2$ is R$^3$. In another embodiment, Q$^1$ is —C(O)—, Q$^2$ is —C(O)—, W is —CH$_2$—, and R$^1$ is —H and R$^2$ is R$^4$. In another embodiment, Q$^1$ is —C(O)—, Q$^2$ is —C(O)—, W is —CH$_2$—, and R$^1$ is —H and R$^2$ is R$^5$. In another embodiment, Q$^1$ is —C(O)—, Q$^2$ is —C(O)—, W is —CH₂—, and R¹ is —H and R² is —O—R⁵. In another embodiment, Q¹ is —C(O)—, Q² is —C(O)—, W is —CH₂—, and R¹ is —H and R² is selected from the group consisting of amino, dimethylamino, hydroxyl,

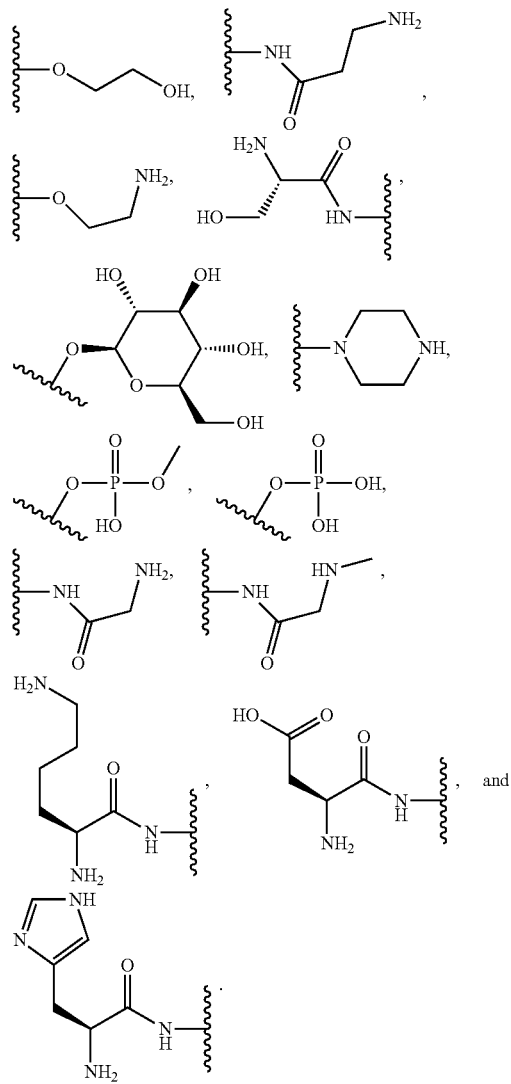

In another embodiment, Q¹ is —C(O)—, Q² is —C(O)—, W is —CH₂—, and R¹ is —OH and R² is —OH, —CH₂NH₂, R³, R⁴, R⁵, or —O—R⁵. In another embodiment, Q¹ is —C(O)—, Q² is —C(O)—, W is —CH₂—, and R¹ is —OH and R² is —OH. In another embodiment, Q¹ is —C(O)—, Q² is —C(O)—, W is —CH₂—, and R¹ is —OH and R² is —CH₂NH₂. In another embodiment, Q¹ is —C(O)—, Q² is —C(O)—, W is —CH₂—, and R¹ is —OH and R² is R³. In another embodiment, Q¹ is —C(O)—, Q² is —C(O)—, W is —CH₂—, and R¹ is —OH and R² is R⁴. In another embodiment, Q¹ is —C(O)—, Q² is —C(O)—, W is —CH₂—, and R¹ is —OH and R² is R⁵. In another embodiment, Q¹ is —C(O)—, Q² is —C(O)—, W is —CH₂—, and R¹ is —OH and R² is —O—R⁵. In another embodiment, Q¹ is —C(O)—, Q² is —C(O)—, W is —CH₂—, and R¹ is —OH and R² is selected from the group consisting of amino, dimethylamino, hydroxyl,

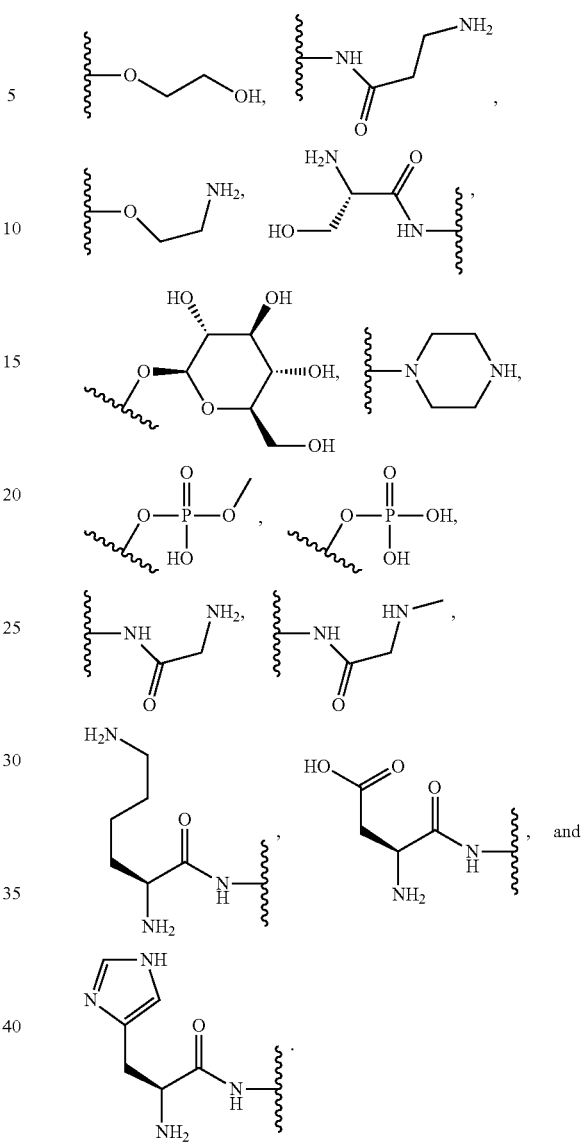

In another embodiment, Q¹ is —C(O)—, Q² is —C(O)—, W is —CH₂—, and R¹ is —NH₂ and R² is —OH, —CH₂NH₂, R³, R⁴, R⁵, or —O—R⁵. In another embodiment, Q¹ is —C(O)—, Q² is —C(O)—, W is —CH₂—, and R¹ is —NH₂ and R² is —OH. In another embodiment, Q¹ is —C(O)—, Q² is —C(O)—, W is —CH₂—, and R¹ is —NH₂ and R² is —CH₂NH₂. In another embodiment, Q¹ is —C(O)—, Q² is —C(O)—, W is —CH₂—, and R¹ is —NH₂ and R² is R³. In another embodiment, Q¹ is —C(O)—, Q² is —C(O)—, W is —CH₂—, and R¹ is —NH₂ and R² is R⁴. In another embodiment, Q¹ is —C(O)—, Q² is —C(O)—, W is —CH₂—, and R¹ is —NH₂ and R² is R⁵. In another embodiment, Q¹ is —C(O)—, Q² is —C(O)—, W is —CH₂—, and R¹ is —NH₂ and R² is —O—R⁵. In another embodiment, Q¹ is —C(O)—, Q² is —C(O)—, W is —CH₂—, and R¹ is —NH₂ and R² is selected from the group consisting of amino, dimethylamino, hydroxyl,

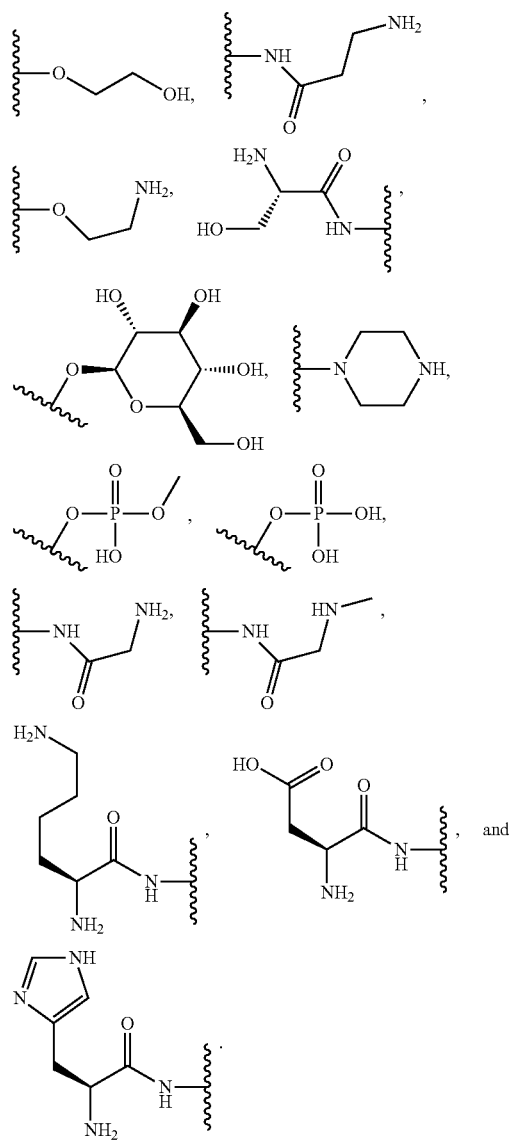

In another embodiment, $Q^1$ is —C(O)—, $Q^2$ is —C(O)—, W is —CH$_2$—, and $R^1$ is alkyl and $R^2$ is —OH, —CH$_2$NH$_2$, $R^3$, $R^4$, $R^5$, or —O—$R^5$. In another embodiment, $Q^1$ is —C(O)—, $Q^2$ is —C(O)—, W is —CH$_2$—, and $R^1$ is alkyl and $R^2$ is —OH. In another embodiment, $Q^1$ is —C(O)—, $Q^2$ is —C(O)—, W is —CH$_2$—, and $R^1$ is alkyl and $R^2$ is —CH$_2$NH$_2$. In another embodiment, $Q^1$ is —C(O)—, $Q^2$ is —C(O)—, W is —CH$_2$—, and $R^1$ is alkyl and $R^2$ is $R^3$. In another embodiment, $Q^1$ is —C(O)—, $Q^2$ is —C(O)—, W is —CH$_2$—, and $R^1$ is alkyl and $R^2$ is $R^4$. In another embodiment, $Q^1$ is —C(O)—, $Q^2$ is —C(O)—, W is —CH$_2$—, and $R^1$ is alkyl and $R^2$ is $R^5$. In another embodiment, $Q^1$ is —C(O)—, $Q^2$ is —C(O)—, W is —CH$_2$—, and $R^1$ is alkyl and $R^2$ is —O—$R^5$. In another embodiment, $Q^1$ is —C(O)—, $Q^2$ is —C(O)—, W is —CH$_2$—, and $R^1$ is alkyl and $R^2$ is selected from the group consisting of amino, dimethylamino, hydroxyl, In another embodiment of Formula I or Ia, $Q^1$ is —C(O)—, $Q^2$ is —C(O)—, W is —CH$_2$—, and $R^1$ is —OH or —OP(O)(OR$^6$)(OH) and $R^2$ is —H. In another embodiment, $Q^1$ is —C(O)—, $Q^2$ is —C(O)—, W is —CH$_2$—, and $R^1$ is —OH and $R^2$ is —H. In another embodiment, $Q^1$ is —C(O)—, $Q^2$ is —C(O)—, W is —CH$_2$—, and $R^1$ is —OP(O)(OR$^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(O)—, $Q^2$ is —C(O)—, and W is —O—. In another embodiment, $Q^1$ is —C(O)—, $Q^2$ is —C(O)—, W is —O—, and $R^1$ is —H and $R^2$ is —OH, —CH$_2$NH$_2$, $R^3$, $R^4$, $R^5$, or —O—$R^5$. In another embodiment, $Q^1$ is —C(O)—, $Q^2$ is —C(O)—, W is —O—, and $R^1$ is —H and $R^2$ is —OH. In another embodiment, $Q^1$ is —C(O)—, $Q^2$ is —C(O)—, W is —O—, and $R^1$ is —H and $R^2$ is —CH$_2$NH$_2$. In another embodiment, $Q^1$ is —C(O)—, $Q^2$ is —C(O)—, W is —O—, and $R^1$ is —H and $R^2$ is $R^3$. In another embodiment, $Q^1$ is —C(O)—, $Q^2$ is —C(O)—, W is —O—, and $R^1$ is —H and $R^2$ is $R^4$. In another embodiment, $Q^1$ is —C(O)—, $Q^2$ is —C(O)—, W is —O—, and $R^1$ is —H and $R^2$ is $R^5$. In another embodiment, $Q^1$ is —C(O)—, $Q^2$ is —C(O)—, W is —O—, and $R^1$ is —H and $R^2$ is —O—$R^5$. In another embodiment, $Q^1$ is —C(O)—, $Q^2$ is —C(O)—, W is —O—, and $R^1$ is —H and $R^2$ is selected from the group consisting of amino, dimethylamino, hydroxyl,

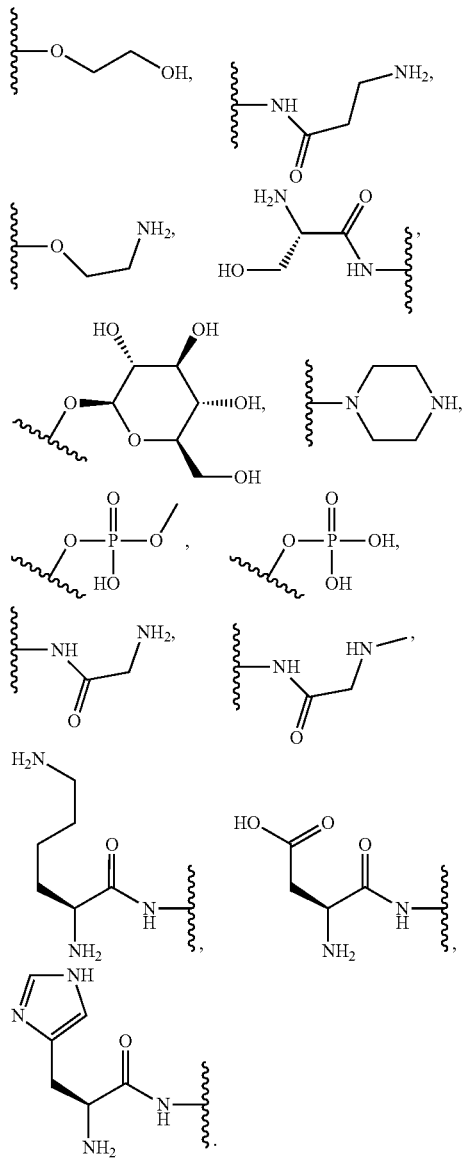

In another embodiment, $Q^1$ is —C(O)—, $Q^2$ is —C(O)—, W is —O—, and $R^1$ is —OH and $R^2$ is —OH, —$CH_2NH_2$, $R^3$, $R^4$, $R^5$, or —O—$R^5$. In another embodiment, $Q^1$ is —C(O)—, $Q^2$ is —C(O)—, W is —O—, and $R^1$ is —OH and $R^2$ is —OH. In another embodiment, $Q^1$ is —C(O)—, $Q^2$ is —C(O)—, W is —O—, and $R^1$ is —OH and $R^2$ is —$CH_2NH_2$. In another embodiment, $Q^1$ is —C(O)—, $Q^2$ is —C(O)—, W is —O—, and $R^1$ is —OH and $R^2$ is $R^3$. In another embodiment, $Q^1$ is —C(O)—, $Q^2$ is —C(O)—, W is —O—, and $R^1$ is —OH and $R^2$ is $R^4$. In another embodiment, $Q^1$ is —C(O)—, $Q^2$ is —C(O)—, W is —O—, and $R^1$ is —OH and $R^2$ is $R^5$. In another embodiment, $Q^1$ is —C(O)—, $Q^2$ is —C(O)—, W is —O—, and $R^1$ is —OH and $R^2$ is —O—$R^5$. In another embodiment, $Q^1$ is —C(O)—, $Q^2$ is —C(O)—, W is —O—, and $R^1$ is —OH and $R^2$ is selected from the group consisting of amino, dimethylamino, hydroxyl,

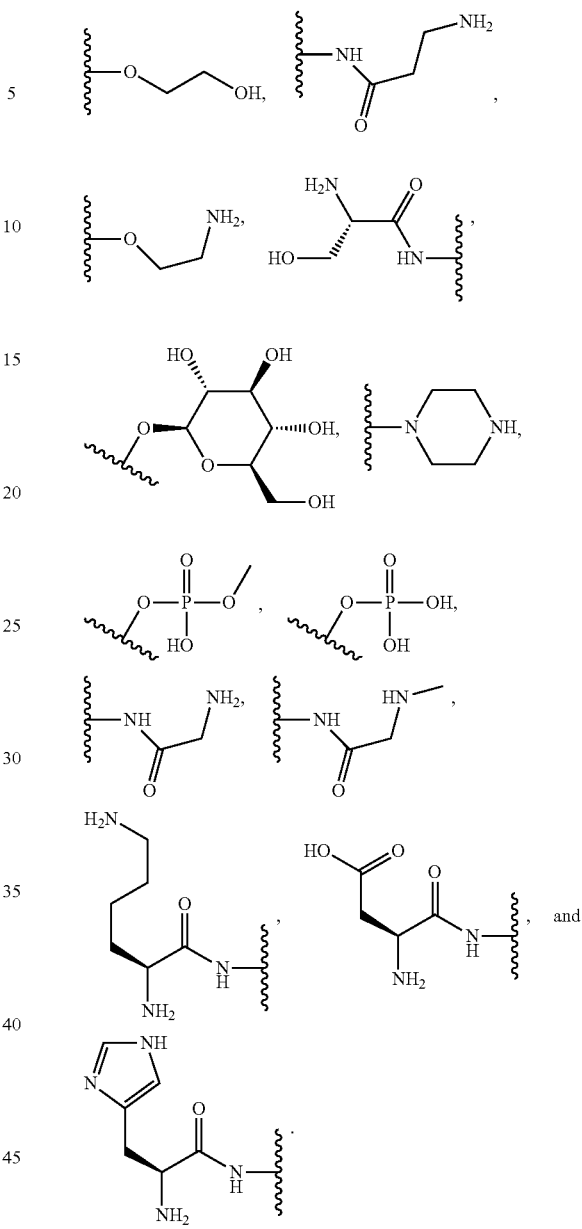

In another embodiment, $Q^1$ is —C(O)—, $Q^2$ is —C(O)—, W is —O—, and $R^1$ is —$NH_2$ and $R^2$ is —OH, —$CH_2NH_2$, $R^3$, $R^4$, $R^5$, or —O—$R^5$. In another embodiment, $Q^1$ is —C(O)—, $Q^2$ is —C(O)—, W is —O—, and $R^1$ is —$NH_2$ and $R^2$ is —OH. In another embodiment, $Q^1$ is —C(O)—, $Q^2$ is —C(O)—, W is —O—, and $R^1$ is —$NH_2$ and $R^2$ is —$CH_2NH_2$. In another embodiment, $Q^1$ is —C(O)—, $Q^2$ is —C(O)—, W is —O—, and $R^1$ is —$NH_2$ and $R^2$ is $R^3$. In another embodiment, $Q^1$ is —C(O)—, $Q^2$ is —C(O)—, W is —O—, and $R^1$ is —$NH_2$ and $R^2$ is $R^4$. In another embodiment, $Q^1$ is —C(O)—, $Q^2$ is —C(O)—, W is —O—, and $R^1$ is —$NH_2$ and $R^2$ is $R^5$. In another embodiment, $Q^1$ is —C(O)—, $Q^2$ is —C(O)—, W is —O—, and $R^1$ is —$NH_2$ and $R^2$ is —O—$R^5$. In another embodiment, $Q^1$ is —C(O)—, $Q^2$ is —C(O)—, W is —O—, and $R^1$ is —$NH_2$ and $R^2$ is selected from the group consisting of amino, dimethylamino,

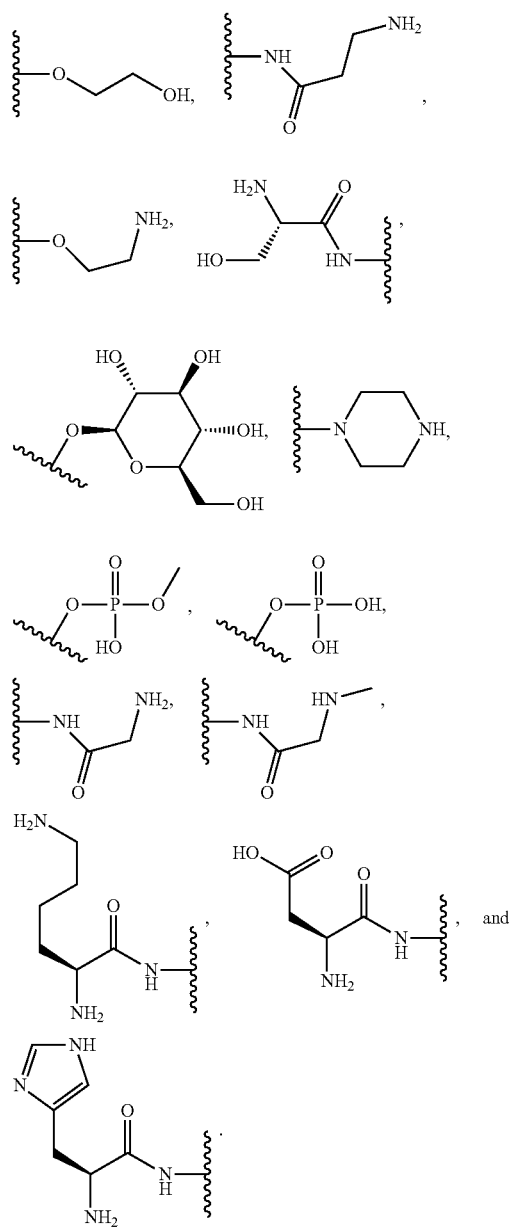
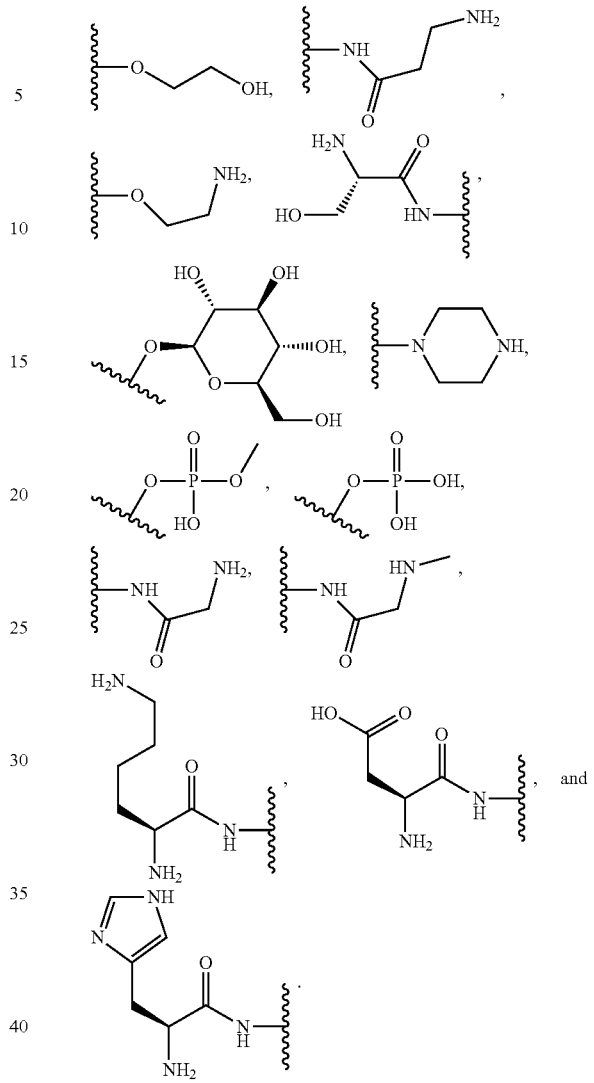

In another embodiment, $Q^1$ is —C(O)—, $Q^2$ is —C(O)—, W is —O—, and $R^1$ is alkyl and $R^2$ is —OH, —CH$_2$NH$_2$, $R^3$, $R^4$, $R^5$, or —O—$R^5$. In another embodiment, $Q^1$ is —C(O)—, $Q^2$ is —C(O)—, W is —O—, and $R^1$ is alkyl and $R^2$ is —OH. In another embodiment, $Q^1$ is —C(O)—, $Q^2$ is —C(O)—, W is —O—, and $R^1$ is alkyl and $R^2$ is —CH$_2$NH$_2$. In another embodiment, $Q^1$ is —C(O)—, $Q^2$ is —C(O)—, W is —O—, and $R^1$ is alkyl and $R^2$ is $R^3$. In another embodiment, $Q^1$ is —C(O)—, $Q^2$ is —C(O)—, W is —O—, and $R^1$ is alkyl and $R^2$ is $R^4$. In another embodiment, $Q^1$ is —C(O)—, $Q^2$ is —C(O)—, W is —O—, and $R^1$ is alkyl and $R^2$ is $R^5$. In another embodiment, $Q^1$ is —C(O)—, $Q^2$ is —C(O)—, W is —O—, and $R^1$ is alkyl and $R^2$ is —O—$R^5$. In another embodiment, $Q^1$ is —C(O)—, $Q^2$ is —C(O)—, W is —O—, and $R^1$ is alkyl and $R^2$ is selected from the group consisting of amino, dimethylamino, hydroxyl, In another embodiment of Formula I or Ia, $Q^1$ is —C(O)—, $Q^2$ is —C(O)—, W is —O—, and $R^1$ is —OH or —OP(O)(OR$^6$)(OH) and $R^2$ is —H. In another embodiment, $Q^1$ is —C(O)—, $Q^2$ is —C(O)—, W is —O—, and $R^1$ is —OH and $R^2$ is —H. In another embodiment, $Q^1$ is —C(O)—, $Q^2$ is —C(O)—, W is —O—, and $R^1$ is —OP(O)(OR$^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(O)—, $Q^2$ is —C(O)—, and W is —NH—. In another embodiment, $Q^1$ is —C(O)—, $Q^2$ is —C(O)—, W is —NH—, and $R^1$ is —H and $R^2$ is —OH, —CH$_2$NH$_2$, $R^3$, $R^4$, $R^5$, or —O—$R^5$. In another embodiment, $Q^1$ is —C(O)—, $Q^2$ is —C(O)—, W is —NH—, and $R^1$ is —H and $R^2$ is —OH. In another embodiment, $Q^1$ is —C(O)—, $Q^2$ is —C(O)—, W is —NH—, and $R^1$ is —H and $R^2$ is —CH$_2$NH$_2$. In another embodiment, $Q^1$ is —C(O)—, $Q^2$ is —C(O)—, W is —NH—, and $R^1$ is —H and $R^2$ is $R^3$. In another embodiment, $Q^1$ is —C(O)—, $Q^2$ is —C(O)—, W is —NH—, and $R^1$ is —H and $R^2$ is $R^4$. In another embodiment, $Q^1$ is —C(O)—, $Q^2$ is —C(O)—, W is —NH—, and $R^1$ is —H and $R^2$ is $R^5$. In another embodiment, $Q^1$ is —C(O)—, $Q^2$ is —C(O)—, W is —NH—, and $R^1$ is —H and $R^2$ is —O—$R^5$. In another embodiment, $Q^1$ is —C(O)—, $Q^2$ is —C(O)—, W is —NH—, and $R^1$ is —H and $R^2$ is selected from the group consisting of amino, dimethylamino, hydroxyl,

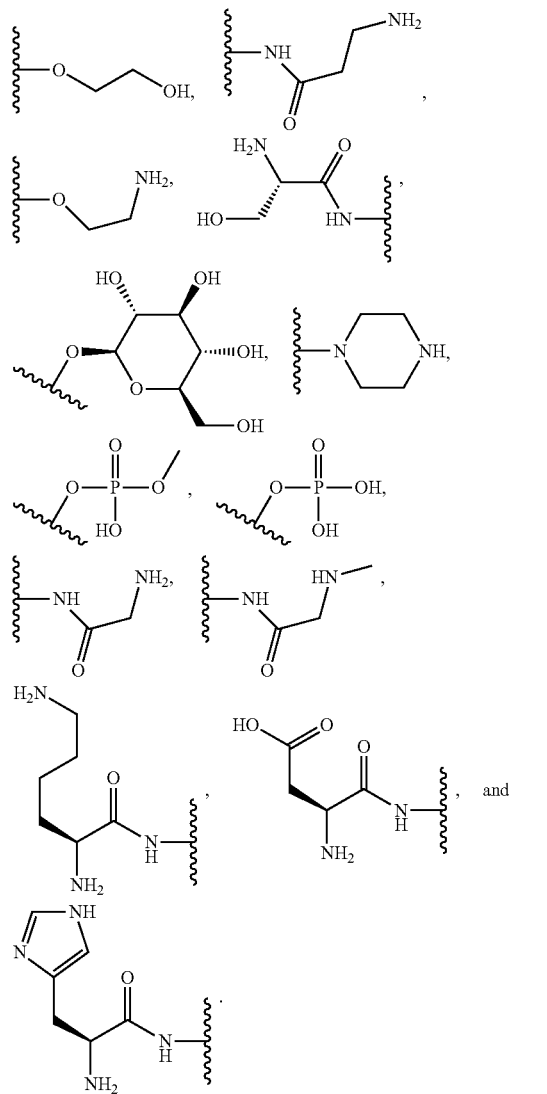

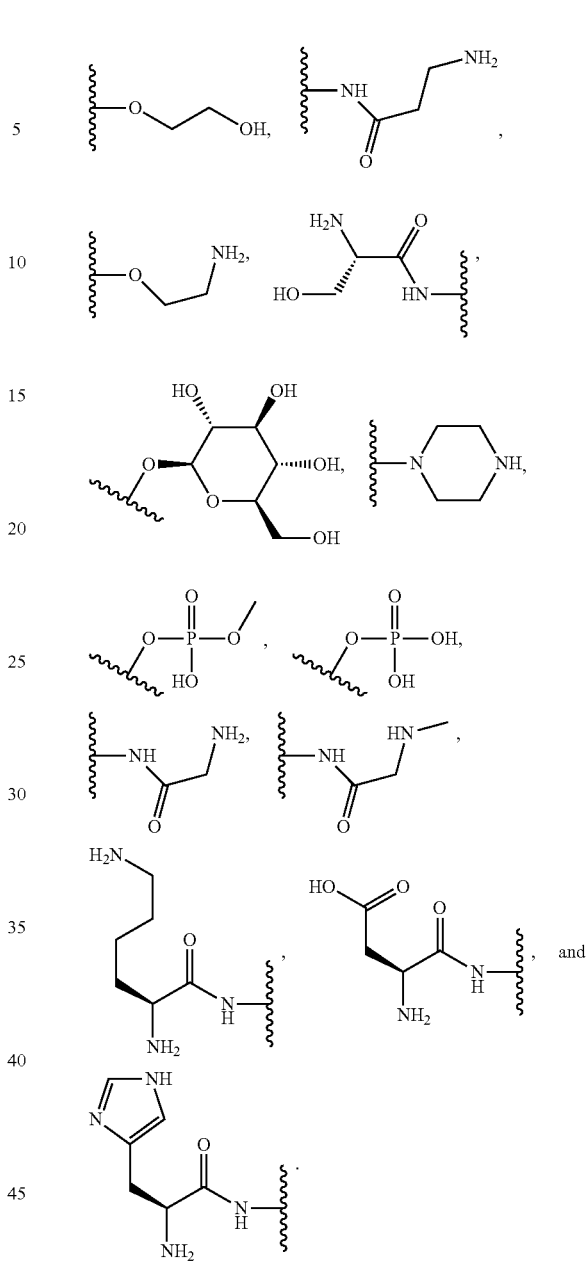

In another embodiment, $Q^1$ is —C(O)—, $Q^2$ is —C(O)—, W is —NH—, and $R^1$ is —OH and $R^2$ is —OH, —$CH_2NH_2$, $R^3$, $R^4$, $R^5$, or —O—$R^5$. In another embodiment, $Q^1$ is —C(O)—, $Q^2$ is —C(O)—, W is —NH—, and $R^1$ is —OH and $R^2$ is —OH. In another embodiment, $Q^1$ is —C(O)—, $Q^2$ is —C(O)—, W is —NH—, and $R^1$ is —OH and $R^2$ is —$CH_2NH_2$. In another embodiment, $Q^1$ is —C(O)—, $Q^2$ is —C(O)—, W is —NH—, and $R^1$ is —OH and $R^2$ is $R^3$. In another embodiment, $Q^1$ is —C(O)—, $Q^2$ is —C(O)—, W is —NH—, and $R^1$ is —OH and $R^2$ is $R^4$. In another embodiment, $Q^1$ is —C(O)—, $Q^2$ is —C(O)—, W is —NH—, and $R^1$ is —OH and $R^2$ is $R^5$. In another embodiment, $Q^1$ is —C(O)—, $Q^2$ is —C(O)—, W is —NH—, and $R^1$ is —OH and $R^2$ is —O—$R^5$. In another embodiment, $Q^1$ is —C(O)—, $Q^2$ is —C(O)—, W is —NH—, and $R^1$ is —OH and $R^2$ is selected from the group consisting of amino, dimethylamino, hydroxyl, In another embodiment, $Q^1$ is —C(O)—, $Q^2$ is —C(O)—, W is —NH—, and $R^1$ is —$NH_2$ and $R^2$ is —OH, —$CH_2NH_2$, $R^3$, $R^4$, $R^5$, or —O—$R^5$. In another embodiment, $Q^1$ is —C(O)—, $Q^2$ is —C(O)—, W is —NH—, and $R^1$ is —$NH_2$ and $R^2$ is —OH. In another embodiment, $Q^1$ is —C(O)—, $Q^2$ is —C(O)—, W is —NH—, and $R^1$ is —$NH_2$ and $R^2$ is —$CH_2NH_2$. In another embodiment, $Q^1$ is —C(O)—, $Q^2$ is —C(O)—, W is —NH—, and $R^1$ is —$NH_2$ and $R^2$ is $R^3$. In another embodiment, $Q^1$ is —C(O)—, $Q^2$ is —C(O)—, W is —NH—, and $R^1$ is —$NH_2$ and $R^2$ is $R^4$. In another embodiment, $Q^1$ is —C(O)—, $Q^2$ is —C(O)—, W is —NH—, and $R^1$ is —$NH_2$ and $R^2$ is $R^5$. In another embodiment, $Q^1$ is —C(O)—, $Q^2$ is —C(O)—, W is —NH—, and $R^1$ is —$NH_2$ and $R^2$ is —O—$R^5$. In another embodiment, $Q^1$ is —C(O)—, $Q^2$ is —C(O)—, W is —NH—, and $R^1$ is —$NH_2$ and $R^2$ is selected from the group consisting of amino, dimethylamino, hydroxyl,

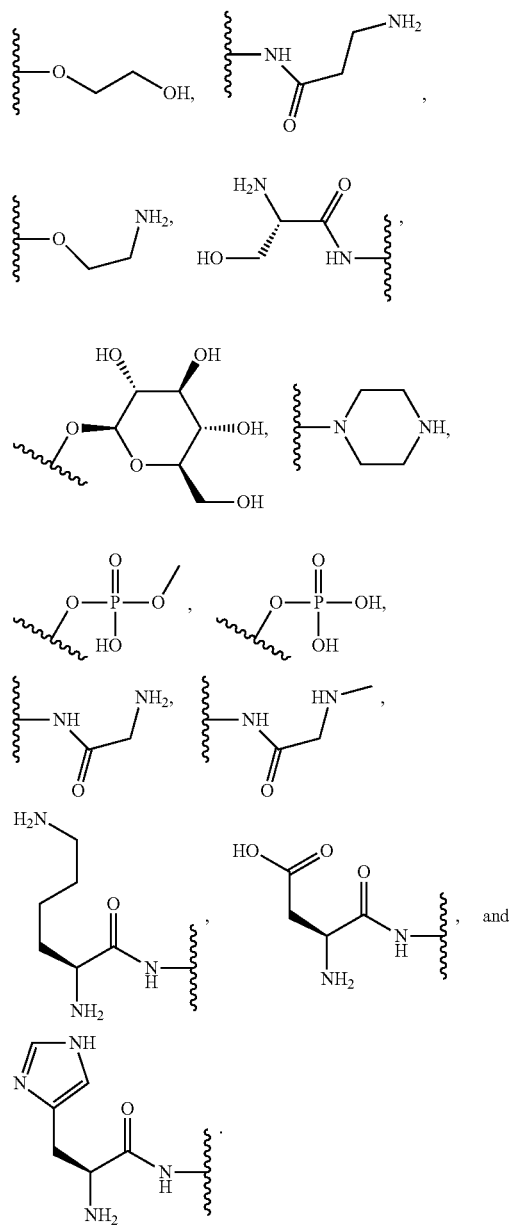

In another embodiment, $Q^1$ is —C(O)—, $Q^2$ is —C(O)—, W is —NH—, and $R^1$ is alkyl and $R^2$ is —OH, —CH$_2$NH$_2$, $R^3$, $R^4$, $R^5$, or —O—$R^5$. In another embodiment, $Q^1$ is —C(O)—, $Q^2$ is —C(O)—, W is —NH—, and $R^1$ is alkyl and $R^2$ is —OH. In another embodiment, $Q^1$ is —C(O)—, $Q^2$ is —C(O)—, W is —NH—, and $R^1$ is alkyl and $R^2$ is —CH$_2$NH$_2$. In another embodiment, $Q^1$ is —C(O)—, $Q^2$ is —C(O)—, W is —NH—, and $R^1$ is alkyl and $R^2$ is $R^3$. In another embodiment, $Q^1$ is —C(O)—, $Q^2$ is —C(O)—, W is —NH—, and $R^1$ is alkyl and $R^2$ is $R^4$. In another embodiment, $Q^1$ is —C(O)—, $Q^2$ is —C(O)—, W is —NH—, and $R^1$ is alkyl and $R^2$ is $R^5$. In another embodiment, $Q^1$ is —C(O)—, $Q^2$ is —C(O)—, W is —NH—, and $R^1$ is alkyl and $R^2$ is —O—$R^5$. In another embodiment, $Q^1$ is —C(O)—, $Q^2$ is —C(O)—, W is —NH—, and $R^1$ is alkyl and $R^2$ is selected from the group consisting of amino, dimethylamino, hydroxyl, In another embodiment of Formula I or Ia, $Q^1$ is —C(O)—, $Q^2$ is —C(O)—, W is —NH—, and $R^1$ is —OH or —OP(O)(O$R^6$)(OH) and $R^2$ is —H. In another embodiment, $Q^1$ is —C(O)—, $Q^2$ is —C(O)—, W is —NH—, and $R^1$ is —OH and $R^2$ is —H. In another embodiment, $Q^1$ is —C(O)—, $Q^2$ is —C(O)—, W is —NH—, and $R^1$ is —OP(O)(O$R^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(O)—, $Q^2$ is —CH$_2$—, and W is —CH$_2$—. In another embodiment, $Q^1$ is —C(O)—, $Q^2$ is —CH$_2$—, W is —CH$_2$—, and $R^1$ is —H and $R^2$ is —OH, —CH$_2$NH$_2$, $R^3$, $R^4$, $R^5$, or —O—$R^5$. In another embodiment, $Q^1$ is —C(O)—, $Q^2$ is —CH$_2$—, W is —CH$_2$—, and $R^1$ is —H and $R^2$ is —OH. In another embodiment, $Q^1$ is —C(O)—, $Q^2$ is —CH$_2$—, W is —CH$_2$—, and $R^1$ is —H and $R^2$ is —CH$_2$NH$_2$. In another embodiment, $Q^1$ is —C(O)—, $Q^2$ is —CH$_2$—, W is —CH$_2$—, and $R^1$ is —H and $R^2$ is $R^3$. In another embodiment, $Q^1$ is —C(O)—, $Q^2$ is —CH$_2$—, W is —CH$_2$—, and $R^1$ is —H and $R^2$ is $R^4$. In another embodiment, $Q^1$ is —C(O)—, $Q^2$ is —CH$_2$—, W is —CH$_2$—, and $R^1$ is —H and $R^2$ is $R^5$. In another embodiment, $Q^1$ is —C(O)—, $Q^2$ is —CH$_2$—, W is —CH₂—, and R¹ is —H and R² is —O—R⁵. In another embodiment, Q¹ is —C(O)—, Q² is —CH₂—, W is —CH₂—, and R¹ is —H and R² is selected from the group consisting of amino, dimethylamino, hydroxyl,

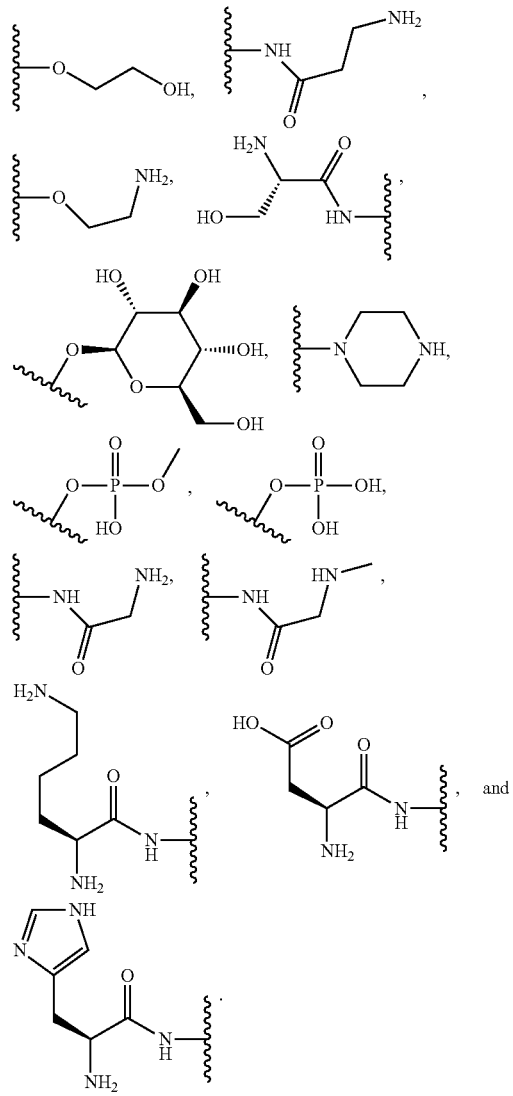

In another embodiment, Q¹ is —C(O)—, Q² is —CH₂—, W is —CH₂—, and R¹ is —OH and R² is —OH, —CH₂NH₂, R³, R⁴, R⁵, or —O—R⁵. In another embodiment, Q¹ is —C(O)—, Q² is —CH₂—, W is —CH₂—, and R¹ is —OH and R² is —OH. In another embodiment, Q¹ is —C(O)—, Q² is —CH₂—, W is —CH₂—, and R¹ is —OH and R² is —CH₂NH₂. In another embodiment, Q¹ is —C(O)—, Q² is —CH₂—, W is —CH₂—, and R¹ is —OH and R² is R³. In another embodiment, Q¹ is —C(O)—, Q² is —CH₂—, W is —CH₂—, and R¹ is —OH and R² is R⁴. In another embodiment, Q¹ is —C(O)—, Q² is —CH₂—, W is —CH₂—, and R¹ is —OH and R² is R⁵. In another embodiment, Q¹ is —C(O)—, Q² is —CH₂—, W is —CH₂—, and R¹ is —OH and R² is —O—R⁵. In another embodiment, Q¹ is —C(O)—, Q² is —CH₂—, W is —CH₂—, and R¹ is —OH and R² is selected from the group consisting of amino, dimethylamino, hydroxyl,

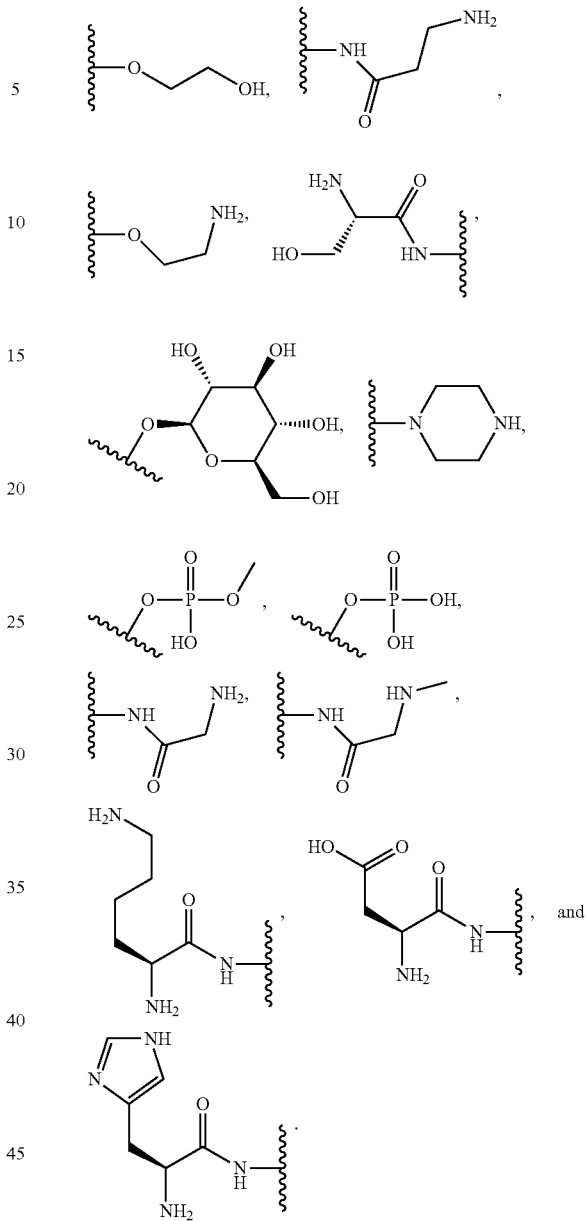

In another embodiment, Q¹ is —C(O)—, Q² is —CH₂—, W is —CH₂—, and R¹ is —NH₂ and R² is —OH, —CH₂NH₂, R³, R⁴, R⁵, or —O—R⁵. In another embodiment, Q¹ is —C(O)—, Q² is —CH₂—, W is —CH₂—, and R¹ is —NH₂ and R² is —OH. In another embodiment, Q¹ is —C(O)—, Q² is —CH₂—, W is —CH₂—, and R¹ is —NH₂ and R² is —CH₂NH₂. In another embodiment, Q¹ is —C(O)—, Q² is —CH₂—, W is —CH₂—, and R¹ is —NH₂ and R² is R³. In another embodiment, Q¹ is —C(O)—, Q² is —CH₂—, W is —CH₂—, and R¹ is —NH₂ and R² is R⁴. In another embodiment, Q¹ is —C(O)—, Q² is —CH₂—, W is —CH₂—, and R¹ is —NH₂ and R² is R⁵. In another embodiment, Q¹ is —C(O)—, Q² is —CH₂—, W is —CH₂—, and R¹ is —NH₂ and R² is —O—R⁵. In another embodiment, Q¹ is —C(O)—, Q² is —CH₂—, W is —CH₂—, and R¹ is —NH₂ and R² is selected from the group consisting of amino, dimethylamino, hydroxyl,

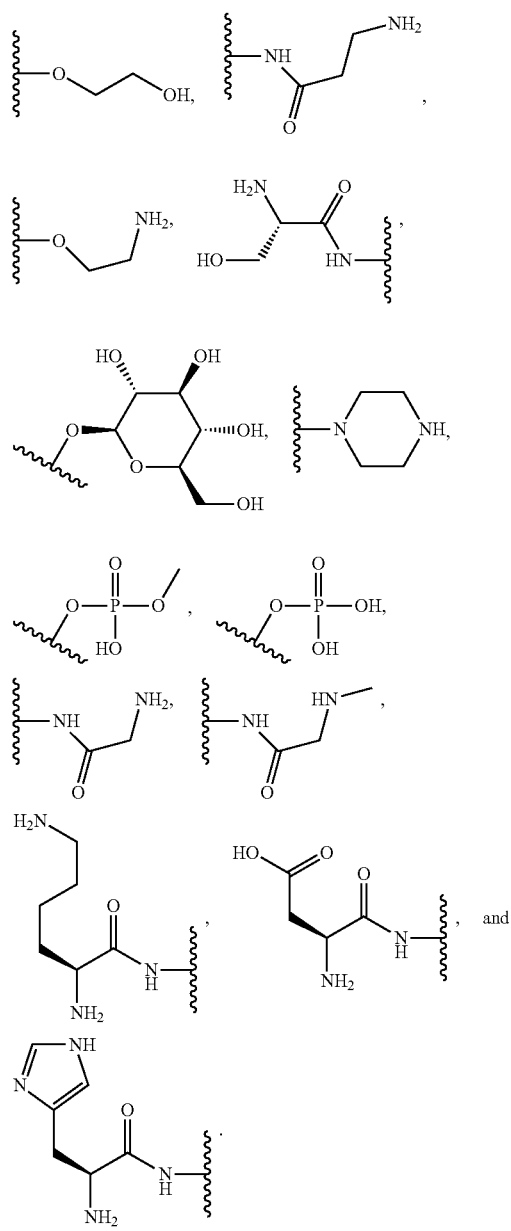

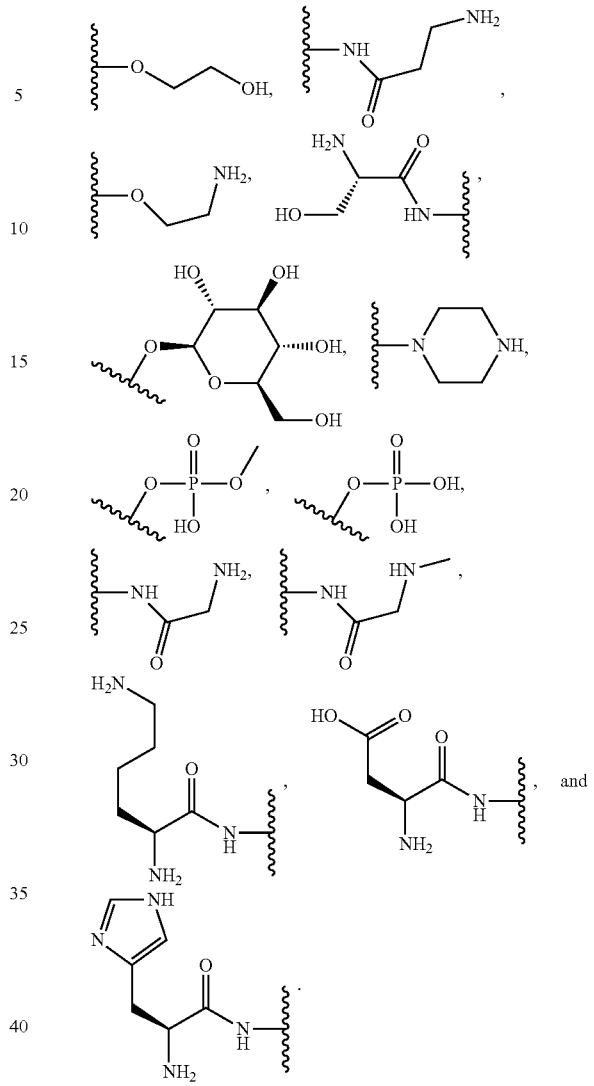

In another embodiment, $Q^1$ is —C(O)—, $Q^2$ is —CH$_2$—, W is —CH$_2$—, and $R^1$ is alkyl and $R^2$ is —OH, —CH$_2$NH$_2$, $R^3$, $R^4$, $R^5$, or —O—$R^5$. In another embodiment, $Q^1$ is —C(O)—, $Q^2$ is —CH$_2$—, W is —CH$_2$—, and $R^1$ is alkyl and $R^2$ is —OH. In another embodiment, $Q^1$ is —C(O)—, $Q^2$ is —CH$_2$—, W is —CH$_2$—, and $R^1$ is alkyl and $R^2$ is —CH$_2$NH$_2$. In another embodiment, $Q^1$ is —C(O)—, $Q^2$ is —CH$_2$—, W is —CH$_2$—, and $R^1$ is alkyl and $R^2$ is $R^3$. In another embodiment, $Q^1$ is —C(O)—, $Q^2$ is —CH$_2$—, W is —CH$_2$—, and $R^1$ is alkyl and $R^2$ is $R^4$. In another embodiment, $Q^1$ is —C(O)—, $Q^2$ is —CH$_2$—, W is —CH$_2$—, and $R^1$ is alkyl and $R^2$ is $R^5$. In another embodiment, $Q^1$ is —C(O)—, $Q^2$ is —CH$_2$—, W is —CH$_2$—, and $R^1$ is alkyl and $R^2$ is —O—$R^5$. In another embodiment, $Q^1$ is —C(O)—, $Q^2$ is —CH$_2$—, W is —CH$_2$—, and $R^1$ is alkyl and $R^2$ is selected from the group consisting of amino, dimethylamino, hydroxyl, In another embodiment of Formula I or Ia, $Q^1$ is —C(O)—, $Q^2$ is —CH$_2$—, W is —CH$_2$—, and $R^1$ is —OH or —OP(O)(OR$^6$)(OH) and $R^2$ is —H. In another embodiment, $Q^1$ is —C(O)—, $Q^2$ is —CH$_2$—, W is —CH$_2$—, and $R^1$ is —OH and $R^2$ is —H. In another embodiment, $Q^1$ is —C(O)—, $Q^2$ is —CH$_2$—, W is —CH$_2$—, and $R^1$ is —OP(O)(OR$^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(O)—, $Q^2$ is —CH$_2$—, and W is —O—. In another embodiment, $Q^1$ is —C(O)—, $Q^2$ is —CH$_2$—, W is —O—, and $R^1$ is —H and $R^2$ is —OH, —CH$_2$NH$_2$, $R^3$, $R^4$, $R^5$, or —O—$R^5$. In another embodiment, $Q^1$ is —C(O)—, $Q^2$ is —CH$_2$—, W is —O—, and $R^1$ is —H and $R^2$ is —OH. In another embodiment, $Q^1$ is —C(O)—, $Q^2$ is —CH$_2$—, W is —O—, and $R^1$ is —H and $R^2$ is —CH$_2$NH$_2$. In another embodiment, $Q^1$ is —C(O)—, $Q^2$ is —CH$_2$—, W is —O—, and $R^1$ is —H and $R^2$ is $R^3$. In another embodiment, $Q^1$ is —C(O)—, $Q^2$ is —CH$_2$—, W is —O—, and $R^1$ is —H and $R^2$ is $R^4$. In another embodiment, $Q^1$ is —C(O)—, $Q^2$ is —CH$_2$—, W is —O—, and $R^1$ is —H and $R^2$ is $R^5$. In another embodiment, $Q^1$ is —C(O)—, $Q^2$ is —CH$_2$—, W is —O—, and $R^1$ is —H and $R^2$ is —O—$R^5$.

In another embodiment, $Q^1$ is —C(O)—, $Q^2$ is —CH$_2$—, W is —O—, and $R^1$ is —H and $R^2$ is selected from the group consisting of amino, dimethylamino, hydroxyl,

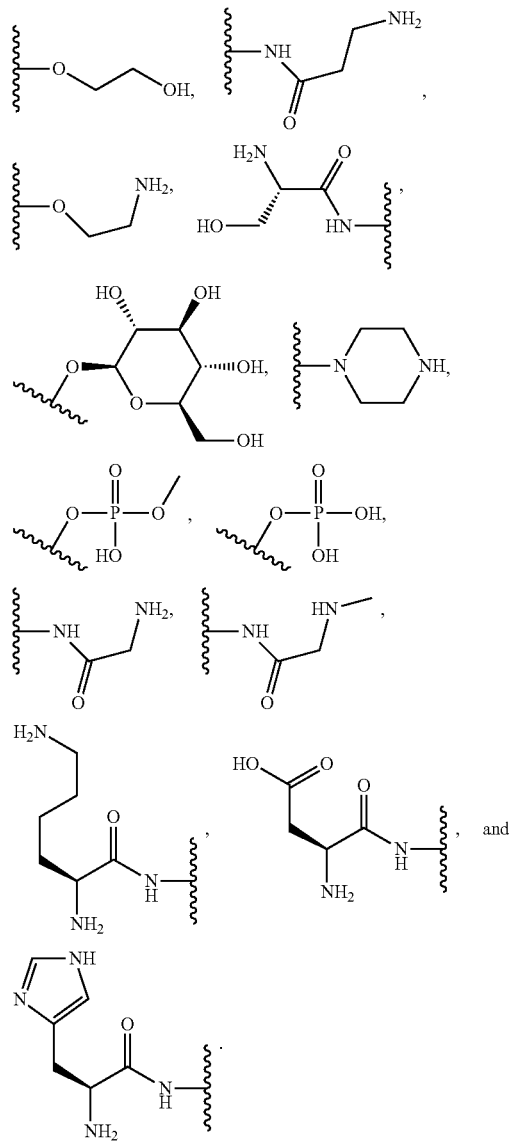

In another embodiment, $Q^1$ is —C(O)—, $Q^2$ is —CH$_2$—, W is —O—, and $R^1$ is —OH and $R^2$ is —OH, —CH$_2$NH$_2$, $R^3$, $R^4$, $R^5$, or —O—$R^5$. In another embodiment, $Q^1$ is —C(O)—, $Q^2$ is —O—, and $R^1$ is —OH and $R^2$ is —OH. In another embodiment, $Q^1$ is —C(O)—, $Q^2$ is —CH$_2$—, W is —O—, and $R^1$ is —OH and $R^2$ is —CH$_2$NH$_2$. In another embodiment, $Q^1$ is —C(O)—, $Q^2$ is —CH$_2$—, W is —O—, and $R^1$ is —OH and $R^2$ is $R^3$. In another embodiment, $Q^1$ is —C(O)—, $Q^2$ is —CH$_2$—, W is —O—, and $R^1$ is —OH and $R^2$ is $R^4$. In another embodiment, $Q^1$ is —C(O)—, $Q^2$ is —CH$_2$—, W is —O—, and $R^1$ is —OH and $R^2$ is $R^5$. In another embodiment, $Q^1$ is —C(O)—, $Q^2$ is —CH$_2$—, W is —O—, and $R^1$ is —OH and $R^2$ is —O—RS. In another embodiment, $Q^1$ is —C(O)—, $Q^2$ is —CH$_2$—, W is —O—, and $R^1$ is —OH and $R^2$ is selected from the group consisting of amino, dimethylamino, hydroxyl,

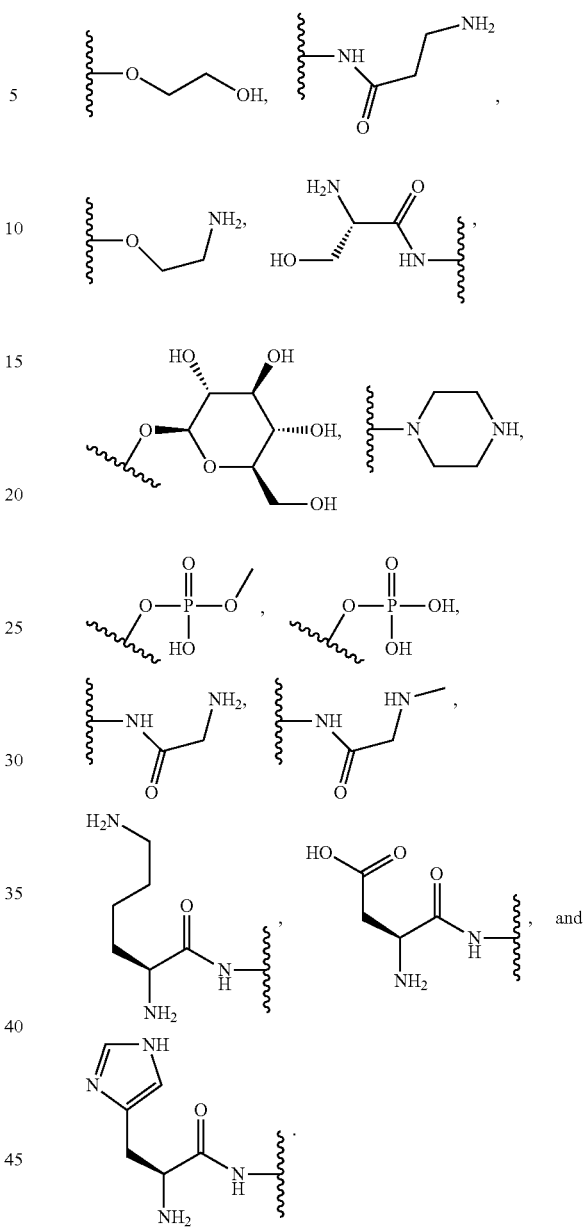

In another embodiment, $Q^1$ is —C(O)—, $Q^2$ is —CH$_2$—, W is —O—, and $R^1$ is —NH$_2$ and $R^2$ is —OH, —CH$_2$NH$_2$, $R^3$, $R^4$, $R^5$, or —O—$R^5$. In another embodiment, $Q^1$ is —C(O)—, $Q^2$ is —CH$_2$—, W is —O—, and $R^1$ is —NH$_2$ and $R^2$ is —OH. In another embodiment, $Q^1$ is —C(O)—, $Q^2$ is —CH$_2$—, W is —O—, and $R^1$ is —NH$_2$ and $R^2$ is —CH$_2$NH$_2$. In another embodiment, $Q^1$ is —C(O)—, $Q^2$ is —CH$_2$—, W is —O—, and $R^1$ is —NH$_2$ and $R^2$ is $R^3$. In another embodiment, $Q^1$ is —C(O)—, $Q^2$ is —CH$_2$—, W is —O—, and $R^1$ is —NH$_2$ and $R^2$ is $R^4$. In another embodiment, $Q^1$ is —C(O)—, $Q^2$ is —CH$_2$—, W is —O—, and $R^1$ is —NH$_2$ and $R^2$ is $R^5$. In another embodiment, $Q^1$ is —C(O)—, $Q^2$ is —CH$_2$—, W is —O—, and $R^1$ is —NH$_2$ and $R^2$ is —O—$R^5$. In another embodiment, $Q^1$ is —C(O)—, $Q^2$ is —CH$_2$—, W is —O—, and $R^1$ is —NH$_2$ and $R^2$ is selected from the group consisting of amino, dimethylamino, hydroxyl,

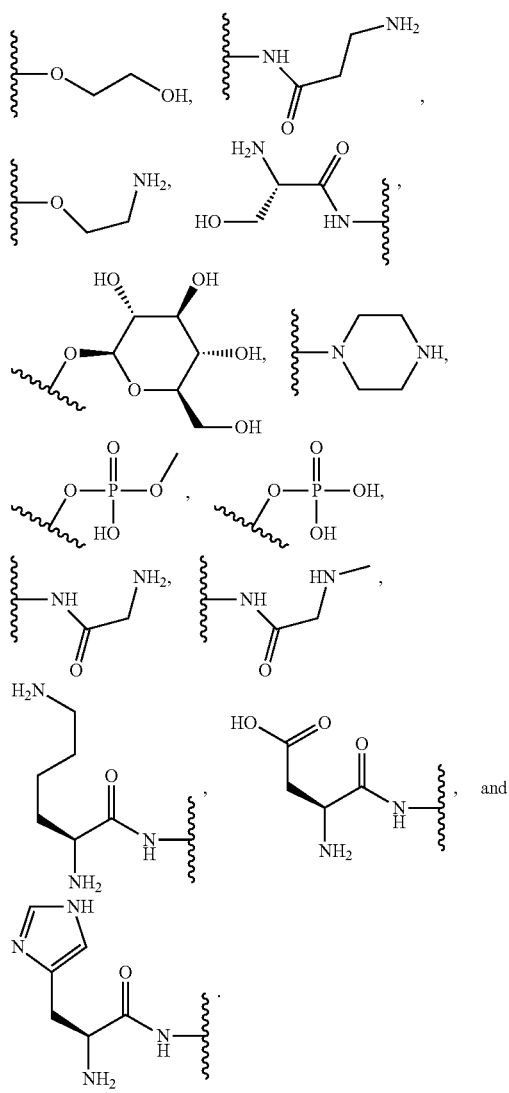

In another embodiment, $Q^1$ is —C(O)—, $Q^2$ is —CH$_2$—, W is —O—, and $R^1$ is alkyl and $R^2$ is —OH, —CH$_2$NH$_2$, $R^3$, $R^4$, $R^5$, or —O—$R^5$. In another embodiment, $Q^1$ is —C(O)—, $Q^2$ is —CH$_2$—, W is —O—, and $R^1$ is alkyl and $R^2$ is —OH. In another embodiment, $Q^1$ is —C(O)—, $Q^2$ is —CH$_2$—, W is —O—, and $R^1$ is alkyl and $R^2$ is —CH$_2$NH$_2$. In another embodiment, $Q^1$ is —C(O)—, $Q^2$ is —CH$_2$—, W is —O—, and $R^1$ is alkyl and $R^2$ is $R^3$. In another embodiment, $Q^1$ is —C(O)—, $Q^2$ is —CH$_2$—, W is —O—, and $R^1$ is alkyl and $R^2$ is $R^4$. In another embodiment, $Q^1$ is —C(O)—, $Q^2$ is —CH$_2$—, W is —O—, and $R^1$ is alkyl and $R^2$ is $R^5$. In another embodiment, $Q^1$ is —C(O)—, $Q^2$ is —CH$_2$—, W is —O—, and $R^1$ is alkyl and $R^2$ is —O—$R^5$. In another embodiment, $Q^1$ is —C(O)—, $Q^2$ is —CH$_2$—, W is —O—, and $R^1$ is alkyl and $R^2$ is selected from the group consisting of amino, dimethylamino, hydroxyl,

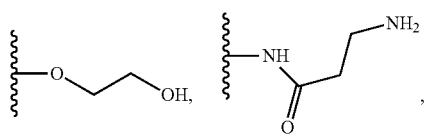

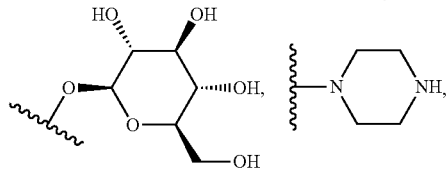

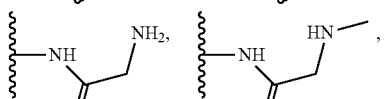

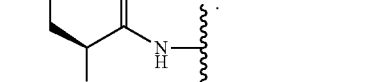

In another embodiment of Formula I or Ia, $Q^1$ is —C(O)—, $Q^2$ is —CH$_2$—, W is —O—, and $R^1$ is —OH or —OP(O)(O$R^6$)(OH) and $R^2$ is —H. In another embodiment, $Q^1$ is —C(O)—, $Q^2$ is —CH$_2$—, W is —O—, and $R^1$ is —OH and $R^2$ is —H. In another embodiment, $Q^1$ is —C(O)—, $Q^2$ is —CH$_2$—, W is —O—, and $R^1$ is —OP(O)(O$R^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(O)—, $Q^2$ is —CH$_2$—, and W is —NH—. In another embodiment, $Q^1$ is —C(O)—, $Q^2$ is —CH$_2$—, W is —NH—, and $R^1$ is —H and $R^2$ is —OH, —CH$_2$NH$_2$, $R^3$, $R^4$, $R^5$, or —O—$R^5$. In another embodiment, $Q^1$ is —C(O)—, $Q^2$ is —CH$_2$—W is —NH—, and $R^1$ is —H and $R^2$ is —OH. In another embodiment, $Q^1$ is —C(O)—, $Q^2$ is —CH$_2$—, W is —NH—, and $R^1$ is —H and $R^2$ is —CH$_2$NH$_2$. In another embodiment, $Q^1$ is —C(O)—, $Q^2$ is —CH$_2$—, W is —NH—, and $R^1$ is —H and $R^2$ is $R^3$. In another embodiment, $Q^1$ is —C(O)—, $Q^2$ is —CH$_2$—, W is —NH—, and $R^1$ is —H and $R^2$ is $R^4$. In another embodiment, $Q^1$ is —C(O)—, $Q^2$ is —CH$_2$—, W is —NH—, and $R^1$ is —H and $R^2$ is $R^5$. In another embodiment, $Q^1$ is —C(O)—, $Q^2$ is —CH$_2$—, W is —NH—, and $R^1$ is —H and $R^2$ is —O—$R^5$. In another embodiment, $Q^1$ is —C(O)—, $Q^2$ is —CH$_2$—, W is —NH—, and $R^1$ is —H and $R^2$ is selected from the group consisting of amino, dimethylamino, hydroxyl,

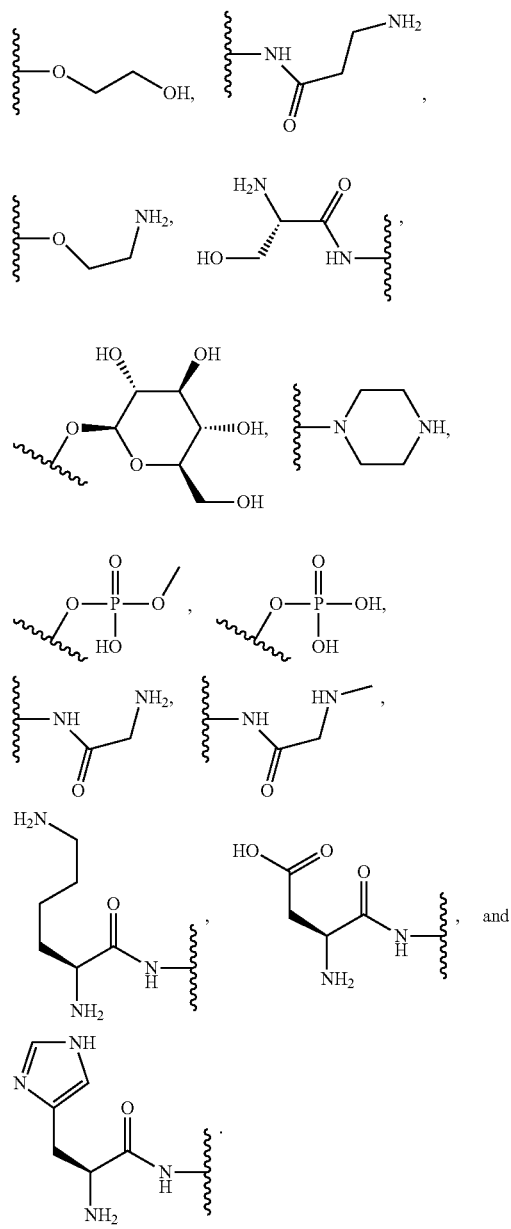
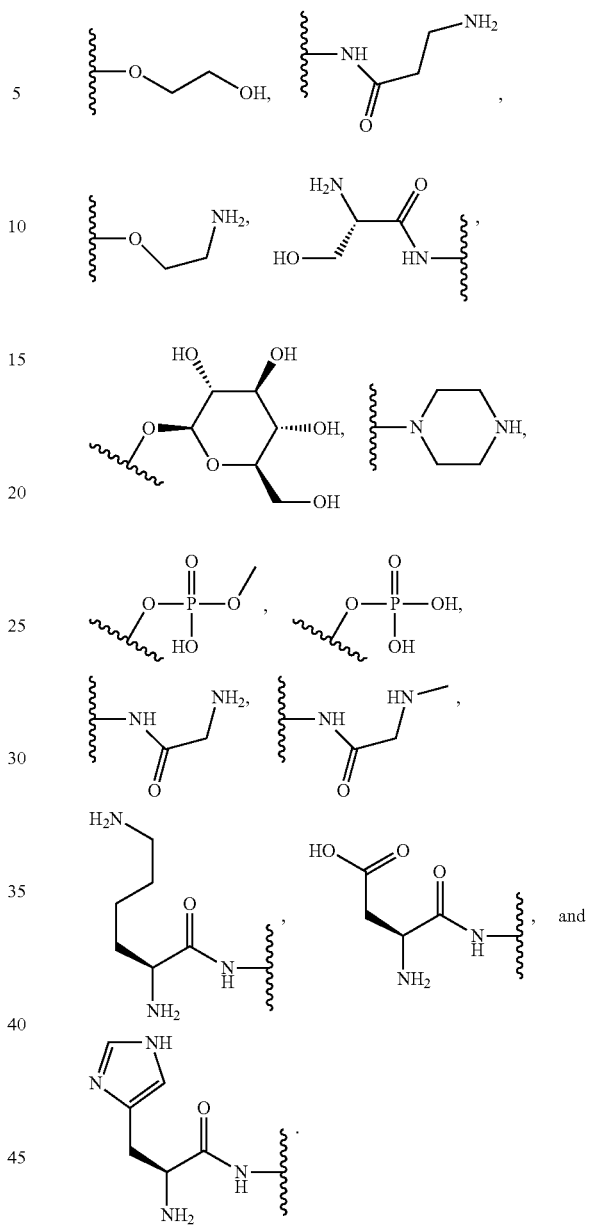

In another embodiment, $Q^1$ is —C(O)—, $Q^2$ is —CH$_2$—, W is —NH—, and $R^1$ is —OH and $R^2$ is —OH, —CH$_2$NH$_2$, $R^3$, $R^4$, $R^5$, or —O—$R^5$. In another embodiment, $Q^1$ is —C(O)—, $Q^2$ is —CH$_2$—, W is —NH—, and $R^1$ is —OH and $R^2$ is —OH. In another embodiment, $Q^1$ is —C(O)—, $Q^2$ is —CH$_2$—, W is —NH—, and $R^1$ is —OH and $R^2$ is —CH$_2$NH$_2$. In another embodiment, $Q^1$ is —C(O)—, $Q^2$ is —CH$_2$—, W is —NH—, and $R^1$ is —OH and $R^2$ is $R^3$. In another embodiment, $Q^1$ is —C(O)—, $Q^2$ is —CH$_2$—, W is —NH—, and $R^1$ is —OH and $R^2$ is $R^4$. In another embodiment, $Q^1$ is —C(O)—, $Q^2$ is —CH$_2$—, W is —NH—, and $R^1$ is —OH and $R^2$ is $R^5$. In another embodiment, $Q^1$ is —C(O)—, $Q^2$ is —CH$_2$—, W is —NH—, and $R^1$ is —OH and $R^2$ is —O—$R^5$. In another embodiment, $Q^1$ is —C(O)—, $Q^2$ is —CH$_2$—, W is —NH—, and $R^1$ is —OH and $R^2$ is selected from the group consisting of amino, dimethylamino, hydroxyl, In another embodiment, $Q^1$ is —C(O)—, $Q^2$ is —CH$_2$—, W is —NH—, and $R^1$ is —NH$_2$ and $R^2$ is —OH, —CH$_2$NH$_2$, $R^3$, $R^4$, $R^5$, or —O—$R^5$. In another embodiment, $Q^1$ is —C(O)—, $Q^2$ is —CH$_2$—, W is —NH—, and $R^1$ is —NH$_2$ and $R^2$ is —OH. In another embodiment, $Q^1$ is —C(O)—, $Q^2$ is —CH$_2$—, W is —NH—, and $R^1$ is —NH$_2$ and $R^2$ is —CH$_2$NH$_2$. In another embodiment, $Q^1$ is —C(O)—, $Q^2$ is —CH$_2$—, W is —NH—, and $R^1$ is —NH$_2$ and $R^2$ is $R^3$. In another embodiment, $Q^1$ is —C(O)—, $Q^2$ is —CH$_2$—, W is —NH—, and $R^1$ is —NH$_2$ and $R^2$ is $R^4$. In another embodiment, $Q^1$ is —C(O)—, $Q^2$ is —CH$_2$—, W is —NH—, and $R^1$ is —NH$_2$ and $R^2$ is $R^5$. In another embodiment, $Q^1$ is —C(O)—, $Q^2$ is —CH$_2$—, W is —NH—, and $R^1$ is —NH$_2$ and $R^2$ is —O—$R^5$. In another embodiment, $Q^1$ is —C(O)—, $Q^2$ is —CH$_2$—, W is —NH—, and $R^1$ is —OH and $R^2$ is selected from the group consisting of amino, dimethylamino, hydroxyl,

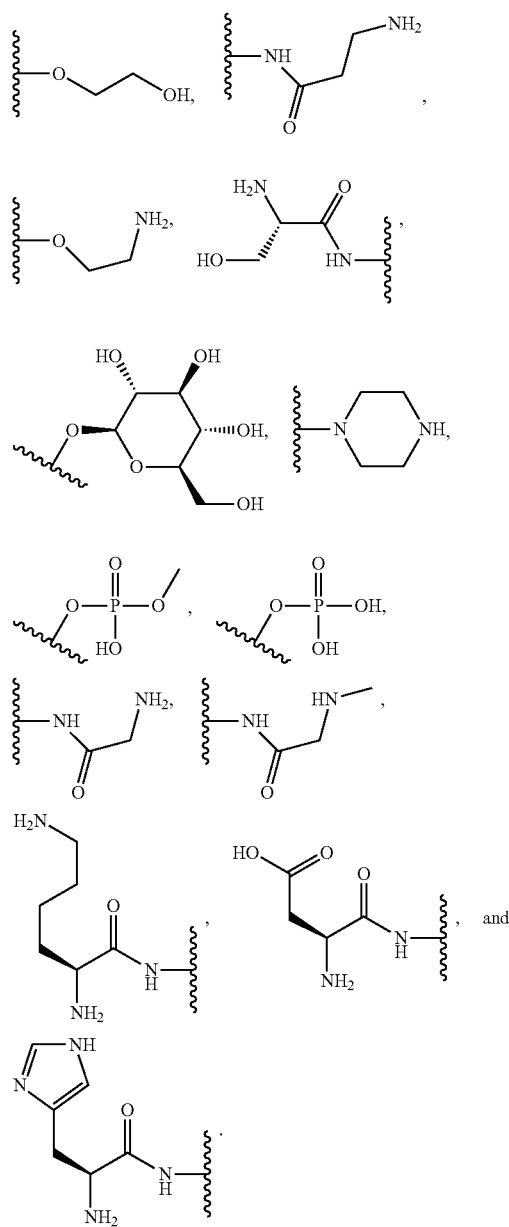
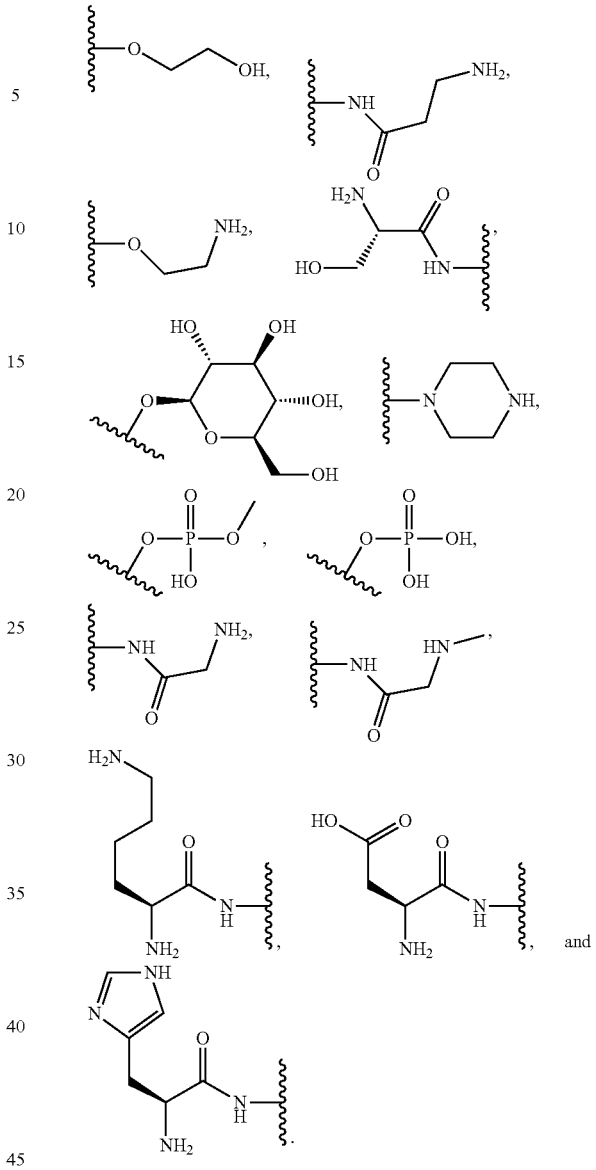

In another embodiment, $Q^1$ is —C(O)—, $Q^2$ is —CH$_2$—, W is —NH—, and $R^1$ is alkyl and $R^2$ is —OH, —CH$_2$NH$_2$, $R^3$, $R^4$, $R^5$, or —O—$R^5$. In another embodiment, $Q^1$ is —C(O)—, $Q^2$ is —CH$_2$—, W is —NH—, and $R^1$ is alkyl and $R^2$ is —OH. In another embodiment, $Q^1$ is —C(O)—, $Q^2$ is —CH$_2$—, W is —NH—, and $R^1$ is alkyl and $R^2$ is —CH$_2$NH$_2$. In another embodiment, $Q^1$ is —C(O)—, $Q^2$ is —CH$_2$—, W is —NH—, and $R^1$ is alkyl and $R^2$ is $R^3$. In another embodiment, $Q^1$ is —C(O)—, $Q^2$ is —CH$_2$—, W is —NH—, and $R^1$ is alkyl and $R^2$ is $R^4$. In another embodiment, $Q^1$ is —C(O)—, $Q^2$ is —CH$_2$—, W is —NH—, and $R^1$ is alkyl and $R^2$ is $R^5$. In another embodiment, $Q^1$ is —C(O)—, $Q^2$ is —CH$_2$—, W is —NH—, and $R^1$ is alkyl and $R^2$ is —O—$R^5$. In another embodiment, $Q^1$ is —C(O)—, $Q^2$ is —CH$_2$—, W is —NH— and $R^1$ is alkyl and $R^2$ is selected from the group consisting of amino, dimethylamino, hydroxyl, In another embodiment of Formula I or Ia, $Q^1$ is —C(O)—, $Q^2$ is —CH$_2$—, W is —NH—, and $R^1$ is —OH or —OP(O)(OR$^6$)(OH) and $R^2$ is —H. In another embodiment, $Q^1$ is —C(O)—, $Q^2$ is —CH$_2$—, W is —NH—, and $R^1$ is —OH and $R^2$ is —H. In another embodiment, $Q^1$ is —C(O)—, $Q^2$ is —CH$_2$—, W is —NH—, and $R^1$ is —OP(O)(OR$^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(O)—, $Q^2$ is —C(H)(OH)—, and W is —CH$_2$—. In another embodiment, $Q^1$ is —C(O)—, $Q^2$ is —C(H)(OH)—, W is —CH$_2$—, and $R^1$ is —H and $R^2$ is —OH, —CH$_2$NH$_2$, $R^3$, $R^4$, $R^5$, or —O—$R^5$. In another embodiment, $Q^1$ is —C(O)—, $Q^2$ is —C(H)(OH)—, W is —CH$_2$—, and $R^1$ is —H and $R^2$ is —OH. In another embodiment, $Q^1$ is —C(O)—, $Q^2$ is —C(H)(OH)—, W is —CH$_2$—, and $R^1$ is —H and $R^2$ is —CH$_2$NH$_2$. In another embodiment, $Q^1$ is —C(O)—, $Q^2$ is —C(H)(OH)—, W is —CH$_2$—, and $R^1$ is —H and $R^2$ is $R^3$. In another embodiment, $Q^1$ is —C(O)—, $Q^2$ is —C(H)(OH)—, W is —CH$_2$—, and R$^1$ is —H and R$^2$ is R$^4$. In another embodiment, Q$^1$ is —C(O)—, Q$^2$ is —C(H)(OH)—, W is —CH$_2$—, and R$^1$ is —H and R$^2$ is R$^5$. In another embodiment, Q$^1$ is —C(O)—, Q$^2$ is —C(H)(OH)—, W is —CH$_2$—, and R$^1$ is —H and R$^2$ is —O—R$^5$. In another embodiment, Q$^1$ is —C(O)—, Q$^2$ is —C(H)(OH)—, W is —CH$_2$—, and R$^1$ is —H and R$^2$ is selected from the group consisting of amino, dimethylamino, hydroxyl

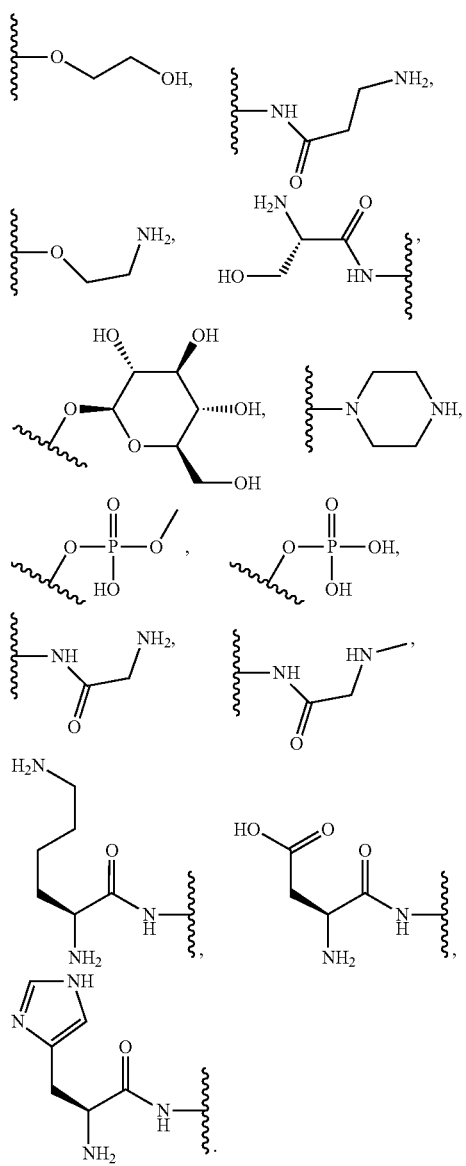

$Q^2$ is —C(H)(OH)—, W is —CH$_2$—, and R$^1$ is —OH and R$^2$ is R$^5$. In another embodiment, Q$^1$ is —C(O)—, Q$^2$ is —C(H)(OH)—, W is —CH$_2$—, and R$^1$ is —OH and R$^2$ is —O—R$^5$. In another embodiment, Q$^1$ is —C(O)—, Q$^2$ is —C(H)(OH)—, W is —CH$_2$—, and R$^1$ is —OH and R$^2$ is selected from the group consisting of amino, dimethylamino, hydroxyl,

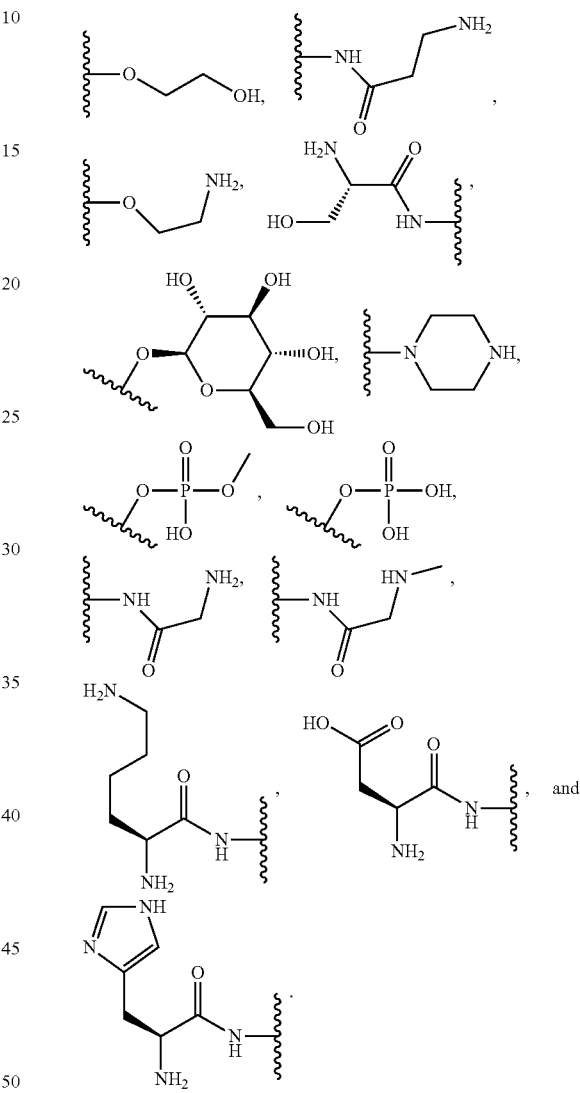

In another embodiment, Q$^1$ is —C(O)—, Q$^2$ is —C(H)(OH)—, W is —CH$_2$—, and R$^1$ is —OH and R$^2$ is —OH, —CH$_2$NH$_2$, R$^3$, R$^4$, R$^5$, or —O—R$^1$. In another embodiment, Q$^1$ is —C(O)—, Q$^2$ is —C(H)(OH)—, W is —CH$_2$—, and R$^1$ is —OH and R$^2$ is —OH. In another embodiment, Q$^1$ is —C(O)—, Q$^2$ is —C(H)(OH)—, W is —CH$_2$—, and R$^1$ is —OH and R$^2$ is —CH$_2$NH$_2$. In another embodiment, Q$^1$ is —C(O)—, Q$^2$ is —C(H)(OH)—, W is —CH$_2$—, and R$^1$ is —OH and R$^2$ is R$^3$. In another embodiment, Q$^1$ is —C(O)—, Q$^2$ is —C(H)(OH)—, W is —CH$_2$—, and R$^1$ is —OH and R$^2$ is R$^4$. In another embodiment, Q$^1$ is —C(O)—, In another embodiment, Q$^1$ is —C(O)—, Q$^2$ is —C(H)(OH)—, W is —CH$_2$—, and R$^1$ is —NH$_2$ and R$^2$ is —OH, —CH$_2$NH$_2$, R$^3$, R$^4$, R$^5$, or —O—R$^5$. In another embodiment, Q$^1$ is —C(O)—, Q$^2$ is —C(H)(OH)—, W is —CH$_2$—, and R$^1$ is —NH$_2$ and R$^2$ is —OH. In another embodiment, Q$^1$ is —C(O)—, Q$^2$ is —C(H)(OH)—, W is —CH$_2$—, and R$^1$ is —NH$_2$ and R$^2$ is —CH$_2$NH$_2$. In another embodiment, Q$^1$ is —C(O)—, Q$^2$ is —C(H)(OH)—, W is —CH$_2$—, and R$^1$ is —NH$_2$ and R$^2$ is R$^3$. In another embodiment, Q$^1$ is —C(O)—, Q$^2$ is —C(H)(OH)—, W is —CH$_2$—, and R$^1$ is —NH$_2$ and R$^2$ is R$^4$. In another embodiment, Q$^1$ is —C(O)—, Q$^2$ is —C(H)(OH)—, W is —CH$_2$—, and R$^1$ is —NH$_2$ and R$^2$ is R$^5$. In another embodiment, Q$^1$ is —C(O)—, Q$^2$ is —C(H)(OH)—, W is —CH$_2$—, and R$^1$ is —NH$_2$ and R$^2$ is —O—R$^5$. In another embodiment, Q$^1$ is —C(O)—, $Q^2$ is —C(H)(OH)—, W is —CH$_2$—, and $R^1$ is —NH$_2$ and $R^2$ is selected from the group consisting of amino, dimethylamino, hydroxyl,

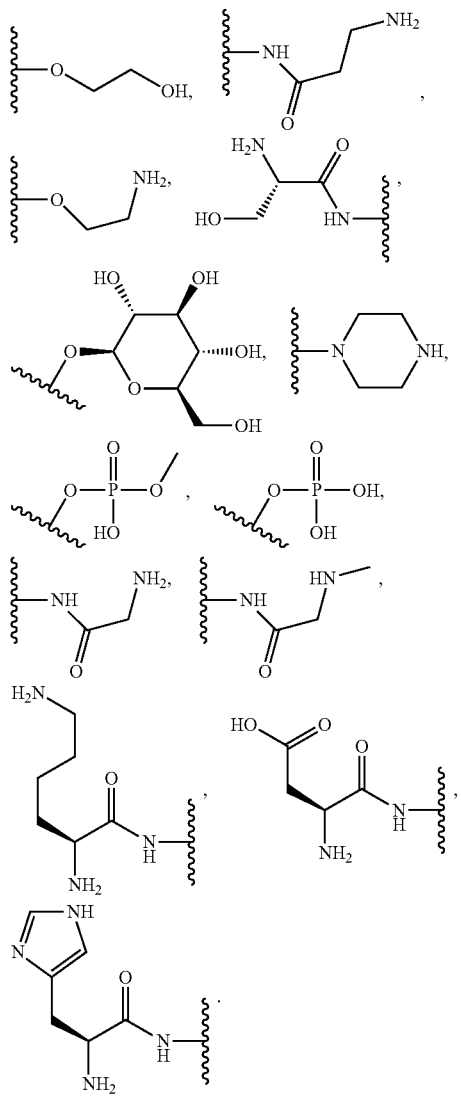

In another embodiment, $Q^1$ is —C(O)—, $Q^2$ is —C(H)(OH)—, W is —CH$_2$—, and $R^1$ is alkyl and $R^2$ is —OH, —CH$_2$NH$_2$, $R^3$, $R^4$, $R^5$, or —O—$R^5$. In another embodiment, $Q^1$ is —C(O)—, $Q^2$ is —C(H)(OH)—, W is —CH$_2$—, and $R^1$ is alkyl and $R^2$ is —OH. In another embodiment, $Q^1$ is —C(O)—, $Q^2$ is —C(H)(OH)—, W is —CH$_2$—, and $R^1$ is alkyl and $R^2$ is —CH$_2$NH$_2$. In another embodiment, $Q^1$ is —C(O)—, $Q^2$ is —C(H)(OH)—, W is —CH$_2$—, and $R^1$ is alkyl and $R^2$ is $R^3$. In another embodiment, $Q^1$ is —C(O)—, $Q^2$ is —C(H)(OH)— W is —CH$_2$—, and $R^1$ is alkyl and $R^2$ is $R^4$. In another embodiment, $Q^1$ is —C(O)—, $Q^2$ is —C(H)(OH)—, W is —CH$_2$—, and $R^1$ is alkyl and $R^2$ is $R^5$. In another embodiment, $Q^1$ is —C(O)—, $Q^2$ is —C(H)(OH)—, W is —CH$_2$—, and $R^1$ is alkyl and $R^2$ is —O—$R^5$. In another embodiment, $Q^1$ is —C(O)—, $Q^2$ is —C(H)(OH)—, W is —CH$_2$—, and $R^1$ is alkyl and $R^2$ is selected from the group consisting of amino, dimethylamino, hydroxyl,

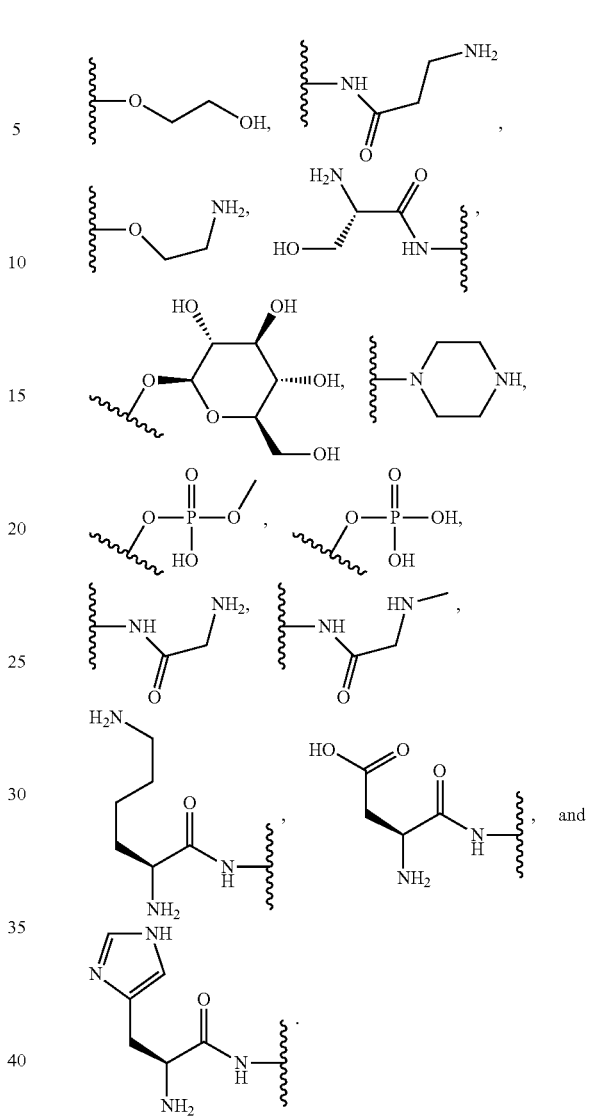

In another embodiment of Formula I or Ia, $Q^1$ is —C(O)—, $Q^2$ is —C(H)(OH)—, W is —CH$_2$—, and $R^1$ is —OH or —OP(O)(OR$^6$)(OH) and $R^2$ is —H. In another embodiment, $Q^1$ is —C(O)—, $Q^2$ is —C(H)(OH)—, W is —CH$_2$—, and $R^1$ is —OH and $R^2$ is —H. In another embodiment, $Q^1$ is —C(O)—, $Q^2$ is —C(H)(OH)—, W is —CH$_2$—, and $R^1$ is —OP(O)(OR$^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(O)—, $Q^2$ is —C(H)(OH)—, and W is —O—. In another embodiment, $Q^1$ is —C(O)—, $Q^2$ is —C(H)(OH)—, W is —O—, and $R^1$ is —H and $R^2$ is —OH, —CH$_2$NH$_2$, $R^3$, $R^4$, $R^5$, or —O—$R^5$. In another embodiment, $Q^1$ is —C(O)—, $Q^2$ is —C(H)(OH)—, W is —O—, and $R^1$ is —H and $R^2$ is —OH. In another embodiment, $Q^1$ is —C(O)—, $Q^2$ is —C(H)(OH)—, W is —O—, and $R^1$ is —H and $R^2$ is —CH$_2$NH$_2$. In another embodiment, $Q^1$ is —C(O)—, $Q^2$ is —C(H)(OH)—, W is —O—, and $R^1$ is —H and $R^2$ is $R^3$. In another embodiment, $Q^1$ is —C(O)—, $Q^2$ is —C(H)(OH)—, W is —O—, and $R^1$ is —H and $R^2$ is $R^4$. In another embodiment, $Q^1$ is —C(O)—, $Q^2$ is —C(H)(OH)—, W is —O—, and $R^1$ is —H and $R^2$ is $R^5$. In another embodiment, $Q^1$ is —C(O)—, $Q^2$ is —C(H)(OH)—, W is —O—, and $R^1$ is —H and $R^2$ is —O—$R^5$. In another embodiment, $Q^1$ is —C(O)—, $Q^2$ is —C(H)(OH)—, W is —O—, and $R^1$ is —H and $R^2$ is selected from the group consisting of amino, dimethylamino, hydroxyl,

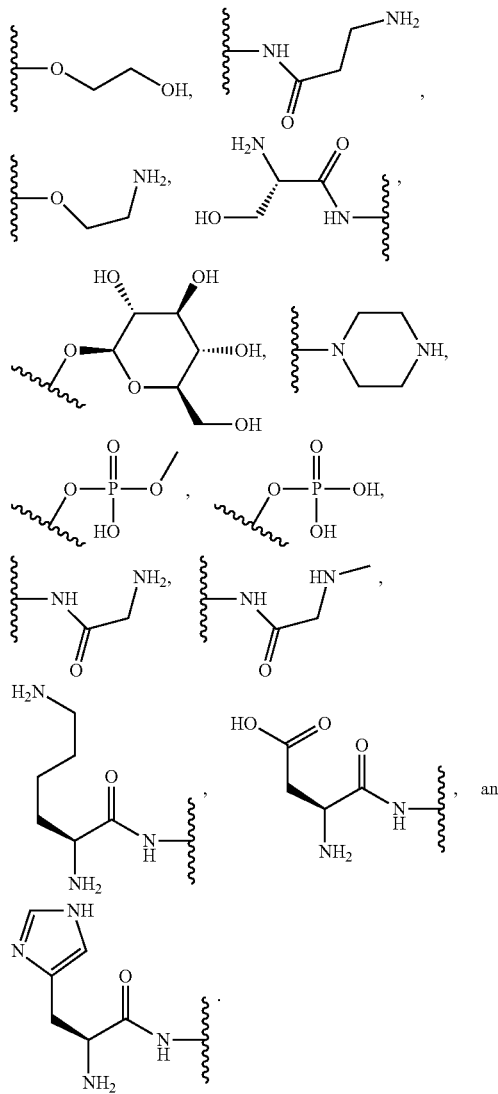

In another embodiment, $Q^1$ is —C(O)—, $Q^2$ is —C(H)(OH)—, W is —O—, and $R^1$ is —OH and $R^2$ is —OH, —$CH_2NH_2$, $R^3$, $R^4$, $R^5$, or —O—$R^5$. In another embodiment, $Q^1$ is —C(O)—, $Q^2$ is —C(H)(OH)—, W is —O—, and $R^1$ is —OH and $R^2$ is —OH. In another embodiment, $Q^1$ is —C(O)—, $Q^2$ is —C(H)(OH)—, W is —O—, and $R^1$ is —OH and $R^2$ is —$CH_2NH_2$. In another embodiment, $Q^1$ is —C(O)—, $Q^2$ is —C(H)(OH)—, W is —O—, and $R^1$ is —OH and $R^2$ is $R^3$. In another embodiment, $Q^1$ is —C(O)—, $Q^2$ is —C(H)(OH)—, W is —O—, and $R^1$ is —OH and $R^2$ is $R^4$. In another embodiment, $Q^1$ is —C(O)—, $Q^2$ is —C(H)(OH)—, W is —O—, and $R^1$ is —OH and $R^2$ is $R^5$. In another embodiment, $Q^1$ is —C(O)—, $Q^2$ is —C(H)(OH)—, W is —O—, and $R^1$ is —OH and $R^2$ is —O—$R^5$. In another embodiment, $Q^1$ is —C(O)—, $Q^2$ is —C(H)(OH)—, W is —O—, and $R^1$ is —OH and $R^2$ is selected from the group consisting of amino, dimethylamino, hydroxyl,

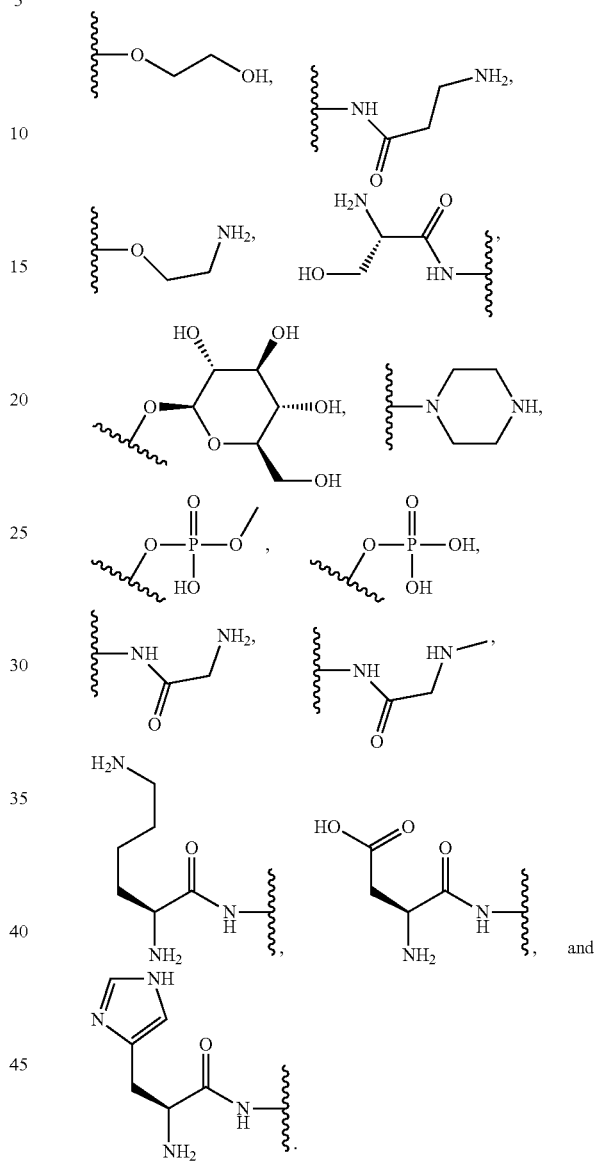

In another embodiment, $Q^1$ is —C(O)—, $Q^2$ is —C(H)(OH)—, W is —O—, and $R^1$ is —$NH_2$ and $R^2$ is —OH, —$CH_2NH_2$, $R^3$, $R^4$, $R^5$, or —O—$R^5$. In another embodiment, $Q^1$ is —C(O)—, $Q^2$ is —C(H)(OH)—, W is —O—, and $R^1$ is —$NH_2$ and $R^2$ is —OH. In another embodiment, $Q^1$ is —C(O)—, $Q^2$ is —C(H)(OH)—, W is —O—, and $R^1$ is —$NH_2$ and $R^2$ is —$CH_2NH_2$. In another embodiment, $Q^1$ is —C(O)—, $Q^2$ is —C(H)(OH)—, W is —O—, and $R^1$ is —$NH_2$ and $R^2$ is $R^3$. In another embodiment, $Q^1$ is —C(O)—, $Q^2$ is —C(H)(OH)—, W is —O—, and $R^1$ is —$NH_2$ and $R^2$ is $R^4$. In another embodiment, $Q^1$ is —C(O)—, $Q^2$ is —C(H)(OH)—, W is —O—, and $R^1$ is —$NH_2$ and $R^2$ is $R^5$. In another embodiment, $Q^1$ is —C(O)—, $Q^2$ is —C(H)(OH)—, W is —O—, and $R^1$ is —$NH_2$ and $R^2$ is —O—$R^5$. In another embodiment, $Q^1$ is —C(O)—, $Q^2$ is —C(H)(OH)—, W is —O—, and $R^1$ is —$NH_2$ and $R^2$ is selected from the group consisting of amino, dimethylamino, hydroxyl,

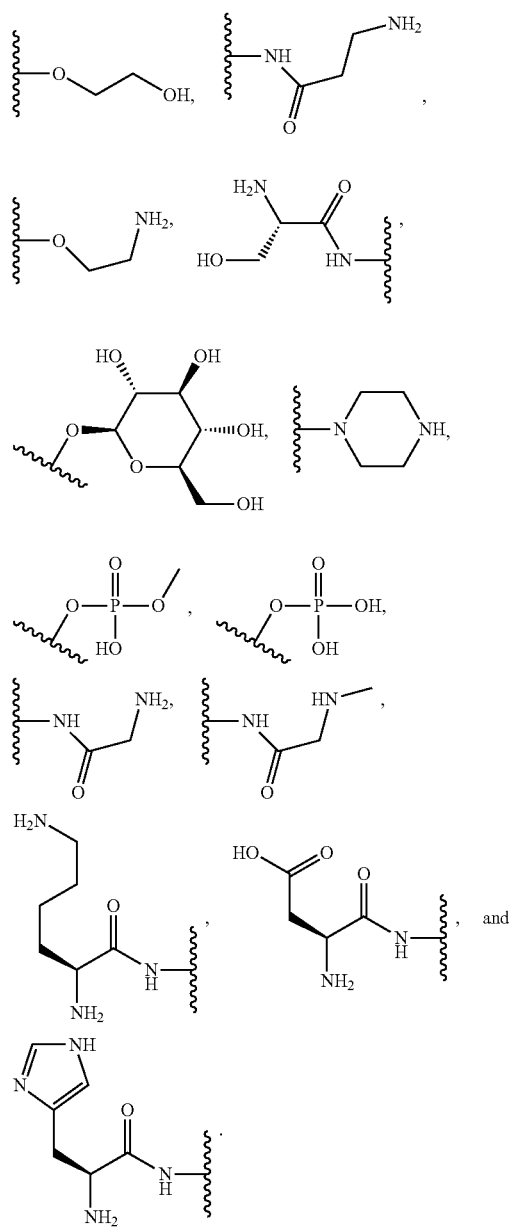

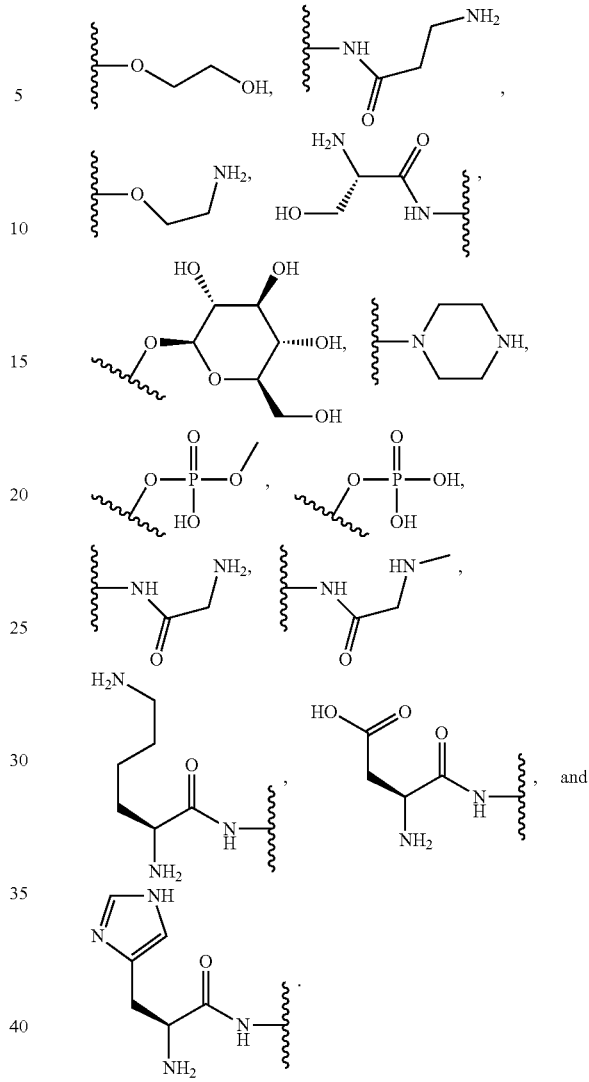

In another embodiment, $Q^1$ is —C(O)—, $Q^2$ is —C(H)(OH)—, W is —O—, and $R^1$ is alkyl and $R^2$ is —OH, —CH$_2$NH$_2$, $R^3$, $R^4$, $R^5$, or —O—$R^5$. In another embodiment, $Q^1$ is —C(O)—, $Q^2$ is —C(H)(OH)—, W is —O—, and $R^1$ is alkyl and $R^2$ is —OH. In another embodiment, $Q^1$ is —C(O)—, $Q^2$ is —C(H)(OH)—, W is —O—, and $R^1$ is alkyl and $R^2$ is —CH$_2$NH$_2$. In another embodiment, $Q^1$ is —C(O)—, $Q^2$ is —C(H)(OH)—, W is —O—, and $R^1$ is alkyl and $R^2$ is $R^3$. In another embodiment, $Q^1$ is —C(O)—, $Q^2$ is —C(H)(OH)—, W is —O—, and $R^1$ is alkyl and $R^2$ is $R^4$. In another embodiment, $Q^1$ is —C(O)—, $Q^2$ is —C(H)(OH)—, W is —O—, and $R^1$ is alkyl and $R^2$ is $R^5$. In another embodiment, $Q^1$ is —C(O)—, $Q^2$ is —C(H)(OH)—, W is —O—, and $R^1$ is alkyl and $R^2$ is —O—$R^5$. In another embodiment, $Q^1$ is —C(O)—, $Q^2$ is —C(H)(OH)—, W is —O—, and $R^1$ is alkyl and $R^2$ is selected from the group consisting of amino, dimethylamino, hydroxyl, In another embodiment of Formula I or Ia, $Q^1$ is —C(O)—, $Q^2$ is —C(H)(OH)—, W is —O—, and $R^1$ is —OH or —OP(O)(OR$^6$)(OH) and $R^2$ is —H. In another embodiment, $Q^1$ is —C(O)—, $Q^2$ is —C(H)(OH)—, W is —O—, and $R^1$ is —OH and $R^2$ is —H. In another embodiment, $Q^1$ is —C(O)—, $Q^2$ is —C(H)(OH)—, W is —O—, and $R^1$ is —OP(O)(OR$^6$)(OH) and $R^2$ is —H. In any one of the foregoing embodiments in this paragraph, $R^6$ may be selected from the group consisting of hydroxyl and methyl.

In one embodiment of Formula I or Ia, $Q^1$ is —C(O)—, $Q^2$ is —C(H)(OH)—, and W is —NH—. In another embodiment, $Q^1$ is —C(O)—, $Q^2$ is —C(H)(OH)—, W is —NH—, and $R^1$ is —H and $R^2$ is —OH, —CH$_2$NH$_2$, $R^3$, $R^4$, $R^5$, or —O—$R^5$. In another embodiment, $Q^1$ is —C(O)—, $Q^2$ is —C(H)(OH)—, W is —NH—, and $R^1$ is —H and $R^2$ is —OH. In another embodiment, $Q^1$ is —C(O)—, $Q^2$ is —C(H)(OH)—, W is —NH—, and $R^1$ is —H and $R^2$ is —CH$_2$NH$_2$. In another embodiment, $Q^1$ is —C(O)—, $Q^2$ is —C(H)(OH)—, W is —NH—, and $R^1$ is —H and $R^2$ is $R^3$. In another embodiment, $Q^1$ is —C(O)—, $Q^2$ is —C(H)(OH)—, W is —NH—, and $R^1$ is —H and $R^2$ is $R^4$. In another embodiment, $Q^1$ is —C(O)—, $Q^2$ is —C(H)(OH)—, W is —NH—, and $R^1$ is —H and $R^2$ is $R^5$. In another embodiment, Q¹ is —C(O)—, Q² is —C(H)(OH)—, W is —NH—, and R¹ is —H and R² is —O—R⁵. In another embodiment, Q¹ is —C(O)—, Q² is —C(H)(OH)—, W is —NH—, and R¹ is —H and R² is selected from the group consisting of amino, dimethylamino, hydroxyl,

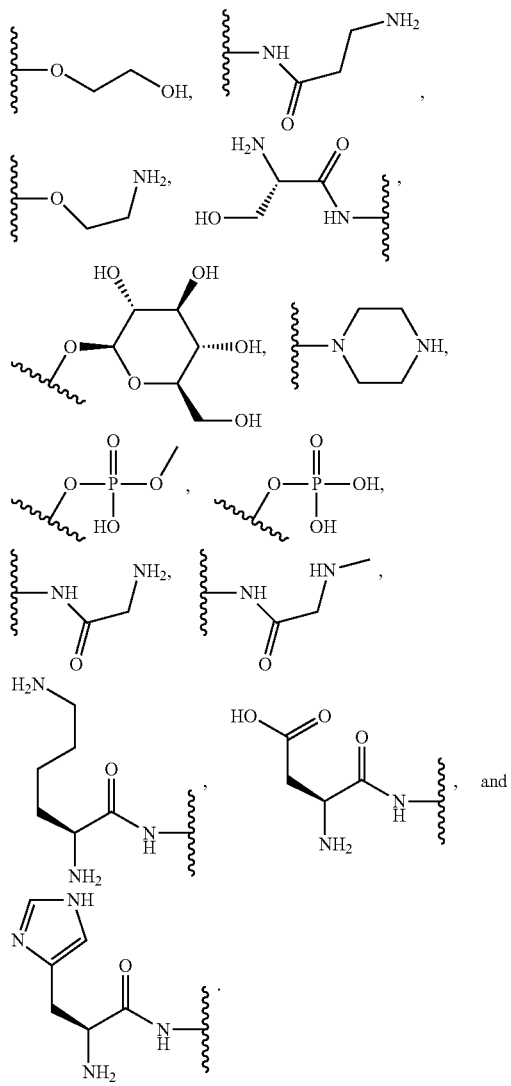

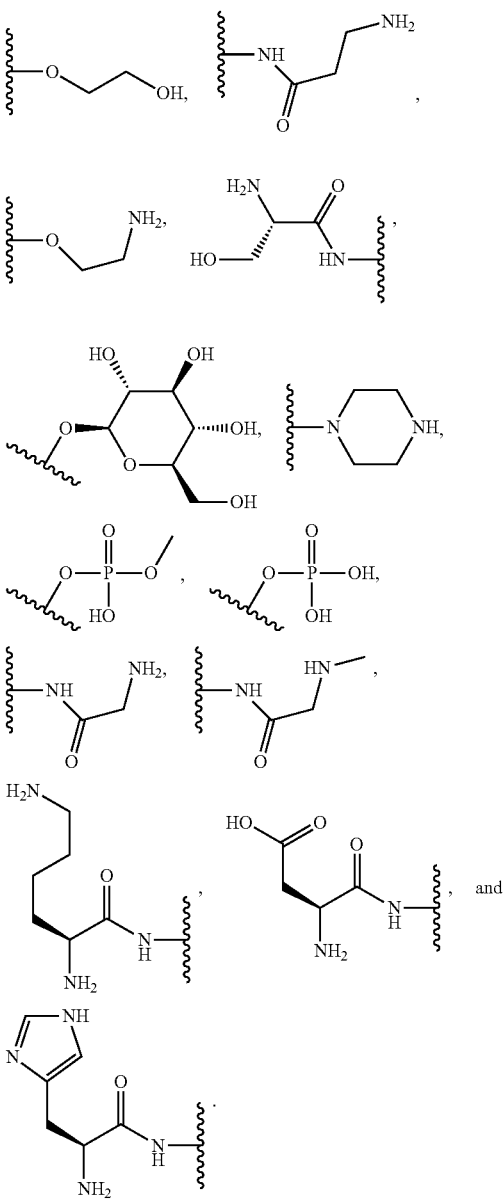

In another embodiment, Q¹ is —C(O)—, Q² is —C(H)(OH)—, W is —NH—, and R¹ is —OH and R² is —OH, —CH₂NH₂, R³, R⁴, R⁵, or —O—R⁵. In another embodiment, Q¹ is —C(O)—, Q² is —C(H)(OH)—, W is —NH—, and R¹ is —OH and R² is —OH. In another embodiment, Q¹ is —C(O)—, Q² is —C(H)(OH)—, W is —NH—, and R¹ is —OH and R² is —CH₂NH₂. In another embodiment, Q¹ is —C(O)—, Q² is —C(H)(OH)—, W is —NH—, and R¹ is —OH and R² is R³. In another embodiment, Q¹ is —C(O)—, Q² is —C(H)(OH)—, W is —NH—, and R¹ is —OH and R² is R⁴. In another embodiment, Q¹ is —C(O)—, Q² is —C(H)(OH)—, W is —NH—, and R¹ is —OH and R² is R⁵. In another embodiment, Q¹ is —C(O)—, Q² is —C(H)(OH)—, W is —NH—, and R¹ is —OH and R² is —O—R⁵. In another embodiment, Q¹ is —C(O)—, Q² is —C(H)(OH)—, W is —NH—, and R¹ is —OH and R² is selected from the group consisting of amino, dimethylamino, hydroxyl, In another embodiment, Q¹ is —C(O)—, Q² is —C(H)(OH)—, W is —NH—, and R¹ is —NH₂ and R² is —OH, —CH₂NH₂, R³, R⁴, R⁵, or —O—R⁵. In another embodiment, Q¹ is —C(O)—, Q² is —C(H)(OH)—, W is —NH—, and R¹ is —NH₂ and R² is —OH. In another embodiment, Q¹ is —C(O)—, Q² is —C(H)(OH)—, W is —NH—, and R¹ is —NH₂ and R² is —CH₂NH₂. In another embodiment, Q¹ is —C(O)—, Q² is —C(H)(OH)—, W is —NH—, and R¹ is —NH₂ and R² is R³. In another embodiment, Q¹ is —C(O)—, Q² is —C(H)(OH)—, W is —NH—, and R¹ is —NH₂ and R² is R⁴. In another embodiment, Q¹ is —C(O)—, Q² is —C(H)(OH)—, W is —NH—, and R¹ is —NH₂ and R² is R⁵. In another embodiment, Q¹ is —C(O)—, Q² is —C(H)(OH)—, W is —NH—, and R¹ is —NH₂ and R² is —O—R⁵. In another embodiment, Q¹ is —C(O)—, Q² is —C(H)(OH)—, W is —NH—, and R¹ is —NH₂ and R² is selected from the group consisting of amino, dimethylamino, hydroxyl,

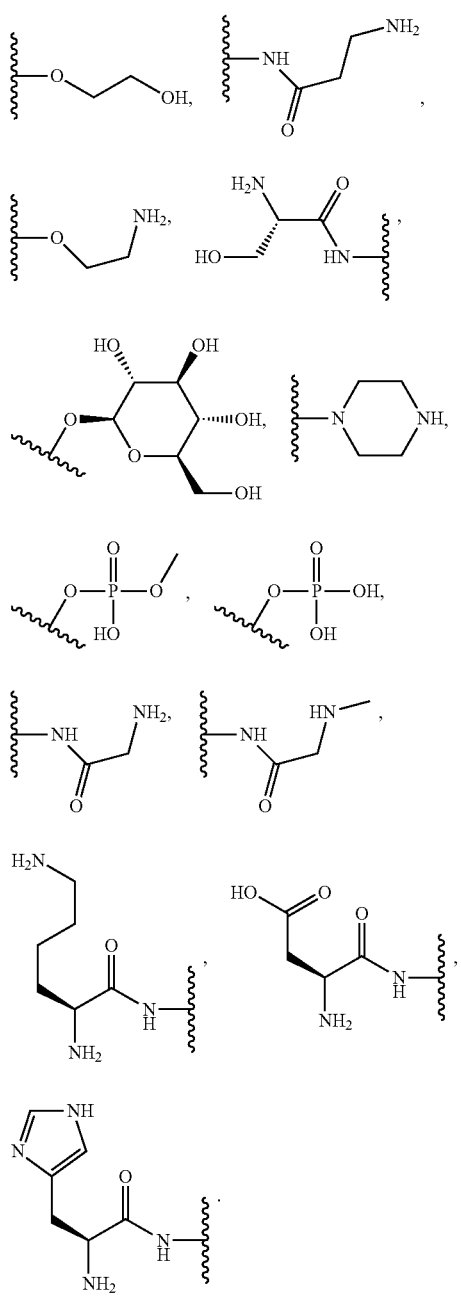

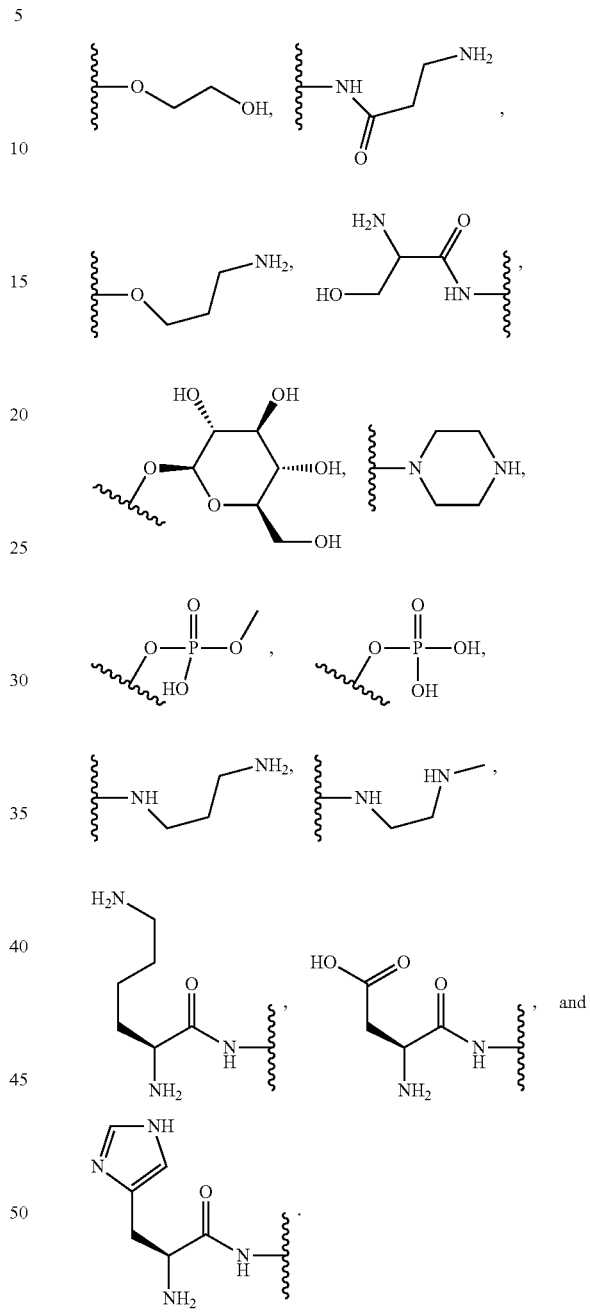

In another embodiment, $Q^1$ is —C(O)—, $Q^2$ is —C(H)(OH)—, W is —NH—, and $R^1$ is alkyl and $R^2$ is —OH, —CH$_2$NH$_2$, $R^3$, $R^4$, $R^5$, or —O—$R^5$. In another embodiment, $Q^1$ is —C(O)—, $Q^2$ is —C(H)(OH)—, W is —NH—, and $R^1$ is alkyl and $R^2$ is —OH. In another embodiment, $Q^1$ is —C(O)—, $Q^2$ is —C(H)(OH)—, W is —NH—, and $R^1$ is alkyl and $R^2$ is —CH$_2$NH$_2$. In another embodiment, $Q^1$ is —C(O)—, $Q^2$ is —C(H)(OH)—, W is —NH—, and $R^1$ is alkyl and $R^2$ is $R^3$. In another embodiment, $Q^1$ is —C(O)—, $Q^2$ is —C(H)(OH)—, W is —NH—, and $R^1$ is alkyl and $R^2$ is $R^4$. In another embodiment, $Q^1$ is —C(O)—, $Q^2$ is —C(H)(OH)—, W is —NH—, and $R^1$ is alkyl and $R^2$ is $R^5$. In another embodiment, $Q^1$ is —C(O)—, $Q^2$ is —C(H)(OH)—, W is —NH—, and $R^1$ is alkyl and $R^2$ is —O—$R^5$. In another embodiment, $Q^1$ is —C(O)—, $Q^2$ is —C(H)(OH)—, W is —NH—, and $R^1$ is alkyl and $R^2$ is selected from the group consisting of amino, dimethylamino, hydroxyl, In another embodiment of Formula I or Ia, $Q^1$ is —C(O)—, $Q^2$ is —C(H)(OH)—, W is —NH—, and $R^1$ is —OH or —OP(O)(OR$^6$)(OH) and $R^2$ is —H. In another embodiment, $Q^1$ is —C(O)—, $Q^2$ is —C(H)(OH)—, W is —NH—, and $R^1$ is —OH and $R^2$ is —H. In another embodiment, $Q^1$ is —C(O)—, $Q^2$ is —C(H)(OH)—, W is —NH—, and $R^1$ is —OP(O)(OR$^6$)(OH) and $R^2$ is —H. In any one of the foregoing embodiments in this paragraph, $R^6$ may be selected from the group consisting of hydroxyl and methyl.

In some examples, set forth herein is a compound having the structure of Formula (Ib):

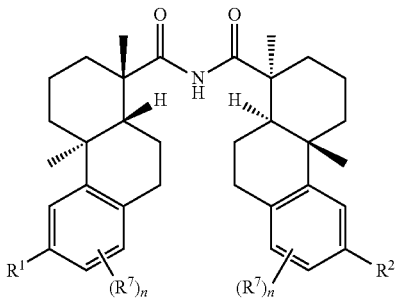

(Ib)

or a pharmaceutically acceptable salt, solvate, or stereoisomeric form, wherein

W is —CH$_2$—, —N(H)—, or —O—;

$R^1$ is —H, —OH, —NH$_2$, alkyl, or —OP(O)(OR$^6$)$_2$;

$R^2$ is —H, —OH, —CH$_2$NH$_2$, $R^3$, $R^4$, $R^1$, or —O—$R^1$, wherein $R^1$ and $R^2$ are not simultaneously —H;

$R^3$ is —N(R$^6$)$_2$;

$R^4$ is —X—Y—Z;

X is selected from the group consisting of —O— and —N(H)—;

Y is selected from the group consisting of alkylene, substituted alkylene (including, without limitation, oxo substitution, (i.e., =O)), heteroalkylene, and substituted heteroalkylene (including, without limitation, oxo substitution (i.e., =O));

Z is selected from the group consisting of —OH and —NH$_2$;

$R^5$ is alkyl, heterocycloalkyl, or substituted heterocycloalkyl, wherein each heterocycloalkyl or substituted heterocycloalkyl includes one, two, or three heteroatoms selected from nitrogen and oxygen, and includes at least one —OH and —CH$_2$OH substituent, or at least one primary or secondary nitrogen, for instance, O-glucose;

each $R^6$ is in each instance, —H, an amino acid residue, an N-alkyl amino acid residue, a peptide, or alkyl; and each $R^7$ is, independently, halo, C$_{1-6}$ alkyl, C$_{1-6}$ alkoxy, —CN, O-glucose, O-amino acid residue, and O-PEG$_n$, wherein each n is an integer from 0-3.

In Formula Ib, in certain embodiments, $R^5$ is heterocycloalkyl or substituted heterocycloalkyl. Useful heterocycloalkyl groups include tetrahydropyranyl, glycosidyl, and piperazinyl. These groups can be substituted or unsubstituted. In certain embodiments, they are unsubstituted. In certain embodiments, they are substituted. Exemplary substituents include at least one hydroxyl, at least one primary nitrogen, or at least one secondary nitrogen.

In certain embodiments of Formula Ib, $R^6$ is independently in each instance an amino acid residue, N-alkyl amino acid residue, or a peptide. Those of skill in the art will recognize that the amino acid residue may be achiral or chiral, for example, L-amino acid or D-amino acid. The amino acids generally include an amino acid side chain. The side chain can be the side chain of any amino acids known to those of skill. In certain embodiments, the side chain is the side chain of histidine, alanine, isoleucine, arginine, leucine, asparagine, lysine, aspartic acid, methionine, cysteine, phenylalanine, glutamic acid, threonine, glutamine, tryptophan, valine, ornithine, selenocysteine, serine, glycine, homoglycine (e.g., β-homoglycine), or tyrosine. Those of skill in the art will recognize that the peptide may be achiral or chiral, for example, including racemic DL-amino acids or non-racemic D- or L-amino acids and diastereomeric mixtures thereof. The side chains of the peptides are as described in the context of amino acids, above. Those of skill in the art will recognize that the N-alkyl amino acid residue includes an alkyl substituent, as defined herein, at the terminal amino group of the amino acid or the terminal amino group of the peptide.

In Formula Ib, in certain embodiments, $R^7$ is halo, C$_{1-6}$ alkyl, C$_{1-6}$ alkoxy, —CN, O-glucose, O-amino acid residue, or O-PEG$_n$, wherein each n is an integer from 0-3. In certain embodiments, O-amino acid residue includes HO-amino acid residue as defined above. In one embodiment, O-PEG$_n$ is where n=0. In another embodiment, O-PEG$_n$ is where n=1. In another embodiment, O-PEG$_n$ is where n=2. In yet another embodiment, O-PEG$_n$ is where n=3.

In one embodiment of Formula Ib, $R^1$ is —OH. In another embodiment, $R^1$ is —OH and $R^2$ is —O—(CH$_2$)$_n$—Z, where n is an integer from one to four. In certain embodiments, $R^1$ is —OH, $R^2$ is —O—(CH$_2$)$_n$—Z, and n is one. In certain embodiments, $R^1$ is —OH, $R^2$ is —O—(CH$_2$)$_n$—Z, and n is two. In certain embodiments, $R^1$ is —OH, $R^2$ is —O—(CH$_2$)$_n$—Z, and n is three. In certain embodiments, $R^1$ is —OH, $R^2$ is —O—(CH$_2$)$_n$—Z, and n is four.

In one embodiment of Formula Ib, $R^1$ is —OH and $R^2$ is —N(H)C(O)—(CH$_2$)$_n$—NH$_2$, where n is an integer from one to four. In certain embodiments, $R^1$ is —OH, $R^2$ is —N(H)C(O)—(CH$_2$)$_n$—NH$_2$, and n is one. In certain embodiments, $R^1$ is —OH, $R^2$ is —N(H)C(O)—(CH$_2$)$_n$—NH$_2$, and n is two. In certain embodiments, $R^1$ is —OH, $R^2$ is —N(H)C(O)—(CH$_2$)$_n$—NH$_2$, and n is three. In certain embodiments, $R^1$ is —OH, $R^2$ is —N(H)C(O)—(CH$_2$)$_n$—NH$_2$, and n is four.

In one embodiment of Formula Ib, $R^1$ is —OH and $R^2$ is —N(H)C(O)—(CRR)$_n$—NH$_2$, where each R is —H, —OH, or —CH$_2$OH, and where n is an integer from one to four. In certain embodiments, $R^1$ is —OH, $R^2$ is —N(H)C(O)—(CRR)$_n$—NH$_2$, each R is —H, and n is an integer from one to four. In certain embodiments, $R^1$ is —OH, $R^2$ is —N(H)C(O)—(CRR)$_n$—NH$_2$, each R is —OH, and n is an integer from one to four. In certain embodiments, $R^1$ is —OH, $R^2$ is —N(H)C(O)—(CRR)$_n$—NH$_2$, each R is —CH$_2$OH, and n is an integer from one to four. In any one of the foregoing embodiments in this paragraph, n is one. In any one of the foregoing embodiments in this paragraph, n is two. In any one of the foregoing embodiments in this paragraph, n is three. In any one of the foregoing embodiments in this paragraph, n is four.

In one embodiment of Formula Ib, $R^1$ is —OH and $R^2$ is N-piperazinyl. In another embodiment, $R^1$ is —OH and $R^2$ is —N(R$^6$)$_2$. In another embodiment, $R^1$ is —OH and $R^2$ is N-serinyl. In yet another embodiment, $R^1$ is —OH and $R^2$ is O-glycosyl.

In one embodiment of Formula Ib, $R^1$ is —OP(O)(OR$^6$)(OH) and $R^2$ is —NH$_2$.

In certain embodiments, provided herein are compounds according to any of Formulae I, Ia, and Ib may be selected from the group consisting of:

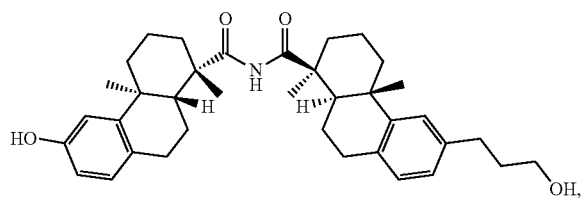

87
-continued
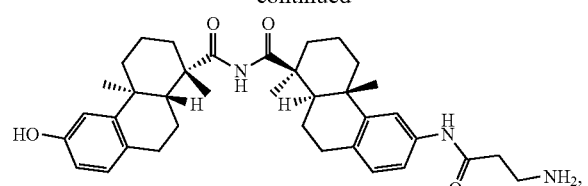
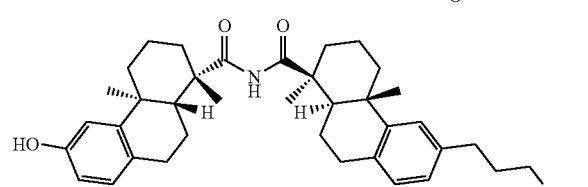
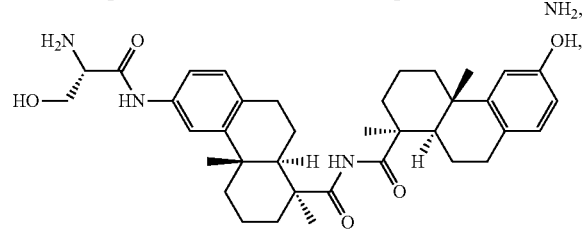
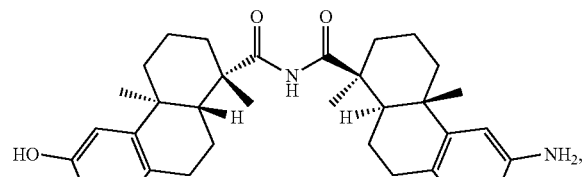
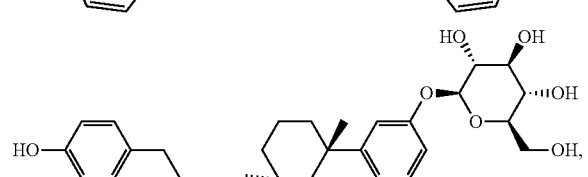
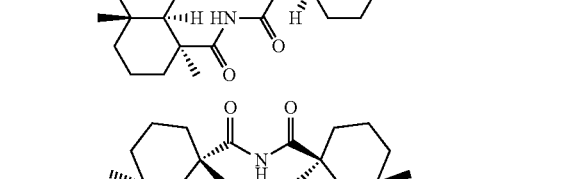
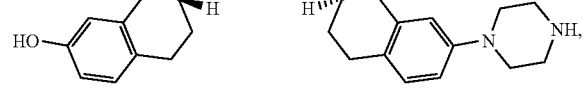
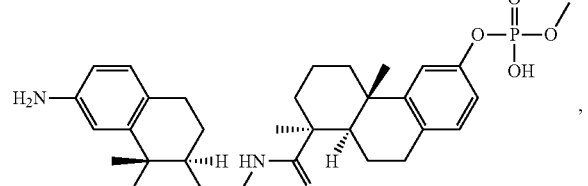
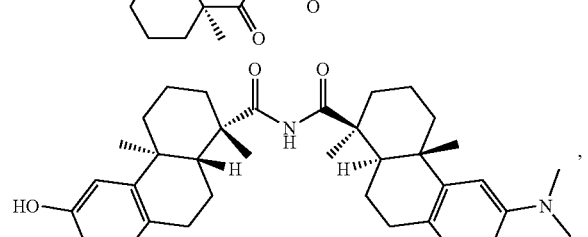
88
-continued
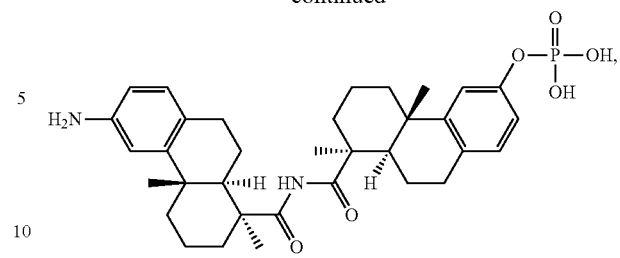
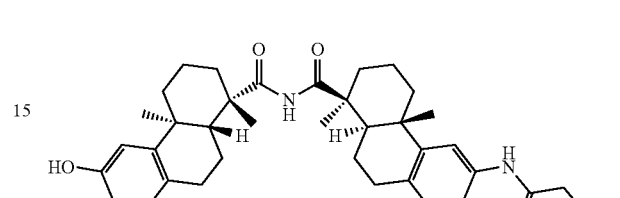
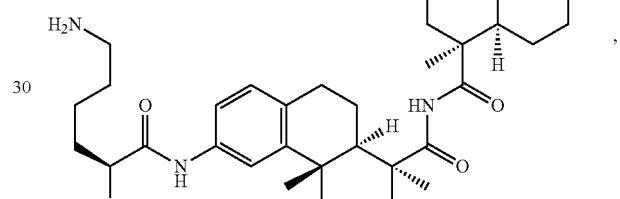
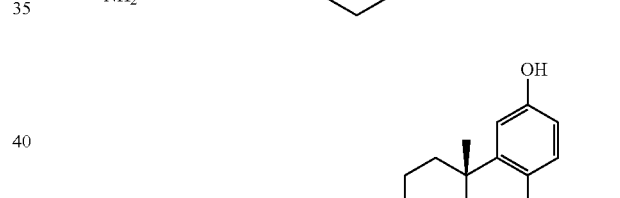
, and
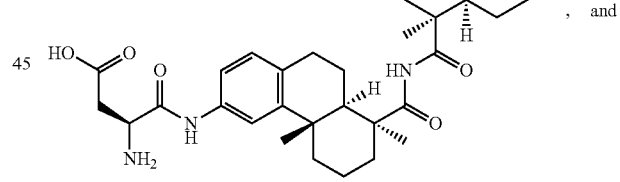
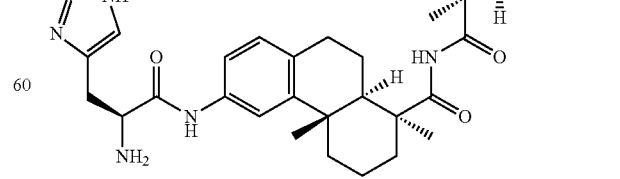
,
or a pharmaceutically acceptable salt, solvate, or stereoisomeric form thereof.

Conjugates Antibody Drug Conjugates (ADCs)
Provided herein are conjugates of Formula A:

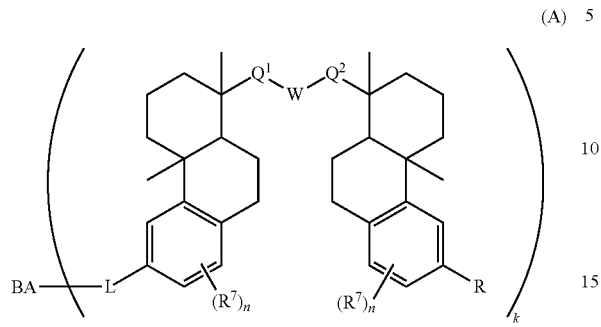

(A)

or a pharmaceutically acceptable salt, solvate, or stereoisomeric form thereof, wherein
L is a linker or X—Y—Z, wherein X is —NH— or —O—; Y is an enzymatically cleavable moiety, a self-immolative group, an acid-labile moiety, $PEG_n$, a sugar moiety, or an enhancement group; and Z is a binding agent linker (BL) wherein Z is covalently bound to BA;
BA is a binding agent;
k is an integer from 1 to 30;
each of $Q^1$ and $Q^2$ is independently —$CH_2$—, —C(O)—, —C(H)(OH)—, or —$C(OH)_2$—;
W is —$CH_2$—, —N(H)—, or —O—; R is —H, —$OR^6$, —OH, —$NH_2$, alkyl, or —$OP(O)(OR^6)_2$;
each $R^6$ is, independently in each instance, —H, an amino acid residue, a peptide, or alkyl; and
wherein $R^1$, $R^2$, $R^3$, $R^4$, and $R^5$ are as described in the context of Formula I.

Exemplary enzymatically cleavable moieties include, but are not limited to, any di- or tri-peptides (e.g., VC-PAB and VA, as described elsewhere herein). Exemplary self-immolative groups are described elsewhere herein. Exemplary acid-labile moieties include, but are not limited to, alkoxamines, ketoxamines, carbonates, or phosphonates. Exemplary enhancement groups are described elsewhere herein. Exemplary reactive moieties are described elsewhere herein. In certain embodiments, Y does not include PEG. In certain embodiments, an amino acid may be used to connect the payload, enhancement group, and antibody (each as described elsewhere herein) to one another, as described and apparent elsewhere herein. Connection of the payload, enhancement group, and antibody via the amino acid may be carried out by amide coupling reactions, thio-Michael additions, or phenol-O-alkylations as would be appreciated by those of skill in the art. For example, the amino acid that connects the payload, enhancement group, and antibody is lysine. By way of further example, in one embodiment, the amino acid that connects the payload, enhancement group, and antibody is D-lysine. By way of further example, in one embodiment, the amino acid that connects the payload, enhancement group, and antibody is aspartic acid. By way of further example, in one embodiment, the amino acid that connects the payload, enhancement group, and antibody is glutamic acid. By way of further example, in one embodiment, the amino acid that connects the payload, enhancement group, and antibody is serine. By way of further example, in one embodiment, the amino acid that connects the payload, enhancement group, and antibody is cysteine. By way of further example, in one embodiment, the amino acid that connects the payload, enhancement group, and antibody is tyrosine.

Provided herein are conjugates of Formula (A):

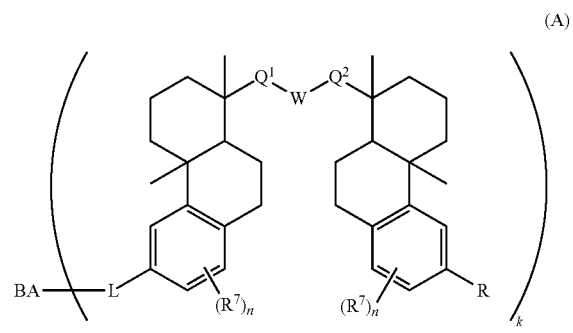

(A)

or a pharmaceutically acceptable salt, solvate, or stereoisomeric form thereof,
wherein
L is a linker;
BA is a binding agent;
k is an integer from 1 to 30;
R is —H, $R^1$ or $R^2$; and
$Q^1$, $Q^2$, W, $R^1$, $R^2$, $R^3$, $R^4$, $R^5$, $R^6$, $R^7$, X, Y, and Z are as described in the context of Formula I. In certain embodiments, R is $R^1$.

Provided herein are compounds of Formula (Aa):

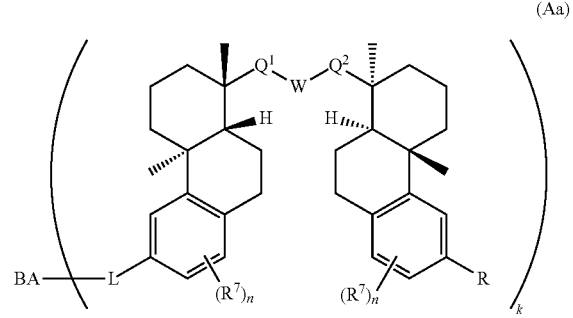

(Aa)

or a pharmaceutically acceptable salt thereof,
wherein
L is a linker;
BA is a binding agent;
k is an integer from 1 to 30;
R is —H, $R^1$ or $R^2$; and
$Q^1$, $Q^2$, W, $R^1$, $R^2$, $R^3$, $R^4$, $R^5$, $R^6$, $R^7$, X, Y, and Z are as described in the context of Formula Ia. In certain embodiments, R is $R^1$.

Provided herein are compounds of Formula (Ab):

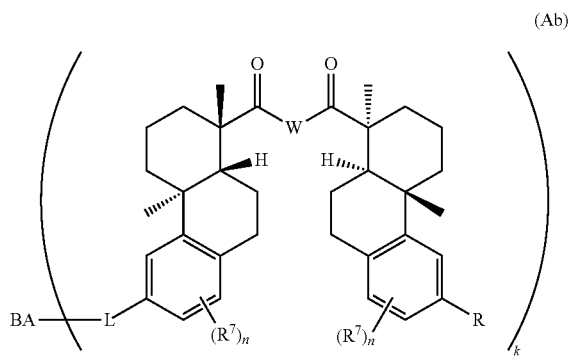

or a pharmaceutically acceptable salt thereof,
wherein
L is a linker;
BA is a binding agent;
k is an integer from 1 to 30;
R is —H, $R^1$ or $R^2$; and
$R^1$, $R^2$, $R^3$, $R^4$, $R^5$, $R^6$, $R^7$, X, Y, and Z are as described in the context of Formula Ib. In certain embodiments, R is $R^1$.

Binding Agents

Suitable binding agents for any of the conjugates provided in the instant disclosure include, but are not limited to, antibodies, lymphokines, hormones, growth factors, viral receptors, interleukins, or any other cell binding or peptide binding molecules or substances.

In some embodiments, the binding agent is an antibody or an antigen-binding fragment thereof. The antibody can be in any form known to those of skill in the art. The term "antibody", as used herein, refers to any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies (or antigen-binding portion thereof) suitable for the compounds herein may be identical to the human germline sequences, or may be naturally or artificially modified. An amino acid consensus sequence may be defined based on a side-by-side analysis of two or more CDRs. The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable, standard technique(s) such as proteolytic digestion or recombinant genetic engineering technique(s) involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add, or delete amino acids, etc. Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated CDR such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$ or $V_L$-$V_L$ dimers. Alternatively, the antigen-binding fragment of an antibody may contain a monomeric $V_H$ or $V_L$ domain. In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$CH_3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60, or more) amino acids which result in a flexible or semi-flexible linkage between adjacent variable and/or constant domains in a single polypeptide molecule. As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art. In certain embodiments described herein, antibodies described herein are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example, in the CDRs and in particular CDR3. However, the term "human antibody", as used herein, is not intended to include antibodies in which CDR sequences derived from the germline of another mammalian species, such as a mouse, have been grafted onto human framework sequences. The term "human antibody" does not include naturally occurring molecules that normally exist without modification or human intervention/manipulation, in a naturally occurring, unmodified living organism. The antibodies of the invention may, in some embodiments, be recombinant human antibodies. The term "recombinant human antibody", as used herein, is intended to include all human antibodies that are prepared, expressed, created, or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created, or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant disclosure encompasses antibodies having one or more mutations in the hinge, $C_H2$ or $C_H3$ region which may be desirable, for example, in production, to improve the yield of the desired antibody form. The antibodies described herein may be isolated antibodies. An "isolated antibody," as used herein, refers to an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the instant disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals. The antibodies used herein can comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure. Antibodies useful for the compounds herein also include antibodies comprising variants of any of the HCVR, LCVR, and/or CDR amino acid sequences disclosed herein having one or more conservative substitutions. The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

In certain embodiments, the antibody comprises a light chain. In certain embodiments, the light chain is a kappa light chain. In certain embodiments, the light chain is a lambda light chain. In certain embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

The antibody can have binding specificity for any antigen deemed suitable to those of skill in the art. In certain embodiments, the antigen is a transmembrane molecule (e.g., receptor) or a growth factor. Exemplary antigens include, but are not limited to, molecules such as class A scavenger receptors including scavenger receptor A (SR-A, or MSR1), macrophage receptor with collagenous structure (MARCO), scavenger receptor with C-type lectin (SRCL), and scavenger receptor A-5 (SCARA5), COLEC12, class B macrophage scavenger receptors including CD36, LIMPII, SRBI, SRBII, class D scavenger receptor CD68, and lysosomal membrane glycoprotein (LAMP), class E scavenger receptor including lectin-like oxidized low density lipoprotein receptor 1 LOX-1 and Dectin-1, class F scavenger receptors including scavenger receptor expressed by endothelial cells-I (SREC-I) and SREC-II as well as multiple epidermal growth factor (EGF)-like domains (MEGF) 10, class G scavenger receptor CXC chemokine ligand 16 (CXCL16), class H scavenger receptors including Fasciclin, EGF-like, lamin type EGF-like and link domain-containing scavenger receptor-1 (FEEL-1) and -2 (FEEL-2), class I scavenger receptor CD163, and class J scavenger receptor receptor for advanced glycation end products (RAGE), other C-type lectin superfamily members including DEC205, CD206, Dectin-2, Mincle, DC-SIGN, and DNGR-1, and other membrane proteins such as B7 family-related member including V-set and Ig domain-containing 4 (VSIG4), Colony stimulating factor 1 receptor (CSF1R), asialoglycoprotein receptor (ASGPR), and Amyloid beta precursor-like protein 2 (APLP-2). In some embodiments, the antigen is PRLR or HER2. In some embodiments, the antibody is an anti-PRLR or anti HER2 antibody.

The binding agent linkers can be bonded to the binding agent, e.g., antibody or antigen-binding molecule, through an attachment at a particular amino acid within the antibody or antigen-binding molecule. Exemplary amino acid attachments that can be used in the context of this aspect of the disclosure include, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA*, 2008, 105:12451-12456), formyl glycine (see, e.g., Carrico et al., *Nat. Chem. Biol.*, 2007, 3:321-322; Agarwal et al., *Proc. Natl. Acad. Sci., USA*, 2013, 110:46-51, and Rabuka et al., *Nat. Protocols*, 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.*, 2001, 13:127-130).

In some examples, the binding agent is an antibody or antigen binding molecule, and the antibody is bonded to the linker through a lysine residue. In some embodiments, the antibody or antigen binding molecule is bonded to the linker through a cysteine residue.

Linkers can also be conjugated to one or more glutamine residues via transglutaminase-based chemo-enzymatic conjugation (see, e.g., Dennler et al., *Bioconjugate Chem.* 2014, 25, 569-578, and WO 2017/147542). For example, in the presence of transglutaminase, one or more glutamine residues of an antibody can be coupled to a primary amine compound. Briefly, in some embodiments, an antibody having a glutamine residue (e.g., a Gln295 residue) is treated with a primary amine compound, described in more detail below, in the presence of the enzyme transglutaminase. Primary amine compounds include, e.g., payloads or linker-payloads, which directly provide antibody drug conjugates via transglutaminase-mediated coupling. Primary amine compounds also include linkers and spacers that are functionalized with reactive groups that can be subsequently treated with further compounds towards the synthesis of antibody drug conjugates. Antibodies comprising glutamine residues can be isolated from natural sources or engineered to comprise one or more glutamine residues. Techniques for engineering glutamine residues into an antibody polypeptide chain (glutaminyl-modified antibodies or antigen binding molecules) are within the skill of the practitioners in the art. In certain embodiments, the antibody is aglycosylated.

In certain embodiments, the antibody or a glutaminyl-modified antibody or antigen binding molecule comprises at least one glutamine residue in at least one polypeptide chain sequence. In certain embodiments, the antibody or a glutaminyl-modified antibody or antigen binding molecule comprises two heavy chain polypeptides, each with one Gln295 residue. In further embodiments, the antibody or a glutaminyl-modified antibody or antigen binding molecule comprises one or more glutamine residues at a site other than a heavy chain 295. Included herein are antibodies of this section bearing Asn297Gln (N297Q) mutation(s) described herein. Included herein are antibodies of this section bearing Gln55 (Q55) residues.

Primary Amine Compounds

The primary amine compound useful for the transglutaminase mediated coupling of an antibody (or antigen binding compound) comprising a glutamine can be any primary amine compound deemed useful by the practitioner of ordinary skill. Generally, the primary amine compound has the formula H$_2$N—R, where R can be any group compatible with the antibody and reaction conditions. In certain embodiments, R is alkyl, substituted alkyl, heteroalkyl, or substituted heteroalkyl.

In some embodiments, the primary amine compound comprises a reactive group or protected reactive group. Useful reactive groups include azides, alkynes, cycloalkynes, thiols, alcohols, ketones, aldehydes, acids, esters, hydrazides, anilines, and amines. In certain embodiments, the reactive group is selected from the group consisting of azide, alkyne, sulfhydryl, cycloalkyne, aldehyde, and carboxyl.

In certain embodiments, the primary amine compound is according to the formula H$_2$N-LL-X, where LL is a divalent spacer and X is a reactive group or protected reactive group. In particular embodiments, LL is a divalent polyethylene glycol (PEG) group. In certain embodiments, X is selected from the group consisting of —SH, —N$_3$, alkyne, aldehyde, and tetrazole. In particular embodiments, X is —N$_3$.

In certain embodiments, the primary amine compound is according to one of the following formulas:

H$_2$N—(CH$_2$)$_n$—X;

H$_2$N—(CH$_2$CH$_2$O)$_n$—(CH$_2$)$_p$—X;

H$_2$N—(CH$_2$)$_n$—N(H)C(O)—(CH$_2$)$_m$—X;

H$_2$N—(CH$_2$CH$_2$O)$_n$—N(H)C(O)—(CH$_2$CH$_2$O)$_m$—(CH$_2$)$_p$—X;

H$_2$N—(CH$_2$)$_n$—C(O)N(H)—(CH$_2$)$_m$—X;

H$_2$N—(CH$_2$CH$_2$O)$_n$—C(O)N(H)—(CH$_2$CH$_2$O)$_m$—(CH$_2$)$_p$—X;

H$_2$N—(CH$_2$)$_n$—N(H)C(O)—(CH$_2$CH$_2$O)$_m$—(CH$_2$)$_p$—X;

H$_2$N—(CH$_2$CH$_2$O)$_n$—N(H)C(O)—(CH$_2$)$_m$—X;

H$_2$N—(CH$_2$)$_n$—C(O)N(H)—(CH$_2$CH$_2$O)$_m$—(CH$_2$)$_p$—X; and

H$_2$N—(CH$_2$CH$_2$O)$_n$—C(O)N(H)—(CH$_2$)$_m$—X;

where n is an integer selected from 1 to 12;
m is an integer selected from 0 to 12;
p is an integer selected from 0 to 2;
and X is selected from the group consisting of —SH, —N$_3$, —C≡CH, —C(O)H, tetrazole, and any of

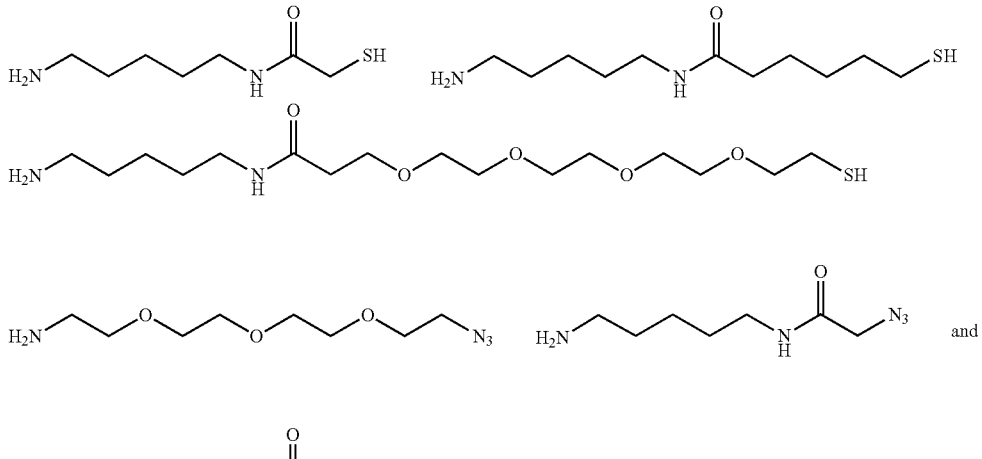

In the above, any of the alkyl (i.e., —CH$_2$—) groups can optionally be substituted, for example, with C$_{1-8}$alkyl, methylformyl, or —SO$_3$H. In certain embodiments, the alkyl groups are unsubstituted.

In certain embodiments, the primary amine compound is selected from the group consisting of:

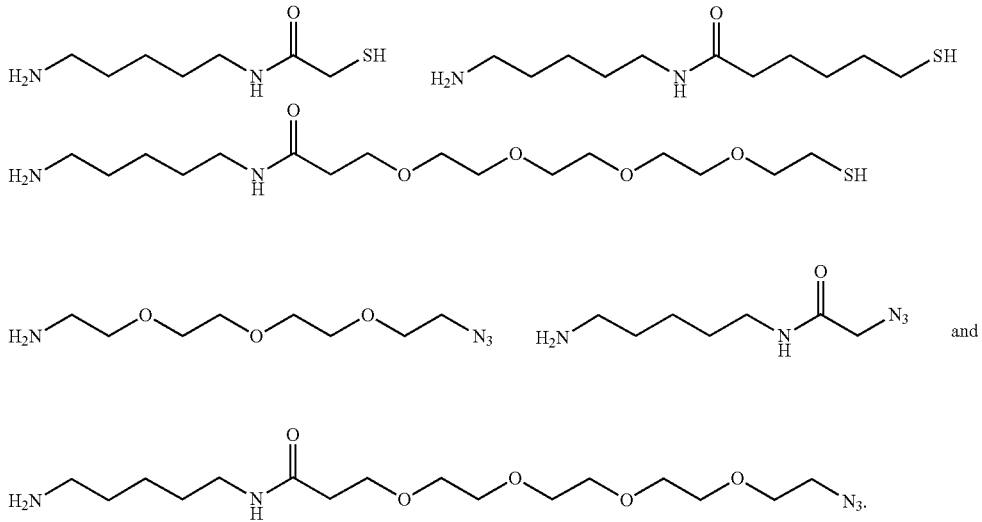

In particular embodiments, the primary amine compound is

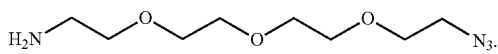

Exemplary conditions for the above reactions are provided in the Examples below.

Linkers

The linker L portion of the conjugates described herein is a moiety, for instance, a divalent moiety, that covalently links a binding agent to a payload compound described herein. In other instances, the linker L is a trivalent or multivalent moiety that covalently links a binding agent to a payload compound described herein. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Payload compounds include compounds of Formula I, Ia, and Ib above, and their residues following bonding or incorporation with linker L. Those of skill in the art will recognize that certain functional groups of the payload moieties are convenient for linking to linkers and/or binding agents. Those groups include amines, hydroxyls, phosphates, and sugars.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety. In some embodiments, the non-cleavable linker is derived from

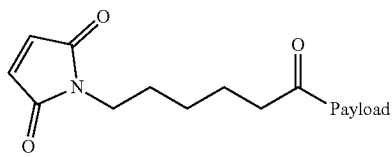

or a residue thereof. In some embodiments, the non-cleavable linker-payload is

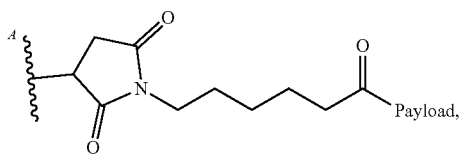

or a regioisomer thereof. In some embodiments, the non-cleavable linker is derived from

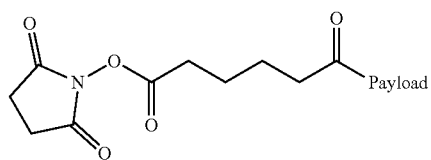

or a residue thereof. In some embodiments, the non-cleavable linker-payload is

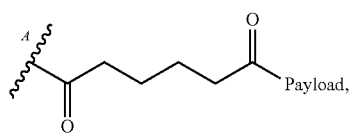

or a regioisomer thereof. In one embodiment, the linker is maleimide cyclohexane carboxylate or 4-(N-maleimidomethyl)cyclohexanecarboxylic acid (MCC). In the structures, $-\overset{A}{\xi}-$ indicates a bond to a binding agent. In the structures, in some examples, $-\overset{A}{\xi}-$ indicates a click chemistry residue which results from the reaction of, for example, a binding agent and a linker payload.

In some embodiments, suitable linkers include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L-, or D-α-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine.

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the linker is:

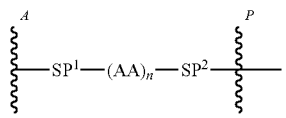

wherein:
SP$^1$ is a spacer;
SP$^2$ is a spacer;

$-\xi^A$ is one or more bonds to the binding agent;

$-\xi^A$ is one or more bonds to the payload;
each AA is an amino acid; and
n is an integer from 1 to 10.

The SP$^1$ spacer is a moiety that connects the (AA)$_n$ moiety to the binding agent (BA) or to a reactive group residue which is bonded to BA. Suitable SP$^1$ spacers include, but are not limited to, those comprising alkylene or polyether, or both. The ends of the spacers, e.g., the portion of the spacer bonded to the binding agent or an AA, can be moieties derived from reactive moieties that are used for purposes of coupling the antibody or an AA to the spacer during chemical synthesis of the conjugate. In certain embodiments, n is 1, 2, 3, or 4. In particular embodiments, n is 2. In particular embodiments, n is 3. In particular embodiments, n is 4.

In some embodiments, the SP$^1$ spacer comprises an alkylene. In some embodiments, the SP$^1$ spacer comprises a C$_{57}$ alkylene. In some embodiments, the SP$^1$ spacer comprises a polyether. In some embodiments, the SP$^1$ spacer comprises a polymer of ethylene oxide such as polyethylene glycol.

In some embodiments, the SP$^1$ spacer is:

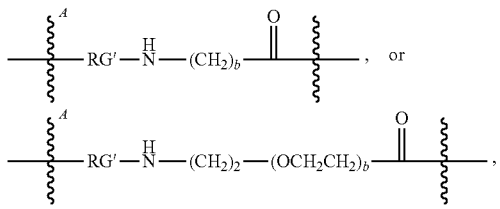

wherein:
RG' is a reactive group residue following reaction of a reactive group RG with a binding agent;

$-\xi^A$ is a bond to the binding agent;

$-\xi^A$ is a bond to (AA)$_n$; and
b is an integer from 2 to 8.

The reactive group RG can be any reactive group known to those of skill in the art to be capable of forming one or more bonds to the binding agent. The reactive group RG is a moiety comprising a portion in its structure that is capable of reacting with the binding agent (e.g., reacting with an antibody at its cysteine or lysine residues, or at an azide moiety, for example, a PEG-N$_3$ functionalized antibody at one or more glutamine residues) to form a compound of Formula A, Aa, or Ab. Following conjugation to the binding agent, the reactive group becomes the reactive group residue (RG'). Illustrative reactive groups include, but are not limited to, those that comprise haloacetyl, isothiocyanate, succinimide, N-hydroxysuccinimide, or maleimide portions that are capable of reacting with the binding agent.

In certain embodiments, reactive groups include, but are not limited to, alkynes. In certain embodiments, the alkynes are alkynes capable of undergoing 1,3-cycloaddition reactions with azides in the absence of copper catalysts such as strained alkynes. Strained alkynes are suitable for strain-promoted alkyne-azide cycloadditions (SPAAC), cycloalkynes, e.g., cyclooctynes, ane benzannulated alkynes. Suitable alkynes include, but are not limited to, dibenzoazacyclooctyne or

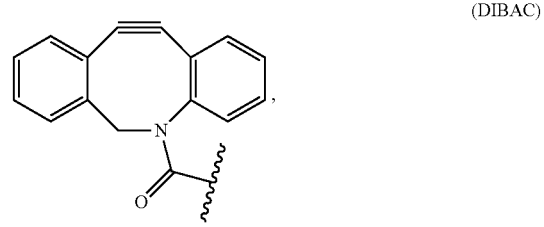 [SMILES: *C(=O)N1Cc2ccccc2C#Cc2ccccc21]

(DIBAC)

dibenzocyclooctyne or

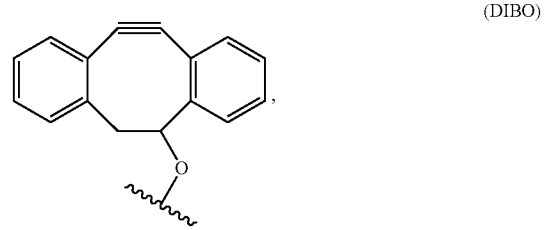 [SMILES: *OC1Cc2ccccc2C#Cc2ccccc21]

(DIBO)

biarylazacyclooctynone or

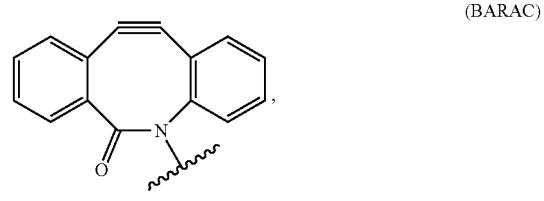 [SMILES: *N1C(=O)c2ccccc2C#Cc2ccccc21]

(BARAC)

difluorinated cyclooctyne or

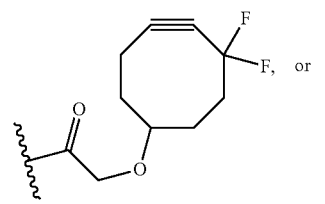

, or

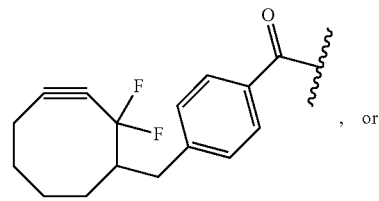

, or

-continued

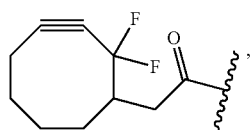
(DIFO)

substituted, e.g., fluorinated alkynes, aza-cycloalkynes, bicycle[6.1.0]nonyne or

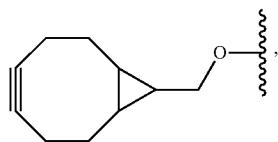
(BCN)

and derivatives thereof. Particularly useful alkynes include

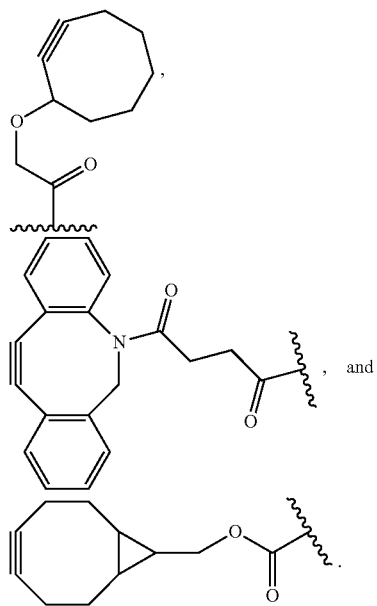

In certain embodiments, the binding agent is bonded directly to RG'. In certain embodiments, the binding agent is bonded to RG' via a spacer, for instance $SP^4$, below. In particular embodiments, the binding agent is bonded to RG' via a PEG spacer. As discussed in detail below, in certain embodiments, the binding agent is prepared by functionalizing with one or more azido groups. Each azido group is capable of reacting with RG to form RG'. In particular embodiments, the binding agent is derivatized with -PEG-$N_3$ linked to a glutamine residue. Exemplary —$N_3$ derivatized binding agents, methods for their preparation, and methods for their use in reacting with RG are provided herein. In certain embodiments, RG is an alkyne suitable for participation in 1,3-cycloadditions, and RG' is a 1,2,3-triazolyl moiety formed from the reaction of RG with an azido-functionalized binding agent. By way of further example, in certain embodiments, RG' is linked to the binding agent as shown in

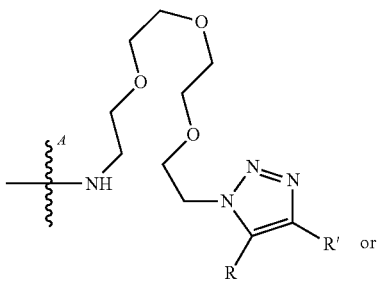 or

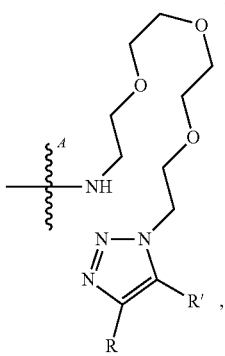, or a mixture of each regioisomer. Each R and R' is as described herein.

The $SP^2$ spacer is a moiety that connects the $(AA)_n$ moiety to the payload. Suitable spacers include, but are not limited to, those described above as $SP^1$ spacers. Further suitable $SP^2$ spacers include, but are not limited to, those comprising alkylene or polyether, or both. The ends of the $SP^2$ spacers, e.g., the portion of the spacer directly bonded to the payload or an AA, can be moieties derived from reactive moieties that are used for purposes of coupling the payload or AA to the $SP^2$ spacer during the chemical synthesis of the conjugate. In some examples, the ends of the $SP^2$ spacers, e.g., the portion of the $SP^2$ spacer directly bonded to the payload or an AA, can be residues of reactive moieties that are used for purposes of coupling the payload or an AA to the spacer during the chemical synthesis of the conjugate.

In some embodiments, the $SP^2$ spacer is selected from the group consisting of —O—, —N($R^6$)—, —$R^{4\dagger}$—, —$R^{5\dagger}$—, —$OR^{5\dagger}$—, and —OP(O)($OR^6$)O—, wherein:

$R^{4\dagger}$ is —Z'—Y—X—;

X is selected from the group consisting of —O— and —N(H)—;

Y is selected from the group consisting of alkylene, substituted alkylene (including, without limitation, oxo substitution, i.e., =O), heteroalkylene, and substituted heteroalkylene;

Z' is selected from the group consisting of —O— and —N(H)—;

$R^{5\dagger}$ is heterocycloalkylene or substituted heterocycloalkylene, wherein each heterocycloalkylene or substituted heterocycloalkylene includes one, two, or three heteroatoms selected from nitrogen and oxygen, including at least two moieties selected from the group consisting of —O—, —N(H)—, and

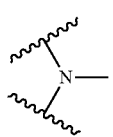

useful for bonding to the remainder of the molecule; and
each $R^6$ is —H, an amino acid residue, a peptide, or alkyl.

In certain embodiments, the SP² spacer is selected from the group consisting of —O—, —N(H)—,

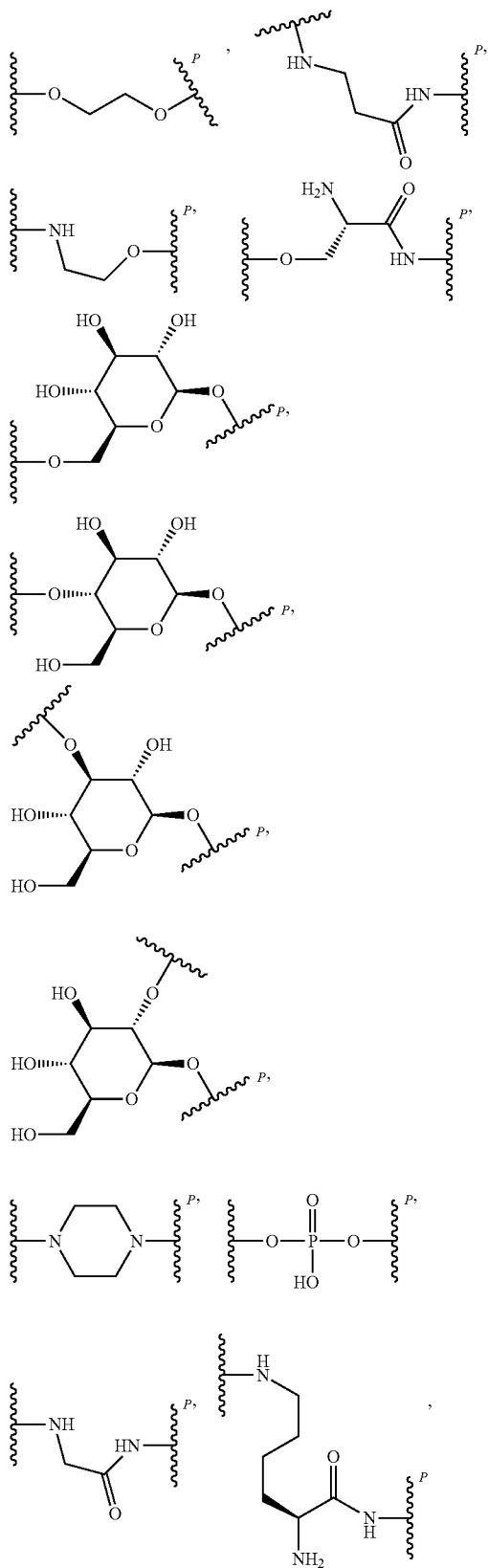

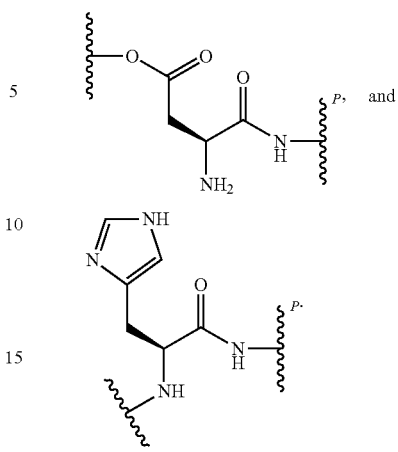

In certain embodiments, each ⁻⸹⁻ᴾ is a bond to the payload, and each ⁻⸹⁻ is a bond to $(AA)_n$.

In the above formulas, each AA is an amino acid or, optionally, ap-aminobenzyloxycarbonyl residue (PABC). If PABC is present, preferably only one PABC is present. Preferably, the PABC residue, if present, is a terminal AA in the $(AA)_n$ group, proximal to the payload. Suitable amino acids for each AA include natural, non-natural, standard, non-standard, proteinogenic, non-proteinogenic, and L-, or D-α-amino acids. In some embodiments, the linker comprises alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, one or more side chains of the amino acids is linked to a side chain group, described below. In some embodiments, n is two. In some embodiments, the $(AA)_n$ is valine-citrulline. In some embodiments, $(AA)_n$ is citrulline-valine. In some embodiments, $(AA)_n$ is valine-alanine. In some embodiments, $(AA)_n$ is alanine-valine. In some embodiments, $(AA)_n$ is valine-glycine. In some embodiments, $(AA)_n$ is glycine-valine. In some embodiments, n is three. In some embodiments, the $(AA)_n$ is valine-citrulline-PABC. In some embodiments, $(AA)_n$ is citrulline-valine-PABC. In some embodiments, $(AA)_n$ is glutamate-valine-citrulline. In some embodiments, $(AA)_n$ is glutamine-valine-citrulline. In some embodiments, $(AA)_n$ is lysine-valine-alanine. In some embodiments, $(AA)_n$ is lysine-valine-citrulline. In some embodiments, n is four. In some embodiments, $(AA)_n$ is glutamate-valine-citrulline-PAB. In some embodiments, $(AA)_n$ is glutamine-valine-citrulline-PABC. Those of skill will recognize PABC as a residue of p-aminobenzyloxycarbonyl with the following structure:

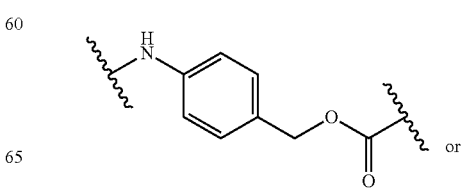

or

-continued
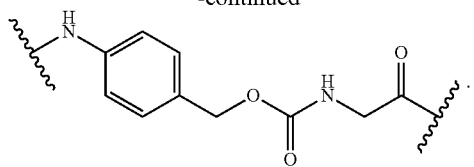
The PABC residue has been shown to facilitate cleavage of certain linkers in vitro and in vivo.
In some embodiments, the linker is:
wherein:
each $\xi^A$ is a bond to the binding agent;
$\xi^A$ each is a bond to the payload;
each $R^9$ is —CH$_3$ or —(CH$_2$)$_3$N(H)C(O)NH$_2$; and
each A is —O—, —N(H)—,
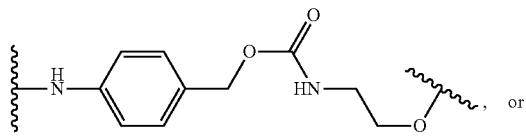, or
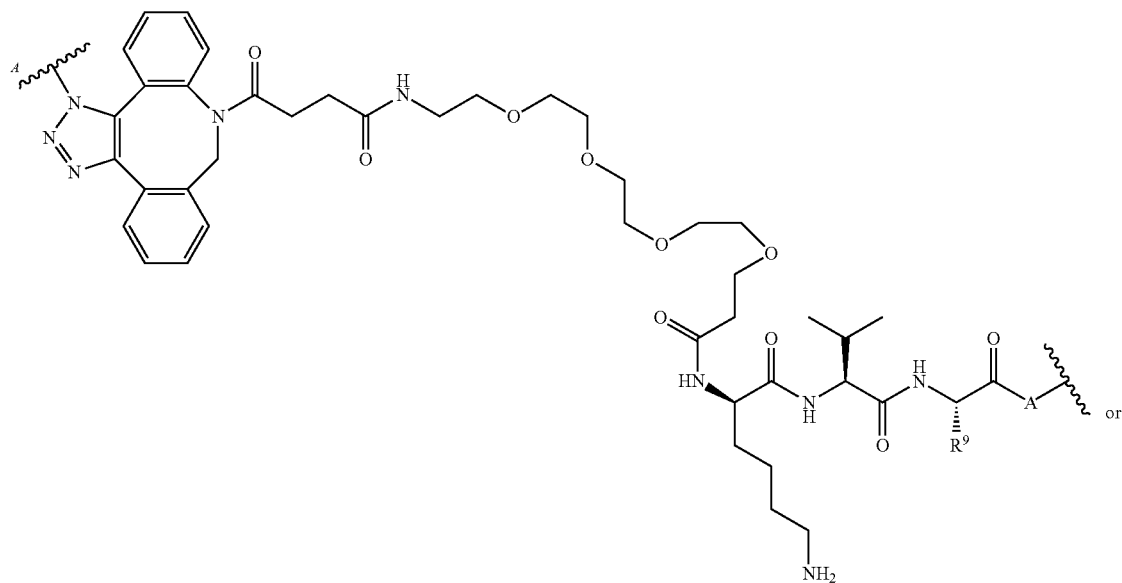 or
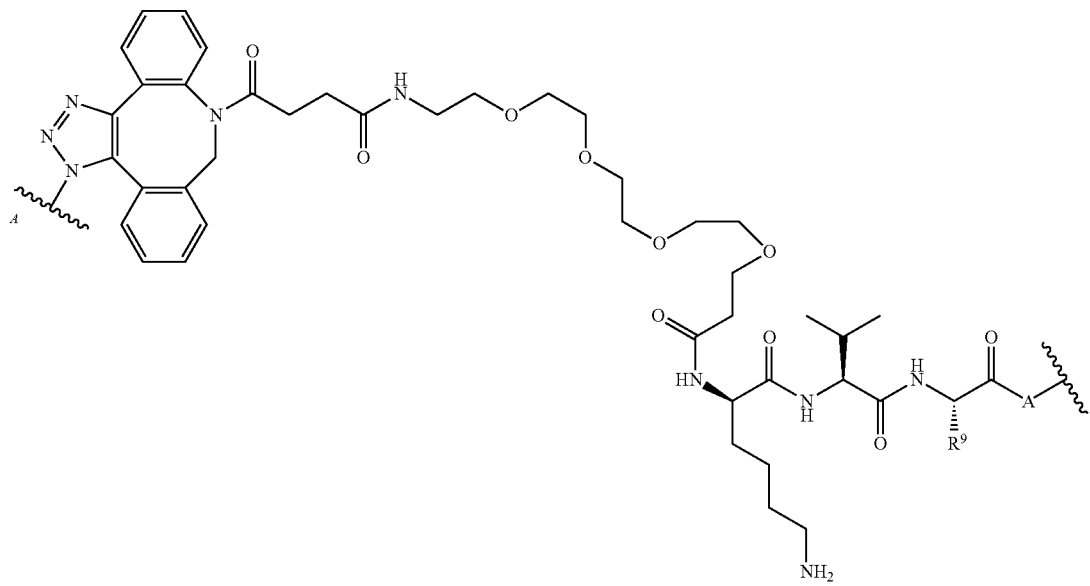

-continued

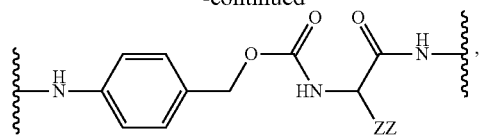

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent.

In some embodiments, the linker is:

wherein:

each ⸯ⟨A⟩ is a bond to the binding agent;

each ⸯ is a bond to the payload;

each $R^9$ is —$CH_3$ or —$(CH_2)_3N(H)C(O)NH_2$; and each A is —O—, —N(H)—,

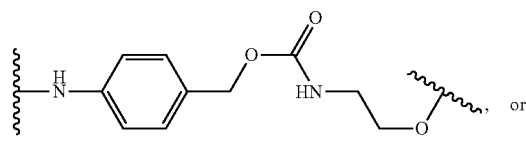, or

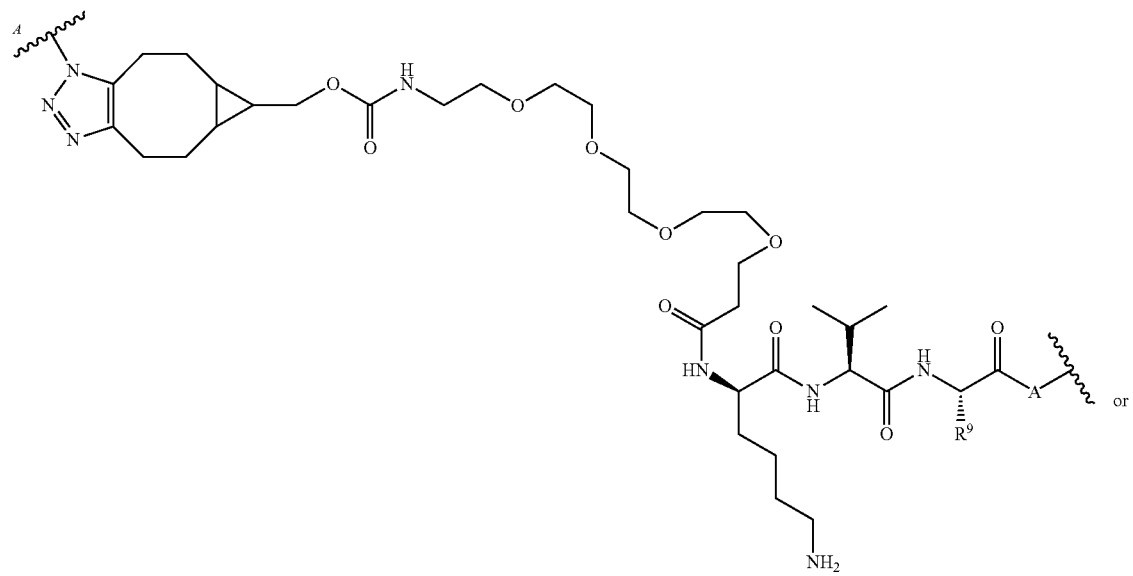, or

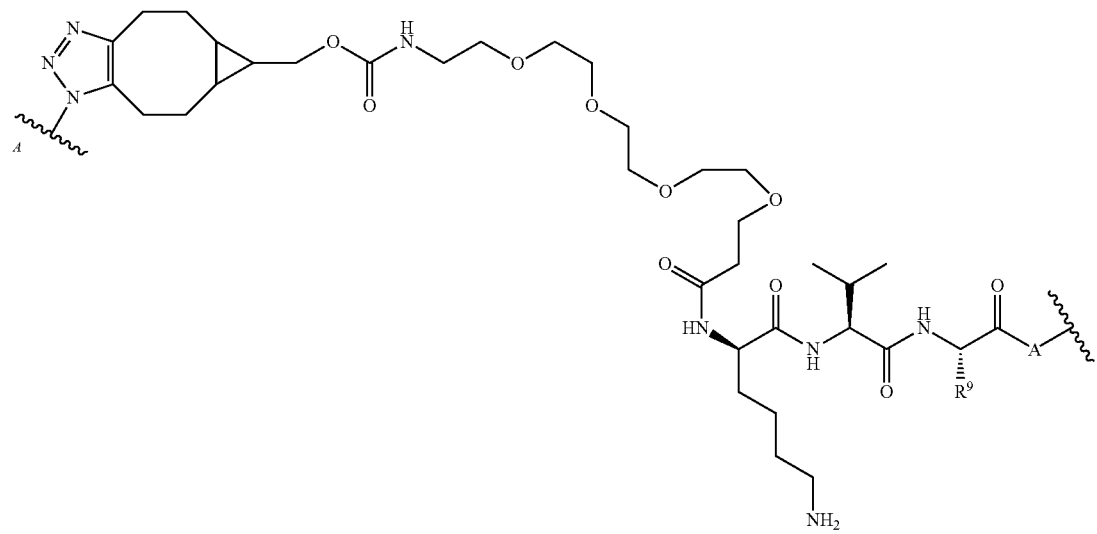

-continued

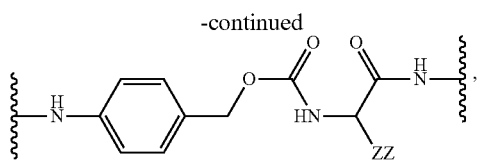

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent.

In any of the above embodiments, the $(AA)_n$ group can be modified with one or more enhancement groups. Advantageously, the enhancement group can be linked to the side chain of any amino acid in $(AA)_n$. Useful amino acids for linking enhancement groups include lysine, asparagine, aspartate, glutamine, glutamate, and citrulline. The link to the enhancement group can be a direct bond to the amino acid side chain, or the link can be indirect via a spacer and/or reactive group. Useful spacers and reactive groups include any described above. The enhancement group can be any group deemed useful by those of skill in the art. For example, the enhancement group can be any group that imparts a beneficial effect to the compound, payload, linker payload, or antibody conjugate including, but not limited to, biological, biochemical, synthetic, solubilizing, imaging, detecting, and reactivity effects, and the like. In certain embodiments, the enhancement group is a hydrophilic group. In certain embodiments, the enhancement group is a cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the enhancement group is capable of improving solubility of the remainder of the conjugate. In certain embodiments, the alkyl, heteroalkyl, alkylenyl, or heteroalkylenyl sulfonic acid is substituted or non-substituted. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_mC(O)NH$—$(CH_2)_{1-5}SO_3H$, —$(CH_2)_n$—N$((CH_2)_{1-5}C(O)NH(CH_2)_{1-5}SO_3H)_2$, —$(CH_2)_n$—C(O)N$((CH_2)_{1-5}C(O)NH(CH_2)_{1-5}SO_3H)_2$, or —$(CH_2CH_2O)_mC(O)N((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)NH—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N$((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N$((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N$((CH_2)_{1-5}C(O)NH(CH_2)_{1-5}SO_3H)_2$, wherein m is 1, 2, 3, 4, or 5. In some embodiments, the linker is:

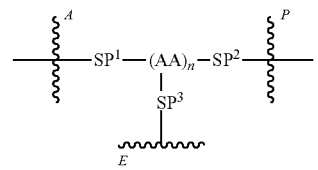

wherein:
SP$^1$ is a spacer;
SP$^2$ is a spacer;
SP$^3$ is a spacer, linked to one AA of $(AA)_n$;

$\overset{A}{\text{-}\xi\text{-}}$ is one or more bonds to the binding agent;

$\overset{P}{\text{-}\xi\text{-}}$ is one or more bonds to the payload;

$\overset{E}{\text{-}\xi\text{-}}$ is one or more bonds to the enhancement group EG;
each AA is an amino acid; and
n is an integer from 1 to 10.

As discussed above, the bond to the binding agent can be direct, or via a spacer. In certain embodiments, the bond to the binding agent is via a PEG spacer to a glutamine residue of the binding agent.

The SP$^1$ spacer group is as described above. The SP$^2$ spacer group is as described above. Each $(AA)_n$ group is as described above.

The SP$^3$ spacer is a moiety that connects the $(AA)_n$ moiety to the enhancement group (EG). Suitable SP$^3$ spacers include, but are not limited to, those comprising alkylene or polyether, or both. The ends of the SP$^3$ spacers, i.e., the portion of the SP$^3$ spacer directly bonded to the enhancement group or an AA, can be moieties derived from reactive moieties that are used for purposes of coupling the enhancement group or an AA to the SP$^3$ spacer during the chemical synthesis of the conjugate. In some examples, the ends of the SP$^3$ spacers, i.e., the portion of the spacer directly bonded to the enhancement group or an AA, can be residues of reactive moieties that are used for purposes of coupling the enhancement group or an AA to the spacer during the chemical synthesis of the conjugate. In certain embodiments, SP$^3$ is a spacer, linked to one and only one AA of $(AA)_n$. In certain embodiments, the SP$^3$ spacer is linked to the side chain of a lysine residue of $(AA)_n$.

In some embodiments, the SP$^3$ spacer is:

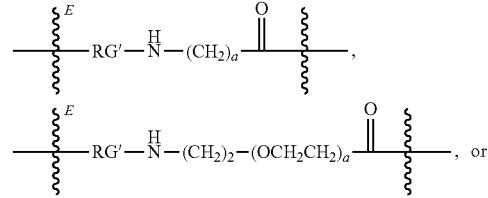

-continued

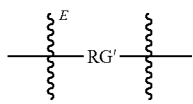

wherein:

RG' is a reactive group residue following reaction of a reactive group RG with an enhancement agent EG;

$-\xi^E$ is a bond to the enhancement agent;

$-\xi$ is a bond to $(AA)_n$; and a is an integer from 2 to 8.

The reactive group RG can be any reactive group known to those of skill in the art to be capable of forming one or more bonds to the enhancement agent. The reactive group RG is a moiety comprising a portion in its structure that is capable of reacting with the binding agent (e.g., reacting with an antibody at its cysteine or lysine residues, or at an azide moiety) to form a compound of Formula A, Aa, or Ab. Following conjugation to the binding agent, the reactive group becomes the reactive group residue (RG'). The reactive group RG can be any reactive group described above. Illustrative reactive groups include, but are not limited to, those that comprise haloacetyl, isothiocyanate, succinimide, N-hydroxysuccinimide, or maleimide portions that are capable of reacting with the binding agent.

In certain embodiments, reactive groups include, but are not limited to, alkynes. In certain embodiments, the alkynes are alkynes capable of undergoing 1,3-cycloaddition reactions with azides in the absence of copper catalysts such as strained alkynes. Strained alkynes are suitable for strain-promoted alkyne-azide cycloadditions (SPAAC), cycloalkynes, e.g., cyclooctynes, ane benzannulated alkynes. Suitable alkynes include, but are not limited to, dibenzoazacyclooctyne or

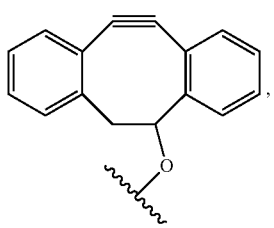
(DIBAC)

dibenzocyclooctyne or

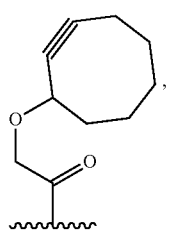
(DIBO)

biarylazacyclooctynone or

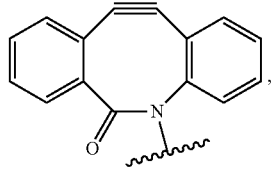
(BARAC)

difluorinated cyclooctyne or

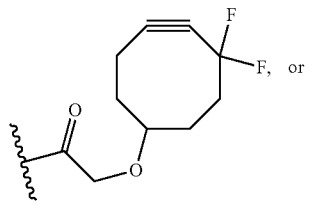
, or

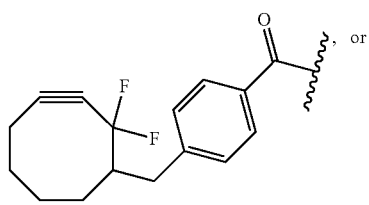
, or

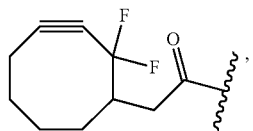
(DIFO)

substituted, e.g., fluorinated alkynes, aza-cycloalkynes, bicycle[6.1.0]nonyne or (BCN)

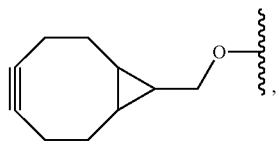

and derivatives thereof. Particularly useful alkynes include

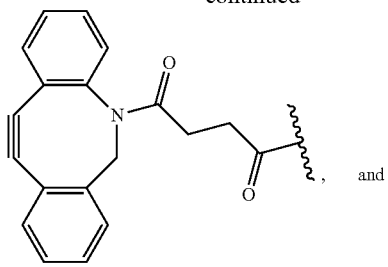, and

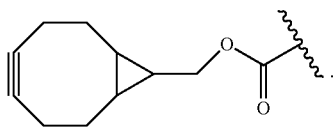.

PEG is PEG3;

SP$^2$ is a spacer;

SP$^3$ is a spacer, linked to one AA of (AA)$_n$;

-$\frac{A}{\xi}$- is one or more bonds to the binding agent;

-$\frac{P}{\xi}$- is one or more bonds to the payload;

-$\frac{E}{\xi}$- is one or more bonds to the enhancement group EG;

each AA is an amino acid; and n is an integer from 1 to 10.

As discussed above, the bond to the binding agent can be direct, or via a spacer. In certain embodiments, the bond to the binding agent is via a PEG spacer to a glutamine residue of the binding agent.

In certain embodiments, the linker is:

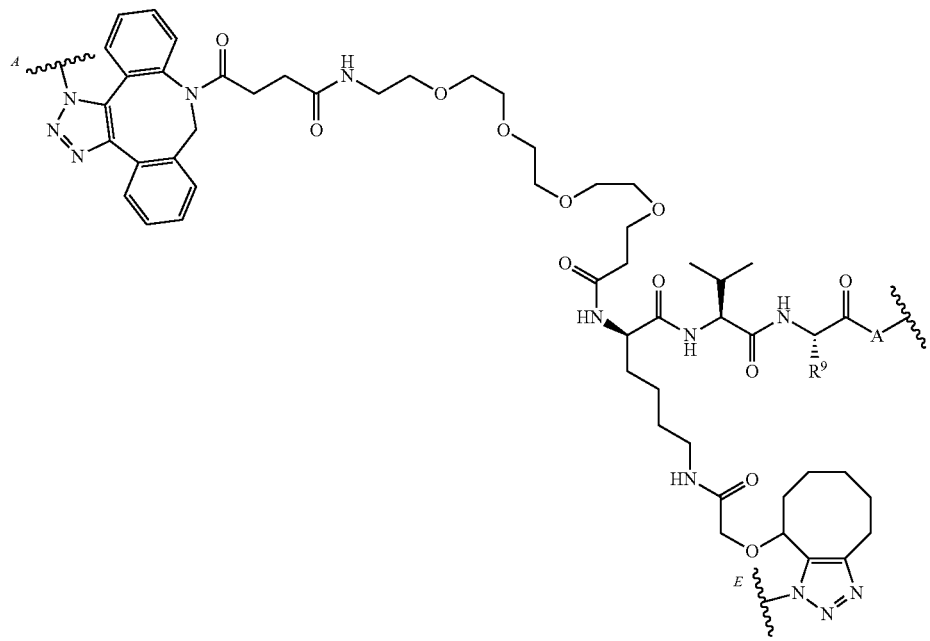

In some embodiments, the linker is:

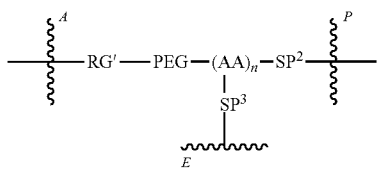

wherein:

RG' is a reactive group residue following reaction of a reactive group RG with a binding agent;

or a pharmaceutically acceptable salt, solvate, or stereoisomeric form thereof, or a regioisomer thereof, or a mixture of regioisomers thereof, wherein:

each -$\frac{A}{\xi}$- is a bond to the binding agent;

each -$\frac{P}{\xi}$- is a bond to the payload;

each -$\frac{E}{\xi}$- is a bond to the enhancement agent;

each R$^9$ is —CH$_3$ or —(CH$_2$)$_3$N(H)C(O)NH$_2$; and each A is —O—, —N(H)—,

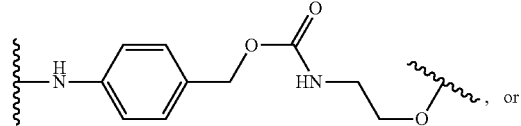, or

-continued

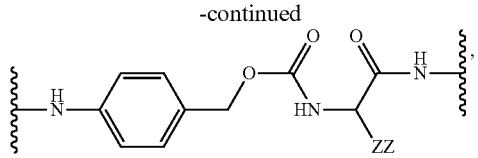

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. In certain embodiments, 1,3-cycloaddition or SPAAC regioisomers, or mixture of regioisomers, are derived from $PEG-N_3$ derivatized antibodies treated with suitable alkynes. For example, in one embodiment, the linker is:

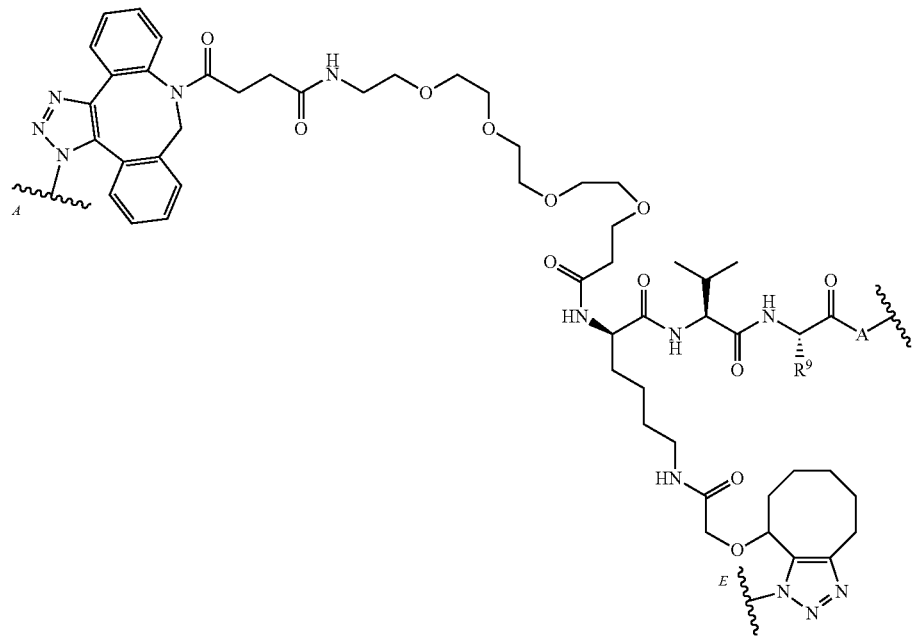

or a pharmaceutically acceptable salt, solvate, or stereoisomeric form thereof, or a regioisomer thereof, or a mixture of regioisomers thereof. By way of further example, the linker is:

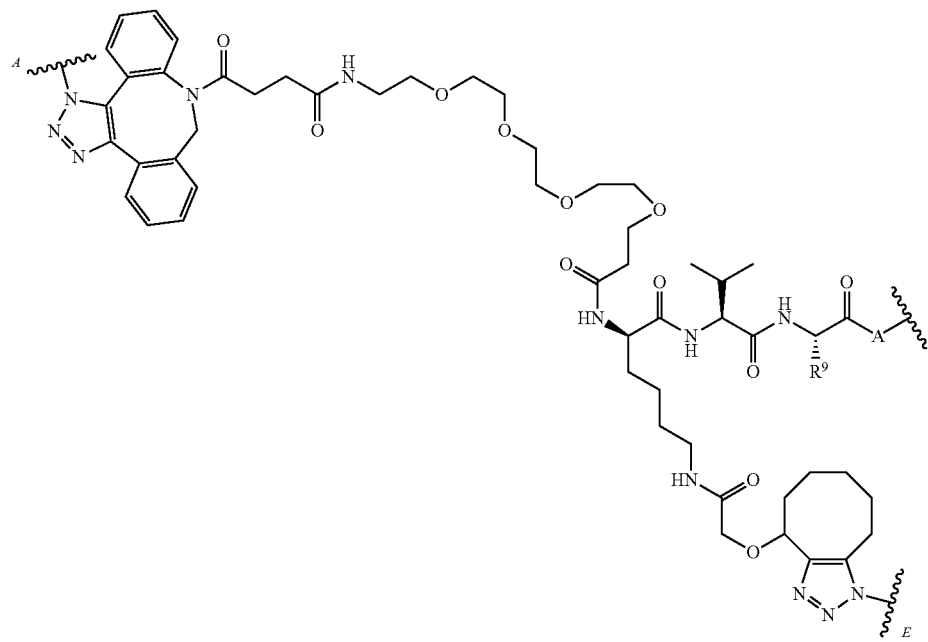

or a pharmaceutically acceptable salt, solvate, or stereoisomeric form thereof, or a regioisomer thereof, or a mixture of regioisomers thereof. By way of further example, in one embodiment, the linker is:

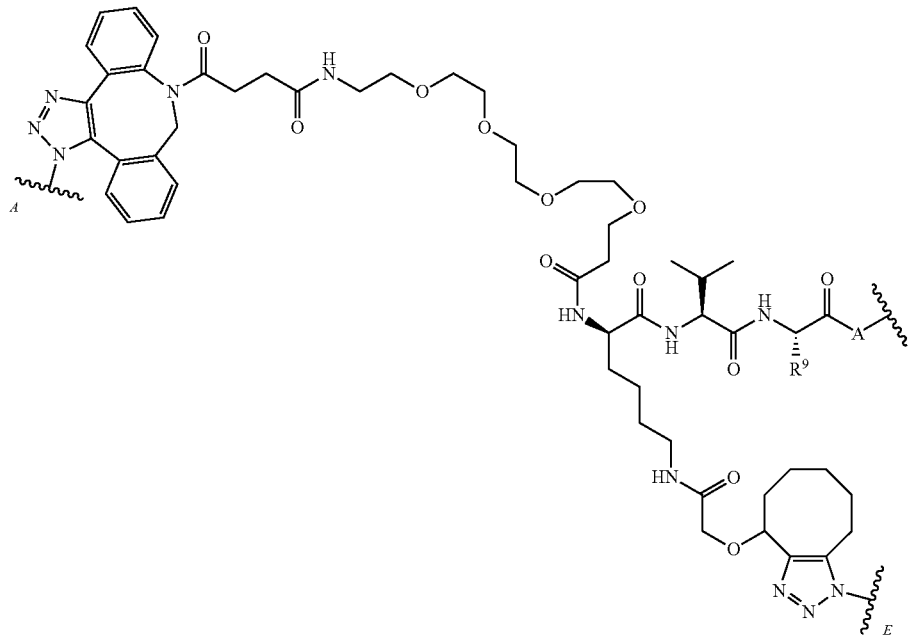

or a pharmaceutically acceptable salt, solvate, or stereoisomeric form thereof, or a regioisomer thereof, or a mixture of regioisomers thereof.

As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_m$—C(O)NH—$(CH_2)_{1-5}SO_3H$, —$(CH_2)_n$—N(($CH_2)_{1-5}$C(O)NH($CH_2)_{1-5}SO_3H)_2$, —$(CH_2)_n$—C(O)N(($CH_2)_{1-5}$C(O)NH($CH_2)_{1-5}SO_3H)_2$, or —$(CH_2CH_2O)_m$—C(O)N(($CH_2)_{1-5}$C(O)NH($CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_m$C(O)NH—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N(($CH_2)_{1-5}$C(O)NH($CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N(($CH_2)_{1-5}$C(O)NH($CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N(($CH_2)_{1-5}$C(O)NH($CH_2)_{1-5}SO_3H)_2$, wherein m is 1, 2, 3, 4, or 5.

In some embodiments, the linker is:

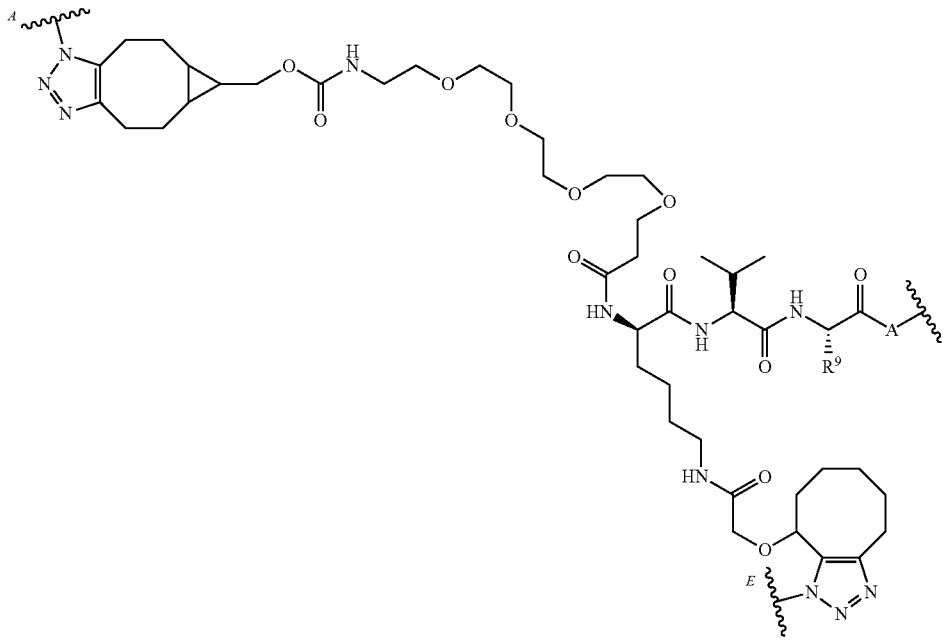

or a pharmaceutically acceptable salt, solvate, or stereoisomeric form thereof, or a regioisomer thereof, or mixture of regioisomers thereof, wherein:

each $-\overset{A}{\underset{}{\xi}}-$ is a bond to the binding agent;

each $-\overset{E}{\underset{}{\xi}}-$ is a bond to the enhancement agent;

each $-\xi-$ is a bond to the payload;
each $R^9$ is $—CH_3$ or $—(CH_2)_3N(H)C(O)NH_2$; and
each A is $—O—$, $—N(H)—$,

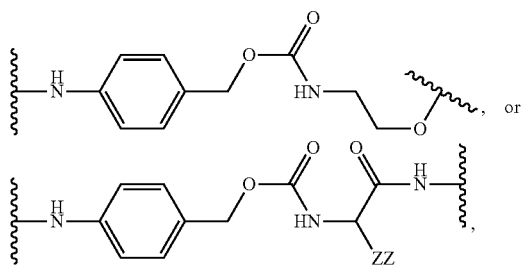

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is $—(CH_2)_{1-5}SO_3H$, $—(CH_2)_n—NH—(CH_2)_{1-5}SO_3H$, $—(CH_2)_n—C(O)NH—(CH_2)_{1-5}SO_3H$, $—(CH_2CH_2O)_m—C(O)NH—(CH_2)_{1-5}SO_3H$, $—(CH_2)_n—N((CH_2)_{1-5}C(O)NH(CH_2)_{1-5}SO_3H)_2$, $—(CH_2)_n—C(O)N((CH_2)_{1-5}C(O)NH(CH_2)_{1-5}SO_3H)_2$, or $—(CH_2CH_2O)_m—C(O)N((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is $—(CH_2)_{1-5}SO_3H$. In another embodiment, the alkyl, heteroalkyl, alkylenyl, or heteroalkylenyl sulfonic acid is $—(CH_2)_n—NH—(CH_2)_{1-5}SO_3H$, wherein n is 1, 2, 3, 4, or 5. In another embodiment, the alkyl, heteroalkyl, alkylenyl, or heteroalkylenyl sulfonic acid is $—(CH_2)_n—C(O)NH—(CH_2)_{1-5}SO_3H$, wherein n is 1, 2, 3, 4, or 5. In another embodiment, the alkyl, heteroalkyl, alkylenyl, or heteroalkylenyl sulfonic acid is $—(CH_2CH_2O)_m—C(O)NH—(CH_2)_{1-5}SO_3H$, wherein m is 1, 2, 3, 4, or 5. In another embodiment, the alkyl, heteroalkyl, alkylenyl, or heteroalkylenyl sulfonic acid is $—(CH_2)_n—N((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is $—(CH_2)_n—C(O)N((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is $—(CH_2CH_2O)_m—C(O)N((CH_2)_{1-5}C(O)NH(CH_2)_{1-5}SO_3H)_2$, wherein m is 1, 2, 3, 4, or 5.

In some embodiments, the linker is:
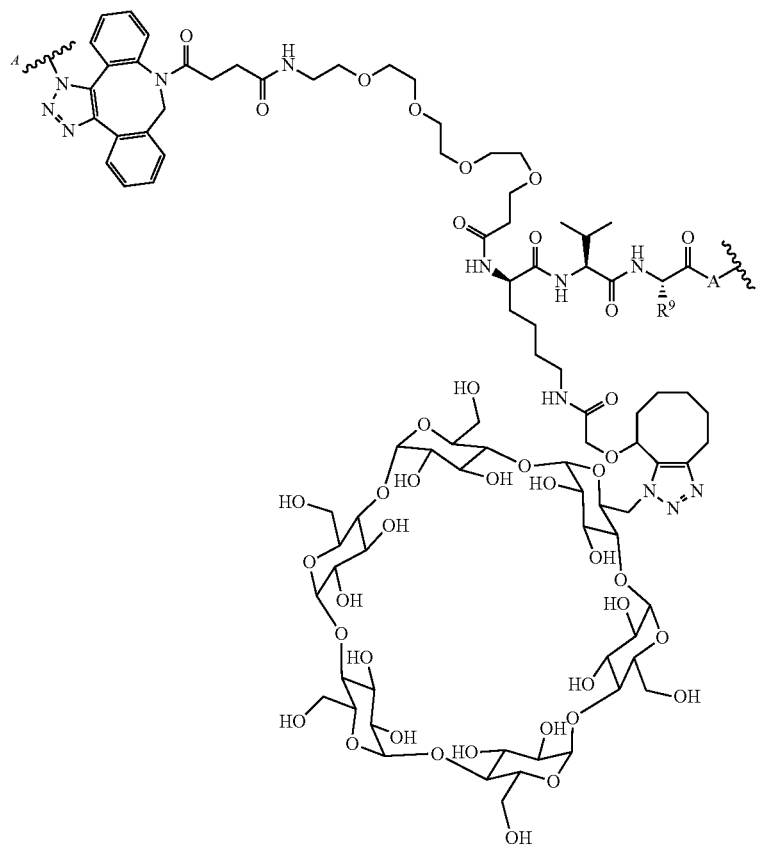
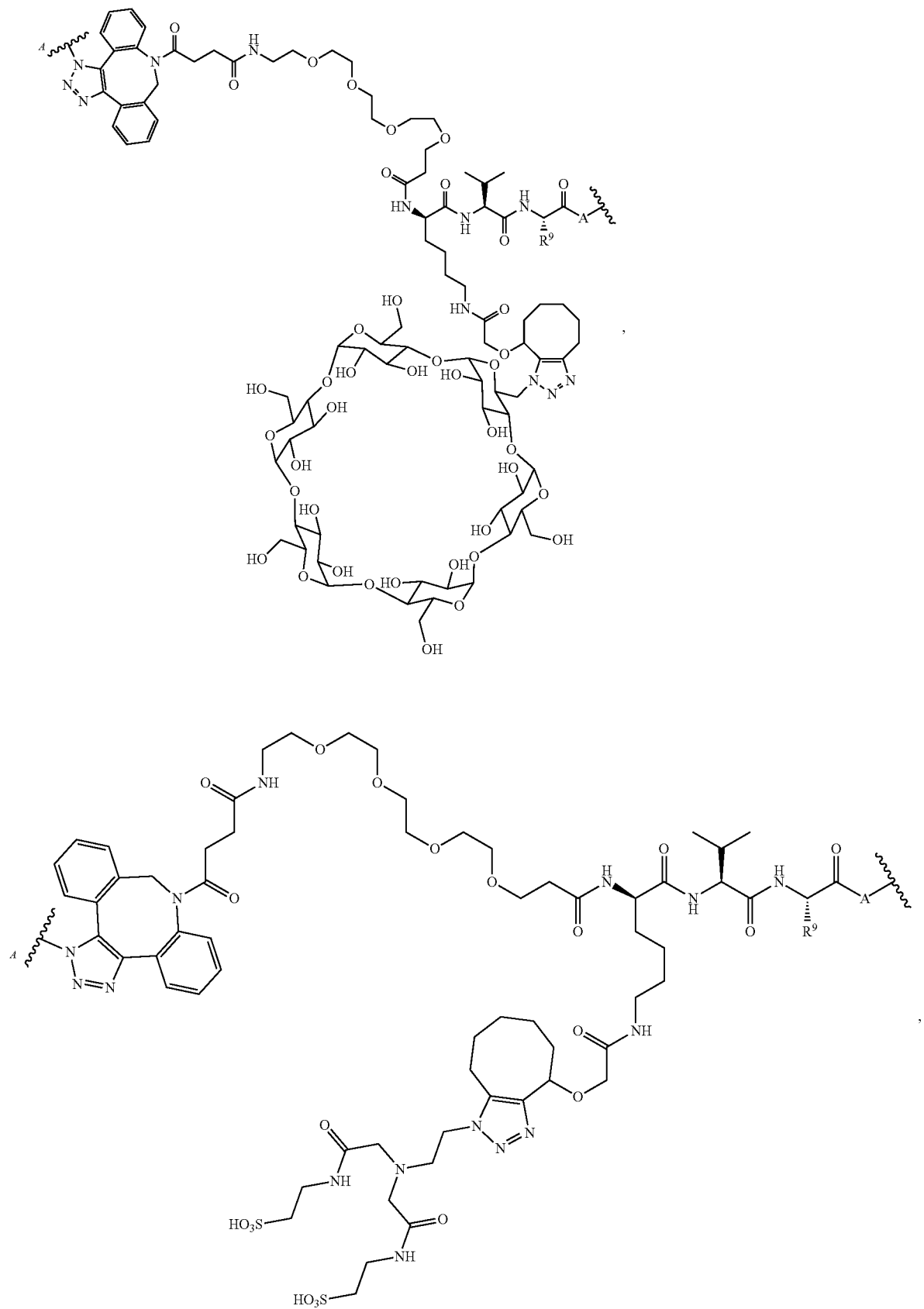

125

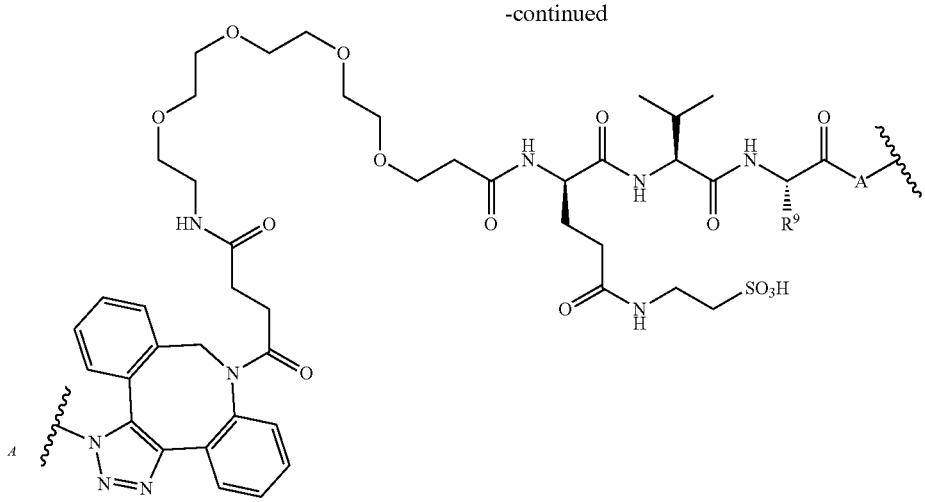

126

-continued

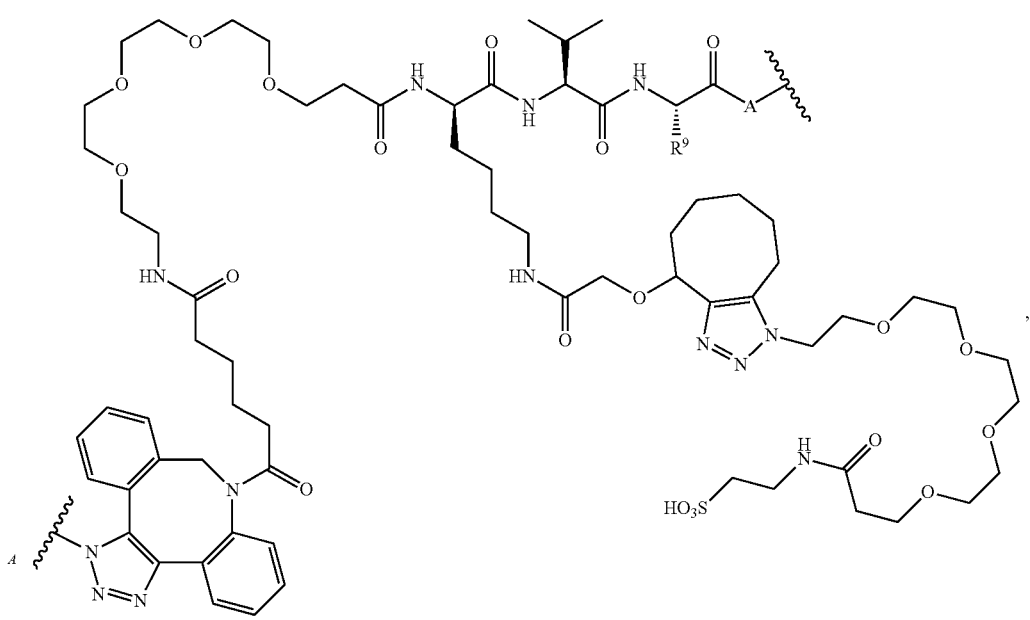

or a pharmaceutically acceptable salt, solvate, or stereoisomeric form thereof, or a regioisomer thereof, or mixture of regioisomers thereof, wherein:

each -§- is a bond to the binding agent;
each -§- is a bond to the payload;
$R^9$ is —$CH_3$ or —$(CH_2)_3N(H)C(O)NH_2$; and
A is —O—, —N(H)—,

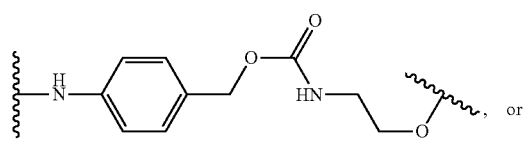 or

-continued

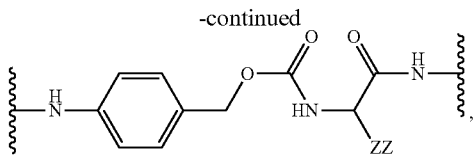

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent.

In some embodiments, the linker is:
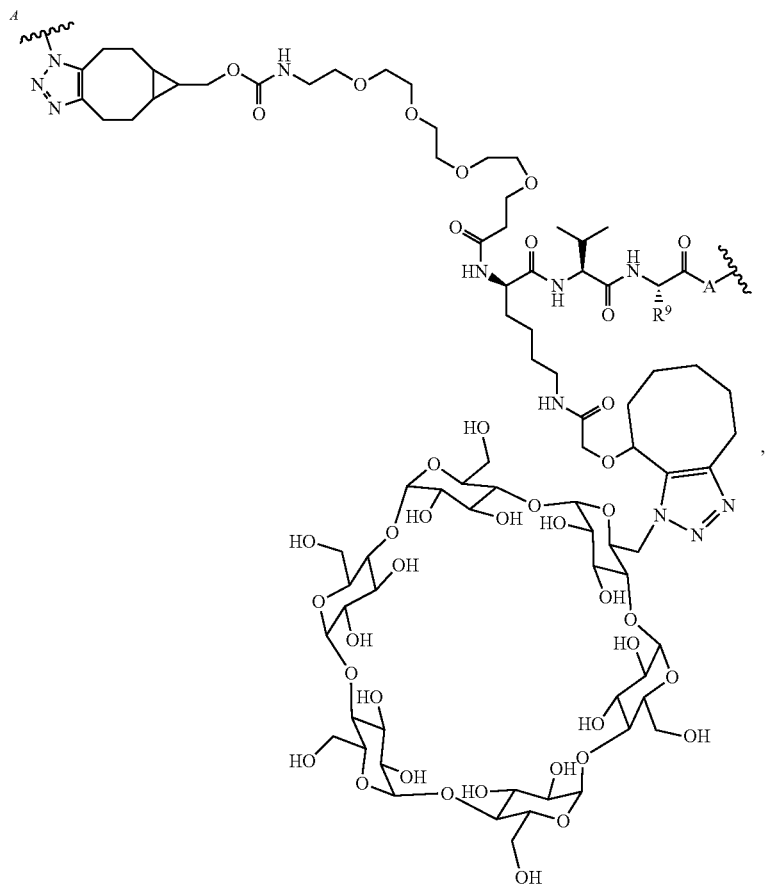
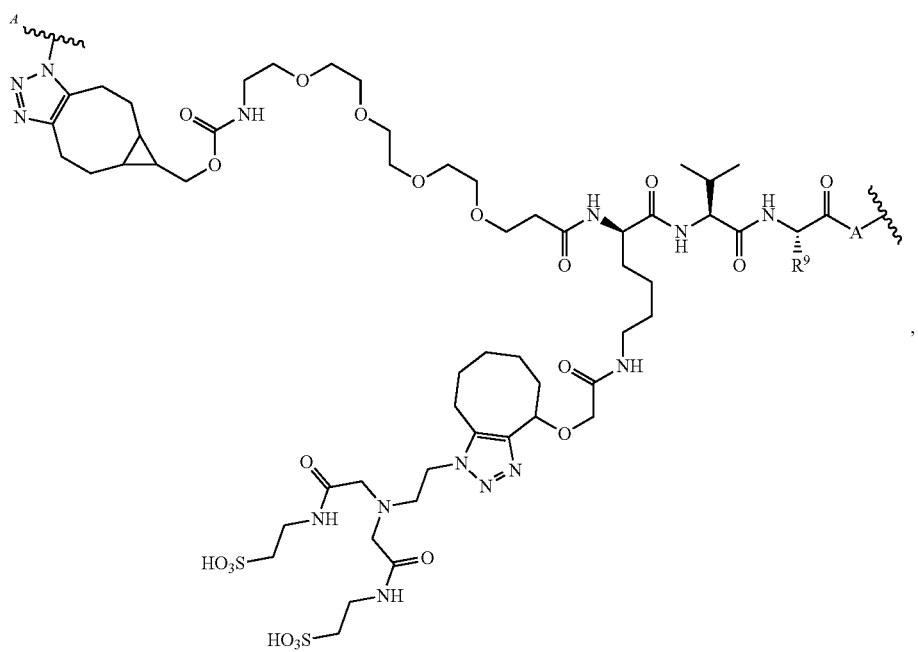

-continued

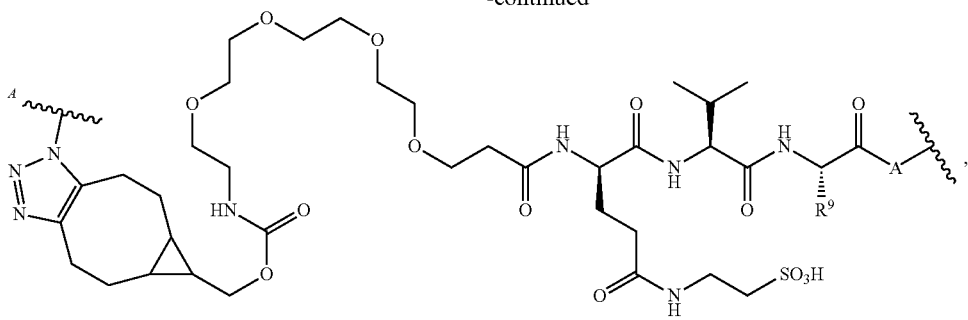

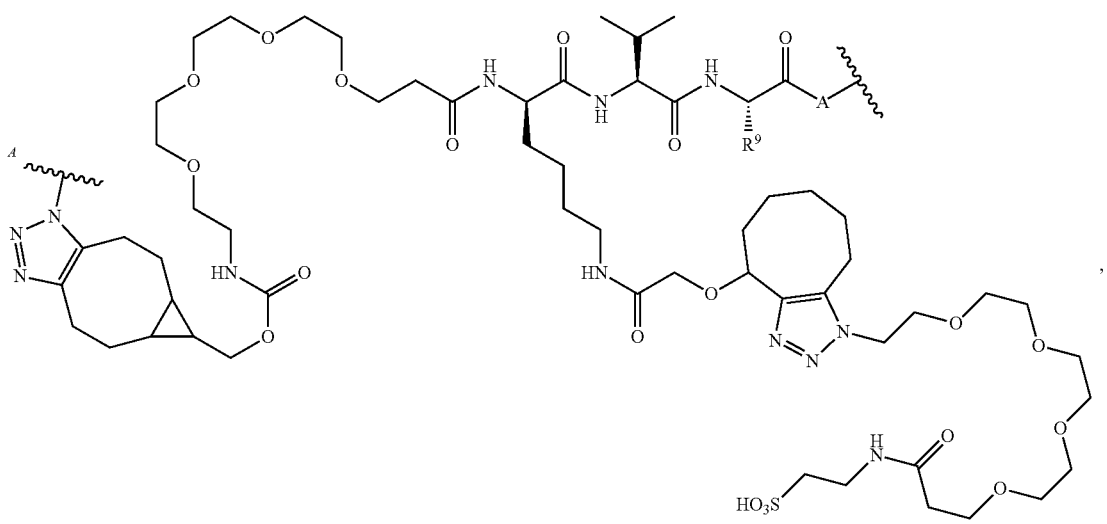

or a pharmaceutically acceptable salt, solvate, or stereoisomeric form thereof, or a regioisomer thereof, or mixture of regioisomers thereof, wherein:

each ⁀§⁀ is a bond to the binding agent;
each ⁀§⁀ is a bond to the payload;
$R^9$ is —$CH_3$ or —$(CH_2)_3N(H)C(O)NH_2$; and
A is —O—, —N(H)—,

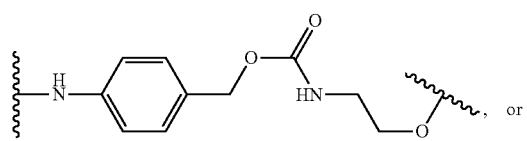 or

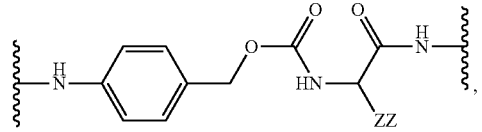

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent.

In some embodiments, the linker is:

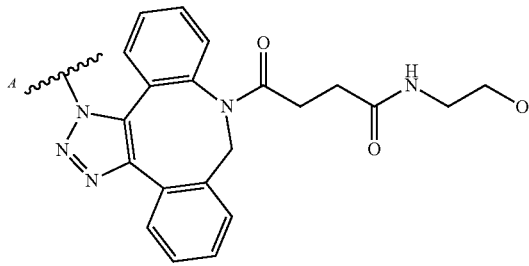

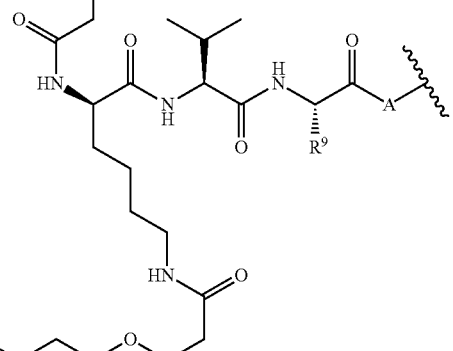

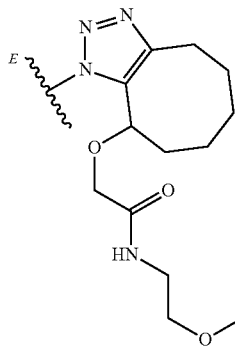

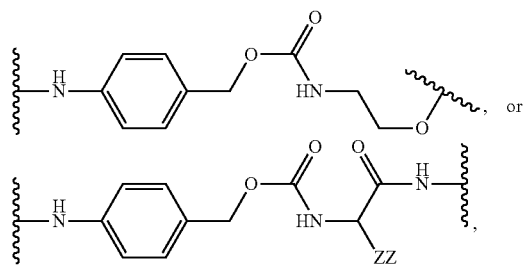

or a pharmaceutically acceptable salt, solvate, or stereoisomeric form thereof, or a regioisomer thereof, or mixture of regioisomers thereof, wherein:

each $-\xi^A$ is a bond to the binding agent;

each $-\xi-$ is a bond to the payload;

each $-\xi^E$ is a bond to the enhancement group;

each $R^9$ is —$CH_3$ or —$(CH_2)_3N(H)C(O)NH_2$; and each A is —O—, —N(H)—, where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_m$—C(O)NH—$(CH_2)_{1-5}SO_3H$, —$(CH_2)_n$—N($(CH_2)_{1-5}C(O)NH(CH_2)_{1-5}SO_3H)_2$, —$(CH_2)_n$—C(O)N($(CH_2)_{1-5}C(O)NH(CH_2)_{1-5}SO_3H)_2$, or —$(CH_2CH_2O)_m$—C(O)N($(CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)NH—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N($(CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N($(CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N($(CH_2)_{1-5}C(O)NH(CH_2)_{1-5}SO_3H)_2$, wherein m is 1, 2, 3, 4, or 5.

In some embodiments, the linker is:

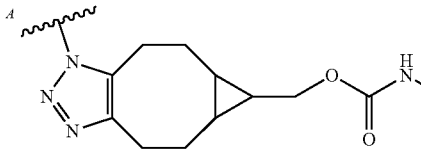

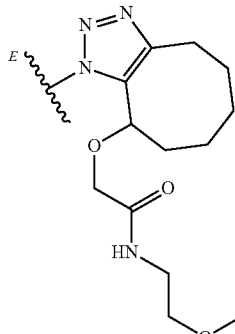

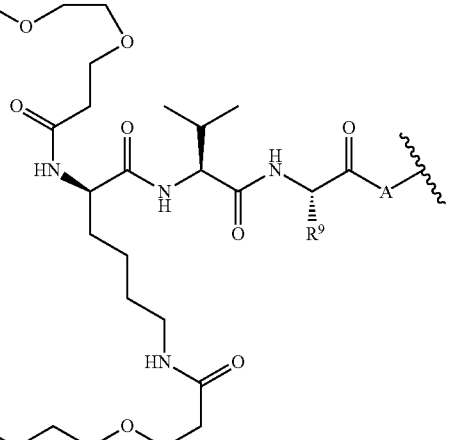

or a pharmaceutically acceptable salt, solvate, or stereoisomeric form thereof, or a regioisomer thereof, or mixture of regioisomers thereof, wherein:

each $-\xi^A-$ is a bond to the binding agent;

each $-\xi-$ is a bond to the payload;

each $R^9$ is —$CH_3$ or —$(CH_2)_3N(H)C(O)NH_2$; and each A is —O—, —N(H)—,

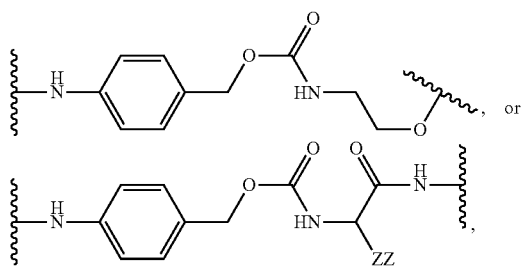

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_mC(O)NH$—$(CH_2)_{1-5}SO_3H$, —$(CH_2)_n$—N($(CH_2)_{1-5}C(O)NH(CH_2)_{1-5}SO_3H)_2$, —$(CH_2)_n$—C(O)N($(CH_2)_{1-5}C(O)NH(CH_2)_{1-5}SO_3H)_2$, or —$(CH_2CH_2O)_mC(O)N((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)NH—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N($(CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N($(CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N($(CH_2)_{1-5}C(O)NH(CH_2)_{1-5}SO_3H)_2$, wherein m is 1, 2, 3, 4, or 5.

In some embodiments, the linker is:
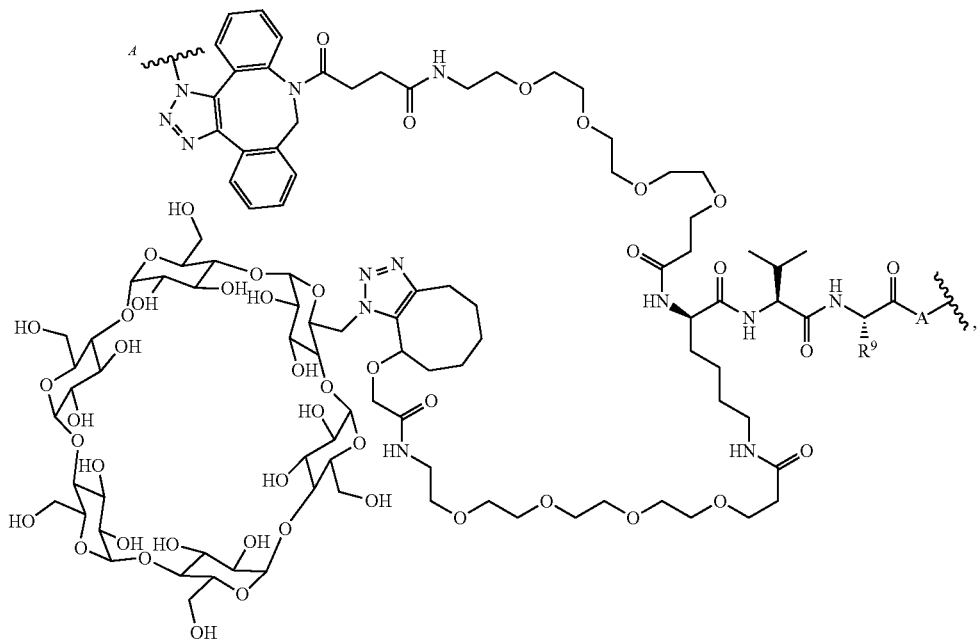
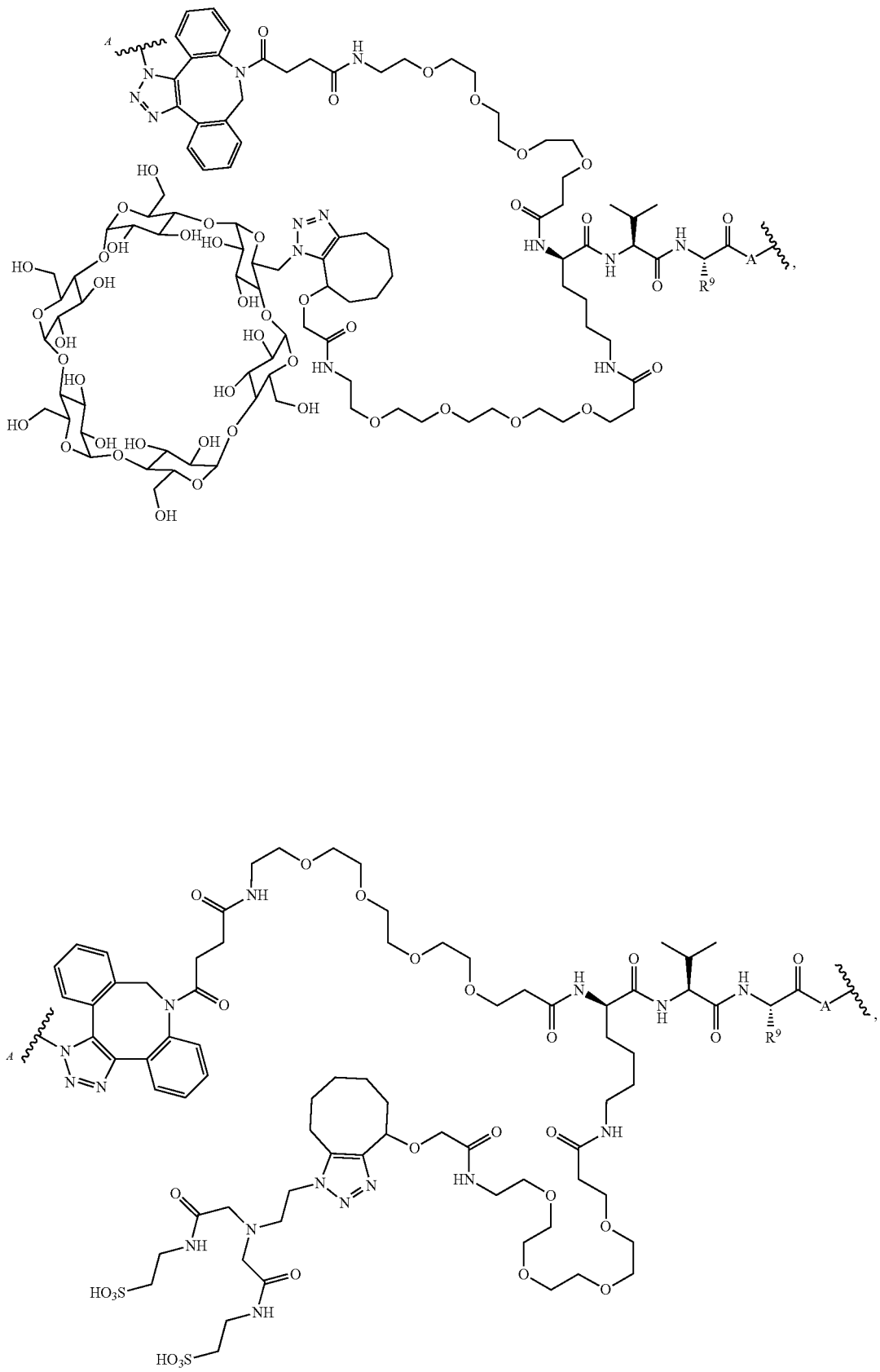

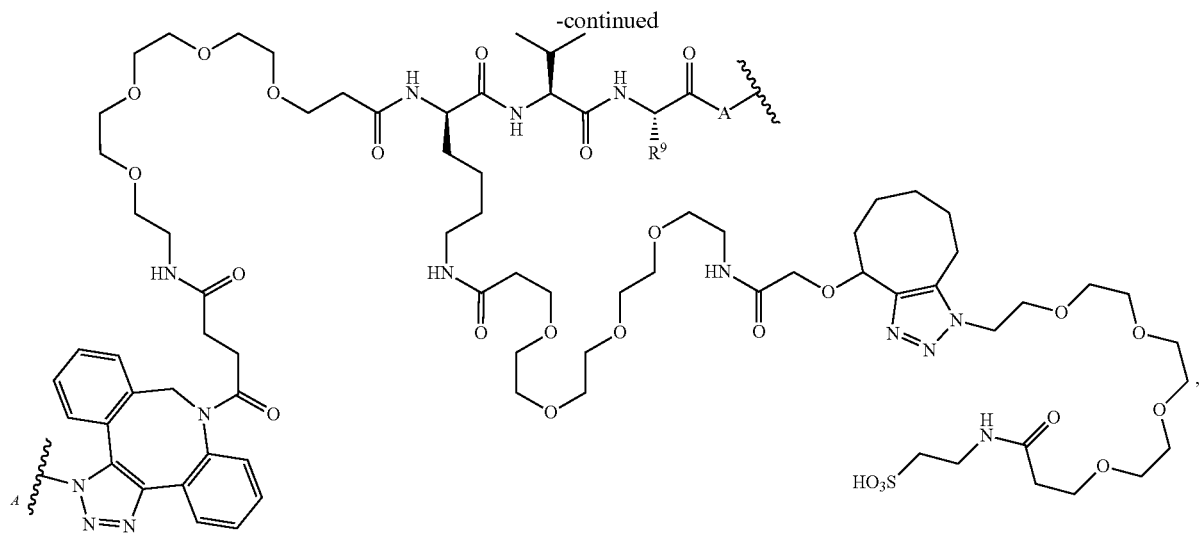

or a pharmaceutically acceptable salt, solvate, or stereoisomeric form thereof, or a regioisomer thereof, or mixture of regioisomers thereof, wherein:

each ⁓⁓⁓ is a bond to the binding agent;
each ⁓⁓⁓ is a bond to the payload;
$R^9$ is —$CH_3$ or —$(CH_2)_3N(H)C(O)NH_2$; and
A is —O—, —N(H)—,

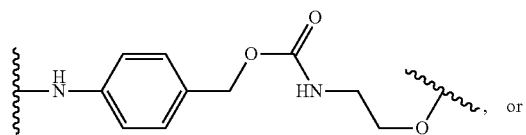

or

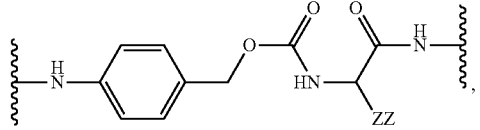

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent.

In some embodiments, the linker is:

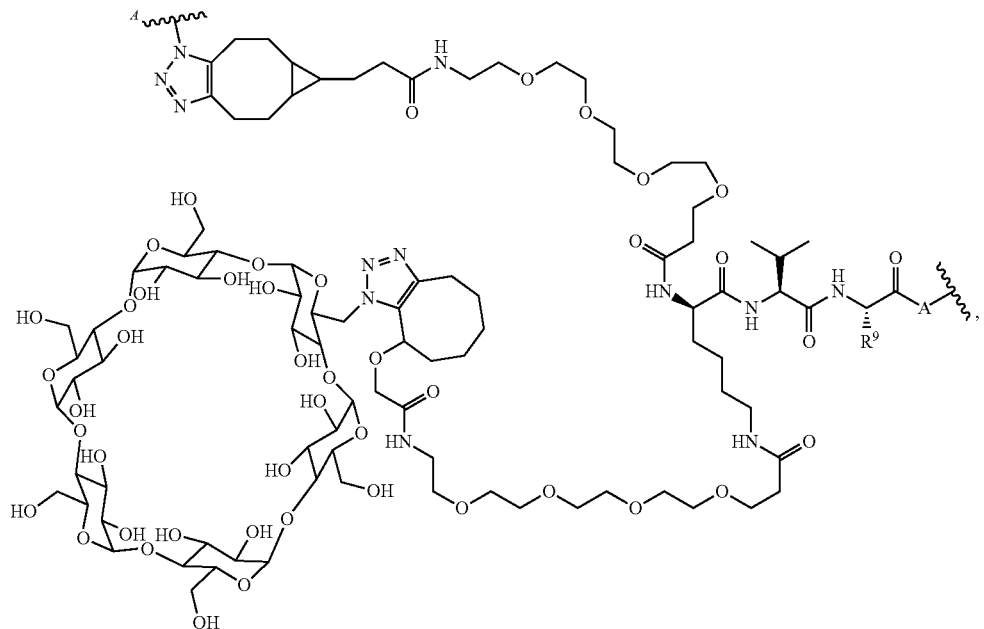

-continued

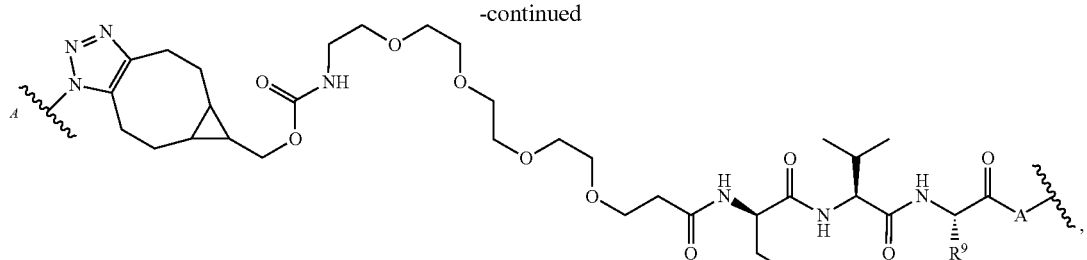

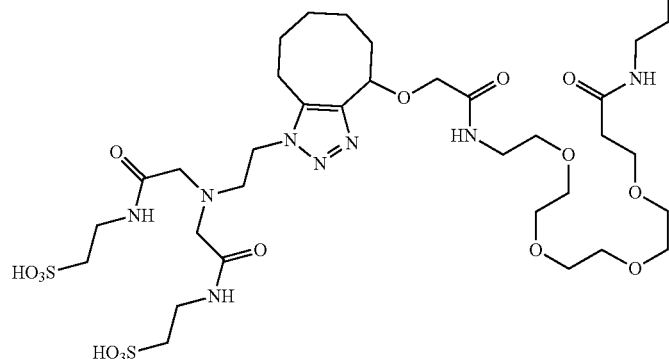

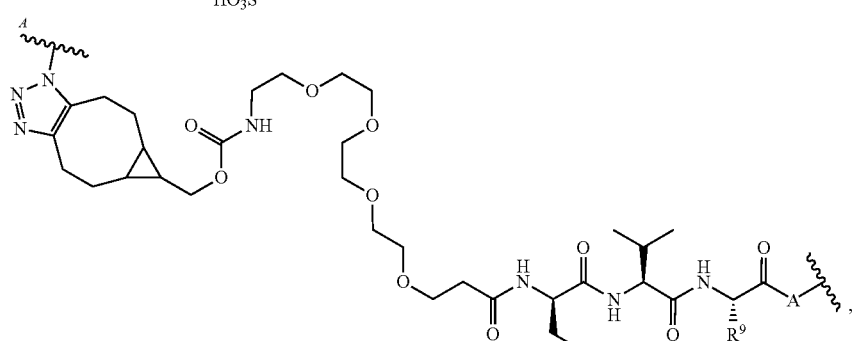

or a pharmaceutically acceptable salt, solvate, or stereoisomeric form thereof, or a regioisomer thereof, or mixture of regioisomers thereof, wherein:

each ⁀A⁀ is a bond to the binding agent;

each ⁀⁀ is a bond to the payload;

R⁹ is —CH₃ or —(CH₂)₃N(H)C(O)NH₂; and

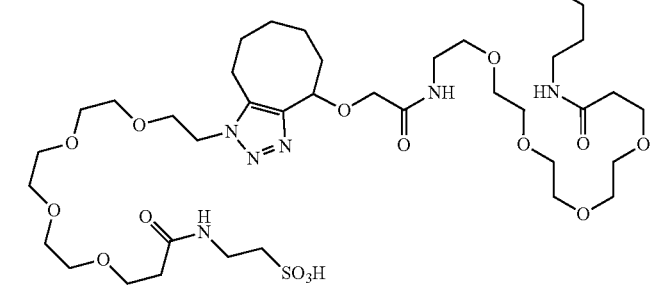 or

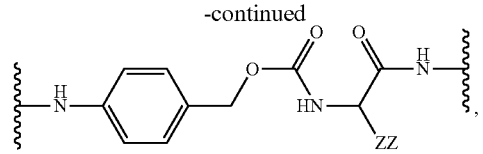

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent.

The above linkers are useful for providing the following conjugates.

In some embodiments, the conjugate is:

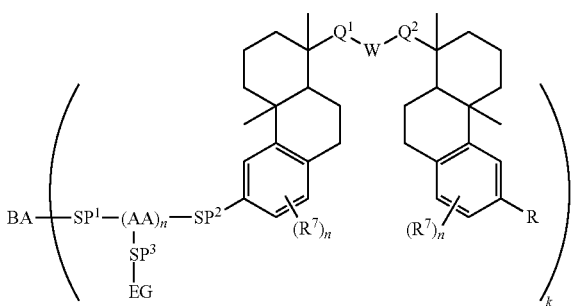

or a pharmaceutically acceptable salt, solvate, or stereoisomeric form thereof, or a regioisomer thereof, wherein:
BA is a binding agent;
each $SP^1$, $SP^2$, and $SP^3$ is a spacer group as described above, where $SP^3$ is linked to one AA of $(AA)_n$;
EG is an enhancement agent;
k is an integer from 1 to 30;
R is —H, $R^1$, or $R^2$; and
$Q^1$, $Q^2$, W, $R^1$, $R^2$, $R^3$, $R^4$, $R^5$, $R^6$, $R^7$, X, Y, Z, and n are as described in the context of Formula I;
each $R^9$ is —$CH_3$ or —$(CH_2)_3N(H)C(O)NH_2$; and
each A, independently in each instance, is —O—, —N(H)—,

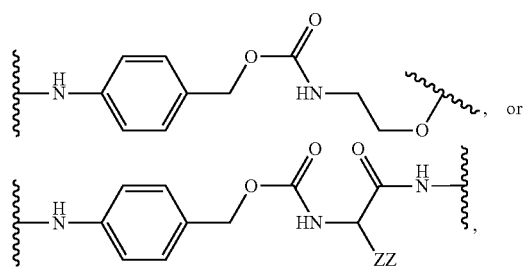

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_m$—C(O)NH—$(CH_2)_{1-5}SO_3H$, —$(CH_2)_n$—N$((CH_2)_{1-5}C(O)NH(CH_2)_{1-5}SO_3H)_2$, —$(CH_2)_n$—C(O)N$((CH_2)_{1-5}C(O)NH(CH_2)_{1-5}SO_3H)_2$, or —$(CH_2CH_2O)_m$—C(O)N$((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_mC(O)NH$—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N$((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N$((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N$((CH_2)_{1-5}C(O)NH(CH_2)_{1-5}SO_3H)_2$, wherein m is 1, 2, 3, 4, or 5. In certain embodiments, R is $R^1$.

In some embodiments, the conjugate is:

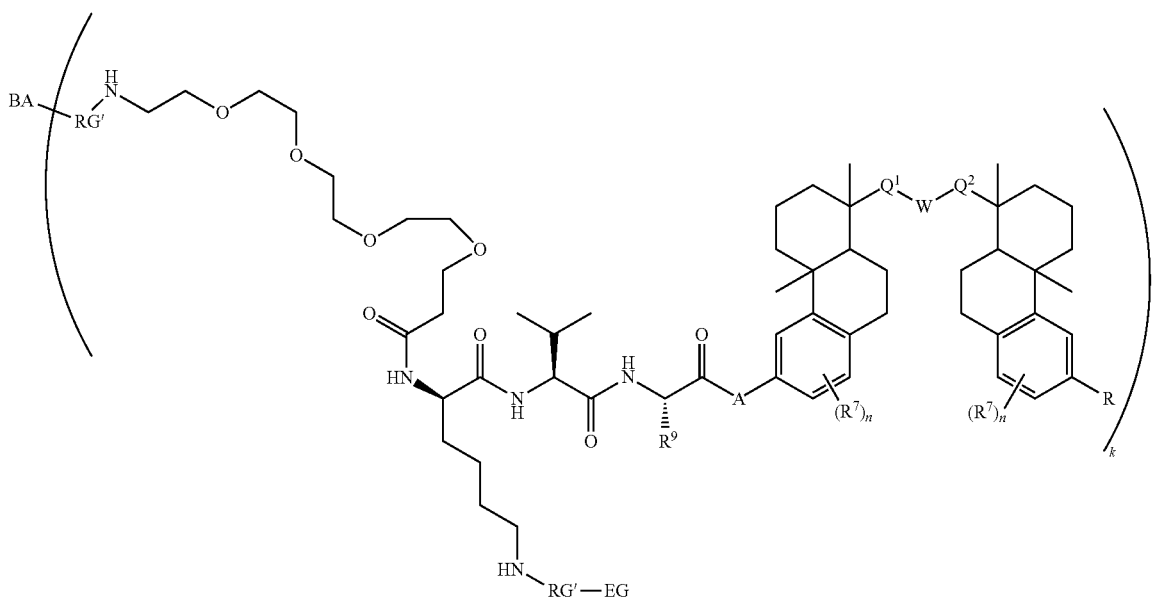

or a pharmaceutically acceptable salt, solvate, or stereoisomeric form thereof, or a regioisomer thereof, wherein:

BA is a binding agent;
each RG' is the residue of a reactive group, as described herein;
EG is an enhancement agent;
k is an integer from 1 to 30;
R is —H, $R^1$, or $R^2$; and
$Q^1$, $Q^2$, W, $R^1$, $R^2$, $R^3$, $R^4$, $R^5$, $R^6$, $R^7$, X, Y, Z, and n are as described in the context of Formula I;
each $R^9$ is —$CH_3$ or —$(CH_2)_3N(H)C(O)NH_2$; and
each A is —O—, —N(H)—,

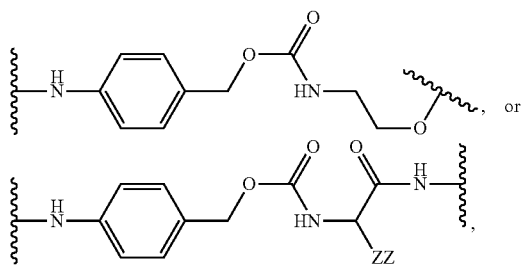

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_m$C(O)NH—$(CH_2)_{1-5}SO_3H$, —$(CH_2)_n$—N(($CH_2)_{1-5}$C(O)NH($CH_2)_{1-5}SO_3H)_2$, —$(CH_2)_n$—C(O)N(($CH_2)_{1-5}$C(O)NH($CH_2)_{1-5}SO_3H)_2$, or —$(CH_2CH_2O)_m$C(O)N(($CH_2)_{1-5}$C(O)NH($CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)NH—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N(($CH_2)_{1-5}$C(O)NH($CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N(($CH_2)_{1-5}$C(O)NH($CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N(($CH_2)_{1-5}$C(O)NH($CH_2)_{1-5}SO_3H)_2$, wherein m is 1, 2, 3, 4, or 5. In certain embodiments, R is $R^1$.

In some embodiments, the conjugate is:

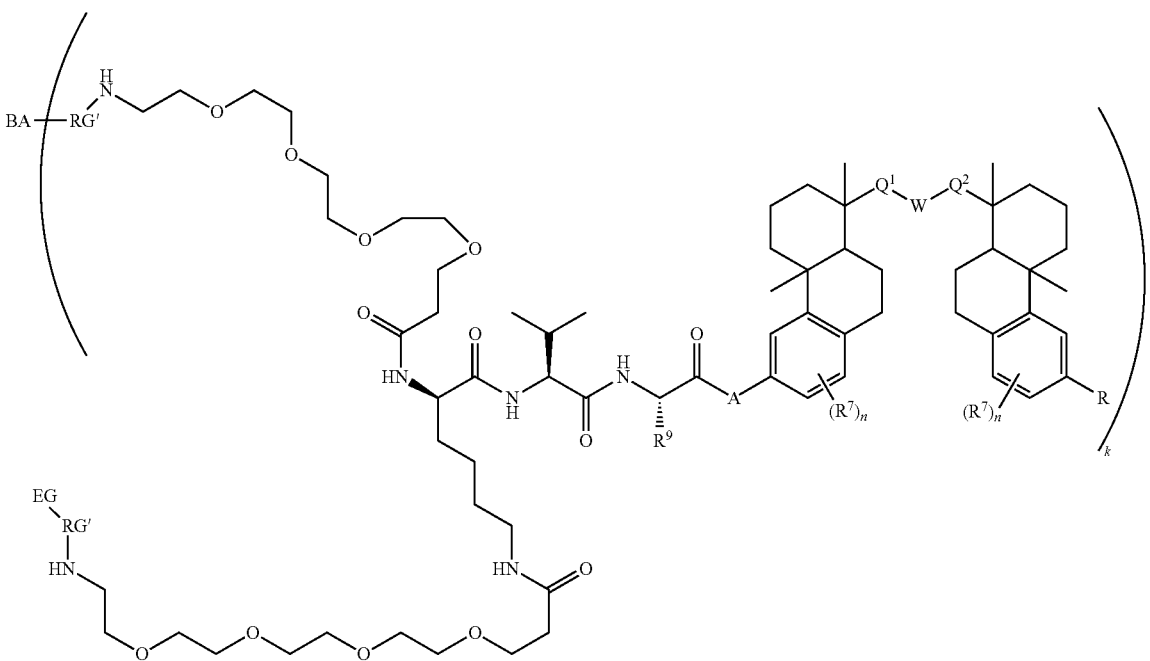

or a pharmaceutically acceptable salt, solvate, or stereoisomeric form thereof, or a regioisomer thereof, wherein:

BA is a binding agent;
each RG' is the residue of a reactive group, as described herein;
EG is an enhancement agent;
k is an integer from 1 to 30;
R is —H, $R^1$, or $R^2$; and
$Q^1$, $Q^2$, W, $R^1$, $R^2$, $R^3$, $R^4$, $R^5$, $R^6$, $R^7$, X, Y, Z, and n are as described in the context of Formula I;
each $R^9$ is —$CH_3$ or —$(CH_2)_3N(H)C(O)NH_2$; and
each A is —O—, —N(H)—,

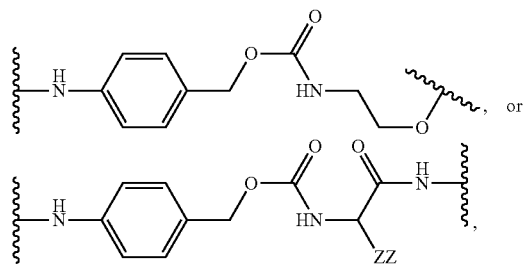

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_mC(O)NH$—$(CH_2)_{1-5}SO_3H$, —$(CH_2)_n$—N$((CH_2)_{1-5}C(O)NH(CH_2)_{1-5}SO_3H)_2$, —$(CH_2)_n$—C(O)N$((CH_2)_{1-5}C(O)NH(CH_2)_{1-5}SO_3H)_2$, or —$(CH_2CH_2O)_m$—C(O)N$((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_mC(O)NH$—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N$((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N$((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N$((CH_2)_{1-5}C(O)NH(CH_2)_{1-5}SO_3H)_2$, wherein m is 1, 2, 3, 4, or 5. In certain embodiments, R is $R^1$.

In some embodiments, the conjugate is:

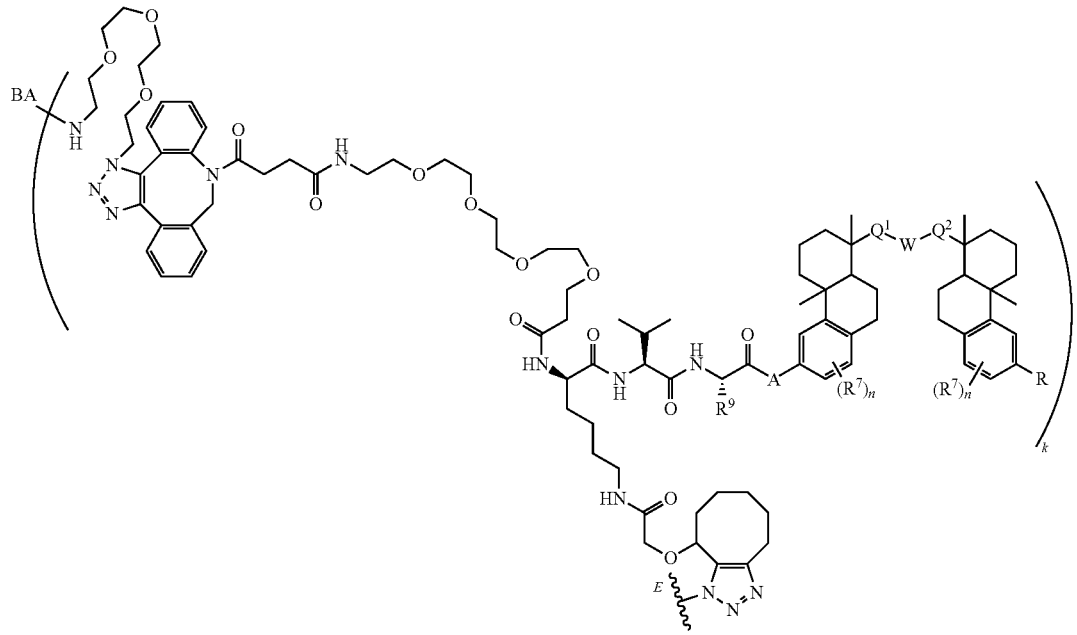

or a pharmaceutically acceptable salt, solvate, or stereoisomeric form thereof, or a regioisomer thereof, wherein:
BA is a binding agent;
k is an integer from 1 to 30;
R is —H, $R^1$, or $R^2$; and
$Q^1$, $Q^2$, W, $R^1$, $R^2$, $R^3$, $R^4$, $R^5$, $R^6$, $R^7$, X, Y, Z, and n are as described in the context of Formula I;

each -ξ-E is a bond to the enhancement group;
each $R^9$ is —$CH_3$ or —$(CH_2)_3N(H)C(O)NH_2$; and
each A is —O—, —N(H)—,

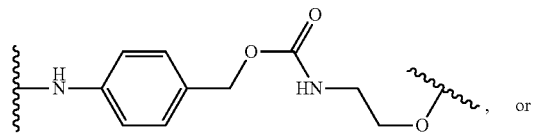, or

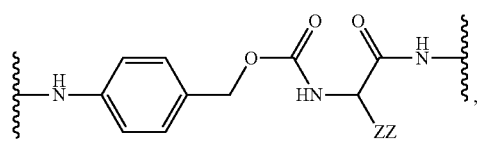, where ZZ is hydrogen, or a side chain for an amino acid as discussed elsewhere herein. For example, in one embodiment, ZZ is $C_{1-6}$ alkyl. By way of further example, in one embodiment, ZZ is $C_{1-8}$ heteroalkyl.

In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_m$—C(O)NH—$(CH_2)_{1-5}SO_3H$, —$(CH_2)_n$—N(($CH_2)_{1-5}C(O)NH(CH_2)_{1-5}SO_3H)_2$, —$(CH_2)_n$—C(O)N(($CH_2)_{1-5}C(O)NH(CH_2)_{1-5}SO_3H)_2$, or —$(CH_2CH_2O)_m$—C(O)N(($CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_m$C(O)NH—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N(($CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N(($CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N(($CH_2)_{1-5}C(O)NH(CH_2)_{1-5}SO_3H)_2$, wherein m is 1, 2, 3, 4, or 5. In certain embodiments, R is $R^1$.

In some embodiments, the conjugate is:

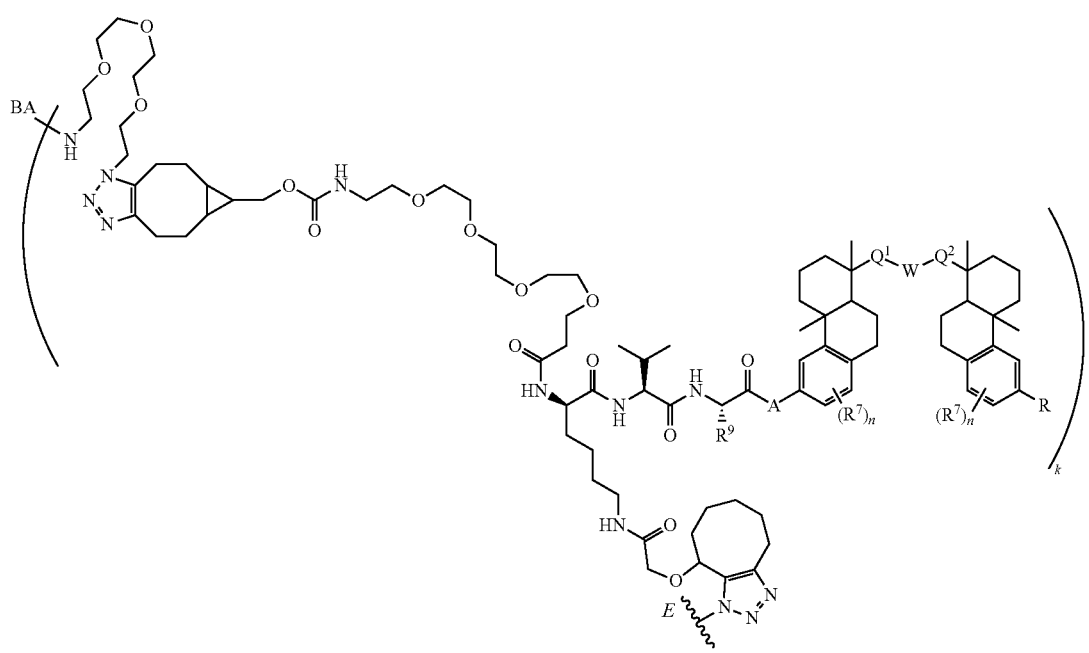

or a pharmaceutically acceptable salt, solvate, or stereoisomeric form thereof, or a regioisomer thereof, wherein:

BA is a binding agent;

k is an integer from 1 to 30;

R is —H, $R^1$, or $R^2$; and $Q^1$, $Q^2$, W, $R^1$, $R^2$, $R^3$, $R^4$, $R^5$, $R^6$, $R^7$, X, Y, Z, and n are as described in the context of Formula I;

each ⁓ξ-E is a bond to the enhancement group;

each $R^9$ is —$CH_3$ or —$(CH_2)_3N(H)C(O)NH_2$; and each A is —O—, —N(H)—,

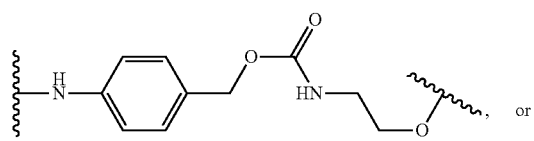

or

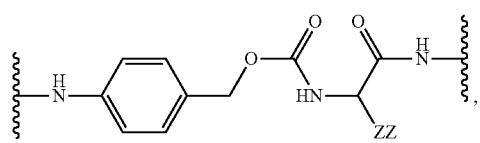

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_mC(O)NH$—$(CH_2)_{1-5}SO_3H$, —$(CH_2)_n$—N($(CH_2)_{1-5}C(O)NH(CH_2)_{1-5}SO_3H)_2$, —$(CH_2)_n$—C(O)N($(CH_2)_{1-5}C(O)NH(CH_2)_{1-5}SO_3H)_2$, or —$(CH_2CH_2O)_mC(O)N((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)NH—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N($(CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N($(CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N($(CH_2)_{1-5}C(O)NH(CH_2)_{1-5}SO_3H)_2$, wherein m is 1, 2, 3, 4, or 5. In certain embodiments, R is $R^1$.

In some embodiments, the conjugate is:

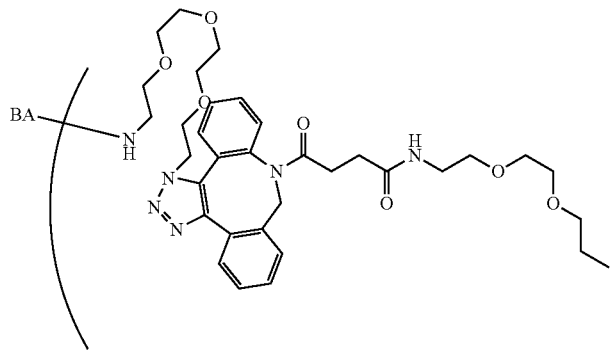

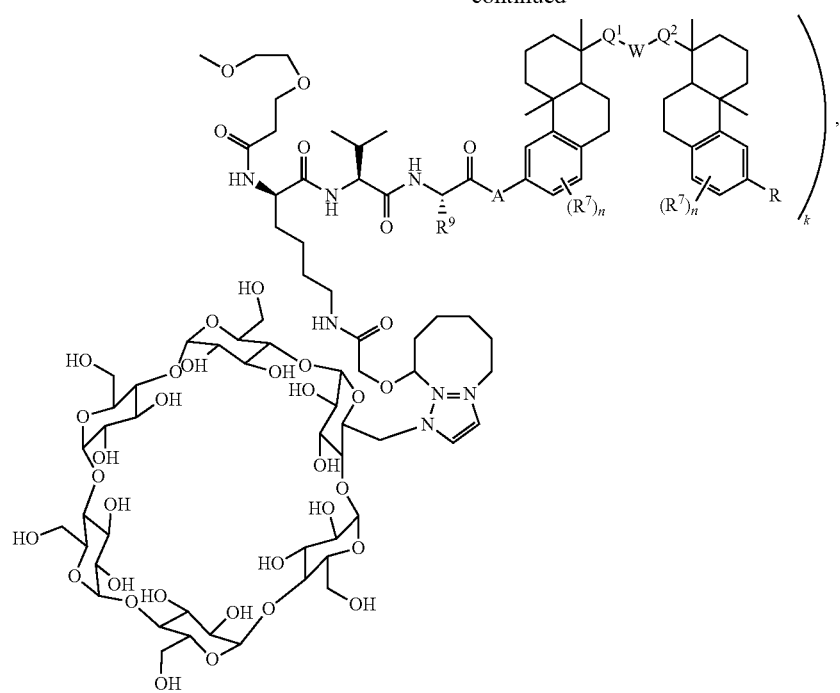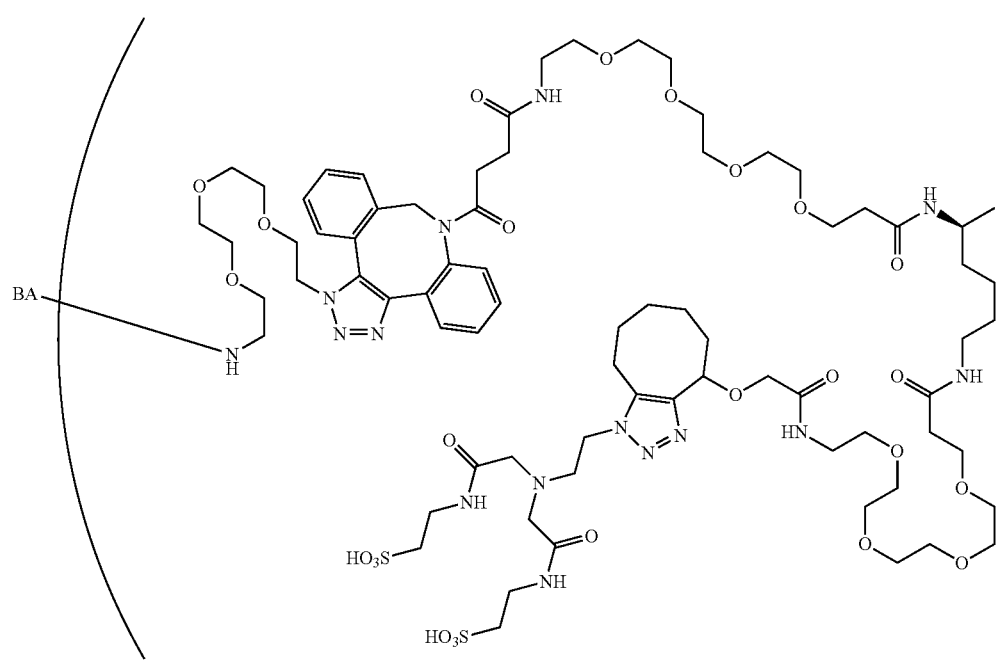

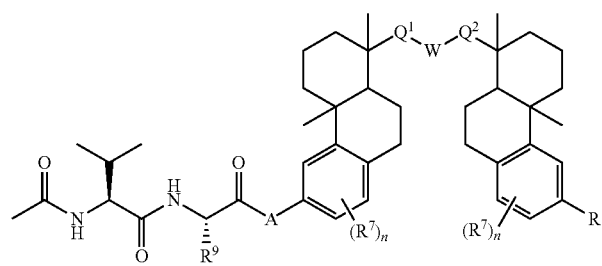
-continued
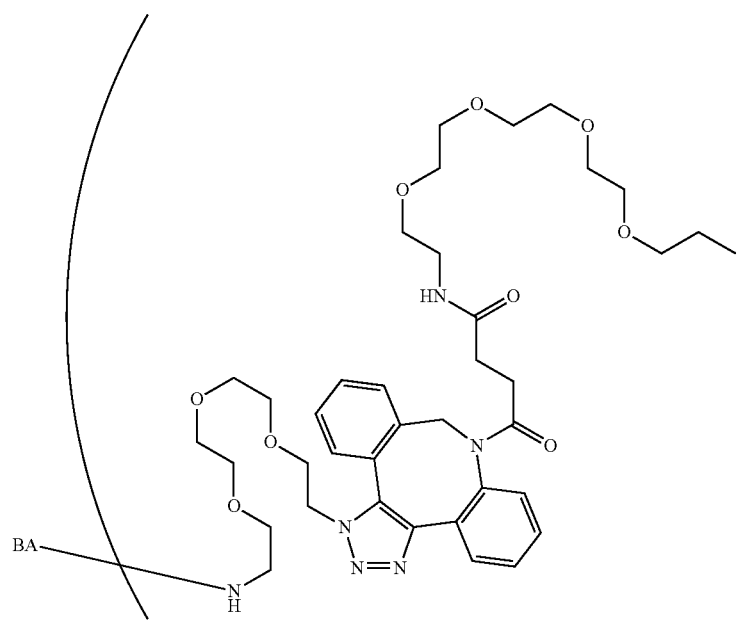

-continued
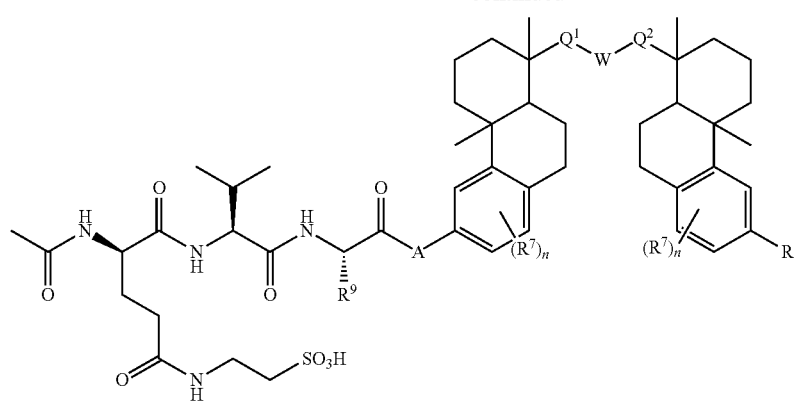
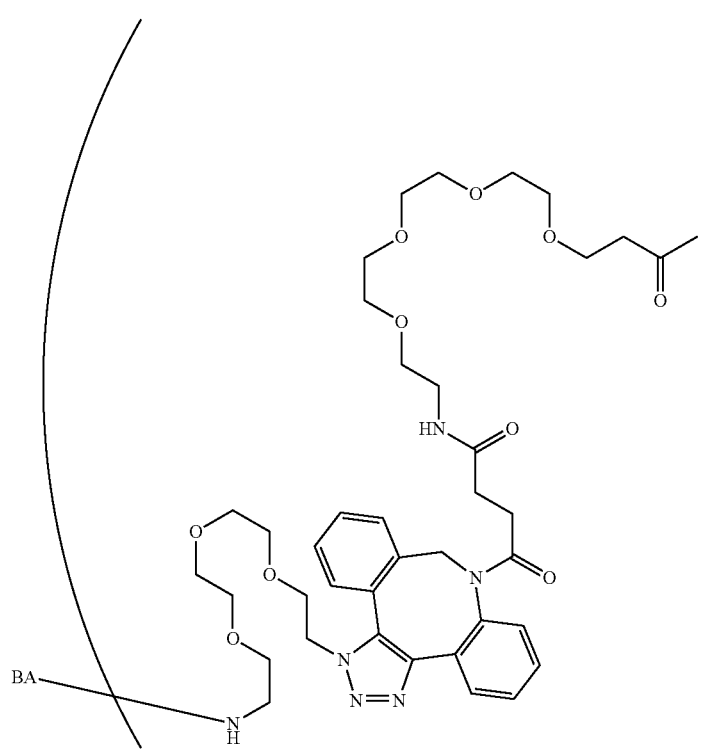

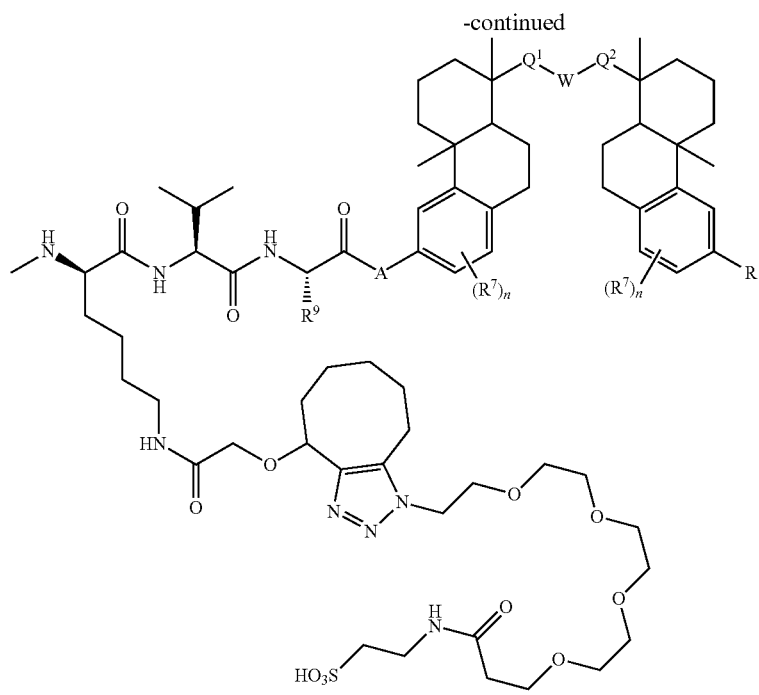

or a pharmaceutically acceptable salt, solvate, or stereoisomeric form thereof, or a regioisomer thereof, wherein:

BA is a binding agent;

k is an integer from 1 to 30;

R is —H, $R^1$, or $R^2$; and $Q^1$, $Q^2$, W, $R^1$, $R^2$, $R^3$, $R^4$, $R^5$, $R^6$, $R^7$, X, Y, Z, and n are as described in the context of Formula I;

each $R^9$ is —$CH_3$ or —$(CH_2)_3N(H)C(O)NH_2$; and each A is —O—, —N(H)—,

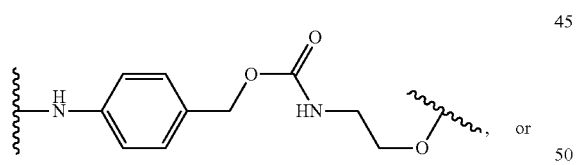 or

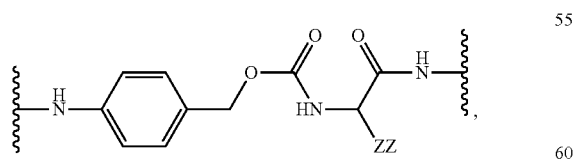

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In some embodiments, the conjugate is:
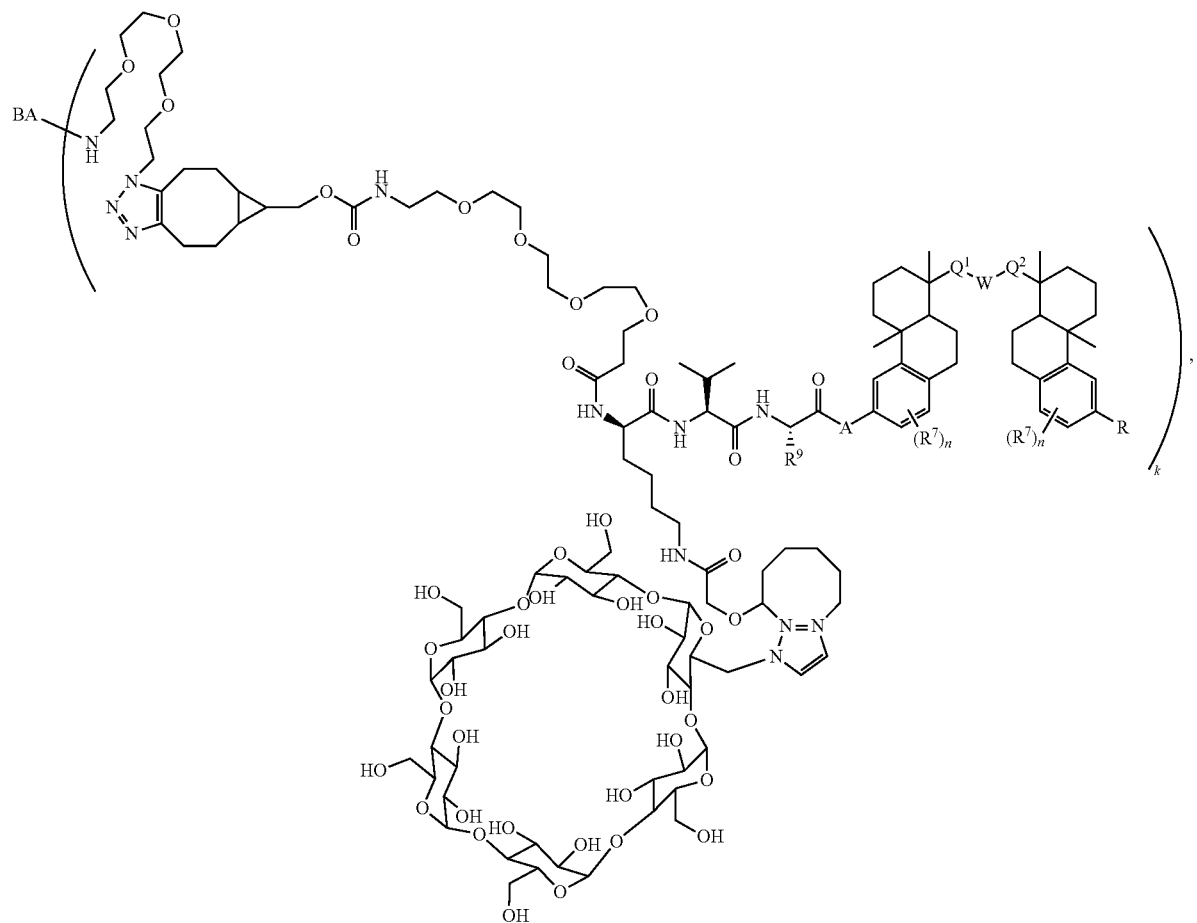
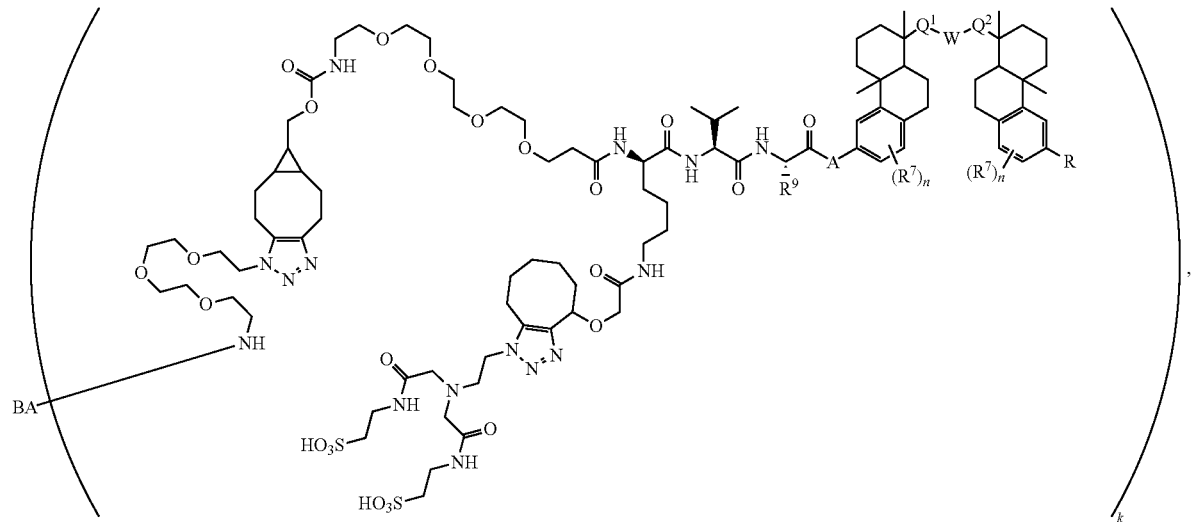

-continued

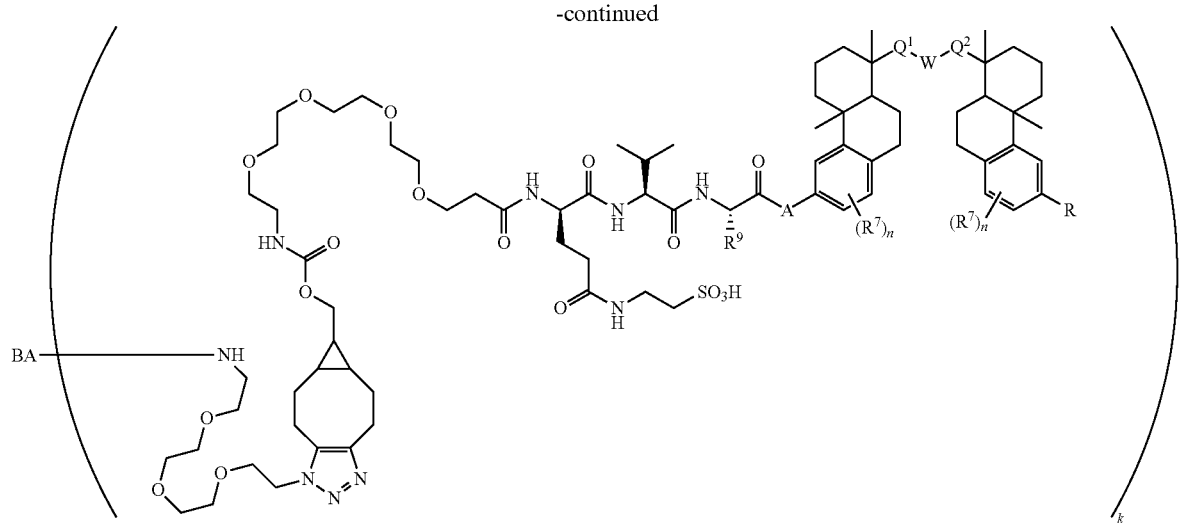

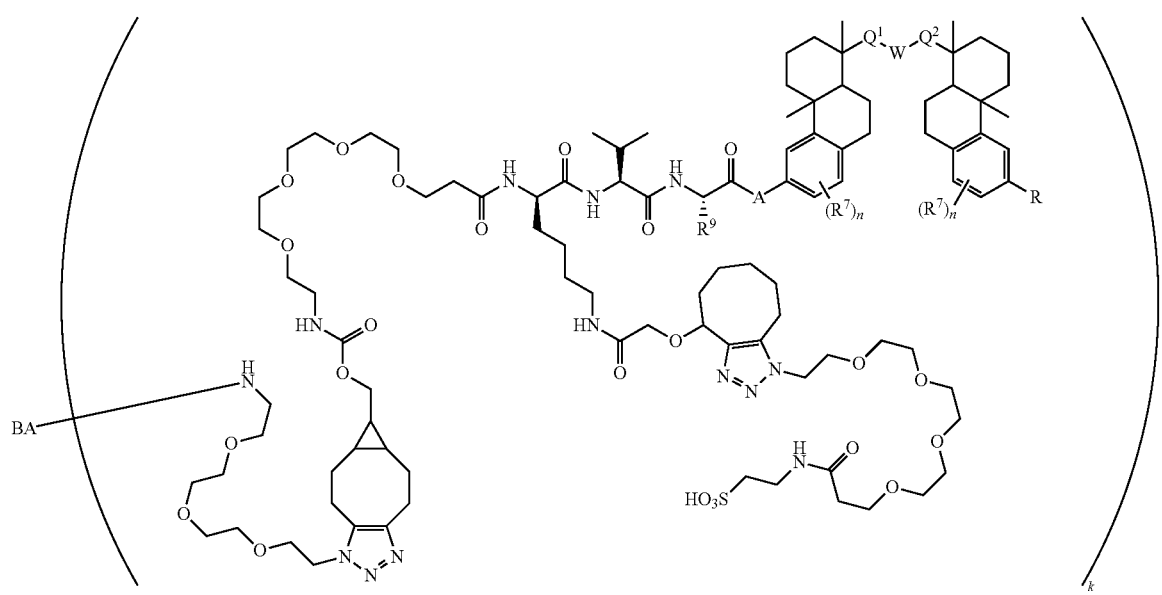

or a pharmaceutically acceptable salt, solvate, or stereoisomeric form thereof, or a regioisomer thereof, wherein:
BA is a binding agent;
k is an integer from 1 to 30;
R is —H, $R^1$, or $R^2$; and
$Q^1$, $Q^2$, W, $R^1$, $R^2$, $R^3$, $R^4$, $R^5$, $R^6$, $R^7$, X, Y, Z, and n are as described in the context of Formula I;
each $R^9$ is —CH$_3$ or —(CH$_2$)$_3$N(H)C(O)NH$_2$; and
each A is —O—, —N(H)—,

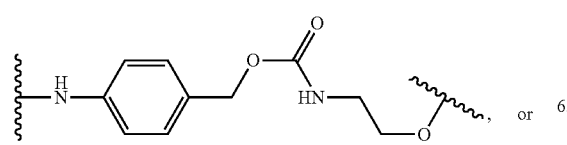 or

-continued

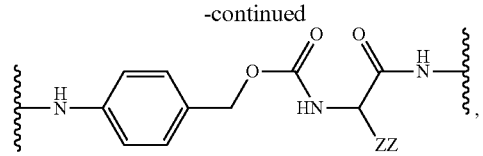

where ZZ is hydrogen, or a side chain for an amino acid as discussed elsewhere herein. For example, in one embodiment, ZZ is C$_{1-6}$ alkyl. By way of further example, in one embodiment, ZZ is C$_{1-6}$ heteroalkyl.

In certain embodiments, R is $R^1$.

In some embodiments, the conjugate is:

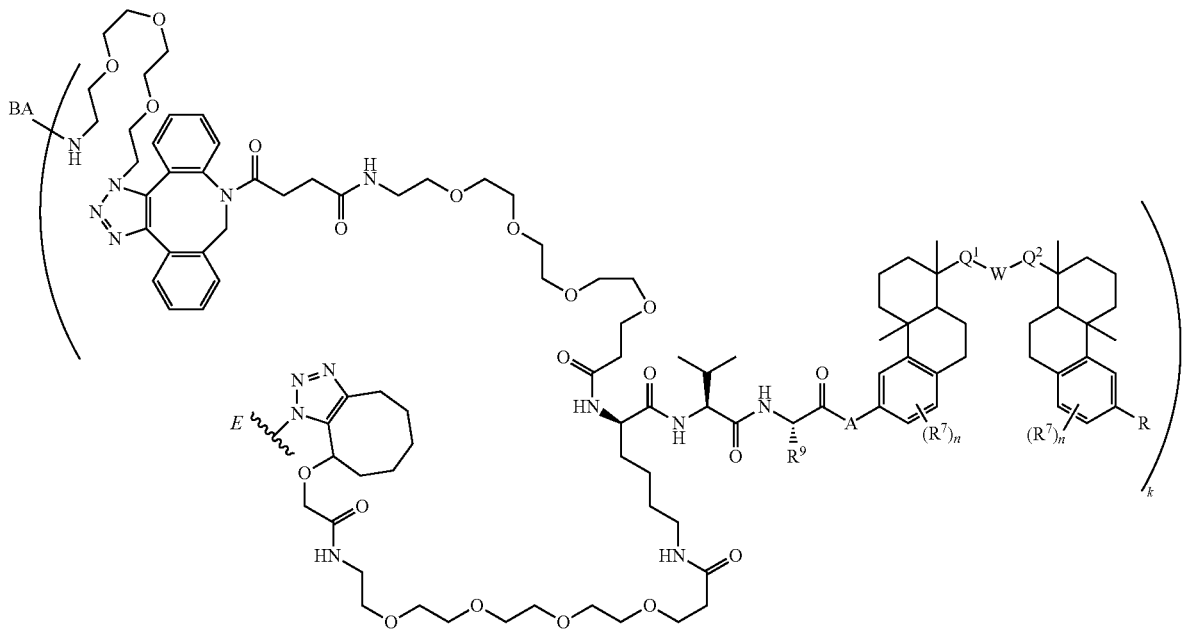

or a pharmaceutically acceptable salt, solvate, or stereoisomeric form thereof, or a regioisomer thereof, wherein:
  BA is a binding agent;
  k is an integer from 1 to 30;
  R is —H, $R^1$, or $R^2$; and
  $Q^1$, $Q^2$, W, $R^1$, $R^2$, $R^3$, $R^4$, $R^5$, $R^6$, $R^7$, X, Y, Z, and n are as described in the context of Formula I;
  each ⸺ξᴱ⸺ is a bond to the enhancement group;
  each $R^9$ is —$CH_3$ or —$(CH_2)_3N(H)C(O)NH_2$; and
  each A is —O—, —N(H)—,

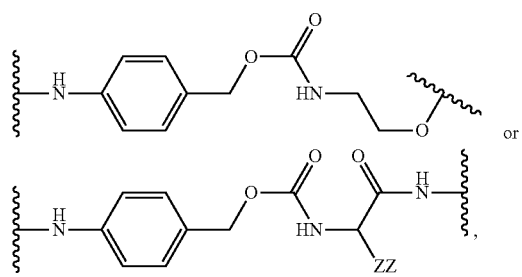

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_m$—C(O)NH—$(CH_2)_{1-5}SO_3H$, —$(CH_2)_n$—N$((CH_2)_{1-5}C(O)NH(CH_2)_{1-5}SO_3H)_2$, —$(CH_2)_n$—C(O)N$((CH_2)_{1-5}C(O)NH(CH_2)_{1-5}SO_3H)_2$, or —$(CH_2CH_2O)_m$—C(O)N$((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_mC(O)NH$—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N$((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N$((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N$((CH_2)_{1-5}C(O)NH(CH_2)_{1-5}SO_3H)_2$, wherein m is 1, 2, 3, 4, or 5. In certain embodiments, R is $R^1$.

In some embodiments, the conjugate is:

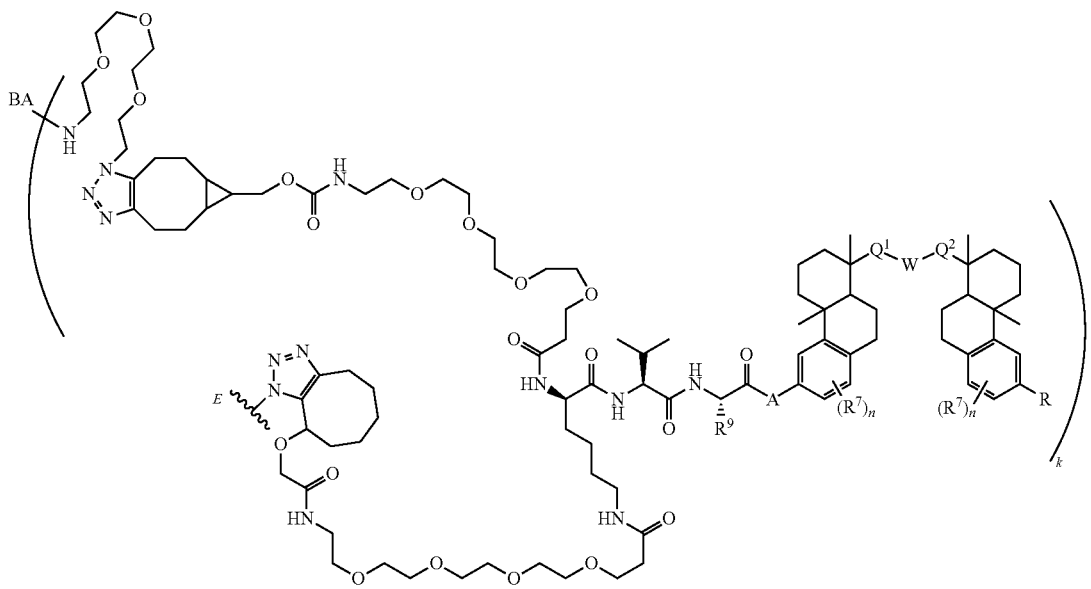

or a pharmaceutically acceptable salt, solvate, or stereoisomeric form thereof, or a regioisomer thereof, wherein:
BA is a binding agent;
k is an integer from 1 to 30;
R is —H, $R^1$, or $R^2$; and
$Q^1$, $Q^2$, W, $R^1$, $R^2$, $R^3$, $R^4$, $R^5$, $R^6$, $R^7$, X, Y, Z, and n are as described in the context of Formula I;
each -ξ-E is a bond to the enhancement group;
each $R^9$ is —$CH_3$ or —$(CH_2)_3N(H)C(O)NH_2$; and
each A is —O—, —N(H)—,

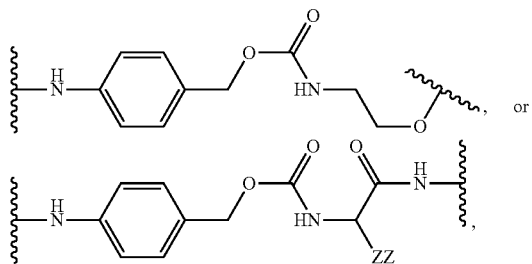

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin.

In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_m$—C(O)NH—$(CH_2)_{1-5}SO_3H$, —$(CH_2)_n$—N$((CH_2)_{1-5}C(O)NH(CH_2)_{1-5}SO_3H)_2$, —$(CH_2)_n$—C(O)N$((CH_2)_{1-5}C(O)NH(CH_2)_{1-5}SO_3H)_2$, or —$(CH_2CH_2O)_m$—C(O)N$((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl, heteroalkyl, alkylenyl, or heteroalkylenyl sulfonic acid is —$(CH_2)_{1-5}SO_3H$. In another embodiment, the alkyl, heteroalkyl, alkylenyl, or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_mC(O)NH$—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N$((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N$((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N$((CH_2)_{1-5}C(O)NH(CH_2)_{1-5}SO_3H)_2$, wherein m is 1, 2, 3, 4, or 5. In certain embodiments, R is $R^1$.

In some embodiments, the conjugate is:
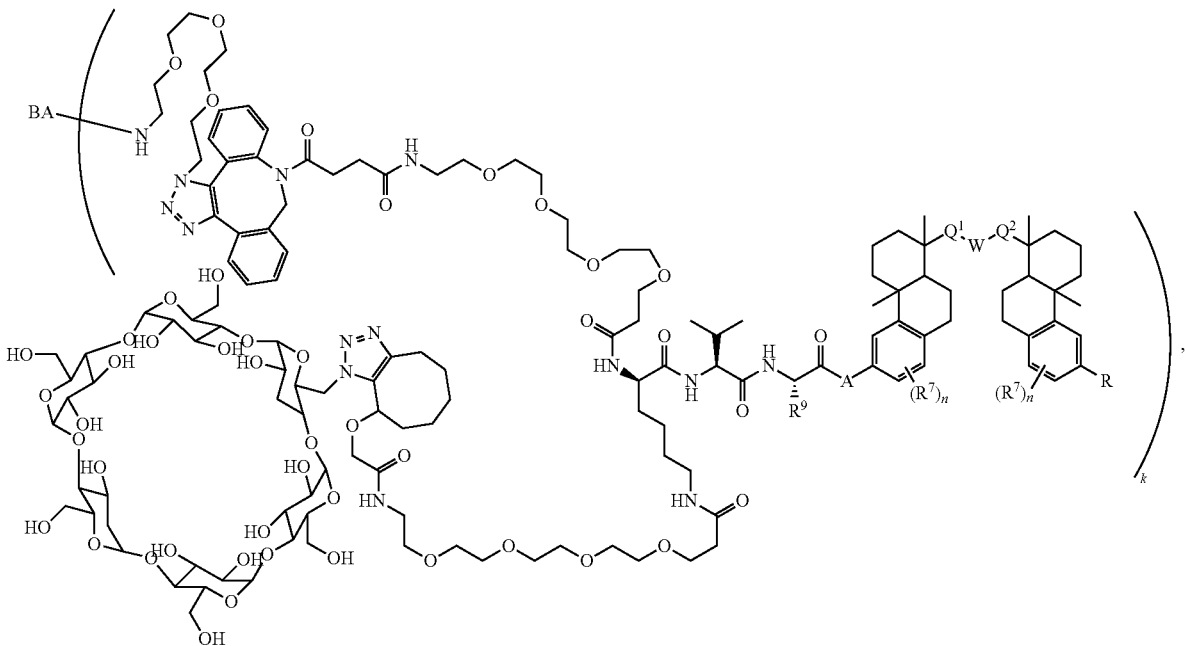
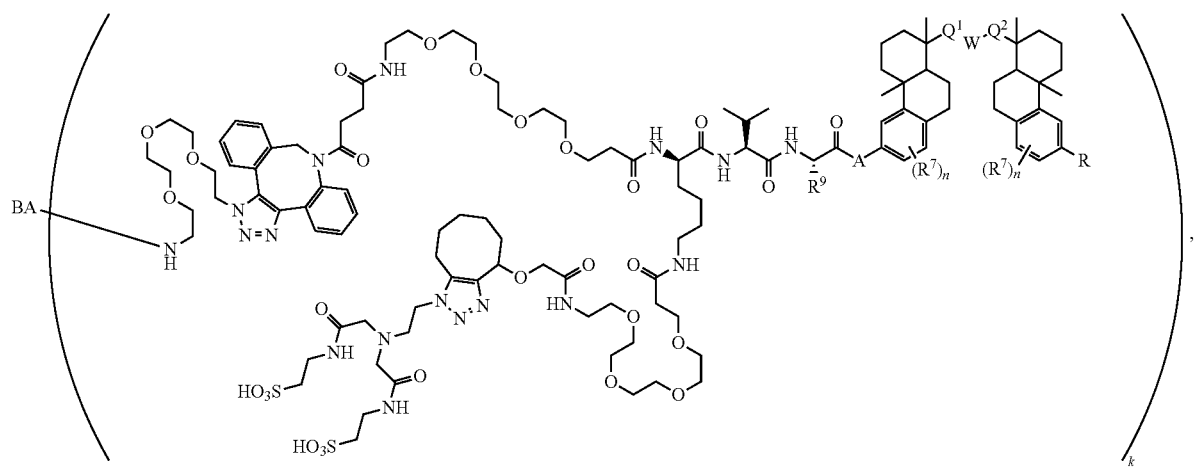
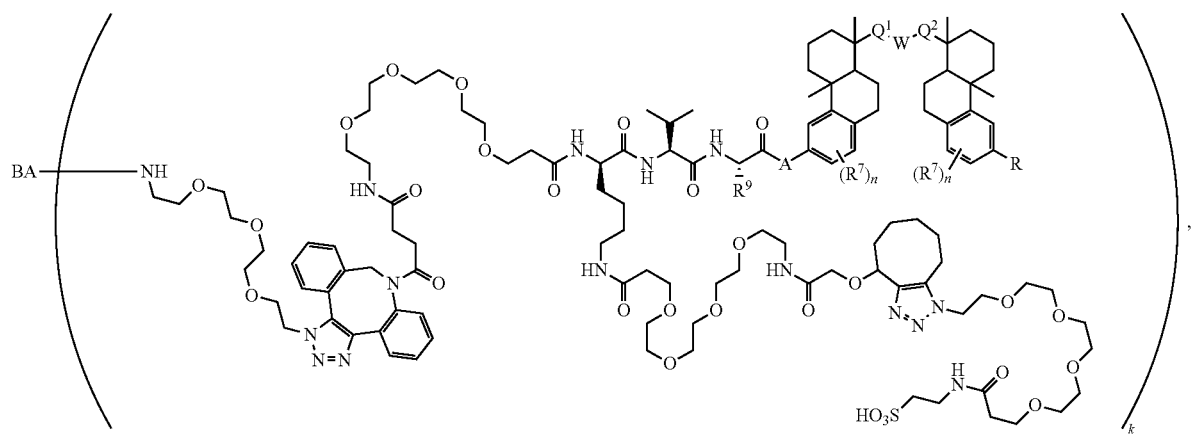

or a pharmaceutically acceptable salt, solvate, or stereoisomeric form thereof, or a regioisomer thereof, wherein:
BA is a binding agent;
k is an integer from 1 to 30;
R is —H, $R^1$, or $R^2$; and
$Q^1$, $Q^2$, W, $R^1$, $R^2$, $R^3$, $R^4$, $R^5$, $R^6$, $R^7$, X, Y, Z, and n are as described in the context of Formula I;
each $R^9$ is —$CH_3$ or —$(CH_2)_3N(H)C(O)NH_2$; and
each A is —O—, —N(H)—,

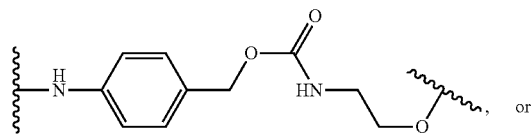, or

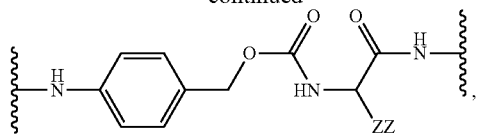, where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In some embodiments, the conjugate is:

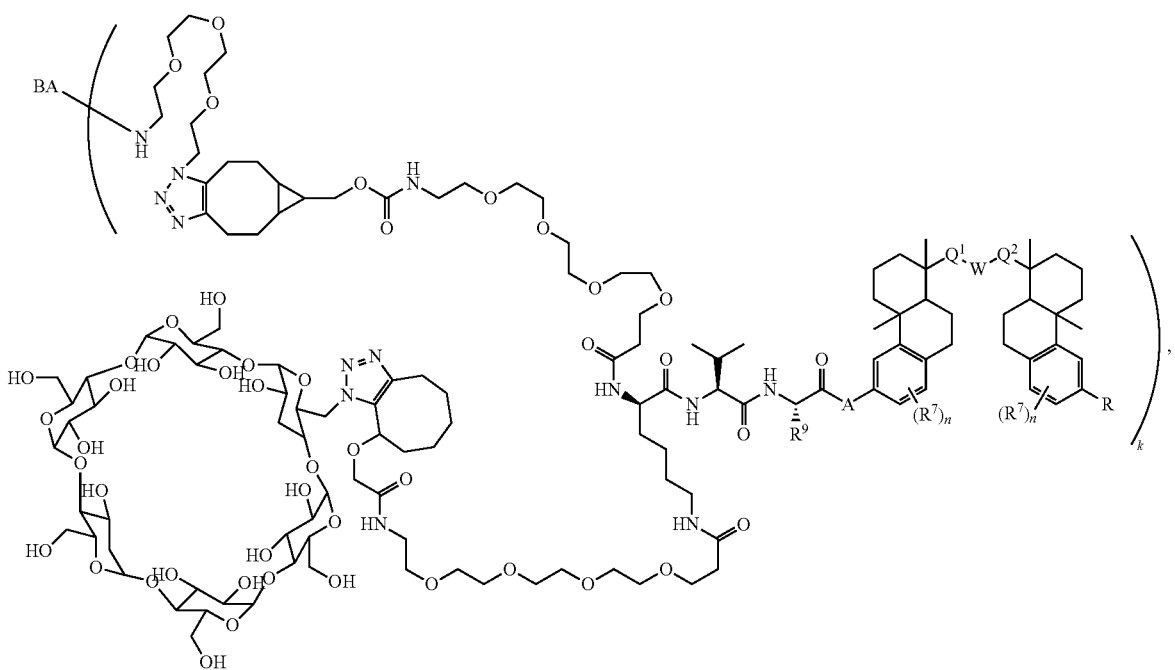

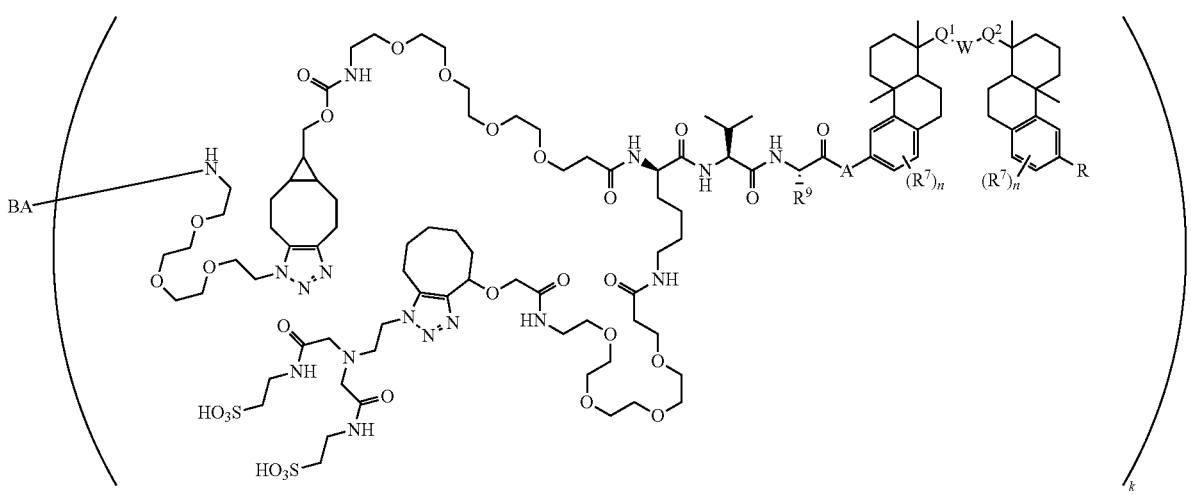

-continued

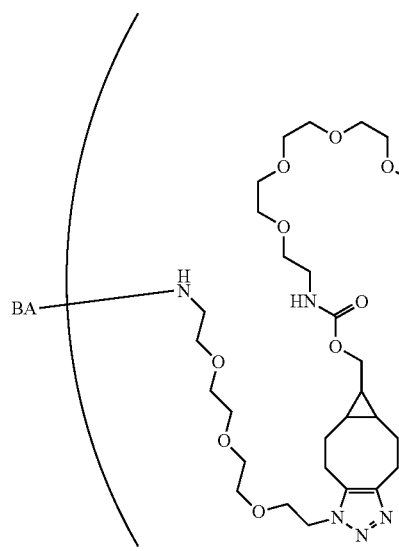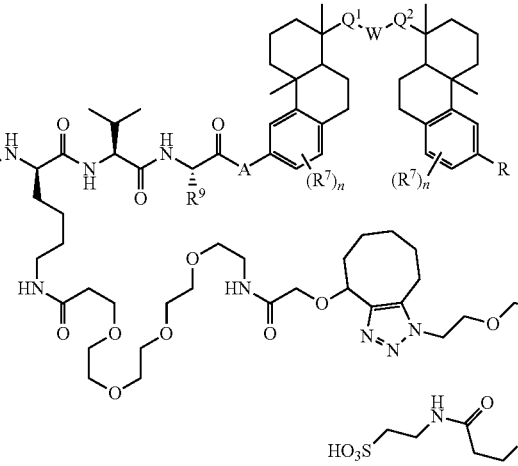

or a pharmaceutically acceptable salt, solvate, or stereoisomeric form thereof, or a regioisomer thereof, wherein:

BA is a binding agent;

k is an integer from 1 to 30;

R is —H, $R^1$, or $R^2$; and $Q^1$, $Q^2$, W, $R^1$, $R^2$, $R^3$, $R^4$, $R^5$, $R^6$, $R^7$, X, Y, Z, and n are as described in the context of Formula I;

each $R^9$ is —$CH_3$ or —$(CH_2)_3N(H)C(O)NH_2$; and each A is —O—, —N(H)—,

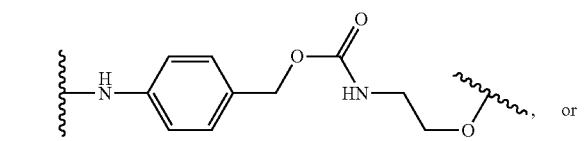 or 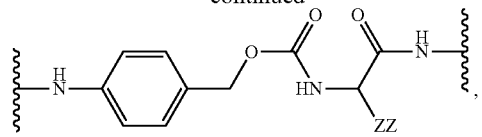, where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In each of the above embodiments, the conjugates can be prepared from binding agents functionalized with azide groups, and residues thereof, as described in the sections below. For convenience, the triazole residue in several structures above is depicted within parentheses. Those of skill will recognize that the trazole can be formed from an azide group of an azide-derivatized binding agent and an alkyne of the linker payload L-P.

In some embodiments, the conjugate is selected from:

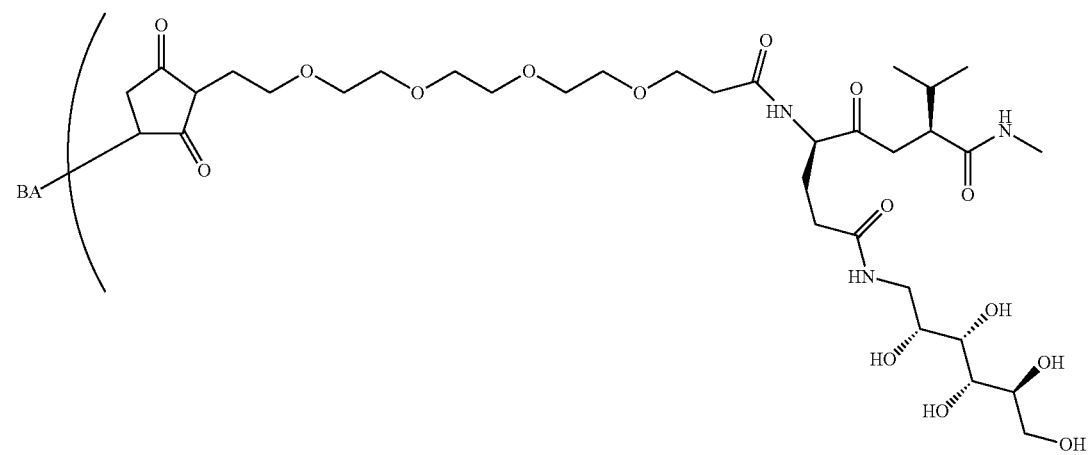

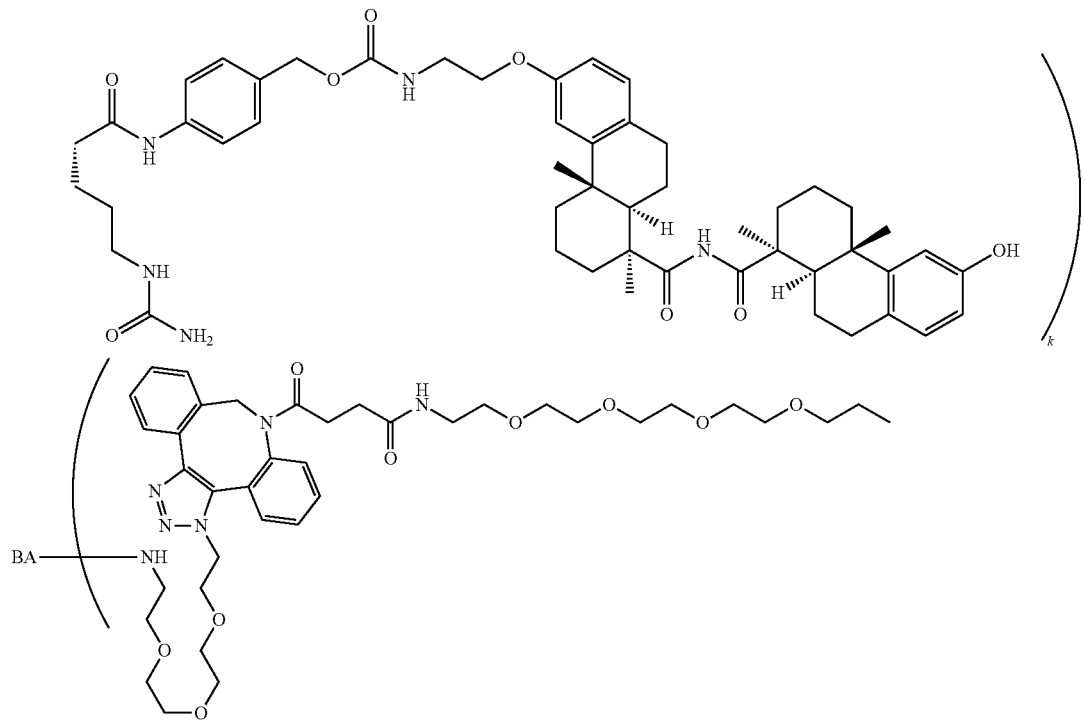
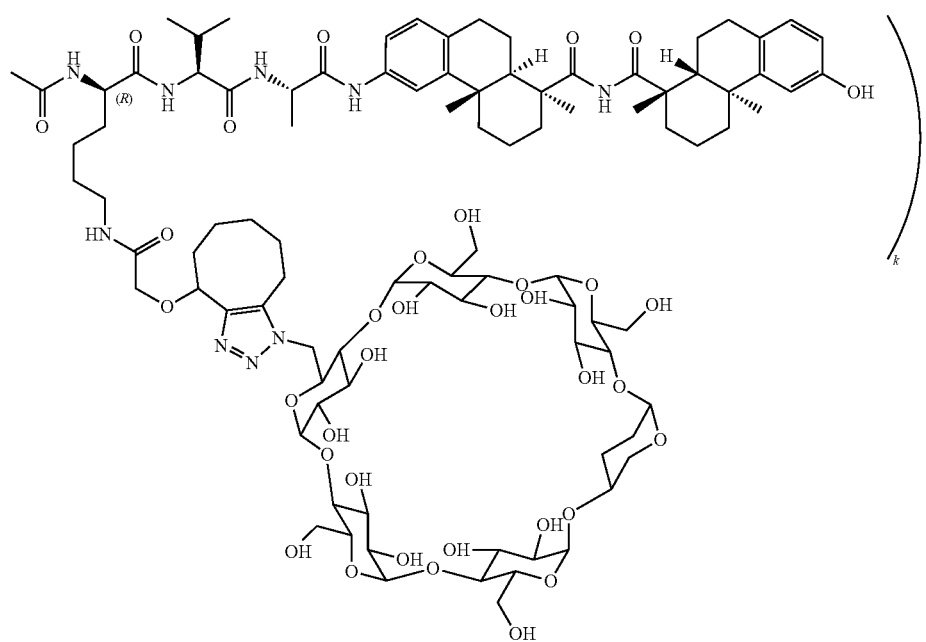
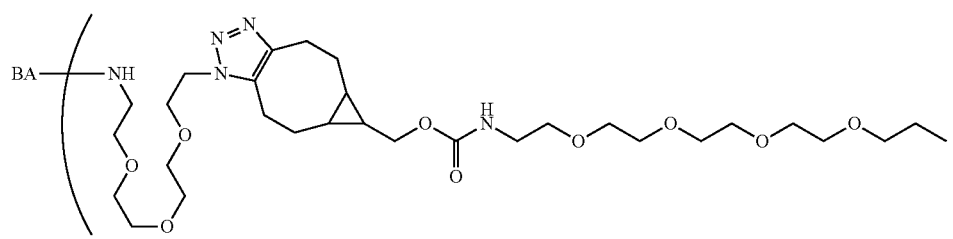

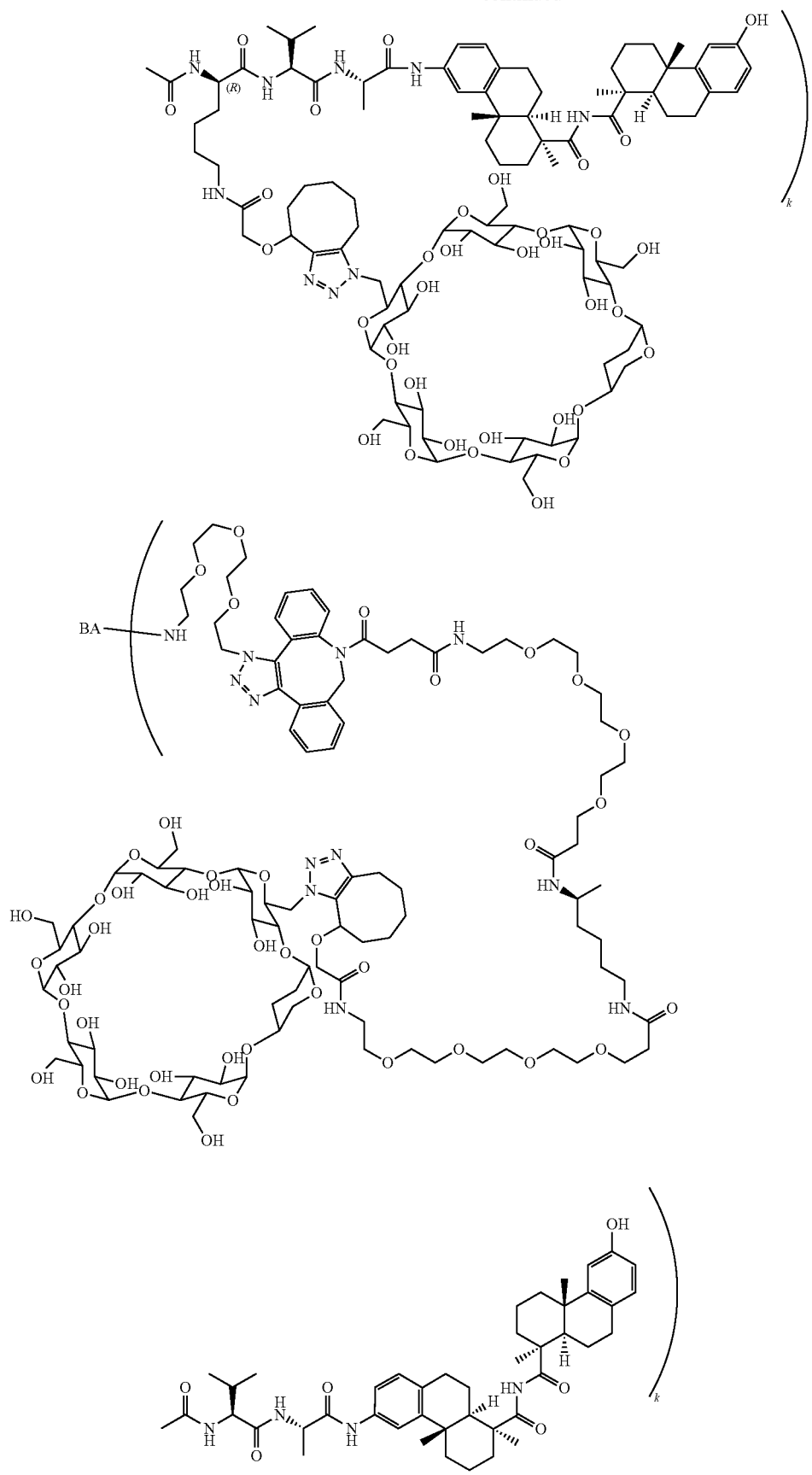

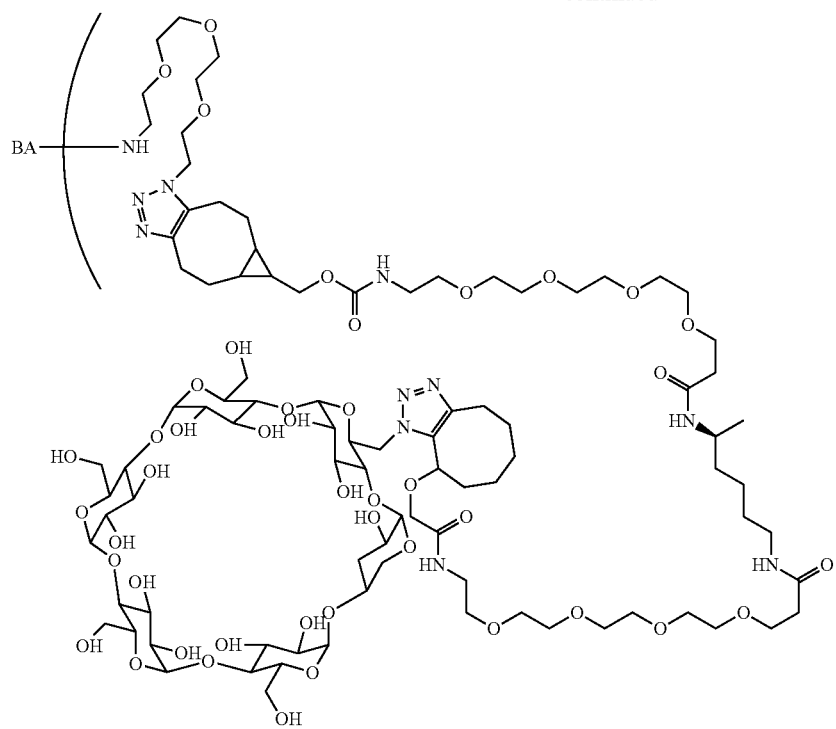
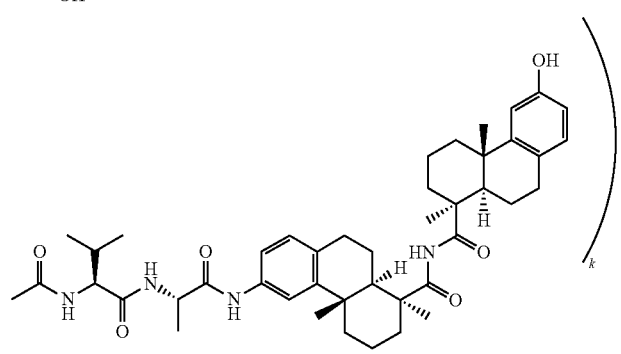
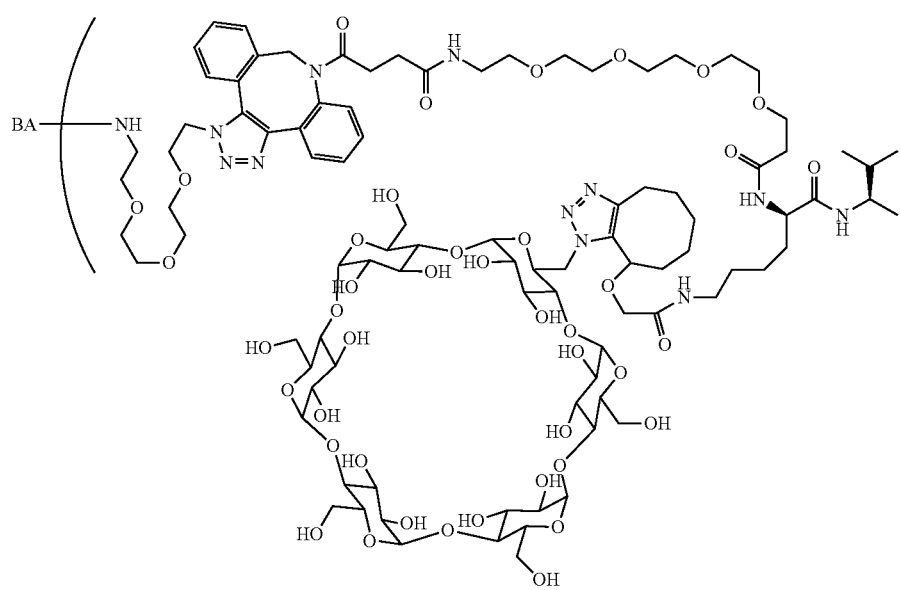

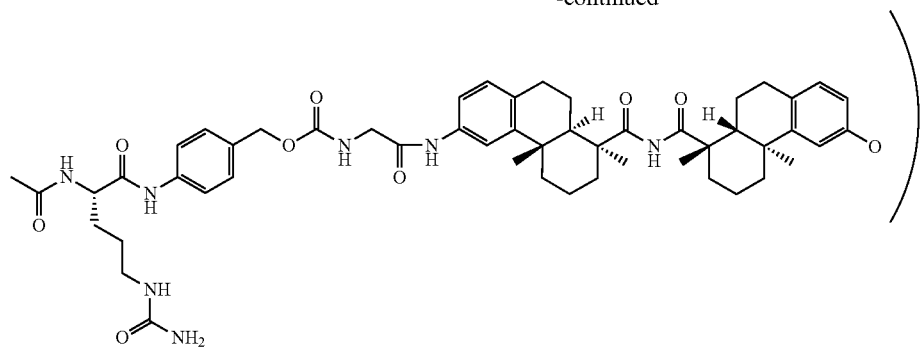
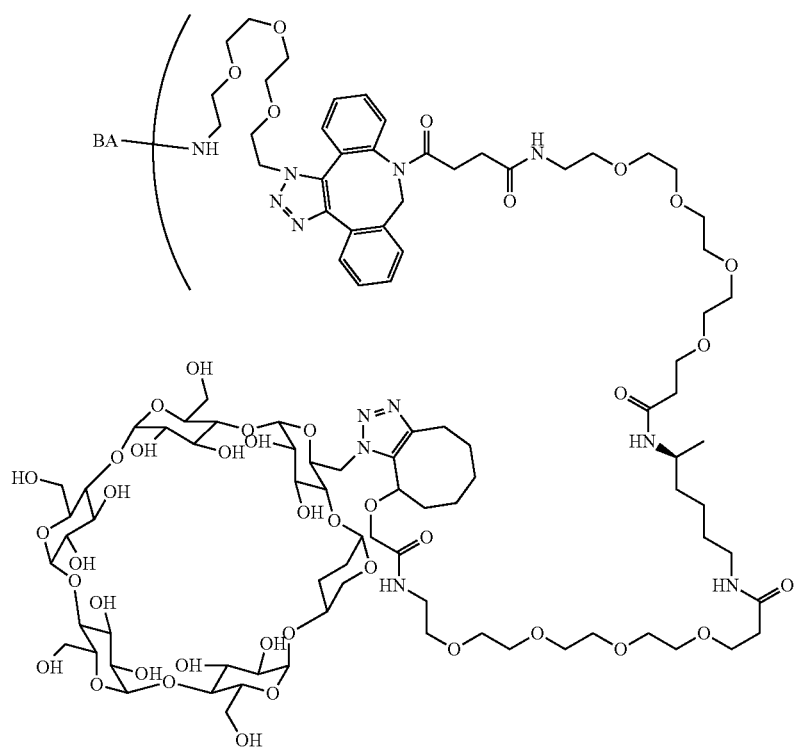
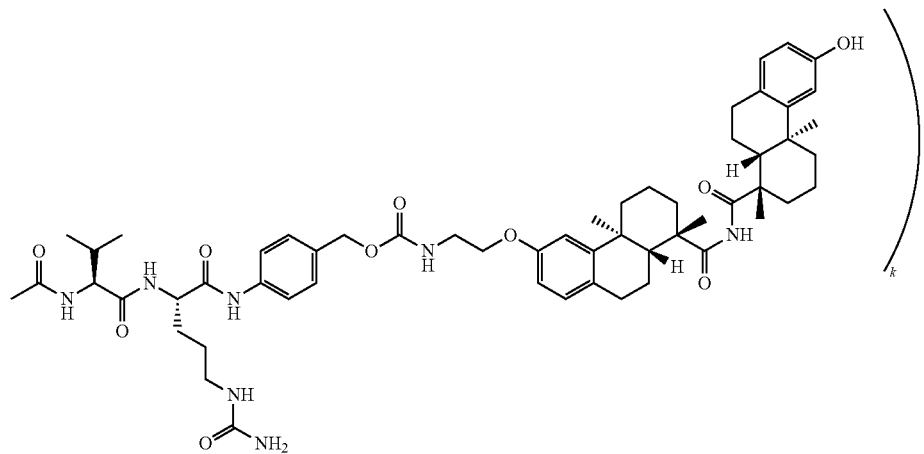

-continued
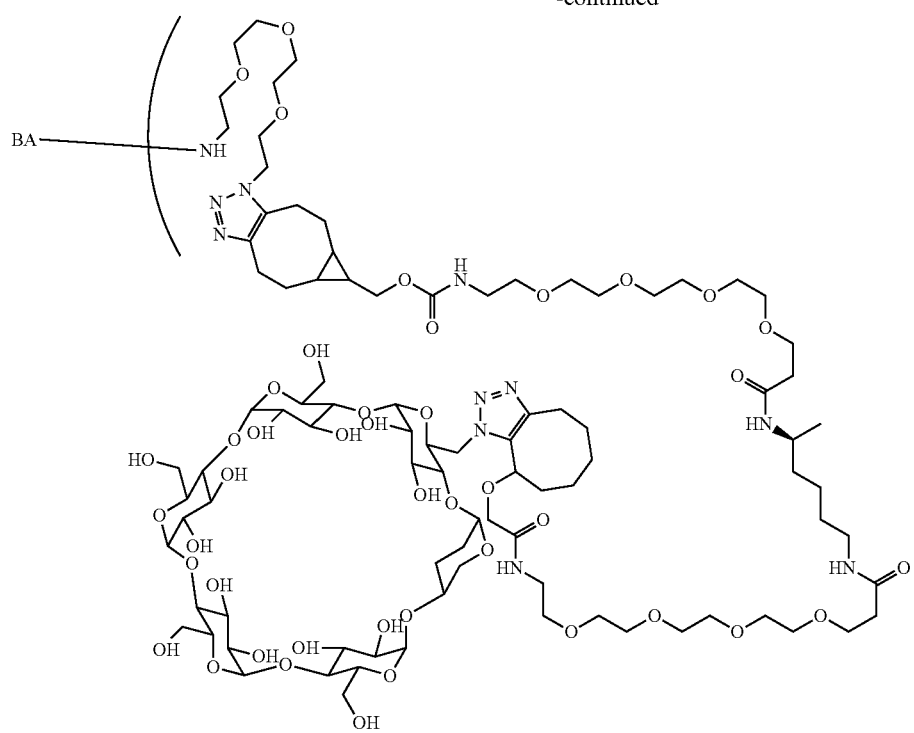
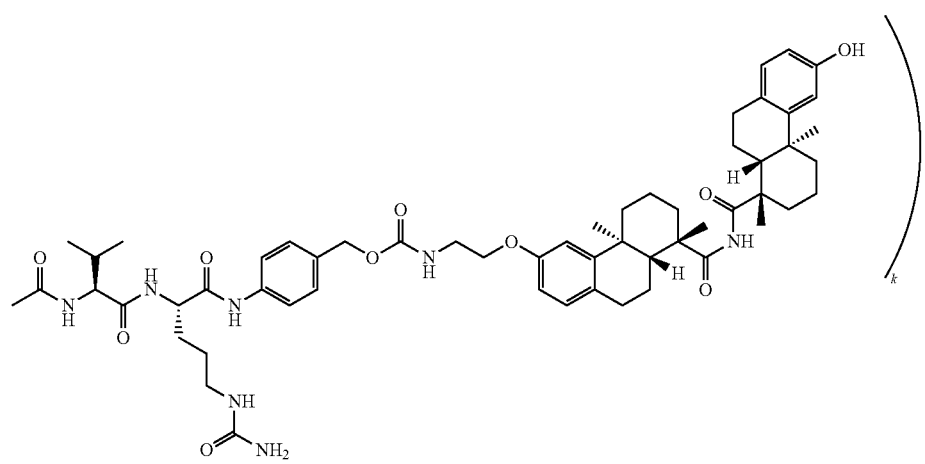

-continued
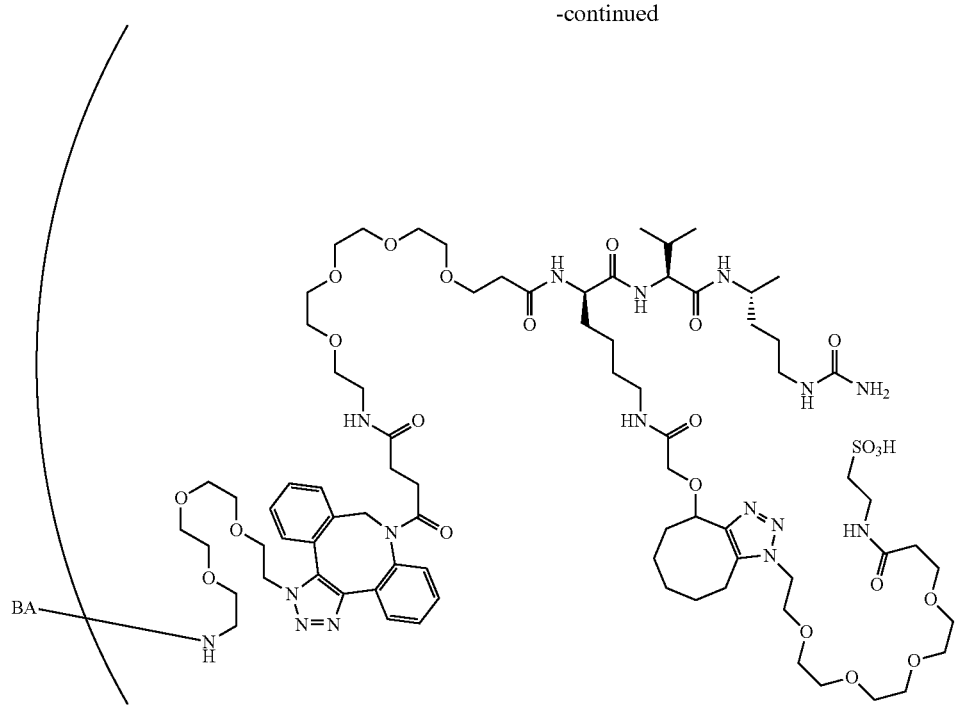
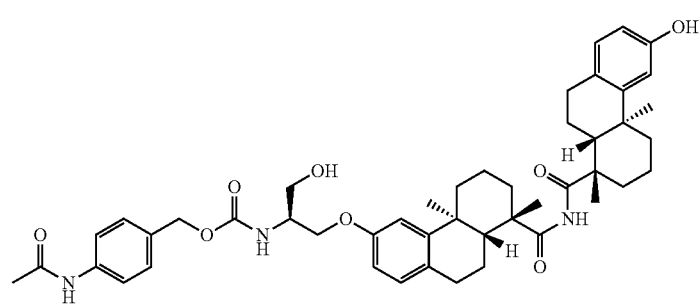

-continued
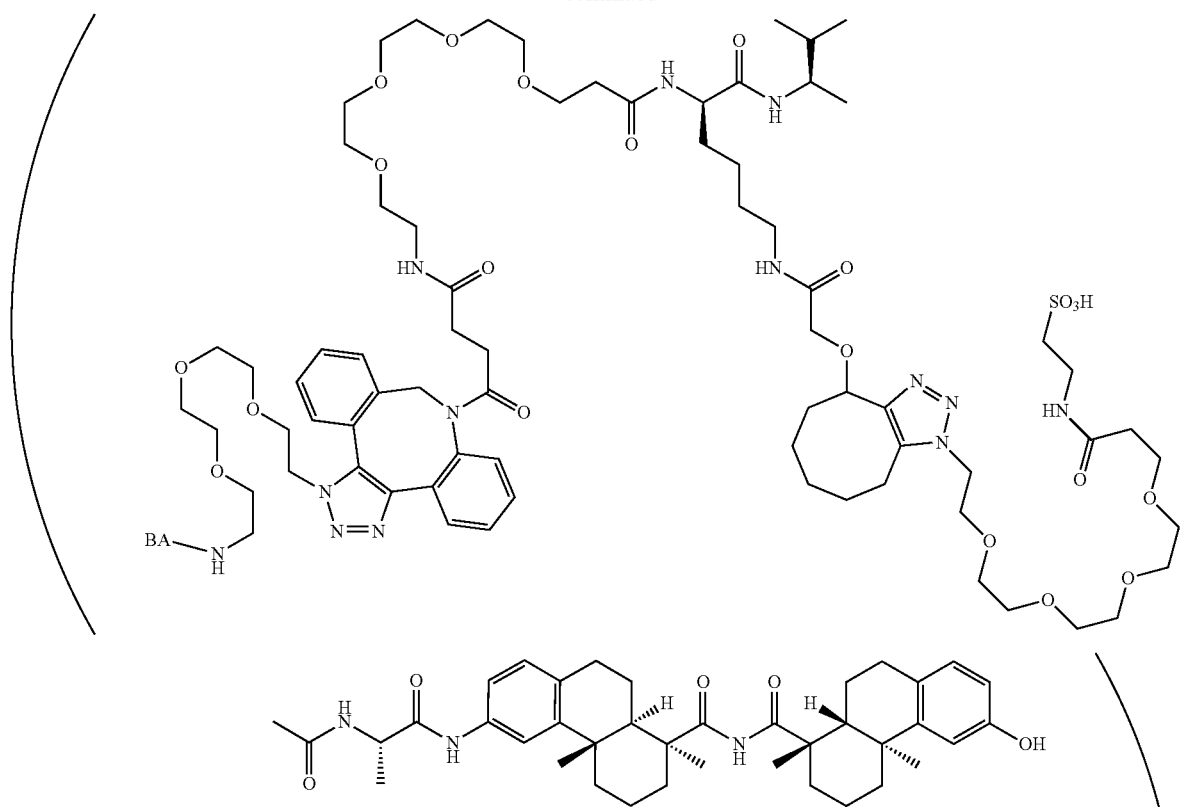
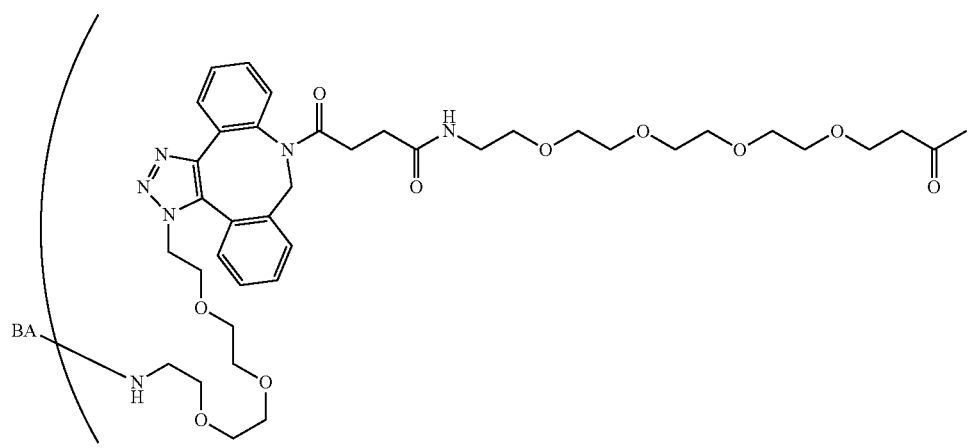

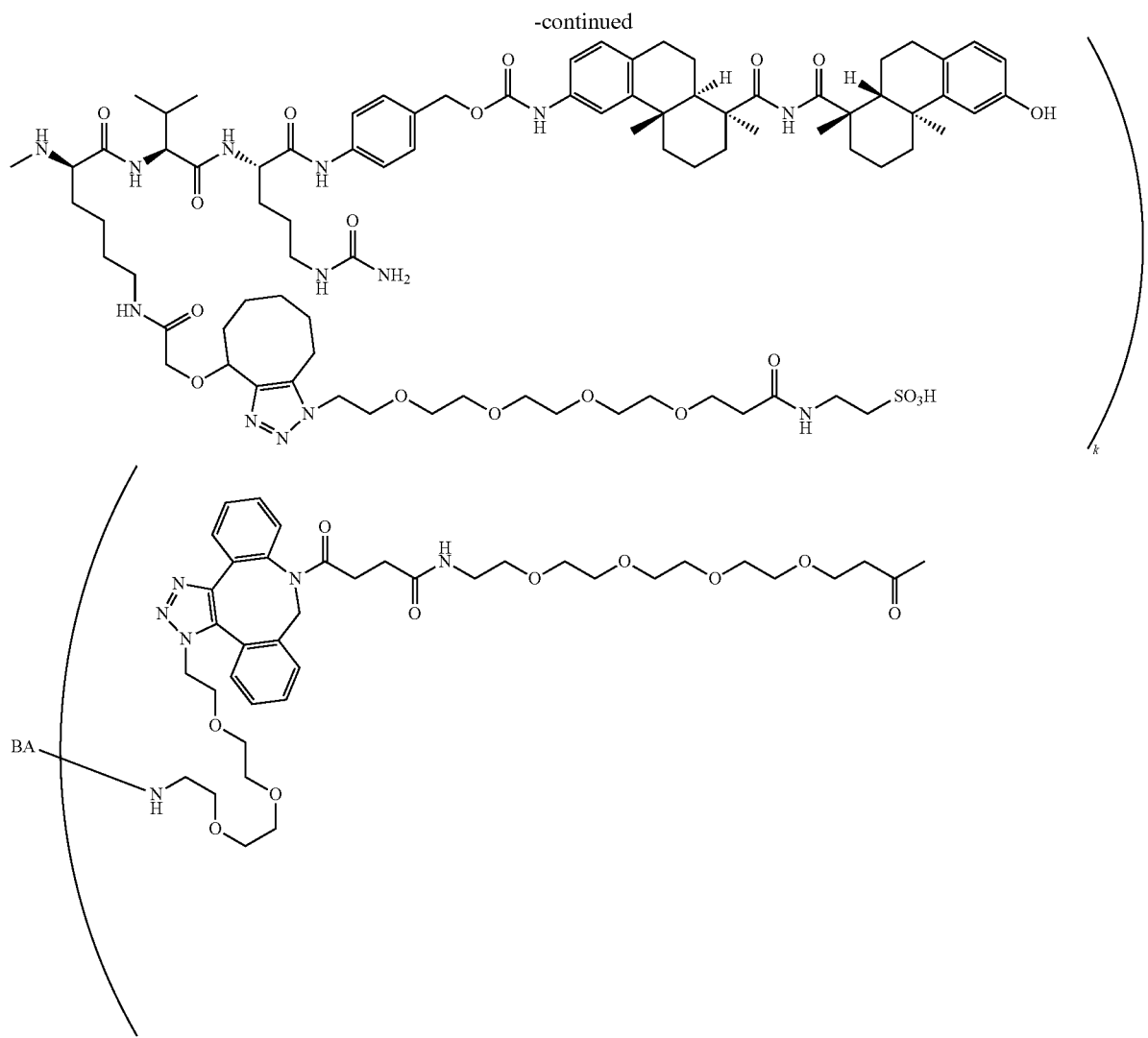
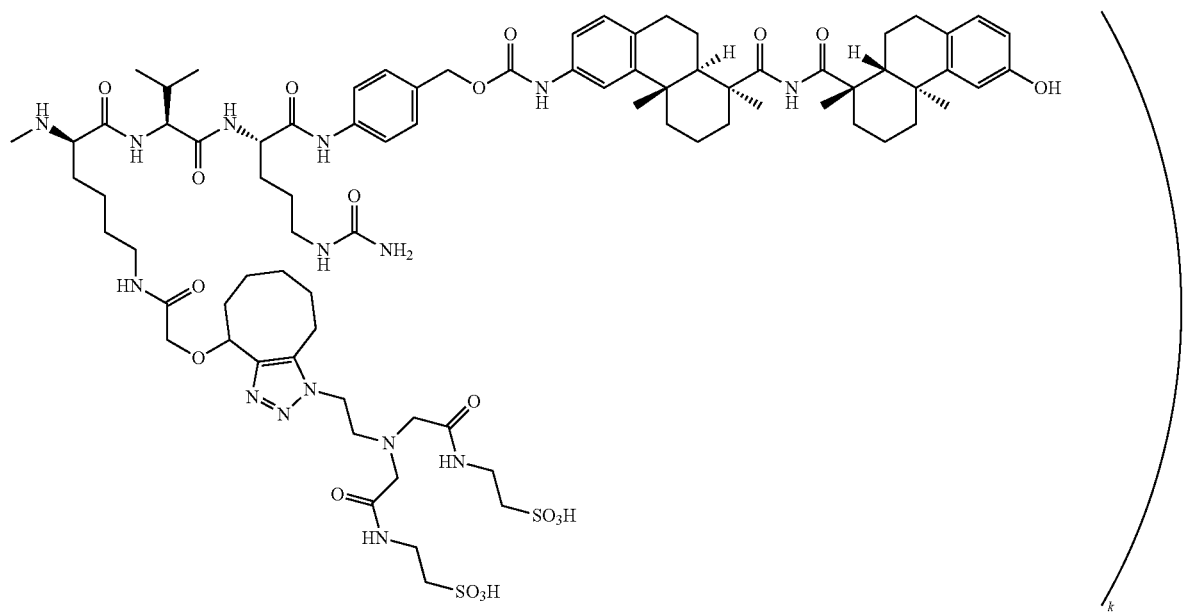

189
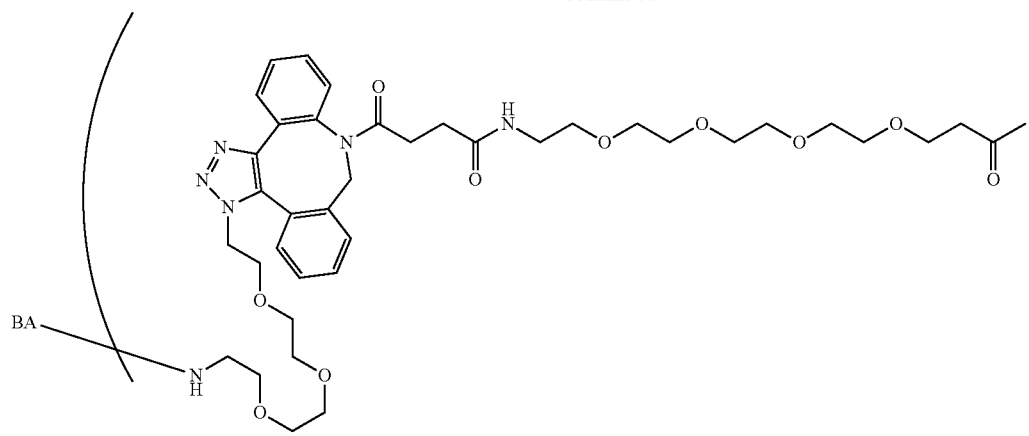
190
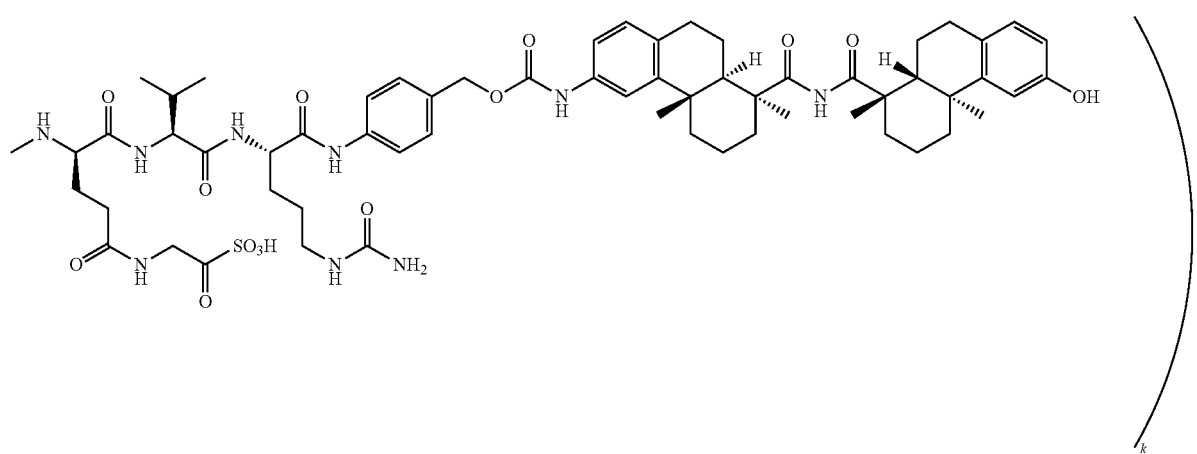
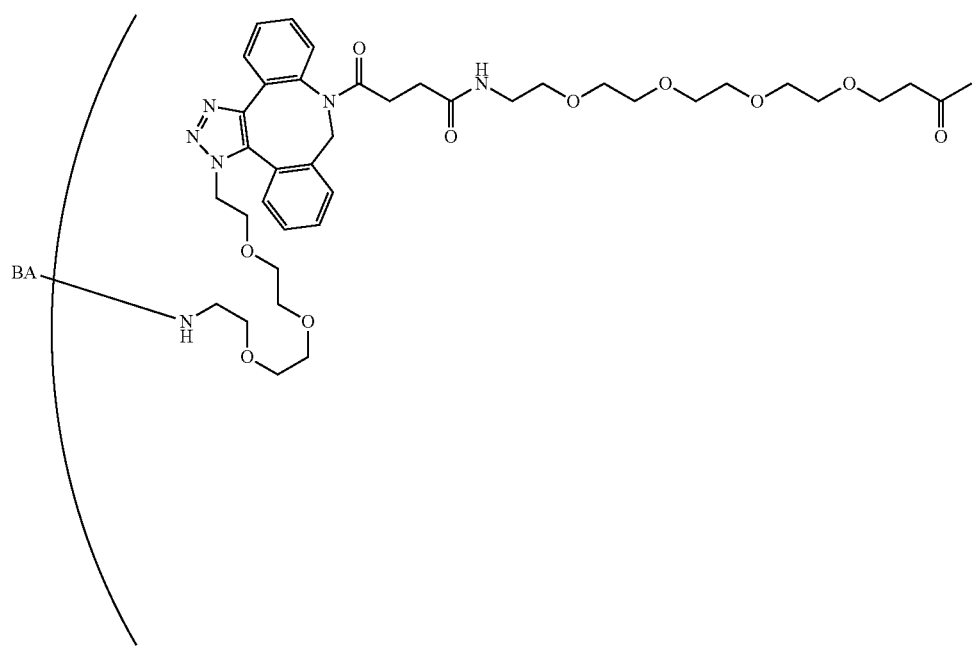

-continued
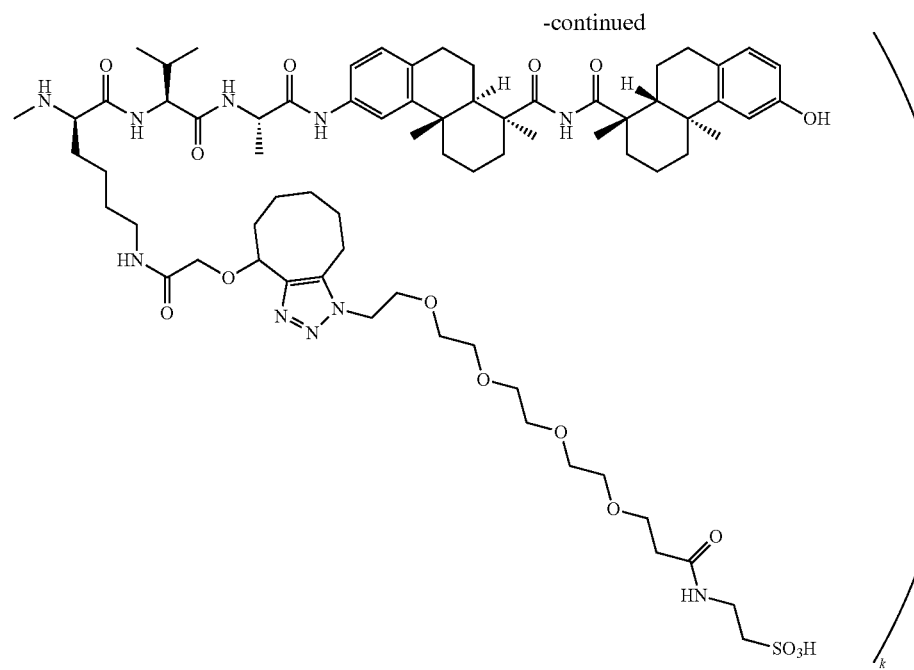

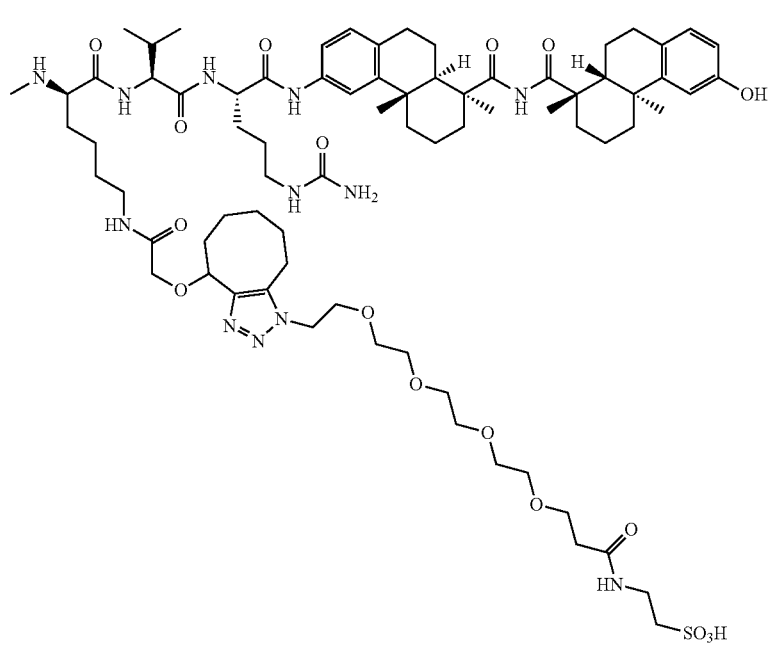
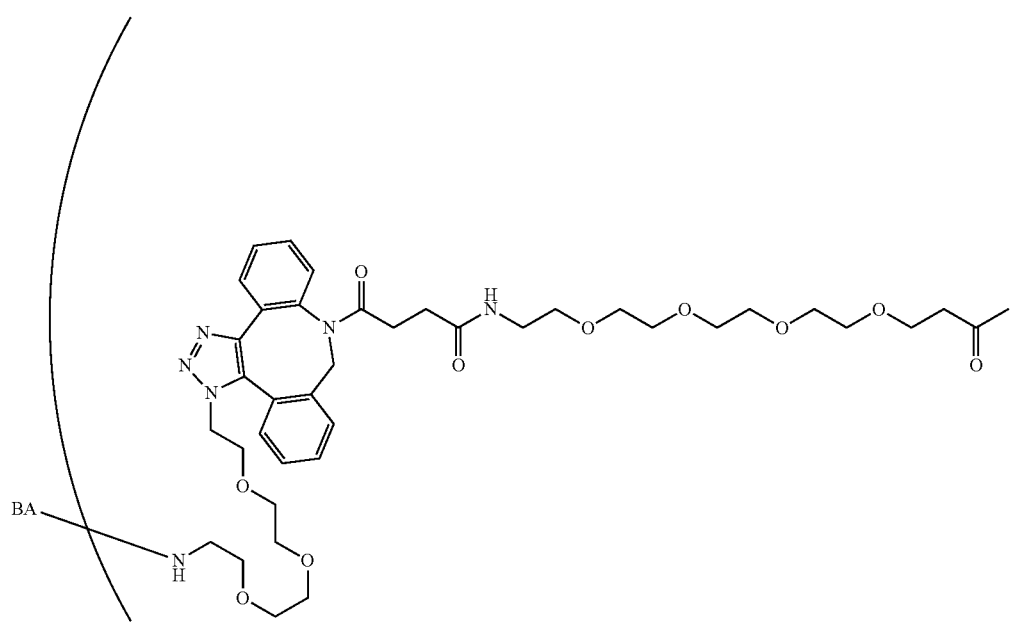

-continued
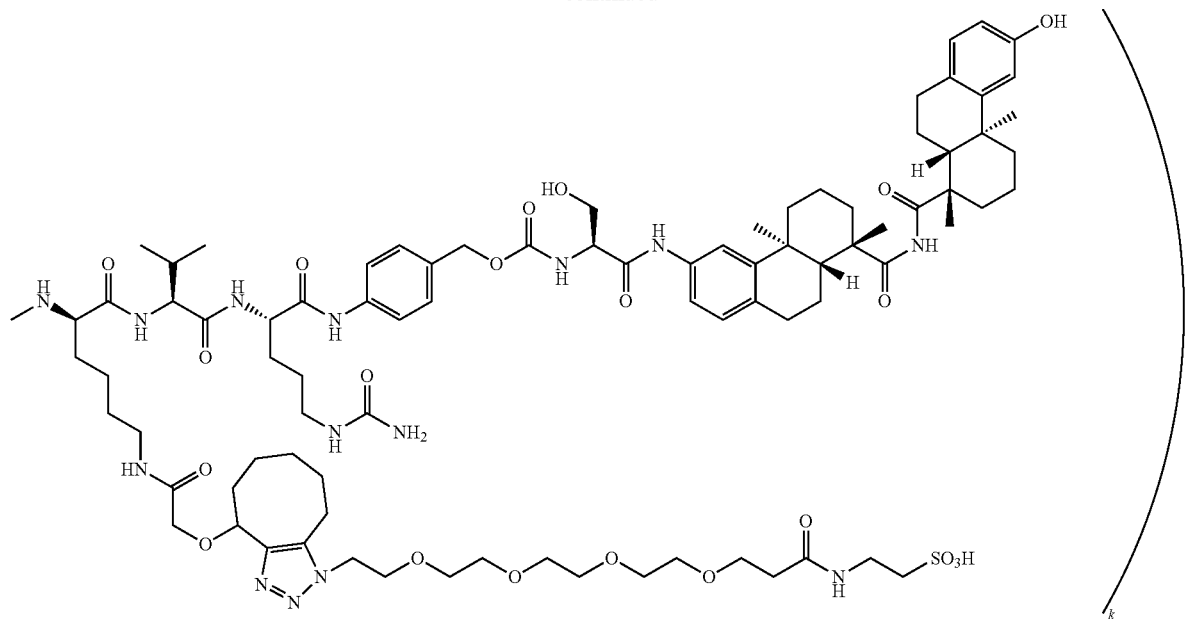
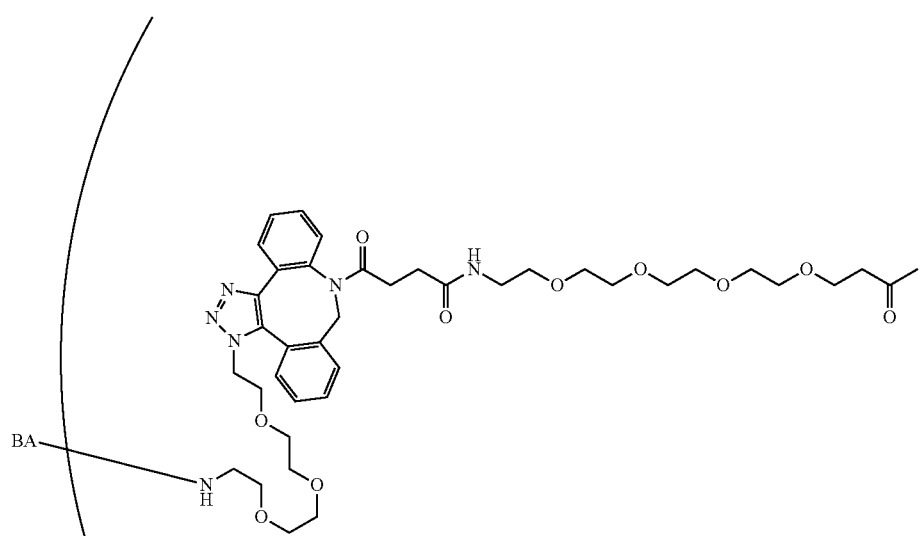

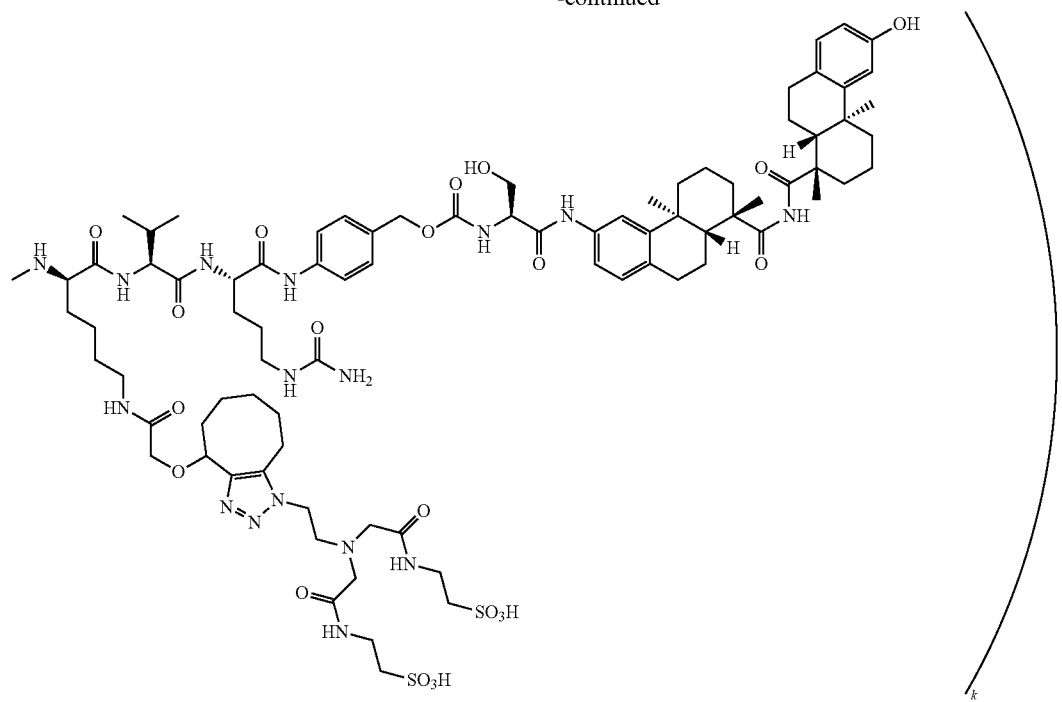
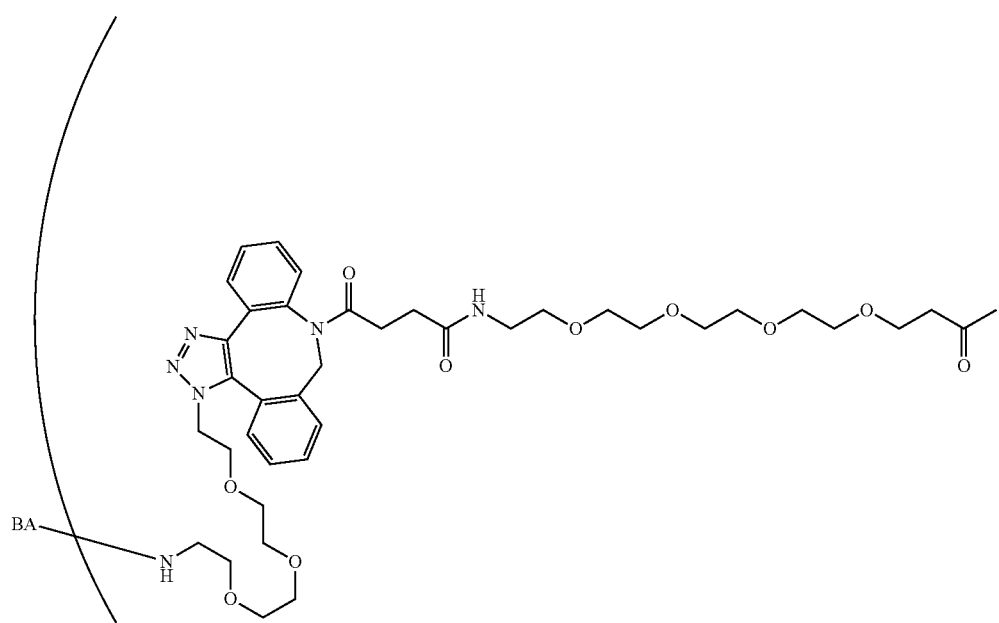

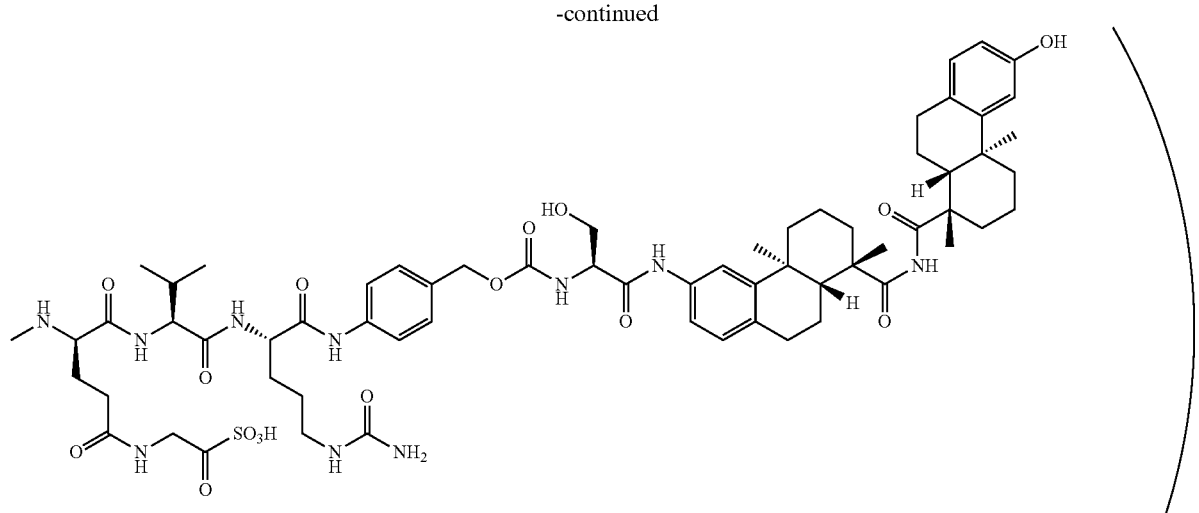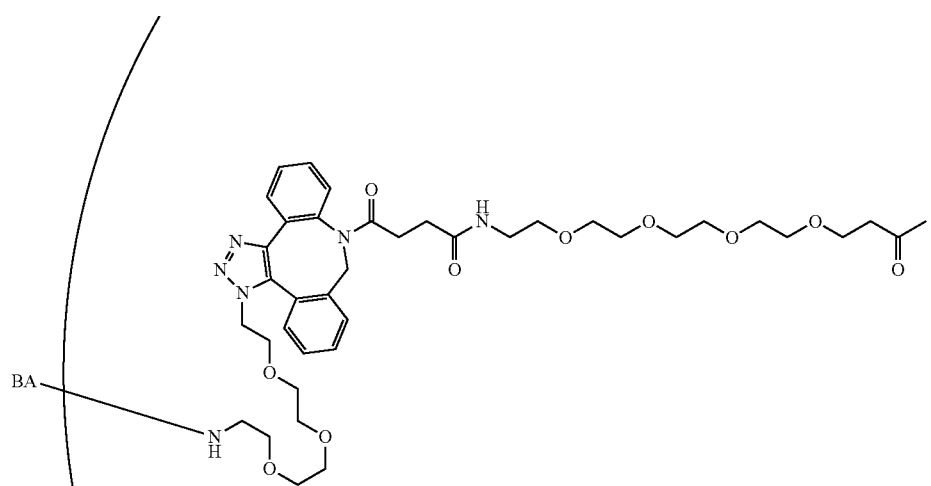

-continued
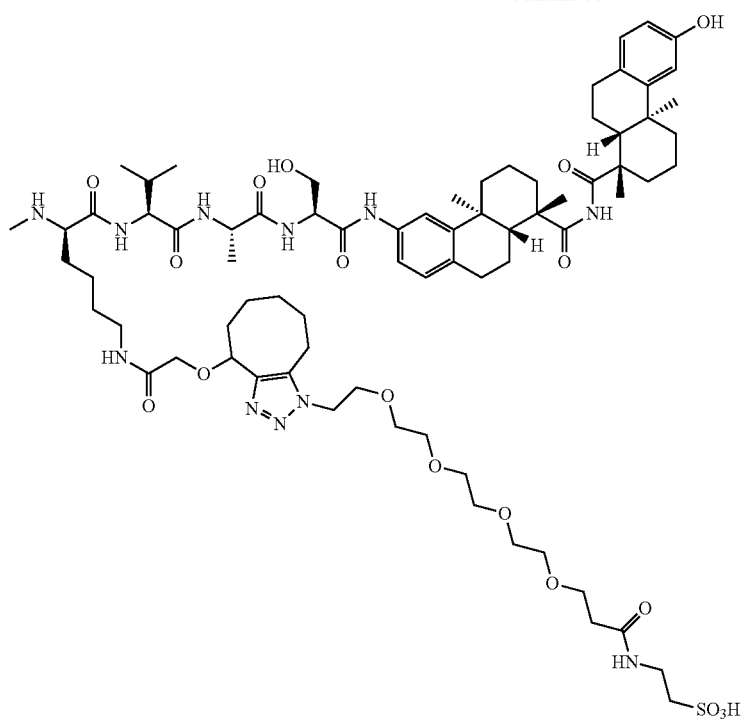
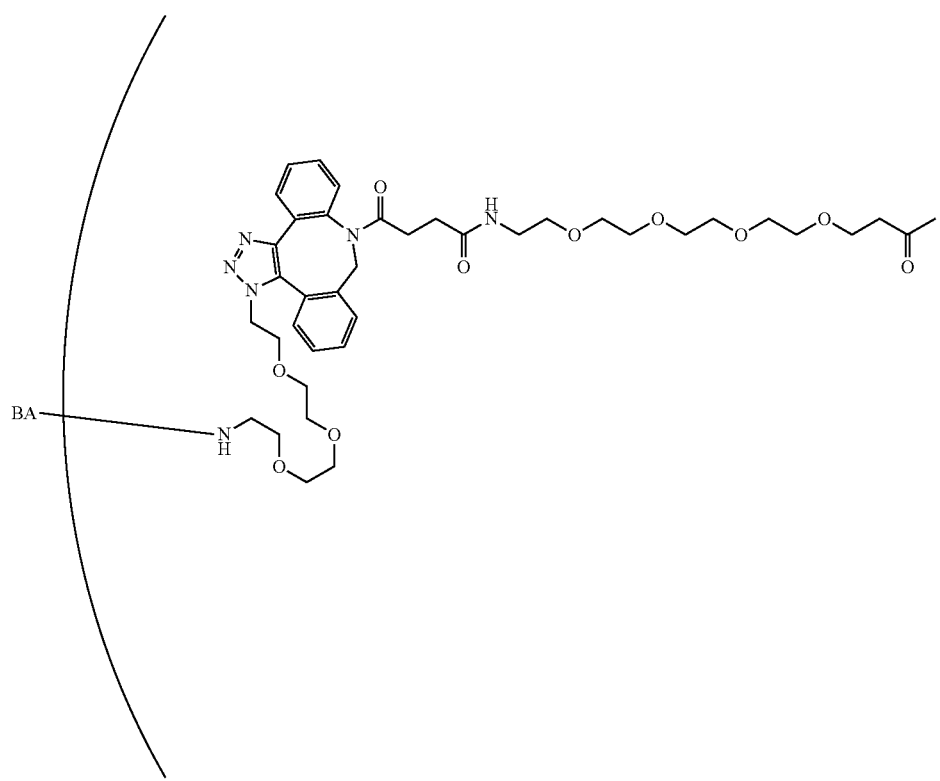

-continued

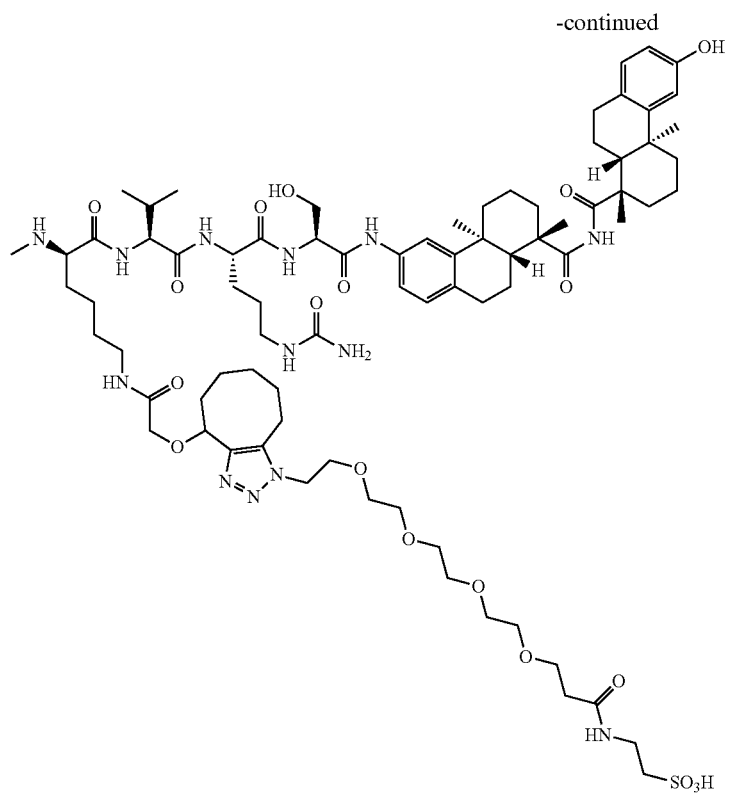

or a regioisomer, or stereoisomeric form pharmaceutically acceptable salt, solvate, thereof.

In the above embodiments, k is an integer from 1 to 30. In certain embodiments, k is an integer from 1 to 8. In certain embodiments, k is an integer from 1 to 4. In certain embodiments, k is 8, 7, 6, 5, 4, 3, 2, or 1. In certain embodiments, k is 4. In certain embodiments, k is 3. In certain embodiments, k is 2. In certain embodiments, k is 1.

Reactive Linker-Payloads

Conjugates provided here can be prepared from reactive linker-paylaods with reactive groups RG as described above. The reactive linker payloads can be linked to enhancement groups and/or binding agents according to the methods described below.

In some embodiments, the reactive linker-payload is:

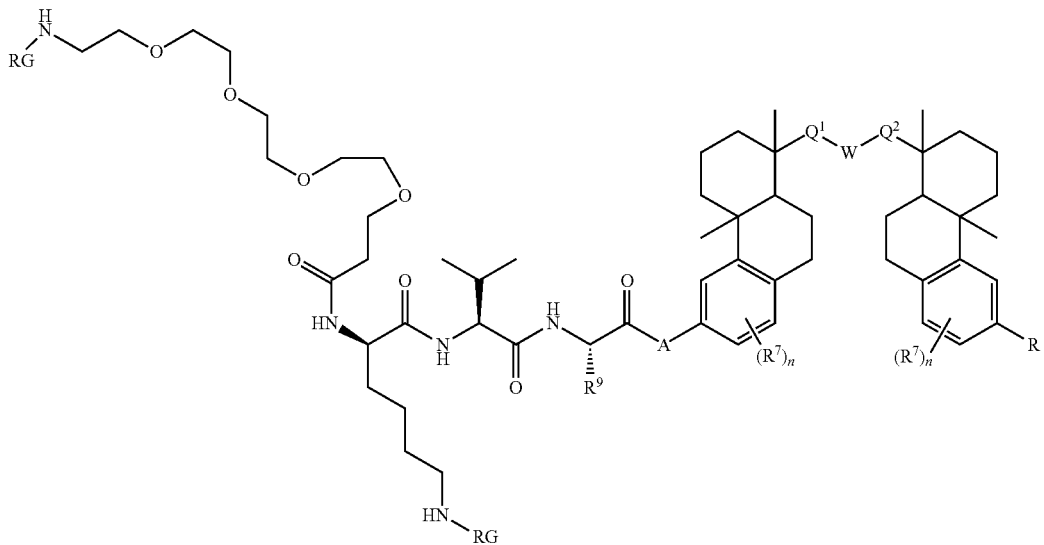

or a pharmaceutically acceptable salt, solvate, or stereoisomeric form thereof, or a regioisomer thereof, wherein:

each RG is a reactive group, as described herein;
R is —H, $R^1$, or $R^2$; and
$Q^1$, $Q^2$, W, $R^1$, $R^2$, $R^3$, $R^4$, $R^5$, $R^6$, $R^7$, X, Y, Z, and n are as described in the context of Formula I;
each $R^9$ is —$CH_3$ or —$(CH_2)_3N(H)C(O)NH_2$; and
each A is —O—, —N(H)—,

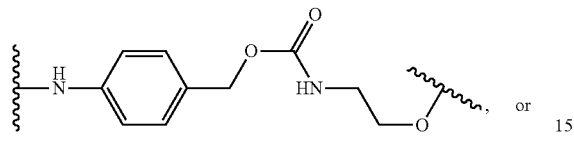, or

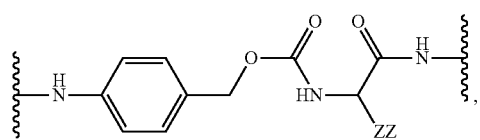, where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.
In certain embodiments, R is $R^1$.
In some embodiments, the reactive linker-payload is:

or a pharmaceutically acceptable salt, solvate, or stereoisomeric form thereof, or a regioisomer thereof, wherein:

each RG is a reactive group, as described herein;
R is —H, $R^1$, or $R^2$; and
$Q^1$, $Q^2$, W, $R^1$, $R^2$, $R^3$, $R^4$, $R^5$, $R^6$, $R^7$, X, Y, Z, and n are as described in the context of Formula I;
each $R^9$ is —$CH_3$ or —$(CH_2)_3N(H)C(O)NH_2$; and
each A is —O—, —N(H)—,

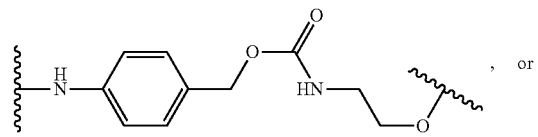, or

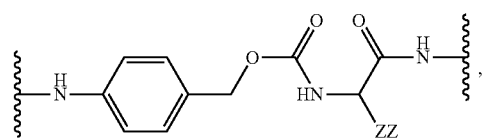, where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.
In certain embodiments, R is $R^1$.

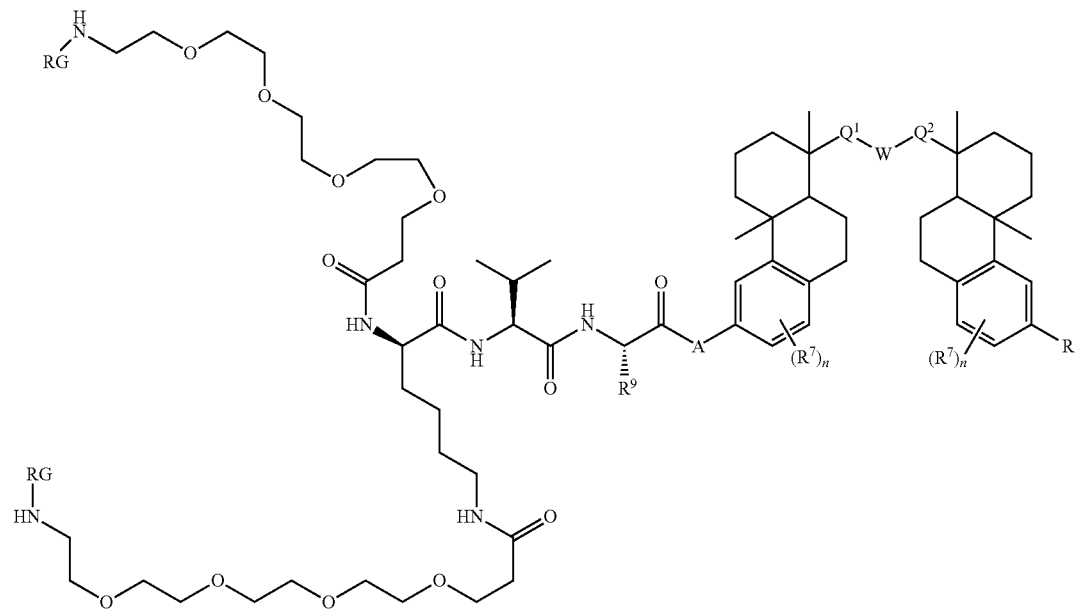

In some embodiments, the reactive linker-payload is:

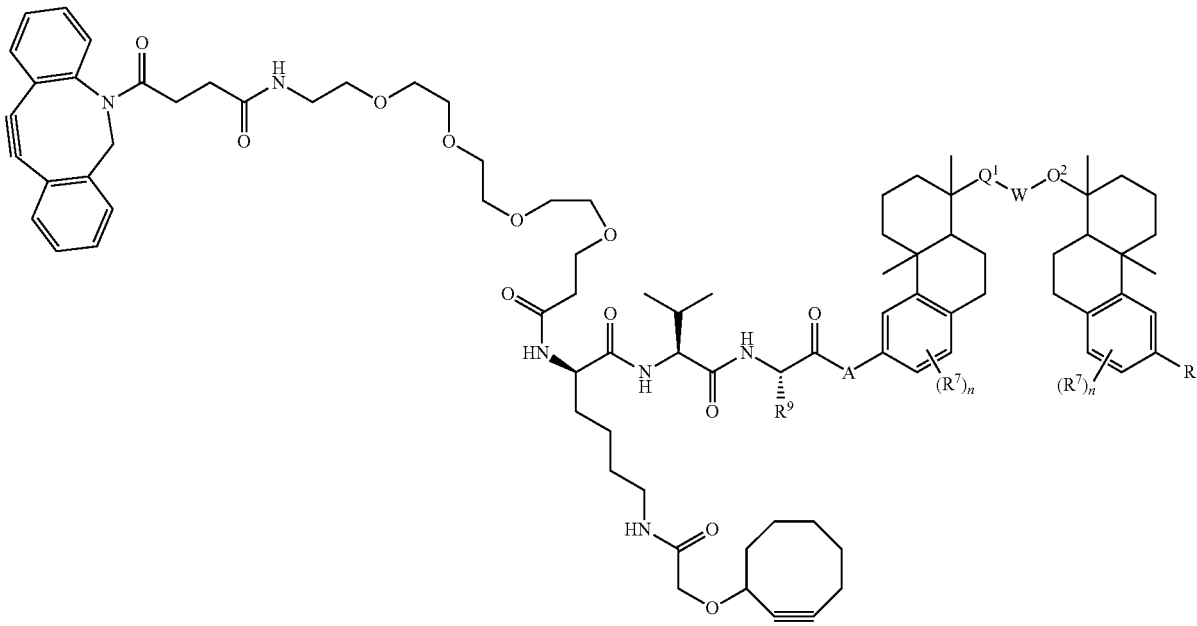

or a pharmaceutically acceptable salt, solvate, or stereoisomeric form thereof, or a regioisomer thereof, wherein:
- R is —H, $R^1$, or $R^2$; and
- $Q^1$, $Q^2$, W, $R^1$, $R^2$, $R^3$, $R^4$, $R^5$, $R^6$, $R^7$, X, Y, Z, and n are as described in the context of Formula I;
- each $R^9$ is —$CH_3$ or —$(CH_2)_3N(H)C(O)NH_2$; and
- each A is —O—, —N(H)—,

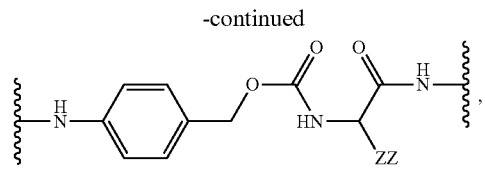

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In some embodiments, the reactive linker-payload is:

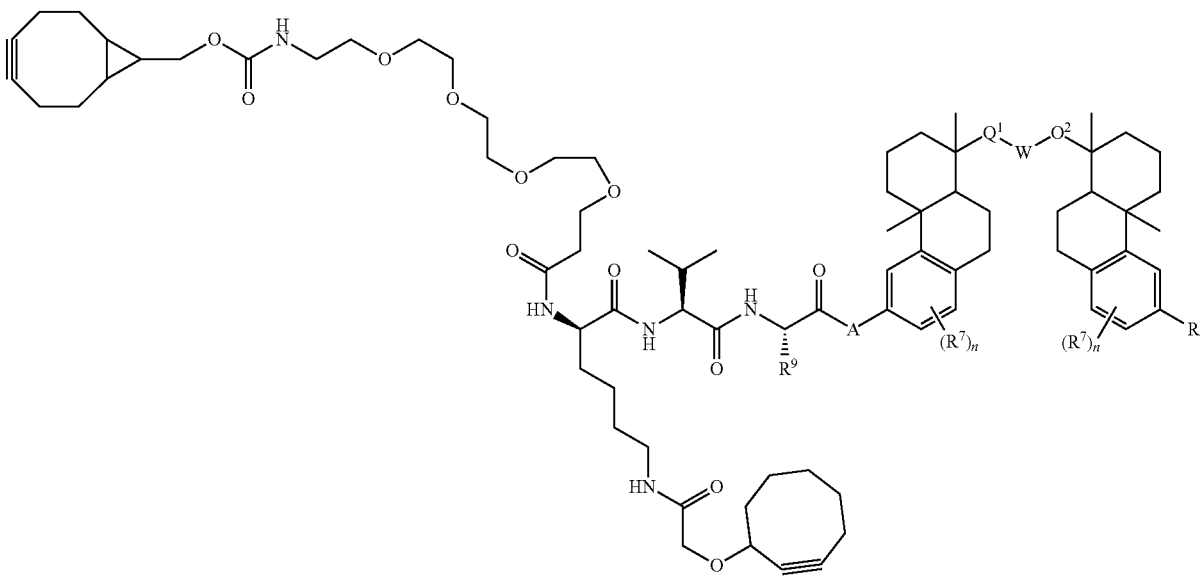

or a pharmaceutically acceptable salt, solvate, or stereoisomeric form thereof, or a regioisomer thereof, wherein:

R is —H, $R^1$, or $R^2$; and $Q^1$, $Q^2$, W, $R^1$, $R^2$, $R^3$, $R^4$, $R^5$, $R^6$, $R^7$, X, Y, Z, and n are as described in the context of Formula I;

each $R^9$ is —$CH_3$ or —$(CH_2)_3N(H)C(O)NH_2$; and each A is —O—, —N(H)—,

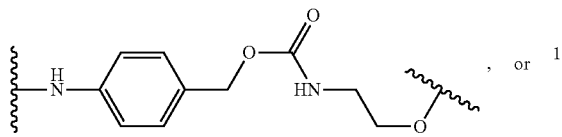

, or

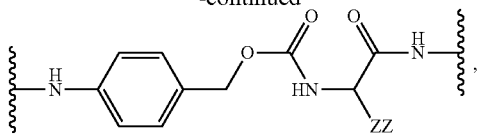

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In some embodiments, the reactive linker-payload is:

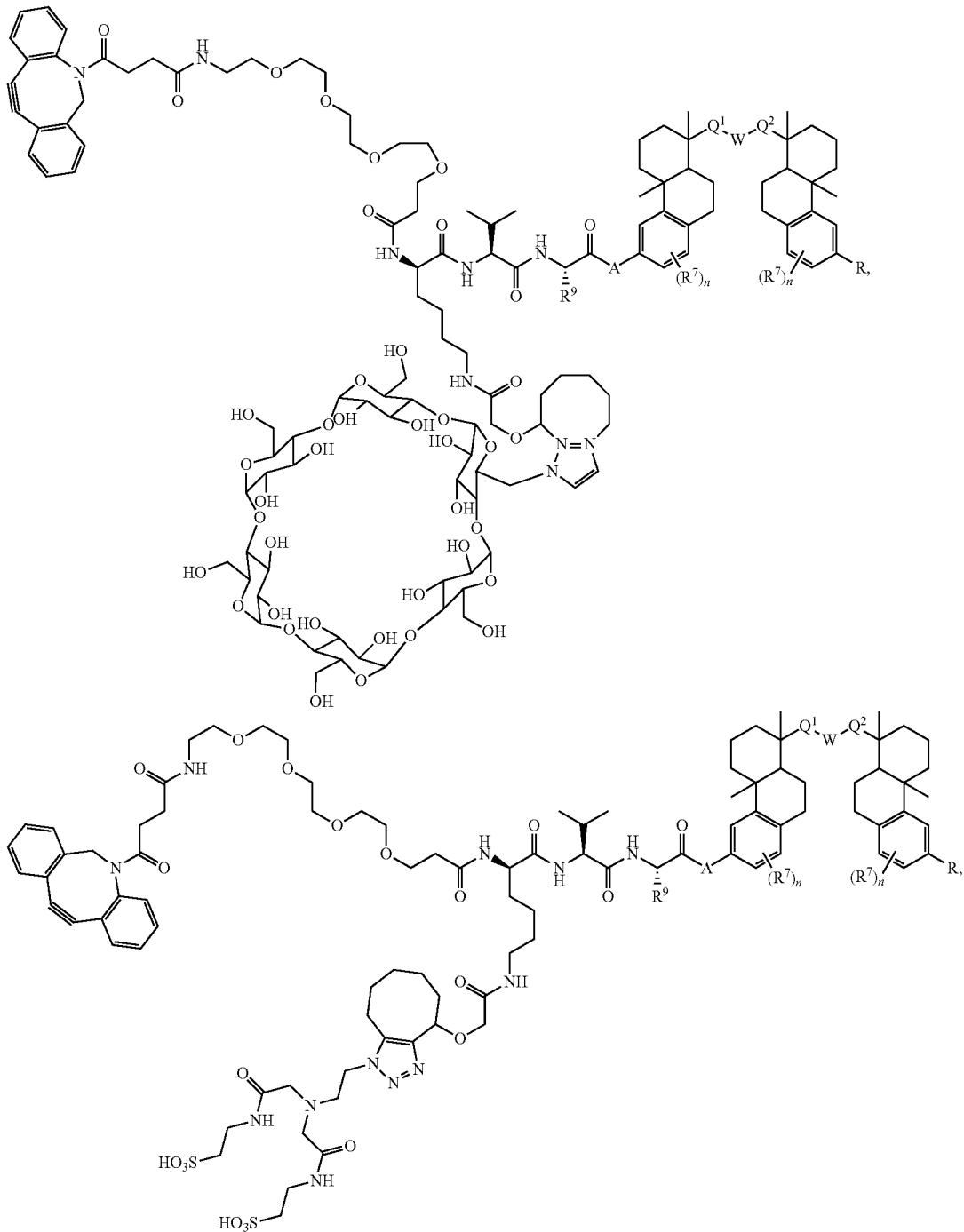

211

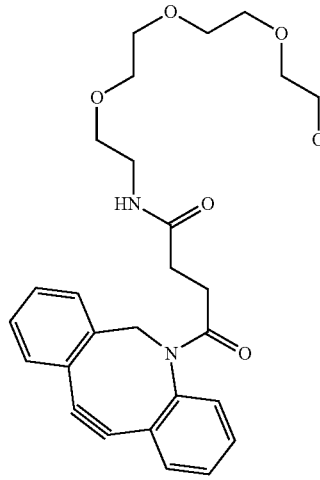
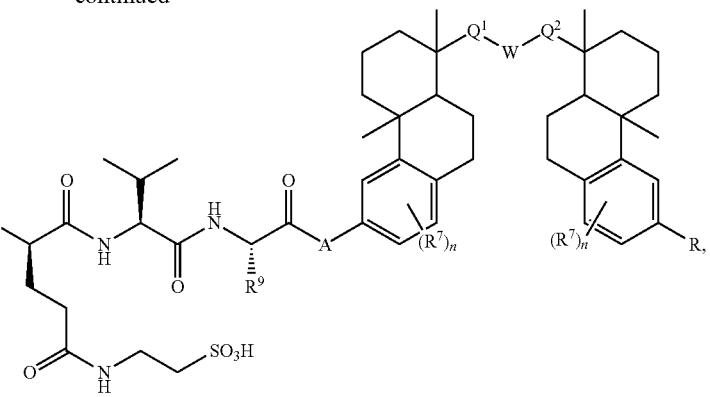

-continued

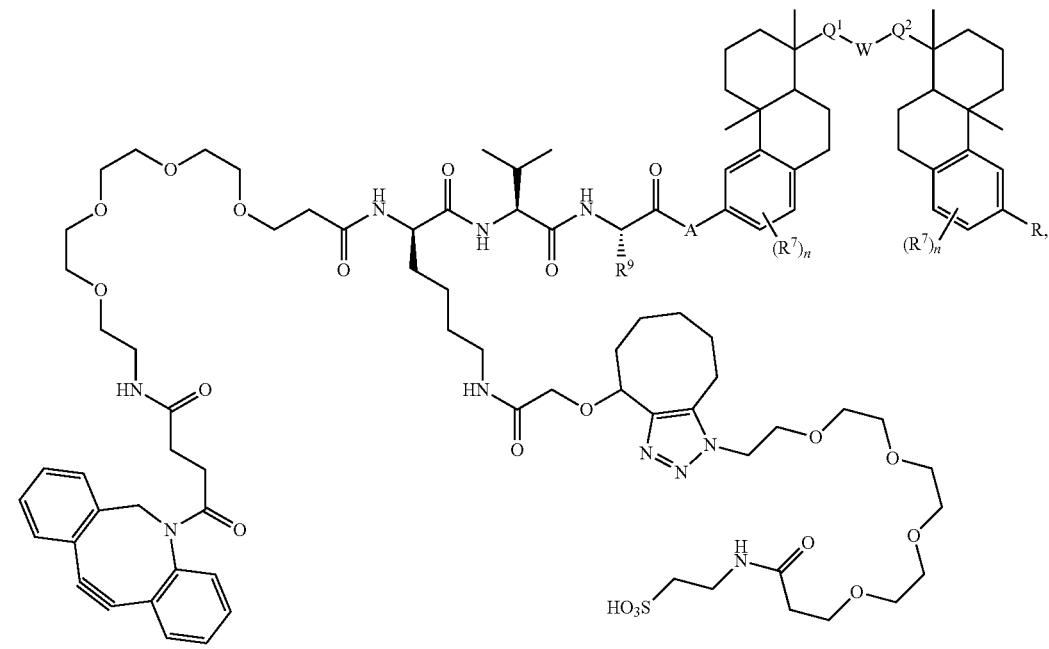

or a pharmaceutically acceptable salt, solvate, or stereoisomeric form thereof, or a regioisomer thereof, wherein.

R is —H, $R^1$, or $R^2$; and $Q^1$, $Q^2$, W, $R^1$, $R^2$, $R^3$, $R^4$, $R^5$, $R^6$, $R^7$, X, Y, Z, and n are as described in the context of Formula I;

each $R^9$ is —$CH_3$ or —$(CH_2)_3N(H)C(O)NH_2$; and each A is —O—, —N(H)—,

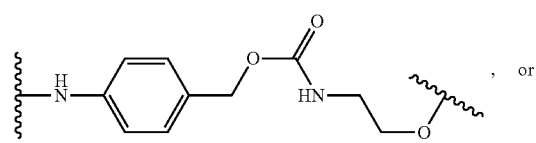

, or

-continued

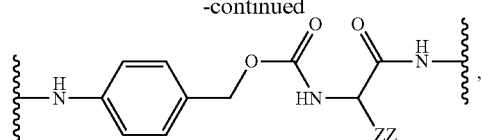

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In some embodiments, the reactive linker-payload is:
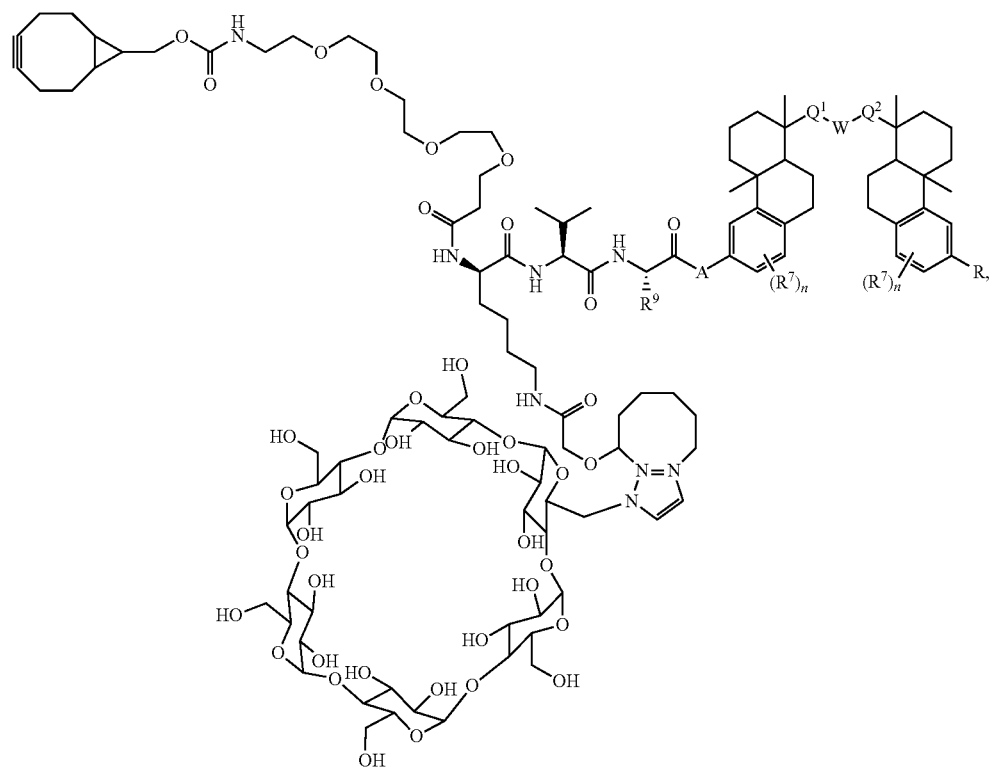
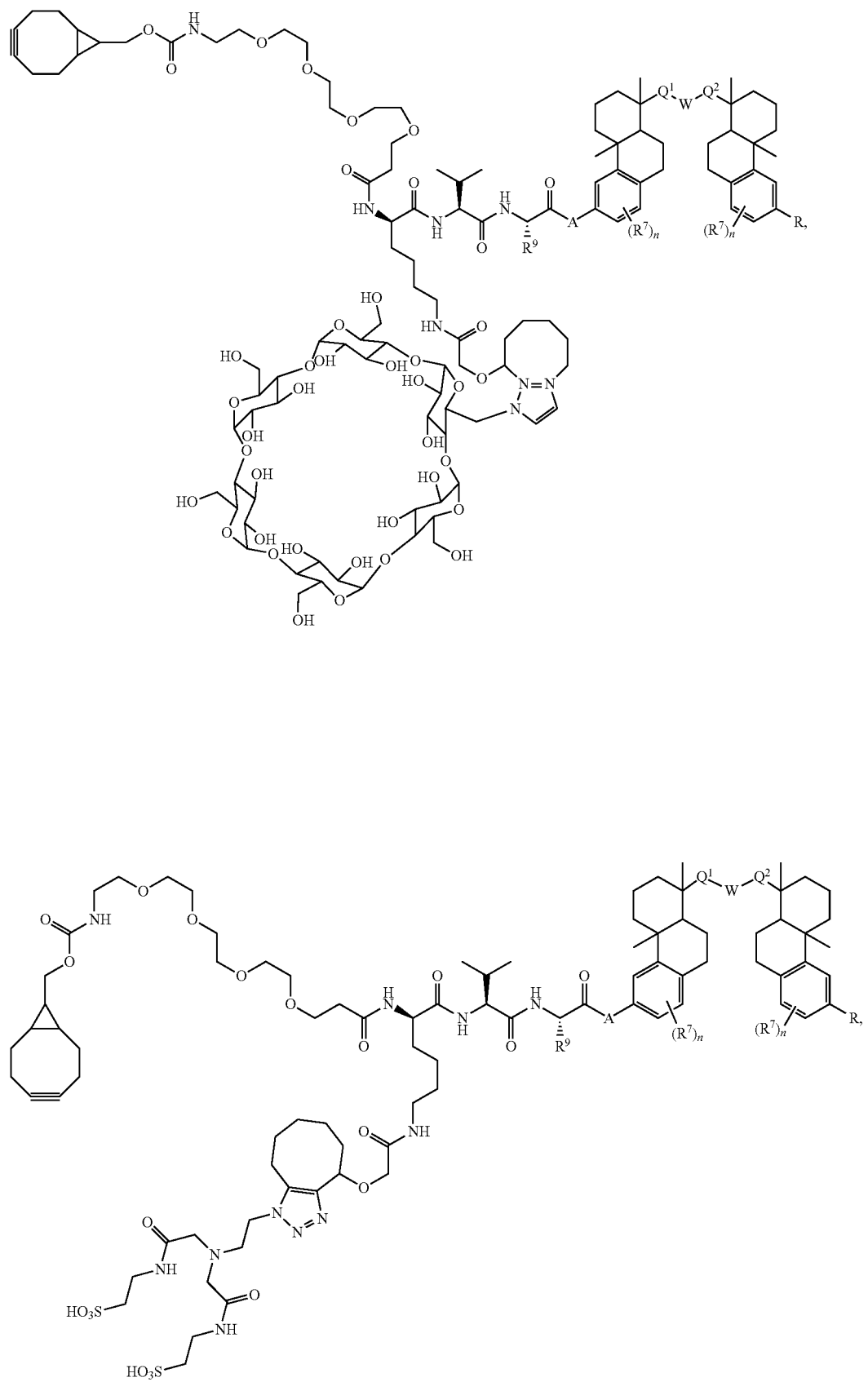

-continued

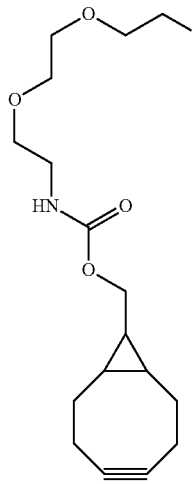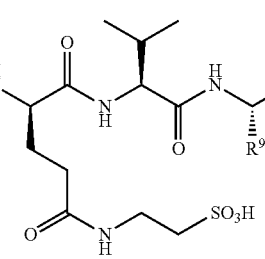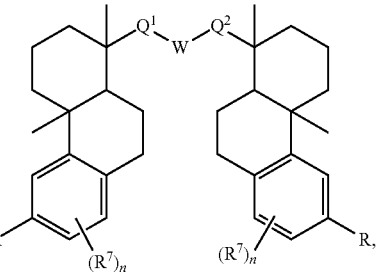

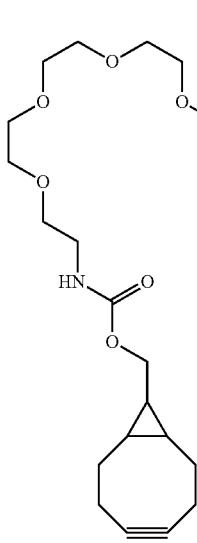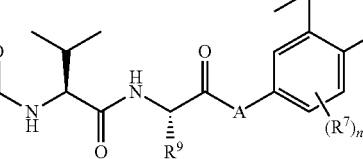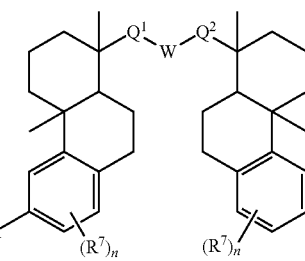

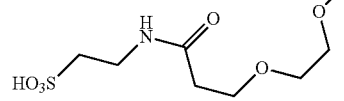

or a pharmaceutically acceptable salt, solvate, or stereoisomeric form thereof, or a regioisomer thereof, wherein:
R is —H, $R^1$, or $R^2$; and
$Q^1$, $Q^2$, W, $R^1$, $R^2$, $R^3$, $R^4$, $R^5$, $R^6$, $R^7$, X, Y, Z, and n are as described in the context of Formula I;
each $R^9$ is —CH$_3$ or —(CH$_2$)$_3$N(H)C(O)NH$_2$; and
each A is —O—, —N(H)—,

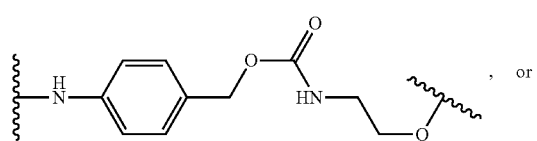, or

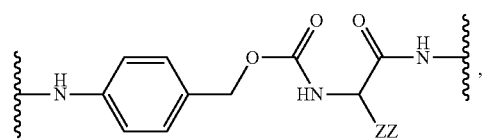

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In some embodiments, the reactive linker-payload is:

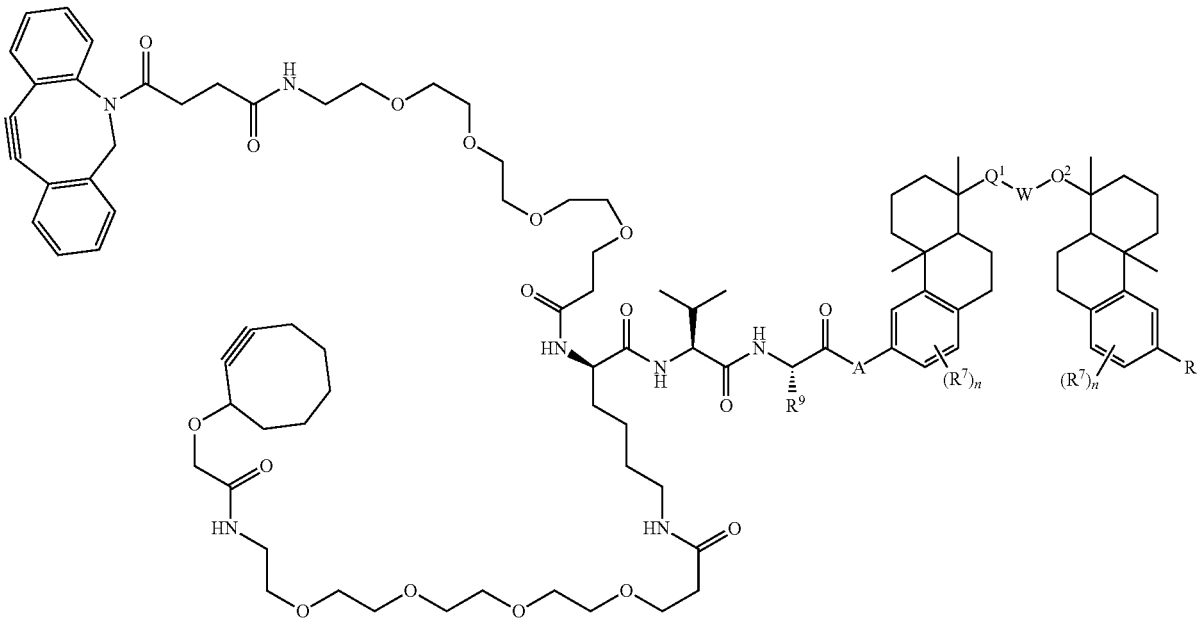

or a pharmaceutically acceptable salt, solvate, or stereoisomeric form thereof, or a regioisomer thereof, wherein:

R is —H, $R^1$, or $R^2$; and $Q^1$, $Q^2$, W, $R^1$, $R^2$, $R^3$, $R^4$, $R^5$, $R^6$, $R^7$, X, Y, Z, and n are as described in the context of Formula I;

each $R^9$ is —$CH_3$ or —$(CH_2)_3N(H)C(O)NH_2$; and each A is —O—, —N(H)—,

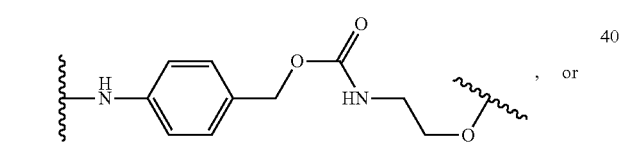, or

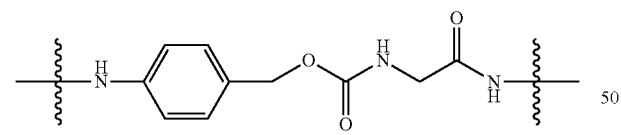

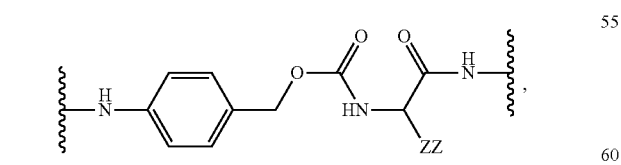

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In some embodiments, the reactive linker-payload is:

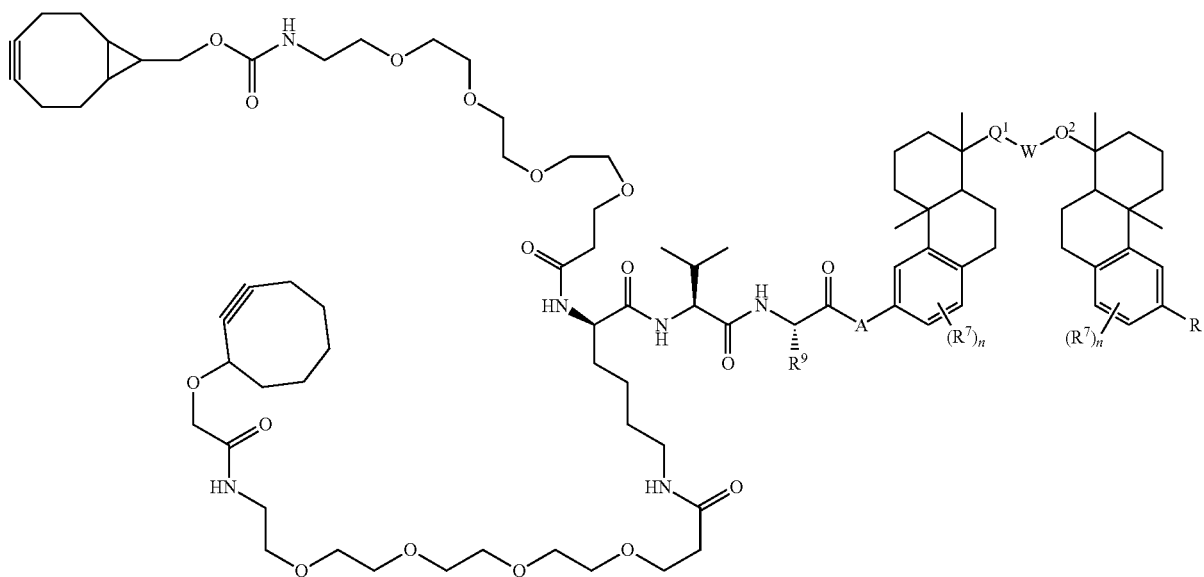

or a pharmaceutically acceptable salt, solvate, or stereoisomeric form thereof, or a regioisomer thereof, wherein:

R is —H, $R^1$, or $R^2$; and $Q^1$, $Q^2$, W, $R^1$, $R^2$, $R^3$, $R^4$, $R^5$, $R^6$, $R^7$, X, Y, Z, and n are as described in the context of Formula I;

each $R^9$ is —$CH_3$ or —$(CH_2)_3N(H)C(O)NH_2$; and each A is —O—, —N(H)—,

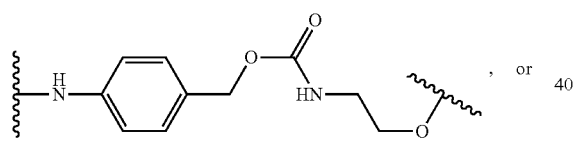

, or

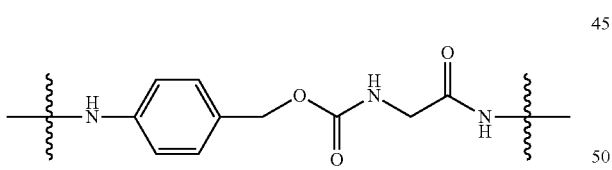

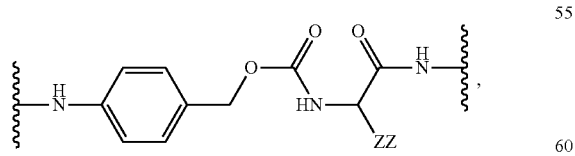

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In some embodiments, the reactive linker-payload is:
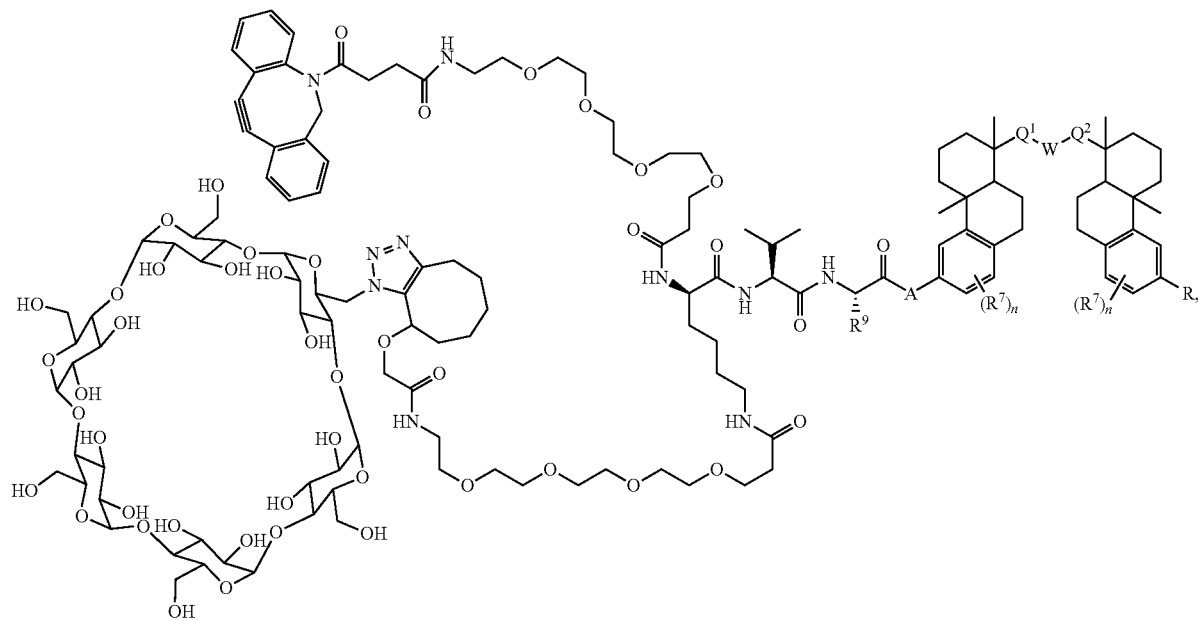
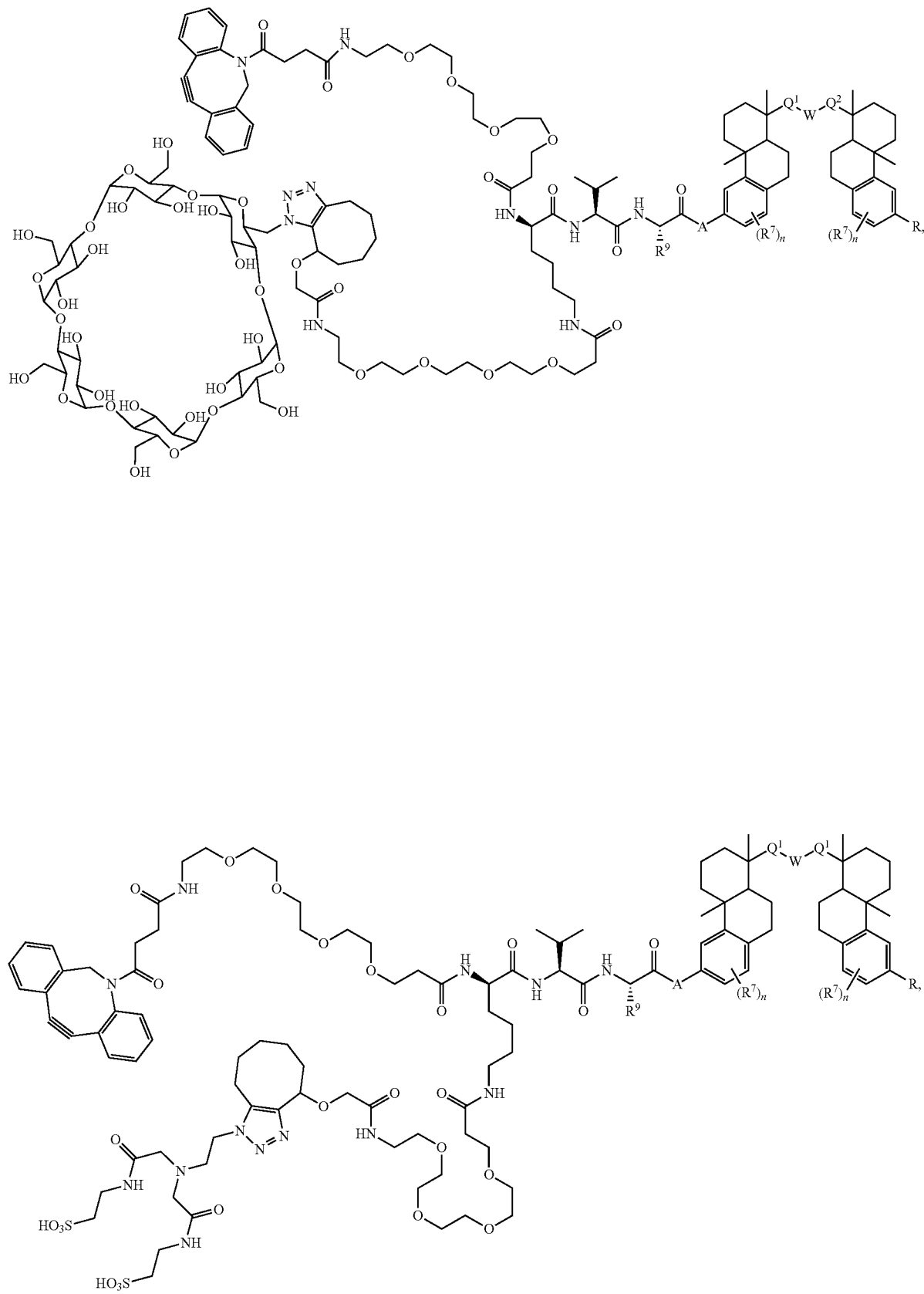

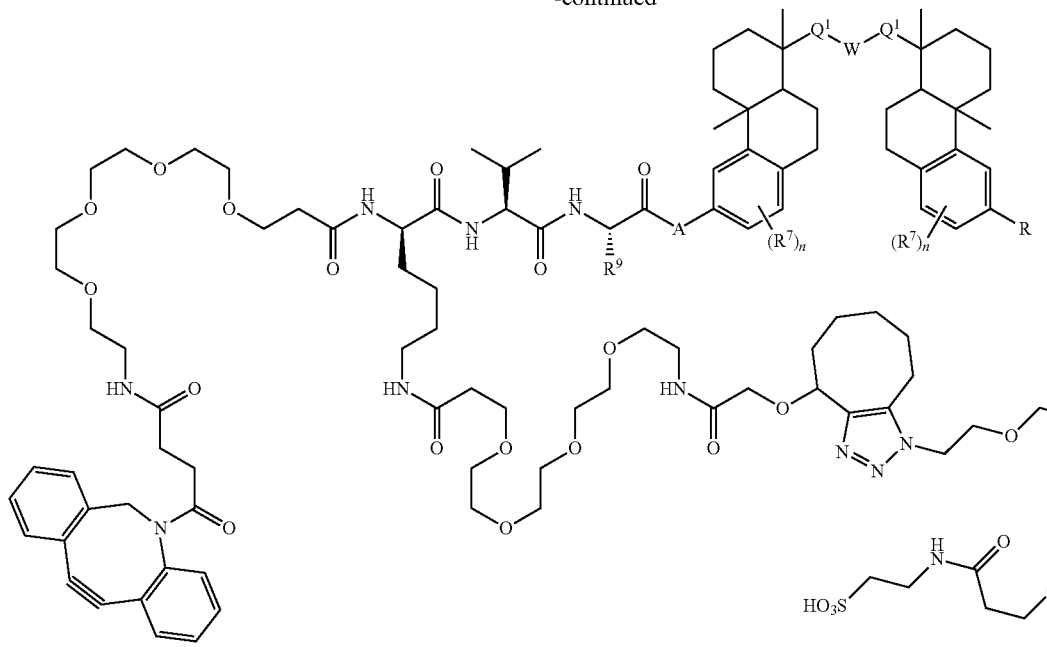

or a pharmaceutically acceptable salt, solvate, or stereoisomeric form thereof, or a regioisomer thereof, wherein:

R is —H, $R^1$, or $R^2$; and $Q^1$, $Q^2$, W, $R^1$, $R^2$, $R^3$, $R^4$, $R^5$, $R^6$, $R^7$, X, Y, Z, and n are as described in the context of Formula I;

each $R^9$ is —$CH_3$ or —$(CH_2)_3N(H)C(O)NH_2$; and each A is —O—, —N(H)—,

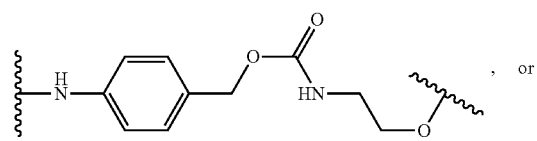 , or

-continued

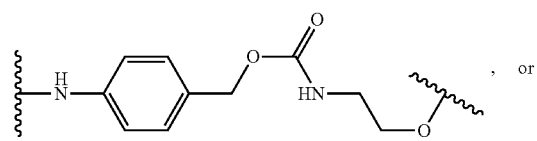

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In some embodiments, the reactive linker-payload is:

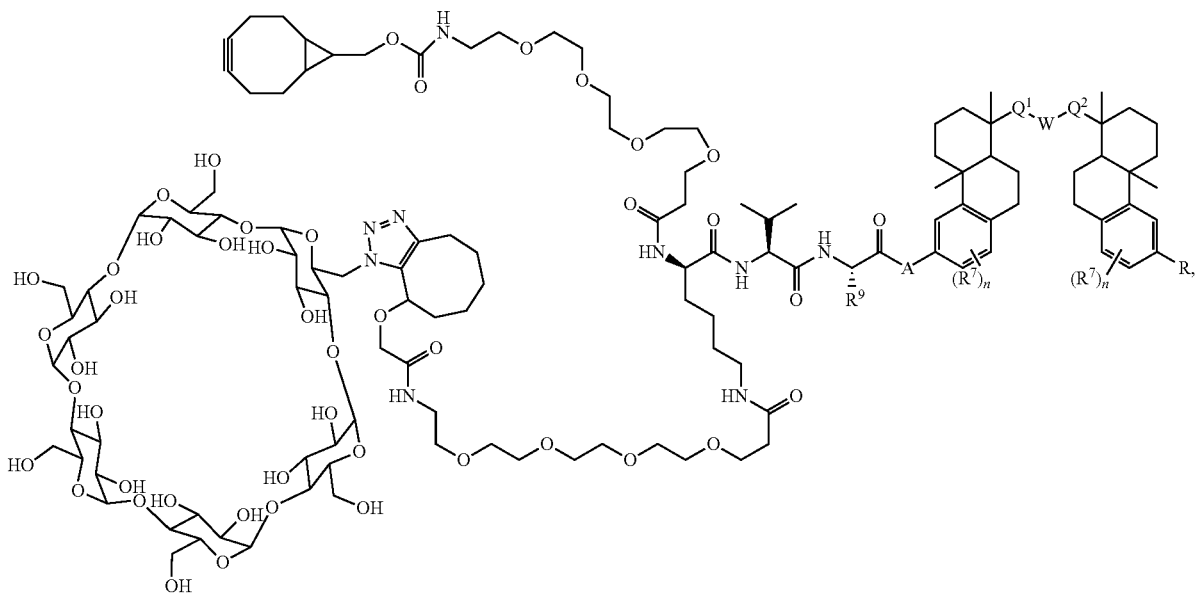

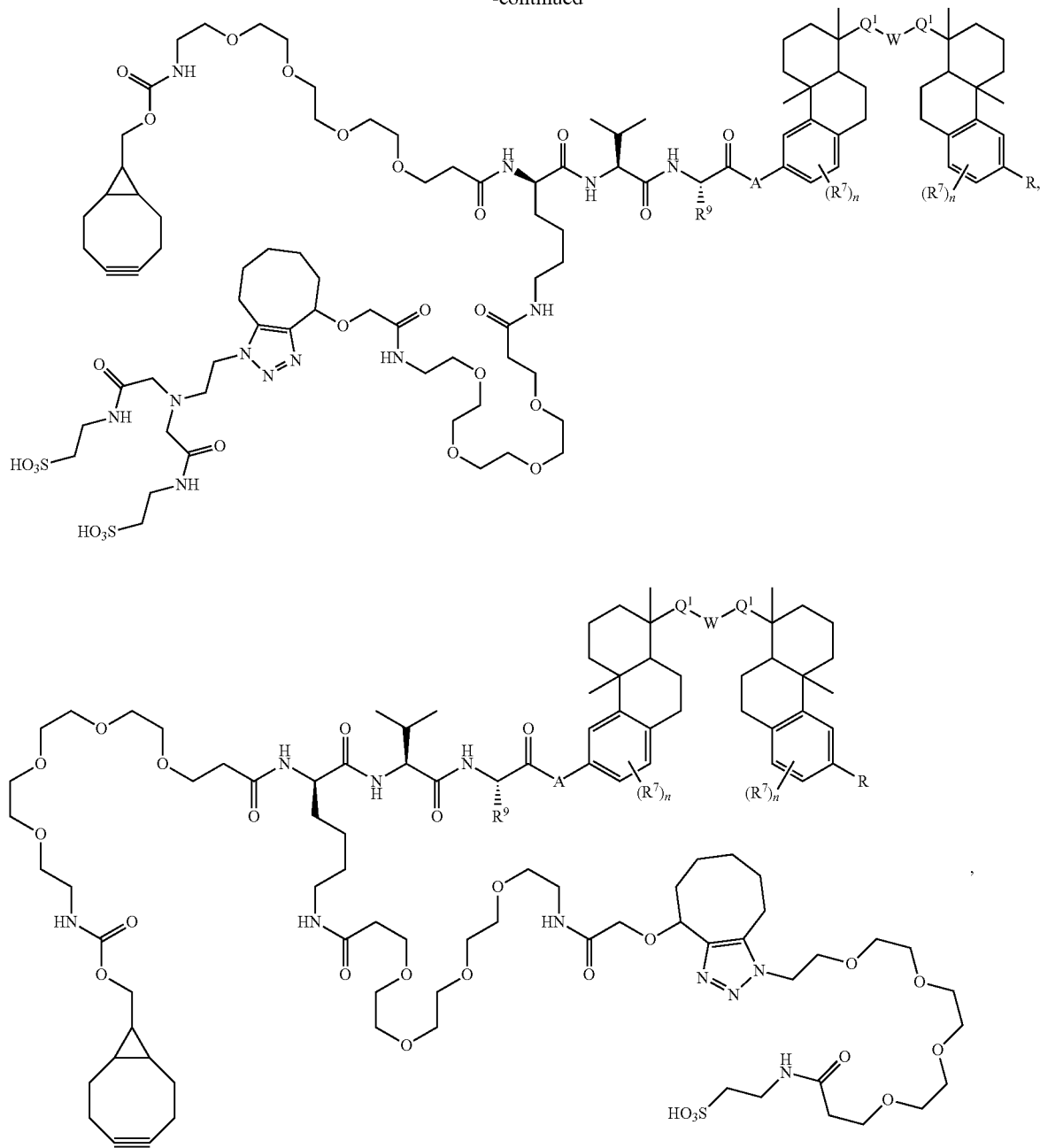

or a pharmaceutically acceptable salt, solvate, or stereoisomeric form thereof, or a regioisomer thereof, wherein:
  R is —H, $R^1$, or $R^2$; and
  $Q^1$, $Q^2$, W, $R^1$, $R^2$, $R^3$, $R^4$, $R^5$, $R^6$, $R^7$, X, Y, Z, and n are as described in the context of Formula I;
  each $R^9$ is —$CH_3$ or —$(CH_2)_3N(H)C(O)NH_2$; and
  each A is —O—, —N(H)—,

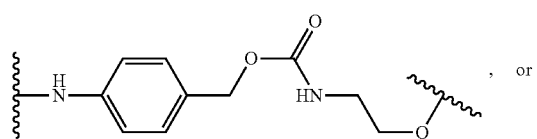, or

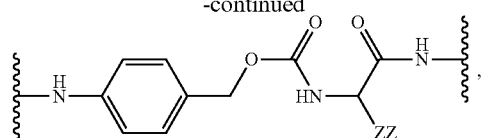

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, R is $R^1$.

In some embodiments, the reactive linker-payload is selected from:

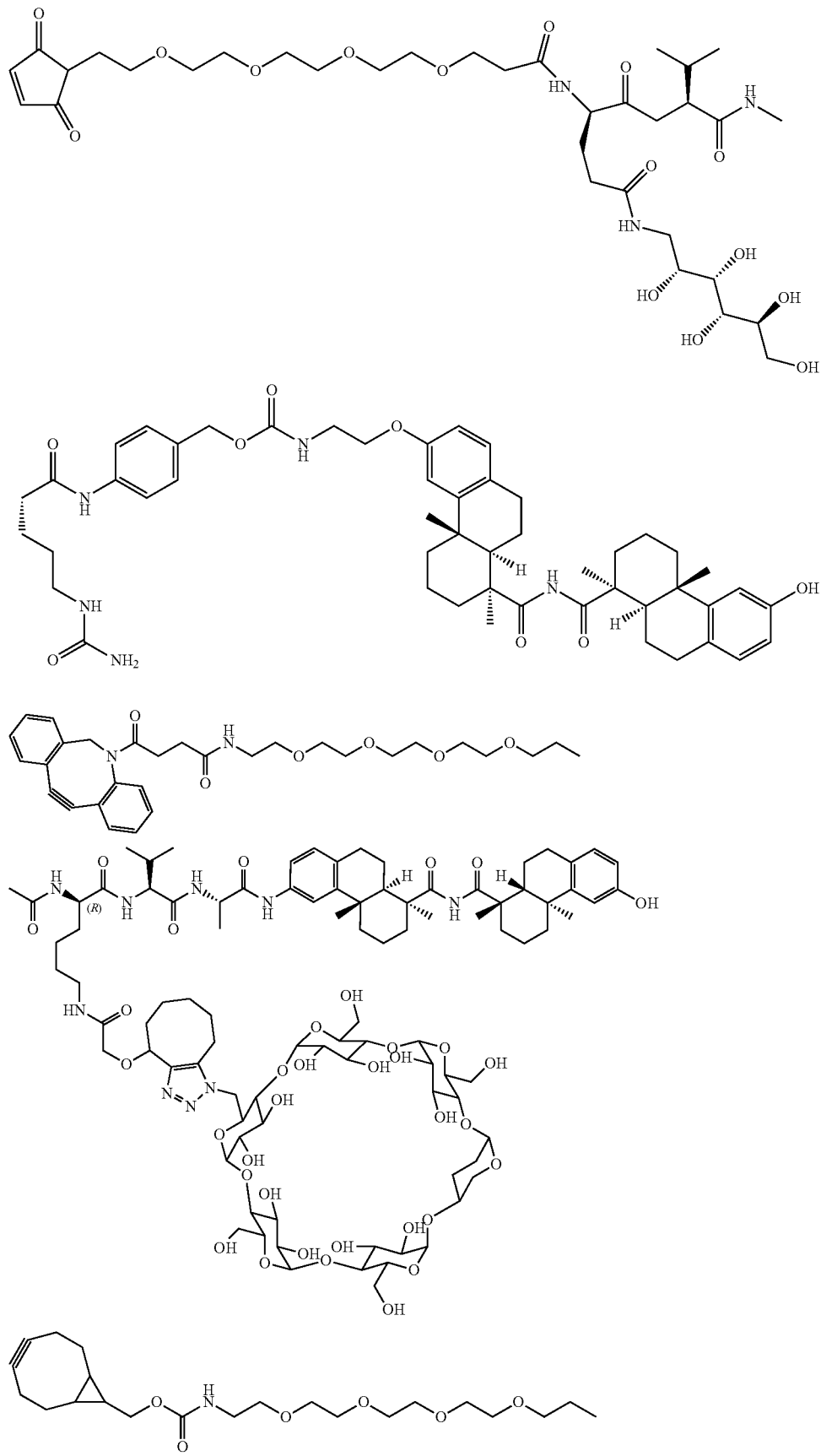

-continued
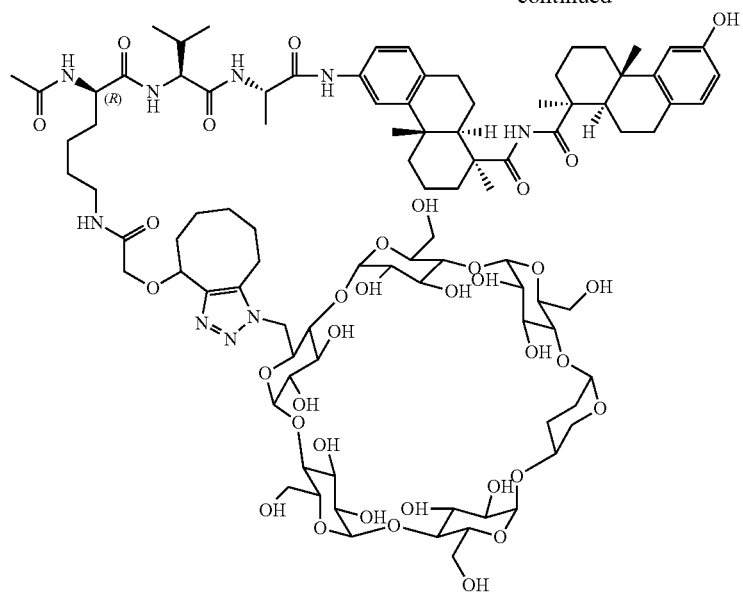
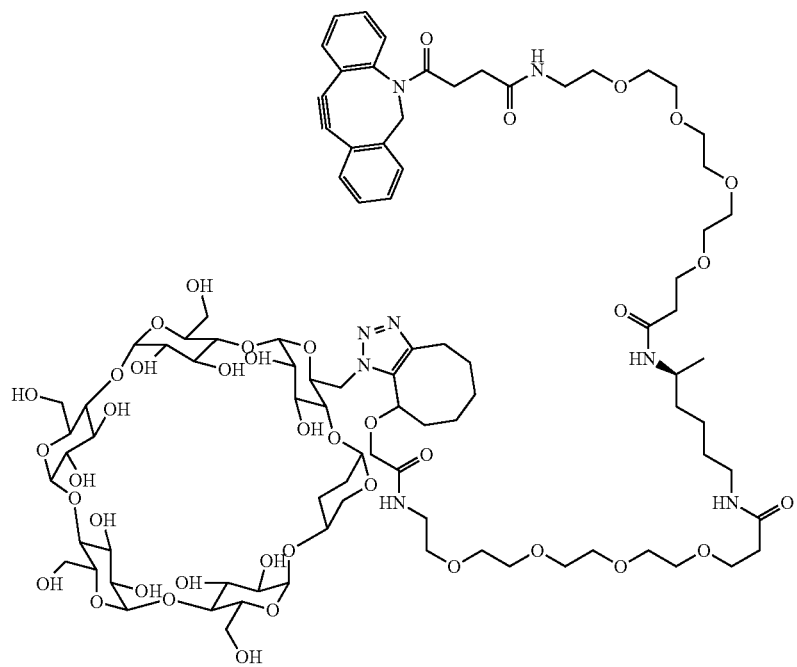
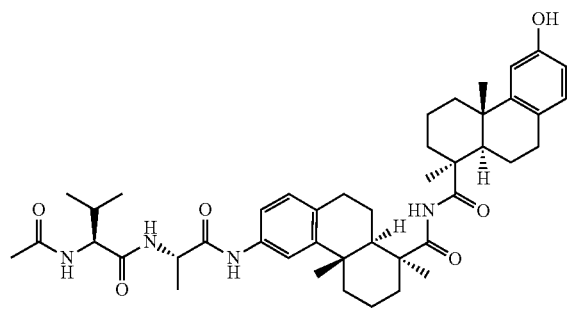

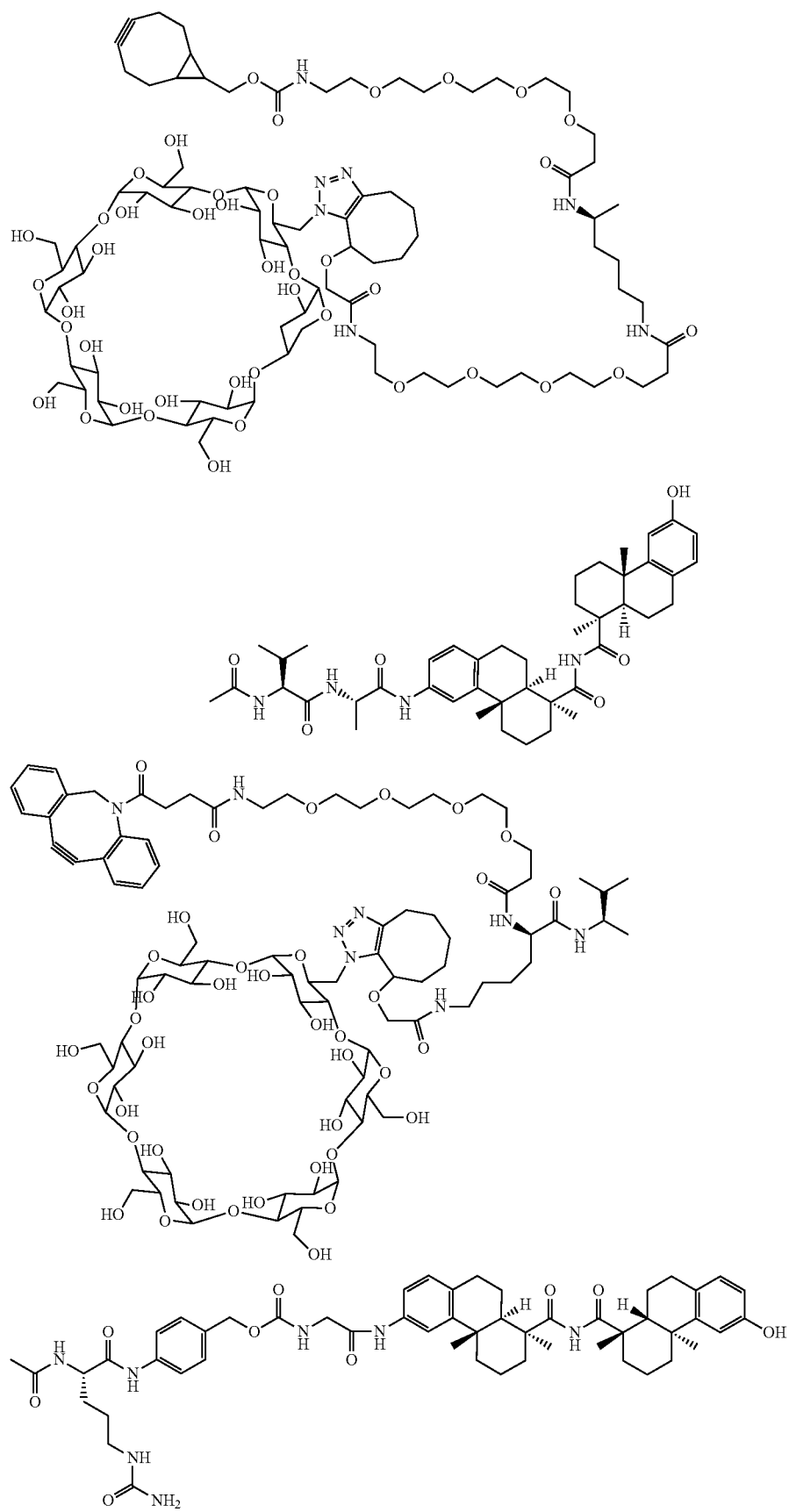

-continued
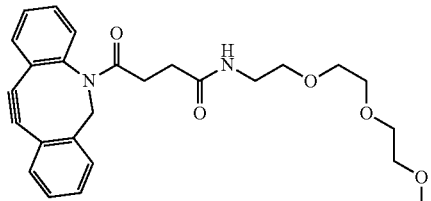
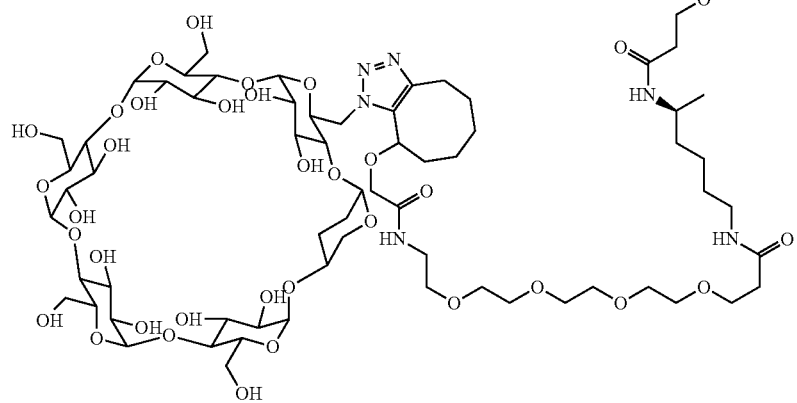
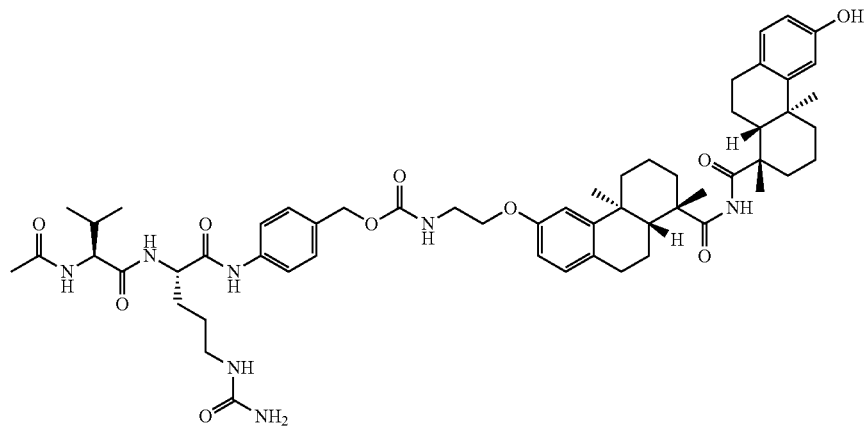
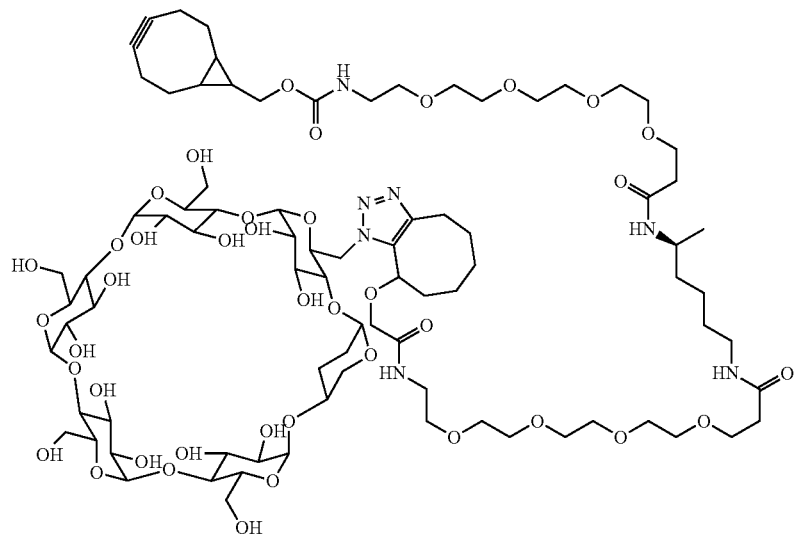

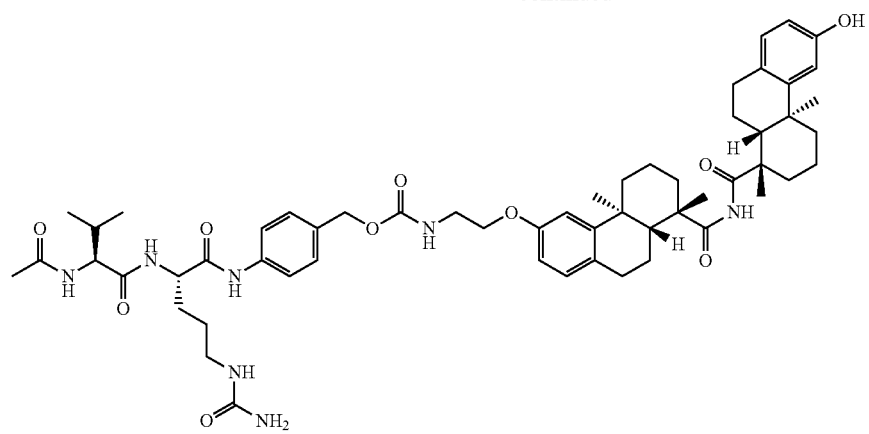
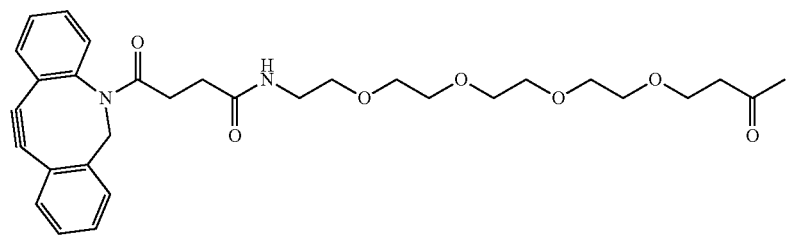
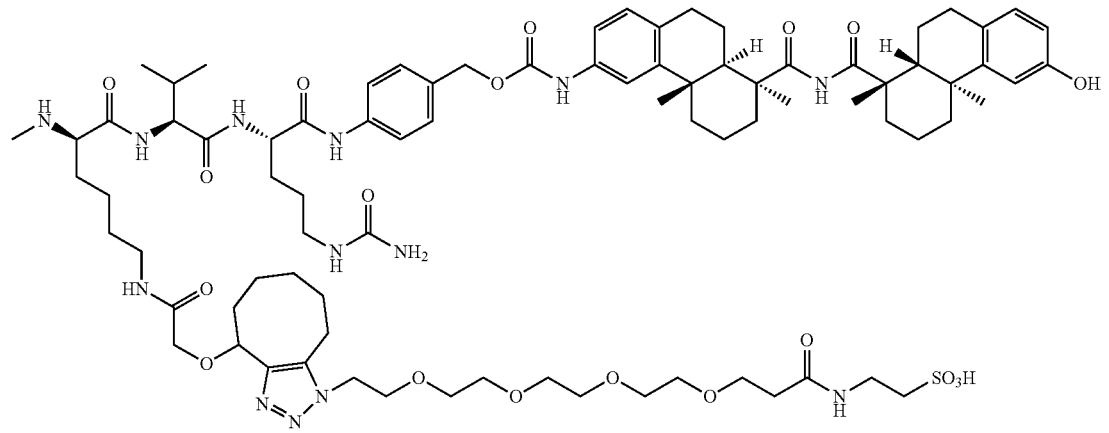
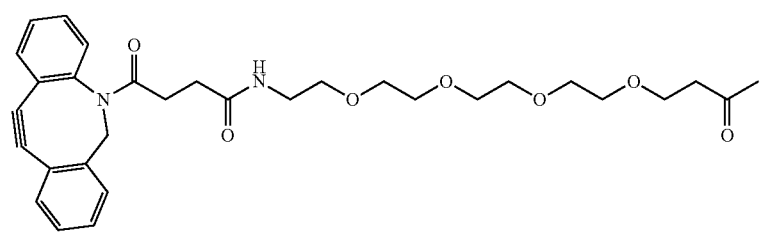

-continued
237
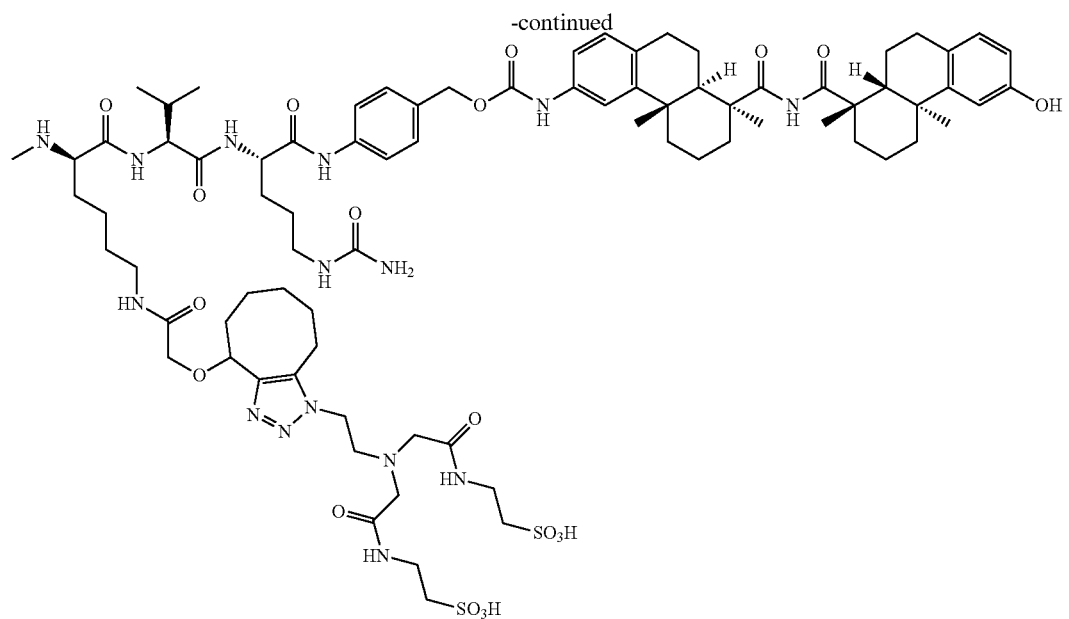
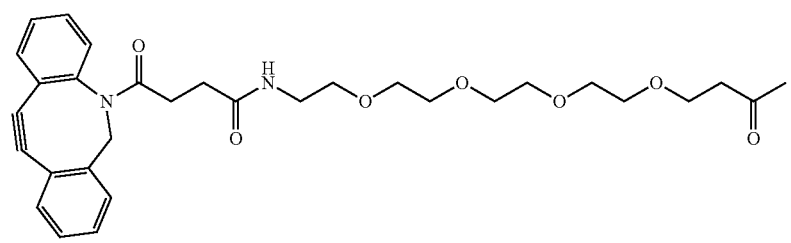
238
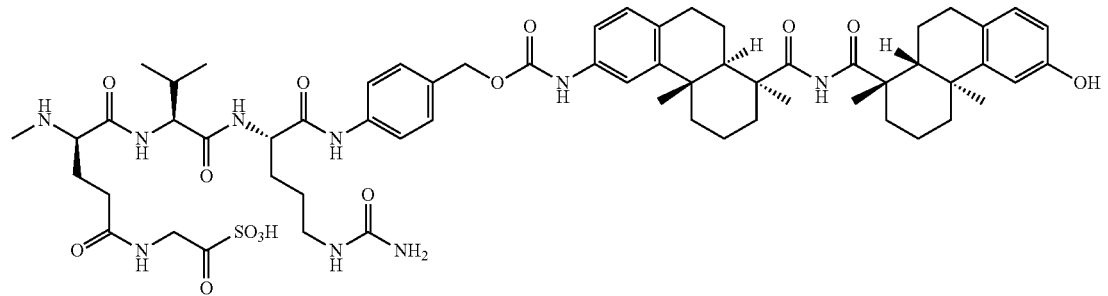
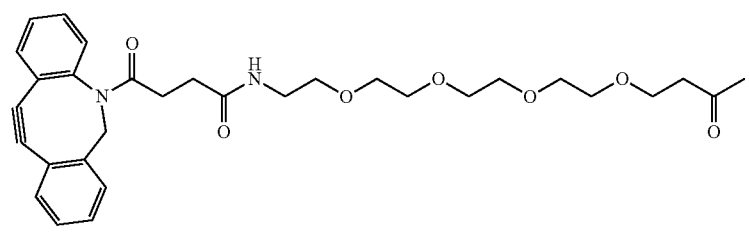

-continued
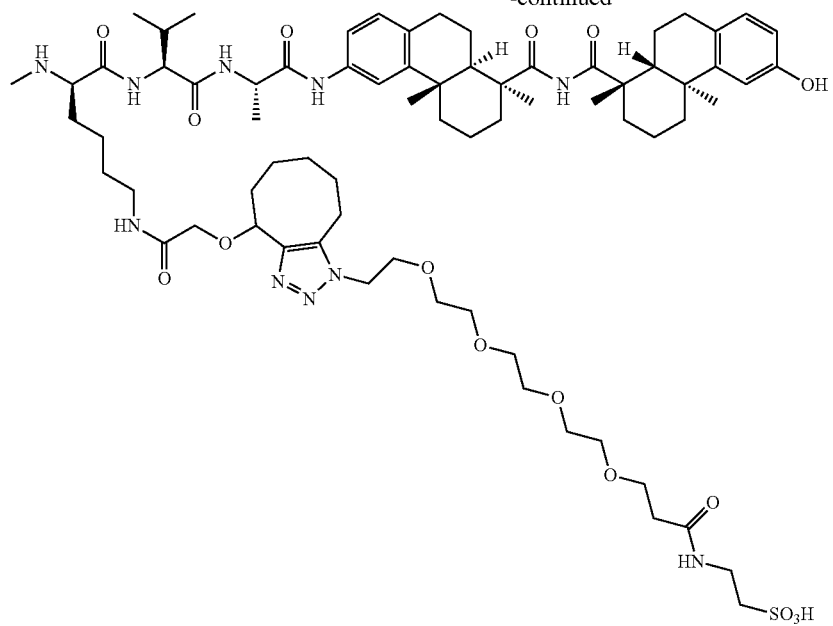
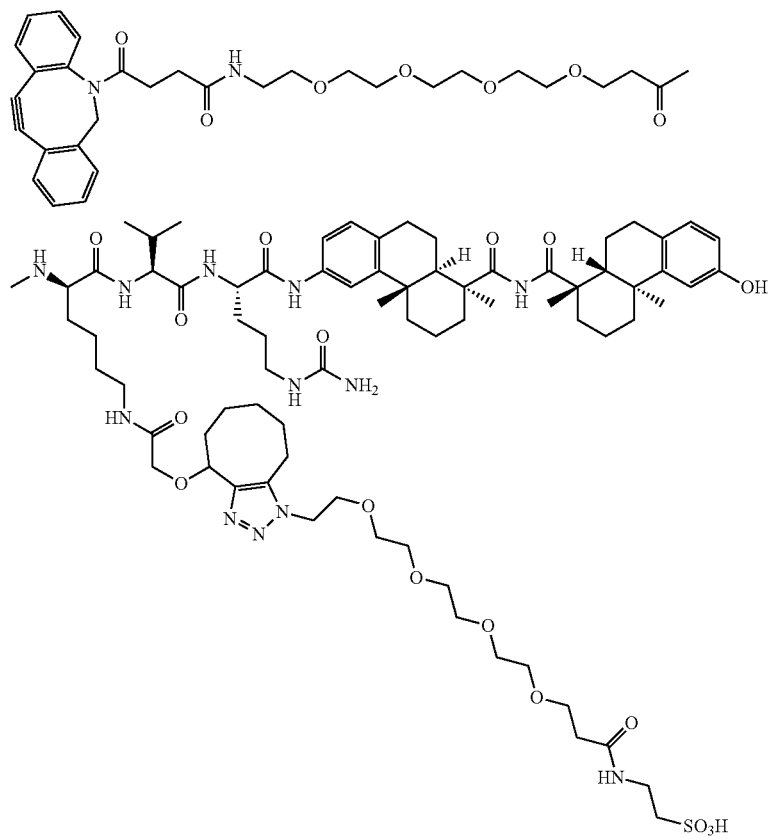
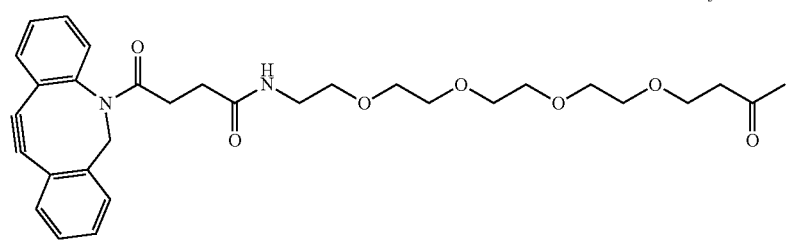

241
242
-continued
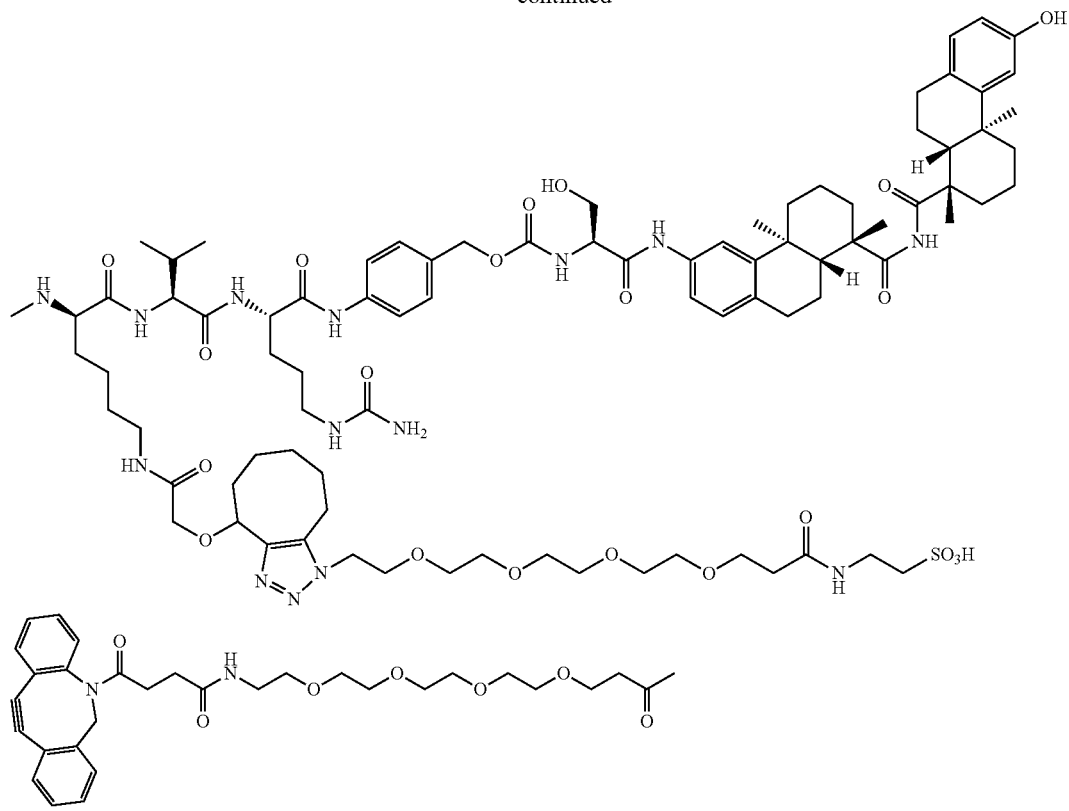
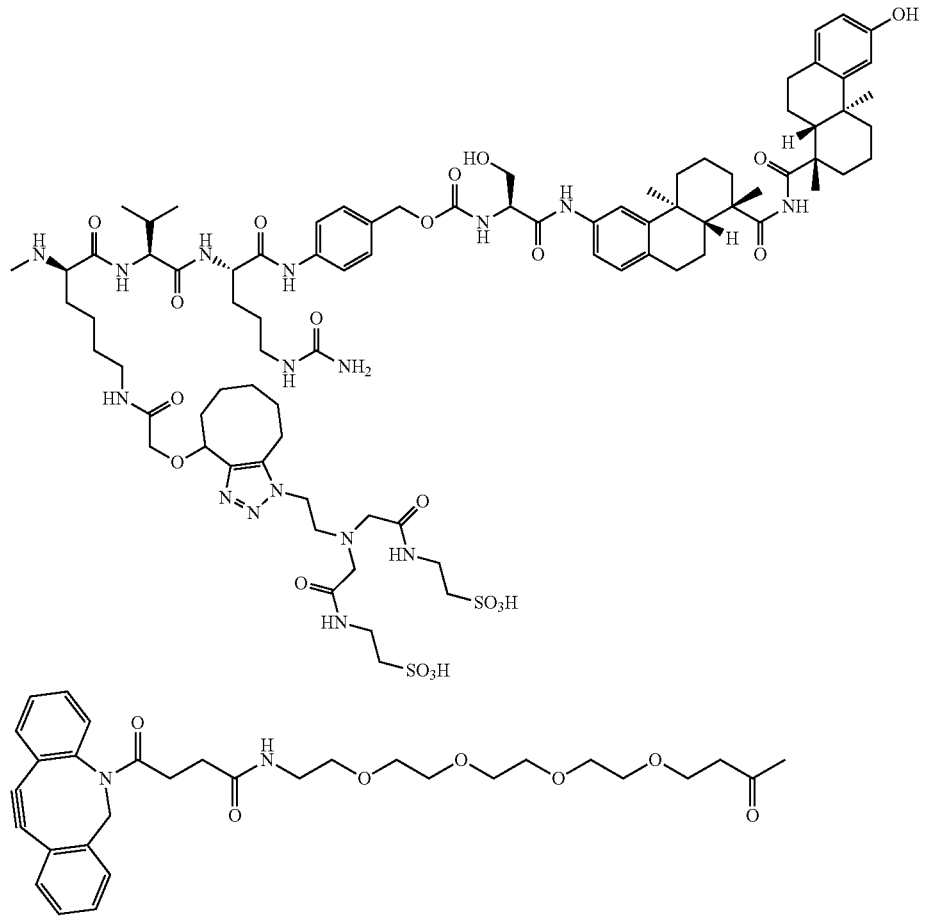

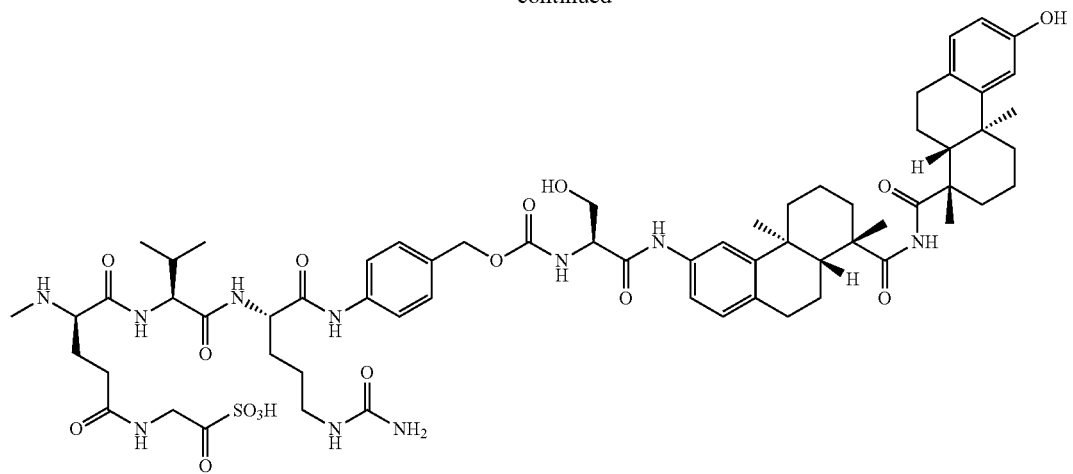
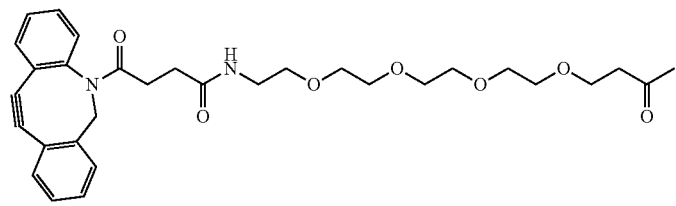
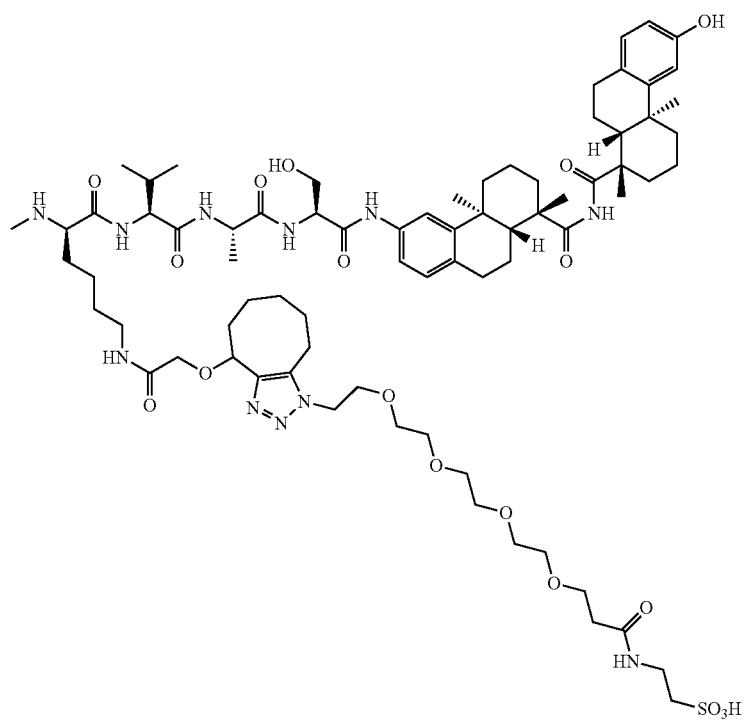
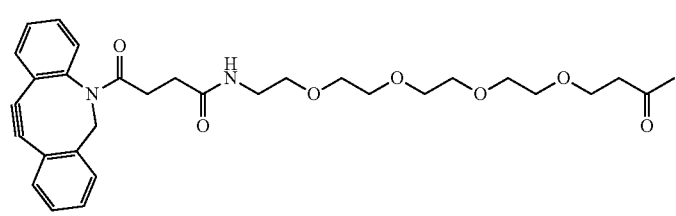

-continued

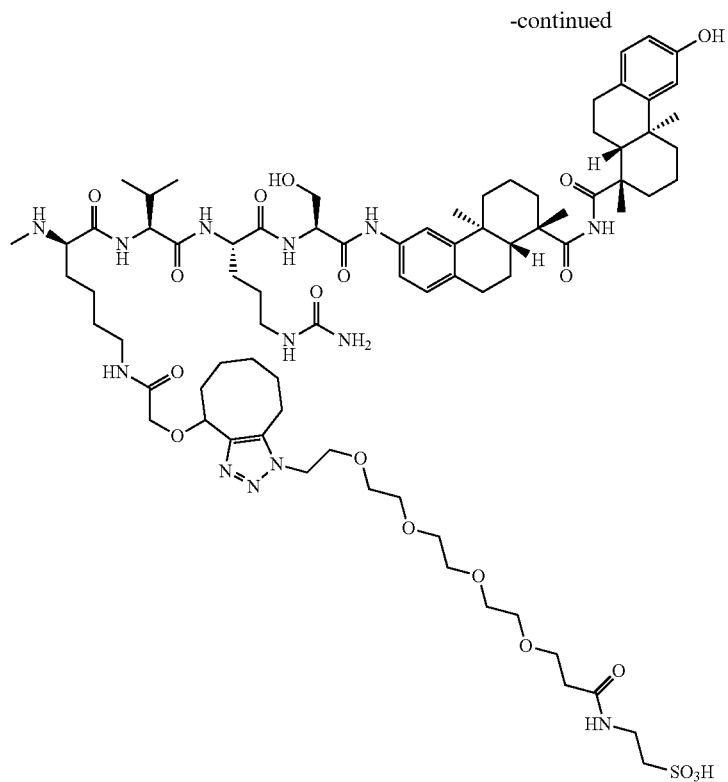

or a regioisomer, or stereoisomeric form pharmaceutically acceptable salt, solvate, thereof.

Methods of Preparing Compounds

The compounds provided herein can be prepared, isolated, or obtained by any method apparent to those of skill in the art. Exemplary methods of preparation are described in detail in the examples below. In certain embodiments, compounds provided herein can be prepared according to Scheme A:

Scheme A. Exemplary Preparation Scheme

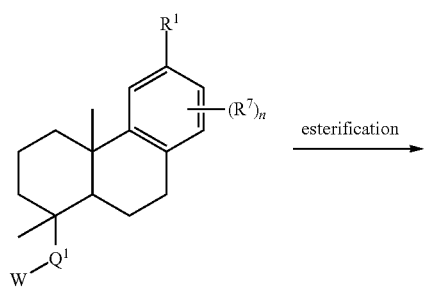 esterification →

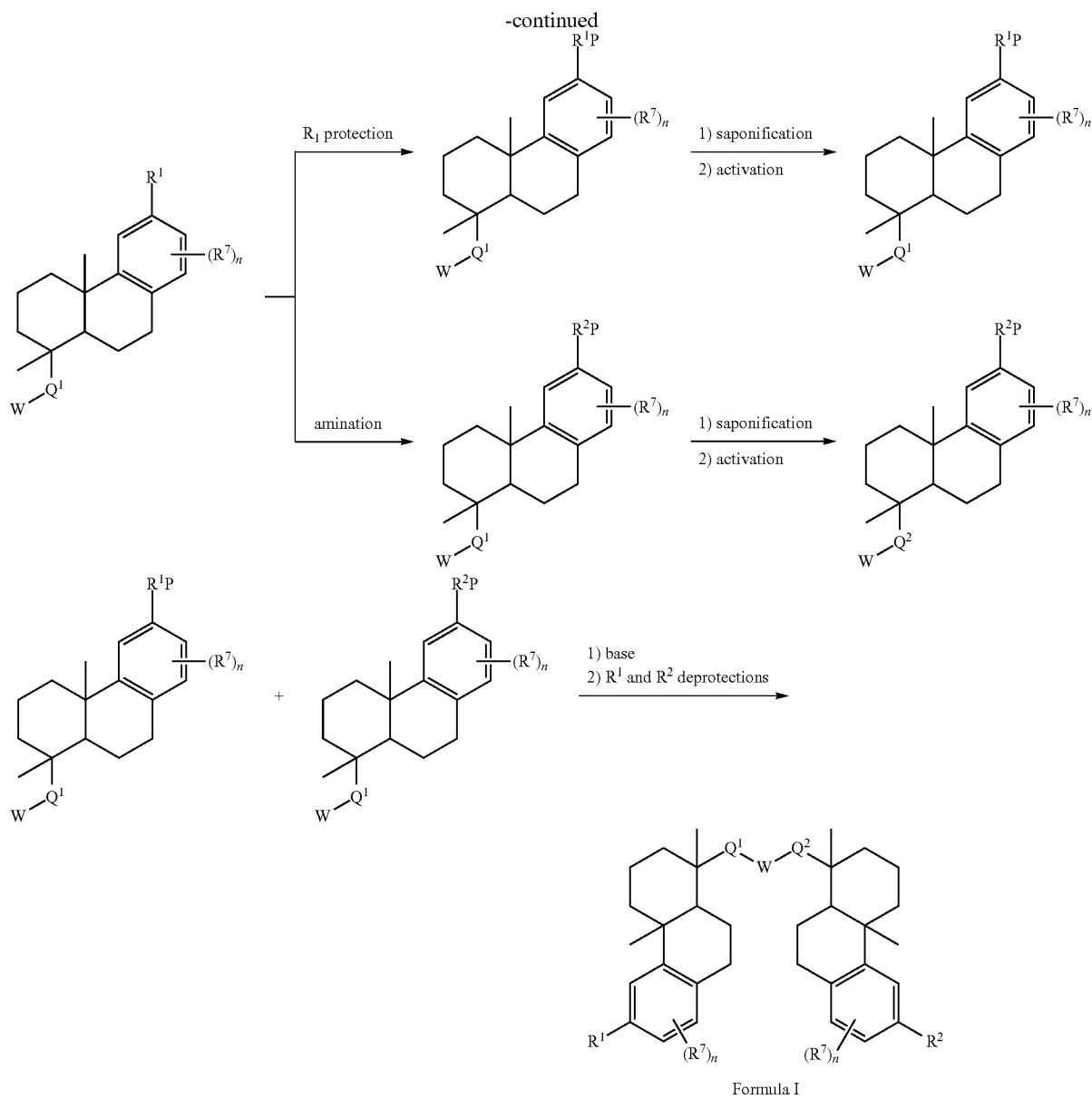

Formula I

In the Exemplary Preparation Scheme, $Q^1$, $Q^2$, $R^1$, $R^2$, $R^7$, W, and n are defined as described in the context of Formula (I). Initial esterification is followed by either protection of $R^1$ and/or amination of $R^1$ to beget $R^2P$. Following protection of $R^1$, a saponification and activation of, for example, a carboxylic acid moiety provides a first coupling partner having $Q^1$. Following amination, saponification, and amidation of, for example, a carboxylic acid moiety, provides a second coupling partner having $Q^2$. Unification of coupling partners having $Q^1$ and $Q^2$, respectively, followed by deprotections of $R^1$ and $R^2$, respectively, provides compounds of Formula I. Exemplary methods of preparation are described in detail in the Examples below.

In certain embodiments, one or more protection or deprotection steps may be included in the methods of preparation described in Scheme A, above.

The linker-payloads described herein can be synthesized by a series of coupling steps.

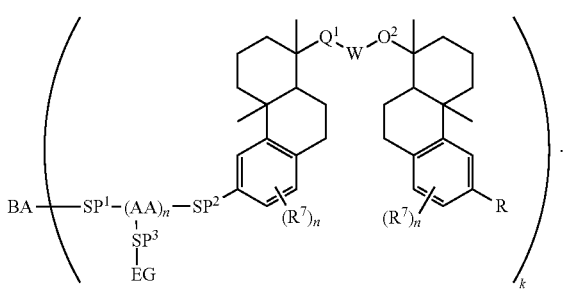

For instance, the payload at the right side can be linked to $SP^2$ via one or more standard coupling reactions. In advantageous embodiments, the payload compounds described herein include free amino groups available for coupling by amide synthesis conditions, described herein. The amino acids of $(AA)_n$ can be added by amide synthesis conditions, for instance, peptide synthesis conditions. The spacer $SP^2$ can be linked to $(AA)_n$ via one or more standard coupling reactions. In advantageous embodiments, the $SP^2$ and $(AA)_n$ groups described herein include free amino or carboxyl groups available for coupling by amide synthesis conditions, described herein. When present, the spacer $SP^3$ can be linked to $(AA)_n$ via one or more standard coupling reactions. In advantageous embodiments, the $SP^3$ and $(AA)_n$ groups described herein include free amino or carboxyl groups available for coupling by amide synthesis conditions, described herein.

The spacer $SP^3$, when present, terminates with a reactive group RG. This reactive group can be linked to the enhancement agent EG via coupling conditions deemed suitable to those of skill in the art. In certain embodiments, spacer $SP^3$ is linked to enhancement agent EG via amide synthesis conditions. In certain embodiments, spacer $SP^3$ is linked to enhancement agent EG via click chemistry. In these embodiments, spacer $SP^3$ terminates with a reactive group suitable for a click reaction, for instance, an azide or an alkyne, and enhancement agent EG comprises a complementary reactive group suitable for a click reaction, for instance an alkyne or an azide. In preferred embodiments, $SP^3$ terminates with a strained alkyne and EG comprises an azide; or $SP^3$ terminates with an carboxylic acid and EG comprises an amine. When EG is a cyclodextrin moiety, the cyclodextrin can comprise an azide. Azido cyclodextrins can be prepared synthetically or obtained from commercial sources. When EG is a sulfonic acid moiety, one end(s) of the EG terminate with a sulfonic acid group(s), and the other end terminates with a primary or secondary amine.

The conjugates described herein can be synthesized by coupling the linker-payloads described herein with a binding agent, for example, an antibody under standard conjugation conditions (see, e.g., Doronina et al. *Nature Biotechnology* 2003, 21, 7, 778, which is incorporated herein by reference in its entirety). When the binding agent is an antibody, the antibody may be coupled to a linker-payload via one or more cysteine or lysine residues of the antibody. Linker-payloads can be coupled to cysteine residues, for example, by subjecting the antibody to a reducing agent, for example, dithiotheritol, to cleave the disulfide bonds of the antibody, purifying the reduced antibody, for example, by gel filtration, and subsequently treating the antibody with a linker-payload containing a suitable reactive moiety, for example, a maleimido group. Suitable solvents include, but are not limited to water, DMA, DMF, and DMSO. Linker-payloads containing a reactive group, for example, an activated ester or acid halide group, can be coupled to lysine residues of the antibody. Suitable solvents include, but are not limited to water, DMA, DMF, and DMSO. Conjugates can be purified using known protein techniques, including, for example, size exclusion chromatography, dialysis, and ultrafiltration/diafiltration.

Binding agents, for example antibodies, can also be conjugated via click chemistry reactions. In some embodiments of said click chemistry reactions, the linker-payload includes a reactive group, for example an alkyne, that is capable of undergoing a 1,3-cycloaddition reaction with an azide. Such suitable reactive groups are described above. The antibody includes one or more azide groups. Such antibodies include antibodies functionalized with, for example, azido-polyethylene glycol groups. In certain embodiments, such functionalized antibody is derived by treating an antibody having at least one glutamine residue, for example, heavy chain Gln295 or Gln55, with a primary amine compound in the presence of the enzyme transglutaminase. In certain embodiments, such functionalized antibody is derived by treating an antibody having at least one glutamine residue, for example, heavy chain Gln297, with a primary amine compound in the presence of the enzyme transglutaminase. Such antibodies include Asn297Gln (N297Q) mutants. In certain embodiments, such functionalized antibody is derived by treating an antibody having at least two glutamine residues, for example, heavy chain Gln295 and heavy chain Gln297, with a primary amine compound in the presence of the enzyme transglutaminase. Such antibodies include Asn297Gln (N297Q) mutants. In certain embodiments, the antibody has two heavy chains as described in this paragraph for a total of two or a total of four glutamine residues.

In certain embodiments, the antibody comprises a glutamine residue at one or more heavy chain positions numbered 295 in the EU numbering system. In the present disclosure, this position is referred to as glutamine 295, or as Gln295, or as Q295. Those of skill will recognize that this is a conserved glutamine residue in the wild type sequence of many antibodies. In other useful embodiments, the antibody can be engineered to comprise a glutamine residue. Techniques for modifying an antibody sequence to include a glutamine residue are within the skill of those in the art (see, e.g., Ausubel et al. Current Protoc. Mol. Biol.).

In certain embodiments, the antibody comprises two glutamine residues, one in each heavy chain. In particular embodiments, the antibody comprises a Q295 residue in each heavy chain. In further embodiments, the antibody comprises one, two, three, four, five, six, seven, eight, or more glutamine residues. These glutamine residues can be in heavy chains, light chains, or in both heavy chains and light chains. Exemplary glutamine residues include Q55. These glutamine residues can be wild-type residues, or engineered residues. The antibodies can be prepared according to standard techniques.

Those of skill will recognize that antibodies are often glycosylated at residue N297, near residue Q295 in a heavy chain sequence. Glycosylation at residue N297 can interfere with a transglutaminase at residue Q295 (Dennler et al., supra). Accordingly, in advantageous embodiments, the antibody is not glycosylated. In certain embodiments, the antibody is deglycoslated or aglycosylated. In particular embodiments, an antibody heavy chain has an N297 mutation. Alternatively stated, the antibody is mutated to no longer have an asparagine residue at position 297. In particular embodiments, an antibody heavy chain has an N297Q mutation. Such an antibody can be prepared by site-directed mutagenesis to remove or disable a glycosylation sequence or by site-directed mutagenesis to insert a glutamine residue at a site without resulting in disabled antibody function or binding. In some embodiments, an antibody having a Q295 residue and/or an N297Q mutation contains one or more additional naturally occurring glutamine residues in their variable regions, which can be accessible to transglutaminase and therefore capable of conjugation to a linker or a linker-payload. An exemplary naturally occurring glutamine residue can be found, e.g., at Q55 of the light chain. In such instances, the antibody conjugated via transglutaminase can have a higher than expected DAR value (e.g., a DAR higher than 4). Any such antibodies can be isolated from natural or artificial sources.

The antibody without interfering glycosylation is then reacted with a primary amine compound. In certain embodiments, an aglycosylated antibody is reacted with a primary amine compound to produce a glutaminyl-modified antibody. In certain embodiments, a deglycosylated antibody is reacted with a primary amine compound to produce a glutaminyl-modified antibody.

The primary amine can be any primary amine that is capable of forming a covalent bond with a glutamine residue in the presence of a transglutaminase. Useful primary amines are described below. The transglutaminase can be any transglutaminase deemed suitable by those of skill in the art. In certain embodiments, the transglutaminase is an enzyme that catalyzes the formation of an isopeptide bond between a free amine group on the primary amine compound and the acyl group on the side chain of a glutamine residue. Transglutaminase is also known as protein-glutamine-γ-glutamyltransferase. In particular embodiments, the transglutaminase is classified as EC 2.3.2.13. The transglutaminase can be from any source deemed suitable. In certain embodiments, the transglutaminase is microbial. Useful transglutaminases have been isolated from *Streptomyces mobaraense, Streptomyces cinnamoneum, Streptomyces griseo-carneum, Streptomyces lavendulae*, and *Bacillus subtilis*. Non-microbial transglutaminases, including mammalian transglutaminases, can also be used. In certain embodiments, the transglutaminase can be produced by any technique or obtained from any source deemed suitable by the practitioner of skill. In particular embodiments, the transglutaminase is obtained from a commercial source.

In particular embodiments, the primary amine compound comprises a reactive group capable of further reaction after transglutamination. In these embodiments, the glutaminyl-modified antibody can be reacted or treated with a reactive payload compound or a reactive linker-payload compound to form an antibody-payload conjugate. In certain embodiments, the primary amine compound comprises an azide.

In certain embodiments, the glutaminyl-modified antibody is reacted or treated with a reactive linker-payload to form an antibody-payload conjugate. The reaction can proceed under conditions deemed suitable by those of skill in the art. In certain embodiments, the glutaminyl-modified antibody is contacted with the reactive linker-payload compound under conditions suitable for forming a bond between the glutaminyl-modified antibody and the linker-payload compound. Suitable reaction conditions are well known to those in the art.

Exemplary reactions are provided in the Examples below.

Pharmaceutical Compositions and Methods of Treatment

Provided herein are methods of treating and preventing diseases, conditions, or disorders comprising administering a therapeutically or prophylactically effective amount or one or more of the compounds disclosed herein, for example, one or more of the compounds of a formula provided herein. Diseases, disorders, and/or conditions include, but are not limited to, those associated with the antigens listed herein.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

Suitable additional therapeutic agents include, but are not limited to: a second glucocorticoid, an autoimmune therapeutic agent, a hormone, a biologic, or a monoclonal antibody. Suitable therapeutic agents also include, but are not limited to any pharmaceutically acceptable salts, acids, or derivatives of a compound set forth herein.

In some embodiments of the methods described herein, multiple doses of a compound described herein (or a pharmaceutical composition comprising a combination of an compound described herein and any of the additional therapeutic agents mentioned herein) may be administered to a subject over a defined time course. The methods according to this aspect of the disclosure comprise sequentially administering to a subject multiple doses of a compound described herein. As used herein, "sequentially administering" means that each dose of the compound is administered to the subject at a different point in time, e.g., on different days separated by a predetermined interval (e.g., hours, days, weeks, or months). The present disclosure includes methods which comprise sequentially administering to the patient a single initial dose of a compound described herein, followed by one or more secondary doses of the compound, and optionally followed by one or more tertiary doses of the compound.

The terms "initial dose," "secondary doses," and "tertiary doses," refer to the temporal sequence of administration of the compounds described herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses can all include the same amount the compound described herein, but generally can differ from one another in terms of frequency of administration. In certain embodiments, the amount of the compound included in the initial, secondary, and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose the compound which is administered to a patient prior to the administration of the very next dose in the sequence with no intervening doses.

The methods according to this aspect of the disclosure may comprise administering to a patient any number of secondary and/or tertiary doses of the compound. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of once a month, then the maintenance doses may be administered to the patient once every six weeks, once every two months, once every three months, etc.

The present disclosure includes pharmaceutical compositions of the compounds and/or conjugates described herein, e.g., the compounds of Formula I, Ia, Ib A, Aa, or Ab, e.g., compositions comprising a compound described herein, a salt, stereoisomer, polymorph thereof, and a pharmaceutically acceptable carrier, diluent, and/or excipient. Examples of suitable carriers, diluents and excipients include, but are not limited to, buffers for maintenance of proper composition pH (e.g., citrate buffers, succinate buffers, acetate buffers, phosphate buffers, lactate buffers, oxalate buffers, and the like), carrier proteins (e.g., human serum albumin), saline, polyols (e.g., trehalose, sucrose, xylitol, sorbitol, and the like), surfactants (e.g., polysorbate 20, polysorbate 80, polyoxolate, and the like), antimicrobials, and antioxidants.

In some examples, set forth herein is a method of treating a disease, disorder or condition comprising administering to a patient having said disorder a therapeutically effective amount of a compound of Formula I, Ia, Ib A, Aa, or Ab or a pharmaceutical composition thereof.

In some examples, set forth herein is a method of preventing a disease, disorder or condition comprising administering to a patient having said disorder a prophylactically effective amount of a compound of Formula I, Ia, Ib A, Aa, or Ab or a pharmaceutical composition thereof.

In some examples, set forth herein are methods for treating or preventing any disease, disorder, or condition responsive to modulation of LXR signaling. In some examples, the disease or disorder is associated with LXR function, LXR polymorphisms, LXR agonist activity, or LXR antagonist activity. In some examples, set forth herein is a method of treating or preventing a disease, disorder, or condition selected from the group consisting of a proliferative disorder, a neurodegenerative disorder, an immunological disorder, an autoimmune disease, an inflammatory disorder, a dermatological disease, a metabolic disease, cardiovascular disease, and a gastrointestinal disease.

The proliferative disorder can be any proliferative disorder known to those of skill. In certain embodiments, proliferative disorders include, without limitation, oncology disorders, where the oncology disorder can be any cancer disorder known to those of skill. In certain embodiments, provided herein are methods of treating or preventing a melanoma. In certain embodiments, provided herein are methods of treating or preventing metastatic melanoma. In certain embodiments, provided herein are methods of treating or preventing lung cancer. In certain embodiments, provided herein are methods of treating or preventing EGFR-tyrosine kinase inhibitor resistant lung cancer. In certain embodiments, provided herein are methods of treating or preventing oral cancer. In certain embodiments, provided herein are methods of treating or preventing oral squamous cell carcinoma. In certain embodiments, provided herein are methods of treating or preventing prostate cancer. In certain embodiments, provided herein are methods of treating or preventing Hodgkin's lymphoma. In certain embodiments, provided herein are methods of treating or preventing breast cancer.

The neurodegenerative disorder can be any neurodegenerative disorder known to those of skill. In certain embodiments, provided herein are methods of treating or preventing Alzheimer's disease. In certain embodiments, provided herein are methods of treating or preventing Parkinson's disease. In certain embodiments, provided herein are methods of treating or preventing Huntington's disease. In certain embodiments, provided herein are methods of treating or preventing amyotrophic lateral sclerosis. In certain embodiments, provided herein are methods of treating or preventing myelin gene expression. In certain embodiments, provided herein are methods of treating or preventing myelination and remyelination conditions, diseases, or disorders.

The immunological disorder can be any immunological disorder known to those of skill. In certain embodiments, provided herein are methods of treating or preventing imflammatory bowel disease. In certain embodiments, provided herein are methods of treating or preventing ulcerative colitis. In certain embodiments, provided herein are methods of treating or preventing Crohn's disease.

The inflammatory disorder can be any inflammatory disorder known to those of skill. In certain embodiments, provided herein are methods of treating or preventing arthritis. In certain embodiments, provided herein are methods of treating or preventing rheumatoid arthritis.

The metabolic disease can be any metabolic disease known to those of skill. In certain embodiments, the metabolic disease is dyslipidemia. Dyslipidemia can be any dyslipidemia known to those of skill. In certain embodiments, dyslipidemia is selected from the group consisting of hyperlipidemia, hypercholesterolemia, hypertriglyceridemia, hyperlipoproteinemia, HDL deficiency, ApoA-I deficiency, and cardiovascular disease such as coronary artery disease (including, for example, treatment and prevention of angina, myocardial infarction, and sudden cardiac death); atherosclerosis (including, for example, treatment and prevention of atherosclerosis); and restenosis (including, for example, preventing or treating atherosclerotic plaques which develop as a consequence of medical procedures such as balloon angioplasty). In certain embodiments, provided herein are methods of treating or preventing diabetes.

The cardiovascular disease can be any cardiovascular disease known to those of skill. In certain embodiments, provided herein are methods of treating or preventing atherosclerosis. In certain embodiments, provided herein are methods of treating or preventing atherosclerosis derived from abnormal macrophage processing. In certain embodiments, provided herein are methods of treating or preventing atherosclerosis derived from the formation of oxidized low-density lipoproteins (oxLDLs), where marcrophages fail to process oxLDLs. In certain embodiments, provided herein are methods of treating or preventing ischemic heart disease. In certain embodiments, provided herein are methods of treating or preventing stroke. In certain embodiments, provided herein are methods of treating or preventing hypertensive heart disease. In certain embodiments, provided herein are methods of treating or preventing aortic aneurysm. In certain embodiments, provided herein are methods of treating or preventing endocarditis. In certain embodiments, provided herein are methods of treating or preventing peripheral artery disease. In certain embodiments, provided herein are methods of treating or preventing combinations of any of the diseases provided in this paragraph.

In some examples, set forth herein is a method for modulating the function of a nuclear receptor. By way of non-limiting example, the function may be selected from expression/secretion of inflammatory mediators (e.g. cytokines, chemokines), cholesterol regulation, cholesterol intake, cholesterol efflux, cholesterol oxidation, migration, chemotaxis, apoptosis and necrosis, an inflammatory activity, lipid regulation, apoptosis, migration, chemotaxis, gene transcription, and protein expression.

EXAMPLES

Provided herein are novel bis-octahydrophenanthrene carboxamides, protein conjugates thereof, and methods for treating diseases, disorders, and conditions including administering the bis-octahydrophenanthrene carboxamides and conjugates.

In some examples, the compound of Formula (I) is a compound identified in Table 1.

TABLE 1

| Cpd # | Structure | MF | MW |
|---|---|---|---|
| 9a | 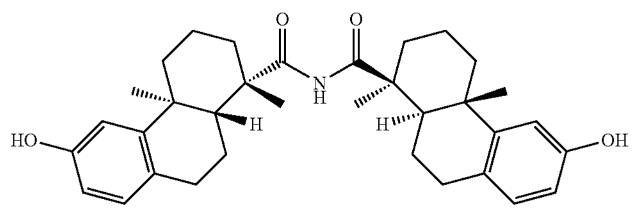 [SMILES: C[C@]1(C(=O)NC(=O)[C@@]2(C)CCC[C@]3(C)c4cc(O)ccc4CC[C@@H]23)CCC[C@]2(C)c3cc(O)ccc3CC[C@@H]12] | $C_{34}H_{43}NO_4$ | 529.71 |
| 9b | 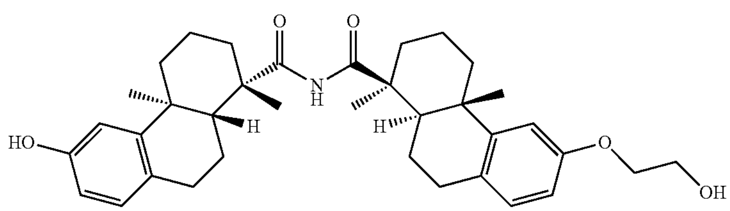 [SMILES: C[C@]1(C(=O)NC(=O)[C@@]2(C)CCC[C@]3(C)c4cc(OCCO)ccc4CC[C@@H]23)CCC[C@]2(C)c3cc(O)ccc3CC[C@@H]12] | $C_{36}H_{47}NO_5$ | 573.76 |
| 9c | 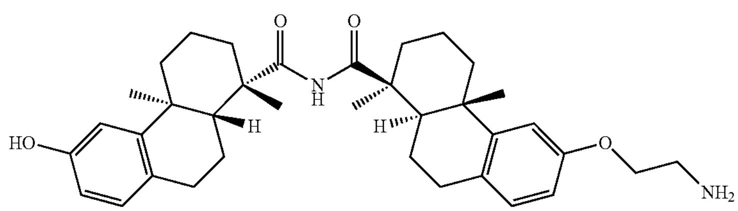 [SMILES: C[C@]1(C(=O)NC(=O)[C@@]2(C)CCC[C@]3(C)c4cc(OCCN)ccc4CC[C@@H]23)CCC[C@]2(C)c3cc(O)ccc3CC[C@@H]12] | $C_{36}H_{48}N_2O_4$ | 695.85 |
| 9d | 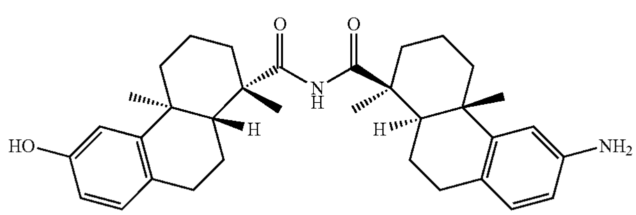 [SMILES: C[C@]1(C(=O)NC(=O)[C@@]2(C)CCC[C@]3(C)c4cc(O)ccc4CC[C@@H]23)CCC[C@]2(C)c3cc(N)ccc3CC[C@@H]12] | $C_{34}H_{44}N_2O_3$ | 528.72 |
| 9e | 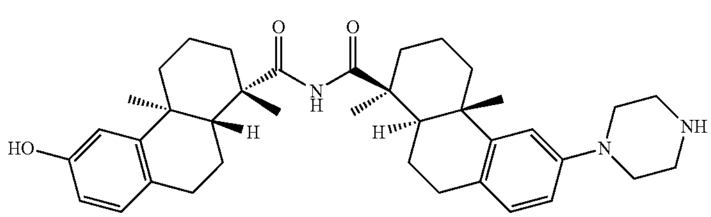 [SMILES: C[C@]1(C(=O)NC(=O)[C@@]2(C)CCC[C@]3(C)c4cc(N5CCNCC5)ccc4CC[C@@H]23)CCC[C@]2(C)c3cc(O)ccc3CC[C@@H]12] | $C_{38}H_{51}N_3O_3$ | 694.85 |

TABLE 1-continued

List of Payloads

| Cpd # | Structure | MF | MW |
|---|---|---|---|
| 9f | 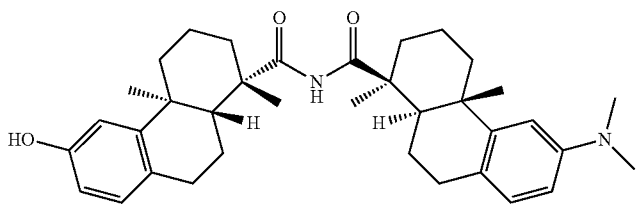 [SMILES: CN(C)c1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2] | $C_{36}H_{48}N_2O_3$ | 556.78 |
| 9g | 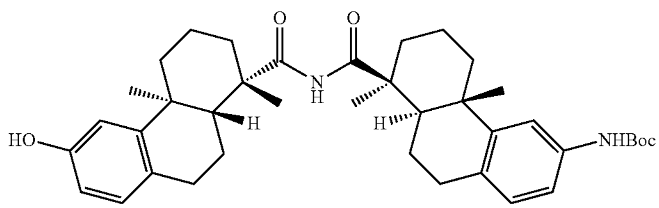 [SMILES: CC(C)(C)OC(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2] | $C_{39}H_{52}N_2O_5$ | 628.85 |
| 9h | 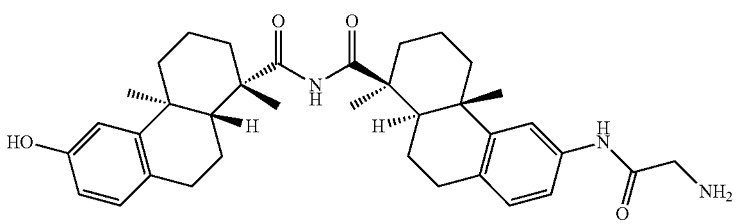 [SMILES: C[C@]1(C(=O)NC(=O)[C@@]2(C)CCC[C@]3(C)c4cc(NC(=O)CN)ccc4CC[C@@H]23)CCC[C@]2(C)c3cc(O)ccc3CC[C@@H]12] | $C_{36}H_{47}N_3O_4$ | 585.78 |
| 9i | 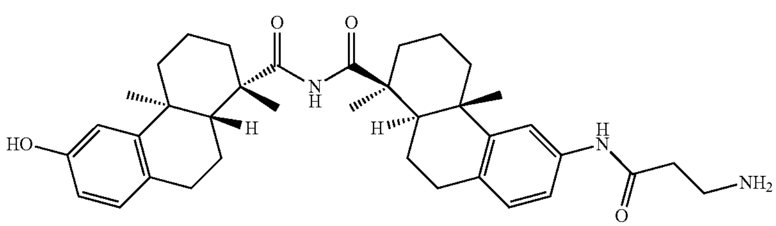 [SMILES: C[C@]1(C(=O)NC(=O)[C@@]2(C)CCC[C@]3(C)c4cc(NC(=O)CCN)ccc4CC[C@@H]23)CCC[C@]2(C)c3cc(O)ccc3CC[C@@H]12] | $C_{37}H_{49}N_3O_4$ | 599.80 |
| 9j | 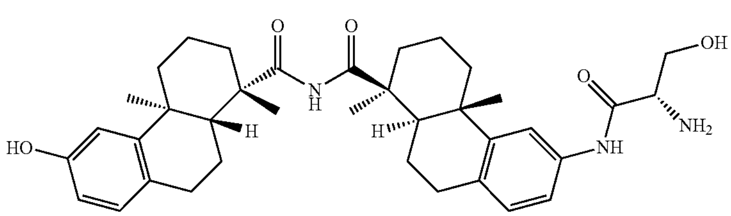 [SMILES: C[C@]1(C(=O)NC(=O)[C@@]2(C)CCC[C@]3(C)c4cc(NC(=O)[C@@H](N)CO)ccc4CC[C@@H]23)CCC[C@]2(C)c3cc(O)ccc3CC[C@@H]12] | $C_{37}H_{49}N_3O_4$ | 615.80 |
| 9k | 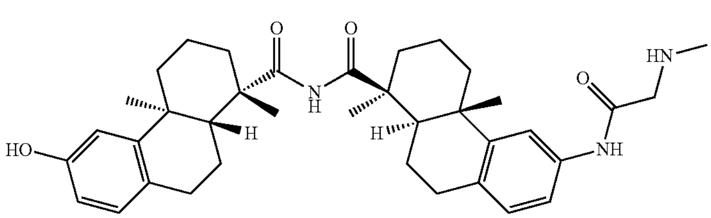 [SMILES: CNCC(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2] | $C_{37}H_{49}N_3O_4$ | 599.37 |

TABLE 1-continued

List of Payloads

| Cpd # | Structure | MF | MW |
|---|---|---|---|
| 9l | 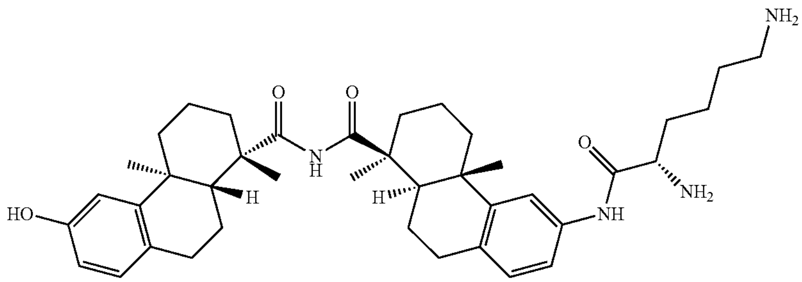 [SMILES: C[C@]1(C(=O)NC(=O)[C@@]2(C)CCC[C@]3(C)c4cc(NC(=O)[C@@H](N)CCCCN)ccc4CC[C@@H]23)CCC[C@]2(C)c3cc(O)ccc3CC[C@@H]12] | $C_{40}H_{56}N_4O_4$ | 656.43 |
| 9m | 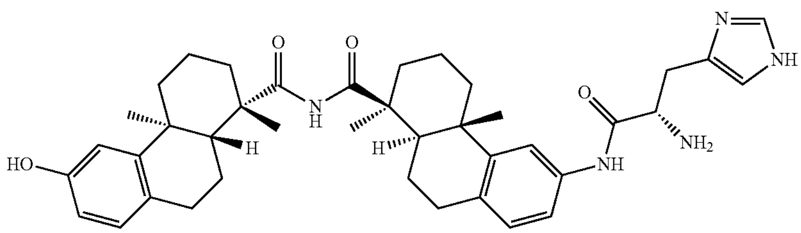 [SMILES: C[C@]1(C(=O)NC(=O)[C@@]2(C)CCC[C@]3(C)c4cc(NC(=O)[C@@H](N)Cc5c[nH]cn5)ccc4CC[C@@H]23)CCC[C@]2(C)c3cc(O)ccc3CC[C@@H]12] | $C_{40}H_{51}N_5O_4$ | 665.39 |
| 9n | 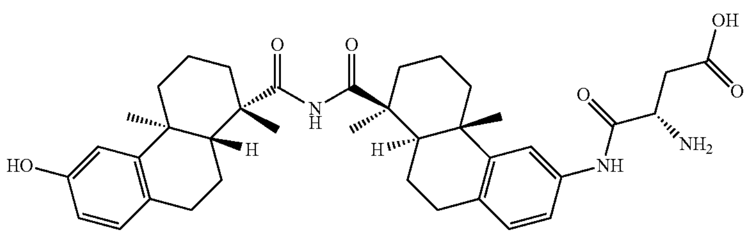 [SMILES: C[C@]1(C(=O)NC(=O)[C@@]2(C)CCC[C@]3(C)c4cc(NC(=O)[C@@H](N)CC(=O)O)ccc4CC[C@@H]23)CCC[C@]2(C)c3cc(O)ccc3CC[C@@H]12] | $C_{38}H_{49}N_3O_6$ | 643.81 |
| 9o | 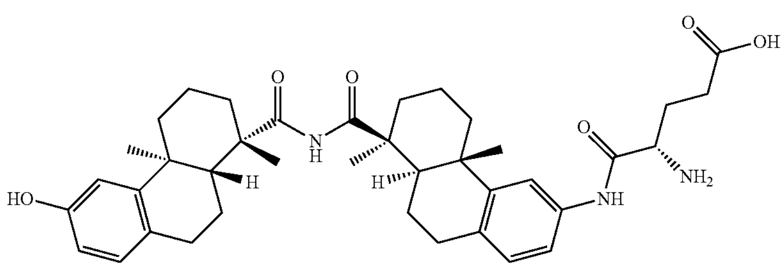 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(O)ccc3CC[C@@H]12] | $C_{39}H_{51}N_3O_6$ | 657.38 |
| 9p | 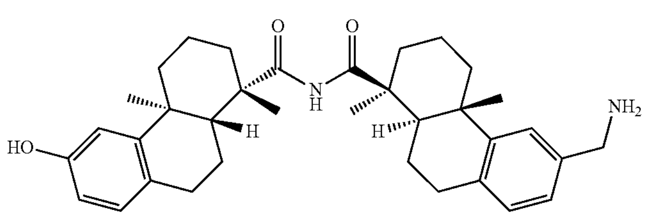 [SMILES: C[C@]1(C(=O)NC(=O)[C@@]2(C)CCC[C@]3(C)c4cc(CN)ccc4CC[C@@H]23)CCC[C@]2(C)c3cc(O)ccc3CC[C@@H]12] | $C_{35}H_{46}N_2O_3$ | 542.35 |
| 9q | 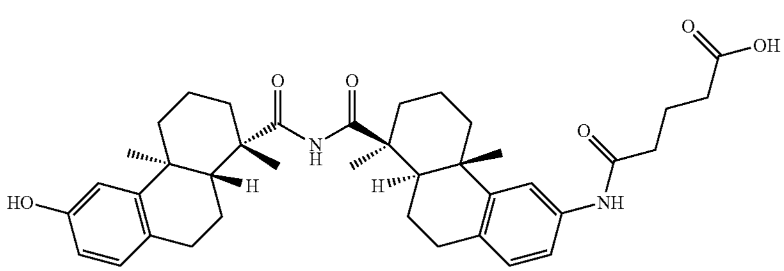 [SMILES: C[C@]1(C(=O)NC(=O)[C@@]2(C)CCC[C@]3(C)c4cc(NC(=O)CCCC(=O)O)ccc4CC[C@@H]23)CCC[C@]2(C)c3cc(O)ccc3CC[C@@H]12] | $C_{39}H_{50}N_2O_6$ | 642.82 |

TABLE 1-continued

List of Payloads

| Cpd # | Structure | MF | MW |
|---|---|---|---|
| 9r | 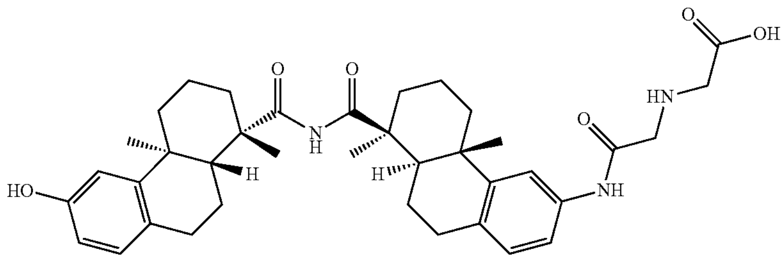 [SMILES: C[C@]1(C(=O)NC(=O)[C@@]2(C)CCC[C@]3(C)c4cc(NC(=O)CNCC(=O)O)ccc4CC[C@@H]23)CCC[C@]2(C)c3cc(O)ccc3CC[C@@H]12] | $C_{38}H_{49}N_3O_6$ | 643.83 |
| 9t | 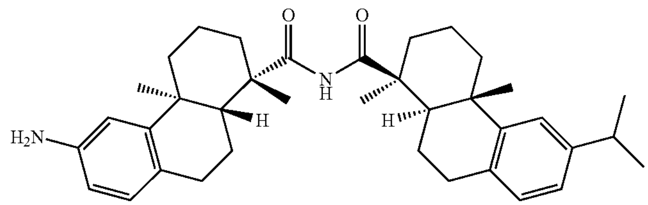 [SMILES: CC(C)c1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] | $C_{37}H_{50}N_2O_2$ | 554.81 |
| 9u | 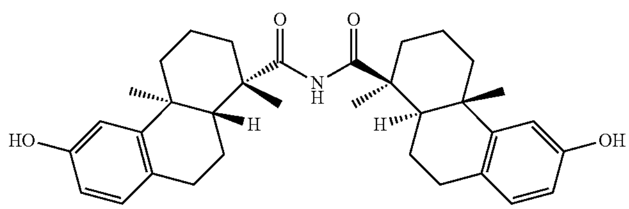 [SMILES: C[C@]1(C(=O)NC(=O)[C@@]2(C)CCC[C@]3(C)c4cc(O)ccc4CC[C@@H]23)CCC[C@]2(C)c3cc(O)ccc3CC[C@@H]12] | $C_{34}H_{45}NO_3$ | 515.73 |
| 15b | 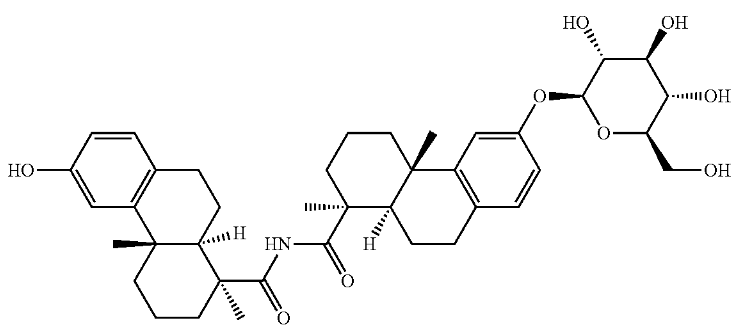 [SMILES: C[C@]1(C(=O)NC(=O)[C@@]2(C)CCC[C@]3(C)c4cc(O[C@@H]5O[C@H](CO)[C@@H](O)[C@H](O)[C@H]5O)ccc4CC[C@@H]23)CCC[C@]2(C)c3cc(O)ccc3CC[C@@H]12] | $C_{40}H_{53}NO_9$ | 691.85 |
| 17b | 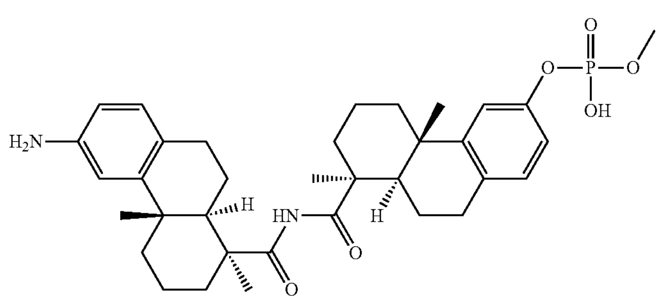 [SMILES: COP(=O)(O)Oc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] | $C_{34}H_{45}N_2P_6P$ | 608.70 |

TABLE 1-continued
List of Payloads
| Cpd # | Structure | MF | MW |
|---|---|---|---|
| 17c | 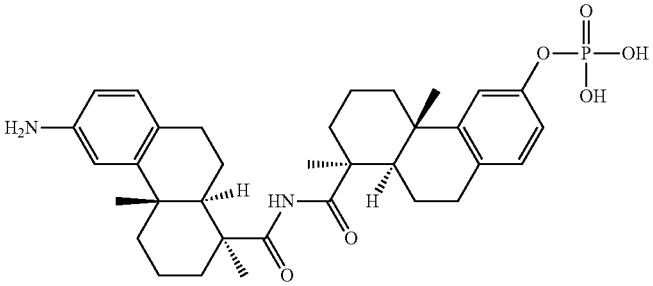 [SMILES: C[C@]1(C(=O)NC(=O)[C@@]2(C)CCC[C@]3(C)c4cc(OP(=O)(O)O)ccc4CC[C@@H]23)CCC[C@]2(C)c3cc(N)ccc3CC[C@@H]12] | $C_{35}H_{47}N_2O_6P$ | 622.73 |
Structure of compound 31
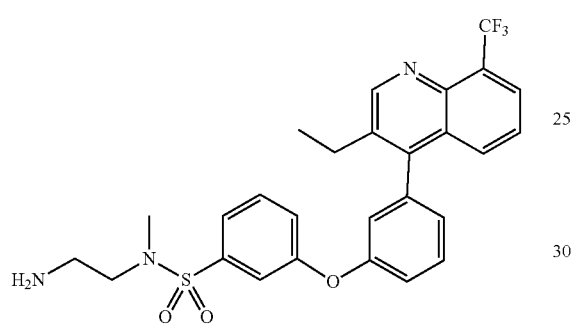
-continued
Structure of T0901317
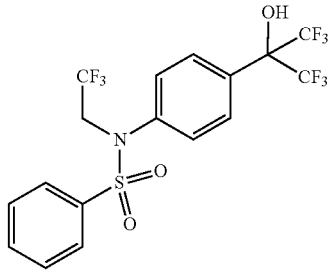
Structure of GW3965
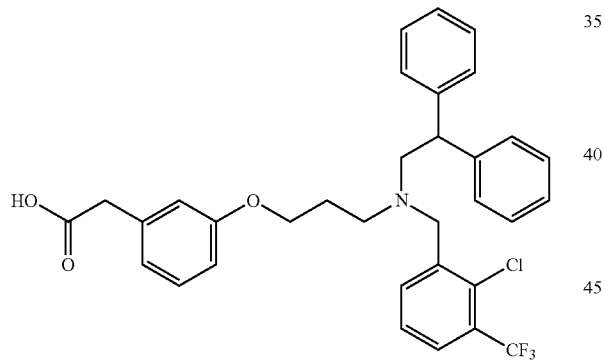
Examples of linker-payloads of the instant disclosure include, but are not limited to, those described in Table 2 below.

TABLE 2

List of Linker-payloads

| Cpd # | Structures |
|---|---|
| LP1 24c | |
| LP2 22d1 | |

TABLE 2-continued
List of Linker-payloads
| Cpd # | Structures |
|---|---|
| LP3 22d2 | 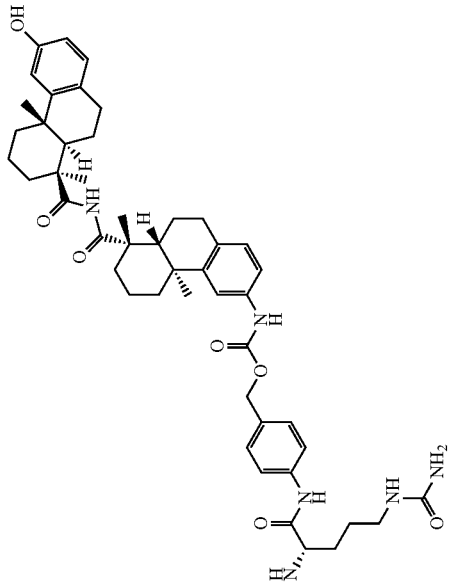 |
| LP4 22j | 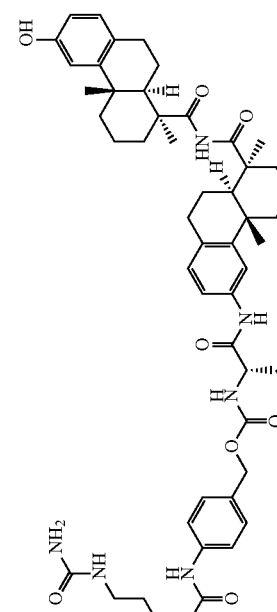 |

TABLE 2-continued
List of Linker-payloads
| Cpd # | Structures |
|---|---|
| LP5 27d1 | 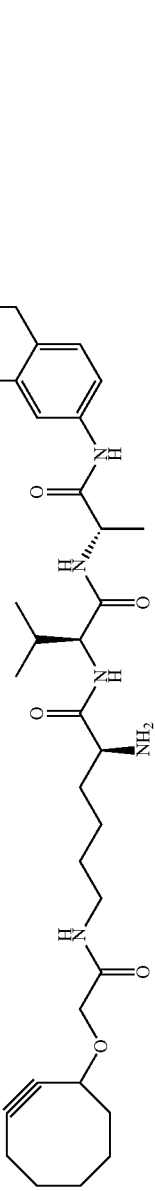 |

TABLE 2-continued
List of Linker-payloads
| Cpd # | Structures |
|---|---|
| LP15 27j | 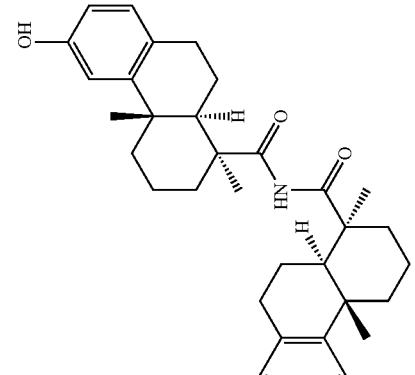 |

TABLE 2-continued

List of Linker-payloads

| Cpd # | Structures |
|---|---|
| LP6 29c1 | |

TABLE 2-continued
List of Linker-payloads
| Cpd # | Structures |
|---|---|
| LP7 29c2 | 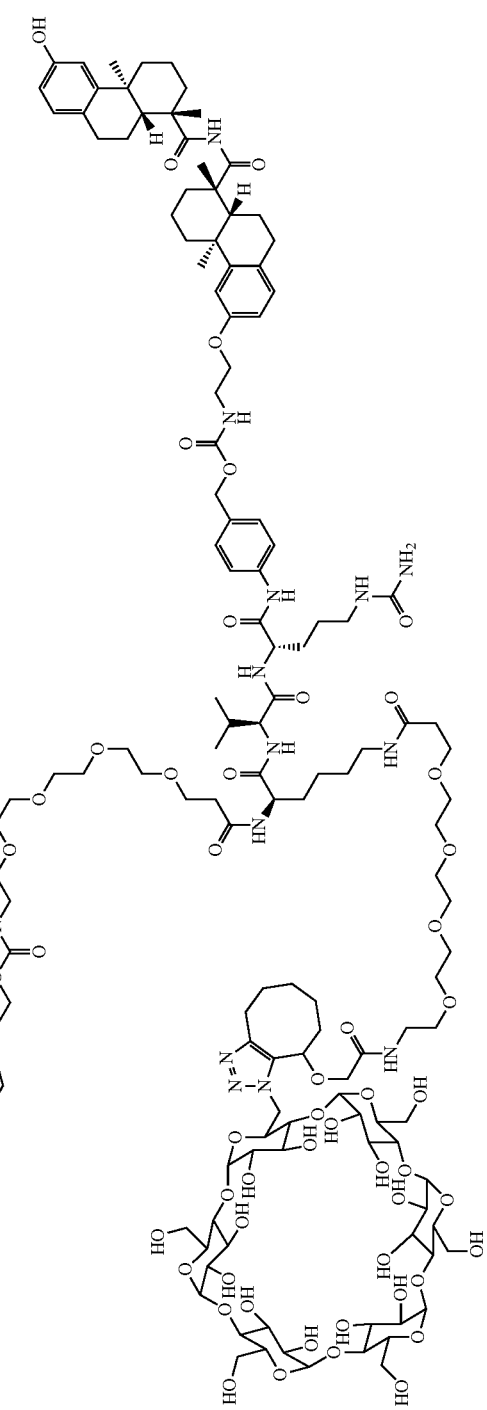 |

TABLE 2-continued
List of Linker-payloads
| Cpd # | Structures |
|---|---|
| 29d1 | 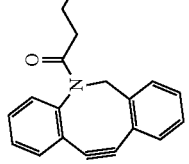 |
LP8

TABLE 2-continued
List of Linker-payloads
| Cpd # | Structures |
|---|---|
| LP9 29d2 | 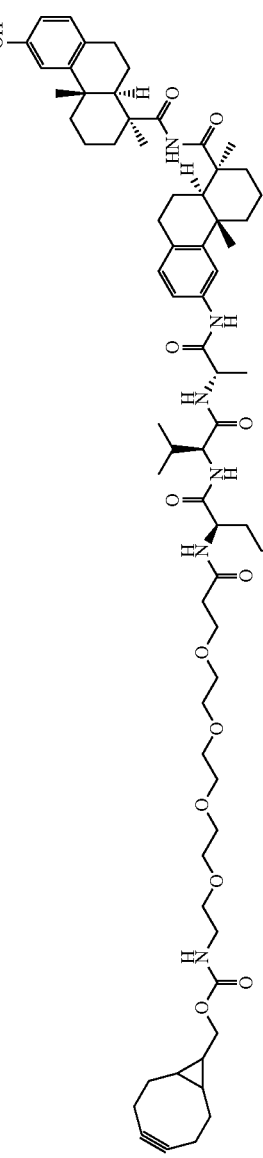 |

TABLE 2-continued
List of Linker-payloads
| Cpd # | Structures |
|---|---|
| LP10 29d3 | 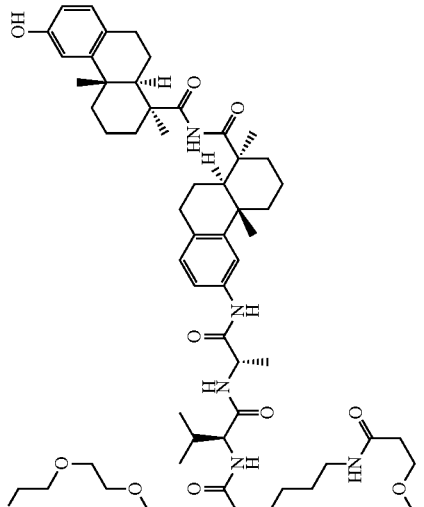 |

TABLE 2-continued
List of Linker-payloads
| Cpd # | Structures |
|---|---|
| LP11 29d4 | 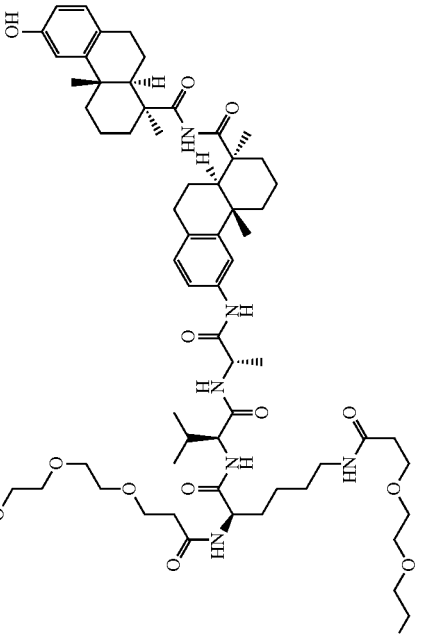 |

TABLE 2-continued
List of Linker-payloads
| Cpd # | Structures |
|---|---|
| LP12 29h | 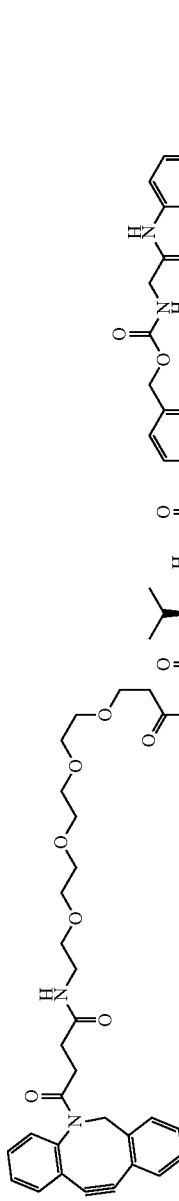 |

TABLE 2-continued
List of Linker-payloads
| Cpd # | Structures |
|---|---|
| LP13 29j | 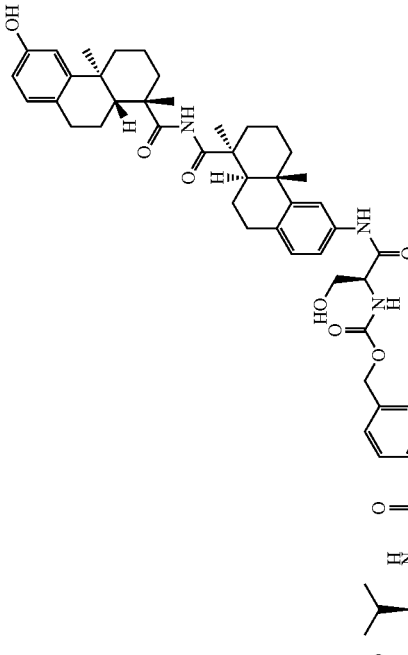 |

TABLE 2-continued
List of Linker-payloads
| Cpd # | Structures |
|---|---|
| LP14 33 | 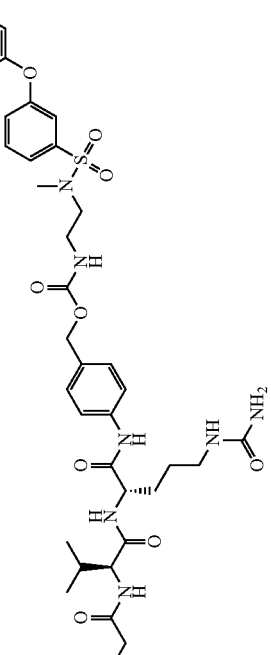 |
| LP39 — | 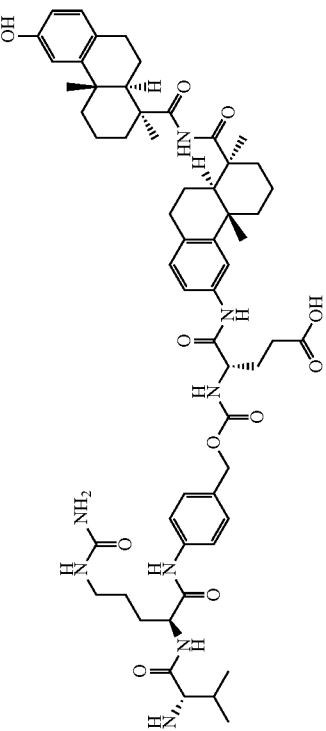 |

TABLE 2-continued
List of Linker-payloads
| Cpd # | Structures |
|---|---|
| LP311 | — 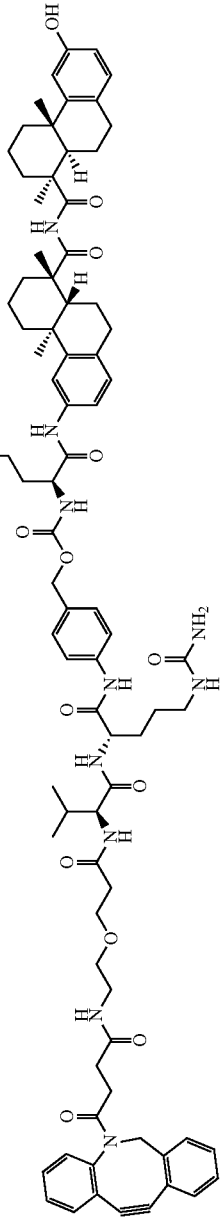 |
| LP18 | — 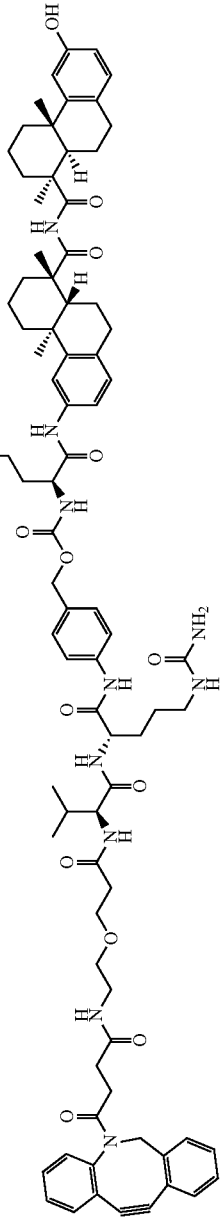 |

TABLE 2-continued

List of Linker-payloads

| Cpd # | Structures |
|---|---|
| LP36 | — |

TABLE 2-continued
List of Linker-payloads
| Cpd # | Structures |
|---|---|
| LP32 | 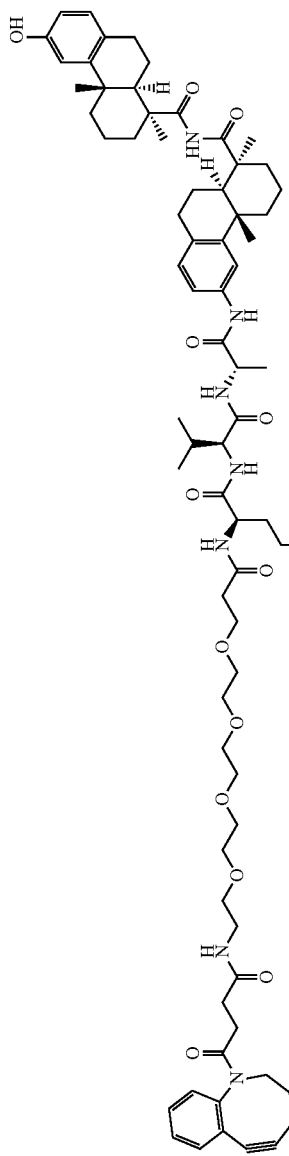 |

Certain embodiments of the invention are illustrated by the following non-limiting examples.

Reagents and solvents were obtained from commercial sources such as Sinopharm Chemical Reagent Co. (SCRC), Sigma-Aldrich, Alfa, or other vendors, unless explicitly stated otherwise.

$^1$H NMR and other NMR spectra were recorded on a Bruker AVIII 400 or Bruker AVIII 500. The data were processed with Nuts software or MestReNova software, measuring proton shifts in parts per million (ppm) downfield from an internal standard tetramethylsilane (TMS).

HPLC-MS measurements were run on an Agilent 1200 HPLC/6100 SQ System using the follow conditions:

Method A for HPLC-MS measurements included, as the Mobile Phase: A: Water (0.01% trifluoroacetic acid (TFA)), B: acetonitrile (0.01% TFA); Gradient Phase: 5% of B increased to 95% of B within 15 minutes (min); Flow Rate: 1.0 mL/min; Column: SunFire C18, 4.6×50 mm, 3.5 µm; Column Temperature: 50° C. Detectors: Analog to Digital Converter (ADC) Evaporative Light-scattering Detector (ELSD), Diode array detector (DAD) (214 nm and 254 nm), electrospray ionization-atmospheric ionization (ES-API).

Method B for HPLC-MS measurements included, as the Mobile Phase: A: Water (10 mM NH$_4$HCO$_3$), B: acetonitrile; Gradient Phase: 5% to 95% of B within 15 min; Flow Rate: 1.0 mL/min; Column: XBridge C18, 4.6×50 mm, 3.5 µm; Column Temperature: 50° C. Detectors: ADC ELSD, DAD (214 nm and 254 nm), mass selective detector (MSD) (ES-API).

LC-MS measurements were run on an Agilent 1200 HPLC/6100 SQ System using the following conditions:

Method A for LC-MS measurement included, as the Instrument: WATERS 2767; column: Shimadzu Shim-Pack, PRC-ODS, 20×250 mm, 15 µm, two connected in series; Mobile Phase: A: Water (0.01% TFA), B: acetonitrile (0.01% TFA); Gradient Phase: 5% of B increased to 95% of B within 3 min; Flow Rate: 1.8-2.3 mL/min; Column: SunFire C18, 4.6×50 mm, 3.5 µm; Column Temperature: 50° C. Detectors: ADC ELSD, DAD (214 nm and 254 nm), ES-API.

Method B for LC-MS measurement included, as the Instrument: Gilson GX-281; column: Xbridge Prep C18 10 um OBD, 19×250 mm; Mobile Phase: A: Water (10 mM NH$_4$HCO$_3$), B: Acetonitrile; Gradient Phase: 5% to 95% of B within 3 min; Flow Rate: 1.8-2.3 mL/min; Column: XBridge C18, 4.6×50 mm, 3.5 µm; Column Temperature: 50° C. Detectors: ADC ELSD, DAD (214 nm and 254 nm), MSD (ES-API).

Preparative high-pressure liquid chromatography (Prep-HPLC) in an acidic or basic solvent system was utilized on a Gilson GX-281 instrument. The acidic solvent system used a Waters SunFire 10 µm C18 column (100 Å, 250×19 mm), and solvent A for prep-HPLC was water/0.05% TFA and solvent B was acetonitrile. The elution conditions were a linear gradient increase of solvent B from 5% to 100% over a time period of 20 min at a flow rate of 30 mL/min. The basic solvent system included a Waters Xbridge 10 µm C18 column (100 Å, 250×19 mm), and solvent A used for prep-HPLC was water/10 mM ammonium bicarbonate (NH$_4$HCO$_3$) and solvent B was acetonitrile. The elution conditions were a linear gradient increase of solvent B from 5% to 100% over a time period of 20 min at a flow rate of 30 mL/min.

Flash chromatography was performed on a Biotage instrument, with Agela Flash Column silica-CS cartridges; Reversed phase flash chromatography was performed on Biotage instrument, with Boston ODS or Agela C18 cartridges.

As used herein, the symbols and conventions used in these processes, schemes, and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the Examples and throughout the specification:

| Abbreviation | Term |
|---|---|
| ADC | Antibody-drug conjugate |
| Aglycosylated antibody | Antibody does not have any glycan |
| API | Atmospheric pressure ionization |
| aq | Aqueous |
| Boc | N-tert-butoxycarbonyl |
| BupH ™ | Thermo Scientific Prod# 28372, containing 100 mM sodium phosphate and 150 mM sodium chloride, potassium free, pH was adjusted from 7.2 to 7.6-7.8 MQ, unless otherwise noted. |
| CD | Cyclodextrin |
| COT | Cyclooctynol |
| Da | Dalton |
| DAD | Diode array detector |
| DAR | Drug to antibody ratio |
| DCM | Dichloromethane |
| DIBAC | 11,12-didehydro-5,6-dihydro-Dibenz[b,g]azocine |
| DIBAC-Suc | 11,12-didehydro-5,6-dihydro-Dibenz[b,f]azocine succinamic acid |
| DIBAC-Suc-PEG4-VC-pAB-PNP | {4-[(2S)-2-[(2S)-2-[1-(4-{2-azatricyclo[10.4.0.0$^{4,9}$]hexadeca-1(12),4(9),5,7,13,15-hexaen-10-yn-2-yl{-4-oxobutanamido)-3,6,9,12-tetraoxapentadecan-15-amido]-3-methylbutanamido]-5-(carbamoylamino)pentanamido]phenyl}methyl 4-nitrophenyl carbonate |
| DIBACT | 3H-Benzo[c]-1,2,3-triazolo[4,5-e][1]benzazocine,8,9-dihydro- |
| DIPEA | Diisopropylethylamine |
| DMF | N,N-dimethylformamide |
| DMSO | Dimethylsulfoxide |
| EC | Enzyme commission |
| ELSD | Evaporative light scattering detector |
| ESI | Electrospray ionization |
| Fmoc | N-(9-fluorenylmethyloxycarbonyl) |
| Fmoc-vcPAB-PNP | N-Fmoc-L-valine-L-citrulline-p-aminobenzyl alcohol p-nitrophenyl carbonate |
| g | Gram |
| HATU | 2-(7-Aza-1H-benzotriazole-1-yl)-1,1,3,3-tetramethyluronium hexafluorophosphate |
| HC | Heavy chain of immunoglobulin |
| HEK | Human embryonic kidney (cells) |
| HPLC | High performance liquid chromatography |
| hr, h, or hrs | Hours |
| LC | Light chain of immunoglobulin |
| LCh | Liquid chromatography |
| MALDI | Matrix-assisted laser desorption/ionization |
| MC | Maleimidocaproyl |
| mg | milligrams |
| min | minutes |
| mL | milliliters |
| mmh | myc-myc-hexahistidine tag |
| uL | microliters |
| mM | millimolar |
| uM | micromolar |
| MMAE | Monomethyl auristatin E |
| MS | Mass spectrometry |
| MsCl | Methanesulfonyl chloride |
| MSD | Mass-selective detector |
| MTG | Microbial transglutaminase (MTG EC 2.3.2.13, Zedira, Darmstadt, Germany) |
| MW | Molecular weight |
| ncADC | Non-Cytotoxic antibody drug conjugate |
| NHS | N-hydroxy succinimide |
| nM | nanomolar |

-continued

| Abbreviation | Term |
|---|---|
| NMR | Nuclear magnetic resonance |
| NOESY | Nuclear Overhauser effect spectroscopy |
| PAB | Para-aminobenzyloxy(carbonyl) |
| PBS | 10 mM sodium phosphate buffer and 150 mM sodium chloride |
| PBSg | 10 mM phosphate, 150 mM sodium chloride, 5% glycerol |
| PEG | Polyethyleneglycol |
| PNP | p-nitrophenyl |
| MC-VC-PAB-PNP | Maleimidocaproyl-L-valine-L-citrulline-p-aminobenzyl alcohol p-nitrophenyl carbonate |
| ppm | Parts per million (chemical shift, δ) |
| RP | Reversed phase |
| rt or RT | Room temperature |
| SDS-PAGE | Sodium dodecylsulfate polyacrylamide gel electrophoresis |
| SEC | Size exclusion chromatography |
| Suc | Succinic acid |
| TCEP | Tris(2-carboxyethyl)phosphine hydrochloride |
| TEA | Triethylamine |
| TMS | tetramethylsilane |
| TFA | Trifluoroacetic acid |
| TG | Transglutaminase |
| THF | Tetrahydrofuran |
| TOF | Time-of-flight |
| UPLC | Ultra Performance Liquid Chromatography |
| UV | Ultraviolet |
| VA | Valine-alanine |
| VC | Valine-citrulline |
| VC-PAB | Valine-citrulline-para-aminobenzyloxy(carbonyl) |

Preparation Methods

Example 1

This example demonstrates general methods for the synthesis of the podocarpic derivatives, 9a to 9r, 9t, and 9u in Table 1, above. This example refers to the compounds numbered from 1 to 9a-p in FIG. 1.

In FIG. 1, the starting material podocarpic acid 1 was originally discovered in plant resins in 1873, and later was reported from several species of Podocarpus (See, e.g., *J. Chem. Soc.* 1938, 1006-1013). The synthesis of compound 4 from podocarpic acid 1 was reported previously (See, e.g., *Bioorg. Med. Chem. Lett.* 2005 15, 2824; *Bioorg. Med. Chem. Lett.* 2005, 15, 4574). Acyl chloride 6a was prepared from treatment of 4 with thionyl chloride; and active ester 6b was prepared from treatment of 4 with 5. The symmetric imide 8a was synthesized from treatment of amide 7a with acid chloride 6a or activated ester 6b, and was then subjected to de-benzylation via hydrogenation to afford imide 9a. Similarly, the asymmetric imides 8b-e and 8g were synthesized from coupling reactions of amides 7b-g with activated ester 6b or acid chloride 6a. Yields for asymmetric imides 8b-e and 8g from 6a were lower compared to yields for symmetric imide 8a, but the yields for 8b-e and 8g using activated ester 6b, were increased from ~40% to 50-85%.

Imides 9a-e were obtained from 8a-e via de-protections of the corresponding protective groups—Bn in 8a, TBS in 8b, or Boc in 8c, 8d, and 8e, respectively. N,N-dimethylated analog 9f was obtained from hydrogenation of 8d in methanol to remove the benzyl group while concomitantly N,N-dimethylating the aniline nitrogen; N-Boc analog 9g was obtained from de-benzylation of 8d. Compounds 9h-o were obtained from amide coupling reactions of 9d with the amino-acid derivatives in the presence of HATU and DIPEA, followed by de-protection of the Boc groups with 10-25% TFA in DCM or by de-protection of the Fmoc groups with 20% piperidine in an organic solvent. The amide coupling reactions of 9d with Fmoc-Gly-OH followed by deprotection of Fmoc provided 9h; Boc-beta-Ala-OH followed by deprotection of Boc provided 9i; Boc-Ser-OH followed by deprotection of Boc provided 9j; Boc-Sar-OH followed by deprotection of Boc provided 9k; Boc-Lys (Boc)-OH followed by deprotection of Boc provided 9l; Boc-His-OH followed by deprotection of Boc provided 9m; Boc-Asp-OtBu followed by deprotection of Boc and —OtBu provided 9n in one pot; and Boc-Glu-OtBu followed by deprotection of Boc and —OtBu provided 9o in one pot, respectively. Compound 9p was synthesized from the amide coupling reaction of 7g with 6b in the presence of LiHMDS to form 8g, followed by Raney Nickel catalyzed reduction of the nitrile to the amine and debenzylation with boron tribromide (BBr₃). Compound 9q was obtained from the amide coupling reaction of 9d with glutaric anhydride. Compound 9r was obtained from the amide coupling reaction of 9d with Boc-iminodiacetic acid followed by Boc deprotection. Compound 9t was obtained from the amide coupling reaction of 7d with an activated ester of dehydroabietic acid (Cas No. 1740-19-8) followed by Boc deprotection.

Example 1a

Synthesis of Payload 9d (FIG. 1a)

Methyl (1S,4aS,10aR)-6-hydroxy-1,4a-dimethyl-1,2,3,4,4a,9,10,10a-octahydrophenanthrene-1-carboxylate (P1-2)

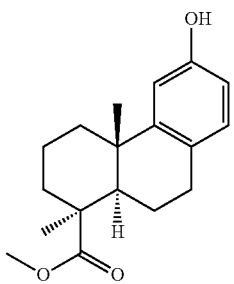 [SMILES: COC(=O)[C@@]1(C)CCC[C@]2(C)c3cc(O)ccc3CC[C@@H]12]

To a solution of podocarpic acid (P1-1, 90 g, 0.33 mol) in methanol (200 mL) and toluene (600 mL) was added with (trimethylsilyl)diazomethane (2 M in hexane, 200 mL). The reaction mixture was stirred at room temperature for 2 hours. The podocarpic acid was then totally consumed according to LCMS. The volatiles were removed in vacuo, and the residue was triturated from petroleum ether (2 L) to give compound P1-2 (91 g, 96% yield) as a white solid. ESI m/z: 289 (M+H)+. $^1$H NMR (400 MHz, DMSO$_{d6}$) δ 8.95 (s, 1H), 6.79 (d, J=8.2 Hz, 1H), 6.63 (d, J=2.4 Hz, 1H), 6.48 (dd, J=8.2, 2.4 Hz, 1H), 3.58 (s, 3H), 2.80-2.55 (m, 2H), 2.20-2.02 (m, 3H), 1.96-1.71 (m, 2H), 1.56-1.45 (m, 2H), 1.27 (t, J=13.5 Hz, 1H), 1.21 (s, 3H), 1.09 (td, J=13.5, 4.1 Hz, 1H), 0.91 (s, 3H) ppm.

Methyl (1S,4aS,10aR)-1,4a-dimethyl-6-(trifluoromethanesulfonyloxy)-1,2,3,4,4a,9,10,10a-octahydrophenanthrene-1-carboxylate (P1-3)

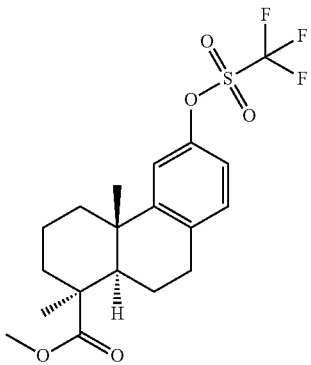 [SMILES: COC(=O)[C@@]1(C)CCC[C@]2(C)c3cc(OS(=O)(=O)C(F)(F)F)ccc3CC[C@@H]12]

To a solution of compound P1-2 (10 g, 35 mmol) in methylene chloride (200 mL) were added pyridine (3.3 g, 42 mmol) and DMAP (0.84 g, 6.9 mmol) under nitrogen atmosphere. The mixture was cooled to −78° C. and was added triflic anhydride (12 g, 42 mmol), and the resulting mixture was allowed to warm to 25° C. and stirred at 25° C. for another 4 hours. The reaction mixture was diluted with DCM (500 mL), washed with water (100 mL), aq. hydrochloride (1 N, 150 mL) and brine (100 mL), dried over sodium sulfate and concentrated in vacuo to give crude compound P1-3 (14 g, 97% crude yield) as viscous oil, which was pure enough for the next step. The crude compound P1-3 could be purified by flash chromatography (0-10% ethyl acetate in petroleum ether) to give pure product as viscous oil. ESI m/z: 421.2 (M+1)+. 1H NMR (400 MHz, CDCl3) δ 7.12 (d, J=2.5 Hz, 1H), 7.10 (d, J=8.5 Hz, 1H), 6.97 (dd, J=8.5, 2.5 Hz, 1H), 3.67 (s, J=3.4 Hz, 3H), 2.93 (dd, J=17.2, 4.4 Hz, 1H), 2.85-2.71 (m, 1H), 2.29 (d, J=13.5 Hz, 1H), 2.25-2.14 (m, 2H), 2.03-1.89 (m, 2H), 1.71-1.61 (m, 1H), 1.56-1.48 (m, 1H), 1.40 (td, J=13.4, 4.2 Hz, 1H), 1.30-1.22 (m, 3H), 1.09 (td, J=13.6, 4.2 Hz, 1H), 1.02 (s, 3H) ppm.

Methyl (1S,4aS,10aR)-6-((tert-butoxycarbonyl)amino)-1,4a-dimethyl-1,2,3,4,4a,9,10,10a-octahydrophenanthrene-1-carboxylate (P1-4)

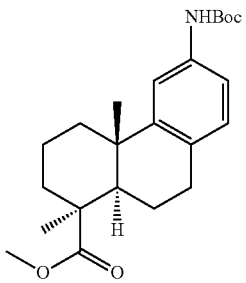 [SMILES: COC(=O)[C@@]1(C)CCC[C@]2(C)c3cc(NC(=O)OC(C)(C)C)ccc3CC[C@@H]12]

To a solution of compound P1-3 (14 g, 34 mmol) and tert-butyl carbamate (BocNH2, 7.9 g, 68 mmol) in tert-butanol (100 mL) were added, successively, cesium carbonate (22 g, 68 mmol), tris(dibenzylideneacetone)dipalladium (0) (Pd2(dba)3, 1.8 g, 2.0 mmol) and X-Phos (1.8 g, 4.0 mmol) at room temperature. The mixture was de-gassed and purged with argon 3 times and was then stirred at 80° C. under argon (balloon) overnight until compound P1-3 was totally consumed, as monitored by TLC. After cooling to room temperature, the reaction mixture was diluted with ethyl acetate and filtered through Celite. The solid was washed with ethyl acetate for 3 times. The combined filtrate was concentrated in vacuo and the residue was purified by silica gel column chromatography (0-6.25% ethyl acetate in petroleum ether) to give compound P1-4 (11 g, 82% yield) as a white solid. ESI m/z: 410 (M+23)+. 1H NMR (500 MHz, DMSO$_{d6}$) δ 9.07 (s, 1H), 7.39 (s, 1H), 7.13 (d, J=8.5 Hz, 1H), 6.87 (d, J=8.3 Hz, 1H), 3.59 (s, 3H), 2.76 (dd, J=16.4, 4.5 Hz, 1H), 2.70-2.61 (m, 1H), 2.16-2.05 (m, 3H), 2.00-1.75 (m, 2H), 1.65-1.50 (m, 2H), 1.45 (s, 9H), 1.31-1.25 (m, 1H), 1.21 (s, 3H), 1.10 (td, J=13.5, 4.1 Hz, 1H), 0.92 (s, 3H) ppm.

(1S,4aS,10aR)-6-{[(tert-Butoxy)carbonyl]amino}-1,4a-dimethyl-1,2,3,4,4a,9,10,10a-octahydrophenanthrene-1-carboxylic Acid (P1-5)

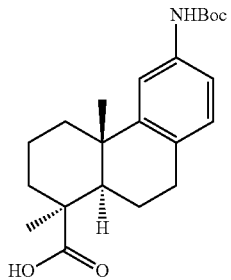 [SMILES: CC(C)(C)OC(=O)Nc1ccc2c(c1)[C@@]1(C)CCC[C@](C)(C(=O)O)[C@@H]1CC2]

To a solution of compound P1-4 (4.9 g, 13 mmol) in DMSO was added potassium tert-butoxide (15 g, 0.13 mol) in one portion at room temperature. The reaction mixture was stirred at 60° C. for 3 hours under argon until the reaction was completed according to LCMS. After cooling to room temperature, the reaction mixture was poured into ice and acidified slowly with aq. hydrochloride (0.5 M) to pH 5, during which the temperature did not exceed 25° C. The precipitates were collected by filtration and washed with water several times. The crude product was further purified by silica gel column chromatography (0-20% ethyl acetate in petroleum ether) to give compound P1-5 (4.5 g, 93% yield) as a white solid. ESI m/z: 318 (M−55)+. 1H NMR (500 MHz, DMSO$_{d6}$) δ 12.08 (s, 1H), 9.08 (s, 1H), 7.40 (s, 1H), 7.11 (s, 1H), 6.87 (d, J=8.3 Hz, 1H), 2.79-2.68 (m, 1H), 2.65 (d, J=12.6 Hz, 1H), 2.17-2.03 (m, 4H), 1.94-1.76 (m, 2H), 1.53 (d, J=13.7 Hz, 1H), 1.46 (d, J=7.4 Hz, 9H), 1.29-1.14 (m, 5H), 1.04 (s, 3H) ppm.

tert-Butyl N-[(4bS,8S,8aR)-8-carbamoyl-4b,8-dimethyl-4b,5,6,7,8,8a,9,10-octahydrophenanthren-3-yl] carbamate (P1-6)

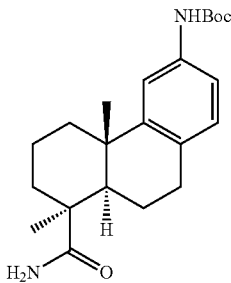

To a solution of P1-5 (4.5 g, 12 mmol) and HATU (4.9 g, 13 mmol) in DMF (50 mL) was added diisopropylethylamine (20 mL, 0.12 mol), and the mixture was stirred at 25° C. for an hour. To the mixture was then added ammonium chloride (16 g, 0.30 mol) and the mixture was stirred at room temperature overnight. The resulting mixture was diluted with ethyl acetate, washed with water and brine, dried over sodium sulfate and concentrated in vacuo. The residue was purified by flash chromatography (0-20% ethyl acetate in petroleum ether) to give compound P1-6 (4.2 g, 94% yield) as a white solid. ESI m/z: 373.3 (M+1)$^+$.
$^1$H NMR (500 MHz, methanol$_{d4}$) δ 7.20 (s, 1H), 6.97 (d, J=7.7 Hz, 1H), 6.80 (d, J=8.3 Hz, 1H), 2.77-2.68 (m, 2H), 2.66-2.55 (m, 1H), 2.20 (d, J=12.9 Hz, 1H), 2.13 (dd, J=13.2, 5.3 Hz, 1H), 2.08 (d, J=14.0 Hz, 1H), 2.03-1.86 (m, 2H), 1.54 (d, J=11.1 Hz, 1H), 1.40 (s, 9H), 1.26 (t, J=26.7 Hz, 1H), 1.18 (s, 3H), 1.14-1.03 (m, 4H) ppm.

Methyl (1S,4aS,10aR)-6-(benzyloxy)-1,4a-dimethyl-1,2,3,4,4a,9,10,10a-octahydrophenanthrene-1-carboxylate (P1-8)

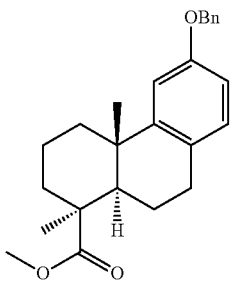 [SMILES: COC(=O)[C@@]1(C)CCC[C@]2(C)c3cc(OCc4ccccc4)ccc3CC[C@@H]12]

A mixture of compound P1-2 (12 g, 40 mmol) and cesium carbonate (14 g, 44 mmol) in DMF (100 mL) was stirred at 20-25° C. for 15 minutes. To the mixture was added benzyl bromide (7.1 mL, 60 mmol) at room temperature. After stirring at room temperature for 4 hours, the resulting mixture was poured into cold water and extracted with ethyl acetate. The combined organic solution was washed with water and brine, dried over sodium sulfate and concentrated in vacuo. The crude product was purified by flash chromatography (0-10% ethyl acetate in petroleum ether) to give the title compound P1-8 (13 g, 89% yield) as a white solid. ESI m/z: 379 (M+H)$^+$. $^1$H NMR (500 MHz, methanol$_{d4}$) δ 7.60-7.20 (m, 5H), 7.00-6.82 (m, 2H), 6.73 (d, J=7.1 Hz, 1H), 5.03 (s, 2H), 3.66 (s, 3H), 2.95-2.58 (m, 2H), 2.36-2.10 (m, 3H), 2.10-1.85 (m, 2H), 1.70-1.48 (m, 2H), 1.44-1.21 (m, 4H), 1.15 (t, J=17.2 Hz, 1H), 1.01 (s, 3H) ppm.

1S,4aS,10aR)-6-(Benzyloxy)-1,4a-dimethyl-1,2,3,4,4a,9,10,10a-octahydrophenanthrene-1-carboxylic Acid (P1-9)

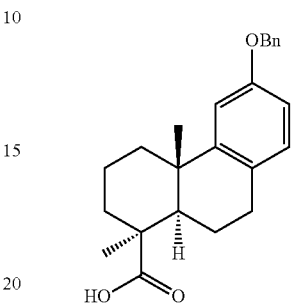

A mixture of compound P1-8 (11 g, 29 mmol) and potassium tert-butoxide (33 g, 0.29 mol) in DMSO (0.19 L) was stirred at 100° C. for an hour until the methyl group was totally removed, as monitored by LCMS and TLC. After cooling to 25° C., the mixture was quenched with aqueous hydrochloride (1 N) and extracted with ethyl acetate. The combined organic solution was washed with brine, dried over sodium sulfate and concentrated in vacuo. The residue was purified by silica gel column chromatography (0-24% ethyl acetate in petroleum ether) to give compound P1-9 (7.5 g, 71% yield) as a white solid. ESI m/z: 365 (M+H)$^+$. $^1$H NMR (500 MHz, methanol$_{d4}$) δ 7.42 (d, J=7.4 Hz, 2H), 7.36 (t, J=7.5 Hz, 2H), 7.30 (t, J=7.3 Hz, 1H), 6.92 (d, J=8.4 Hz, 1H), 6.87 (d, J=2.5 Hz, 1H), 6.72 (dd, J=8.4, 2.5 Hz, 1H), 5.02 (s, 2H), 2.82 (dd, J=16.3, 4.4 Hz, 1H), 2.77-2.65 (m, 1H), 2.24 (d, J=13.2 Hz, 2H), 2.19 (dd, J=13.8, 6.0 Hz, 1H), 2.11-1.96 (m, 2H), 1.64-1.56 (m, 1H), 1.53 (d, J=11.0 Hz, 1H), 1.35 (td, J=13.3, 3.7 Hz, 1H), 1.30 (s, 3H), 1.13 (s, 3H), 1.11-1.05 (m, 1H) ppm.

Pentafluorophenyl (1S,4aS,10aR)-6-(benzyloxy)-1,4a-dimethyl-1,2,3,4,4a,9,10,10a-octahydrophenanthrene-1-carboxylate_(P1-10)

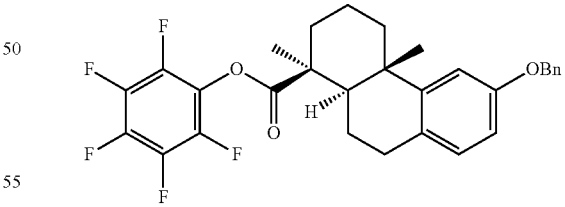

To a solution of P1-9 (9.6 g, 26 mmol) in DMF (100 mL) was added DIPEA (14 mL, 79 mmol), and perfluorophenyl 2,2,2-trifluoroacetate (15 g, 53 mmol). This mixture was stirred at room temperature overnight, and monitored by LCMS. The reaction mixture was then diluted with ether (200 mL) and washed with water (300 mL) and brine (200 mL). The organic solution was dried over sodium sulfate and concentrated in vacuo. The residue was purified by flash chromatography (0-10% ethyl acetate in petroleum ether) to give compound P1-10 (12 g, 88% yield) as a white solid. ESI m/z: 531 (M+H)⁺. ¹H NMR (500 MHz, DMSO$_{d6}$) δ 7.43 (d, J=7.1 Hz, 2H), 7.38 (t, J=7.4 Hz, 2H), 7.31 (t, J=7.2 Hz, 1H), 6.93 (dd, J=10.2, 5.5 Hz, 2H), 6.76 (dd, J=8.4, 2.5 Hz, 2H), 5.05 (s, 2H), 2.81 (dd, J=16.3, 4.5 Hz, 1H), 2.77-2.68 (m, 1H), 2.28-2.19 (m, 2H), 2.18 (dd, J=13.4, 5.6 Hz, 1H), 2.00-1.83 (m, 2H), 1.74 (d, J=11.8 Hz, 1H), 1.65 (d, J=14.1 Hz, 1H), 1.47 (s, 3H), 1.38-1.27 (m, 2H), 1.08 (s, 3H) ppm.

tert-Butyl N-[(4bS,8S,8aR)-8-({[(1S,4aS,10aR)-6-(benzyloxy)-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (P1-11)

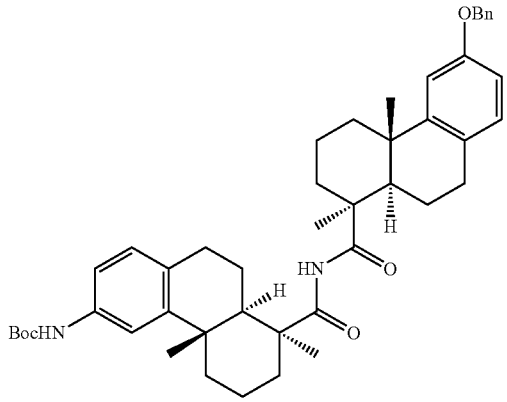 [SMILES: CC(C)(C)OC(=O)Nc1ccc2c(c1)[C@@]1(C)CCC[C@](C)(C(=O)NC(=O)[C@@]3(C)CCC[C@]4(C)c5cc(OCc6ccccc6)ccc5CC[C@@H]34)[C@@H]1CC2]

To a solution of compound P1-6 (2.3 g, 6.2 mmol) in THF (20 mL) was added dropwise n-BuLi (2.5 M in hexane, 5.5 mL, 14 mmol) at −78° C. The reaction was stirred at this temperature for 1 hour. To the mixture was added a solution of P1-10 (3.0 g, 5.6 mmol) in THF (20 mL), and the resulting mixture was then stirred at 10-20° C. overnight until compound P1-10 was consumed, as monitored by LCMS. The reaction was quenched with sat. aq. ammonium chloride and extracted with ethyl acetate. The combined organic solution was washed with water and brine, dried over sodium sulfate and concentrated in vacuo. The residue was purified by flash chromatography (0-30% ethyl acetate in petroleum ether) to give compound P1-11 (1.59 g, 51% yield) as a white solid. ESI m/z: 719 (M+1)⁺.

tert-Butyl N-[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (P1-12)

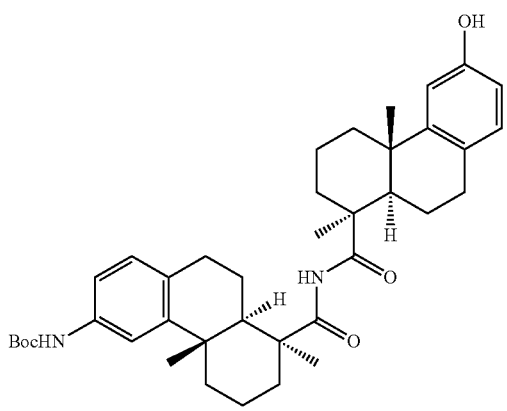 [SMILES: CC(C)(C)OC(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of P1-11 (2.0 g, 2.78 mmol) in ethyl acetate (40 mL) was added wet palladium on carbon (10% Pd, 0.9 g) under nitrogen protection. The mixture was degassed and purged with hydrogen and stirred at room temperature under hydrogen balloon overnight until P1-11 was totally consumed, which was monitored by LCMS. The mixture was filtered through Celite and the filtration was concentrated in vacuo. The residue was purified by silica gel column chromatography (0-55% ethyl acetate in petroleum ether) to give P1-12 (1.06 g, 61% yield) as a white solid. ESI m/z: 629 (M+H)⁺. ¹H NMR (500 MHz, DMSO$_{d6}$) δ 9.10 (s, 1H), 8.98 (s, 1H), 8.11 (s, 1H), 7.40 (s, 1H), 7.15 (d, J=7.5 Hz, 1H), 6.90 (d, J=8.4 Hz, 1H), 6.81 (d, J=8.3 Hz, 1H), 6.63 (d, J=2.3 Hz, 1H), 6.50 (dd, J=8.2, 2.4 Hz, 1H), 2.84 (td, J=16.3, 3.8 Hz, 2H), 2.77-2.64 (m, 2H), 2.30-2.22 (m, 2H), 2.14 (t, J=10.9 Hz, 4H), 2.00-1.80 (m, 4H), 1.65-1.54 (m, 4H), 1.45 (s, 9H), 1.34-1.28 (m, 2H), 1.27 (d, J=2.5 Hz, 6H), 1.15-1.08 (m, 2H), 0.99 (s, 6H) ppm.

(1S,4aS,10aR)—N-[(1S,4aS,10aR)-6-Amino-1,4a-dimethyl-1,2,3,4,4a,9,10,10a-octahydrophenanthrene-1-carbonyl]-6-hydroxy-1,4a-dimethyl-1,2,3,4,4a,9,10,10a-octahydrophenanthrene-1-carboxamide (9d)

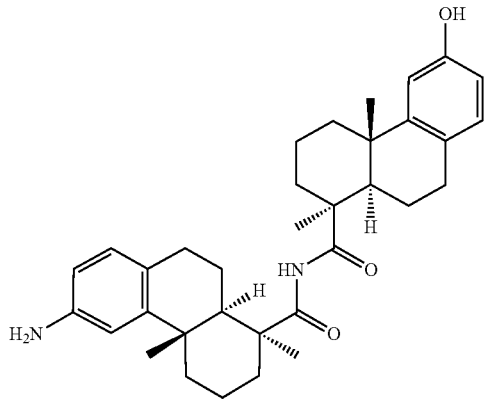 [SMILES: C[C@]1(C(=O)NC(=O)[C@@]2(C)CCC[C@]3(C)c4cc(O)ccc4CC[C@@H]23)CCC[C@]2(C)c3cc(N)ccc3CC[C@@H]12]

To the solution of compound P1-12 (0.17 g, 0.27 mmol) in DCM (10 mL) was added dropwise TFA (3 mL) at room temperature. The reaction mixture was stirred at room temperature for an hour until Boc was removed according to LCMS. The volatiles were removed in vacuo and the residue was purified by prep-HPLC (method B) to give 9d (0.10 g, 70% yield) as a white solid.

ESI m/z: 529.3 (M+1)⁺.

¹H NMR (400 MHz, CDCl₃) δ 8.14 (s, 1H), 6.92 (d, J=8.3 Hz, 1H), 6.86 (d, J=8.1 Hz, 1H), 6.73 (d, J=2.5 Hz, 1H), 6.65-6.57 (m, 2H), 6.50 (dd, J=8.1, 2.3 Hz, 1H), 4.75 (s, 1H), 3.49 (s, 1H), 2.99-2.85 (m, 2H), 2.79 (tt, J=11.6, 5.8 Hz, 2H), 2.34-2.14 (m, 6H), 2.15-1.95 (m, 4H), 1.74-1.51 (m, 5H), 1.46-1.34 (m, 2H), 1.30 (s, 6H), 1.21-1.06 (m, 8H) ppm.

¹H NMR (400 MHz, DMSO$_{d6}$) δ 8.99 (s, 1H), 8.09 (s, 1H), 6.81 (d, J=8.0 Hz, 1H), 6.68 (d, J=8.0 Hz, 1H), 6.63 (d, J=2.5 Hz, 1H), 6.50 (dd, J=8.0, 2.5 Hz, 1H), 6.48 (d, J=2.5 Hz, 1H), 6.34 (dd, J=8.0, 2.5 Hz, 1H), 4.69 (s, 2H), 2.86-2.60 (m, 4H), 2.28-2.10 (m, 6H), 1.94-1.75 (m, 4H), 1.65-1.53 (m, 4H), 1.35-1.20 (m, 8H), 1.20-1.06 (m, 2H), 0.98 (s, 6H) ppm.

$^{13}$C NMR (100 MHz, DMSO$_{d6}$) δ 174.03, 173.92, 155.34, 148.39, 147.63, 146.43, 129.56, 129.09, 124.60, 121.65, 113.23, 112.58, 111.81, 110.77, 52.32, 52.09, 45.56, 45.52, 39.20, 39.36, 38.23, 38.17, 37.18, 37.12, 31.08, 31.00, 27.65, 27.64, 23.08, 23.03, 21.43, 21.27, 19.64, 19.61 ppm.

HPLC (method B): Retention time: 8.92 min, purity: 99.4%. chiral HPLC: >99.9% (in column AD, AS, OD, and OJ).

Optical rotation (α): +2.53° (1.7 g/100 mL THF, 25° C.).

Example 1b

Synthesis of LP8 (FIG. 1b)

(1S,4aS,10aR)-6-((S)-2-((S)-2-Amino-3-methylbutanamido)propanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (LP1-2)

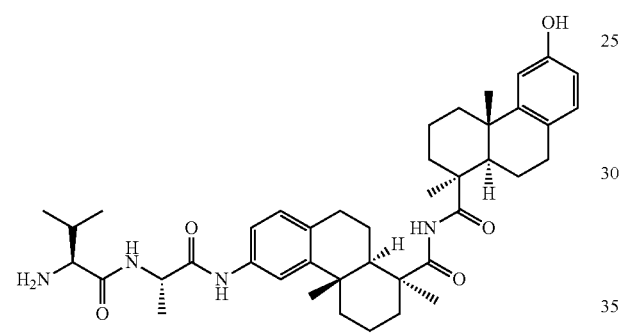

To a solution of 9d (53 mg, 0.10 mmol) in DMF (1 mL) were added Fmoc-Val-Ala-OH (41 mg, 0.10 mmol), HATU (38 mg, 0.1 mmol) and diisopropylethylamine (26 mg, 0.20 mmol) successively. After stirring at 25° C. for 24 hours until 9d was consumed according to LCMS, to the mixture was added piperidine (0.1 mL) and the resulting solution was stirred at 25° C. for another 3 hours. After filtration, the filtrate was directly purified by prep-HPLC (method B) to give compound LP1-2 (45 mg, 64% yield) as a white solid. ESI m/z: 699 (M+1)$^+$. $^1$H NMR (500 MHz, methanol$_{d4}$) δ 8.40 (s, 1H), 7.47 (s, 1H), 7.32 (d, J=8.0 Hz, 1H), 7.03 (d, J=8.3 Hz, 1H), 6.88 (d, J=8.2 Hz, 1H), 6.72 (d, J=2.4 Hz, 1H), 6.56 (dd, J=8.3, 2.4 Hz, 1H), 4.60-4.48 (m, 1H), 3.22-3.11 (m, 1H), 3.02-2.93 (m, 1H), 2.92-2.76 (m, 3H), 2.74-2.70 (m, 1H), 2.43-2.31 (m, 3H), 2.28 (d, J=14.1 Hz, 3H), 2.16-1.96 (m, 3H), 1.81 (s, 1H), 1.78-1.65 (m, 4H), 1.53-1.42 (m, 4H), 1.38 (d, J=5.3 Hz, 6H), 1.33-1.22 (m, 2H), 1.14 (d, J=6.6 Hz, 6H), 1.09 (d, J=18.6 Hz, 6H) ppm.

(1S,4aS,10aR)-6-((2S)-2-((2S)-2-((2R)-2-Amino-6-(2-(cyclooct-2-ynyloxy)acetamido)hexanamido)-3-methylbutanamido)propanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (LP1-4)

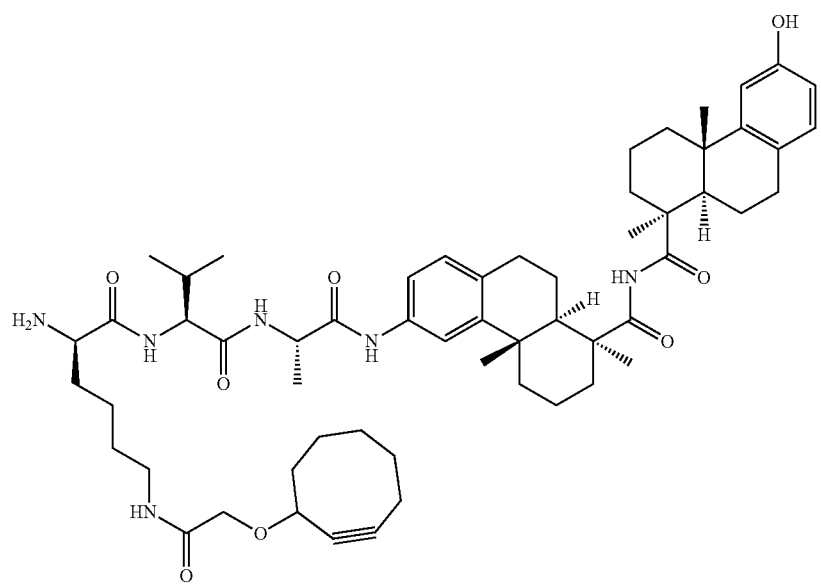 [SMILES: CC(C)[C@H](NC(=O)[C@H](N)CCCCNC(=O)COC1C#CCCCCC1)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of compound LP1-3 (35 mg, 0.064 mmol) in DMF (1 mL) were added HATU (24 mg, 0.064 mmol) and compound LP1-2 (45 mg, 0.064 mmol) in succession at room temperature. The mixture was stirred for a few minutes at room temperature until the mixture was homogenous. To this mixture was added diisopropylethylamine (41 mg, 0.32 mmol) at room temperature by syringe. The resulting mixture was stirred at room temperature overnight (16 hours) until LP1-2 was mostly consumed according to LCMS. To this reaction mixture was then added piperidine (0.1 mL, excess) dropwise at room temperature and the mixture was stirred for another 3 hours until Fmoc was removed, as monitored by LCMS. The reaction mixture was directly purified by reversed phase flash chromatography or prep-HPLC (method B, basic condition) to give compound LP1-4 (30 mg, 47% yield) as a white solid. ESI m/z: 991 (M+1)$^+$.
$^1$H NMR (500 MHz, methanol$_{d4}$) δ 7.51 (d, J=1.5 Hz, 1H), 7.37 (dd, J=8.3, 2.0 Hz, 1H), 7.02 (d, J=8.3 Hz, 1H), 6.89 (d, J=8.4 Hz, 1H), 6.72 (d, J=2.4 Hz, 1H), 6.56 (dd, J=8.3, 2.5 Hz, 1H), 4.64-4.57 (m, 1H), 4.48 (q, J=7.1 Hz, 1H), 4.33-4.27 (m, 1H), 4.20 (d, J=6.7 Hz, 1H), 3.93 (m, 2H), 3.43 (t, J=6.6 Hz, 1H), 3.24 (t, J=6.9 Hz, 2H), 3.02-2.93 (m, 2H), 2.92-2.76 (m, 3H), 2.40-2.32 (m, 2H), 2.33-2.23 (m, 4H), 2.22-2.12 (m, 3H), 2.12-2.00 (m, 5H), 1.99-1.91 (m, 1H), 1.91-1.81 (m, 2H), 1.78-1.66 (m, 6H), 1.66-1.58 (m, 1H), 1.58-1.49 (m, 2H), 1.45 (d, J=7.1 Hz, 6H), 1.38 (d, J=4.0 Hz, 6H), 1.34-1.22 (m, 4H), 1.14 (d, J=7.0 Hz, 6H), 1.06-0.98 (m, 6H) ppm.

(1S,4aS,10aR)—N-{[(1S,4aS,10aR)-6-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]propanamido]-1,4a-dimethyl-1,2,3,4,4a,9,10,10a-octahydrophenanthren-1-yl]carbonyl}-6-hydroxy-1,4a-dimethyl-1,2,3,4,4a,9,10,10a-octahydrophenanthrene-1-carboxamide (LP1-5)

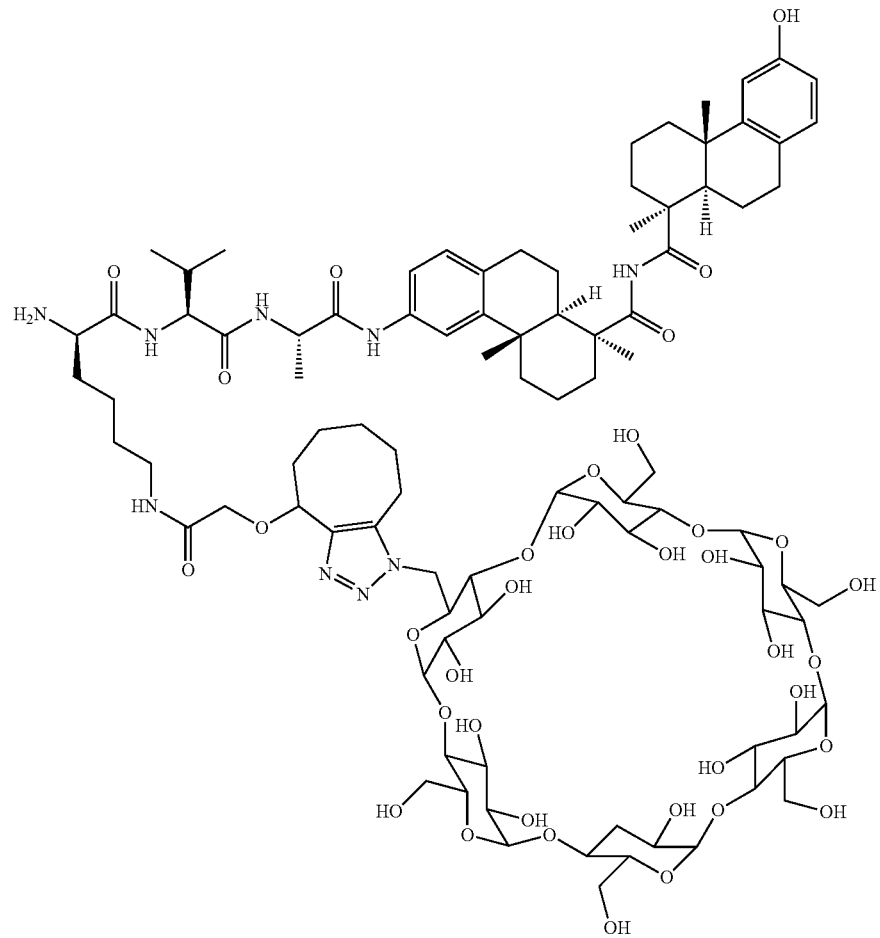 [SMILES: CC(C)[C@H](NC(=O)[C@H](N)CCCCNC(=O)COC1CCCCCc2c1nnn2CC1OC2OC3C(CO)OC(OC4CC(O)C(OC4CO)OC4C(CO)OC(OC5C(CO)OC(OC6C(CO)OC(OC1C(O)C2O)C(O)C6O)C(O)C5O)C(O)C4O)C(O)C3O)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of compound LP1-4 (30 mg, 30 μmol) in DMF (0.5 mL) was added a solution of CD-N$_3$ (60 mg, 60 μmol) in DMF (0.5 mL) at room temperature by syringe. The mixture was stirred at 20-25° C. for 3 days. Compound LP1-4 was mostly consumed according to LCMS. The reaction mixture was directly purified by prep-HPLC (method B) to give compound LP1-5 (14 mg, 23% yield) as a white solid. ESI m/z: 995 (M/2+1)$^+$. $^1$H NMR (500 MHz, methanol$_{d4}$) δ 8.40 (s, 1H), 7.56-7.52 (m, 1H), 7.32 (t, J=7.7 Hz, 1H), 7.03 (d, J=8.4 Hz, 1H), 6.88 (d, J=8.3 Hz, 1H), 6.72 (d, J=2.4 Hz, 1H), 6.56 (dd, J=8.2, 2.3 Hz, 1H), 5.24-5.16 (m, 1H), 5.01-4.95 (m, 6H), 4.65-4.59 (m, 1H), 4.52-4.44 (m, 1H), 4.31-4.22 (m, 2H), 4.13-3.73 (m, 22H), 3.63-3.43 (m, 14H), 3.14-2.72 (m, 7H), 2.45-2.32 (m, 3H), 2.28 (d, J=13.8 Hz, 3H), 2.22-1.85 (m, 11H), 1.82-1.59 (m, 9H), 1.55-1.41 (m, 8H), 1.38 (d, J=5.3 Hz, 6H), 1.31-1.26 (m, 3H), 1.14 (d, J=7.2 Hz, 6H), 1.06-0.93 (m, 6H) ppm.

1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (LP8)

313 314
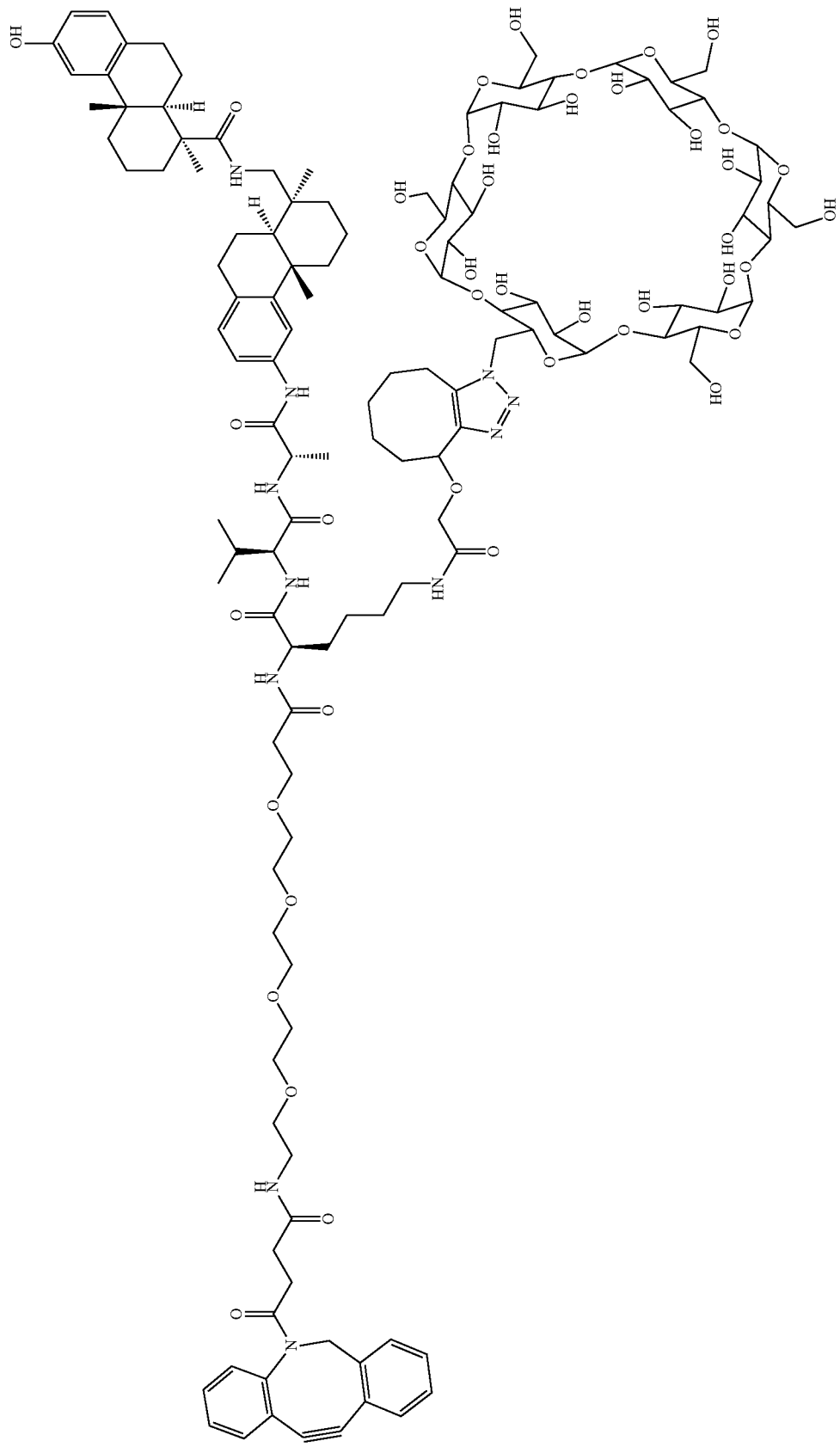

To a solution of compound LP1-5 (14 mg, 7.4 μmol) and DIBAC-Suc-PEG$_4$-OSu (6.5 mg, 10 μmol) in DMF (1 mL) was added triethylamine (2.0 mg, 20 μmol) and the mixture was stirred at 20-25° C. for 16 hours. Most of the volatiles were removed in vacuo and the residue was purified by prep-HPLC (method B) to give compound LP8 (5.0 mg, 27% yield) as a white solid. ESI m/z: 1261 (M/2+1)$^+$. $^1$H NMR (500 MHz, methanol$_{d4}$) δ 7.69-7.44 (m, 6H), 7.41-7.30 (m, 3H), 7.26 (d, J=6.8 Hz, 1H), 7.04-6.96 (m, 1H), 6.88 (d, J=8.4 Hz, 1H), 6.72 (d, J=1.9 Hz, 1H), 6.56 (dd, J=8.3, 2.4 Hz, 1H), 5.25-5.18 (m, 1H), 5.17-5.08 (m, 1H), 5.01-4.94 (m, 4H), 4.61 (s, 16H), 4.53-4.13 (m, 5H), 4.03-3.80 (m, 18H), 3.74-3.64 (m, 3H), 3.63-3.41 (m, 23H), 3.28-2.76 (m, 12H), 2.76-2.65 (m, 1H), 2.56-2.44 (m, 2H), 2.42-2.31 (m, 4H), 2.30-2.23 (m, 4H), 2.18-1.92 (m, 9H), 1.79-1.55 (m, 9H), 1.49-1.34 (m, 9H), 1.33-1.22 (m, 3H), 1.18-1.10 (m, 6H), 1.06-0.94 (m, 6H) ppm.

Example 1c

Synthesis of LP32 (FIG. 1c)

(1S,4aS,10aR)—N-{[(1S,4aS,10aR)-6-[(2S)-2-[(2S)-2-[(2R)-2-Amino-6-{2-[(1-{[41,42,43,44,45,46,47,48,49,50,51,52,53,54,55,56-hexadecahydroxy-10,15,20,25,30,35,40-heptakis(hydroxymethyl)-2,4,7,9,12,14,17,19,22,24,27,29,32,34,37,39-hexadecaoxanonacyclo[36.2.2.2$^{3,6}$.2$^{8,11}$.2$^{13,16}$.2$^{18,21}$.2$^{23,26}$.2$^{28,31}$.2$^{33,36}$]hexapentacontan-5-yl]methyl}-1H,4H,5H,6H,7H,8H,9H-cycloocta[d][1,2,3]triazol-4-yl)oxy]acetamido}hexanamido]-3-methylbutanamido]propanamido]-1,4a-dimethyl-1,2,3,4,4a,9,10,10a-octahydrophenanthren-1-yl]carbonyl}-6-hydroxy-1,4a-dimethyl-1,2,3,4,4a,9,10,10a-octahydrophenanthrene-1-carboxamide (LP2-5)

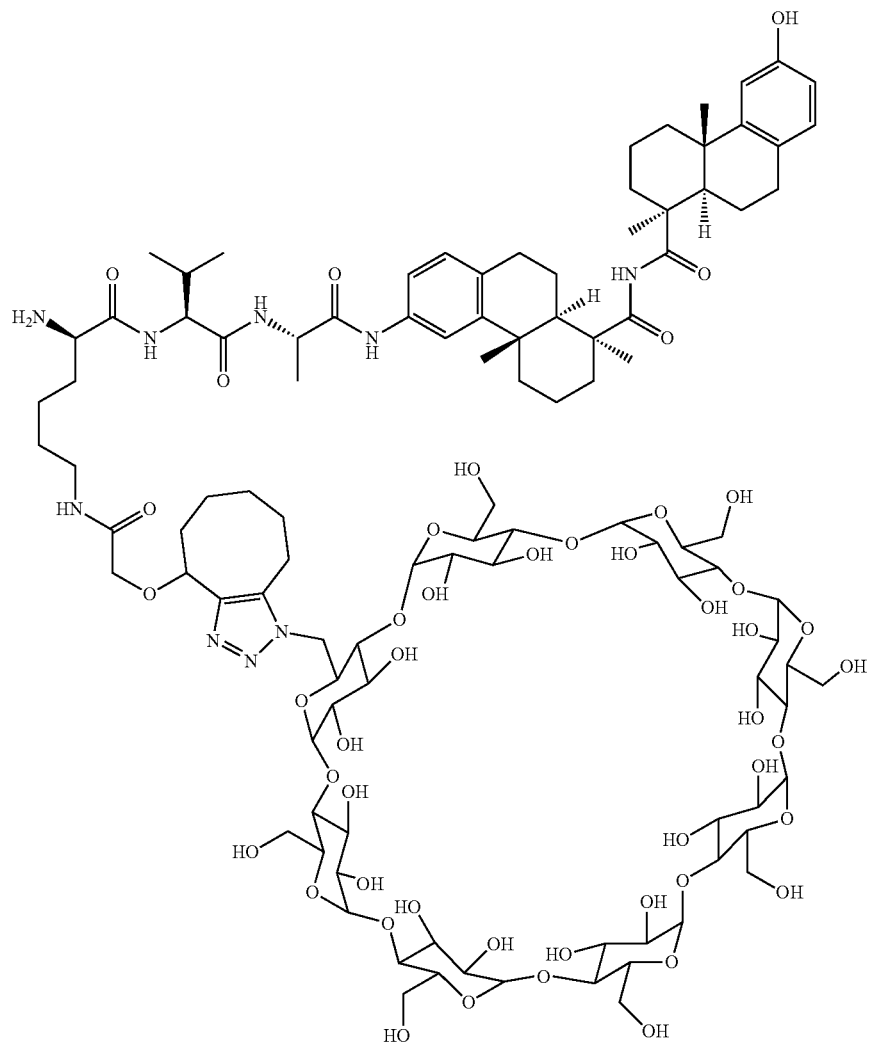 [SMILES: CC(C)[C@H](NC(=O)[C@H](N)CCCCNC(=O)COC1CCCCCc2c1nnn2CC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of compound LP1-4 (30 mg, 0.030 mmol) in DMF (2 mL) was added γCD-N$_3$ (0.12 mg, 0.091 mmol). The mixture was stirred at RT for 16 hours, which was monitored by LCMS. The mixture was filtered through membrane and the filtrate was then purified by prep-HPLC (method A) to give compound LP2-5 (40 mg, 57% yield) as a white solid. ESI m/z: 1157.6 (M/2+1)$^+$. $^1$H NMR (500 MHz, DMSO$_{d6}$) δ 9.82 (s, 1H), 9.00 (s, 1H), 8.55 (d, J=9.0 Hz, 1H), 8.39 (d, J=6.5 Hz, 1H), 8.11-8.04 (m, 4H), 7.93-7.88 (m, 1H), 7.45 (s, 1H), 7.35 (d, J=8.0 Hz, 1H), 6.97 (d, J=8.5 Hz, 1H), 6.81 (d, J=8.5 Hz, 1H), 6.63 (s, 1H), 6.50 (d, J=11 Hz, 1H), 5.89-5.68 (m, 16H), 5.16-4.32 (m, 19H), 3.94-3.80 (m, 4H), 3.69-3.51 (m, 50H), 3.18-2.64 (m, 8H), 2.33-1.85 (m, 12H), 1.65-1.11 (m, 25H), 0.99 (d, J=9.5 Hz, 6H), 0.89-0.83 (m, 6H) ppm.

1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[41,42,43,44,45,46,47,48,49,50,51,52,53,54,55,56-hexadecahydroxy-10,15,20,25,30,35,40-heptakis(hydroxymethyl)-2,4,7,9,12,14,17,19,22,24,27,29,32,34,37,39-hexadecaoxanonacyclo[36.2.2.2$^{3,6}$.2$^{8,11}$.2$^{13,16}$.2$^{18,21}$.2$^{23,26}$.2$^{28,31}$.2$^{33,36}$]hexapentacontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (LP32)

319
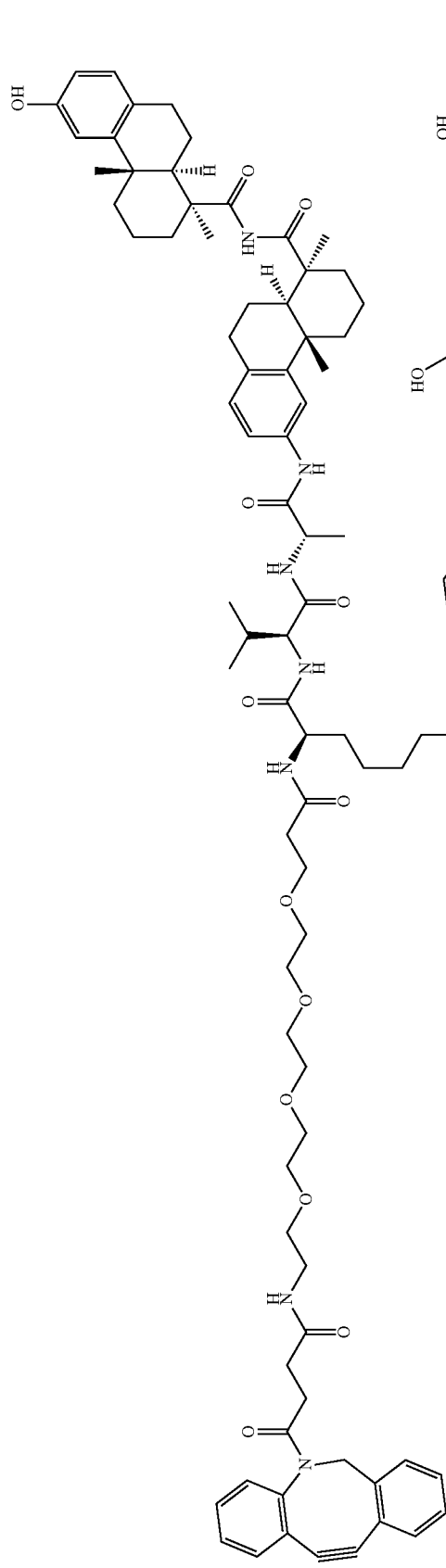
320
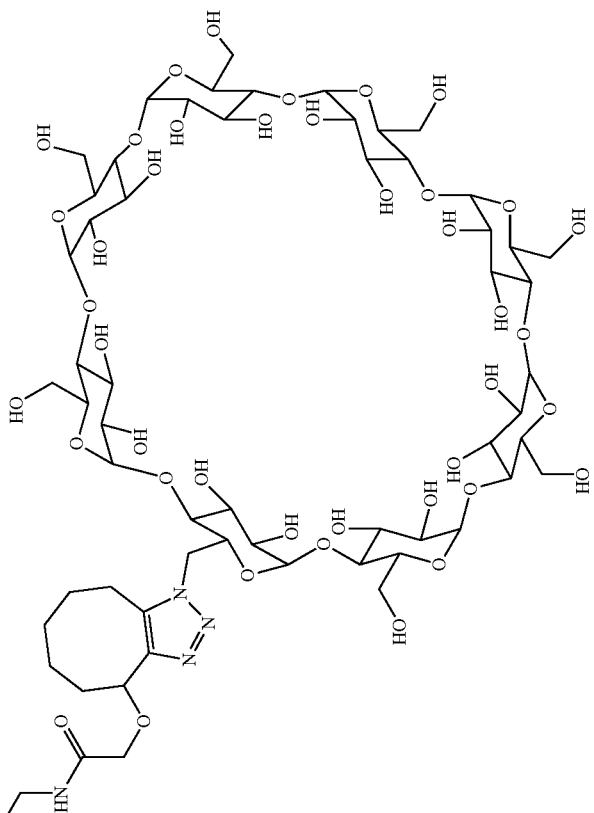

To a solution of compound LP2-6 (4.3 mg, 7.8 μmol) in anhydrous DMF (1 mL) was added HATU (3.0 mg, 7.8 μmol). The mixture was stirred at 10° C. for 10 minutes before compound LP2-5 (15 mg, 6.5 μmol) and DIPEA (1.7 mg, 13 μmol) was added. The mixture was stirred at RT for 2 hours until LP2-5 was totally consumed, as monitored by LCMS. The mixture was filtered through a membrane and the filtrate was purified by prep-HPLC (method B) to give compound LP32 (6.0 mg, 32% yield) as a white solid. ESI m/z: 1424.2 (M/2+1)$^+$. $^1$H NMR (500 MHz, DMSO$_{d6}$) δ 9.26 (s, 1H), 8.95 (s, 1H), 8.24-7.98 (m, 4H), 7.81 (d, J=5.6 Hz, 1H), 7.72 (t, J=5.5 Hz, 1H), 7.67 (d, J=8.1 Hz, 1H), 7.61 (d, J=7.4 Hz, 1H), 7.55 (s, 1H), 7.53-7.25 (m, 7H), 6.95 (d, J=8.5 Hz, 1H), 6.81 (d, J=8.4 Hz, 1H), 6.63 (d, J=2.1 Hz, 1H), 6.50 (dd, J=8.2, 2.1 Hz, 1H), 5.94-5.58 (m, 15H), 5.39-4.43 (m, 17H), 4.37-4.24 (m, 3H), 4.13-4.08 (m, 1H), 3.98-3.33 (m, 52H), 3.26-2.52 (m, 18H), 2.40-1.18 (m, 48H), 1.18-0.63 (m, 19H) ppm. Solubility: 0.075 mg/mL H$_2$O.

Example 1d

Synthesis of LP13 (FIG. 1*d*)

{4-[(2S)-2-[(2S)-2-[(2R)-2-Amino-6-{2-[(1-{[31,32, 33,34,35,36,37,38,39,40,41,42-dodecahydroxy-10, 15,20,25,30-pentakis(hydroxymethyl)-2,4,7,9,12,14, 17,19,22,24,27,29-dodecaoxaheptacyclo [26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1, 2,3]triazol-4-yl)oxy]acetamido}hexanamido]-3-methylbutanamido]-5-(carbamoylamino) pentanamido]phenyl}methyl N-[(1S)-1-{[(4bS,8S, 8aR)-8-({[(1S,4aS,10aR)-6-hydroxy-1,4a-dimethyl-1,2,3,4,4a,9,10,10a-octahydrophenanthren-1-yl] formamido}carbonyl)-4b,8-dimethyl-4b,5,6,7,8,8a,9, 10-octahydrophenanthren-3-yl]carbamoyl}-2-hydroxyethyl]carbamate (LP5-1)

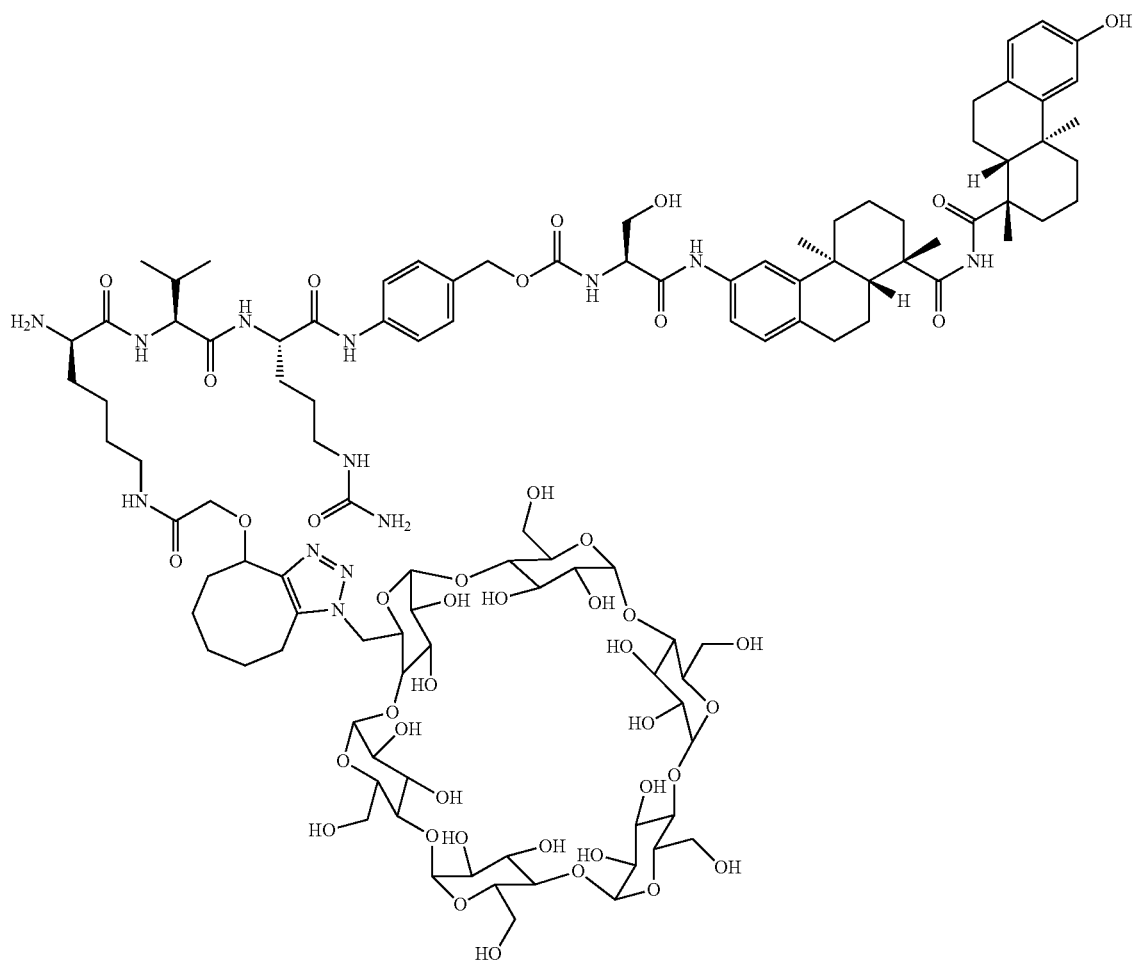 [SMILES: CC(C)[C@H](NC(=O)[C@H](N)CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of compound LP15 (20 mg, 15 μmol) in DMF (1 mL) was added a solution of CD-N$_3$ (46 mg, 45 μmol) in acetonitrile (2 mL) and water (2 mL) at RT. The mixture was stirred at 30° C. for 16 hours. Compound LP15 was mostly consumed according to LCMS. The reaction mixture was directly purified by prep-HPLC (method B) to give compound LP5-1 (20 mg, 57% yield) as a white solid. ESI m/z: 1156.0 (M/2+1)$^+$. {4—[(2S)-2-[(2S)-2-[(2R)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (LP13)

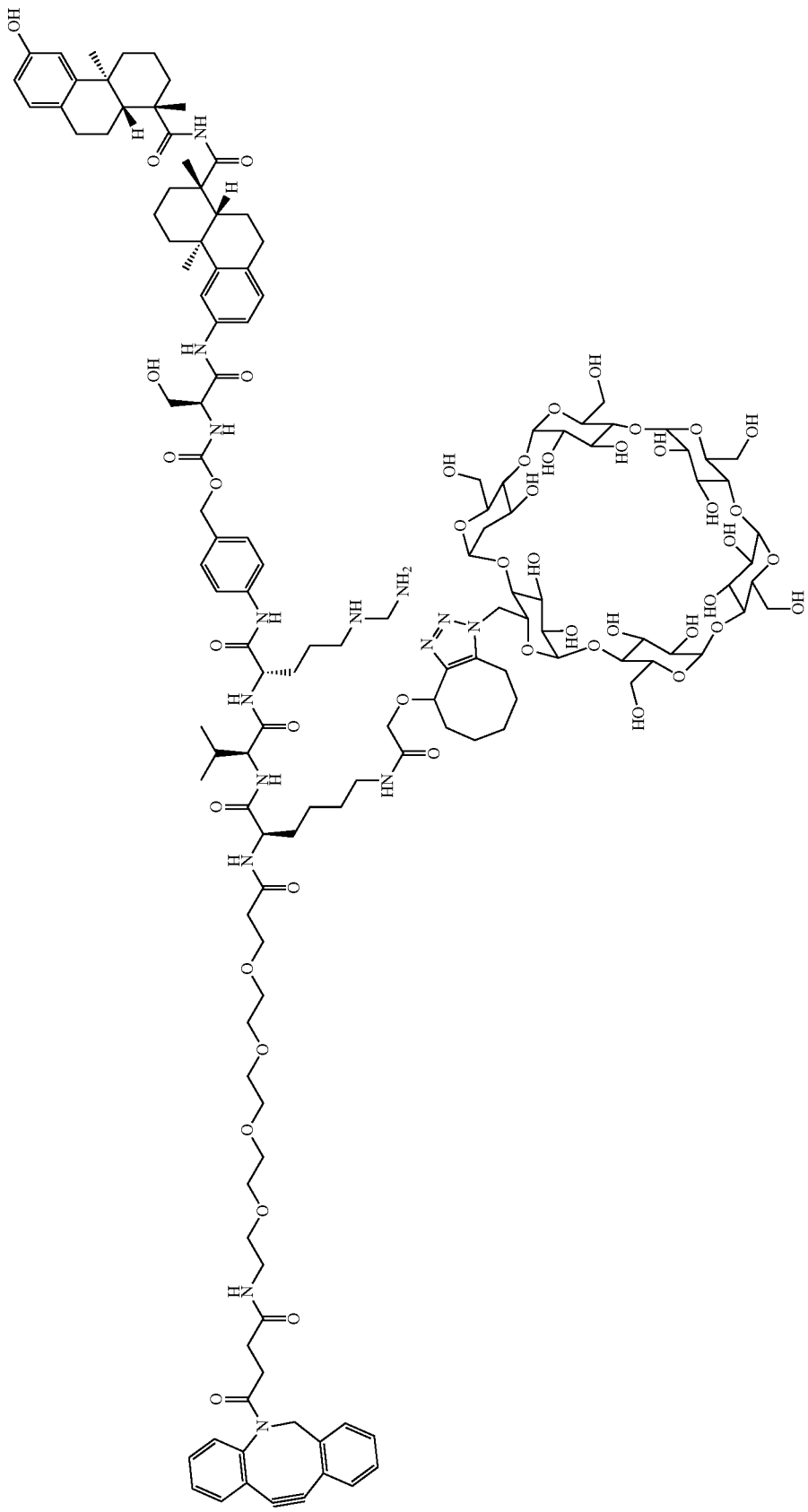

To a solution of DIBAC-PEG$_4$-acid LP5-2 (4.3 mg, 7.8 μmol) in DMF (1 mL) were added HATU (3.0 mg, 3.6 μmol) and DIPEA (1.7 mg, 13 μmol) at RT. The resulting mixture was stirred at RT for 10 minutes. To the mixture was then added LP5-1 (15 mg, 6.5 μmol). The reaction mixture was stirred at 30° C. for 2 hours until the reaction completed, as monitored by LCMS. The reaction mixture was filtered and purified by prep-HPLC (method B) to give LP13 (10 mg, 42% yield) as a white solid. ESI m/z: 1424.3 (M/2+1)$^+$. $^1$H NMR (500 MHz, DMSO$_{d6}$) δ 9.81-9.67 (m, 2H), 8.99 (s, 1H), 8.20-8.06 (m, 5H), 7.85-7.22 (m, 18H), 6.97-6.49 (m, 2H), 5.98 (s, 1H), 5.65-5.33 (m, 15H), 5.14-4.92 (m, 5H), 4.82-4.72 (m, 6H), 4.60-4.54 (m, 4H), 4.36-4.28 (m, 3H), 4.18-3.96 (m, 3H), 3.85-3.55 (m, 27H), 3.49-3.39 (m, 23H), 3.28-3.08 (m, 8H), 2.94-2.57 (m, 4H), 2.42-2.07 (m, 8H), 1.99-1.45 (m, 22H), 1.28-1.11 (m, 23H), 1.05-0.95 (m, 6H), 0.89-0.79 (m, 7H) ppm.

Example 1e

Synthesis of LP36 (FIG. 1e)

1-Azido-15-oxo-3,6,9,12-tetraoxa-16-azaoctadecane-18-sulfonic Acid (L6-2)

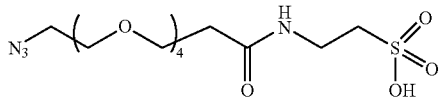

To a solution of azido-PEG$_4$-NHS (L6-1, 0.10 g, 0.26 mmol) in anhydrous DMF (4 mL) were added taurine (39 mg, 0.31 mmol) and DIPEA (15 mg, 0.52 mmol). The mixture was stirred at 25° C. overnight. The mixture was filtered and the filtrate was purified by prep-HPLC (method A) to give compound LP6-2 (80 mg, 78% yield) as colorless oil. ESI m/z: 399.1 (M+H)$^+$. $^1$H NMR (500 MHz, D$_2$O) δ 3.69 (t, J=6.0 Hz, 2H), 3.64-3.59 (m, 14H), 3.49 (t, J=6.5 Hz, 2H), 3.41 (t, J=4.5 Hz, 2H), 3.00 (t, J=7.0 Hz, 2H), 2.45 (t, J=6.0 Hz, 2H) ppm.

2-{1-[4-({[(5R)-5-Amino-5-{[(1S)-1-{[(1S)-1-({4-[({[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamoyl}oxy)methyl]phenyl}carbamoyl)-4-(carbamoylamino)butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic Acid (LP6-3)

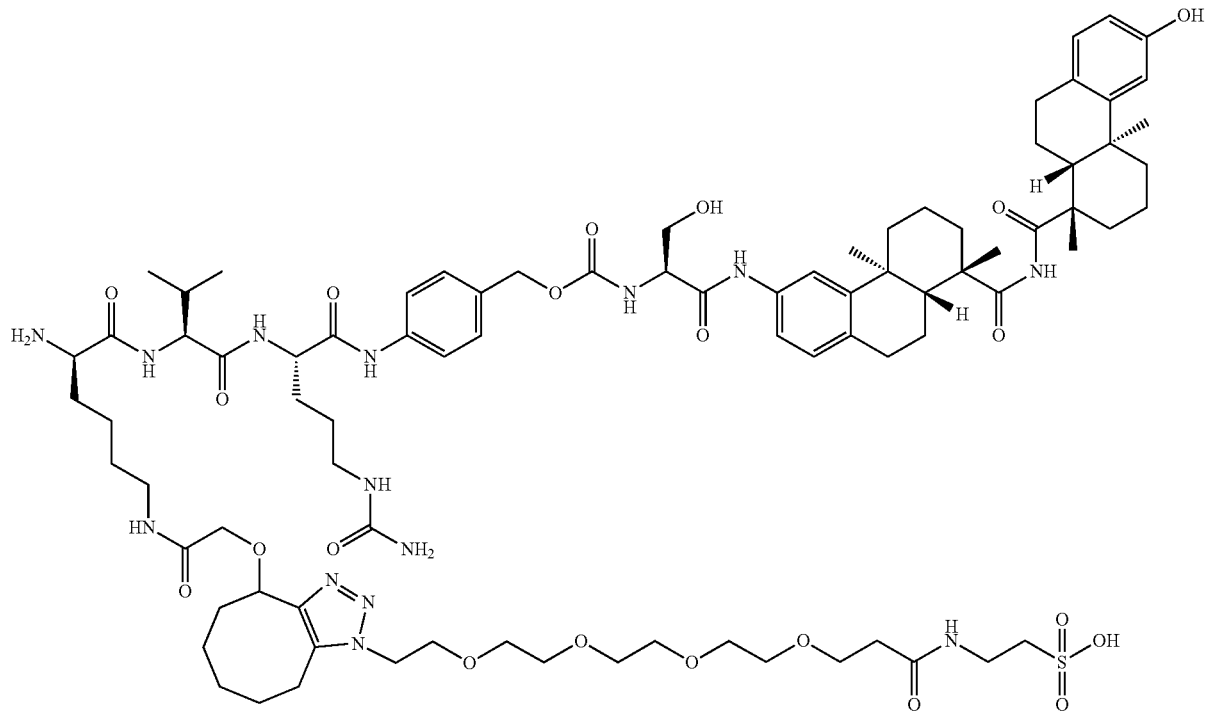 [SMILES: CC(C)[C@H](NC(=O)[C@H](N)CCCCNC(=O)COC1CCCCCc2c1nnn2CCOCCOCCOCCOCCC(=O)NCCS(=O)(=O)O)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of compound LP6-2 (20 mg, 50 μmol) in water (1 mL) was added dropwise sat. aq. sodium bicarbonate solution at 0° C. until pH~ 7. To the stirred solution was then added a solution of compound LP15 (28 mg, 21 μmol) in acetontrile (1 mL) by syringe. The mixture was stirred at 25° C. overnight. The reaction mixture was monitored by LCMS until compound LP15 was totally consumed. The reaction mixture was filtered and purified by prep-HPLC (method A) to give compound LP6-3 (15 mg, 41% yield) as a white solid. ESI m/z: 856.5 (M/2+1)$^+$.

2-{1-[4-({[(5R)-5-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-5-{[(1S)-1-{[(1S)-1-({4-[({[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamoyl}oxy)methyl]phenyl}carbamoyl)-4-(carbamoylamino)butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic Acid (LP36)

1H), 5.39-5.33 (m, 1H), 5.14-5.09 (m, 5H), 4.61 (s, 18H), 4.50-4.43 (m, 2H), 4.33-4.30 (m, 1H), 3.99 (s, 2H), 3.89-3.85 (m, 3H), 3.73-3.42 (m, 28H), 3.25-2.72 (m, 8H), 2.45 (t, J=7.5 Hz, 2H), 2.36-1.96 (m, 18H), 1.81-1.51 (m, 12H), 1.45-1.32 (m, 15H), 1.12-0.89 (m, 12H) ppm.

Example 1f

Synthesis of LP18 (FIG. 1f)

1-Azido-15-oxo-3,6,9,12-tetraoxa-16-azaoctadecane-18-sulfonic Acid (L18-2)

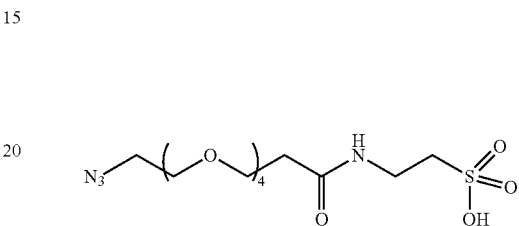

To a solution of azido-PEG$_4$-NHS (L18-1, 0.10 g, 0.26 mmol) in anhydrous DMF (4 mL) were added taurine (39

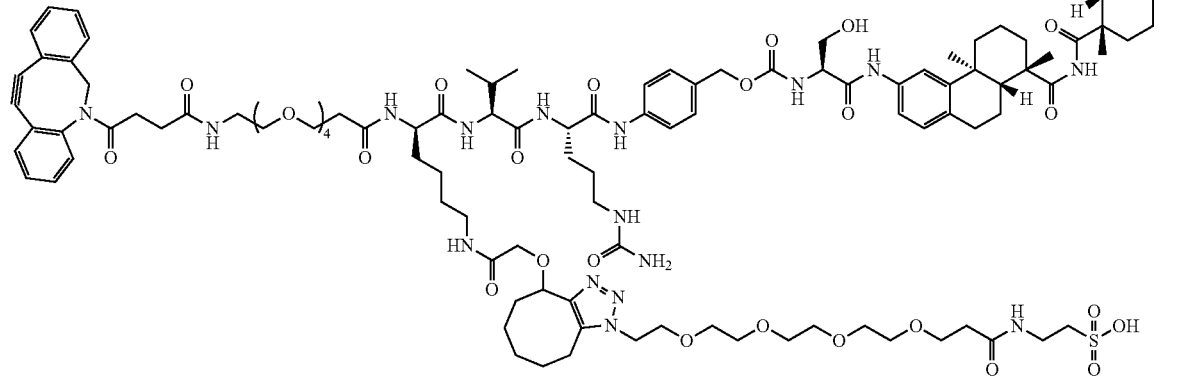

To a solution of compound LP6-3 (15 mg, 8.8 μmol) and commercially available DIBAC-Suc-PEG$_4$-OSu LP6-4 (5.7 mg, 8.8 μmol, CAS 1427004-19-0) in DMF (1 mL) was added DIPEA (2.3 mg, 18 μmol) and the mixture was stirred at RT for 2 hours. Most of the volatiles were removed in vacuo and the residue was purified by prep-HPLC (method B) to give LP36 (6.0 mg, 30% yield) as a white solid. ESI m/z: 1123.8 (M/2+H)$^+$, 749.5 (M/3+H)$^+$. $^1$H NMR (500 MHz, methanol$_{d4}$) δ 7.76-7.16 (m, 14H), 7.06-7.00 (m, 1H), 6.88 (d, J=8.5 Hz, 1H), 6.72-6.71 (m, 1H), 6.56-6.55 (m, mg, 0.31 mmol) and DIPEA (15 mg, 0.52 mmol). The mixture was stirred at 25° C. overnight. The mixture was filtered and the filtrate was purified by prep-HPLC (method A) to give compound LP18-2 (80 mg, 78% yield) as colorless oil. ESI m/z: 399.1 (M+H)$^+$. $^1$H NMR (500 MHz, D$_2$O) δ 3.69 (t, J=6.0 Hz, 2H), 3.64-3.59 (m, 14H), 3.49 (t, J=6.5 Hz, 2H), 3.41 (t, J=4.5 Hz, 2H), 3.00 (t, J=7.0 Hz, 2H), 2.45 (t, J=6.0 Hz, 2H) ppm.

1-(4-(2-((R)-5-Amino-6-((S)-1-((S)-1-((4bS,8S,
8aR)-8-((1S,4aS,10aR)-6-hydroxy-1,4a-dimethyl-1,
2,3,4,4a,9,10,10a-octahydrophenanthrene-1-carbo-
nylcarbamoyl)-4b,8-dimethyl-4b,5,6,7,8,8a,9,10-
octahydrophenanthren-3-ylamino)-1-oxopropan-2-
ylamino)-3-methyl-1-oxobutan-2-ylamino)-6-
oxohexylamino)-2-oxoethoxy)-4,5,6,7,8,9-
hexahydro-1H-cycloocta[d][1,2,3]triazol-1-yl)-15-
oxo-3,6,9,12-tetraoxa-16-azaoctadecane-18-sulfonic
acid (LP18-3)

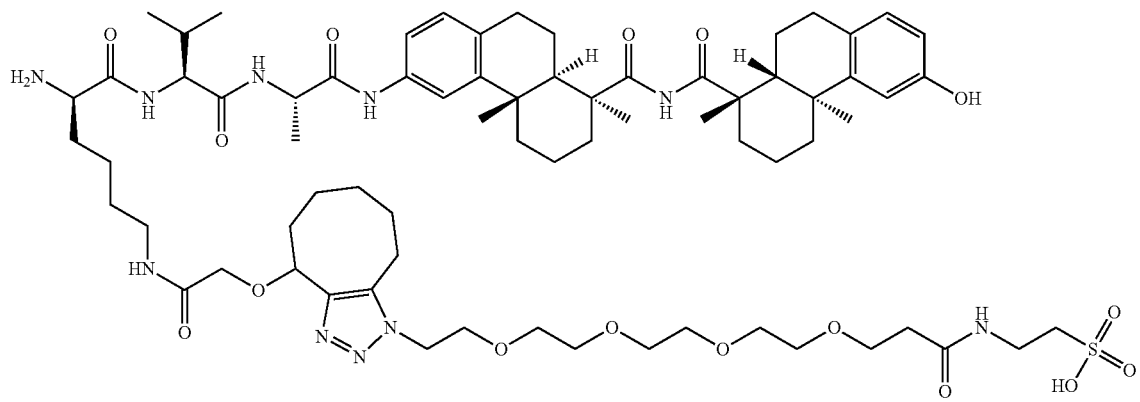 [SMILES: CC(C)[C@H](NC(=O)[C@H](N)CCCCNC(=O)COC1CCCCCc2c1nnn2CCOCCOCCOCCOCCC(=O)NCCS(=O)(=O)O)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of compound LP1-4 (40 mg, 40 μmol) in DMF (1 mL) was added azide LP18-2 (40 mg, 0.10 mmol) at RT. The reaction was stirred at RT for 16 hours, until LCMS showed complete reaction. The reaction mixture was directly purified by prep-HPLC to give compound LP18-3 (43 mg, 77% yield) as a white solid. ESI m/z: 695.4 (M/2+H)$^+$.

2-{1-[4-({[(5R)-5-[1-(4-{2-Azatricyclo[10.4.0.0$^{4,9}$]
hexadeca-1(12),4(9),5,7,13,15-hexaen-10-yn-2-yl}-
4-oxobutanamido)-3,6,9,12-tetraoxapentadecan-15-
amido]-5-{[(1S)-1-{[(1S)-1-{[(4bS,8S,8aR)-8-
({[(1S,4aS,10aR)-6-hydroxy-1,4a-dimethyl-1,2,3,4,
4a,9,10,10a-octahydrophenanthren-1-yl]
formamido}carbonyl)-4b,8-dimethyl-4b,5,6,7,8,8a,9,
10-octahydrophenanthren-3-yl]carbamoyl}ethyl]
carbamoyl}-2-methylpropyl]carbamoyl}pentyl]
carbamoyl}methoxy)-1H,4H,5H,6H,7H,8H,9H-
cycloocta[d][1,2,3]triazol-1-yl]-3,6,9,12-
tetraoxapentadecan-15-amido}ethane-1-sulfonic
Acid (LP18)

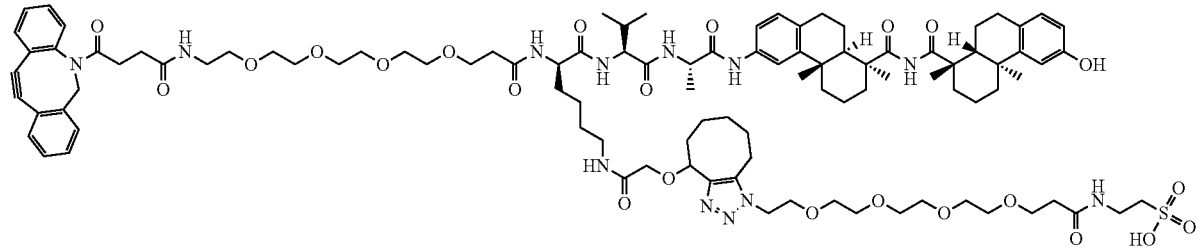 [SMILES: CC(C)[C@H](NC(=O)[C@@H](CCCCNC(=O)COC1CCCCCc2c1nnn2CCOCCOCCOCCOCCC(=O)NCCS(=O)(=O)O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of compound LP18-3 (30 mg, 22 μmol) in DMF (1 mL) were added a solution of DIBAC-suc-PEG$_4$-OSu (LP18-4, 14 mg, 22 μmol) in DMF (1 mL) and DIPEA (4 mg, 32 μmol) successively at RT. The reaction mixture was stirred at RT for 2 hours. The reaction mixture was directly purified by prep-HPLC (method B) to give compound LP18 (15 mg, 37% yield) as a white solid. ESI m/z: 642 (M/3+H)$^+$. $^1$H NMR (400 MHz, DMSO$_{d6}$) δ 9.68-9.27 (m, 1H), 8.99 (s, 1H), 8.23-7.85 (m, 4H), 7.79-7.71 (m, 2H), 7.76-7.42 (m, 6H), 7.39-7.28 (m, 3H), 7.21 (s, 1H), 7.09 (s, 1H), 6.96-6.93 (m, 2H), 6.81 (d, J=8.4 Hz, 1H), 6.63 (d, J=2.4 Hz, 1H), 6.50 (dd, J=8.4 Hz, 2.4 Hz, 1H), 5.02 (d, J=14.0 Hz, 1H), 4.93-4.72 (m, 1H), 4.53-4.09 (m, 5H), 3.82-3.75 (m, 4H), 3.62-3.53 (m, 3H), 3.51-3.38 (m, 23H), 3.30-3.27 (m, 6H), 3.12-2.67 (m, 10H), 2.61-2.54 (m, 4H), 2.39-1.52 (m, 31H), 1.45-1.08 (m, 18H), 1.01-0.98 (m, 6H), 0.90-0.82 (m, 6H) ppm.

Example 1g

Synthesis of Payload 9j, Payload 9o, and Payload 9l

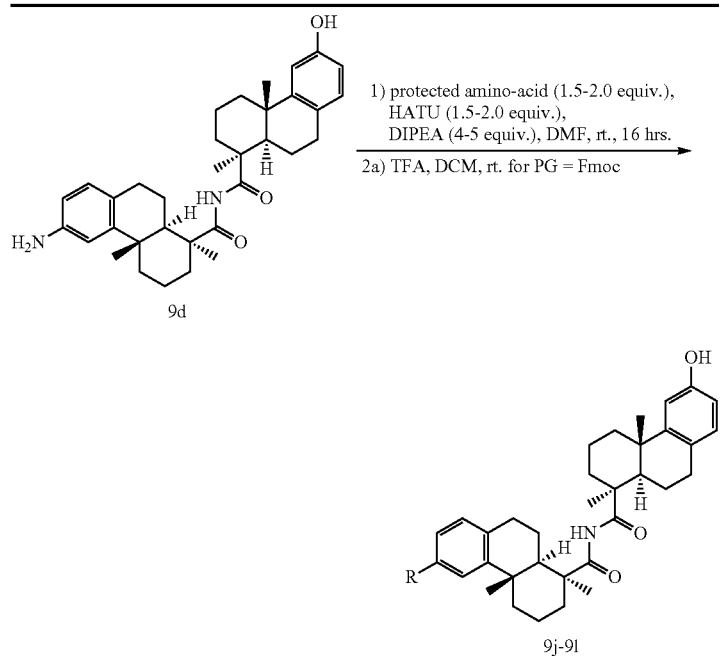

| Cpd | R | PG | Yield |
|---|---|---|---|
| 9j | NHC(O)(S)—CH(CH$_2$OH)NH$_2$ (Ser) | Fmoc | 51% |
| 9o | NHC(O)(S)—CH(CH$_2$CH$_2$COOH)NH$_2$ (Glu) | tBu, Boc | 46% |
| 9l | NHC(O)(S)—CH((CH$_2$)$_4$NH$_2$)NH$_2$ (Lys) | Boc, Boc | 49% |

Payload 9j (1S,4aS,10aR)-6-((S)-2-Amino-3-hydroxypropanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (9j)

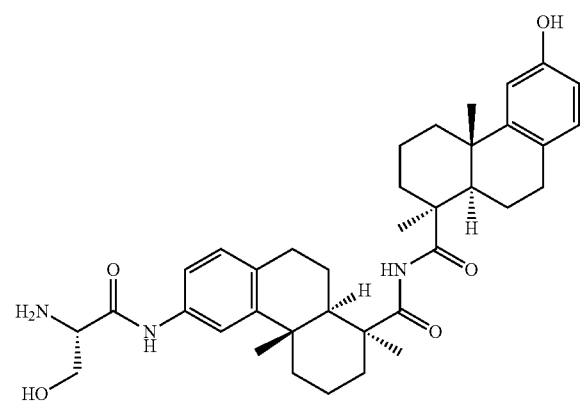 [SMILES: C[C@]1(C(=O)NC(=O)[C@@]2(C)CCC[C@]3(C)c4cc(NC(=O)[C@@H](N)CO)ccc4CC[C@@H]23)CCC[C@]2(C)c3cc(O)ccc3CC[C@@H]12]

To a solution of Fmoc-Ser-OH (33 mg, 0.1 mmol) in DMF (1 mL) were added HATU (38 mg, 0.1 mmol), and DIPEA (39 mg, 0.3 mmol) at 25° C. The resulting mixture was stirred at this temperature for an hour. To the mixture was then added 9d (30 mg, 0.06 mmol). After the reaction mixture was stirred at 25° C. for 16 hours and 9d was totally consumed (monitored by LCMS), piperidine (0.2 mL) was added into the mixture, which was stirred for another 30 min at room temperature. The residue was directly purified by prep-HPLC (method B) to give 9j (18 mg, 51% yield) as a white solid. ESI m/z: 616 (M+1)$^+$. $^1$H NMR (500 MHz, DMSO$_{d6}$) δ 9.74 (br s, 1H), 9.00 (s, 1H), 8.11 (s, 1H,), 7.58 (s, 1H), 7.41 (dd, J=8.2, 2.0 Hz, 1H), 6.96 (d, J=8.4 Hz, 1H), 6.82 (d, J=8.3 Hz, 1H), 6.63 (d, J=2.3 Hz, 1H), 6.50 (dd, J=8.2, 2.4 Hz, 1H), 4.82 (t, J=5.5 Hz, 1H), 3.62-3.45 (m, 2H), 2.97-2.67 (m, 4H), 2.67-2.61 (m, 2H), 2.33-2.21 (m, 2H), 2.21-2.03 (m, 4H), 1.96-1.77 (m, 4H), 1.70-1.50 (m, 4H), 1.43-1.37 (m, 1H), 1.36-1.20 (m, 8H), 1.23-1.06 (m, 2H), 1.06-0.93 (m, 6H) ppm.

Payload 9o (4S)-4-Amino-4-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}butanoic acid; Trifluoroacetic Acid Salt (9o)

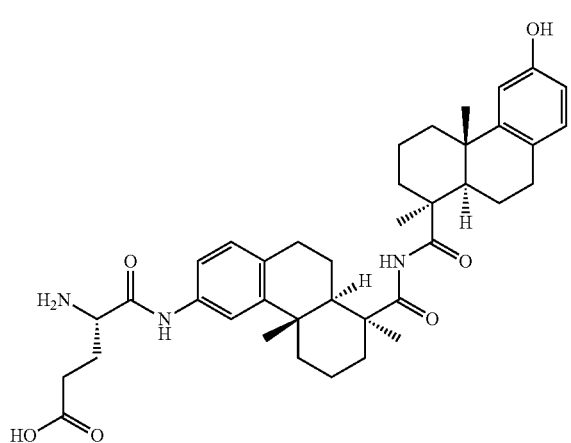 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(O)ccc3CC[C@@H]12]

Payload 9l (1S,4aS,10aR)—N-[(1S,4aS,10aR)-6-Hydroxy-1,4a-dimethyl-1,2,3,4,4a,9,10,10a-octahydrophenanthrene-1-carbonyl]-6-[(2S)-2,6-diaminohexanamido]-1,4a-dimethyl-1,2,3,4,4a,9,10,10a-octahydrophenanthrene-1-carboxamide; Trifluoroacetic Acid Salt (9l)

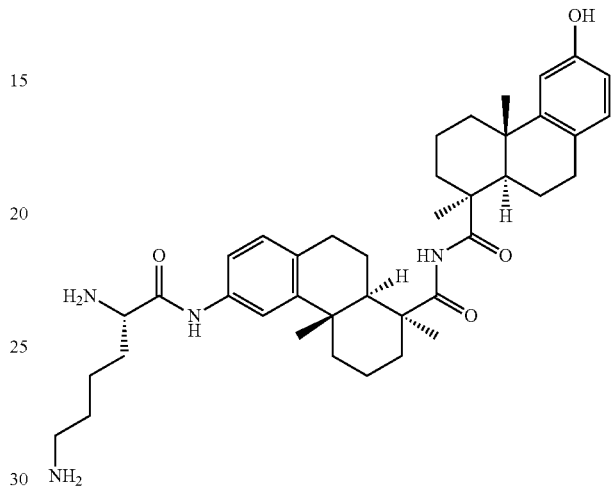

To a solution of OtBu-N-Boc-Glu-OH (15 mg, 0.05 mmol) in DMF (1 mL) was added HATU (19 mg, 0.05 mmol), and DIPEA (13 mg, 0.1 mmol) at 25° C. The resulting mixture was stirred at this temperature for an hour. To the mixture was then added 9d (14 mg, 0.026 mmol). After stirring at 25° C. for 16 hours and 9d was totally consumed (monitored by LCMS), the reaction mixture was diluted with ethyl acetate and washed with water and brine. The organic solution was dried over sodium sulfate and concentrated in vacuo. The residue was dissolved in DCM (1 mL) and to the solution was added TFA (0.1 mL) slowly at room temperature. The mixture was stirred at room temperature for 2 hours. The volatiles were removed in vacuo and the residue was purified by prep-HPLC (method A) to give 9o (8 mg, 46% yield) as a white solid. ESI m/z: 658.3 (M+1)$^+$. $^1$H NMR (400 MHz, DMSO$_{d6}$) δ 10.32 (s, 1H), 9.00 (s, 1H), 8.12 (s, 1H), 7.48 (s, 1H), 7.35 (d, J=8.2 Hz, 1H), 7.02 (d, J=8.4 Hz, 1H), 6.82 (d, J=8.3 Hz, 1H), 6.63 (d, J=2.1 Hz, 1H), 6.50 (dd, J=8.2, 2.3 Hz, 1H), 3.87 (t, J=6.5 Hz, 1H), 2.97-2.67 (m, 4H), 2.41-2.22 (m, 4H), 2.22-2.08 (m, 4H), 2.05-1.97 (m, 2H), 1.94-1.80 (m, 4H), 1.69-1.52 (m, 4H), 1.42-1.22 (m, 8H), 1.22-1.06 (m, 2H), 1.02 (s, 3H), 0.99 (s, 3H) ppm. $^{19}$F NMR (376 MHz, DMSO$_{d6}$) δ -73.50 ppm.

To a solution of Boc-Lys-OH (15 mg, 0.05 mmol) in DMF (1 mL) was added HATU (19 mg, 0.05 mmol), and DIPEA (13 mg, 0.1 mmol) at 25° C. The resulting mixture was stirred at this temperature for an hour. To the mixture was then added 9d (15 mg, 0.028 mmol). After stirring at 25° C. for 16 hours and 9d was totally consumed (monitored by LCMS), the reaction mixture was diluted with ethyl acetate and washed with water and brine. The organic solution was dried over sodium sulfate and concentrated in vacuo. The residue (Boc-9l) was dissolved in DCM (1 mL) and to the solution was added TFA (0.1 mL) slowly at room temperature. The mixture was stirred at room temperature for 2 hours. The volatiles were removed in vacuo and the residue was purified by prep-HPLC (method A) to give 9l (9 mg, 49% yield) as a white solid. ESI m/z: 657.5 (M+1)$^+$. $^1$H NMR (400 MHz, DMSO$_{d6}$) δ 10.33 (s, 1H), 9.01 (s, 1H), 8.13 (s, 1H), 7.78 (br s, 6H), 7.51 (s, 1H), 7.34 (d, J=8.1 Hz, 1H), 7.02 (d, J=8.5 Hz, 1H), 6.82 (d, J=8.6 Hz, 1H), 6.63 (s, 1H), 6.51 (d, J=8.3 Hz, 1H), 3.82 (s, 1H), 2.89 (s, 1H), 2.82-2.67 (m, 5H), 2.29 (s, 2H), 2.15 (s, 4H), 1.85 (s, 6H), 1.64-1.51 (m, 6H), 1.28 (d, J=6.8 Hz, 10H), 1.13 (s, 2H), 1.01 (s, 3H), 0.99 (s, 3H) ppm. $^{19}$F NMR (376 MHz, DMSO$_{d6}$) δ -73.53 ppm.

Example 1h

Synthesis of LP15 (FIG. 1g)

{4-[(2S)-2-[(2S)-2-Amino-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (LP4-2)

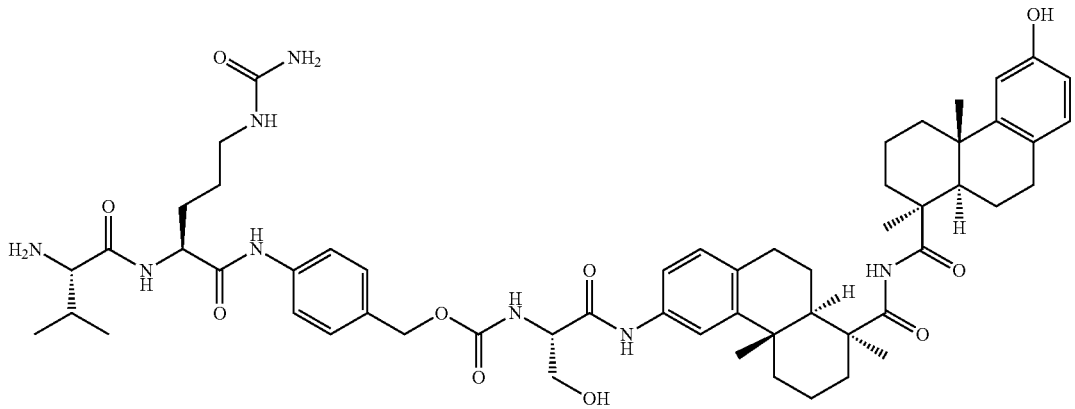 [SMILES: CC(C)[C@H](N)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of Fmoc-vc-PAB-PNP (LP4-1, 58 mg, 76 µmol) and 9j (36 mg, 58 µmol) in DMF (3 mL) was added HOBt (7.9 mg, 58 µmol) and DIPEA (15 mg, 0.12 mmol), and the mixture was stirred at 30° C. for 16 hours. Compound 9j was then totally consumed according to LCMS. To the resulting mixture was added diethylamine (0.1 mL) and the reaction was stirred at RT for an hour until Fmoc was removed, as monitored by LCMS. After the reaction was filtered, the filtrate was directly purified by prep-HPLC (method B) to give compound LP4-2 (36 mg, 48% yield) as a light yellow solid. ESI m/z: 1021 (M+1)$^+$.

$^1$H NMR (400 MHz, DMSO$_{d6}$) δ 10.02 (s, 1H), 9.82 (s, 1H), 9.00 (s, 1H), 8.69-8.65 (m, 1H), 8.11-8.00 (m, 4H), 7.65-7.53 (m, 3H), 7.40-7.30 (m, 3H), 7.30-7.20 (m, 1H), 6.96 (d, J=8.0 Hz, 1H), 6.81 (d, J=8.0 Hz, 1H), 6.65-6.61 (m, 1H), 6.50 (dd, J=8.0 Hz, 2.0 Hz, 1H), 6.00-5.95 (m, 1H), 5.48 (s, 2H), 5.00-4.95 (m, 3H), 4.60-4.40 (m, 1H), 4.25-4.20 (m, 1H), 3.65-3.55 (m, 4H), 3.15-2.55 (m, 10H), 2.40-2.20 (m, 3H), 2.20-2.00 (m, 5H), 2.00-1.80 (m, 4H), 1.86-1.55 (m, 6H), 1.27 (d, J=4.8 Hz, 9H), 1.20-1.10 (m, 2H), 0.97-0.90 (m, 6H) ppm.

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (LP15)

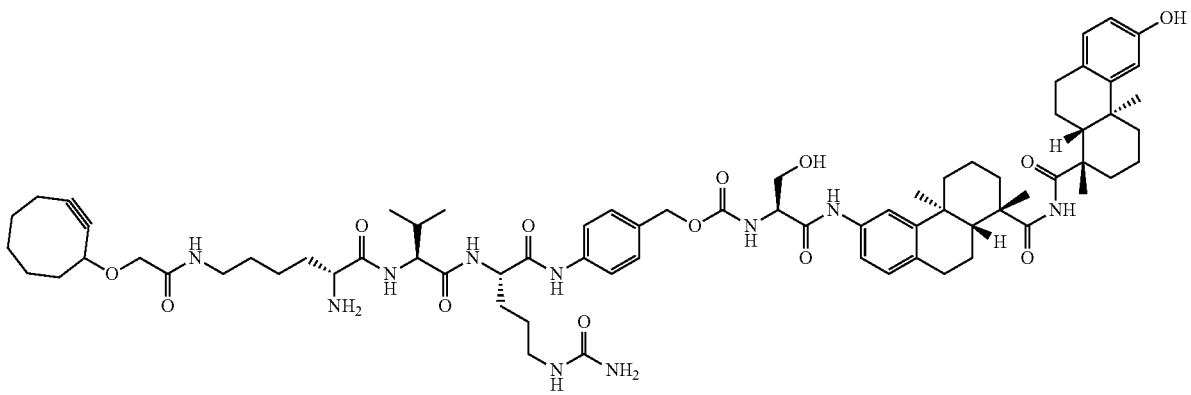 [SMILES: CC(C)[C@H](NC(=O)[C@H](N)CCCCNC(=O)COC1C#CCCCCC1)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of compound LP4-3 (24 mg, 44 µmol) in DMF (2 mL) was added HATU (17 mg, 44 µmol) and compound LP4-2 (35 mg, 34 µmol) in succession at RT. The mixture was stirred for a few minutes at RT until the mixture was homogenous. To this mixture was added DIPEA (8.8 mg, 68 µmol) at RT by syringe. The resulting mixture was stirred at RT for 2 hours until the LP4-2 was mostly consumed according to LCMS. To this reaction mixture was then added diethylamine or piperidine (0.1 mL, excess) dropwise at RT and the mixture was stirred for an hour until Fmoc group was removed, as monitored by LCMS. (Note: Both diethylamine and piperidine were effective.) The reaction mixture was directly purified by prep-HPLC (method B) to give compound LP15 (15 mg, 33% yield) as a white solid. ESI m/z: 1313.6 (M+H)$^+$. $^1$H NMR (500 MHz, methanol$_{d4}$) δ 7.59 (d, J=8.5 Hz, 2H), 7.51 (s, 1H), 7.36-7.26 (m, 3H), 7.01 (d, J=8.5 Hz, 1H), 6.88 (d, J=8.0 Hz, 1H), 6.72-6.71 (m, 1H), 6.57-6.54 (m, 1H), 5.09 (s, 2H), 4.64-4.52 (m, 1H), 4.35-4.28 (m, 2H), 4.21 (d, J=7.0 Hz, 1H), 4.01-3.98 (m, 1H), 3.88-3.84 (m, 3H), 3.43 (t, J=6.5 Hz, 1H), 3.26-3.10 (m, 4H), 3.00-2.76 (m, 3H), 2.38-2.24 (m, 7H), 2.19-2.02 (m, 9H), 1.98-1.78 (m, 4H), 1.74-1.54 (m, 12H), 1.45-1.26 (m, 14H), 1.13 (s, 6H), 1.00 (t, J=7.5 Hz, 6H) ppm.

Example 1i

Synthesis of LP311 (FIG. 1*h*)

tert-Butyl N-[(1S)-1-{[(4bS,8S,8aR)-8-{[(1S,4aS, 10aR)-6-hydroxy-1,4a-dimethyl-1,2,3,4,4a,9,10,10a-octahydrophenanthrene-1-carbonyl]carbamoyl}-4b, 8-dimethyl-4b,5,6,7,8,8a,9,10-octahydrophenanthren-3-yl]carbamoyl}-5-{[(9H-fluoren-9-ylmethoxy)carbonyl]amino}pentyl] Carbamate (LP11-1)

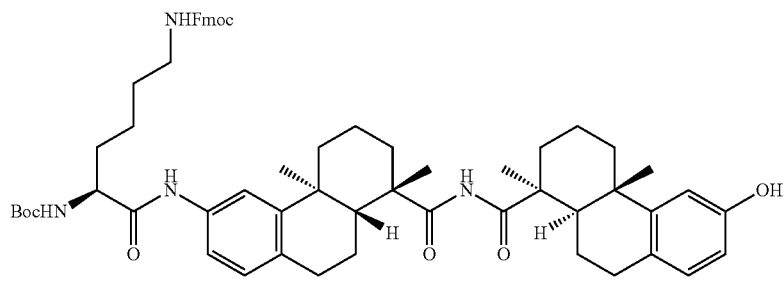

To a solution of N-Boc-N-Fmoc-L-Lysine (0.21 g, 0.45 mmol) in DMF (2 mL) was added HATU (0.24 g, 0.64 mmol) and DIPEA (0.15 g, 1.1 mmol) at RT. The resulting mixture was stirred at RT for 3 minutes. To the mixture was then added payload 9d (0.20 g, 0.38 mmol). The reaction mixture was stirred at RT for 15 minutes until the reaction completed, as monitored by LCMS. The reaction mixture was filtered and purified by prep-HPLC (method B) to give compound LP11-1 (0.10 g, 27% yield) as a white solid. ESI m/z: 979 (M+1)$^+$.

9H-Fluoren-9-ylmethyl N-[(5S)-5-amino-5-{[(4bS, 8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9, 10-octahydrophenanthren-3-yl]carbamoyl}pentyl] carbamate (LP11-2)

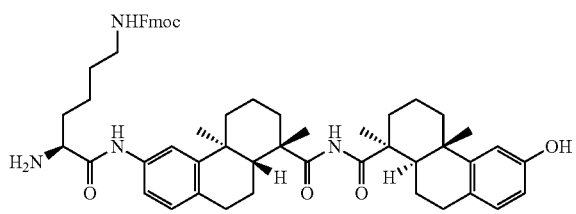

To a solution of compound LP11-1 (0.10 g, 0.10 mmol) in DCM was added TFA (2 mL) at RT. The resulting mixture was stirred at RT for an hour until Boc was totally removed according to LCMS. The volatiles were removed in vacuo. The residue was purified by reversed phase flash chromatography (0-100% acetonitrile in aq. ammonium bicarbonate (10 mM)) to give compound LP11-2 (77 mg, 86% yield) as a white solid. ESI m/z: 879 (M+1)$^+$. $^1$H NMR (400 MHz, DMSO$_{d6}$) δ 9.87-9.52 (m, 1H), 9.00 (s, 1H), 8.11 (s, 1H), 7.92-7.81 (m, 2H), 7.71-7.48 (m, 3H), 7.44-7.22 (m, 6H), 7.00-6.90 (m, 1H), 6.82 (d, J=8.3 Hz, 1H), 6.66-6.60 (m, 1H), 6.54-6.47 (m, 1H), 4.38-4.14 (m, 3H), 3.27-3.17 (m, 1H), 3.01-2.93 (m, 2H), 2.90-2.66 (m, 4H), 2.33-2.06 (m, 7H), 1.94-1.78 (m, 4H), 1.67-1.51 (m, 5H), 1.48-1.07 (m, 16H), 1.03-0.92 (m, 6H) ppm.

{4-[(2S)-2-[(2S)-2-[1-(4-{2-Azatricyclo[10.4.0.0^{4,9}]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}-5-{[(9H-fluoren-9-ylmethoxy)carbonyl]amino}pentyl]carbamate (LP11-3)

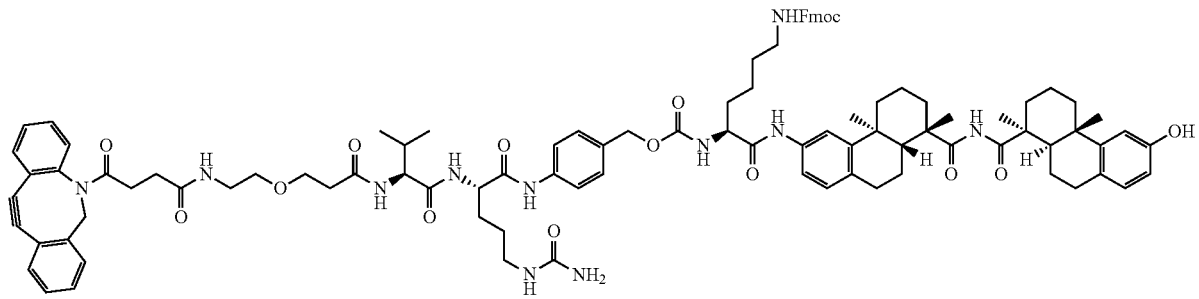

To a mixture of compound LP11-2 (57 mg, 65 μmol) and compound LP9-5 (0.10 g, 96 μmol) in DMF (3 mL) were added HOBt (30 mg, 0.22 mmol) and DIPEA (0.11 g, 0.81 mmol), and the mixture was stirred at RT for an hour, which was monitored by LCMS. The reaction mixture was purified by reversed phase flash chromatography (0-100% acetonitrile in aq. ammonium bicarbonate (10 mM)) to give compound LP11-3 (97 mg, 81% yield) as a white solid. ESI m/z: 909 (M/2+1)$^+$.

{4-[(2S)-2-[(2S)-2-[1-(4-{2-Azatricyclo[10.4.0.0^{4,9}]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-[(1S)-5-amino-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}pentyl]carbamate (LP311)

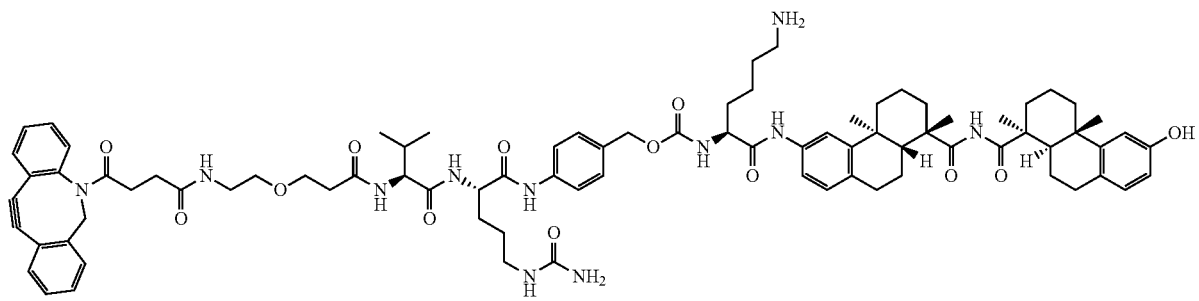 [SMILES: CC(C)[C@H](NC(=O)CCOCCNC(=O)CCC(=O)N1Cc2ccccc2C#Cc2ccccc21)C(=O)N[C@@H](CCCNC(N)=O)C(=O)Nc1ccc(COC(=O)N[C@@H](CCCCN)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of compound LP11-3 (97 mg, 53 μmol) in DMF (3 mL) was added diethylamine (45 mg, 0.62 mmol). The mixture was stirred at RT for 2 hours until Fmoc was totally removed according to LCMS. The reaction mixture was directly purified by prep-HPLC (method B) to give compound LP311 (40 mg, 47% yield) as a white solid. ESI m/z: 798 (M/2+1)$^+$. $^1$H NMR (500 MHz, DMSO$_{d6}$) δ 9.99 (s, 1H), 9.85 (s, 1H), 9.00 (s, 1H), 8.21-8.10 (m, 2H), 7.88 (d, J=8.5 Hz, 1H), 7.82-7.59 (m, 6H), 7.55-7.43 (m, 5H), 7.41-7.29 (m, 5H), 6.98 (d, J=8.2 Hz, 1H), 6.84 (d, J=8.3 Hz, 1H), 6.66 (s, 1H), 6.53 (d, J=8.1 Hz, 1H), 6.06-5.96 (m, 1H), 5.50-5.38 (m, 2H), 5.09-4.92 (m, 3H), 4.45-4.35 (m, 1H), 4.28-4.21 (m, 1H), 4.14-4.04 (m, 1H), 3.67-3.58 (m, 4H), 3.52-3.45 (m, 13H), 3.14-2.69 (m, 9H), 2.63-2.56 (m, 1H), 2.50-2.44 (m, 1H), 2.43-2.37 (m, 1H), 2.33-2.13 (m, 7H), 2.06-1.85 (m, 6H), 1.82-1.56 (m, 9H), 1.51-1.23 (m, 17H), 1.21-1.13 (m, 2H), 1.10-0.80 (m, 12H) ppm.

Example 1j

Synthesis of LP39 (FIG. 1i)

1-(4-{2-Azatricyclo[10.4.0.0⁴,⁹]hexadeca-1(12),4(9),
5,7,13,15-hexaen-10-yn-2-yl}-4-oxobutanamido)-N-
[(1S)-1-{[(1S)-4-(carbamoylamino)-1-{[4-(hy-
droxymethyl)phenyl]carbamoyl}butyl]carbamoyl}-
2-methylpropyl]-3,6,9,12-tetraoxapentadecan-15-
amide (LP9-3)

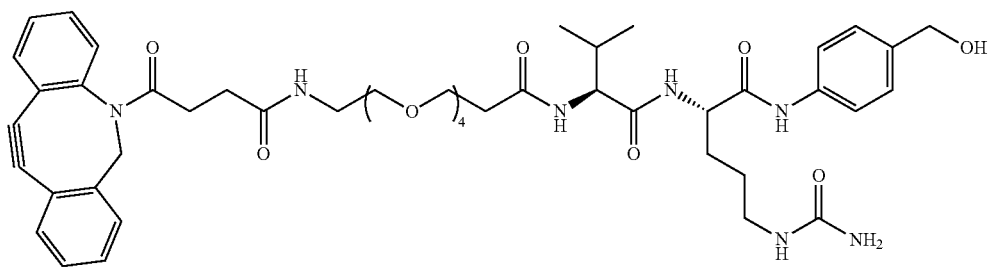

To a solution of compound LP9-2 (0.30 g, 0.54 mmol) in DMF (10 mL) were added HATU (0.31 g, 0.81 mmol) and DIPEA (0.14 g, 1.1 mmol) successively at room temperature. The mixture was stirred at room temperature for 15 minutes. To the reaction solution was added VC-PAB-OH (LP9-1, CAS: 159857-79-1, 0.21 g, 0.54 mmol) at RT, and the resulting mixture was stirred at RT for 3 hours; reaction progress monitored by LCMS. The reaction mixture was filtered through a filtering membrane and the filtrate was directly purified by reversed flash chromatography (0-100% acetonitrile in water (with 10 mmol/L ammonium bicarbonate)) to give compound LP9-2 (0.30 g, 60% yield) as a white solid. ESI m/z: 617 (M+H)⁺.

{4-[(2S)-2-[(2S)-2-[1-(4-{2-Azatricyclo[10.4.0.0⁴,⁹]
hexadeca-1(12),4(9),5,7,13,15-hexaen-10-yn-2-yl}-
4-oxobutanamido)-3,6,9,12-tetraoxapentadecan-15-
amido]-3-methylbutanamido]-5-(carbamoylamino)
pentanamido]phenyl}methyl 4-nitrophenyl
Carbonate (LP9-5)

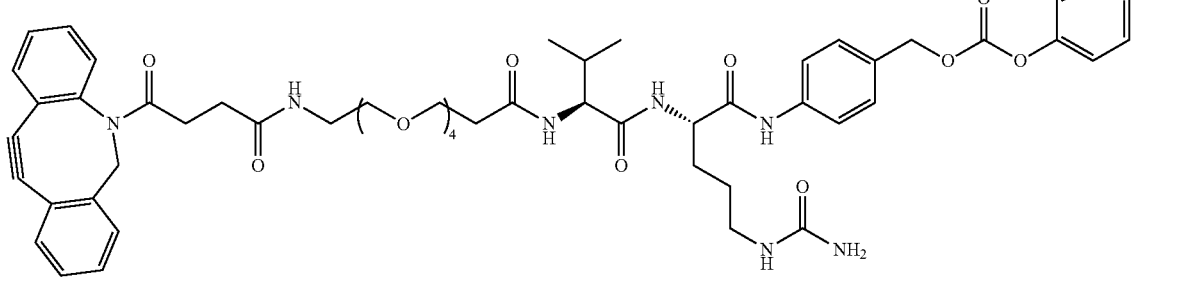

To a solution of compound LP9-3 (0.15 g, 0.16 mmol) in DMF (10 mL) was added bis(4-nitrophenyl) carbonate (LP9-4, 0.15 g, 0.49 mmol) and DIPEA (63 mg, 0.49 mmol) successively at 0° C. The mixture was then stirred at RT for 3 hours until LP9-3 was mostly consumed, as monitored by LCMS. The reaction mixture was filtered through a filtering membrane and the filtrate was directly purified by reversed flash chromatography (0-100% acetonitrile in water (with 10 mmol/L ammonium bicarbonate)) to give compound LP9-5 (50 mg, 28% yield) as a white solid. ESI m/z: 1079 (M+H)⁺.

(4S)-4-{[({4-[(2S)-2-[(2S)-2-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxa-pentadecan-15-amido]-3-methylbutanamido]-5-(carbamoylamino)pentanamido]phenyl}methoxy)carbonyl]amino}-4-{[(4bS,8S,8aR)-8-{[(1S,4aS,10aR)-6-hydroxy-1,4a-dimethyl-1,2,3,4,4a,9,10,10a-octahydrophenanthrene-1-carbonyl] carbamoyl}-4b,8-dimethyl-4b,5,6,7,8,8a,9,10-octahydrophenanthren-3-yl]carbamoyl}butanoic Acid (LP39)

mediates 7b and 7c were prepared from phenol-O-alkylation of 7f with 10b and 10c, respectively. The intermediates 7d and 7e were synthesized starting from conversion of phenol 2 to triflate 11, followed by Buchwald coupling conditions to introduce the masked amino functionality of 12d and 12e; then acidic de-protection of 12d and 12e followed by basic hydrolysis to convert the esters to the acids 13d and 13e, respectively; finally, Boc-protection of 13d and 13e provided 14d and 14e, respectively, which were further carried into the amide coupling reactions with ammonium salt to provide 7d and 7e, respectively. The intermediate 7g was

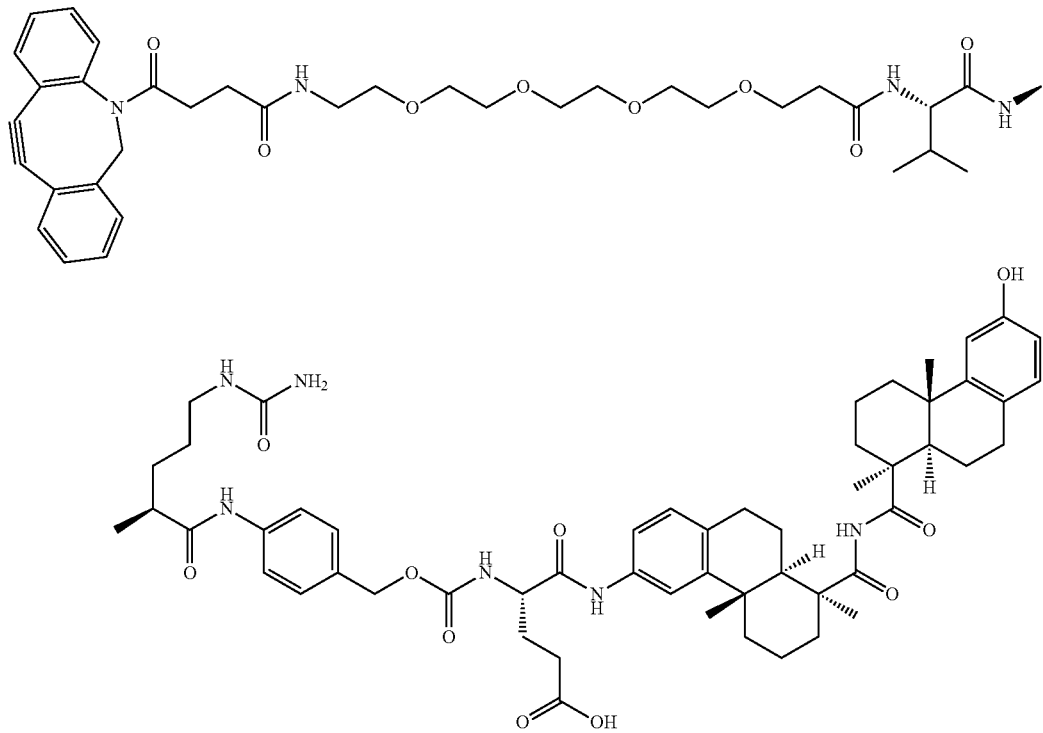

To a mixture of compound 9o (50 mg, 76 µmol) and compound LP9-5 (0.10 g, 96 µmol) in DMF (1 mL) were added HOBt (16 mg, 0.12 mmol) and DIPEA (39 mg, 0.31 mmol), and the mixture was stirred at RT for an hour, which was monitored by LCMS. The reaction mixture was purified by prep-HPLC (method B) to give compound LP39 (40 mg, 33% yield) as a white solid. ESI m/z: 799 (M/2+1)⁺. $^1$H NMR (500 MHz, DMSO$_{d6}$) δ 10.02 (s, 1H), 9.03 (s, 1H), 8.20-8.07 (m, 2H), 7.94-7.87 (m, 1H), 7.82-7.76 (m, 1H), 7.70-7.57 (m, 4H), 7.54-7.42 (m, 4H), 7.40-7.26 (m, 6H), 6.99-6.91 (m, 1H), 6.85-6.79 (m, 1H), 6.63 (s, 1H), 6.53-6.47 (m, 1H), 6.03 (s, 1H), 5.44 (s, 2H), 5.07-4.88 (m, 3H), 4.42-4.32 (m, 1H), 4.27-4.20 (m, 1H), 4.11-4.02 (m, 1H), 3.63-3.55 (m, 3H), 3.51-3.41 (m, 13H), 3.11-2.58 (m, 10H), 2.40-2.10 (m, 11H), 2.00-1.55 (m, 15H), 1.46-1.09 (m, 14H), 1.05-0.94 (m, 6H), 0.99-0.77 (m, 7H) ppm.

Example 2

This example demonstrates general methods for making the key intermediates, 7b-7f. The chemical syntheses for making 7b-7e were shown in FIG. 2.

The amide 7f was prepared from an amide coupling reaction of 1 with NH₄Cl catalyzed by HATU. The interprepared from an amide coupling reaction of 1 with 2,4-dimethoxybenzylamine to form 7g-1, followed by conversion to the triflate analog 7g-2 with triflic anhydride. The cyano analog 7g-3 was prepared using zinc cyanide, and a final deprotection was achieved with TFA to remove 2,4-dimethoxy-benzyl moiety.

Alternatively, 13d was prepared starting from Boc-protection of podocarpic acid 1 to form E2, followed by conversion to triflate E3. Intermediate E3 was stable to purification via normal-phase column chromatography, and was further treated with diphenylmethanimine under Buchwald conditions to afford a mixture of E4-1, E4-2, E4-3, and 13d, which were hydrolyzed in aq. HCl in THF (v/v=1:1) in one pot to provide 13d in 28% total yield.

Example 3

This example demonstrates a method for making the intermediate 7a. This example refers to the compound numbering in FIG. 1.

Step 1: making (1S,4aS,10aR)-Methyl-6-hydroxy-1,4a-dimethyl-1,2,3,4,4a,9,10,10a-octahydrophenanthrene-1-carboxylate (2)

To a solution of podocarpic acid (1, 0.20 g, 0.73 mmol) in methanol (1.4 mL) and toluene (5.2 mL) was added (trimethylsilyl)diazomethane (2M in hexane, 0.45 mL). The reaction mixture was stirred at 10-25° C. overnight. After podocarpic acid was totally consumed based on LC-MS, the volatiles were removed in vacuo, and the residue was purified by flash chromatography (0-35% ethyl acetate in petroleum ether) to provide compound 2 (0.21 g, 98% yield) as a white solid. ESI m/z: 289 (M+H)$^+$. $^1$H NMR (400 MHz, DMSO-$_{d6}$) δ 8.95 (s, 1H), 6.79 (d, J=8.2 Hz, 1H), 6.63 (d, J=2.4 Hz, 1H), 6.48 (dd, J=8.2, 2.4 Hz, 1H), 3.58 (s, 3H), 2.80-2.55 (m, 2H), 2.20-2.02 (m, 3H), 1.96-1.71 (m, 2H), 1.56-1.45 (m, 2H), 1.27 (t, J=13.5 Hz, 1H), 1.21 (s, 3H), 1.09 (td, J=13.5, 4.1 Hz, 1H), 0.91 (s, 3H) ppm.

Step 2: making (1S,4aS,10aR)-Methyl 6-(benzyloxy)-1,4a-dimethyl-1,2,3,4,4a,9,10,10a-octahydrophenanthrene-1-carboxylate (3)

To a solution of compound 2 (0.10 g, 0.35 mmol) in DMF (1.2 mL) was added cesium carbonate (0.12 g, 0.38 mmol) and the mixture was stirred at 20-25° C. for 15 min. To the mixture was then added benzyl bromide (88 mg, 0.52 mmol) at rt, and the resulting mixture was stirred for an additional 4 hours, then poured into water and extracted with ethyl acetate. The combined organics were washed with water and brine, dried over sodium sulfate, and concentrated in vacuo. The crude product was purified by flash chromatography (10-35% ethyl acetate in petroleum ether) to give compound 3 (0.13 g, 99% yield) as a white solid. ESI m/z: 379 (M+H)$^+$. $^1$H NMR (500 MHz, methanol$_{d4}$) δ 7.60-7.20 (m, 5H), 7.00-6.82 (m, 2H), 6.73 (d, J=7.1 Hz, 1H), 5.03 (s, 2H), 3.66 (s, 3H), 2.95-2.58 (m, 2H), 2.36-2.10 (m, 3H), 2.10-1.85 (m, 2H), 1.70-1.48 (m, 2H), 1.44-1.21 (m, 4H), 1.15 (t, J=17.2 Hz, 1H), 1.01 (s, 3H) ppm.

Step 3: making (1S,4aS,10aR)-6-(Benzyloxy)-1,4a-dimethyl-1,2,3,4,4a,9,10,10a-octahydrophenanthrene-1-carboxylic Acid (4)

To a mixture of compound 3 (0.10 g, 0.26 mmol) in DMSO (1.7 mL) was added potassium tert-butoxide (0.30 g, 2.6 mmol), and the mixture was stirred at 100° C. for 2 hours until the reaction was completed, as monitored by LC-MS and TLC. After the reaction was cooled to 25° C., the mixture was quenched with aqueous hydrochloride (1N) to pH 2, and extracted with ethyl acetate. The combined organics were washed with brine, dried over sodium sulfate, and concentrated in vacuo. The residue was purified by flash chromatography (20-35% ethyl acetate in petroleum ether) to provide compound 4 (92 mg, 95% yield) as a white solid. ESI m/z: 365 (M+H)$^+$. $^1$H NMR (500 MHz, methanol$_{d4}$) δ 7.42 (d, J=7.4 Hz, 2H), 7.36 (t, J=7.5 Hz, 2H), 7.30 (t, J=7.3 Hz, 1H), 6.92 (d, J=8.4 Hz, 1H), 6.87 (d, J=2.5 Hz, 1H), 6.72 (dd, J=8.4, 2.5 Hz, 1H), 5.02 (s, 2H), 2.82 (dd, J=16.3, 4.4 Hz, 1H), 2.77-2.65 (m, 1H), 2.24 (d, J=13.2 Hz, 2H), 2.19 (dd, J=13.8, 6.0 Hz, 1H), 2.11-1.96 (m, 2H), 1.64-1.56 (m, 1H), 1.53 (d, J=11.0 Hz, 1H), 1.35 (td, J=13.3, 3.7 Hz, 1H), 1.30 (s, 3H), 1.13 (s, 3H), 1.11-1.05 (m, 1H) ppm.

Step 4: making (1S,4aS,10aR)-6-(Benzyloxy)-1,4a-dimethyl-1,2,3,4,4a,9,10,10a-octahydrophenanthrene-1-carbonyl chloride (6a)

To a solution of compound 4 (0.10 g, 0.27 mmol) in 1,2-dichloroethane (DCE) (2 mL) was added thionyl chloride (0.20 mL), and the reaction was then stirred at 90° C. for 3 h. After the reaction was cooled to rt, the volatiles were removed in vacuo and the crude product was used for the next step without further purification.

Alternative Step 4: making (1S,4aS,10aR)-Perfluorophenyl-6-(benzyloxy)-1,4a-dimethyl-1,2,3,4,4a,9,10,10a-octahydrophenanthrene-1-carboxylate (6b)

To a solution of 4 (0.50 g, 1.4 mmol) in DMF (5 mL) was added DIPEA (0.51 g, 4.1 mmol), and then perfluorophenyl 2,2,2-trifluoroacetate 5 (0.77 g, 2.7 mmol). This mixture was stirred at 25° C. overnight, and was then diluted with ether (80 mL). The organic mixture was washed with water (10 mL) and brine (10 mL), dried over sodium sulfate, and concentrated in vacuo. The residue was purified by flash chromatography (0-15% ethyl acetate in petroleum ether) to give ester 6b (0.46 g, 63% yield) as a white solid. $^1$H NMR (500 MHz, acetone$_{d6}$) δ 7.33 (d, J=7.4 Hz, 2H), 7.24 (t, J=7.5 Hz, 2H), 7.17 (t, J=7.3 Hz, 1H), 6.86-6.80 (m, 2H), 6.63 (dd, J=8.4, 2.5 Hz, 1H), 4.95 (s, 2H), 2.78-2.57 (m, 3H), 2.28-2.19 (m, 2H), 2.14 (dd, J=13.5, 5.9 Hz, 1H), 2.02-1.81 (m, 1H), 1.63 (d, J=11.5 Hz, 1H), 1.60-1.52 (m, 1H), 1.40 (s, 3H), 1.29 (td, J=13.4, 3.8 Hz, 1H), 1.22 (td, J=13.8, 4.1 Hz, 1H), 1.05 (s, 3H) ppm.

Step 5: making (1S,4aS,10aR)-6-(Benzyloxy)-1,4a-dimethyl-1,2,3,4,4a,9,10,10a-octahydrophenanthrene-1-carboxamide (7a)

A solution of compound 4 (50 mg, 0.14 mmol) and HATU (57 mg, 0.15 mmol) in DMF was stirred at 25° C. for 15 min. To the solution were added DIPEA (89 mg, 0.69 mmol) and ammonium chloride (25 mg, 0.48 mmol) at 25° C., and the resulting mixture was then stirred for additional 4 h, poured into water, and extracted with ethyl acetate. The combined organics were washed with water and brine, dried over sodium sulfate, and concentrated in vacuo. The crude product was purified by flash chromatography (0-35% ethyl acetate in petroleum ether) to give 7a (48 mg, 91% yield) as a white solid. ESI m/z: 364 (M+1)$^+$. $^1$H NMR (500 MHz, methanol$_{d4}$) δ 7.63-7.22 (m, 5H), 7.02-6.82 (m, 2H), 6.78 (d, J=7.1 Hz, 1H), 5.10 (s, 2H), 2.95-2.58 (m, 2H), 2.36-2.10 (m, 3H), 2.10-1.85 (m, 2H), 1.70-1.48 (m, 2H), 1.44-1.21 (m, 4H), 1.15 (t, J=17.2 Hz, 1H), 1.01 (s, 3H) ppm.

Example 4

This example demonstrates methods for making the intermediates 7b-7g. This example refers to the compound numbering in FIG. 2.

(1S,4aS,10aR)-6-Hydroxy-1,4a-dimethyl-1,2,3,4,4a,9,10,10a-octahydrophenanthrene-1-carboxamide (7f)

To a solution of podocarpic acid 1 (0.30 g, 1.1 mmol) in DMF (4 mL) were added HATU (0.46 g, 1.2 mmol), DIPEA (0.57 g, 4.4 mmol) and ammonium chloride (0.23 g, 4.4 mmol), and the solution was stirred at 10-25° C. for 16 h. The mixture was poured into water, and extracted with ethyl acetate. The combined organics were washed with brine, dried over sodium sulfate, and concentrated in vacuo. The residue was purified by flash chromatography (0-35% ethyl acetate in petroleum ether) to give the desired compound (0.77 g, 100% yield) as an oil. ESI m/z: 274.1 (M+1)$^+$. $^1$H NMR (500 MHz, methanol$_{d4}$) δ 6.82 (d, J=8.3 Hz, 1H), 6.71 (d, J=2.4 Hz, 1H), 6.58-6.47 (m, 1H), 2.79 (dd, J=16.1, 4.1

Hz, 1H), 2.71-2.60 (m, 1H), 2.29-2.13 (m, 3H), 2.13-1.95 (m, 2H), 1.67-1.56 (m, 1H), 1.48 (d, J=11.6 Hz, 1H), 1.36 (td, J=13.2, 4.0 Hz, 1H), 1.27 (s, 3H), 1.19 (dt, J=8.9, 4.5 Hz, 1H), 1.16 (s, 3H) ppm.

(1S,4aS,10aR)-6-(2-(tert-Butyldimethylsilyloxy) ethoxy)-1,4a-dimethyl-1,2,3,4,4a,9,10,10a-octahydrophenanthrene-1-carboxamide (7b)

To a solution of 7f (0.33 g, 0.47 mmol) in DMF (2.5 mL) was added cesium carbonate (0.60 g, 1.8 mmol) and (2-bromoethoxy)(tert-butyl)dimethylsilane (10b, 0.45 g, 2.1 mmol). After the reaction was stirred for 8 h under nitrogen, the mixture was poured into water (30 mL) and ethyl acetate (30 mL). The organics were separated and washed with brine, dried with anhydrous sodium sulfate, and concentrated in vacuo. The residue was purified by silica gel column chromatography (20-35% ethyl acetate in petroleum ether) to give compound 7b (0.21 g, 87% yield). ESI m/z: 432.2 (M+1)$^+$. $^1$H NMR (500 MHz, methanol$_{d4}$) δ 6.79 (d, J=8.4 Hz, 1H), 6.69 (d, J=2.2 Hz, 1H), 6.53 (dd, J=8.3, 1.5 Hz, 1H), 3.84 (dd, J=14.3, 4.1 Hz, 4H), 2.71 (dd, J=16.1, 4.6 Hz, 1H), 2.64-2.47 (m, 1H), 2.20-2.02 (m, 3H), 2.01-1.84 (m, 2H), 1.52 (d, J=14.0 Hz, 1H), 1.37 (d, J=12.2 Hz, 1H), 1.25 (td, J=13.2, 3.3 Hz, 1H), 1.16 (s, 3H), 1.12-0.99 (m, 4H), 0.81 (s, 9H), 0.00 (s, 6H) ppm.

tert-Butyl 2-((4bS,8S,8aR)-8-carbamoyl-4b,8-dimethyl-4b,5,6,7,8,8a,9,10-octahydrophenanthren-3-yloxy)ethylcarbamate (7c)

Following the procedure for making 7b, 7c (60 mg, 40% yield) as a white solid was obtained from 7f treated with 10c. ESI m/z: 360.9 (M−55)$^+$, 438.9 (M+23)$^+$.

tert-Butyl-(4bS,8S,8aR)-8-carbamoyl-4b,8-dimethyl-4b,5,6,7,8,8a,9,10-octahydrophenanthren-3-ylcarbamate (7d)

Step 1: making (1S,4aS,10aR)-Methyl-1,4a-dimethyl-6-(trifluoromethylsulfonyloxy)-1,2,3,4,4a,9,10,10a-octahydrophenanthrene-1-carboxylate (11)

To a solution of compound 2 (0.33 g, 1.1 mmol) in DCM (6 mL) were added 2,6-lutidine (0.15 g, 1.4 mmol) and DMAP (28 mg, 0.23 mmol). The mixture was cooled to −78° C. and triflic anhydride (0.39 g, 1.4 mmol) was added. The resulting mixture was allowed to warm to 25° C. and stirred at 25° C. for an additional 4 h. The reaction mixture was diluted with ethyl acetate (50 mL), and the organics were washed with water (6 mL), aq. hydrochloride (1 N, 10 mL) and brine (10 mL), then dried over sodium sulfate, and concentrated in vacuo. The residue was purified by flash chromatography (0-10% ethyl acetate in petroleum ether) to give compound 11 (0.43 g, 89% yield) as a viscous oil. ESI m/z: 421.2 (M+1)$^+$. $^1$H NMR (400 MHz, CDCl$_3$) δ 7.12 (d, J=2.5 Hz, 1H), 7.10 (d, J=8.5 Hz, 1H), 6.97 (dd, J=8.5, 2.5 Hz, 1H), 3.67 (s, J=3.4 Hz, 3H), 2.93 (dd, J=17.2, 4.4 Hz, 1H), 2.85-2.71 (m, 1H), 2.29 (d, J=13.5 Hz, 1H), 2.25-2.14 (m, 2H), 2.03-1.89 (m, 2H), 1.71-1.61 (m, 1H), 1.56-1.48 (m, 1H), 1.40 (td, J=13.4, 4.2 Hz, 1H), 1.30-1.22 (m, 3H), 1.09 (td, J=13.6, 4.2 Hz, 1H), 1.02 (s, 3H) ppm.

Step 2: making (1S,4aS,10aR)-6-amino-1,4a-dimethyl-1,2,3,4,4a,9,10,10a-octahydrophenanthrene-1-carboxylic Acid (13d)

To a mixture of cesium carbonate (0.62 g, 1.9 mmol), X-phos (50 mg, 0.11 mmol) and Pd$_2$(dba)$_3$ (50 mg, 55 μmol) in tert-butanol (5 mL) under an atmosphere of argon were added a solution of compound 11 (0.40 g, 0.95 mmol) in tert-butanol (5 mL) and then diphenylmethanimine (0.26 g, 1.4 mmol). After the reaction was stirred at 100° C. for 30 min under argon, the reaction mixture was cooled to rt, diluted with DCM, and filtered through Celite to remove insoluble residues. The filtrate was washed with water, dried over anhydrous sodium sulfate, and concentrated in vacuo. To the residue (crude 12d) was added hydrochloride in methanol (4N, 2 mL) and the resulting solution was stirred at 25° C. for 5 h. The volatiles were removed in vacuo and the residue was purified by flash chromatography (0-20% ethyl acetate in petroleum ether) to give 12d'-methyl ester (0.28 g) as a white solid aniline-ester. ESI m/z: 288 (M+1)$^+$, $^1$H NMR (400 MHz, DMSO-$_{d6}$) δ 9.72 (s, 2H), 7.22 (s, 1H), 7.11 (d, J=8.1 Hz, 1H), 7.01 (d, J=8.1 Hz, 1H), 3.58 (s, 3H), 2.86 (dd, J=17.0, 4.5 Hz, 1H), 2.79-2.66 (m, 1H), 2.21-2.05 (m, 3H), 1.97-1.76 (m, 2H), 1.55 (t, J=13.7 Hz, 2H), 1.30 (td, J=13.2, 3.7 Hz, 1H), 1.22 (s, 3H), 1.10 (td, J=13.4, 4.0 Hz, 1H), 0.93 (s, 3H) ppm. To a mixture of 12d'-methyl ester (0.12 g, 0.42 mmol) in DMF (3 mL) was added with sodium ethanethiolate (0.37 g, 4.2 mmol), and the resulting mixture was stirred at 60° C. for 16 h. After the reaction was cooled to rt, the resulting mixture was diluted with water and acidified with aq. hydrochloride (1 N, 20 mL). The aqueous solution was extracted with ethyl acetate and the organics were separated and concentrated in vacuo to give crude 13d (0.14 g), which was used in the next step directly. ESI m/z: 274.2 (M+1)$^+$.

An alternative way to prepare 13d via E2, E3, and E4 is described as follows:

Step 1: making (tert-Butyl carbonic) (1S,4aS, 10aR)-6-hydroxy-1,4a-dimethyl-1,2,3,4,4a,9,10,10a-octahydrophenanthrene-1-carboxylic Anhydride (E2)

To a mixture of podocarpic acid (1, 0.40 g, 1.5 mmol) and sodium carbonate (0.31 g, 2.9 mmol) in t-BuOH (10 mL) was added di-tert-butyl dicarbonate (0.35 g, 1.6 mmol). The reaction mixture was stirred at 10-25° C. for 16 h. The reaction was monitored by TLC and LCMS until the podocarpic acid was consumed. The resulting mixture was poured into ethyl acetate (100 mL) and the organics were washed with water (20 mL×2) and brine (50 mL). The organic solution was dried over sodium sulfate and concentrated in vacuo. The crude product was purified by flash chromatography (0-20% ethyl acetate in petroleum ether) to give the title compound E2 (0.41 g, 76% yield) as a viscous oil. ESI m/z: 319.2 (M−55)$^+$. $^1$H NMR (400 MHz, DMSO-$_{d6}$) δ 8.95 (s, 1H), 6.79 (d, J=8.0 Hz, 1H), 6.64 (d, J=2.5 Hz, 1H), 6.49 (dd, J=8.0, 2.5 Hz, 1H), 2.76-2.72 (m, 1H), 2.67-2.60 (m, 1H), 2.16-2.03 (m, 3H), 1.85-1.78 (m, 2H), 1.60-1.57 (m, 2H), 1.46 (s, 9H), 1.33-1.27 (m, 4H), 1.21-1.15 (m, 1H), 1.04 (s, 3H) ppm.

Step 2: making (tert-Butyl carbonic) (1S,4aS, 10aR)-1,4a-dimethyl-6-(trifluoromethylsulfonyloxy)-1,2,3,4,4a,9,10,10a-octahydrophenanthrene-1-carboxylic Anhydride (E3)

To a solution of compound E2 (0.30 g, 0.80 mmol) in DCM (16 mL) were added pyridine (95 mg, 1.2 mmol) and DMAP (10 mg, 0.080 mmol) under nitrogen atmosphere. The mixture was cooled to −20° C. and triflic anhydride (0.27 g, 0.96 mmol) was added by syringe. The resulting mixture was allowed to warm to 25° C. and stirred at 25° C.

for additional 2 h. The reaction mixture was diluted with ethyl acetate (50 mL), and the organics were washed with water (6 mL), aq. hydrochloride (1 N, 10 mL), and brine (10 mL), then dried over sodium sulfate and concentrated in vacuo. The residue was purified by flash chromatography (0-10% ethyl acetate in petroleum ether) to give compound E3 (0.27 g, 66% yield) as a viscous oil. ESI m/z: 529.2 (M+Na)$^+$. $^1$H NMR (400 MHz, DMSO-$d_6$) δ 7.37 (d, J=2.0 Hz, 1H), 7.23-7.17 (m, 2H), 2.95-2.90 (m, 1H), 2.82-2.75 (m, 1H), 2.30-2.28 (m, 1H), 2.12-2.09 (m, 1H), 1.90-1.80 (m, 2H), 1.68-1.66 (m, 1H), 1.62-1.59 (m, 1H), 1.46 (s, 9H), 1.33-1.27 (m, 4H), 1.26-1.17 (m, 1H), 1.08 (s, 3H) ppm.

Step 3: making (1S,4aS,10aR)-6-Amino-1,4a-dimethyl-1,2,3,4,4a,9,10,10a-octahydrophenanthrene-1-carboxylic Acid (13d)

To a stirred solution of compound E3 (0.20 g, 0.40 mmol) and diphenylmethanimine (0.086 g, 0.48 mmol) in tert-butanol (10 mL) were added cesium carbonate (0.33 g, 1.0 mmol), X-phos (38 mg, 80 μmol) and Pd$_2$(dba)$_3$ (37 mg, 40 μmol) under an atmosphere of argon. The reaction mixture was stirred under argon at 90° C. for 3 h, monitored by LCMS, and E4-1, E4-2, E4-3, and 13d were detected in the LCMS spectra at that time. The reaction mixture was cooled, diluted with DCM (30 ml) and filtered through Celite to remove inorganics. The filtrate was washed with water, dried over anhydrous sodium sulfate and concentrated in vacuo. The residue was dissolved in THF (5 mL) and acidified with aq. HCl (2 N, 5 mL). The reaction was then stirred at 25° C. and monitored by LCMS. After 16 h, LCMS showed most of E4-1 and E4-2 were converted to 13d. The reaction mixture was neutralized with saturated aq. sodium bicarbonate to pH 8 and extracted with ethyl acetate (20 mL×3). The combined organics were dried over sodium sulfate and concentrated in vacuo. The crude product was purified by flash chromatography (0-50% ethyl acetate in petroleum ether) to give the title compound 13d (30 mg, 56% yield for 2 steps) as a white solid. ESI m/z: 274.2 (M+H)$^+$.

Step 4: making (1S,4aS,10aR)-6-(tert-Butoxycarbonylamino)-1,4a-dimethyl-1,2,3,4,4a,9,10,10a-octahydrophenanthrene-1-carboxylic Acid (14d)

To a solution of 13d (0.12 g) in tert-butanol (5 mL) were added sodium carbonate (0.12 g, 1.1 mmol), di-tert-butyl dicarbonate (0.48 g, 2.2 mmol), and DMAP (20 mg, 0.16 mmol), and the mixture was then stirred at 60° C. for 16 h. The volatiles were removed in vacuo and the residue was diluted with DCM (20 mL). The organics were separated, washed with saturated aqueous citric acid, dried over sodium sulfate, and concentrated in vacuo. The residue was purified by flash chromatography (0-35% ethyl acetate in petroleum ether) to give compound 14d (0.11 g, 67% yield in 3 steps from 11) as a white solid. ESI m/z: 318.2 (M−tBu+1)$^+$. $^1$H NMR (500 MHz, DMSO-$d_6$) δ 12.08 (s, 1H), 9.08 (s, 1H), 7.40 (s, 1H), 7.11 (s, 1H), 6.87 (d, J=8.3 Hz, 1H), 2.79-2.68 (m, 1H), 2.65 (d, J=12.6 Hz, 1H), 2.17-2.03 (m, 4H), 1.94-1.76 (m, 2H), 1.53 (d, J=13.7 Hz, 1H), 1.46 (d, J=7.4 Hz, 9H), 1.29-1.14 (m, 5H), 1.04 (s, 3H) ppm.

Step 5: making tert-Butyl-(4bS,8S,8aR)-8-carbamoyl-4b,8-dimethyl-4b,5,6,7,8,8a,9,10-octahydrophenanthren-3-ylcarbamate (7d)

To a solution of 14d (0.11 g, 0.30 mmol) in DMF (2.4 mL) were added HATU (0.12 g, 0.32 mmol) and DIPEA (0.5 mL, 3.0 mmol), and the mixture was stirred at 25° C. for an hour. To the mixture was then added ammonium chloride (0.40 g, 7.5 mmol), and the mixture was stirred at 15-25° C. for additional 16 h. The resulting mixture was diluted with ethyl acetate (40 mL); the organics were separated and washed with water (10 mL) and brine (10 mL), dried over sodium sulfate, and concentrated in vacuo. The residue was purified by flash chromatography (0-20% ethyl acetate in petroleum ether) to give compound 7d (84 mg, 75% yield) as a white solid. ESI m/z: 373.3 (M+1)$^+$. $^1$H NMR (500 MHz, methanol-$d_4$) δ 7.20 (s, 1H), 6.97 (d, J=7.7 Hz, 1H), 6.80 (d, J=8.3 Hz, 1H), 2.77-2.68 (m, 2H), 2.66-2.55 (m, 1H), 2.20 (d, J=12.9 Hz, 1H), 2.13 (dd, J=13.2, 5.3 Hz, 1H), 2.08 (d, J=14.0 Hz, 1H), 2.03-1.86 (m, 2H), 1.54 (d, J=11.1 Hz, 1H), 1.40 (s, 9H), 1.26 (t, J=26.7 Hz, 1H), 1.18 (s, 3H), 1.14-1.03 (m, 4H) ppm.

tert-Butyl-4-((4bS,8S,8aR)-8-carbamoyl-4b,8-dimethyl-4b,5,6,7,8,8a,9,10-octahydrophenanthren-3-yl)piperazine-1-carboxylate (7e)

Step 1: making (1S,4aS,10aR)-1,4a-Dimethyl-6-(piperazin-1-yl)-1,2,3,4,4a,9,10,10a-octahydrophenanthrene-1-carboxylic Acid (14e)

To a solution of compound 11 (0.40 g, 0.95 mmol) and tert-butyl piperazine-1-carboxylate (0.29 g, 1.5 mmol) in tert-butanol (5 mL) under atmosphere of argon were added cesium carbonate (0.62 g, 1.9 mmol), X-phos (50 mg, 0.11 mmol) and Pd$_2$(dba)$_3$ (50 mg, 55 μmol). After the reaction was stirred at 100° C. for 30 min under argon, the reaction mixture was cooled, diluted with DCM and filtered through Celite to remove inorganics. The filtrate was washed with water, dried over anhydrous sodium sulfate and concentrated in vacuo. The residue was purified by silica gel column chromatography (20-35% ethyl acetate in petroleum ether) to give 12e (0.42 g) as a yellow solid. ESI m/z: 457.1 (M+1)$^+$. A solution of 12e (0.23 g, 0.5 mmol) in DMSO (5 mL) was treated with potassium tert-butoxide (0.25 g, 2.2 mmol) at 100° C. for an hour. After the reaction was cooled to rt, to the mixture of the crude 13e was added di-tertbutyl dicarbonate (0.92 g, 4.3 mmol) at 20-25° C., and the resulting mixture was stirred at 25° C. for 4 hours. The reaction mixture was then diluted with ethyl acetate (100 mL), the organics were washed with water, dried over sodium sulfate, and concentrated in vacuo. The residue was purified by silica gel column chromatography (0-35% ethyl acetate in petroleum ether) to give compound 14e (0.15 g, 79% yield in 3 steps from 11) as a yellow solid. ESI m/z: 443 (M+1)$^+$.

Step 2: making tert-Butyl-4-((4bS,8S,8aR)-8-carbamoyl-4b,8-dimethyl-4b,5,6,7,8,8a,9,10-octahydrophenanthren-3-yl)piperazine-1-carboxylate (7e)

To a solution of 14e (0.10 g, 0.30 mmol) and HATU (0.12 g, 0.32 mmol) in DMF (2.4 mL) was added DIPEA (0.5 mL, 3.0 mmol), and the resulting solution was stirred at 25° C. for an hour. To the mixture was then added ammonium chloride (0.40 g, 7.5 mmol), and the resulting mixture was stirred at 15-25° C. for additional 16 h. The resulting mixture was diluted with ethyl acetate (40 mL), and the organics were washed with water (10 mL) and brine (10 mL), dried over sodium sulfate, and concentrated in vacuo. The residue was purified by flash chromatography (0-20% ethyl acetate in petroleum ether) to give compound 7e (96 mg, 87% yield) as a white solid. ESI m/z: 442 (M+1)+.

(1S,4aS,10aR)-6-Hydroxy-1,4a-dimethyl-1,2,3,4,4a,9,10,10a-octahydrophenanthrene-1-carboxamide (7g)

Step 1: making (1S,4aS,10aR)—N-(2,4-Dimethoxybenzyl)-6-hydroxy-1,4a-dimethyl-1,2,3,4,4a,9,10,10a-octahydrophenanthrene-1-carboxamide (7g-1)

Following the procedure for making 7f, the coupling reaction of compound 1 with 2,4-dimethoxybenzylamine provided 7g-1 (0.57 g, 93% yield) as a light yellow solid. ESI m/z: 424.1 (M+1)+. $^1$H NMR (500 MHz, DMSO-$_{d6}$) δ 8.90 (s, 1H), 7.33 (t, J=5.7 Hz, 1H), 7.06 (d, J=8.3 Hz, 1H), 6.77 (d, J=8.2 Hz, 1H), 6.60 (d, J=2.4 Hz, 1H), 6.51 (d, J=2.3 Hz, 1H), 6.48-6.42 (m, 2H), 4.28-4.02 (m, 2H), 3.77 (s, 3H), 3.72 (s, 3H), 2.74-2.67 (m, 1H), 2.62-2.53 (m, 1H), 2.24-2.05 (m, 3H), 2.02-1.90 (m, 1H), 1.90-1.78 (m, 1H), 1.56-1.45 (m, 1H), 1.42-1.22 (m, 2H), 1.19 (s, 3H), 1.09-1.01 (m, 1H), 0.87 (s, 3H) ppm.

Step 2: making (4bS,8S,8aR)-8-(2,4-Dimethoxybenzylcarbamoyl)-4b,8-dimethyl-4b,5,6,7,8,8a,9,10-octahydrophenanthren-3-yl trifluoromethanesulfonate (7g-2)

Following the procedure of for making 11, 7g-2 was obtained (0.59 g, 96% yield) as a white solid. ESI m/z: 556.2 (M+1)+. $^1$H NMR (500 MHz, DMSO-$_{d6}$) δ 7.43 (t, J=5.7 Hz, 1H), 7.31 (d, J=2.3 Hz, 1H), 7.22-7.11 (m, 2H), 7.06 (d, J=8.3 Hz, 1H), 6.52 (d, J=2.3 Hz, 1H), 6.45 (dd, J=8.3, 2.3 Hz, 1H), 4.17 (d, J=5.7 Hz, 2H), 3.77 (s, 3H), 3.72 (s, 3H), 2.92-2.82 (m, 1H), 2.78-2.65 (m, 1H), 2.27-2.15 (m, 3H), 2.03-1.86 (m, 2H), 1.57-1.48 (m, 1H), 1.42-1.17 (m, 5H), 1.10-1.05 (m, 1H), 0.91 (s, J=5.9 Hz, 3H) ppm.

Step 3: making (1S,4aS,10aR)-6-Cyano-N-(2,4-dimethoxybenzyl)-1,4a-dimethyl-1,2,3,4,4a,9,10,10a-octahydrophenanthrene-1-carboxamide (7g-3)

To a solution of compound 7g-2 (0.20 g, 0.36 mmol) in DMF (3.6 mL) were added tetrakis(triphenylphosphine)palladium (42 mg, 36 µmol) and zinc cyanide (84 mg, 0.72 mmol) under nitrogen. The mixture was stirred under nitrogen at 110° C. for 4 h until the reaction was completed, monitored by LCMS. After the reaction was cooled to rt, the reaction mixture was diluted with ethyl acetate (100 mL) and the organics were washed with water (20 mL) and brine (20 mL). The organics were dried over sodium sulfate and concentrated in vacuo. The residue was purified by flash chromatography (10-20% ethyl acetate in petroleum ether) to give the title compound 7g-3 (0.13 g, 82% yield) as a white solid. ESI m/z: 433.2 (M+1)+. $^1$H NMR (500 MHz, DMSO-$_{d6}$) δ 7.74 (d, J=1.1 Hz, 1H), 7.47 (dd, J=7.9, 1.4 Hz, 1H), 7.44 (t, J=5.7 Hz, 1H), 7.20 (d, J=8.0 Hz, 1H), 7.06 (d, J=8.3 Hz, 1H), 6.51 (d, J=2.3 Hz, 1H), 6.45 (dd, J=8.3, 2.3 Hz, 1H), 4.16 (d, J=5.6 Hz, 2H), 3.77 (s, 3H), 3.72 (s, 3H), 3.05-2.87 (m, 1H), 2.82-2.70 (m, 1H), 2.36-2.28 (m, 1H), 2.26-2.16 (m, 2H), 2.01-1.85 (m, 2H), 1.58-1.48 (m, 1H), 1.45-1.17 (m, 5H), 1.13-1.05 (m, 1H), 0.91 (s, 3H) ppm.

Step 4: making (1S,4aS,10aR)-6-Cyano-1,4a-dimethyl-1,2,3,4,4a,9,10,10a-octahydrophenanthrene-1-carboxamide (7g)

To a solution of compound 7g-3 (0.12 g, 0.28 mmol) in DCM (3 mL) was added TFA (3 mL) dropwise at 0° C. The resulting mixture was allowed to warm and then stirred at 25° C. for 48 h. The desired mass was detected by LCMS as major peak. The volatiles were removed in vacuo and the residue was purified by flash chromatography (20-40% ethyl acetate in petroleum ether) to give the title compound 7g (70 mg, 71% yield) as a white solid. ESI m/z: 283.2 (M+1)+. $^1$H NMR (500 MHz, DMSO-$_{d6}$) δ 7.76 (d, J=1.3 Hz, 1H), 7.48 (dd, J=7.9, 1.5 Hz, 1H), 7.21 (d, J=8.0 Hz, 1H), 6.84 (d, J=11.8 Hz, 2H), 3.00-2.85 (m, 1H), 2.84-2.69 (m, 1H), 2.41-2.27 (m, 1H), 2.22-2.15 (m, 1H), 2.15-2.09 (m, 1H), 2.04-1.89 (m, 2H), 1.56-1.48 (m, 1H), 1.40-1.20 (m, 2H), 1.16 (s, 3H), 1.11-1.00 (m, 4H) ppm.

Example 5

This example demonstrates methods for making the intermediates 8a-e and 8g. This example refers to the compound numbering in FIG. 1.

General Procedures for Compounds 8a-e and 8g:

A solution of one of intermediates 7a-g (40-100 mg) in THF (0.5-2 mL) was prepared to make the concentration 0.06-0.28 M. To the solution was added lithium bis(trimethylsilyl)amide (LiHMDS) (1 M in hexane, 1.2 equiv.) dropwise at −78° C., and the resulting mixture was stirred at −78° C. for 2 h. To the mixture was added a solution of 6a (0.9-2.2 equiv.) or 6b (1.2 equiv.) in THF (1 mL), and the resulting mixture was then stirred at 10-20° C. overnight. After 7a-g was consumed as monitored by LCMS, the reaction was quenched with saturated. aq. ammonium chloride and extracted with ethyl acetate. The combined organics were washed with water and brine, dried over sodium sulfate, and concentrated in vacuo. The residue was purified by flash chromatography (0-35% ethyl acetate in petroleum ether) to give 8a-e and 8g as a white solid.

(1S,4aS,10aR)-6-(Benzyloxy)-N-((1S,4aS,10aR)-6-(benzyloxy)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (8a): The synthetic procedure of 8a was similar to what was reported in Bioorg. Med. Chem. Lett. 2005, 15, 2824-2828, but LiHMDS was replaced with NaHMDS. 8a (60 mg, 31% yield) was obtained from treatment of 7a (0.10 g, 0.28 mmol) with 6a (0.10 g, 0.26 mmol). ESI m/z: 710 (M+1)+. $^1$H NMR (400 MHz, CDCl$_3$) δ 8.16 (s, 1H), 7.46-7.28 (m, 10H), 6.97 (dd, J=8.4, 3.0 Hz, 2H), 6.88 (dd, J=5.8, 2.6 Hz, 2H), 6.75 (dt, J=8.4, 2.9 Hz, 2H), 5.02 (s, 4H), 2.98-2.89 (m, 1H), 2.89-2.71 (m, 3H), 2.33-2.14 (m, 6H), 2.12-1.93 (m, 4H), 1.72-1.61 (m, 4H), 1.45-1.40 (m, 2H), 1.38 (s, 3H), 1.31 (s, 3H), 1.22-1.09 (m, 8H) ppm.

(1S,4aS,10aR)-6-(Benzyloxy)-N-((1S,4aS,10aR)-6-(2-(tert-butyldimethylsilyloxy)ethoxy)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (8b): Compound 8b (34 mg, 38% yield) was obtained from treatment of 7b (50 mg, 0.12 mmol) with 6a (0.10 g, 0.26 mmol). ESI m/z: 779 (M+1)+.

tert-Butyl 2-((4bS,8S,8aR)-8-((1S,4aS,10aR)-6-(benzyloxy)-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-yloxy)ethylcarbamate (8c): Compound 8c (0.11 g, 60% yield) was obtained from treatment of 7c (0.10 g, 0.24 mmol) with 6b (0.15 g, 0.29 mmol). ESI m/z: 763 (M+1)+. $^1$H NMR (500 MHz, CDCl$_3$) δ 8.14 (s, 1H), 7.37-7.33 (m, 2H), 7.32-7.28 (m, 2H), 7.26-7.22 (m, 1H), 6.91 (s, 1H), 6.90 (s, 1H), 6.80 (d, J=2.5 Hz, 1H), 6.72 (s, 1H), 6.69 (dd, J=8.4, 2.6 Hz, 1H), 6.60 (dd, J=8.4, 2.5 Hz, 1H), 4.95 (s, 2H), 3.90 (t, J=5.0 Hz, 2H), 3.61

(s, 1H), 3.44 (s, 2H), 2.87 (dd, J=16.2, 4.1 Hz, 2H), 2.80-2.67 (m, 2H), 2.25-2.11 (m, 6H), 2.06-1.89 (m, 4H), 1.67-1.54 (m, 4H), 1.45-1.29 (m, 11H), 1.24 (s, 6H), 1.14-1.03 (m, 8H) ppm.

tert-Butyl-(4bS,8S,8aR)-8-((1S,4aS,10aR)-6-(benzyloxy)-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylcarbamate (8d): Compound 8d (37 mg, 46% yield) was obtained from treatment of 7d (42 mg, 0.11 mmol) with 6b (72 mg, 0.14 mmol). ESI m/z: 719 (M+1)$^+$.

tert-Butyl-4-((4bS,8S,8aR)-8-((1S,4aS,10aR)-6-(benzyloxy)-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-yl)piperazine-1-carboxylate (8e): Compound 8e (80 mg, 99% yield) was obtained from treatment of 7e (45 mg, 0.10 mmol) with 6b (65 mg, 0.12 mmol). ESI m/z: 788.4 (M+1)$^+$.

(1S,4aS,10aR)-6-(Benzyloxy)-N-((1S,4aS,10aR)-6-cyano-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (8g): Compound 8g (83 mg, 67% yield) was obtained from treatment of 7g (56 mg, 0.20 mmol) with 6b (0.16 g, 0.30 mmol). ESI m/z: 629.2 (M+1)$^+$. $^1$H NMR (500 MHz, DMSO-$_{d6}$) δ 8.14 (s, 1H), 7.79 (s, 1H), 7.51 (dd, J=7.9, 1.4 Hz, 1H), 7.44-7.40 (m, 2H), 7.40-7.35 (m, 2H), 7.33-7.29 (m, 1H), 7.25 (d, J=8.0 Hz, 1H), 6.94 (d, J=8.6 Hz, 1H), 6.89 (d, J=2.5 Hz, 1H), 6.78-6.71 (m, 1H), 5.04 (s, 2H), 3.20-2.98 (m, 1H), 2.92-2.80 (m, 2H), 2.78-2.68 (m, 1H), 2.39-2.21 (m, 5H), 2.22-2.11 (m, 2H), 1.95-1.79 (m, 4H), 1.69-1.53 (m, 4H), 1.31-1.22 (m, 7H), 1.21-1.08 (m, 2H), 1.02 (s, 3H), 1.01 (s, 3H) ppm.

Example 6

This example demonstrates methods for making the final compound 9a in Table 1, above. This example refers to the compound numbering in FIG. 1.

(1S,4aS,10aR)-6-Hydroxy-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (9a) was reported in *Bioorg. Med. Chem. Lett.* 2005, 15, 2824-2828; the synthetic procedure was similar as reported, and the hydrogenation was under atmospheric pressure instead of 45 psi. To a solution of 8a (50 mg, 70 μmol) in ethyl acetate (2 mL) was added wet Pd/C (10%, 20 mg) under nitrogen. The mixture was purged with hydrogen 3 times, and stirred at 15-25° C. under an atmosphere of hydrogen for 16 h. The mixture was filtered through Celite to remove Pd/C, and the filtrate was concentrated in vacuo. The residue was purified by flash chromatography (0-20% ethyl acetate in petroleum ether) to give 9a (10 mg, 27% yield) as a white solid. ESI m/z: 530 (M+1)$^+$. $^1$H NMR (400 MHz, CDCl$_3$) δ 8.16 (s, 1H), 6.93 (d, J=8.4 Hz, 2H), 6.73 (d, J=2.6 Hz, 2H), 6.64-6.59 (m, 2H), 3.00-2.85 (m, 2H), 2.88-2.71 (m, 2H), 2.34-2.16 (m, 6H), 2.15-1.96 (m, 4H), 1.49-1.35 (m, 4H), 1.31 (s, 6H), 1.30-1.08 (m, 4H), 1.08 (s, 6H) ppm.

Example 7

This example demonstrates methods for making the final compound 9b in Table 1, above. This example refers to the compound numbering in FIG. 1.

(1S,4aS,10aR)-6-Hydroxy-N-((1S,4aS,10aR)-6-(2-hydroxyethoxy)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (9b)

Step 1:

To a solution of 8b (37 mg, 44 μmol) in THF (1.4 mL) was added TBAF (1 M in THF, 0.09 mL) and the mixture was stirred at 25° C. for 2 h. Removing THF in vacuo afforded the crude hydroxyl intermediate, which was used in the next step without purification. ESI m/z: 664 (M+1). $^1$H NMR (500 MHz, methanol-$_{d4}$) δ 7.42 (d, J=7.4 Hz, 2H), 7.36 (t, J=7.5 Hz, 2H), 7.29 (t, J=7.3 Hz, 1H), 6.97 (d, J=2.3 Hz, 1H), 6.96 (d, J=2.3 Hz, 1H), 6.87 (dd, J=4.4, 2.6 Hz, 2H), 6.75 (dd, J=8.4, 2.5 Hz, 1H), 6.72 (dd, J=8.4, 2.5 Hz, 1H), 5.03 (s, 2H), 4.02-3.98 (m, 2H), 3.87-3.83 (m, 2H), 2.94 (d, J=16.3 Hz, 2H), 2.82 (dd, J=18.2, 8.2 Hz, 2H), 2.40-2.20 (m, 5H), 2.16-1.95 (m, 4H), 1.77-1.62 (m, 3H), 1.59-1.49 (m, 1H), 1.48-1.32 (m, 8H), 1.25 (tt, J=13.8, 3.8 Hz, 2H), 1.12 (d, J=13.3 Hz, 6H), 0.98 (t, J=7.4 Hz, 1H) ppm.

Step 2:

To a solution of the crude hydroxyl intermediate (20 mg, 30 μmol) in ethyl acetate (2 mL) was added wet Pd/C (10%, 20 mg) under nitrogen. This mixture was purged with hydrogen 3 times, and stirred at 20-25° C. under an atmosphere of hydrogen for 16 h. The mixture was filtered through Celite to remove Pd/C and the filtrate was concentrated in vacuo. The residue was purified by flash chromatography (0-35% ethyl acetate in petroleum ether) to give 9b (4 mg, 23% yield) as a white solid. ESI m/z: 574.2 (M+1)$^+$. $^1$H NMR (500 MHz, CDCl$_3$) δ 8.16 (s, 1H), 7.02-6.87 (m, 2H), 6.85-6.72 (m, 2H), 6.72-6.57 (m, 2H), 4.08-4.01 (m, 2H), 3.99-3.89 (m, 2H), 3.01-2.87 (m, 2H), 2.87-2.68 (m, 2H), 2.33-2.15 (m, 6H), 2.14-1.97 (m, 4H), 1.78-1.58 (m, 5H), 1.50-1.35 (m, 2H), 1.36-1.25 (m, 7H), 1.22-1.07 (m, 8H) ppm.

Example 8

This example demonstrates methods for making the final compound 9c in Table 1, above. This example refers to the compound numbering in FIG. 1.

(1S,4aS,10aR)-6-(2-Aminoethoxy)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (9c)

Method 1: To a solution of 8c (0.11 g, 0.16 mmol) in ethyl acetate (5 mL) was added wet Pd/C (10%, 30 mg) under nitrogen. The mixture was purged with hydrogen 3 times and stirred at 15-25° C. for 16 h. The mixture was filtered through Celite and the filtrate was concentrated in vacuo to give the de-benzylated intermediate (94 mg) as a white solid. ESI m/z: 673 (M+1)$^+$. $^1$H NMR (400 MHz, methanol-$_{d4}$) δ 6.95 (d, J=8.5 Hz, 1H), 6.90-6.82 (m, 2H), 6.72-6.66 (m, 2H), 6.54 (dd, J=8.3, 2.4 Hz, 1H), 3.94 (t, J=5.6 Hz, 2H), 3.43-3.34 (m, 2H), 2.98-2.86 (m, 2H), 2.86-2.72 (m, 2H), 2.38-2.30 (m, 3H), 2.26 (d, J=13.8 Hz, 3H), 2.15-1.94 (m, 4H), 1.75-1.63 (m, 4H), 1.44 (s, 9H), 1.39-1.32 (m, 8H), 1.31-1.20 (m, 2H), 1.12 (d, J=5.0 Hz, 6H) ppm. A mixture of the de-benzylated intermediate (90 mg) in methanol (0.5 mL) was treated with HCl in dioxane (4 M, 0.5 mL) at 15-25° C. for 16 h. The volatiles were removed in vacuo and the residue was purified by prep-HPLC (method B) to give 9c (40 mg, 52% yield) as a white solid. ESI m/z: 573.3 (M+1)⁺. ¹H NMR (400 MHz, methanol-$d_4$) δ 8.41 (s, 1H, NH of imidine), 6.99 (d, J=8.4 Hz, 1H), 6.90 (d, J=2.5 Hz, 1H), 6.87 (d, J=8.4 Hz, 1H), 6.76 (dd, J=8.3, 2.5 Hz, 1H), 6.69 (d, J=2.5 Hz, 1H), 6.54 (dd, J=8.3, 2.5 Hz, 1H), 4.17 (t, J=5.0 Hz, 2H), 3.40-3.22 (m, 2H), 2.99-2.71 (m, 4H), 2.41-2.21 (m, 6H), 2.15-1.93 (m, 4H), 1.75-1.64 (m, 4H), 1.47-1.33 (m, 8H), 1.27-1.25 (m, 2H), 1.12 (s, 3H), 1.09 (s, 3H) ppm.

Method 2: To a solution of 9b (25 mg, 44 μmol) in toluene (1 mL) were added phthalimide (10 mg, 65 μmol), triphenylphosphine (23 mg, 88 μmol) and diisopropyl azodicarboxylate (DIAD, 18 mg, 88 μmol). After the reaction was stirred at 20-25° C. for 24 h, the reaction mixture was diluted with ethyl acetate (40 mL), the organics were washed with water (20 mL), dried over anhydrous sodium sulfate, and concentrated. The residue was dissolved in ethanol (5 mL) and the ethanolic solution was then treated with hydrazine (0.3 mL). This mixture was stirred at 90° C. for 3 h. After the reaction was cooled, the volatiles were removed in vacuo, and the residue was triturated with acetonitrile (10 mL). The mixture was stirred at 25° C. for 10 minutes and filtered. The solids were washed with acetonitrile (10 mL) and the combined filtrate was concentrated in vacuo. The crude product was purified by prep-HPLC (method B) to give 9c (11 mg, 44% yield) as a white solid. ESI m/z: 573.4 (M+1)⁺.

Example 9

This example demonstrates methods for making the final compound 9d in Table 1, above. This example refers to the compound numbering in FIG. 1.

(1S,4aS,10aR)-6-Amino-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (9d)

Step 1:

To a solution of 8d (0.84 g, 1.3 mmol) in ethyl acetate (50 mL) was added wet Pd/C (10%, 0.15 g) under nitrogen. The mixture was purged with hydrogen and stirred at 15-25° C. under a hydrogen balloon for 16 h. The mixture was filtered through Celite and the filtrate was concentrated in vacuo. The residue was purified by silica gel column chromatography (0-50% ethyl acetate in petroleum ether) to give 9g (0.66 g, 90% yield) as a white solid. ESI m/z: 629 (M+1)⁺. ¹H NMR (500 MHz, DMSO-$d_6$) δ 9.12 (s, 1H), 9.00 (s, 1H), 8.12 (s, 1H), 7.39 (d, J=17.8 Hz, 1H), 7.15 (d, J=7.4 Hz, 1H), 6.90 (d, J=8.4 Hz, 1H), 6.82 (d, J=8.3 Hz, 1H), 6.64 (d, J=2.3 Hz, 1H), 6.51 (dd, J=8.2, 2.4 Hz, 1H), 2.85 (td, J=16.3, 3.8 Hz, 2H), 2.79-2.64 (m, 2H), 2.33-2.22 (m, 2H), 2.21-2.09 (m, 4H), 1.96-1.77 (m, 4H), 1.68-1.54 (m, 4H), 1.46 (s, 9H), 1.34-1.24 (m, 8H), 1.20-1.10 (m, 2H), 0.99 (s, 6H) ppm.

Step 2:

To a solution of 9g in methanol (0.5 mL) was added HCl in dioxane (4 M, 0.5 mL) at 0° C., and the resulting solution was stirred at 15-25° C. for 16 h. The volatiles were removed in vacuo and the residue was purified by prep-HPLC (method B) to give 9d (1.3 mg, 44% yield) as a white solid. ESI m/z: 529.3 (M+1)⁺.

The 500 MHz NMR data in DMSO-$d_6$ (ppm) for 9d were summarized in Table 3 as follows.

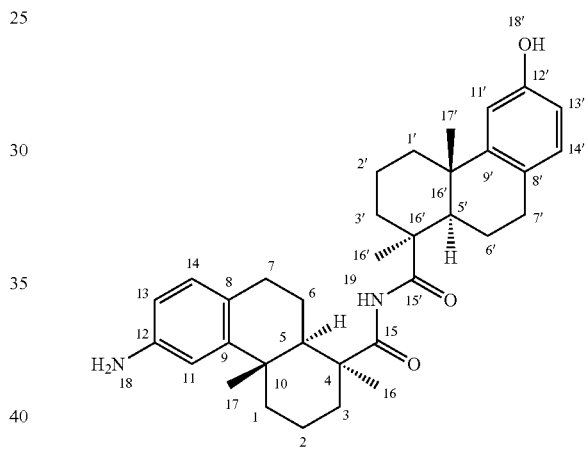

TABLE 3

| Atom # | ¹H NMR | ¹³C NMR | Atom # | ¹H NMR | ¹³C NMR |
|---|---|---|---|---|---|
| 1 | 1.30 (Ha), 2.14 (He) | 39.2 | 1' | 1.30 (Ha), 2.14 (He) | 39.36 |
| 2 | 1.54 (Ha), 1.84 (He) | 19.61 | 2' | 1.54 (Ha), 1.84 (He) | 19.64 |
| 3 | 1.13 (Ha), 2.14 (He) | 37.12 | 3' | 1.13 (Ha), 2.14 (He) | 37.18 |
| 4 | — | 45.52 | 4' | — | 45.56 |
| 5 | 1.6 | 52.09 | 5' | 1.6 | 52.32 |
| 6 | 1.84 (Ha), 2.23 (He) | 21.27 | 6' | 1.84 (Ha), 2.23 (He) | 21.43 |
| 7 | 2.75 | 31 | 7' | 2.75 | 31.08 |
| 8 | — | 121.65 | 8' | — | 124.6 |
| 9 | — | 147.63 | 9' | — | 148.39 |
| 10 | — | 38.17 | 10' | — | 38.23 |
| 11 | 6.48 | 110.77 | 11' | 6.63 | 111.81 |
| 12 | — | 146.43 | 12' | — | 155.34 |
| 13 | 6.34 | 112.58 | 13' | 6.5 | 113.23 |
| 14 | 6.68 | 129.09 | 14' | 6.81 | 129.56 |
| 15 | — | 173.92 | 15' | — | 174.03 |
| 16 | 1.26 | 27.65 | 16' | 1.26 | 27.64 |
| 17 | 0.98 | 23.03 | 17' | 0.98 | 23.08 |
| 18 (N) | 4.69 | | 18' (O) | 8.99 | |
| 19 (N) | 8.09 | | | | |

¹H NMR (500 MHz, CDCl₃) δ 8.14 (s, 1H), 6.92 (d, J=8.3 Hz, 1H), 6.86 (d, J=8.1 Hz, 1H), 6.73 (d, J=2.5 Hz, 1H), 6.65-6.57 (m, 2H), 6.50 (dd, J=8.1, 2.3 Hz, 1H), 4.75 (s, 1H), 3.49 (s, 1H), 2.99-2.85 (m, 2H), 2.79 (tt, J=11.6, 5.8 Hz, 2H), 2.34-2.14 (m, 6H), 2.15-1.95 (m, 4H), 1.74-1.51 (m, 5H), 1.46-1.34 (m, 2H), 1.30 (s, 6H), 1.21-1.06 (m, 8H) ppm.

$^1$H NMR (500 MHz, DMSO-$_{d6}$) δ 8.99 (s, 1H), 8.09 (s, 1H), 6.81 (d, J=8.0 Hz, 1H), 6.68 (d, J=8.0 Hz, 1H), 6.63 (d, J=2.5 Hz, 1H), 6.50 (dd, J=8.0, 2.5 Hz, 1H), 6.48 (d, J=2.5 Hz, 1H), 6.34 (dd, J=8.0, 2.5 Hz, 1H), 4.69 (s, 2H), 2.86-2.60 (m, 4H), 2.28-2.10 (m, 6H), 1.94-1.75 (m, 4H), 1.65-1.53 (m, 4H), 1.35-1.20 (m, 8H), 1.20-1.06 (m, 2H), 0.98 (s, 6H) ppm.

$^{13}$C NMR (100 MHz, DMSO-$_{d6}$) δ 174.03, 173.92, 155.34, 148.39, 147.63, 146.43, 129.56, 129.09, 124.60, 121.65, 113.23, 112.58, 111.81, 110.77, 52.32, 52.09, 45.56, 45.52, 39.20, 39.36, 38.23, 38.17, 37.18, 37.12, 31.08, 31.00, 27.65, 27.64, 23.08, 21.43, 21.27, 19.64, 19.61 ppm.

HPLC (method B): Retention time (Rt): 8.92 min, purity: 99.4%. chiral HPLC: >99.9% (in column AD, AS, OD and OJ). Optical rotation [α]$^{25}$: +2.53° (1.7 g/100 mL THF).

Example 10

This example demonstrates methods for making the final compound 9e in Table 1, above. This example refers to the compound numbering in FIG. 1.

(1S,4aS,10aR)—N-((1S,4aS,10aR)-1,4a-Dimethyl-6-(piperazin-1-yl)-1,2,3,4,4a,9,10,10a-octahydrophenanthrene-1-carbonyl)-6-hydroxy-1,4a-dimethyl-1,2,3,4,4a,9,10,10a-octahydrophenanthrene-1-carboxamide (9e)

To a solution of 8e (61 mg, 77 μmol) in ethyl acetate (1 mL) was added wet Pd/C (10%, 5 mg) under nitrogen. The mixture was purged with hydrogen 3 times and stirred under hydrogen at 30° C. for 16 h. The mixture was filtered through Celite and the filtrate was concentrated in vacuo to give the de-benzylated intermediate (54 mg, ESI m/z: 698 (M+1)$^+$), which was dissolved in methanol (0.5 mL) and treated with HCl in dioxane (4 M, 0.5 mL) at 15-25° C. for 16 h. The volatiles were removed in vacuo and the residue was purified by prep-HPLC (method B) to give 9e (10 mg, 22% yield) as a white solid. ESI m/z: 598 (M+1)$^+$. $^1$H NMR (400 MHz, methanol-$_{d4}$) δ 8.40 (s, 1H, NH), 7.00 (d, J=8.3 Hz, 1H), 6.92 (d, J=2.5 Hz, 1H), 6.87 (d, J=8.3 Hz, 1H), 6.80 (dd, J=8.3, 2.4 Hz, 1H), 6.70 (d, J=2.5 Hz, 1H), 6.54 (dd, J=8.2, 2.4 Hz, 1H), 3.36 (m, 8H), 3.02-2.71 (m, 4H), 2.42-2.20 (m, 6H), 2.15-1.92 (m, 4H), 1.79-1.59 (m, 4H), 1.52-1.18 (m, 10H), 1.12 (d, J=9.1 Hz, 6H) ppm.

Example 11

This example demonstrates methods for making the final compound 9f in Table 1, above. This example refers to the compound numbering in FIG. 1.

(1S,4aS,10aR)-6-(Dimethylamino)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (9f)

To a solution of compound 8d (36 mg, 50 μmol) in methanol (0.5 mL) was added with HCl in dioxane (4 N, 0.5 mL, 2 mmol) at 0° C., and the resulting mixture was stirred at 20-25° C. for 16 h. The reaction was monitored by LC-MS until compound 8d was consumed. The volatiles were removed in vacuo to give 27 mg of the free amine intermediate, which was dissolved in methanol (2 mL), followed by the addition of Pd/C (10%, 5 mg) under nitrogen. The reaction mixture was purged with hydrogen and stirred at 20-25° C. under a hydrogen balloon for 16 h. The N-methylation occurred with methanol under acidic conditions. The mixture was filtered through Celite, and the filtrate was concentrated in vacuo. The residue was purified by prep-HPLC (method B) to give 9f (10 mg, 36% yield) as a white solid. ESI m/z: 557 (M+H)$^+$. $^1$H NMR (400 MHz, CDCl$_3$) δ 8.15 (s, 1H), 6.99-6.90 (m, 2H), 6.73 (d, J=2.6 Hz, 1H), 6.68-6.58 (m, 3H), 4.69 (s, 1H), 2.98-2-2.85 (m, 8H), 2.87-2.72 (m, 2H), 2.35-2.16 (m, 6H), 2.15-1.98 (m, 4H), 1.66 (d, J=14.5 Hz, 4H), 1.5-1.34 (m, 2H), 1.31 (s, 3H), 1.31 (s, 3H) 1.19 (s, 3H), 1.17-1.08 (m, 5H) ppm.

Example 12

This example demonstrates methods for making the final compound 9g in Table 1, above. This example refers to the compound numbering in FIG. 1.

tert-Butyl (4bS,8S,8aR)-8-((1S,4aS,10aR)-6-hydroxy-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylcarbamate (9g)

To a solution of 8d (0.84 g, 1.3 mmol) in ethyl acetate (50 mL) was added wet Pd/C (10%, 0.15 g) under nitrogen. The mixture was purged with hydrogen and stirred at 15-25° C. under a hydrogen balloon for 16 h until 8d was totally consumed, which was monitored by LCMS. The mixture was filtered through Celite and the filtrate was concentrated in vacuo. The residue was purified by silica gel column chromatography (0-50% ethyl acetate in petroleum ether) to give 9g (0.66 g, 90% yield) as a white solid. ESI m/z: 629 (M+1)$^+$. $^1$H NMR (500 MHz, DMSO-$_{d6}$) δ 9.12 (s, 1H), 9.00 (s, 1H), 8.12 (s, 1H), 7.39 (d, J=17.8 Hz, 1H), 7.15 (d, J=7.4 Hz, 1H), 6.90 (d, J=8.4 Hz, 1H), 6.82 (d, J=8.3 Hz, 1H), 6.64 (d, J=2.3 Hz, 1H), 6.51 (dd, J=8.2, 2.4 Hz, 1H), 2.85 (td, J=16.3, 3.8 Hz, 2H), 2.79-2.64 (m, 2H), 2.33-2.22 (m, 2H), 2.21-2.09 (m, 4H), 1.96-1.77 (m, 4H), 1.68-1.54 (m, 4H), 1.46 (s, 9H), 1.34-1.24 (m, 8H), 1.20-1.10 (m, 2H), 0.99 (s, 6H) ppm.

Example 13

This example demonstrates methods for making the final compound 9h in Table 1, above. This example refers to the compound numbering in FIG. 1.

(1S,4aS,10aR)-6-(2-Aminoacetamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (9h)

To a solution of Fmoc-Gly-OH (30 mg, 0.1 mmol) in DMF (1 mL) were added HATU (38 mg, 0.1 mmol), and DIPEA (39 mg, 0.3 mmol) at 25° C. The resulting mixture was stirred at this temperature for an hour. To the mixture was then added 9d (30 mg, 0.06 mmol), and the reaction mixture was stirred at 25° C. for 16 h until 9d was totally consumed (as monitored by LCMS). To the mixture was added piperidine (0.2 mL), and the resulting mixture was stirred for additional 30 min at rt. The volatiles were removed in vacuo and the residue was directly purified by prep-HPLC (method B) to give 9h (17 mg, 51% yield) as a white solid. ESI m/z: 586 (M+1)$^+$. $^1$H NMR (500 MHz, DMSO-$_{d6}$) δ 9.70 (br s, 1H, CONH-Ph), 9.03 (s, 1H, OH), 8.12 (s, 1H, NH of imidine), 7.52 (s, 1H), 7.41 (dd, J=8.3, 1.8 Hz, 1H), 6.97 (d, J=8.4 Hz, 1H), 6.82 (d, J=8.3 Hz, 1H), 6.64 (d, J=2.3 Hz, 1H), 6.51 (dd, J=8.2, 2.3 Hz, 1H), 3.22 (s, 2H), 2.95-2.63 (m, 4H), 2.33-2.23 (m, 2H), 2.23-2.08 (m, 4H), 1.98-1.77 (m, 4H), 1.71-1.51 (m, 4H), 1.37-1.23 (m, 8H), 1.20-1.09 (m, 2H), 1.01 (s, 3H), 0.99 (s, 3H) ppm.

Example 14

This example demonstrates methods for making the final compound 9i in Table 1, above. This example refers to the compound numbering in FIG. 1.

(1S,4aS,10aR)-6-(3-Aminopropanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (9i)

To a solution of Boc-β-Ala-OH (38 mg, 0.2 mmol) in DMF (1 mL) were added HATU (76 mg, 0.2 mmol), and DIPEA (52 mg, 0.4 mmol) at 25° C. The resulting solution was stirred at this temperature for an hour. To the solution was then added 9d (53 mg, 0.1 mmol), and the resulting mixture was stirred at 25° C. for 16 h until 9d was totally consumed (as monitored by LCMS). The reaction mixture was diluted with ethyl acetate, and washed with water and brine. The organics were dried over sodium sulfate, and concentrated in vacuo. The residue was dissolved in DCM (2 mL) and to the solution was slowly added TFA (0.2 mL) at rt. The mixture was stirred at rt for 2 h, and the volatiles were removed in vacuo and the residue was purified by prep-HPLC (method B) to give 9i (30 mg, 50% yield) as a white solid. ESI m/z: 600 (M+1)$^+$. $^1$H NMR (500 MHz, methanol-$_{d4}$) δ 7.38 (s, 1H), 7.20 (d, J=8.2 Hz, 1H), 6.90 (d, J=8.3 Hz, 1H), 6.76 (d, J=8.3 Hz, 1H), 6.60 (d, J=2.3 Hz, 1H), 6.43 (dd, J=8.2, 2.3 Hz, 1H), 2.93 (t, J=6.5 Hz, 2H), 2.90-2.80 (m, 2H), 2.80-2.63 (m, 2H), 2.47 (t, J=6.5 Hz, 2H), 2.30-2.12 (m, 6H), 2.02-1.85 (m, 4H), 1.65-1.54 (m, 4H), 1.37-1.28 (m, 2H), 1.26 (s, 3H), 1.25 (s, 3H), 1.21-1.11 (m, 2H), 1.02 (s, 3H), 1.01 (s, 3H) ppm.

Example 15

This example demonstrates methods for making the final compound 9j in Table 1, above. This example refers to the compound numbering in FIG. 1.

(1S,4aS,10aR)-6-((S)-2-Amino-3-hydroxypropanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (9j)

Using the same procedure for preparing 9h except replacing Fmoc-Gly-OH with Fmoc-Ser-OH, 9j (18 mg, 51% yield) as a white solid was obtained. ESI m/z: 616 (M+1)$^+$. $^1$H NMR (500 MHz, DMSO-$_{d6}$) δ 9.74 (br s, 1H, CONH-Ph), 9.00 (s, 1H, OH), 8.11 (s, 1H, NH of imidine), 7.58 (s, 1H), 7.41 (d, J=8.2, 2.0 Hz, 1H), 6.96 (d, J=8.4 Hz, 1H), 6.82 (d, J=8.3 Hz, 1H), 6.63 (d, J=2.3 Hz, 1H), 6.50 (dd, J=8.2, 2.4 Hz, 1H), 4.82 (t, J=5.5 Hz, 1H, OH on Ser), 3.62-3.45 (m, 3H), 2.97-2.61 (m, 4H), 2.33-2.21 (m, 2H), 2.21-2.03 (m, 4H), 1.96-1.77 (m, 4H), 1.70-1.50 (m, 4H), 1.36-1.20 (m, 8H), 1.23-1.06 (m, 2H), 1.06-0.93 (m, 6H) ppm.

Example 16

This example demonstrates methods for making the final compound 9k in Table 1, above. This example refers to the compound numbering in FIG. 1.

(1S,4aS,10aR)—N-((1S,4aS,10aR)-1,4a-Dimethyl-6-(2-(methylamino)acetamido)-1,2,3,4,4a,9,10,10a-octahydrophenanthrene-1-carbonyl)-6-hydroxy-1,4a-dimethyl-1,2,3,4,4a,9,10,10a-octahydrophenanthrene-1-carboxamide; Trifluoroacetic Acid Salt (9k)

Following the procedures for preparing 9i except replacing Boc-β-Ala-OH with N-Boc-Sar-OH, 9k (27 mg, 28% yield, TFA salt) was obtained as a white solid after purification by prep-HPLC (method A). ESI m/z: 600.5 (M+1)$^+$. $^1$H NMR (400 MHz, DMSO-$_{d6}$) δ 10.33 (s, 1H), 8.99 (s, 1H), 8.74 (s, 2H), 8.12 (s, 1H), 7.47 (s, 1H), 7.32 (dd, J=8.3, 1.6 Hz, 1H), 7.03 (d, J=8.4 Hz, 1H), 6.82 (d, J=8.1 Hz, 1H), 6.63 (d, J=2.3 Hz, 1H), 6.50 (dd, J=8.2, 2.4 Hz, 1H), 3.87 (s, 2H), 2.97-2.66 (m, 4H), 2.62 (s, 3H), 2.37-2.23 (m, 2H), 2.21-2.06 (m, 4H), 2.00-1.77 (m, 4H), 1.70-1.50 (m, 4H), 1.38-1.23 (m, 8H), 1.21-1.08 (m, 2H), 1.01 (s, 3H), 0.99 (s, 3H) ppm. $^{19}$F NMR (376 MHz, DMSO-$_{d6}$) δ− 73.43 ppm.

Example 17

This example demonstrates methods for making the final compound 9l in Table 1, above. This example refers to the compound numbering in FIG. 1.

(1S,4aS,10aR)—N-[(1S,4aS,10aR)-6-Hydroxy-1,4a-dimethyl-1,2,3,4,4a,9,10,10a-octahydro-phenanthrene-1-carbonyl]-6-[(2S)-2,6-diamino-hexanamido]-1,4a-dimethyl-1,2,3,4,4a,9,10,10a-octahydrophenanthrene-1-carboxamide; Trifluoroacetic Acid Salt (9l)

Following the procedures for preparing 9i except replacing Boc-β-Ala-OH with Boc-Lys-OH, compound 9l (9 mg, 49% yield) was obtained as a white solid. ESI m/z: 657.5 (M+1)$^+$. $^1$H NMR (400 MHz, DMSO-$_{d6}$) δ 10.33 (s, 1H), 9.01 (s, 1H), 8.13 (s, 1H), 7.78 (br s, 6H), 7.51 (s, 1H), 7.34 (d, J=8.1 Hz, 1H), 7.02 (d, J=8.5 Hz, 1H), 6.82 (d, J=8.6 Hz, 1H), 6.63 (s, 1H), 6.51 (d, J=8.3 Hz, 1H), 3.82 (s, 1H), 2.89 (s, 1H), 2.82-2.67 (m, 5H), 2.29 (s, 2H), 2.15 (s, 4H), 1.85 (s, 6H), 1.64-1.51 (m, 6H), 1.28 (d, J=6.8 Hz, 10H), 1.13 (s, 2H), 1.01 (s, 3H), 0.99 (s, 3H) ppm. $^{19}$F NMR (376 MHz, DMSO a6) 8-73.53 ppm.

Example 18

This example demonstrates methods for making the final compound 9m in Table 1, above. This example refers to the compound numbering in FIG. 1.

(1S,4aS,10aR)—N-[(1S,4aS,10aR)-6-Hydroxy-1,4a-dimethyl-1,2,3,4,4a,9,10,10a-octahydro-phenanthrene-1-carbonyl]-6-[(2S)-2-amino-3-(1H-imidazol-4-yl)propanamido]-1,4a-dimethyl-1,2,3,4,4a,9,10,10a-octahydrophenanthrene-1-carboxamide; trifluoroacetic acid salt (9m)

Following the procedures for preparing 9i except replacing Boc-β-Ala-OH with Boc-His-OH, 9m (11 mg, 60% yield) was obtained as a white solid. ESI m/z: 666.3 (M+1)⁺. ¹H NMR (500 MHz, DMSO-$d_6$) δ 10.39 (s, 1H), 9.02 (s, 1H), 8.74 (s, 1H), 8.45 (br s, 2H), 8.13 (s, 1H), 7.42 (s, 1H), 7.36 (s, 1H), 7.31-7.27 (dd, J=8.3 Hz, 1.7 Hz, 1H), 7.02 (d, J=8.4 Hz, 1H), 6.82 (d, J=8.3 Hz, 1H), 6.63 (d, J=2.2 Hz, 1H), 6.51 (dd, J=8.2, 2.3 Hz, 1H), 4.20 (t, J=6.8 Hz, 1H), 3.28-3.13 (m, 2H), 2.95-2.63 (m, 4H), 2.34-2.22 (m, 2H), 2.22-2.08 (m, 4H), 1.93-1.81 (m, 4H), 1.66-1.56 (m, 4H), 1.37-1.22 (m, 8H), 1.22-1.08 (m, 2H), 1.01 (s, 3H), 0.99 (s, 3H) ppm. ¹⁹F NMR (376 MHz, DMSO-$d_6$) δ −73.64 ppm.

Example 19

This example demonstrates methods for making the final compound 9n in Table 1, above. This example refers to the compound numbering in FIG. 1.

(3S)-3-Amino-3-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}propanoic Acid (9n)

Following the procedures for preparing 9i except replacing Boc-β-Ala-OH with OtBu-N-Boc-Asp-OH, 9n (11 mg, 62% yield) was obtained as a white solid. ESI m/z: 644.3 (M+1)⁺. ¹H NMR (500 MHz, DMSO-$d_6$) δ 10.34 (br s, 1H), 9.03 (br s, 1H), 8.12 (s, 1H), 7.53 (s, 1H), 7.34 (dd, J=8.3, 1.8 Hz, 1H), 6.98 (d, J=8.4 Hz, 1H), 6.81 (d, J=8.3 Hz, 1H), 6.63 (d, J=2.3 Hz, 1H), 6.50 (dd, J=8.2, 2.3 Hz, 1H), 3.79-3.74 (m, 1H), 2.93-2.69 (m, 5H), 2.37-2.23 (m, 3H), 2.22-2.08 (m, 4H), 1.95-1.78 (m, 4H), 1.66-1.54 (m, 4H), 1.42-1.22 (m, 8H), 1.19-1.09 (m, 2H), 1.00 (s, 3H), 0.99 (s, 3H) ppm.

Example 20

This example demonstrates methods for making the final compound 9o in Table 1, above. This example refers to the compound numbering in FIG. 1.

(4S)-4-Amino-4-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}butanoic acid; Trifluoroacetic Acid Salt (9o)

Following the procedures for preparing 9i except replacing Boc-β-Ala-OH with OtBu-N-Boc-Glu-OH, 9o (8 mg, 46% yield) was obtained as a white solid. ESI m/z: 658.3 (M+1)⁺. ¹H NMR (400 MHz, DMSO-$d_6$) δ 10.32 (s, 1H), 9.00 (s, 1H), 8.12 (s, 1H), 7.48 (s, 1H), 7.35 (d, J=8.2 Hz, 1H), 7.02 (d, J=8.4 Hz, 1H), 6.82 (d, J=8.3 Hz, 1H), 6.63 (d, J=2.1 Hz, 1H), 6.50 (dd, J=8.2, 2.3 Hz, 1H), 3.87 (t, J=6.5 Hz, 1H), 2.97-2.67 (m, 4H), 2.41-2.22 (m, 4H), 2.22-2.08 (m, 4H), 2.05-1.97 (m, 2H), 1.94-1.80 (m, 4H), 1.69-1.52 (m, 4H), 1.42-1.22 (m, 8H), 1.22-1.06 (m, 2H), 1.02 (s, 3H), 0.99 (s, 3H) ppm. ¹⁹F NMR (376 MHz, DMSO-$d_6$) δ− 73.50 ppm.

Example 21

Figure 3A:
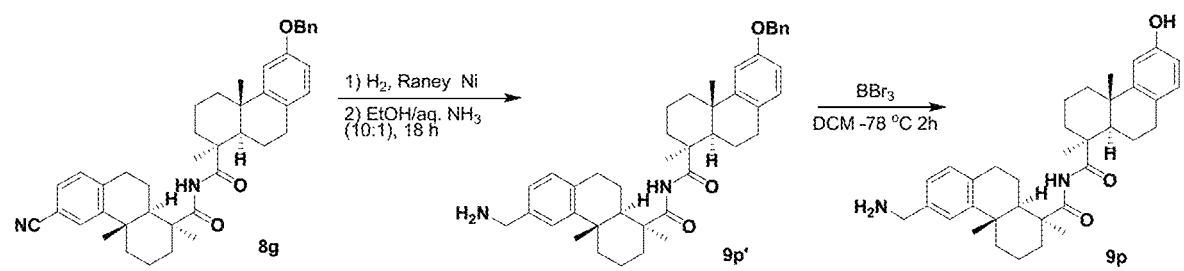

This example demonstrates methods for making the final compound 9p in Table 1, above. This example refers to the compound numbering in FIG. 1 and the synthesis was shown in FIG. 3a.

Step 1: Making (1S,4aS,10aR)-6-(Aminomethyl)-N-((1S,4aS,10aR)-6-(benzyloxy)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide; Trifluoroacetic Acid Salt (9p')

To a solution of 8g (70 mg, 0.11 mmol) in ethanol (15 mL) under nitrogen, was added Raney Ni (0.10 g) at 0° C., followed by the addition of conc. aq. ammonia solution (1.5 mL). The resulting mixture was purged with hydrogen and stirred under an atmosphere of hydrogen via balloon for 18 h. The reduction was deemed complete by LCMS. The solution was filtered through Celite and the filtrate was concentrated in vacuo to give a crude material (67 mg, 95% yield) as a white solid, 7 mg of which was purified by prep-HPLC (method A) to provide 9p' (4 mg, TFA salt) for NMR analysis. ESI m/z: 633.4 (M+1)⁺. ¹H NMR (400 MHz, DMSO-$d_6$) δ 9.21 (s, 2H), 9.01 (s, 1H), 8.13 (s, 1H), 7.52-7.34 (m, 6H), 7.18 (d, J=8.0 Hz, 1H), 7.10 (d, J=7.9 Hz, 1H), 6.82 (d, J=8.3 Hz, 1H), 6.63 (d, J=2.2 Hz, 1H), 6.51 (dd, J=8.2, 2.3 Hz, 1H), 4.19-4.03 (m, 4H), 3.00-2.93 (m, 1H), 2.87-2.77 (m, 2H), 2.75-2.64 (m, 1H), 2.35-2.24 (m, 3H), 2.22-2.09 (m, 3H), 1.96-1.74 (m, 4H), 1.71-1.51 (m, 4H), 1.38-1.22 (m, 8H), 1.21-1.08 (m, 2H), 1.03 (s, 3H), 0.99 (s, 3H) ppm. ¹⁹F NMR (376 MHz, DMSO-$d_6$) δ −73.53 ppm.

Step 2: Making (1S,4aS,10aR)-6-(Aminomethyl)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide; Trifluoroacetic Acid Salt (9p)

To a solution of compound 9p' (60 mg, 95 μmol) in DCM (5 mL) was added dropwise boron tribromide (1 M in DCM, 1 mL) under an atmosphere of argon at −78° C. The resulting mixture was stirred at −78° C. for an hour until the benzyl group was totally removed according to LCMS. The mixture was then quenched with methanol (5 mL) dropwise at −78° C. and the reaction was allowed to warm to room temperature. The solution was diluted with DCM (50 mL) and washed with sat. aq. sodium bicarbonate (20 mL×2). The organics were dried over sodium sulfate and concentrated in vacuo. The residue was purified by prep-HPLC (method A) to give the title compound 9p (15 mg, 30% yield, TFA salt) as a white solid. ESI m/z: 543.2 (M+1)⁺. ¹H NMR (500 MHz, DMSO-$d_6$) δ 9.02 (s, 1H), 8.14 (s, 1H), 8.09 (br s, 3H), 7.40 (s, 1H), 7.15 (d, J=7.9 Hz, 1H), 7.09 (d, J=7.9 Hz, 1H), 6.82 (d, J=8.3 Hz, 1H), 6.64 (d, J=2.3 Hz, 1H), 6.51 (dd, J=8.2, 2.4 Hz, 1H), 3.96 (d, J=4.7 Hz, 2H), 3.00-2.91 (m, 1H), 2.87-2.76 (m, 2H), 2.75-2.66 (m, 1H), 2.36-2.24 (m, 3H), 2.22-2.10 (m, 3H), 1.97-1.78 (m, 4H), 1.68-1.53 (m, 4H), 1.35-1.23 (m, 8H), 1.16 (qd, J=14.0, 3.6 Hz, 2H), 1.03 (s, 3H), 0.99 (s, 3H) ppm. ¹⁹F NMR (376 MHz, DMSO-$d_6$) δ −73.53 ppm.

Example 22

This example demonstrates methods for making the final compound 9q in Table 1, above. This example refers to the compound numbering in FIG. 1.

4-{[(4bS,8S,8aR)-8-{[(1S,4aS,10aR)-6-Hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}butanoic Acid (9q)

To a 4 mL-screw-capped vial were added compound 9d (15 mg, 28 μmol) and glutaric anhydride (5.0 mg, 43 μmol).

The mixed solids were dissolved in THF (0.2 mL). The mixture was stirred at rt for 16 hours until the reaction was completed, as monitored by LCMS. The mixture was diluted with methanol (2 mL). The solution was filtered and the filtrate was purified by prep-HPLC (method B) to give compound 9q (10 mg, 56% yield) as a white solid. ESI m/z: 643.3 (M+1)$^+$. $^1$H NMR (500 MHz, DMSO$_{d6}$) δ 9.73 (s, 1H), 8.99 (s, 1H), 8.11 (s, 1H), 7.48 (s, 1H), 7.33 (dd, J=8.3, 1.7 Hz, 1H), 6.94 (d, J=8.4 Hz, 1H), 6.81 (d, J=8.3 Hz, 1H), 6.63 (d, J=2.3 Hz, 1H), 6.50 (dd, J=8.2, 2.3 Hz, 1H), 2.94-2.60 (m, 4H), 2.33-2.07 (m, 10H), 1.96-1.51 (m, 10H), 1.37-1.21 (m, 8H), 1.14 (t, J=14.1 Hz, 2H), 1.00 (s, 3H), 0.98 (s, 3H) ppm.

Example 23

Figure 3B:
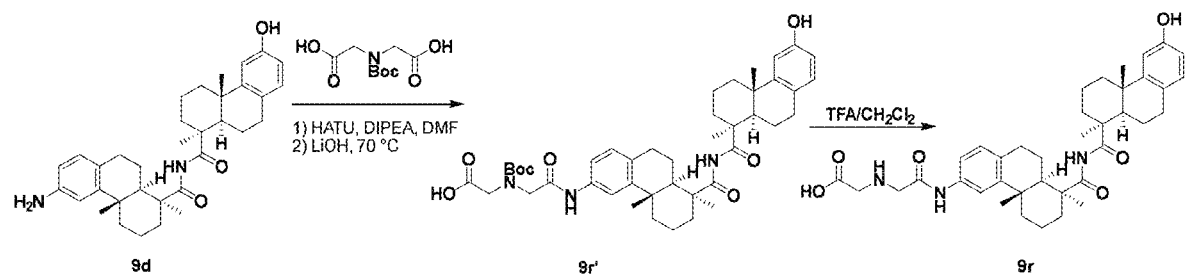

This example demonstrates methods for making the final compound 9r in Table 1, above. This example refers to the compound numbering in FIG. 1 and the synthesis was shown in FIG. 3b.

2-[({[(4bS,8S,8aR)-8-{[(1S,4aS,10aR)-6-Hydroxy-1, 4a-dimethyl-1,2,3,4,4a,9,10,10a-octahydro-phenanthrene-1-carbonyl]carbamoyl}-4b,8-dim-ethyl-4b,5,6,7,8,8a,9,10-octahydrophenanthren-3-yl] carbamoyl}methyl)amino]acetic Acid; Trifluoroacetic Acid Salt (9r)

To a solution of Boc-iminodiacetic Acid (30 mg, 0.13 mmol) in DMF (0.5 mL) were added HATU (60 mg, 0.16 mmol), and DIPEA (72 mg, 0.56 mmol) at 25° C. The resulting mixture was stirred at this temperature for an hour. The reaction mixture was cooled to 10-15° C., and to the mixture was then added 9d (30 mg, 57 μmol). After the reaction was stirred at 10-15° C. for 3 hours, 9d was totally consumed (as monitored by LCMS). To the reaction mixture was added aq. lithium hydroxide (1 M, 0.5 mL). The mixture was then stirred at 70° C. for 2 hours. After the reaction was cooled to rt and filtered through a syringe filter membrane, the filtrate was directly separated by reversed phase flash chromatography (5-90% acetonitrile in water (with 0.1% TFA) to afford white solids. The solids were dissolved in DCM (0.4 mL) and to the solution was added TFA (0.1 mL) slowly at rt, and the reaction was stirred at rt for 2 hours. The volatiles were removed in vacuo and the residue was purified by prep-HPLC (method B) to give 9r (10 mg, 28% yield) as a white solid. ESI m/z: 644.4 (M+1)$^+$. $^1$H NMR (500 MHz, DMSO$_{d6}$) δ 10.24 (s, 1H), 9.00 (s, 1H), 8.12 (s, 1H), 7.48 (s, 1H), 7.32 (d, J=7.9 Hz, 1H), 7.01 (d, J=8.5 Hz, 1H), 6.82 (d, J=8.3 Hz, 1H), 6.67-6.60 (m, 1H), 6.51 (d, J=8.4 Hz, 1H), 3.88-3.76 (m, 4H), 2.96-2.61 (m, 5H), 2.32-2.22 (m, 2H), 2.19-2.08 (m, 4H), 1.97-1.78 (m, 4H), 1.69-1.54 (m, 4H), 1.39-1.20 (m, 8H), 1.22-1.08 (m, 2H), 1.01 (s, 3H), 0.99 (s, 3H) ppm. $^{19}$F NMR (376 MHz, DMSO$_{d6}$) δ −73.44 ppm.

Example 24

Figure 3C:
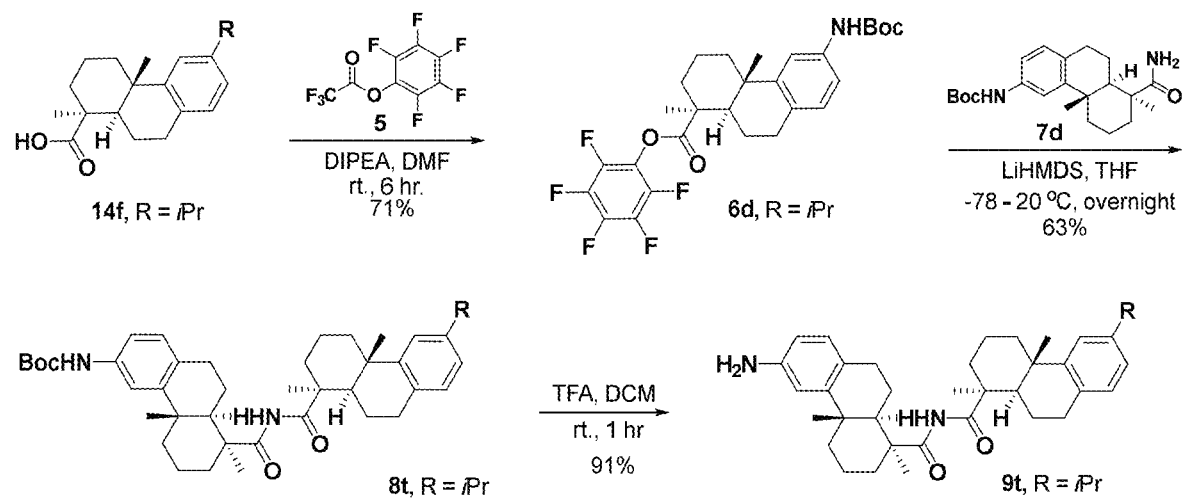

This example demonstrates methods for making the final compound 9t in Table 1, above. This example refers to the compound numbering in FIG. 1, and the synthesis is shown in FIG. 3c.

(1S,4aS,10aR)-6-Amino-N-((1R,4aS,10aR)-7-iso-propyl-1,4a-dimethyl-1,2,3,4,4a,9,10,10a-octahydro-phenanthrene-1-carbonyl)-1,4a-dimethyl-1,2,3,4,4a, 9,10,10a-octahydrophenanthrene-1-carboxamide (9t)

Step 1: making (1R,4aS,10aR)-Perfluorophenyl 7-isopropyl-1,4a-dimethyl-1,2,3,4,4a,9,10,10a-octa-hydrophenanthrene-1-carboxylate (6d)

Using the same procedure for making 6b except replacing 4 with 14f (dehydroabietic acid, CAS No. 1740-19-8, 0.50 g, 1.7 mmol), compound 6d (0.30 g, 39% yield) as colorless oil was obtained after flash chromatography (5% ethyl acetate in petroleum ether). $^1$HNMR (500 MHz, DMSO$_{d6}$) δ 7.2 (d, J=7.0 Hz, 1H), 7.00-6.99 (m, 1H), 6.88 (s, 1H), 2.94-2.78 (m, 3H), 2.38-2.36 (m, 1H), 2.25-2.23 (m, 1H), 2.02-1.73 (m, 5H), 1.46-1.40 (m, 2H), 1.36 (s, 3H), 1.19 (s, 3H), 1.15 (d, J=7.0 Hz, 6H) ppm.

Step 2: making tert-Butyl (4bS,8S,8aR)-8-((1R,4aS, 10aR)-7-isopropyl-1,4a-dimethyl-1,2,3,4,4a,9,10, 10a-octahydrophenanthrene-1-carbonylcarbamoyl)-4b,8-dimethyl-4b,5,6,7,8,8a,9,10-octahydrophenanthren-3-ylcarbamate (8t)

Using the same procedure for making 8d, an amide coupling reaction of 7d (40 mg, 0.11 mmol) with 6d (60 mg, 0.13 mmol) provided pure 8t (10 mg, 14% yield). ESI m/z: 655 (M+1)$^+$.

Step 3: making (1S,4aS,10aR)-6-Amino-N-((1R, 4aS,10aR)-7-isopropyl-1,4a-dimethyl-1,2,3,4,4a,9, 10,10a-octahydrophenanthrene-1-carbonyl)-1,4a-dimethyl-1,2,3,4,4a,9,10,10a-octahydrophenanthrene-1-carboxamide (9t)

To a solution of compound 8t (10 mg, 15 μmol) in DCM (2 mL) was added dropwise TFA (0.2 mL) at 0° C. The reaction was stirred at 0° C. for an hour until Boc was removed, which was monitored by LCMS. The reaction mixture was diluted with DCM (20 mL) and washed with sat. aq. sodium bicarbonate, water and brine. The organic solution was dried over sodium sulfate and concentrated in vacuo to give compound 9t (5 mg, 59% yield) as a white solid. ESI m/z: 555.2 (M+1)$^+$. $^1$H NMR (500 MHz, methanol-$d_4$) δ 7.19 (d, J=8.0 Hz, 1H), 7.00 (d, J=9.5 Hz, 1H), 6.88 (s, 1H), 6.81 (d, J=8.5 Hz, 1H), 6.72 (d, J=2.5 Hz, 1H), 6.55-6.53 (m, 1H), 2.88-2.74 (m, 5H), 2.43-2.40 (m, 1H), 2.31-2.28 (m, 3H), 2.11-1.99 (m, 2H), 1.94-1.86 (m, 2H), 1.81-1.67 (m, 4H), 1.52-1.46 (m, 2H), 1.42 (s, 4H), 1.35 (s, 3H), 1.32-1.30 (m, 3H), 1.26 (s, 3H), 1.23 (s, 3H), 1.21 (s, 3H), 1.13 (s, 3H) ppm.

Example 25

Figure 3D:
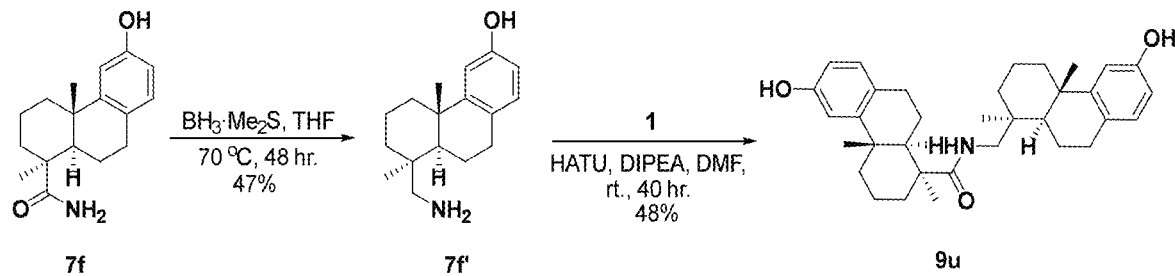

This example demonstrates methods for making the final compound 9u in Table 1, above. This example refers to the compound numbering in FIG. 1, and the synthesis is shown in FIG. 3d.

Step 1: making (4bS,8S,8aR)-8-(Aminomethyl)-4b, 8-dimethyl-4b,5,6,7,8,8a,9,10-octahydro-phenanthren-3-ol (7f)

To a solution of 7f (0.10 g, 0.37 mmol) in THF (10 mL) was added borane-methyl sulfide complex (2 M in THF, 1.9 mL, 3.7 mmol) by syringe at rt. The mixture was then stirred at 70° C. for 48 hours until the reaction was completed, as monitored by LC-MS. After the reaction was cooled, the reaction mixture was poured into cold methanol (50 mL) at 0-5° C. The volatiles were removed in vacuo. The residue was purified by prep-HPLC (method B) to afford compound 7f' (45 mg, 47% yield) as a white solid. ESI m/z: 260.2 (M+1)$^+$.

Step 2: making (1S,4aS,10aR)—N-{[(1S,4aS, 10aR)-6-Hydroxy-1,4a-dimethyl-1,2,3,4,4a,9,10, 10a-octahydrophenanthren-1-yl]methyl}-6-hydroxy-1,4a-dimethyl-1,2,3,4,4a,9,10,10a-octahydrophenanthrene-1-carboxamide (9u)

To a solution of podocarpic acid 1 (10 mg, 36 μmol) in DMF (0.5 mL) were added HATU (21 mg, 55 μmol) and DIPEA (14 mg, 0.11 mmol) at 25° C. The resulting mixture was stirred at this temperature for 16 hours. To the mixture was then added compound 7f' (10 mg, 39 μmol). After the reaction was stirred at 25° C. for 40 hours, which was monitored by LCMS, the reaction mixture was directly purified by prep-HPLC (method A) to give compound 9u (9 mg, 48% yield) as a white solid. ESI m/z: 516.3 (M+1)$^+$. $^1$H NMR (500 MHz, DMSO-$_{d6}$) δ 8.93 (br s, 2H), 6.77 (dd, J=8.2, 5.3 Hz, 2H), 6.70 (t, J=5.9 Hz, 1H), 6.62 (s, 2H), 6.47 (dt, J=8.2, 2.1 Hz, 2H), 3.70-3.62 (m, 1H), 2.87-2.55 (m, 5H), 2.22-2.09 (m, 4H), 2.02-1.80 (m, 4H), 1.72-1.13 (m, 14H), 1.10-1.04 (m, 1H), 1.01 (s, 3H), 0.93 (s, 3H), 0.87-0.81 (m, 1H) ppm.

Example 26

Figure 3E:
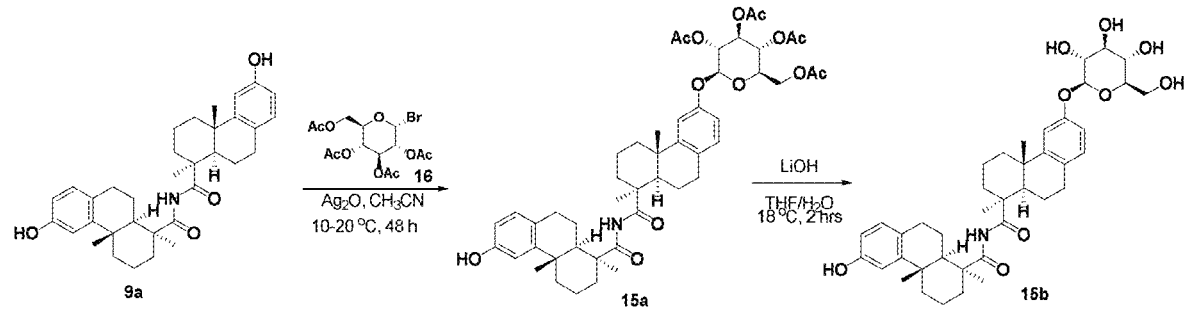

This example demonstrates a method for making compound 15b in Table 1, above. This example refers to the compound numbering in FIG. 1, and the synthesis is shown in FIG. 3e.

The glucose-analog 15b was obtained from basic hydrolysis of acetyl ester 15a, where 15a was formed by treating bis-phenol 9a with bromo-glucose 16.

(1S,4aS,10aR)—N-((1S,4aS,10aR)-1,4a-dimethyl-6-((2S,3R,4S,5S,6R)-3,4,5-trihydroxy-6-(hydroxymethyl)tetrahydro-2H-pyran-2-yloxy)-1,2,3,4,4a,9,10, 10a-octahydrophenanthrene-1-carbonyl)-6-hydroxy-1,4a-dimethyl-1,2,3,4,4a,9,10,10a-octahydrophenanthrene-1-carboxamide (15b)

To a solution of 9a (10 mg, 19 μmol) in acetonitrile (0.2 mL) was added [(2R,3R,4S,5R,6S)-3,4,5-tris(acetyloxy)-6-bromooxan-2-yl]methyl acetate (16, 10 mg, 24 μmol) and silver(I) oxide (15 mg, 64 μmol). The resulting mixture was stirred at 10-20° C. for 48 h. The mixture was filtered through Celite and the filtrate was concentrated in vacuo. The residue (crude 15a) was dissolved in THF/water (v/v=4, 1 mL) and to the solution was added lithium hydroxide (0.50 mg, 0.021 mmol). After the reaction was stirred at 18° C. for 2 h, the mixture was filtered and the filtrate was directly purified by prep-HPLC (method B) to give 15b (2 mg, 15% yield) as a white solid. ESI m/z: 692 (M+1)$^+$. $^1$H NMR (500 MHz, DMSO-$_{d6}$) δ 9.01 (s, 1H), 8.13 (s, 1H), 6.96-6.89 (m, 2H), 6.85-6.75 (m, 2H), 6.66-6.61 (m, 1H), 6.57 (s, 1H), 5.26 (d, J=5.1 Hz, 1H), 5.07 (d, J=4.4 Hz, 1H), 4.99 (d, J=6.1 Hz, 1H), 4.80 (d, J=7.8 Hz, 1H), 4.52-4.49 (m, 1H), 2.32-2.22 (m, 4H), 2.21-2.09 (m, 4H), 1.93-1.78 (m, 5H), 1.66-1.54 (m, 4H), 1.32-1.22 (m, 14H), 1.15 (s, 3H), 1.00 (d, J=7.7 Hz, 6H) ppm.

Example 27

Figure 4:
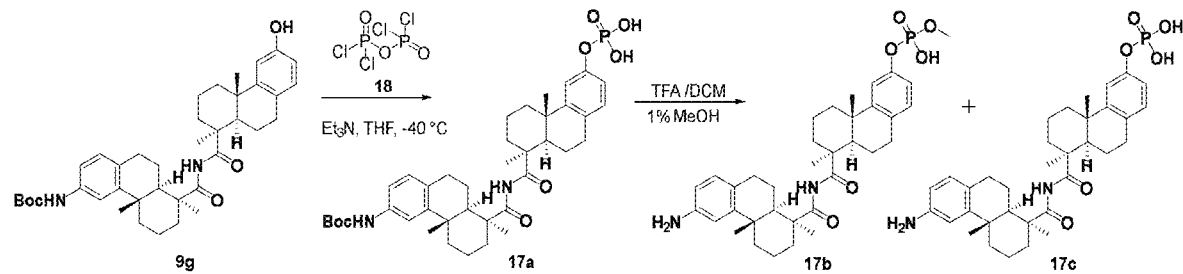

This example demonstrates a method for making compounds 17b and 17c in Table 1, above. This example refers to the compound numbering in FIG. 4.

The phosphoric acid-analog 17a was obtained from the treatment of phenol 9g with diphosphoryl chloride 18. Compounds 17b and 17c were obtained from the acidic deprotection of 17a with TFA. The phosphoric acid-analog 17c was soluble in water under basic and neutral conditions, but not stable at pH 5, and was converted to methoxy phosphate 17b in the presence of methanol; the latter was found to be stable at pH 5-8.

(4bS,8S,8aR)-8-((1S,4aS,10aR)-6-Amino-1,4a-dimethyl-1,2,3,4,4a,9,10,10a-octahydrophenanthrene-1-carbonylcarbamoyl)-4b,8-dimethyl-4b,5,6,7,8,8a,9, 10-octahydrophenanthren-3-yl methyl hydrogen phosphate (17b); (4bS,8S,8aR)-8-((1S,4aS,10aR)-6-Amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-yl dihydrogen phosphate (17c)

To a stirred solution of 9g (10 mg, 16 μmol) in THF (0.1 mL) at −40° C. was added diphosphoryl chloride 18 (10 mg, 40 μmol) and TEA (16 mg, 0.16 mmol). After the reaction was stirred at −40° C. for an hour, the reaction mixture was quenched with water and the pH was adjusted with saturated aqueous sodium bicarbonate solution to pH 8. The solution was then acidified with aqueous hydrochloride (1 N) to pH 2, and extracted with ethyl acetate. The combined organics were washed with brine, dried over sodium sulfate, and concentrated to provide a crude 17a. To a solution of 17a (11 mg) in about 1% methanol in methylene chloride (1 mL) was added TFA (0.1 mL), and the resulting mixture was stirred at 25° C. for an hour. The volatiles were removed, and the residue was purified by prep-HPLC (method B) to provide 17b (3 mg, 310% yield) as a white solid and 17c (2 mg, 20% yield) as a white solid.

For 17b: ESI m/z: 623 (M+1)$^+$. $^1$H NMR (500 MHz, DMSO-$_{d6}$) δ 8.13 (s, 1H), 7.04 (s, 1H), 7.00 (d, J=8.4 Hz, 1H), 6.96-6.89 (m, 1H), 6.89-6.84 (m, 2H), 6.76-6.67 (m, 1H), 3.60 (d, J=11.4 Hz, 3H), 2.89 (t, J=17.0 Hz, 2H), 2.81-2.68 (m, 1H), 2.56-2.50 (m, 4H), 2.33-2.23 (m, 2H), 2.16 (d, J=12.3 Hz, 4H), 1.93-1.80 (m, 4H), 1.67-1.55 (m, 4H), 1.33-1.20 (m, 8H), 1.15 (t, J=10.4 Hz, 2H), 1.00 (s, 6H) ppm.

For 17c: ESI m/z: 609 (M+1)$^+$. $^1$H NMR (500 MHz, DMSO-$_{d6}$) δ 8.11 (s, 1H), 7.20 (s, 1H), 7.00-6.91 (m, 2H), 6.86 (d, J=8.5 Hz, 1H), 6.68 (d, J=8.1 Hz, 1H), 6.48 (s, 1H), 6.34 (d, J=7.9 Hz, 1H), 2.87 (d, J=14.4 Hz, 2H), 2.80-2.57 (m, 5H), 2.31-2.22 (m, 2H), 2.19-2.07 (m, 4H), 1.95-1.73 (m, 4H), 1.69-1.48 (m, 4H), 1.27 (d, J=5.9 Hz, 8H), 1.21-1.06 (m, 2H), 0.99 (s, 6H) ppm.

Example 28

The structures, calculated Log P values, MS and HPLC results for the above compounds were summarized in Table 4.

TABLE 4

Chemical-Physical Properties of Payload

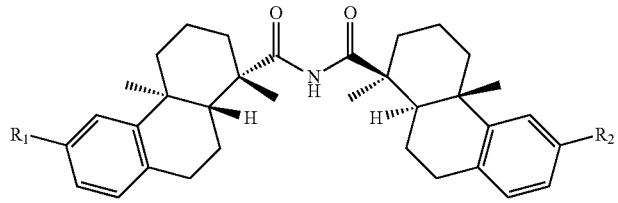

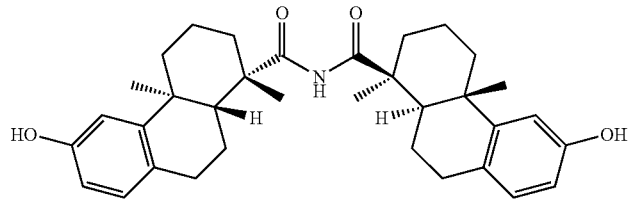 [SMILES: C[C@]1(C(=O)NC(=O)[C@@]2(C)CCC[C@]3(C)c4cc(O)ccc4CC[C@@H]23)CCC[C@]2(C)c3cc(O)ccc3CC[C@@H]12]

9u

| | R1 | R2 | CLogP | MS M + H (100%) | HPLC Purity (%) | HPLC Rt (min) |
|---|---|---|---|---|---|---|
| 9a | OH | OH | +++ | 530.3 | 100 | 2.01 |
| 9b | OH | OCH$_2$CH$_2$OH | +++ | 574.2 | 100 | 2.00 |
| 9c | OH | OCH$_2$CH$_2$NH$_2$ | +++ | 572.4 | 100 | 8.72 |
| 9d | OH | NH$_2$ | +++ | 529.3 | 95 | 8.66 |
| 9e | OH | N-Piperazine | +++ | 598.4 | 100 | 8.99 |
| 9f | OH | N(CH$_3$)$_2$ | +++ | 557.4 | 95 | 10.07 |
| 9h | OH | NH-Gly | +++ | 586.2 | 100 | 7.51 |
| 9i | OH | NH-β-Ala | +++ | 600.3 | 97 | 8.43 |
| 9j | OH | NH-Ser | ++ | 616.3 | 92 | 6.38 |
| 9k | OH | NH-Sar | +++ | 599.4 | 99 | 7.55 |
| 9l | OH | NH-Lys | +++ | 657.5 | 96 | 6.82 |
| 9m | OH | NH-His | +++ | 666.3 | 99 | 6.85 |
| 9n | OH | NH-Asp | ++ | 644.3 | 99 | 6.69 |
| 9o | OH | NH-Glu | ++ | 658.3 | 100 | 7.41 |
| 9p | OH | CH$_2$ NH$_2$ | +++ | 526.2 | 99 | 7.48 |
| 9q | OH | NHCO(CH$_2$)$_3$CO$_2$H | +++ | 643.3 | 100 | 9.35 |
| 9r | OH | NHCOCH$_2$NH$_2$CH$_2$CO$_2$H | + | 644.4 | 100 | 7.7 |
| 9t | NH2 | iPr | +++ | 555.2 | 98 | 11.4 |
| 9u | OH | OH | +++ | 516.3 | 100 | 10.6 |
| 15b | OH | Glucose | ++ | 692.2 | 90 | 7.24 |
| 17b | NH2 | OPO$_3$HMe | +++ | 623.2 | 99 | 6.42 |
| 17c | NH2 | OPO$_3$H$_2$ | +++ | 609.1 | 98 | 5.83 |

6 < +++ < 9; 4 < ++ < 6; 2 < + < 4

Example 29

Figure 5:
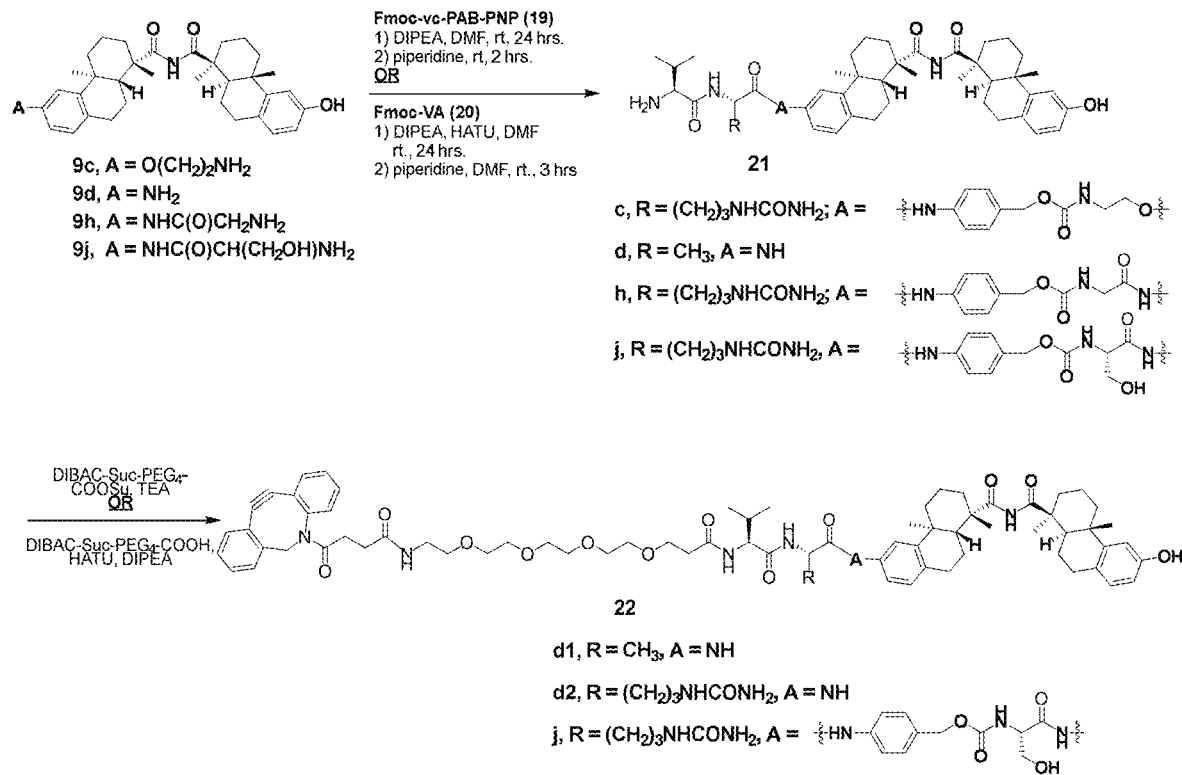

This example demonstrates general methods for making VA-payloads, VC-payloads, and VC-PAB-payloads, represented by compounds 21c, 21d, 21h, and 21j. This example refers to the compound numbering in FIG. 5.

Compound 21d was obtained from an amide coupling reaction of 9d with Fmoc-VA-acid (20) followed by standard Fmoc deprotection conditions. Compounds 21c, 21d, 21h, and 21j were obtained from treatment of 9c, 9d, 9h or 9j with Fmoc-L-valine-L-citrulline-p-aminobenzyl alcohol p-nitrophenyl carbonate (Fmoc-VC-PAB-PNP, 19) followed by standard Fmoc deprotection conditions, respectively.

4-((S)-2-((S)-2-Amino-3-methylbutanamido)-5-ureidopentanamido)benzyl 2-((4bS,8S,8aR)-8-((1S,4aS,10aR)-6-hydroxy-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-yloxy)ethylcarbamate (21c)

To a solution of 9c (18 mg, 31 μmol) in DMF was added Fmoc-VC-PAB-PNP 19 (16 mg, 21 μmol) and DIPEA (20 mg, 0.16 mmol), and the mixture was stirred at 20-25° C. for 24 h. To the resulting mixture was added piperidine (0.1 mL), and the mixture was stirred at 25° C. for additional 2 h until Fmoc was removed from the intermediate as monitored by LC-MS. The mixture was filtered through a membrane, and the filtrate was directly purified by prep-HPLC (method B) to give 21c (14 mg, 50% yield) as a white solid. ESI m/z: 978 (M+1)$^+$. $^1$H NMR (500 MHz, DMSO-$d_6$) δ 10.22 (s, 1H), 9.04 (s, 1H), 8.71 (d, J=7.5 Hz, 1H), 8.12 (s, 2H), 7.59 (d, J=8.3 Hz, 2H), 7.42 (t, J=5.4 Hz, 1H), 7.29 (d, J=8.2 Hz, 2H), 6.94 (d, J=8.5 Hz, 1H), 6.84-6.76 (m, 2H), 6.67 (d, J=8.4 Hz, 1H), 6.64 (s, 1H), 6.51 (dd, J=8.1, 2.0 Hz, 1H), 6.12 (s, 1H), 5.52 (s, 2H), 4.96 (s, 2H), 4.51 (d, J=5.1 Hz, 1H), 3.92 (s, 2H), 3.66 (d, J=5.7 Hz, 1H), 3.32 (d, J=5.6 Hz, 2H), 3.13-2.93 (m, 2H), 2.85 (t, J=18.0 Hz, 2H), 2.77-2.63 (m, 2H), 2.26 (d, J=7.2 Hz, 2H), 2.22-2.03 (m, 4H), 1.89-1.82 (m, 4H), 1.79-1.69 (m, 1H), 1.68-1.53 (m, 4H), 1.46-1.40 (m, 2H), 1.27 (d, J=3.3 Hz, 8H), 1.19-1.08 (m, 4H), 1.03-0.89 (m, 12H) ppm.

(1S,4aS,10aR)-6-((S)-2-((S)-2-Amino-3-methylbutanamido)propanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (21d)

To a solution of 9d (53 mg, 0.10 mmol) in DMF (1 mL) were added Fmoc-Val-Ala-OH 20 (41 mg, 0.10 mmol), HATU (38 mg, 0.1 mmol), and DIPEA (26 mg, 0.20 mmol). After the reaction was stirred at 25° C. for 24 h, 9d was consumed according to LC-MS. To the mixture was then added piperidine (0.1 mL) and the resulting solution was stirred at 25° C. for another 3 h. The mixture was filtered, and the filtrate was concentrated in vacuo and the residue was directly purified by prep-HPLC (method B) to give compound 21d (45 mg, 64% yield) as a white solid. ESI m/z: 699 (M+1)$^+$. $^1$H NMR (500 MHz, methanol-d4) δ 8.40 (s, 1H), 7.47 (s, 1H), 7.32 (d, J=8.0 Hz, 1H), 7.03 (d, J=8.3 Hz, 1H), 6.88 (d, J=8.2 Hz, 1H), 6.72 (d, J=2.4 Hz, 1H), 6.56 (dd, J=8.3, 2.4 Hz, 1H), 4.60-4.48 (m, 1H), 3.22-3.11 (m, 1H), 3.02-2.93 (m, 1H), 2.92-2.76 (m, 3H), 2.74-2.70 (m, 1H), 2.43-2.31 (m, 3H), 2.28 (d, J=14.1 Hz, 3H), 2.16-1.96 (m, 3H), 1.81 (s, 1H), 1.78-1.65 (m, 4H), 1.53-1.42 (m, 4H), 1.38 (d, J=5.3 Hz, 6H), 1.33-1.22 (m, 2H), 1.14 (d, J=6.6 Hz, 6H), 1.09 (d, J=18.6 Hz, 6H) ppm.

{4-[(2S)-2-[(2S)-2-Amino-3-methylbutanamido]-5-(carbamoylamino)pentanamido]phenyl} methyl N-({[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl)carbamate (21h)

Using the same procedure for making 21c, except 9h was used instead of 9c. 21h (85 mg, 32% yield) was obtained as a white solid. ESI m/z: 990 (M+1)$^+$. $^1$H NMR (500 MHz, methanol-$d_4$) δ 8.40 (s, 1H, NH of imidine), 7.58 (d, J=8.5 Hz, 2H), 7.50 (s, 1H), 7.37 (d, J=8.5 Hz, 2H), 7.30 (d, J=7.5 Hz, 1H), 7.02 (d, J=8.3 Hz, 1H), 6.88 (d, J=8.3 Hz, 1H), 6.72 (d, J=2.4 Hz, 1H), 6.56 (dd, J=8.2, 2.5 Hz, 1H), 5.10 (s, 2H), 4.66-4.52 (m, 1H), 3.92 (s, 2H), 3.75 (d, J=5.7 Hz, 1H), 3.26-3.03 (m, 3H), 3.02-2.75 (m, 4H), 2.42-2.22 (m, 7H), 2.14-1.98 (m, 5H), 1.97-1.87 (m, 1H), 1.85-1.59 (m, 6H), 1.40 (t, J=15.9 Hz, 8H), 1.34-1.27 (m, 3H), 1.16-1.12 (m, 6H), 1.10 (d, J=6.9 Hz, 3H), 1.07 (d, J=6.9 Hz, 3H) ppm.

{4-[(2S)-2-[(2S)-2-Amino-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (21j)

Using the same procedure for making 21c, except 9j was used instead of 9c. 21j (22 mg, 40% yield) was obtained as a white solid. ESI m/z: 1021 (M+1)$^+$. $^1$H NMR (400 MHz, DMSO-$d_6$) δ 10.02 (s, 1H), 9.82 (s, 1H), 9.00 (s, 1H), 8.69-8.65 (m, 1H), 8.11-8.00 (m, 4H), 7.65-7.53 (m, 3H), 7.40-7.30 (m, 3H), 7.30-7.20 (m, 1H), 6.96 (d, J=8.0 Hz, 1H), 6.81 (d, J=8.0 Hz, 1H), 6.65-6.61 (m, 1H), 6.50 (dd, J=8.0 Hz, 2.0 Hz, 1H), 6.00-5.95 (m, 1H), 5.48 (s, 2H), 5.00-4.95 (m, 3H), 4.60-4.40 (m, 1H), 4.25-4.20 (m, 1H), 3.65-3.55 (m, 4H), 3.15-2.55 (m, 10H), 2.40-2.20 (m, 3H), 2.20-2.00 (m, 5H), 2.00-1.80 (m, 4H), 1.86-1.55 (m, 6H), 1.27 (d, J=4.8 Hz, 9H), 1.20-1.10 (m, 2H), 0.97-0.90 (m, 6H) ppm.

Example 30

This example demonstrates general methods for making the linker-payloads 22d1, 22d2, and 22j. This example refers to the compound numbering in FIG. 5.
General Procedure to Make Linker-Payload 22:

To a solution of compound 21 (5-30 mg, 1 equiv.) in DMF (0.5 mL) were added a solution of commercially available DIBAC-Suc-PEG$_4$-COOSu or DIBAC-Suc-PEG$_4$-COOH, or BCN-PEG$_4$-COOSu (1.2 equiv.) in THF (0.5 mL) and then TEA (2 equiv.) at rt. The mixture was stirred at rt until 21 was consumed, as monitored by LC-MS. The reaction mixture was concentrated in vacuo and the residue was directly purified by prep-HPLC to yield 22 as a white solid.

Example 31

This example demonstrates general methods for making the linker-payload 22d1. This example refers to the compound numbering in FIG. 5.

1-(4-{2-Azatricyclo[10.4.0.0$^{4,9}$]hexadeca-1(12),4(9),5,7,13,15-hexaen-10-yn-2-yl}-4-oxobutanamido)-N-[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]-3,6,9,12-tetraoxapentadecan-15-amide (22d1)

Using the General procedure to make linker-payload 22, 22d1 (10 mg, 28% yield) was obtained as a white solid. ESI m/z: 1234 (M+H)$^+$. $^1$H NMR (500 MHz, methanol-$d_4$) δ 7.65 (d, J=7.4 Hz, 1H), 7.62-7.51 (m, 2H), 7.48-7.43 (m, 3H), 7.39-7.30 (m, 2H), 7.27-7.23 (m, 1H), 7.00 (d, J=8.5 Hz, 1H), 6.88 (d, J=8.0 Hz, 1H), 6.72 (d, J=2.4 Hz, 1H), 6.57-6.54 (m, 1H), 5.15-5.10 (m, 1H), 4.62 (s, 6H), 4.52-4.45 (m, 1H), 4.22-4.02 (m, 1H), 3.77-3.64 (m, 3H), 3.60-3.51 (m, 11H), 3.46-3.41 (m, 2H), 3.24 (t, J=5.5 Hz, 2H), 2.99-2.66 (m, 5H), 2.57-2.51 (m, 1H), 2.37-2.24 (m, 6H), 2.21-2.12 (m, 1H), 2.09-1.95 (m, 5H), 1.74-1.65 (m, 4H), 1.47-1.41 (m, 4H), 1.39-1.35 (m, 6H), 1.31-1.22 (m, 2H), 1.14-1.10 (m, 6H), 1.05-0.97 (m, 6H) ppm.

Example 32

This example demonstrates general methods for making the linker-payload 22d2. This example refers to the compound numbering in FIG. 5.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (22d2)

Using the General procedure to make linker-payload 22, 22d2 (7 mg, 44% yield) was obtained as a white solid. ESI m/z: 735.0 (M/2+H)⁺. ¹H NMR (500 MHz, methanol-$d_4$) δ 7.65-7.62 (m, 3H), 7.59-7.57 (m, 1H), 7.44-7.42 (m, 3H), 7.39-7.18 (m, 7H), 6.96 (d, J=8.5 Hz, 1H), 6.88 (d, J=8.0 Hz, 1H), 6.71 (s, 1H), 6.56-6.54 (m, 1H), 5.15-5.10 (m, 3H), 4.64 (s, 5H), 4.53-4.49 (m, 1H), 4.22 (d, J=8.0 Hz, 1H), 3.77-3.66 (m, 3H), 3.59-3.51 (m, 11H), 3.45-3.42 (m, 2H), 3.24 (t, J=5.5 Hz, 2H), 3.15-3.08 (m, 1H), 2.96-2.90 (m, 2H), 2.84-2.68 (m, 3H), 2.55 (t, J=6.0 Hz, 2H), 2.40-2.33 (m, 3H), 2.28-1.91 (m, 11H), 1.75-1.58 (m, 5H), 1.36-1.22 (m, 11H), 1.12-1.11 (m, 5H), 1.01-0.98 (m, 6H) ppm.

Example 33

This example demonstrates general methods for making the linker-payload 22j. This example refers to the compound numbering in FIG. 5.

{4-[(2S)-2-[(2S)-2-[1-(4-{2-Azatricyclo[10.4.0.0⁴,⁹] hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino) pentanamido]phenyl}methyl N-[(1S)-1-{[(4bS,8S, 8aR)-8-({[(1S,4aS,10aR)-6-hydroxy-1,4a-dimethyl-1,2,3,4,4a,9,10,10a-octahydrophenanthren-1-yl] formamido}carbonyl)-4b,8-dimethyl-4b,5,6,7,8,8a,9, 10-octahydrophenanthren-3-yl]carbamoyl}-2-hydroxyethyl]carbamate (22j)

Using the General procedure to make linker-payload 22, 22j (8 mg, 26% yield) was obtained as a white solid. ESI m/z: 778 (M/2+H)⁺. ¹H NMR (500 MHz, DMSO-$d_6$) δ 10.02 (s, 1H), 9.82 (s, 1H), 9.00 (s, 1H), 8.11 (m, 2H), 7.88 (d, J=8.5 Hz, 1H), 7.80-7.75 (m, 1H), 7.70-7.66 (m, 1H), 7.65-7.53 (m, 4H), 7.53-7.45 (m, 3H), 7.40-7.25 (m, 7H), 6.96 (d, J=8.5 Hz, 1H), 6.81 (d, J=8.0 Hz, 1H), 6.63 (d, J=2.5 Hz, 1H), 6.50 (dd, J=8.0 Hz, 2.0 Hz, 1H), 6.00-5.95 (m, 1H), 5.41 (s, 2H), 5.10-5.05 (m, 4H), 4.43-4.33 (m, 1H), 4.25-4.10 (m, 2H), 3.65-3.55 (m, 5H), 3.50-3.40 (m, 12H), 3.30-3.25 (m, 2H), 3.15-2.55 (m, 10H), 2.40-2.20 (m, 5H), 2.20-2.10 (m, 4H), 2.00-1.90 (m, 2H), 1.86-1.70 (m, 5H), 1.64-1.54 (m, 6H), 1.50-1.25 (m, 9H), 1.20-1.10 (m, 2H), 1.00 (m, 6H), 0.86 (d, J=6.5 Hz, 3H), 0.82 (d, J=6.5 Hz, 3H) ppm.

Example 34

Figure 6:
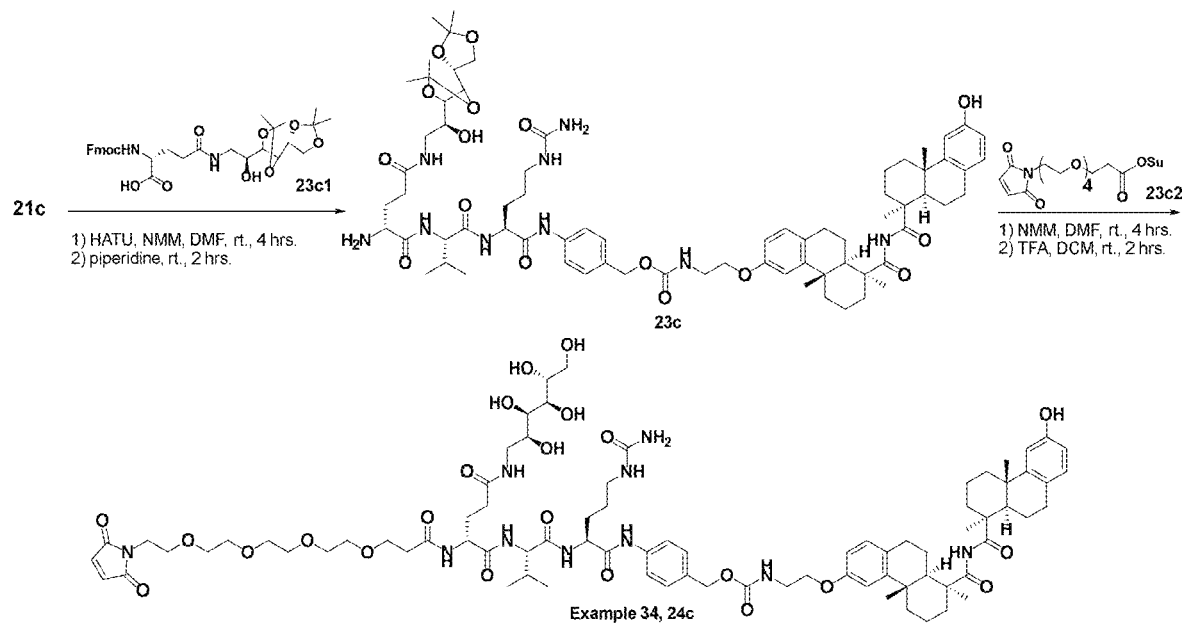

This example demonstrates general methods for making the linker-payloads that could be conjugated to an antibody via cysteine conjugation, represented by compound 24c. This example refers to the compound numbering in FIG. 6.

The amide coupling reaction of 21c with substituted Glu-acid (23c1) afforded 23c, which was treated with MC-PEG₄-CO₂Su ester (23c2) to afford the linker-payload 24c.

{4-[(2S)-5-(Carbamoylamino)-2-[(2S)-2-[(2R)-2-[1-(2,5-dioxo-2,5-dihydro-1H-pyrrol-1-yl)-3,6,9,12-tetraoxapentadecan-15-amido]-4-{[(2R,3S,4S,5S)-2, 3,4,5,6-pentahydroxyhexyl]carbamoyl}butanamido]-3-methylbutanamido]pentanamido]phenyl}methyl N-(2-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl] oxy}ethyl)carbamate (24c)

Step 1:
To a solution of 23c1 (15 mg, 25 µmol) in DMF (1 mL) were added compound 21c (14 mg, 14 µmol), HATU (9.5 mg, 25 µmoL) and NMM (4.9 mg, 49 µmoL). After the reaction was stirred at 25° C. for 4 h, 21c was consumed according to LC-MS. The resulting mixture was treated with piperidine (0.1 mL) and allowed to stir for 2 h. The mixture was directly purified by prep-HPLC to give 23c (8.0 mg, 45% yield) as a white solid. ESI m/z: 675 (M/2+1)⁺.
Step 2:
To a solution of 23c (10 mg, 7.4 µmol) in DMF (1 mL) were added 23c2 (7 mg, 22 µmol) and N-methylmorpholine (2.0 mg, 20 µmol), and the resulting mixture was stirred at 25° C. for 4 h. After the volatiles were removed in vacuo, the residue was then dissolved in DCM (1 mL) and to the solution was added TFA (0.1 mL). The resulting mixture was stirred at 25° C. for 2 h and was then concentrated in vacuo, and the residue was purified by prep-HPLC (method B) to give 24c (4.0 mg, 30% yield) as a white solid. ESI m/z: 1598 (M+1)⁺. ¹H NMR (500 MHz, DMSO-$d_6$) δ 9.71 (s, 1H), 8.98 (s, 1H), 8.20 (d, J=6.9 Hz, 1H), 8.13-8.08 (m, 2H), 8.06 (d, J=8.1 Hz, 1H), 7.74 (t, J=5.5 Hz, 1H), 7.61 (d, J=8.4 Hz, 2H), 7.40 (t, J=5.9 Hz, 1H), 7.27 (d, J=8.5 Hz, 2H), 7.02 (s, 2H), 6.93 (d, J=8.3 Hz, 1H), 6.84-6.77 (m, 2H), 6.67 (d, J=10.5 Hz, 1H), 6.63 (d, J=2.2 Hz, 1H), 6.50 (dd, J=8.2, 2.3 Hz, 1H), 5.98 (t, J=5.8 Hz, 1H), 5.40 (s, 2H), 4.95 (s, 2H), 4.33 (s, 3H), 4.23-4.13 (m, 1H), 3.92 (t, J=5.9 Hz, 2H), 3.62-3.54 (m, 6H), 3.51-3.45 (m, 18H), 3.07-2.62 (m, 9H), 2.43-2.35 (m, 2H), 2.32-2.21 (m, 4H), 2.19-2.09 (m, 6H), 2.09-2.01 (m, 1H), 1.93-1.70 (m, 8H), 1.68-1.53 (m, 6H), 1.51-1.33 (m, 2H), 1.27 (d, J=3.2 Hz, 9H), 1.14 (t, J=12.4 Hz, 2H), 1.00 (d, J=11.9 Hz, 6H), 0.87 (dd, J=20.2, 6.8 Hz, 6H) ppm.

Example 35

Figure 7:
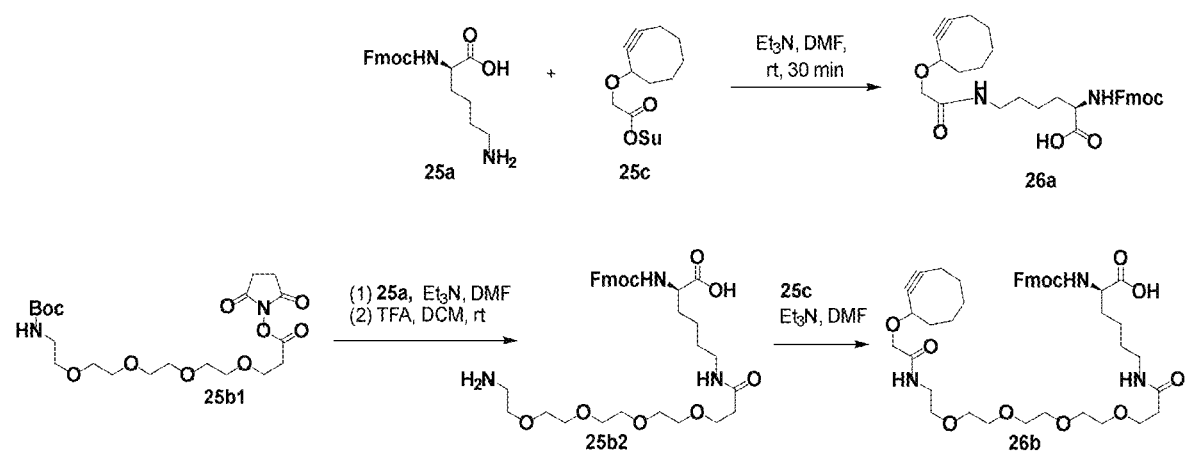
Figure 8:
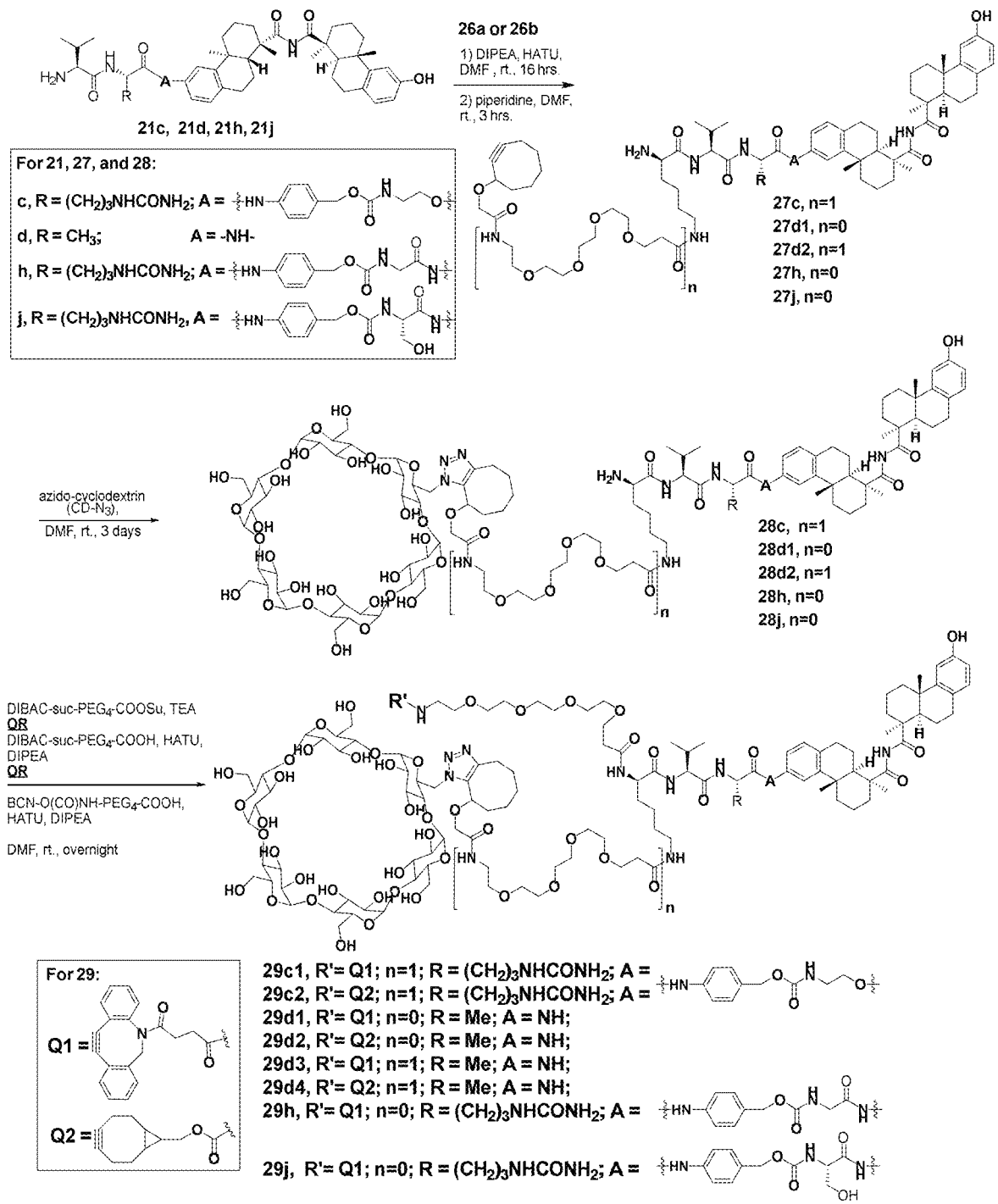

This example demonstrates general methods for making the linker-payloads that could be conjugated to an antibody via a click reaction of an azide with an alkyne. The synthesis of the intermediates for the linkers is shown in FIG. 7, and the synthesis of the linker-payloads is shown in FIG. 8. This example refers to the compound numbering in FIGS. 7 and 8.

FIG. 7 shows the synthesis of COT-(PEG₄)$_n$—(N²—Fmoc)dLys 26a and 26b. The amide coupling reaction of N²-Fmoc-D-lysine 25a with commercially available ester 25c provided 26a. The amide coupling reaction of N²-Fmoc-D-lysine 25a with commercially available ester 25b1, followed by Boc deprotection, provided 25b2; the amide coupling reaction of 25b2 with 25c provided 26b.

FIG. 8 shows a general synthesis of the linker-payloads 29, such as 29c1, 29c2, 29d1, 29d2, 29d3, 29d4, 29h, and 29j. The synthesis of linker-payloads 29 started from the amide coupling reactions of 26a or 26b with 21c, 21d, 21h, and 21j, independently, followed by Fmoc deprotection to form 27c, 27d1, 27d2, 27h, and 27j, independently, each of which underwent a 2+3 cyclization with cyclodextrin-azide to provide 28c, 28d1, 28d2, 28h, and 28j, respectively. Finally, amide coupling reactions of 28c, 28d1, 28d2, 28h, and 28j, with commercially available DIBAC-Suc-PEG₄-NHS ester or BCN-Carbamate-PEG₄-acid provided 29c1, 29c2, 29d1, 29d2, 29d3, 29d4, 29h, and 29j, respectively.

Example 36

This example demonstrates general methods for the synthesis of the intermediates for the linkers 26a and 26b. This example refers to the compound numbering in FIG. 7.

(2R)-6-[2-(Cyclooct-2-yn-1-yloxy)acetamido]-2-{[(9H-fluoren-9-ylmethoxy)carbonyl]amino}hexanoic Acid (26a)

To a solution of commercially available 25c (65 mg, 0.23 mmol) and Fmoc-D-Lys-OH (85 mg, 0.23 mmol) in DMF (2 mL) was added TEA (52 mg, 0.51 mmol), and the mixture was then stirred at rt for 30 min. The mixture was then concentrated in vacuo and the residue was directly purified by reversed phase flash chromatography (0-100% acetonitrile in water (0.05% TFA)) to give 26a (85 mg, yield 70%) as a white solid. ESI m/z: 533 (M+H)$^+$. $^1$H NMR (500 MHz, methanol-d4): δ 7.70 (d, J=7.5 Hz, 2H), 7.59 (t, J=8.0 Hz, 2H), 7.30 (t, J=7.5 Hz, 2H), 7.22 (t, J=7.4 Hz, 2H), 4.35-4.22 (m, 2H), 4.22-4.09 (m, 2H), 4.09-3.99 (m, 1H), 3.94-3.81 (m, 1H), 3.79-3.67 (m, 1H), 3.15 (t, J=6.9 Hz, 2H), 2.17-1.96 (m, 3H), 1.96-1.86 (m, 1H), 1.85-1.66 (m, 4H), 1.66-1.41 (m, 5H), 1.41-1.25 (m, 3H) ppm.

(24R)-24-(((9H-Fluoren-9-yl)methoxy)carbonylamino)-1-(cyclooct-2-ynyloxy)-2,18-dioxo-6,9,12,15-tetraoxa-3,19-diazapentacosan-25-oic Acid (26b)

Step 1:
To a mixture of compound 25b1 (4.6 g, 10 mmol) and Fmoc-(D)Lys-OH (25a, 3.6 g, 10 mmol) in DMF (10 mL) was added triethylamine (2.0 g, 20 mmol). The reaction mixture was stirred at 25° C. for an hour and then was diluted with DCM (100 mL) and washed with water and brine. The organics were dried over anhydrous sodium sulfate and concentrated in vacuo. The residue was purified by silica gel column chromatography (0-5% methanol in methylene chloride) to give 25b2' as a colorless oil (5.5 g, 77% yield). ESI m/z: 716.2 (M+H)$^+$. $^1$H NMR (500 MHz, DMSO-$d_6$) δ 7.89 (d, J=7.5 Hz, 2H), 7.84-7.80 (m, 1H), 7.74-7.72 (d, J=7.5 Hz, 2H), 7.61-7.59 (m, 1H), 7.42 (t, J=7.5 Hz, 2H), 7.33 (t, J=7.5 Hz, 2H), 6.76-6.74 (m, 1H), 4.28-4.21 (m, 3H), 3.93-3.85 (m, 1H), 3.58 (t, J=6.5 Hz, 2H), 3.48-3.47 (m, 12H), 3.16 (d, J=5.5 Hz, 1H), 3.07-2.97 (m, 2H), 2.28 (t, J=6.5 Hz, 2H), 2.02-1.94 (m, 1H), 1.71-1.56 (m, 2H), 1.36 (s, 9H), 1.23-1.15 (m, 6H) ppm.
Step 2:
To a solution of 25b2' (0.60 g, 0.84 mmol) in DCM (10 mL) was added TFA (2.0 mL) dropwise at 0° C. The reaction mixture was allowed to warm and stirred at 25° C. overnight until compound 25b2' was totally consumed by TLC. The volatiles were removed in vacuo to provide a residue: ESI m/z: 616.3 (M+H)$^+$.
Step 3:
To a solution of the above residue in DMF (10 mL) was added compound 25c (0.27 g, 0.98 mmol). A small amount of the reaction mixture was tested on wet pH paper and the pH of the reaction mixture was adjusted from pH 7 to 8 by addition of TEA (about 1.0 mL). The reaction was stirred at 25° C., monitored by LCMS, and completed in half an hour. The reaction mixture was then diluted with DCM (100 mL) and water (100 mL). The resulting mixture was acidified with hydrochloride (2 N) to pH 2. The organics were washed with water (80 mL) and brine, dried over anhydrous sodium sulfate, and concentrated in vacuo. The residue was purified by silica gel column chromatography (0-5% methanol in methylene chloride) to give the 26b as a colorless oil (0.38 g, 49% yield). ESI m/z: 780.3 (M+H)$^+$. $^1$H NMR (400 MHz, CDCl$_3$) δ 7.75 (d, J=7.6 Hz, 2H), 7.61 (t, J=7.6 Hz, 2H), 7.39 (t, J=7.6 Hz, 2H), 7.32-7.27 (m, 2H), 7.05-7.01 (m, 1H), 6.86-6.83 (m, 1H), 5.85 (d, J=7.6 Hz, 1H), 4.38-4.37 (m, 3H), 4.27-4.15 (m, 2H), 4.11-4.05 (m, 1H), 3.91-3.87 (m, 1H), 3.69 (t, J=5.6 Hz, 2H), 3.62-3.47 (m, 17H), 3.28-3.19 (m, 2H), 2.46 (t, J=5.6 Hz, 2H), 2.27-2.01 (m, 3H), 1.91-1.72 (m, 5H), 1.66-1.55 (m, 4H), 1.42-1.34 (m, 3H) ppm.

Example 37

This example demonstrates the methods for making the linker-payloads 27c, 27d1, 27d2, 27h, and 27j. This example refers to the compound numbering in FIG. 8.
General Procedures to Make the Intermediate Linker-Payload 27:
To a solution of compound 26a or 26b (1 equiv.) in DMF (30-50 mg of 26a or 26b per mL of DMF) were subsequently added HATU (1 equiv.) and—independently—compound 21c, 21d, 21h, or 21j (1 equiv.) at rt. The mixture was stirred at rt until the mixture was homogenous. To this mixture was slowly added DIPEA (5 equiv.) at rt via a syringe. The resulting mixture was stirred at rt overnight (16 h) until, independently, 21c, 21d, 21h, or 21j was consumed according to LC-MS. To the reaction mixture was then added piperidine (0.1 mL, excess) dropwise at rt, and the mixture was stirred for an additional 3 h until the Fmoc group was removed as monitored by LC-MS. The reaction mixture was directly purified by reversed phase flash chromatography or prep-HPLC (method B, basic condition) to—independently—give compounds 27c, 27d1, 27d2, 27h, and 27j, respectively, as white solids.

Example 38

This example demonstrates the methods for making the linker-payload 27c. This example refers to the compound numbering in FIG. 8.

{4-[(2S)-2-[(2S)-2-[(2R)-2-Amino-6-{1-[2-(cyclooct-2-yn-1-yloxy)acetamido]-3,6,9,12-tetraoxapentadecan-15-amido}hexanamido]-3-methylbutanamido]-5-(carbamoylamino)pentanamido]phenyl}methyl N-(2-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]oxy}ethyl)carbamate (27c)

Compound 27c (40 mg, 30% yield) as a white solid was obtained from the amide coupling reaction of 21c (85 mg, 87 μmol) with 26b (68 mg, 87 μmol), following the general procedure to make 27. ESI m/z: 759 (M/2+1)$^+$. $^1$H NMR (500 MHz, DMSO-$d_6$) δ 10.01 (s, 1H), 9.00 (s, 1H), 8.24-8.09 (m, 1H), 8.06-7.74 (m, 1H), 7.64-7.36 (m, 3H), 7.28 (d, J=8.3 Hz, 2H), 6.94 (d, J=8.5 Hz, 1H), 6.82 (d, J=8.4 Hz, 2H), 6.68 (d, J=7.6 Hz, 1H), 6.64 (s, 1H), 6.51 (d, J=6.4 Hz, 1H), 6.00 (s, 1H), 5.42 (s, 1H), 4.96 (s, 2H), 4.39 (s, 1H), 4.28-2.21 (m, 2H), 4.05 (s, 2H), 3.93 (t, J=5.6 Hz, 2H), 3.86-3.79 (m, 2H), 3.59 (t, J=6.5 Hz, 2H), 3.53-3.47 (m, 11H), 3.43 (t, J=5.9 Hz, 2H), 3.36 (s, 6H), 3.24 (dt, J=12.8, 6.1 Hz, 3H), 3.10-2.91 (m, 4H), 2.85 (t, J=17.2 Hz, 2H), 2.75-2.69 (m, 2H), 2.34-2.10 (m, 10H), 2.10-1.66 (m, 12H), 1.67-1.54 (m, 8H), 1.47-1.24 (m, 16H), 1.14 (t, J=13.3 Hz, 2H), 1.01 (d, J=11.8 Hz, 6H), 0.88 (s, 3H) 0.84 (s, 3H) ppm.

Example 39

This example demonstrates the methods for making the linker-payload 27d1. This example refers to the compound numbering in FIG. 8.

(1S,4aS,10aR)-6-((2S)-2-((2S)-2-((2R)-2-Amino-6-(2-(cyclooct-2-ynyloxy)acetamido)hexanamido)-3-methylbutanamido)propanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (27d1)

Compound 27d (30 mg, 47% yield) as a white solid was obtained from the amide coupling reaction of 26a (35 mg, 0.064 mmol) with 21d1 (45 mg, 0.064 mmol), following the general procedure to make 27. ESI m/z: 991 (M+1)$^+$. $^1$H NMR (500 MHz, methanol-$d_4$) δ 7.51 (d, J=1.5 Hz, 1H), 7.37 (dd, J=8.3, 2.0 Hz, 1H), 7.02 (d, J=8.3 Hz, 1H), 6.89 (d, J=8.4 Hz, 1H), 6.72 (d, J=2.4 Hz, 1H), 6.56 (dd, J=8.3, 2.5 Hz, 1H), 4.64-4.57 (m, 1H), 4.48 (q, J=7.1 Hz, 1H), 4.33-4.27 (m, 1H), 4.20 (d, J=6.7 Hz, 1H), 3.93 (m, 2H), 3.43 (t, J=6.6 Hz, 1H), 3.24 (t, J=6.9 Hz, 2H), 3.02-2.93 (m, 2H), 2.92-2.76 (m, 3H), 2.40-2.32 (m, 2H), 2.33-2.23 (m, 4H), 2.22-2.12 (m, 3H), 2.12-2.00 (m, 5H), 1.99-1.91 (m, 1H), 1.91-1.81 (m, 2H), 1.78-1.66 (m, 6H), 1.66-1.58 (m, 1H), 1.58-1.49 (m, 2H), 1.45 (d, J=7.1 Hz, 6H), 1.38 (d, J=4.0 Hz, 6H), 1.34-1.22 (m, 4H), 1.14 (d, J=7.0 Hz, 6H), 1.06-0.98 (m, 6H) ppm.

Example 40

This example demonstrates the methods for making the linker-payload 27d2. This example refers to the compound numbering in FIG. 8.

N-[(5R)-5-Amino-5-{[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}pentyl]-1-[2-(cyclooct-2-yn-1-yloxy)acetamido]-3,6,9,12-tetraoxapentadecan-15-amide (27d2)

Compound 27d2 (54 mg, 50% yield) as a white solid was obtained from the amide coupling reaction of 21d (60 mg, 0.086 mmol) with 26b, following the general procedure to make 27. ESI m/z: 620 (M/2+1)$^+$. $^1$H NMR (500 MHz, methanol-$d_4$) δ 7.61-7.48 (m, 1H), 7.35-7.29 (m, 1H), 7.02 (d, J=8.3 Hz, 1H), 6.88 (d, J=8.3 Hz, 1H), 6.71 (d, J=1.8 Hz, 1H), 6.56 (dd, J=8.2, 1.7 Hz, 1H), 4.52-4.44 (m, 1H), 4.27 (dd, J=21.9, 7.2 Hz, 2H), 4.03 (dd, J=15.1, 2.4 Hz, 1H), 3.96 (dt, J=22.5, 6.5 Hz, 1H), 3.89 (dd, J=15.1, 3.1 Hz, 1H), 3.75 (t, J=5.8 Hz, 2H), 3.64 (t, J=8.6 Hz, 12H), 3.60-3.54 (m, 3H), 3.44 (dd, J=11.7, 5.9 Hz, 2H), 3.23 (t, J=6.7 Hz, 2H), 3.02-2.91 (m, 1H), 2.91-2.74 (m, 3H), 2.46 (t, J=5.9 Hz, 2H), 2.40-2.31 (m, 3H), 2.26-2.22 (m, 5H), 2.21-1.79 (m, 12H), 1.77-1.65 (m, 6H), 1.62-1.53 (m, 3H), 1.47-1.43 (m, 5H), 1.38 (s, 3H), 1.37 (s, 3H), 1.33-1.22 (m, 3H), 1.14 (s, 3H), 1.12 (s, 3H), 1.06-0.95 (m, 6H) ppm.

Example 41

This example demonstrates the methods for making the linker-payload 27h. This example refers to the compound numbering in FIG. 8.

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-({[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl) carbamate (27h)

Compound 27h (65 mg, 62% yield) as a white solid was obtained from the amide coupling reaction of 21h (80 mg, 64 μmol) with 26a (53 mg, 97 μmol), following the general procedure to make 27. ESI m/z: 1283 (M+1)$^+$. $^1$H NMR (500 MHz, methanol-$d_4$) δ 7.53-7.33 (m, 3H), 7.28-7.14 (m, 3H), 6.89 (d, J=8.4 Hz, 1H), 6.76 (d, J=8.3 Hz, 1H), 6.60 (d, J=2.5 Hz, 1H), 6.43 (dd, J=8.3, 2.5 Hz, 1H), 4.97 (s, 2H), 4.53-4.46 (m, 2H), 4.41 (dd, J=8.9, 5.0 Hz, 1H), 4.18 (t, J=6.0 Hz, 1H), 4.09 (d, J=7.1 Hz, 1H), 3.92-3.72 (m, 4H), 3.31 (t, J=6.6 Hz, 1H), 3.16-3.05 (m, 3H), 3.06-2.97 (m, 1H), 2.90-2.62 (m, 4H), 2.27-2.09 (m, 7H), 2.09-1.87 (m, 7H), 1.86-1.68 (m, 4H), 1.66-1.40 (m, 12H), 1.36-1.22 (m, 10H), 1.20-1.09 (m, 3H), 1.01 (s, 3H), 1.01 (s, 3H), 0.89 (t, J=7.0 Hz, 6H) ppm.

Example 42

This example demonstrates the methods for making the linker-payload 27j. This example refers to the compound numbering in FIG. 8.

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (27j)

Compound 27j (15 mg, 33% yield) was obtained as a white solid, following the general procedure to make 27. ESI m/z: 1313.6 (M+H)$^+$. $^1$H NMR (500 MHz, methanol-$d_4$) δ 7.59 (d, J=8.5 Hz, 2H), 7.51 (s, 1H), 7.36-7.26 (m, 3H), 7.01 (d, J=8.5 Hz, 1H), 6.88 (d, J=8.0 Hz, 1H), 6.72-6.71 (m, 1H), 6.57-6.54 (m, 1H), 5.09 (s, 2H), 4.64-4.52 (m, 1H), 4.35-4.28 (m, 2H), 4.21 (d, J=7.0 Hz, 1H), 4.01-3.98 (m, 1H), 3.88-3.84 (m, 3H), 3.43 (t, J=6.5 Hz, 1H), 3.26-3.10 (m, 4H), 3.00-2.76 (m, 3H), 2.38-2.24 (m, 7H), 2.19-2.02 (m, 9H), 1.98-1.78 (m, 4H), 1.74-1.54 (m, 12H), 1.45-1.26 (m, 14H), 1.13 (s, 6H), 1.00 (t, J=7.5 Hz, 6H) ppm.

Example 43

This example demonstrates the methods for making the linker-payloads 28c, 28d1, 28d2, 28h, and 28j. This example refers to the compound numbering in FIG. 8.

General Procedure to Make Intermediate Linker-Payload 28:

To a solution of compound 27 (30 mg, 1 equiv.) in DMF (0.5 mL) was added a solution of α-cyclodextrin azide (CD-N$_3$, ESI m/z: 1020 (M+Na)$^+$, 2 equiv.; see *Synthetic Communications*, 2002, 32(21), 3367-3372.) in DMF (0.5 mL) at rt via a syringe. The mixture was stirred at 20-25° C. for 3 days. Compound 27 was consumed based on LC-MS analysis. The reaction mixture was concentrated in vacuo and the residue was directly purified by prep-HPLC (method B) or reversed phase flash chromatography (0-100% acetonitrile in water with 10% ammonium bicarbonate) to give compound 28 as a white solid.

Example 44

This example demonstrates the methods for making the linker-payload 28c. This example refers to the compound numbering in FIG. 8.

{4-[(2S)-2-[(2S)-2-[(2R)-2-Amino-6-(1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-9-yl)oxy]acetamido}-3,6,9,12-tetraoxapentadecan-15-amido)hexanamido]-3-methylbutanamido]-5-(carbamoylamino)pentanamido]phenyl}methyl N-(2-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]oxy}ethyl)carbamate (28c)

Compound 28c (51 mg, 78% yield) as a white solid was obtained from the (2+3) click reaction of 27c (40 mg, 26 μmol) with CD-N$_3$ (52 μmol), following the general procedure to make 28. ESI m/z: 1258 (M/2+1)$^+$. $^1$H NMR (500 MHz, DMSO-$_{d6}$) δ 10.08 (s, 1H), 9.09-8.91 (m, 1H), 8.56 (d, J=8.7 Hz, 1H), 8.39 (d, J=7.3 Hz, 1H), 8.12 (s, 1H), 8.07 (s, 1H), 7.85-7.78 (m, 2H), 7.58 (d, J=8.5 Hz, 2H), 7.41 (s, 1H), 7.29 (d, J=8.5 Hz, 2H), 6.94 (d, J=8.5 Hz, 1H), 6.85-6.78 (m, 2H), 6.68 (d, J=8.3 Hz, 1H), 6.63 (s, 1H), 6.51 (d, J=8.2 Hz, 1H), 6.06 (s, 1H), 5.50 (br s, 15H), 5.15 (s, 1H), 4.96 (s, 3H), 4.85-4.78 (m, 12H), 4.70 (s, 3H), 4.56 (s, 3H), 4.39 (s, 5H), 3.89-3.75 (m, 14H), 3.74-3.56 (m, 8H), 3.54-3.39 (m, 8H), 3.38-3.29 (m, 7H), 3.14 (s, 2H), 3.01 (d, J=5.5 Hz, 5H), 2.86-2.8 (m, 2H), 2.74 (s, 4H), 2.32-2.23 (m, 5H), 2.16 (d, J=11.2 Hz, 3H), 2.00 (d, J=6.6 Hz, 2H), 1.93-1.86 (m, 5H), 1.77-1.54 (m, 10H), 1.46-1.42 (m, 6H), 1.30-1.27 (m 11H), 1.14 (s, 3H), 1.00 (d, J=12.5 Hz, 6H), 0.88 (s, 3H) 0.84 (s, 3H) ppm.

Example 45

This example demonstrates the methods for making the linker-payload 28d1. This example refers to the compound numbering in FIG. 8.

(1S,4aS,10aR)—N-{[(1S,4aS,10aR)-6-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo [26.2.2.23,6.28,11.213,16.218,21.223,26]dotetracontan-5-yl]methyl}-1H,4H,5H,6H,7H,8H,9H-cycloocta[d][1,2,3]triazol-4-yl)oxy]acetamido}hexanamido]-3-methylbutanamido]propanamido]-1,4a-dimethyl-1,2,3,4,4a,9,10,10a-octahydrophenanthren-1-yl]carbonyl}-6-hydroxy-1,4a-dimethyl-1,2,3,4,4a,9,10,10a-octahydrophenanthrene-1-carboxamide (28d1)

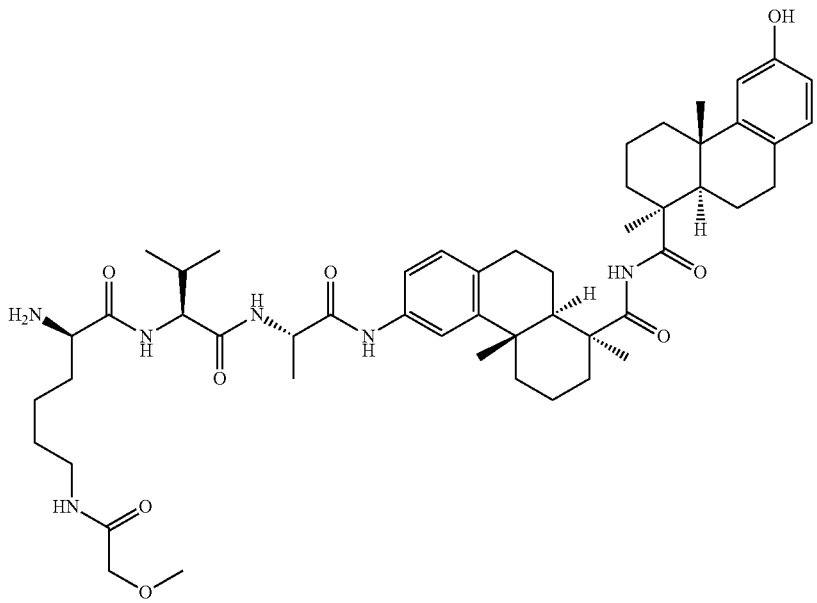

-continued

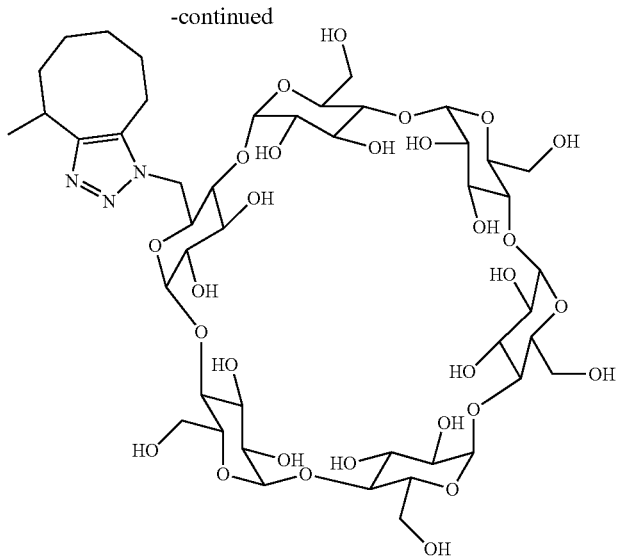

Compound 28d1 (14 mg, 23% yield) as a white solid was obtained from the (2+3) click reaction of 27d1 (30 mg, 30 µmol) with CD-$N_3$ (60 µmol), following the general procedure to make 28. ESI m/z: 995 (M/2+1)$^+$. $^1$H NMR (500 MHz, methanol-d4) δ 8.40 (s, 1H, imide-H), 7.56-7.52 (m, 1H), 7.32 (t, J=7.7 Hz, 1H), 7.03 (d, J=8.4 Hz, 1H), 6.88 (d, J=8.3 Hz, 1H), 6.72 (d, J=2.4 Hz, 1H), 6.56 (dd, J=8.2, 2.3 Hz, 1H), 5.24-5.16 (m, 1H), 5.01-4.95 (m, 6H), 4.65-3.43 (m, 40H), 3.14-2.72 (m, 7H), 2.55-1.26 (m, 44H), 1.16 (s, 3H), 1.13 (s, 3H), 1.09-0.93 (m, 6H) ppm.

Example 46

This example demonstrates the methods for making the linker-payload 28d2. This example refers to the compound numbering in FIG. 8.

N-[(5R)-5-Amino-5-{[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}pentyl]-1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-9-yl)oxy]acetamido}-3,6,9,12-tetraoxapentadecan-15-amide (28d2)

Compound 28d2 (30 mg, 72% yield) as a white solid was obtained from the (2+3) click reaction of 27d2 (23 mg, 19 µmol) with CD-$N_3$ (38 µmol), following the general procedure to make 28. ESI m/z: 1118 (M/2+1)$^+$. $^1$H NMR (500 MHz, DMSO-$d_6$) δ 9.91-9.85 (m, 1H), 9.13-8.90 (m, 1H), 8.58 (t, J=9.3 Hz, 2H), 8.50-8.47 (m, 1H), 8.17-8.00 (m, 6H), 7.88-7.78 (m, 2H), 7.53-7.49 (m, 1H), 7.36-7.30 (m, 1H), 6.97 (d, J=8.5 Hz, 1H), 6.82 (d, J=8.3 Hz, 1H), 6.63 (s, 1H), 6.51 (d, J=8.3 Hz, 1H), 5.52-5.50 (m, 11H), 5.14 (s, 1H), 4.86-4.67 (m, 10H), 4.54 (d, J=12.9 Hz, 2H), 4.46-4.32 (m, 5H), 4.06-3.94 (m, 3H), 3.89-3.76 (m, 4H), 3.73-3.61 (m, 5H), 3.57 (t, J=6.5 Hz, 3H), 3.53-3.34 (m, 12H), 3.33-3.19 (m, 4H), 3.17-3.08 (m, 3H), 3.00 (dd, J=12.6, 6.2 Hz, 3H), 2.91-2.68 (m, 8H), 2.31-2.22 (m, 5H), 2.18-2.07 (m, 6H), 1.93-1.78 (m, 6H), 1.74-1.35 (m, 15H), 1.28 (d, J=6.6 Hz, 17H), 1.19-1.06 (m, 5H), 1.01-0.94 (m, 9H), 0.89-0.79 (m, 6H) ppm.

Example 47

This example demonstrates the methods for making the linker-payload 28h. This example refers to the compound numbering in FIG. 8.

{4-[(2S)-2-[(2S)-2-[(2R)-2-Amino-6-{2-[(1-{[31,32,33,34,35,36,37,38,39,40, 41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,2H,3H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-({[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl)carbamate (28h)

Compound 28h (67 mg, 76% yield) as a white solid was obtained from the (2+3) click reaction of 27h (60 mg, 47 µmol) with CD-$N_3$ (94 µmol), following the general procedure to make 28. ESI m/z: 1141 (M/2+1)$^+$. $^1$H NMR (500 MHz, methanol-$d_4$) δ 8.40 (s, 1H), 7.65-7.45 (m, 3H), 7.40-7.26 (m, 3H), 7.02 (d, J=8.3 Hz, 1H), 6.88 (d, J=8.3 Hz, 1H), 6.72 (d, J=2.4 Hz, 1H), 6.56 (dd, J=8.3, 2.4 Hz, 1H), 5.24-5.16 (m, 1H), 5.10 (s, 2H), 5.02-4.93 (m, 4H), 4.66-4.51 (m, 2H), 4.43-4.22 (m, 2H), 4.15-3.73 (m, 22H), 3.64-3.42 (m, 12H), 3.37 (s, 3H), 3.24-3.03 (m, 4H), 3.01-2.75 (m, 6H), 2.42-2.25 (m, 6H), 2.18-1.98 (m, 8H), 1.94-1.58 (m, 15H), 1.56-1.50 (m, 3H), 1.47-1.40 (m, 3H), 1.38 (s, 3H), 1.37 (s, 3H), 1.34-1.25 (m, 4H), 1.16-1.10 (m, 6H), 1.09-0.93 (m, 7H) ppm.

Example 48

This example demonstrates the methods for making the linker-payload 28j. This example refers to the compound numbering in FIG. 8.

{4-[(2S)-2-[(2S)-2-[(2R)-2-Amino-6-{2-[(1-{[31,32,
33,34,35,36,37,38,39,40,41,42-dodecahydroxy-10,
15,20,25,30-pentakis(hydroxymethyl)-2,4,7,9,12,14,
17,19,22,24,27,29-dodecaoxaheptacyclo
[26.2.2.2$^{3,6}$.2$^{8,11}$.2$^{13,16}$.2$^{18,21}$.2$^{23,26}$]dotetracontan-5-
yl]methyl}-1H,4H,5H,6H,7H,8H,9H-cycloocta[d][1,
2,3]triazol-4-yl)oxy]acetamido}hexanamido]-3-
methylbutanamido]-5-(carbamoylamino)
pentanamido]phenyl}methyl N-[(1S)-1-{[(4bS,8S,
8aR)-8-({[(1S,4aS,10aR)-6-hydroxy-1,4a-dimethyl-
1,2,3,4,4a,9,10,10a-octahydrophenanthren-1-yl]
formamido}carbonyl)-4b,8-dimethyl-4b,5,6,7,8,8a,9,
10-octahydrophenanthren-3-yl]carbamoyl}-2-
hydroxyethyl]carbamate (28j)

Compound 28j (20 mg, 57% yield) was obtained as a white solid from the (2+3) click reaction of 27j with CD-N$_3$ following the general procedure to make 28. ESI m/z: 1156.0 (M/2+1)$^+$. $^1$H NMR (500 MHz, DMSO$_{d6}$) δ 9.81-9.67 (m, 2H), 8.99 (s, 1H), 8.20-8.06 (m, 5H), 7.85-7.22 (m, 18H), 6.97-6.49 (m, 2H), 5.98 (s, 1H), 5.65-5.33 (m, 15H), 5.14-4.92 (m, 5H), 4.82-4.72 (m, 6H), 4.60-4.54 (m, 4H), 4.36-4.28 (m, 3H), 4.18-3.96 (m, 3H), 3.85-3.55 (m, 27H), 3.49-3.39 (m, 23H), 3.28-3.08 (m, 8H), 2.94-2.57 (m, 4H), 2.42-2.07 (m, 8H), 1.99-1.45 (m, 22H), 1.28-1.11 (m, 23H), 1.05-0.95 (m, 6H), 0.89-0.79 (m, 7H) ppm.

Example 49

This example demonstrates the methods for making the linker-payloads 29c1, 29c2, 29d1, 29d2, 29d3, 29d4, 29h, and 29j. This example refers to the compound numbering in FIG. 8.

General Procedure to Make Linker-Payload 29:

To a solution of compound 28 (5-30 mg, 1 equiv.) in DMF (0.5 mL) were added a solution of commercially available DIBAC-Suc-PEG$_4$-OSu or BCN-PEG$_4$-NHS ester (1.2 equiv.) in THF (0.5 mL) and then TEA (2 equiv.) at rt. The mixture was stirred at rt until 28 was consumed, as monitored by LC-MS. The reaction mixture was concentrated in vacuo and the residue was directly purified by prep-HPLC to yield 29 as a white solid.

Example 50

This example demonstrates the methods for making the linker-payload 29c1. This example refers to the compound numbering in FIG. 8.

{4-[(2S)-2-[(2S)-2-[(2R)-2-[1-(4-{2-Azatricyclo
[10.4.0.0$^{4,9}$]hexadeca-1(12),4(9),5,7,13,15-hexaen-
10-yn-2-yl}-4-oxobutanamido)-3,6,9,12-tetraoxa-
pentadecan-15-amido]-6-(1-{2-[(1-{[31,32,33,34,35,
36,37,38,39,40,41,42-dodecahydroxy-10,15,20,25,
30-pentakis(hydroxymethyl)-2,4,7,9,12,14,17,19,22,
24,27,29-dodecaoxaheptacyclo[26.2.2.2$^{3,6}$.2$^{8,11}$.
2$^{13,16}$.2$^{18,21}$.2$^{23,26}$]dotetracontan-5-yl]methyl}-1H,
4H,5H,6H,7H,8H,9H-cycloocta[d][1,2,3]triazol-9-
yl)oxy]acetamido}-3,6,9,12-tetraoxapentadecan-15-
amido)hexanamido]-3-methylbutanamido]-5-
(carbamoylamino)pentanamido]phenyl}methyl-N-
(2-{[(4bS,8S,8aR)-8-({[(1S,4aS,10aR)-6-hydroxy-1,
4a-dimethyl-1,2,3,4,4a,9,10,10a-
octahydrophenanthren-1-yl]formamido}carbonyl)-
4b,8-dimethyl-4b,5,6,7,8,8a,9,10-
octahydrophenanthren-3-yl]oxy}ethyl)carbamate
(29c1)

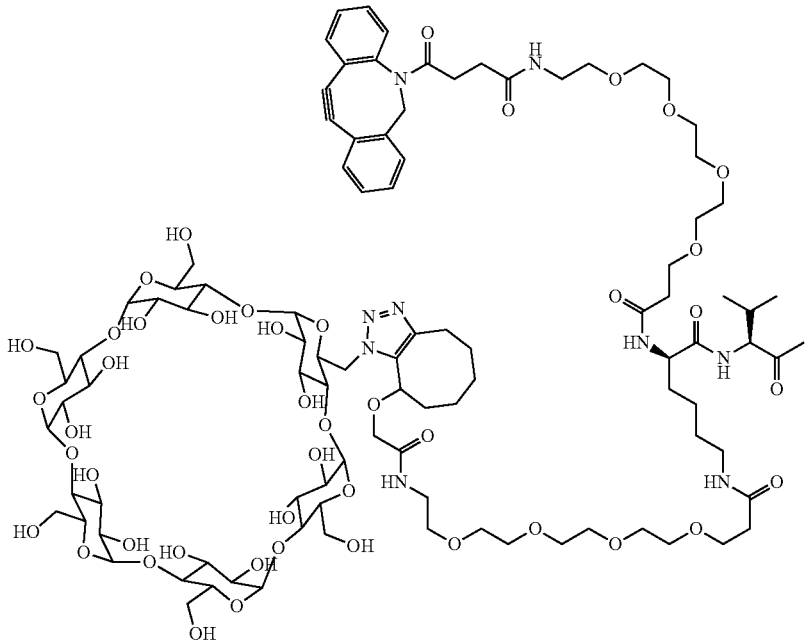

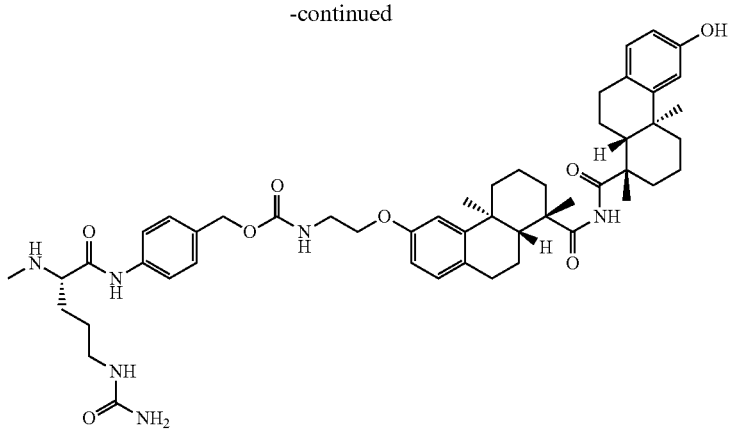

Compound 29c1 (12 mg, 39% yield) was obtained as a white solid following the general procedure to make 29.

$C_{148}H_{213}N_{15}O_{53}$, Exact mass: 3048.4. ESI m/z: 1017 (M/3+1)$^+$. $^1$H NMR (500 MHz, DMSO$_{d6}$) δ 9.68 (s, 1H), 8.21-8.04 (m, 3H), 7.88-7.74 (m, 2H), 7.71-7.56 (m, 3H), 7.52-7.21 (m, 8H), 6.93 (d, J=8.6 Hz, 1H), 6.84-6.77 (m, 1H), 6.70-6.58 (m, 2H), 6.51 (d, J=8.1 Hz, 1H), 6.01 (s, 1H), 5.78-5.33 (m, 12H), 5.22-4.51 (m, 14H), 4.43-4.12 (m, 4H), 4.07-3.55 (m, 35H), 3.53-3.33 (m, 38H), 3.33-2.52 (m, 32H), 2.43-1.21 (m, 41H), 1.20-0.77 (m, 14H) ppm.

Example 51

This example demonstrates the methods for making the linker-payload 29c2. This example refers to the compound numbering in FIG. 8.

{Bicyclo[6.1.0]non-4-yn-9-yl}methyl N-(14-{[(1R)-1-{[(1S)-1-{[(1S)-1-{[4-({[(2-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]oxy}ethyl)carbamoyl]oxy}methyl)phenyl]carbamoyl}-4-(carbamoylamino)butyl]carbamoyl}-2-methylpropyl]carbamoyl}-5-(1-{2-[(1-{[31,32,33,34,35,36,37,38,39,40,41,42-dodecahydroxy-10,15,20,25,30-pentakis (hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-9-yl)oxy]acetamido}-3,6,9,12-tetraoxapentadecan-15-amido)pentyl]carbamoyl}-3,6,9,12-tetraoxatetradecan-1-yl)carbamate (29c2)

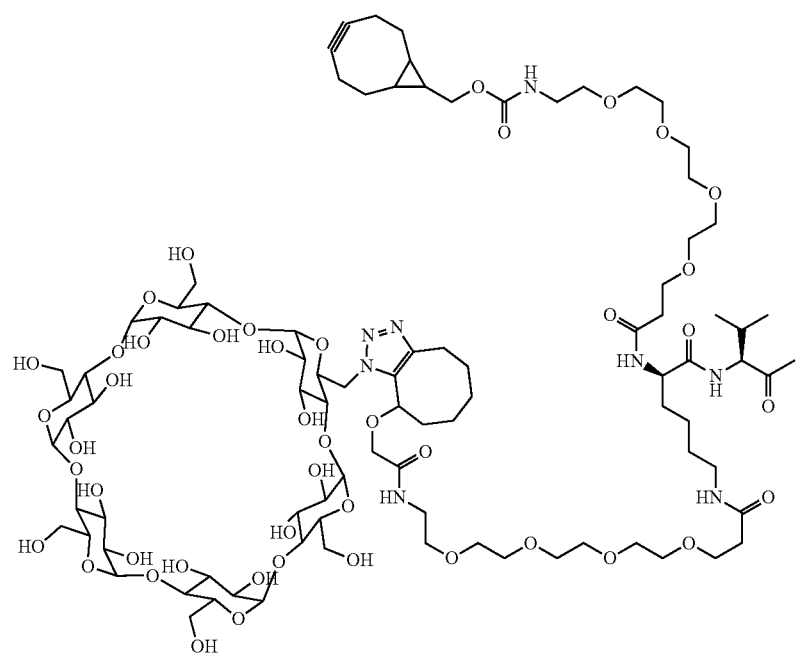

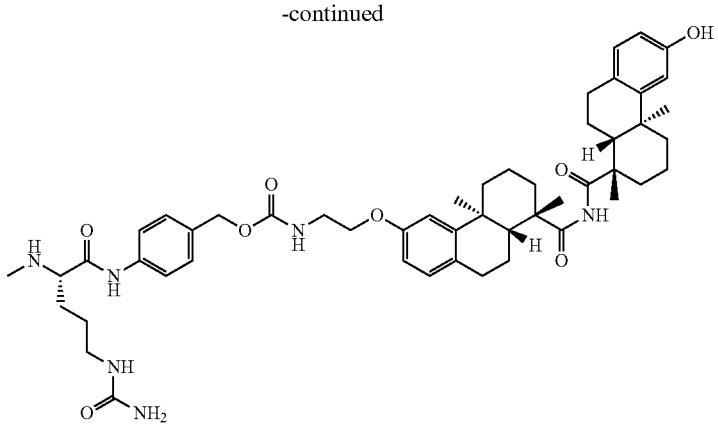

Compound 29c2 (5 mg, 210% yield) was obtained as a white solid following the general procedure to make 29.

$C_{140}H_2N_{14}O_{53}$, Exact mass: 2937.4. ESI m/z: 1470 (M/2+1)$^+$. $^1$H NMR (500 MHz, DMSO$_{d6}$) δ 9.68 (s, 1H), 9.00 (s, 1H), 8.21-8.03 (m, 2H), 7.62 (d, J=8.4 Hz, 2H), 7.27 (d, J=8.3 Hz, 2H), 6.93 (d, J=8.8 Hz, 1H), 6.81 (d, J=8.4 Hz, 1H), 6.80 (s, 1H), 6.67 (d, J=8.6 Hz, 1H), 6.63 (s, 1H), 6.50 (d, J=7.9 Hz, 1H), 5.99 (s, 1H), 5.64-5.37 (m, 12H), 5.14 (s, 1H), 5.00-4.50 (m, 13H), 4.38-4.29 (m, 3H), 4.20-4.13 (m, 1H), 4.09-3.97 (m, 10H), 3.95-3.89 (m, 2H), 3.86-3.54 (m, 23H), 3.52-3.33 (m, 28H), 3.16-2.61 (m, 17H), 2.45-1.20 (m, 66H), 1.18-0.80 (m, 21H) ppm.

Example 52

This example demonstrates the methods for making the linker-payload 29d1. This example refers to the compound numbering in FIG. 8.

1-(4-{2-Azatricyclo[10.4.0.04,9]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (29d1)

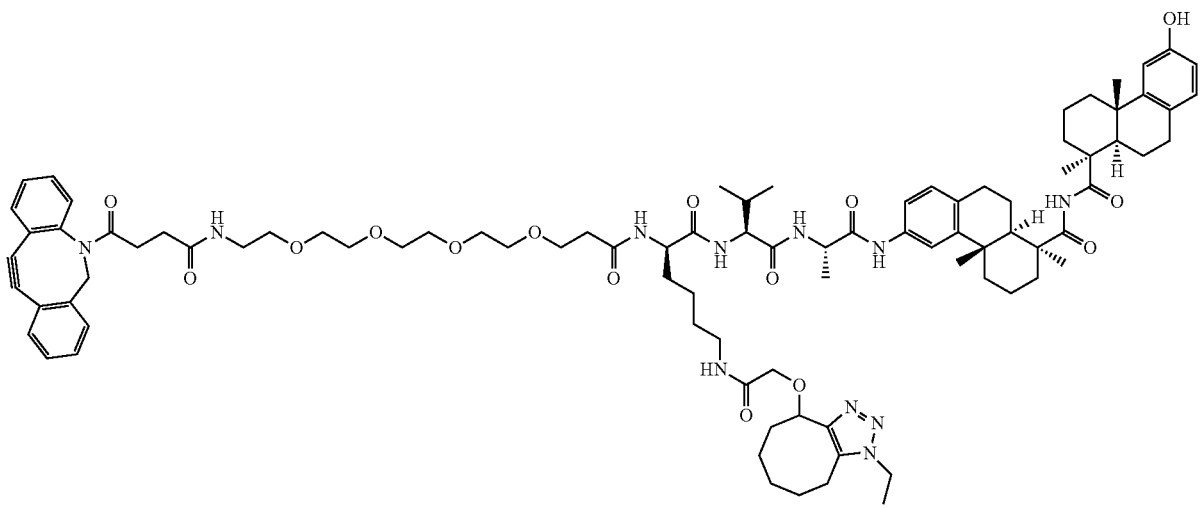

-continued

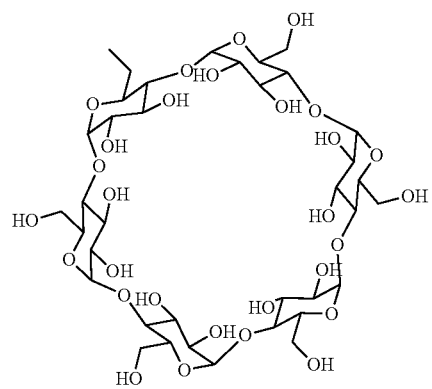

Compound 29d1 (5.0 mg, 27% yield) was obtained as a white solid following the general procedure to make 29.

$C_{124}H_{175}N_{11}O_{44}$, Exact mass: 2522.2. ESI m/z: 1261 (M/2+1)+. $^1$H NMR (500 MHz, methanol-$d_4$) δ 7.69-7.44 (m, 6H), 7.41-7.30 (m, 3H), 7.26 (d, J=6.8 Hz, 1H), 7.04-6.96 (m, 1H), 6.88 (d, J=8.4 Hz, 1H), 6.72 (d, J=1.9 Hz, 1H), 6.56 (dd, J=8.3, 2.4 Hz, 1H), 5.25-4.94 (m, 6H), 4.75-4.55 (m, 16H), 4.53-3.41 (m, 49H), 3.33-1.20 (m, 53H), 1.18-1.10 (m, 6H), 1.06-0.94 (m, 6H) ppm.

Example 53

This example demonstrates the methods for making the linker-payload 29d2. This example refers to the compound numbering in FIG. 8.

{Bicyclo[6.1.0]non-4-yn-9-yl}methyl N-(14-{[(1R)-1-{[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$] dotetracontan-5-yl]methyl}-1H,4H,5H,6H,7H,8H,9H-cycloocta[d][1,2,3]triazol-4-yl)oxy]acetamido}pentyl]carbamoyl}-3,6,9,12-tetraoxatetradecan-1-yl) carbamate (29d2)

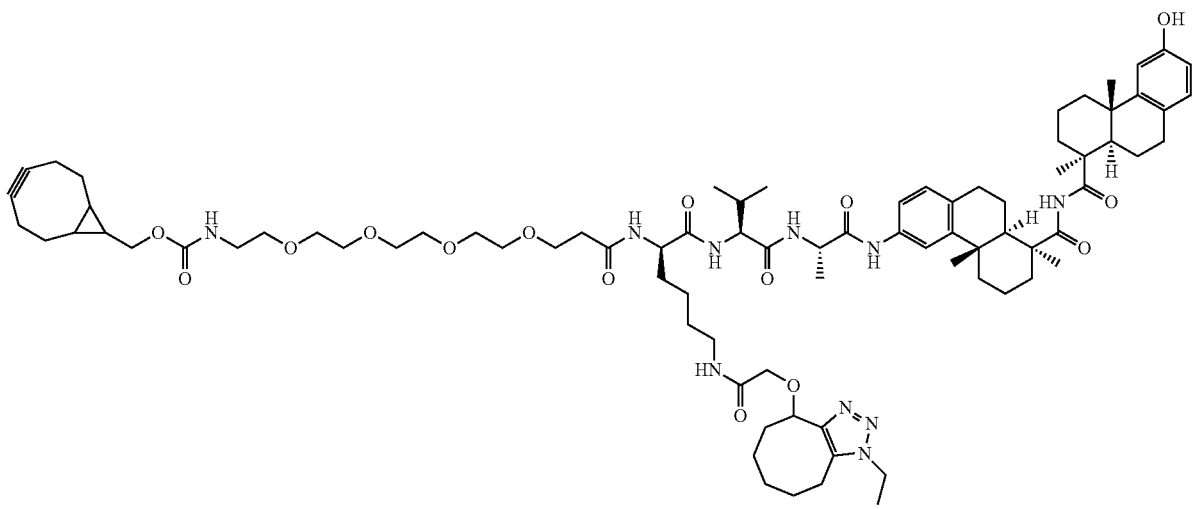

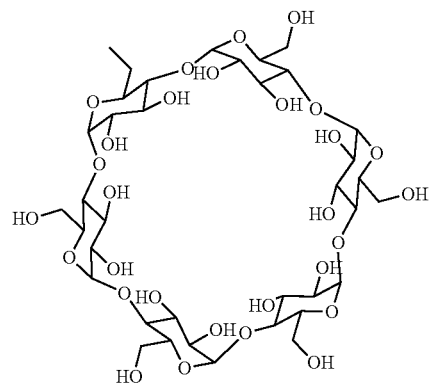

Compound 29d2 (16 mg, 43% yield) was obtained as a white solid following the general procedure to make 29.

$C_{116}H_{174}N_{10}O_{44}$, Exact mass: 2411.2. ESI m/z: 1206 (M/2+1)+. $^1$H NMR (500 MHz, methanol-d4) δ 7.62 (s, 1H), 7.39 (d, J=8.2 Hz, 1H), 7.03 (d, J=8.4 Hz, 1H), 6.89 (d, J=8.3 Hz, 1H), 6.72 (d, J=2.3 Hz, 1H), 6.56 (dd, J=8.2, 2.4 Hz, 1H), 5.21 (t, J=2.8 Hz, 1H), 4.99-4.95 (m, 4H), 4.65-3.43 (m, 57H), 3.31-2.74 (m, 11H), 2.55-1.22 (m, 55H), 1.16 (s, 3H), 1.13 (s, 3H), 1.06-0.87 (m, 9H) ppm.

Example 54

This example demonstrates the methods for making the linker-payload 29d3. This example refers to the compound numbering in FIG. 8.

1-(4-{2-Azatricyclo[10.4.0.0$^{4,9}$]hexadeca-1(12),4(9), 5,7,13,15-hexaen-10-yn-2-yl}-4-oxobutanamido)-N-[(1R)-1-{[(1S)-1-{[(1S)-1-{[(4bS,8S,8aR)-8-{[(1S, 4aS,10aR)-6-hydroxy-1,4a-dimethyl-1,2,3,4,4a,9,10, 10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}-5-(1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H, 6H,7H,8H,9H-cycloocta[d][1,2,3]triazol-9-yl)oxy] acetamido}-3,6,9,12-tetraoxapentadecan-15-amido) pentyl]-3,6,9,12-tetraoxapentadecan-15-amide
(29d3)

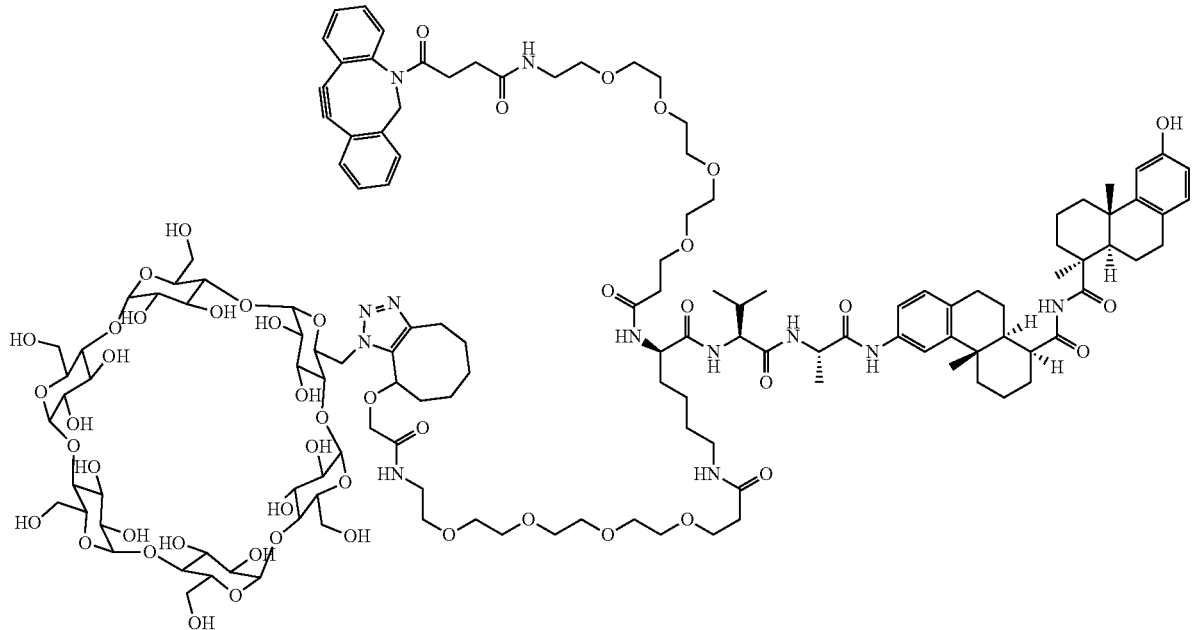 [SMILES: CC(C)[C@H](NC(=O)[C@@H](CCCCNC(=O)CCOCCOCCOCCOCCNC(=O)COC1CCCCCc2nnn(CC3OC4OC5C(CO)OC(OC6C(CO)OC(OC7C(CO)OC(OC8C(CO)OC(OC9C(CO)OC(OC3C(O)C4O)C(O)C9O)C(O)C8O)C(O)C7O)C(O)C6O)C(O)C5O)c21)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@H](C(=O)NC(=O)[C@@]3(C)CCC[C@]4(C)c5cc(O)ccc5CC[C@@H]34)[C@@H]1CC2]

Compound 29d3 was obtained as a white solid (8 mg, 32% yield) following the general procedure to make 29.

$C_{135}H_{196}N_{12}O_{49}$, Exact mass: 2769.3. ESI m/z: 1385.9 (M/2+1)$^+$. $^1$H NMR (500 MHz, DMSO$_{d6}$) δ 9.71-9.30 (br s, 0.6H), 9.01 (s, 1H), 8.29-7.99 (m, 4H), 7.89-7.76 (m, 3H), 7.74-7.60 (m, 2H), 7.58-7.27 (m, 7H), 7.01-6.92 (m, 1H), 6.82 (d, J=8.1 Hz, 1H), 6.68-6.48 (m, 2H), 5.71-5.45 (m, 12H), 5.17-4.69 (m, 2H), 4.90-4.50 (m, 12H), 4.44-3.54 (m, 33H), 3.54-3.41 (m, 38H), 3.33-2.54 (m, 15H), 2.43-1.19 (m, 44H), 1.18-0.66 (m, 18H) ppm.

Example 55

This example demonstrates the methods for making the linker-payload 29d4. This example refers to the compound numbering in FIG. 8.

{Bicyclo[6.1.0]non-4-yn-9-yl}methyl N-(14-{[(1R)-1-{[(1S)-1-{[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}-5-(1-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo [26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-9-yl)oxy]acetamido}-3,6,9,12-tetraoxapentadecan-15-amido)pentyl]carbamoyl}-3,6,9,12-tetraoxatetradecan-1-yl) carbamate (29d4)

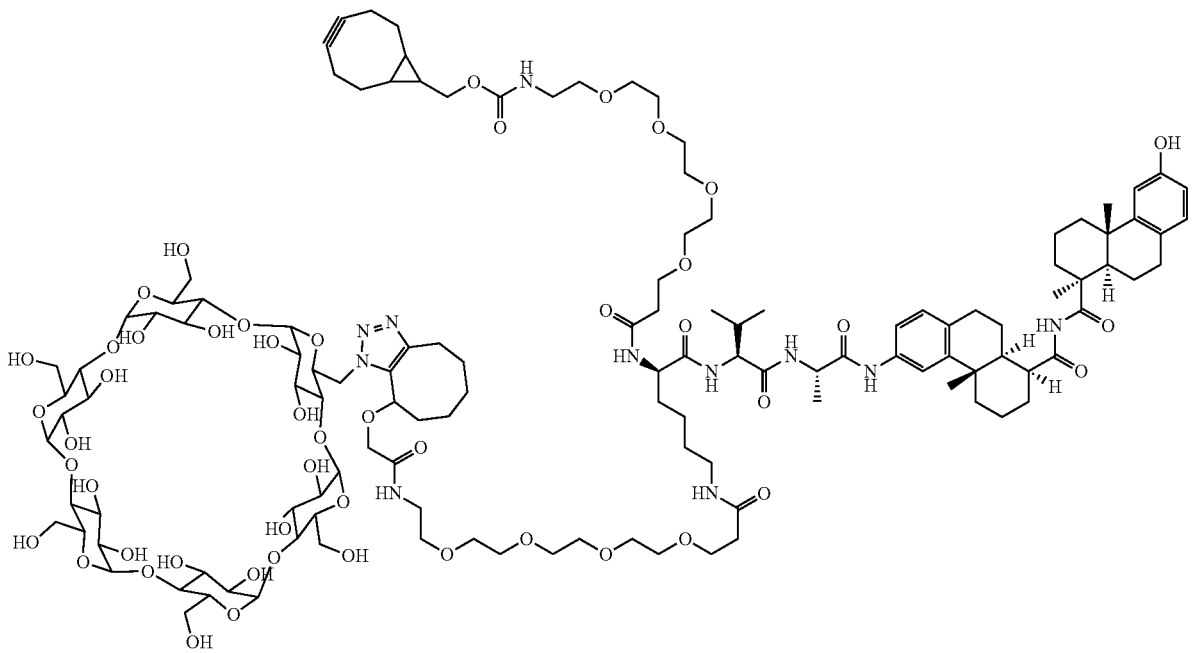 [SMILES: CC(C)[C@H](NC(=O)[C@@H](CCCCNC(=O)CCOCCOCCOCCOCCNC(=O)COC1CCCCCc2nnn(CC3OC4OC5C(CO)OC(OC6C(CO)OC(OC7C(CO)OC(OC8C(CO)OC(OC9C(CO)OC(OC3C(O)C4O)C(O)C9O)C(O)C8O)C(O)C7O)C(O)C6O)C(O)C5O)c21)NC(=O)CCOCCOCCOCCOCCNC(=O)OCC1C2CCC#CCCC21)C(=O)N[C@@H](C)C(=O)Nc1ccc2c(c1)[C@@]1(C)CCC[C@H](C(=O)NC(=O)[C@@]3(C)CCC[C@]4(C)c5cc(O)ccc5CC[C@@H]34)[C@@H]1CC2]

Compound 29d4 (2 mg, 14% yield) was obtained as a white solid following the general procedure to make 29.

$C_{148}H_{213}N_{15}O_{53}$, Exact mass: 3048.4. ESI m/z: 1017 (M/3+1)$^+$, $^1$H NMR (500 MHz, DMSO$_{d6}$) δ 9.68 (s, 1H), 8.21-8.04 (m, 3H), 7.88-7.74 (m, 2H), 7.71-7.56 (m, 3H), 7.52-7.21 (m, 8H), 6.93 (d, J=8.6 Hz, 1H), 6.84-6.77 (m, 1H), 6.70-6.58 (m, 2H), 6.51 (d, J=8.1 Hz, 1H), 6.01 (s, 1H), 5.78-5.33 (m, 12H), 5.22-4.51 (m, 14H), 4.43-4.12 (m, 4H), 4.07-3.55 (m, 35H), 3.53-3.33 (m, 38H), 3.33-2.52 (m, 32H), 2.43-1.21 (m, 41H), 1.20-0.77 (m, 14H) ppm.

Example 56

This example demonstrates the methods for making the linker-payload 29h. This example refers to the compound numbering in FIG. 8.

1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (29h)

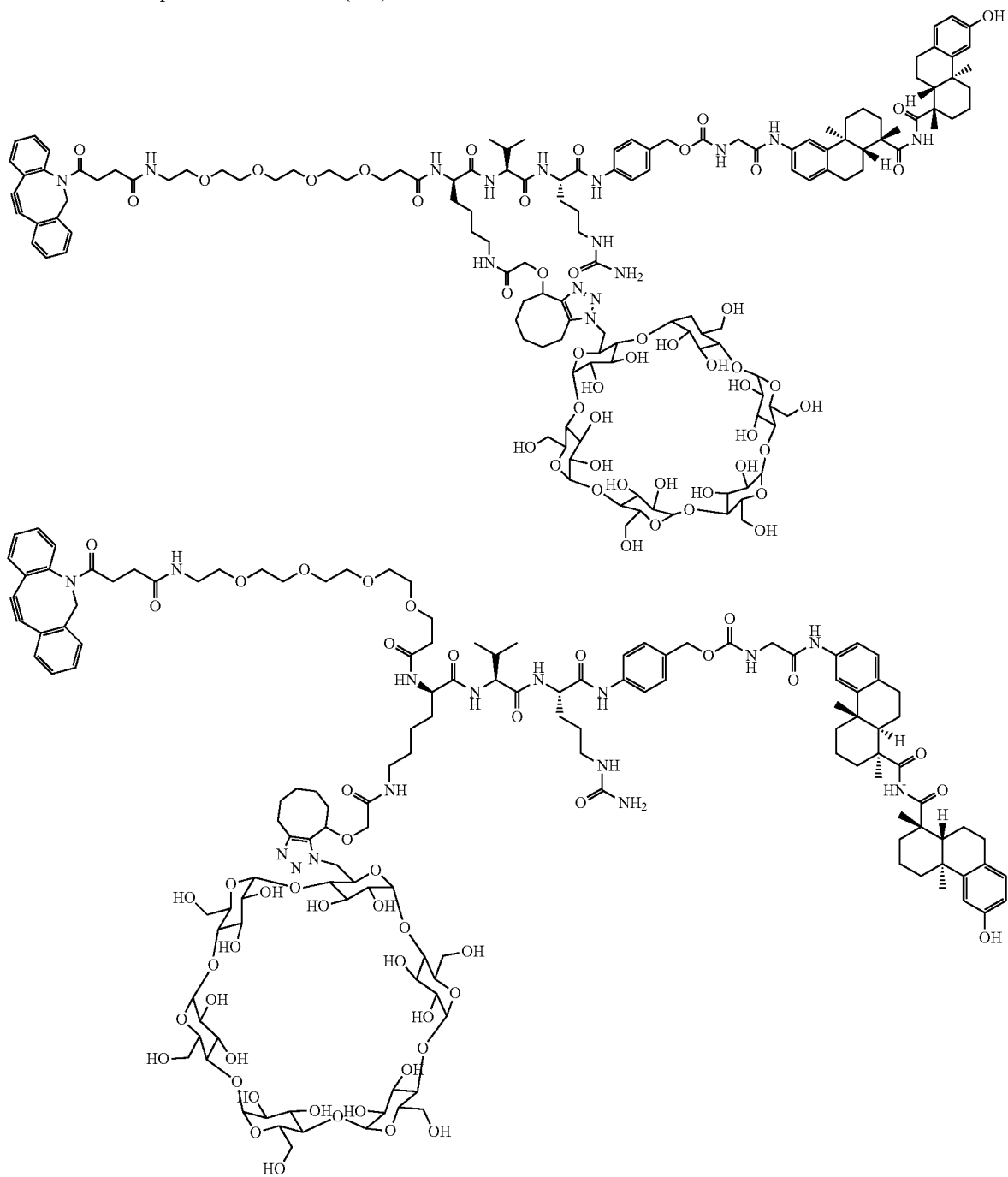

Compound 29h (28 mg, 35% yield) was obtained as a white solid (mixture of regioisomers at the triazole) following the general procedure to make 29.

$C_{137}H_{191}N_{15}O_{48}$, exact mass: 2814.3. ESI m/z: 1409 (M/2+1)$^+$. H NMR (500 MHz, DMSO$_{d6}$) δ 9.79 (s, 1H), 9.68 (s, 1H), 8.99 (s, 1H), 8.24-8.05 (m, 3H), 7.86-7.73 (m, 2H), 7.71-7.58 (m, 3H), 7.54-7.42 (m, 4H), 7.42-7.25 (m, 5H), 6.96 (d, J=8.5 Hz, 1H), 6.81 (d, J=8.4 Hz, 1H), 6.63 (s, 1H), 6.57-6.45 (m, 1H), 5.99 (s, 1H), 5.69-5.31 (m, 12H), 5.17-4.49 (m, 14H), 4.39-3.95 (m, 5H), 3.90-3.51 (m, 25H), 3.50-3.33 (m, 32H), 3.33-2.53 (m, 21H), 2.44-1.20 (m, 41H), 1.21-0.77 (m, 16H) ppm.

Example 57

This example demonstrates the methods for making the linker-payload 29j. This example refers to the compound numbering in FIG. 8.

{4-[(2S)-2-[(2S)-2-[(2R)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo [26.2.2.2$^{3,6}$.2$^{8,11}$.2$^{13,16}$.2$^{18,21}$.2$^{23,26}$]dotetracontan-5-yl]methyl}-1H,4H,H,6H,7H,8H,9H-cyclooocta[d][1,2,3]triazol-4-yl)oxy]acetamido}hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (29j)

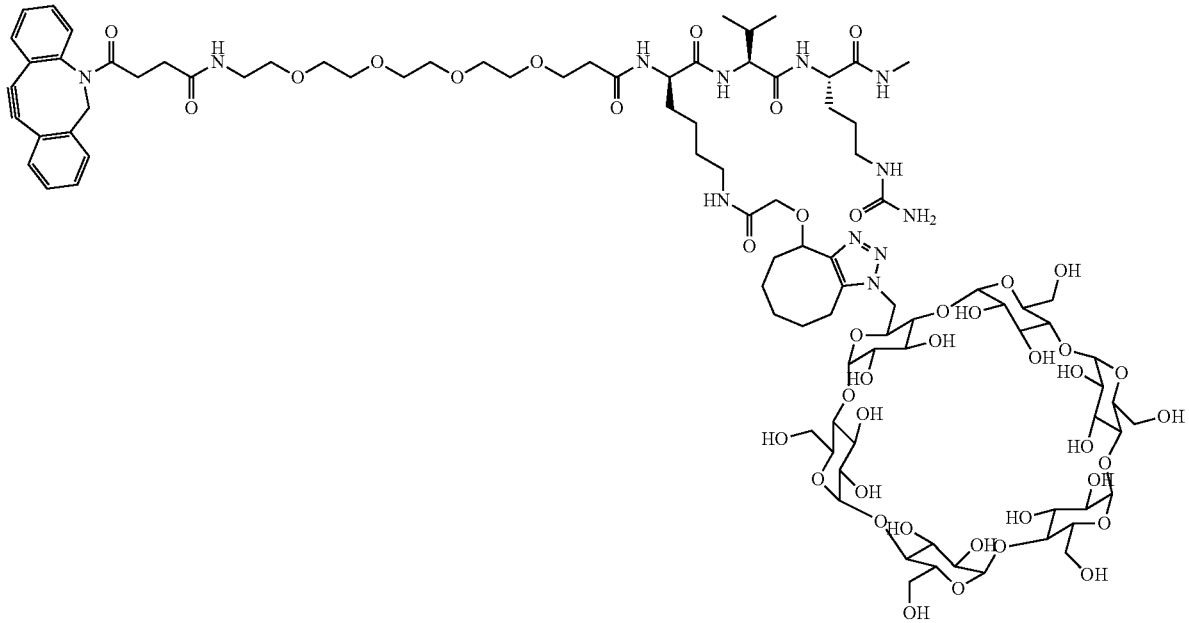

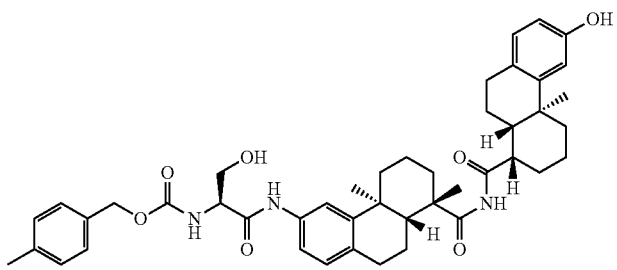

-continued

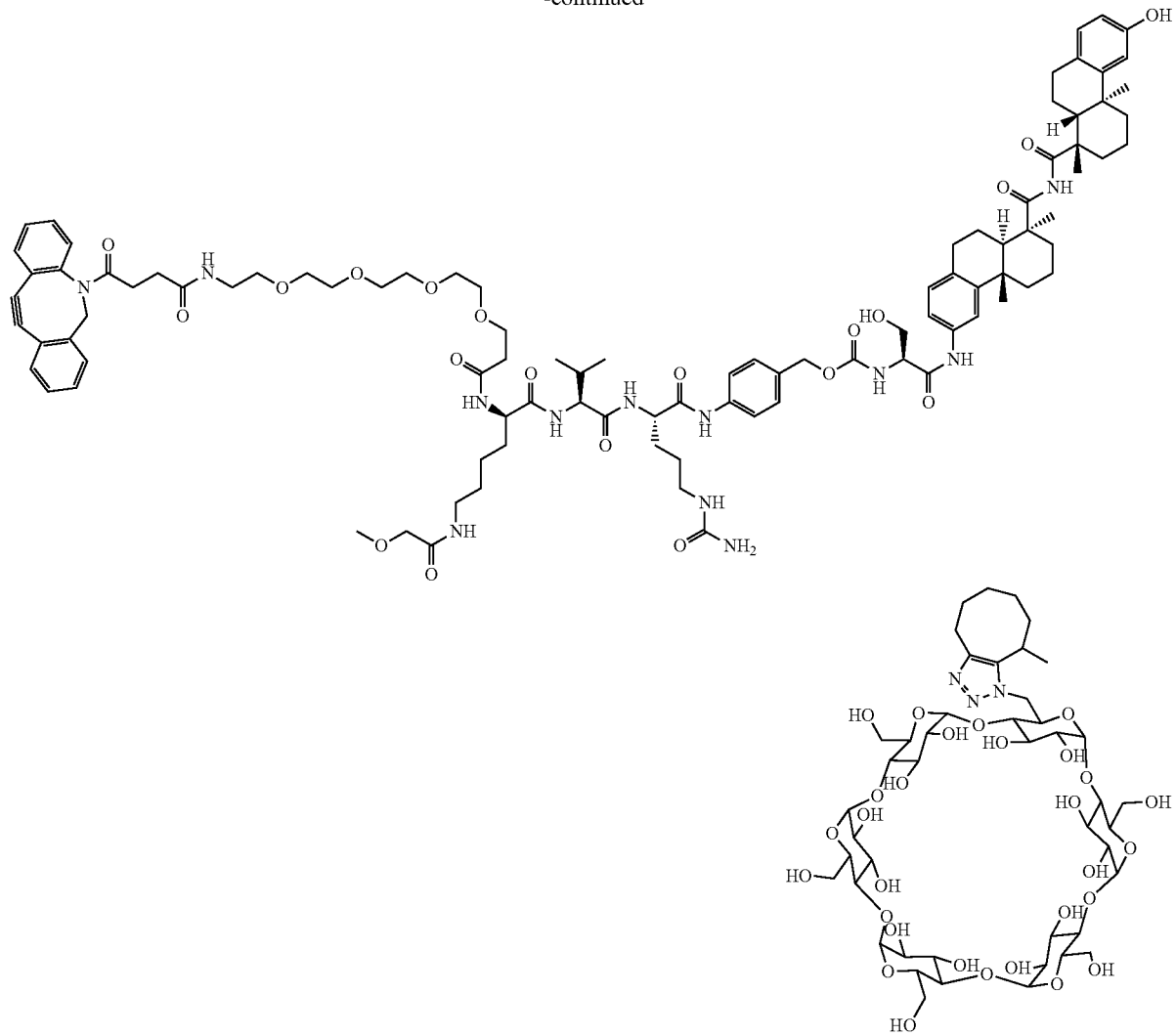

Compound 29j (10 mg, 42% yield) was obtained as a white solid (mixture of regioisomers at the triazole) following the general procedure to make 29.

$C_{138}H_{193}N_{15}O_{49}$, Exact mass: 2844.3. ESI m/z: 1424.3 $(M/2+H)^+$. $^1H$ NMR (500 MHz, DMSO$_{d6}$) δ 9.81 (s, 1H), 9.65 (s, 1H), 8.97 (s, 1H), 8.28-8.04 (m, 3H), 7.91-7.73 (m, 2H), 7.73-7.16 (m, 12H), 6.95 (d, J=8.8 Hz, 1H), 6.81 (d, J=7.8 Hz, 1H), 6.73-6.59 (m, 1H), 6.59-6.44 (m, 1H), 5.98 (s, 1H), 5.71-5.27 (m, 12H), 5.23-4.48 (m, 14H), 4.43-3.93 (m, 5H), 4.09-3.50 (m, 24H), 3.51-3.33 (m, 31H), 3.33-2.53 (m, 17H), 2.42-1.08 (m, 51H), 1.06-0.67 (m, 14H) ppm.

Example 58

This example demonstrates the methods for making the linker-payload 33. This example refers to the compound numbering in FIG. 9.

{4-[(2S)-2-[(2S)-2-[1-(4-{2-Azatricyclo[10.4.0.0$^{(4,9)}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-{2-[N-methyl(3-{3-[3-ethyl-8-(trifluoromethyl)quinolin-4-yl]phenoxy}benzene)sulfonamido]ethyl}carbamate (33)

N-(2-Aminoethyl)-3-(3-(3-ethyl-8-(trifluoromethyl)quinolin-4-yl)phenoxy)-N-methylbenzenesulfonamide (31) was reported as a potent LXR agonist having a binding affinity of 1.5 nM to LXRα and 12 nM to LXRβ (See, Bioconjug Chem. 2015 26(11), 2216-22).

Figure 9:
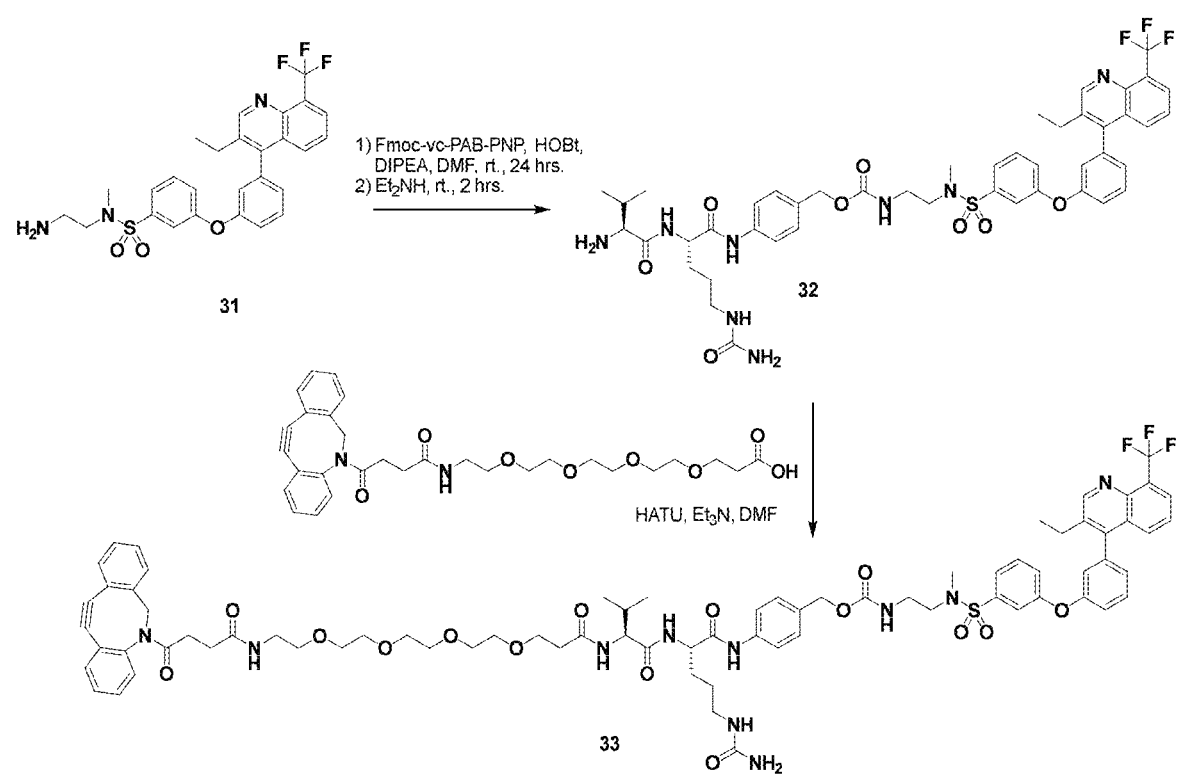

The synthesis of the linker-payload 33 via two amide coupling reactions is shown in FIG. 9. The first amide coupling reaction of 31 with Fmoc-VC-PAB-PNP catalyzed by HOBt followed by Fmoc deprotection under basic conditions formed 32, and the second amide coupling reaction of 32 with commercially available DIBAC-suc-PEG$_4$-acid formed 33.

Step 1:

To a mixture of 31 (0.14 g, 0.26 mmol) in DMF (5 mL) were subsequently added Fmoc-vc-PAB-PNP (0.26 g, 0.34 mmol), HOBt (46 mg, 0.34 mmol), and DIPEA (89 mg, 0.68 mmol) at rt. After the reaction was stirred at 20-25° C. for 24 h, 31 was totally consumed according to LC-MS analysis. To the reaction mixture was added Et$_2$NH (0.5 mL) and the resulting mixture was stirred at 25° C. for additional 2 h. LC-MS showed the Fmoc group was totally removed at that time. The volatiles were removed in vacuo and the residue was purified by prep-HPLC (Method A) to give 32 (75 mg, 30% yield) as a white solid. ESI m/z: 935 (M+H)$^+$. $^1$H NMR (400 MHz, methanol-$d_4$) δ 8.97 (s, 1H), 8.06 (d, J=7.2 Hz, 1H), 7.71-7.52 (m, 7H), 7.40-7.37 (m, 2H), 7.31-7.27 (m, 3H), 7.18 (d, J=7.2 Hz, 1H), 7.06-7.04 (m, 1H), 5.00 (s, 2H), 4.55-4.52 (m, 1H), 3.25-3.06 (m, 7H), 2.74 (s, 3H), 2.73-2.60 (m, 2H), 2.06-1.54 (m, 5H), 1.18 (t, J=7.2 Hz, 3H), 0.98 (d, J=6.8 Hz, 3H), 0.93 (d, J=6.8 Hz, 3H) ppm.

Step 2:

To a solution of DIBAC-suc-PEG$_4$-acid (8.0 mg, 14 µmol) in DMF (1 mL) was added HATU (8.0 mg, 20 µmol) at rt. The mixture was stirred at 25° C. for an hour and to the mixture was subsequently added 32 (13 mg, 14 µmol) and TEA (13 mg, 28 µmol). The mixture was stirred at 25° C. for additional 2 h. The reaction was monitored by LC-MS until 32 was consumed. The volatiles were removed in vacuo and the residue was purified by prep-HPLC (Method B) to give 33 (7.0 mg, 35% yield) as a white solid. ESI m/z: 735 (M/2+H)$^+$. $^1$H NMR (400 MHz, methanol-$d_4$) δ 8.96 (s, 1H), 8.06 (d, J=7.2 Hz, 1H), 7.71-7.52 (m, 9H), 7.43-7.18 (m, 12H), 7.05 (s, 1H), 5.13-5.09 (m, 1H), 5.00 (s, 2H), 4.52-4.46 (m, 1H), 4.20 (d, J=6.8 Hz, 1H), 3.77-3.65 (m, 3H), 3.58-3.51 (m, 12H), 3.44-3.39 (m, 2H), 3.22 (t, J=6.0 Hz, 4H), 3.14-3.03 (m, 3H), 2.73-2.62 (m, 6H), 2.53 (t, J=6.0 Hz, 2H), 2.40-2.31 (m, 1H), 2.20-1.86 (m, 5H), 1.79-1.51 (m, 3H), 1.17 (t, J=7.6 Hz, 3H), 0.97 (t, J=6.0 Hz, 6H) ppm.

Example 59

Summarized in Table 2 are the structures of the linker-payloads 22, 24, 27, 29, and 33. Summarized in Table 5 are the molecular formulae, molecular weights, calculated Log P values, MS, and HPLC results for the linker-payloads.

TABLE 5

Chemical-Physical Properties of Linker-Payload

| | Cpd # | cLogP | MF | MW | MS m/z (100%) | HPLC R$_t$ Method A or B (min) | HPLC Purity (%) |
|---|---|---|---|---|---|---|---|
| LP1 | 24c | + | C$_{81}$H$_{116}$N$_{10}$O$_{23}$ | 1597.8 | 1598.7 [M + H] | 6.70 (A) 7.72 (B) | 100 |
| LP2 | 22d1 | +++ | C$_{72}$H$_{92}$N$_6$O$_{12}$ | 1233.53 | 617.3 [M/2 + H] | 9.21 (B) | 100 |
| LP3 | 22d2 | ++ | C$_{38}$H$_{51}$N$_3$O$_3$ | 597.39 | 598.4 [M + H] | 8.99 (B) | 100 |
| LP4 | 22j | ++ | C$_{86}$H$_{110}$N$_{10}$O$_{17}$ | 1555.8 | 778.4 [M/2 + H] | 7.21 (B) | 96.6 |
| LP5 | 27d1 | ++ | C$_{58}$H$_{82}$N$_6$O$_8$ | 990.62 | 991.3 [M + H] | 6.5 (B) | 100 |
| LP6 | 29c1 | + | C$_{137}$H$_{191}$N$_{15}$O$_{48}$ | 2818.1 | 939.5 [M/3 + H] | 6.62 (B) | 100 |
| LP7 | 29c2 | + | C$_{148}$H$_{213}$N$_{15}$O$_{53}$ | 3050.3 | 1017.3 [M/3 + H] | 6.68 (B) | 96 |
| LP8 | 29d1 | + | C$_{124}$H$_{175}$N$_{11}$O$_{44}$ | 2523.8 | 841.8 [M/3 + H] | 6.19 (B) | 98 |
| LP9 | 29d2 | + | C$_{116}$H$_{174}$N$_{10}$O$_{44}$ | 2412.7 | 1215.2 [(M + H2O)/2 + H] | 6.37 (B) | 100 |
| LP10 | 29d3 | + | C$_{135}$H$_{196}$N$_{12}$O$_{49}$ | 2771.1 | 924.5 [M/3 + H] | 6.42 (B) | 100 |
| LP11 | 29d4 | + | C$_{127}$H$_{195}$N$_{11}$O$_{49}$ | 2660 | 837.2 [(M-BCN)/3 + H] | 6.33 (B) | 100 |
| LP12 | 29h | + | C$_{137}$H$_{191}$N$_{15}$O$_{48}$ | 2818.1 | 939.5 [M/3 + H] | 6.62 (B) | 100 |
| LP13 | 29j | + | C$_{138}$H$_{193}$N$_{15}$O$_{49}$ | 2846.08 | 1424.3 [M/2 + H] | 6.12 (B) | 100 |
| LP15 | 27j | ++ | C$_{72}$H$_{100}$N$_{10}$O$_{13}$ | 1313.62 | 657.5 [M/2 + H] 1313.6 [M + H, 5%] | 8.16 (B) | 96 |
| LP14 | 33 | ++ | C$_{76}$H$_{87}$F$_3$N$_{10}$O$_{15}$S | 1469.6 | 735.3 [M/2 + H] | 9.34 (B) | 96 |

9 < +++;
7 < ++ < 9;
−2 < + < 2

Example 60

This example demonstrates a method for making non-site-specific conjugated drug(s) to an antibody using a thiol-maleimide reaction.

Conjugation through antibody cysteines was performed in two steps using the methods similar to those for making Adcetris®-like ADCs (See, *Mol. Pharm.* 2015, 12(6), 1863-71).

A monoclonal antibody (mAb) is reduced with dithiothreitol or TCEP. After gel filtration, 24c in DMSO solution is added to the reduced antibody, and the mixture is adjusted to appropriate pH. The reaction is allowed to stir. The resulting conjugate are purified by SEC. The DAR (UV) values are determined using the measured absorbances of the ncADC and the extinction coefficients of the antibody and 24c.

Example 61

This example demonstrates a method for site-specific conjugation, generally, for a payload to an antibody or antigen-binding fragment thereof. This example refers to FIG. 10.

Figure 10:
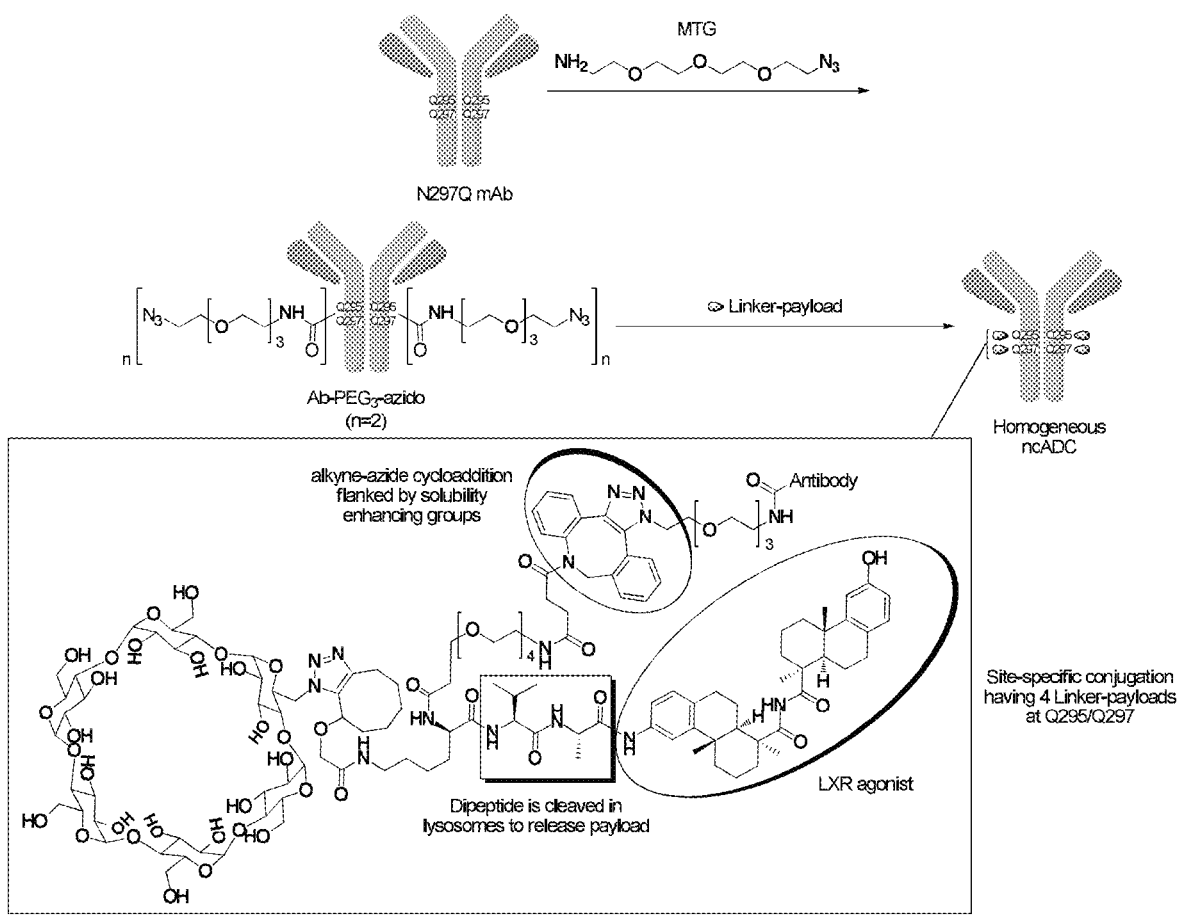

In one example, the site-specific conjugates were produced by Microbial transglutaminase (MTG EC 2.3.2.13, Zedira, Darmstadt, Germany) (hereinafter "MTG-based") two-step conjugation of N297Q antibody. The first step was a MTG-based enzymatic attachment of a small molecule, such as azide-PEG3-amine, to the mutated antibody. The second step employed the attachment of a linker-payload to the azido-functionalized antibody via a [2+3] cycloaddition, for example, the 1,3-dipolar cycloaddition between the azides and the cyclooctynes (aka copper-free click chemistry). See, Baskin, J. M.; Prescher, J. A.; Laughlin, S. T.; Agard, N. J.; Chang, P. V.; Miller, I. A.; Lo, A.; Codelli, J. A.; Bertozzi, C. R. *PNAS* 2007, 104 (43), 16793-7. Shown in FIG. 10 is an example of a linker-payload having a DIBAC moiety conjugated with an azido-functionalized antibody via a [2+3] cycloaddition. This process provided the site-specific and stoichiometric conjugates in about 50-80% isolated yield.

Example 62

This example demonstrates a method for making an azido-functionalized antibody drug conjugate.

Figure 12:
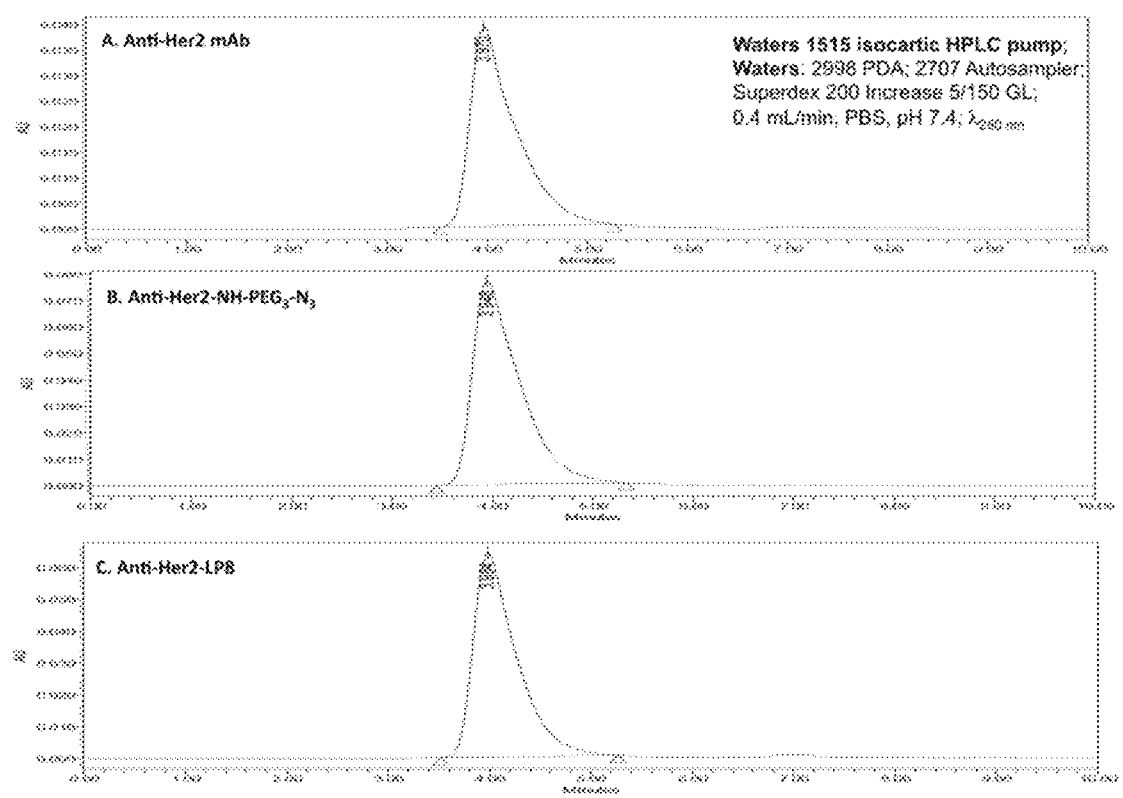
FIG. 12 shows SEC of anti-Her2 Ab, anti-Her2-PEG₃-N₃, and anti-Her2-LP8.
Figure 13:
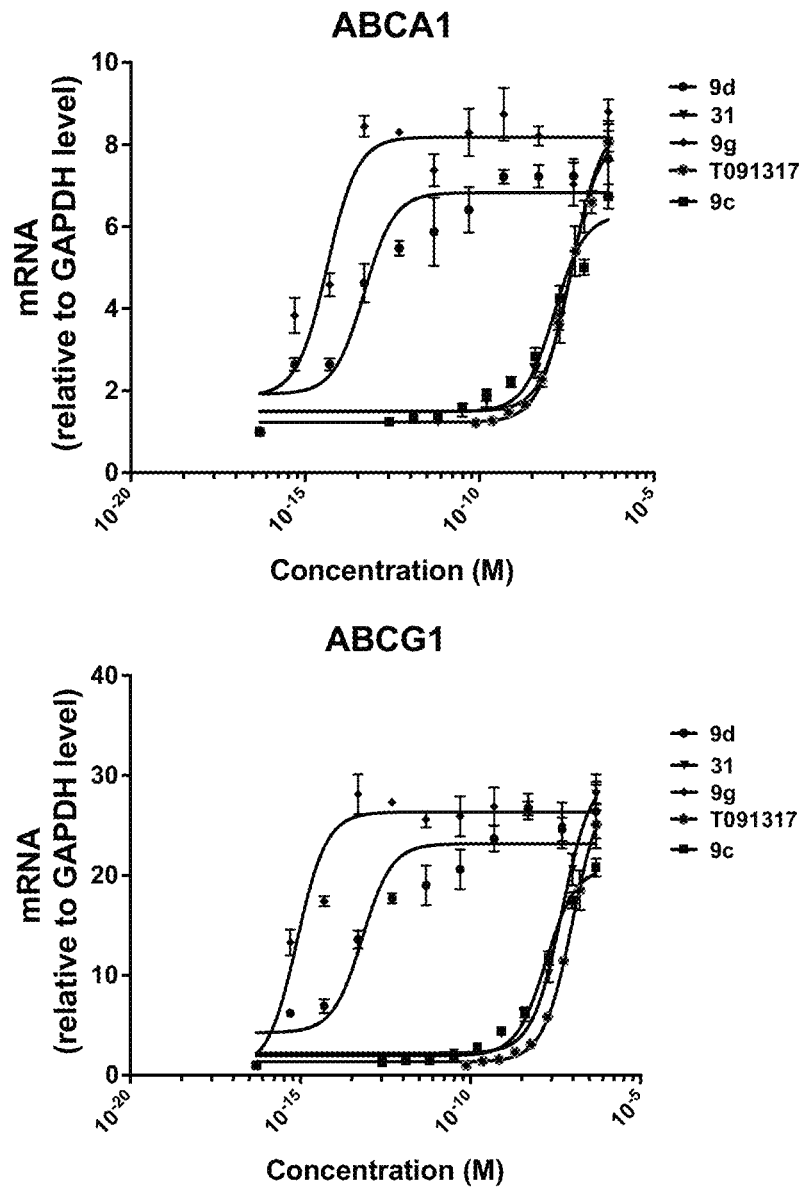
FIG. 13 shows Activation of ABCA1 and ABCG1 genes by LXR agonists.

Aglycosylated human antibody IgG (IgG1, IgG4, etc.) or a human IgG1 isotype in BupH™ (pH 6.5-8.0) was mixed with >200 molar equivalents of azido-dPEG$_3$-amine (MW=218.26 g/mol). The resulting solution was mixed with transglutaminase (25 U/mL; 5U MTG per mg of antibody, from Zedira, Darmstadt, Germany, or Ajinomoto, Japan) resulting in a final concentration of the antibody at 0.5-5 mg/mL, and the solution was kept at pH 6.5-8.0 and then incubated at 37° C. for 4-24 h while gently shaking. The reaction was monitored by ESI-MS. Upon reaction completion, the excess amine and MTG were removed by SEC (see FIG. 12) or protein A column eluting with acidic buffer and then neutralizing with Tris buffer (pH8), to generate the azido-functionalized antibody. This product was analyzed by SDS-PAGE (see FIG. 11) and ESI-MS (see FIG. 13). The azido-dPEG$_3$-amine added to two sites—Q295 and Q297-of the antibody resulting in an 804 Da increase for the 4DAR aglycosylated antibody-PEG$_3$-azide conjugate. The conjugation sites were identified and confirmed at $EEQ^{Link}_{er}YQ^{Linker}STYR$ for the 4DAR azido-functionalized antibody via peptide sequence mapping of trypsin digested heavy chains.

Example 63

This example demonstrates a method for making site-specific conjugates of a drug to an antibody using click chemistry reactions.

The site-specific aglycosylated antibody drug conjugates with a human IgG (IgG1, IgG4, etc.) containing an N297Q mutation (EU numbering) in Table 6 were prepared by a [2+3] click reaction between azido-functionalized antibodies with an alkyne containing linker-payload. As shown in Table 6, Anti Her2-PEG$_3$-N$_3$ was conjugated to linker-payloads (LPs) in Table 2: LP2, LP3, LP4, LP5, LP6, LP7, LP8, LP10, LP11, LP12, LP13, and LP14. As shown in Table 6, Anti PRLR-PEG$_3$-N$_3$ was conjugated to LPs in Table 2: LP5, LP6, LP7, LP8, LP10, LP11, LP12, LP13, and LP14. As shown in Table 6, isotype-control-PEG3-N3 was conjugated to LP2, LP3, LP4, LP5, LP6, LP7, LP8, LP10, LP11, LP12, LP13, and LP14 in Table 2.

For the conjugation, an azido-functionalized aglycosylated human IgG1 antibody (mAb-PEG$_3$-N$_3$) and a linker-payload (LP) conjugate was prepared by incubating mAb-PEG$_3$-N$_3$ (1-3 mg/mL) in an aqueous medium (e.g., PBS, PBS containing 5% glycerol, HBS) with ≥6 molar equivalents of an LP dissolved in a suitable organic solvent, such as DMSO, DMF or DMA (i.e., the reaction mixture contains 5-20% organic solvent, v/v) at 24° C. to 37° C. for over 6 h. The progress of the reaction was monitored by ESI-MS and the absence of mAb-PEG$_3$-N$_3$ indicated the completion of the conjugation. The excess amount of the LP and organic solvent were removed by SEC via elution with PBS, or via protein A column eluting with acidic buffer followed by neutralization with Tris (pH 8). The purified conjugates were analyzed by SEC, SDS-PAGE, and ESI-MS. Shown in Table 6 is a list of non-cytotoxic antibody conjugates (ncADCs) from the corresponding LPs, their molecular weights, and ESI-DAR values.

Summarized in Table 6 were the naked antibodies (anti-Her2 antibody, anti-PRLR antibody, and isotype control antibody), azido-functionalized antibodies (anti-Her2 antibody-PEG$_3$-N$_3$, anti-PRLR antibody-PEG3-N3, and isotype control antibody-PEG3-N3, and their antibody drug conjugates. In Table 6, Ab refers to an antibody, mAb refers to a monoclonal antibody, Ab-N$_3$ refers to an azido-functionalized antibody, Ab-PEG$_3$-N$_3$ refers to an azido-functionalized antibody with a PEG$_3$ spacer, and ncADC refers to a non-cytotoxic antibody drug conjugate. For convenience, the Anti Her2-LP(X) and Anti PRLR-LP(X) nomenclature—within Table 6 and other Tables herein—where X indicates a particular linker-payload (e.g., LP2 or LP10, etc.) embraces the presence of a PEG$_3$ spacer (e.g., from anti-Her2 antibody-PEG$_3$-N$_3$ or anti-PRLR antibody-PEG$_3$-N$_3$), as described herein.

TABLE 6

| List of Antibody, Antibody-PEG$_3$-N$_3$, and LXR Agonist-ncADCs | | | | |
|---|---|---|---|---|
| Ab, Ab-N$_3$, or ncADC | MS m/z (ncADC) | LP # | MW (LP) | DAR (ESI-MS) |
| Anti Her2 mAb | 145132 | | | |
| Anti Her2-PEG$_3$-N$_3$ | 145930 | NH$_2$-PEG$_3$-N$_3$ | 218.26 | 4 |
| Anti Her2-LP2 | 150880 | LP2 | 1232.7 | 3.8 |
| Anti Her2-LP3 | 151830 | LP3 | 1467.8 | 3.9 |
| Anti Her2-LP4 | 152175 | LP4 | 1554.8 | 3.8 |

TABLE 6-continued

List of Antibody, Antibody-PEG$_3$-N$_3$, and LXR Agonist-ncADCs

| Ab, Ab-N$_3$, or ncADC | MS m/z (ncADC) | LP # | MW (LP) | DAR (ESI-MS) |
|---|---|---|---|---|
| Anti Her2-LP5 | 149925 | LP5 | 990.0 | 4 |
| Anti Her2-LP6 | 158153 | LP6 | 3050.3 | 4 |
| Anti Her2-LP7 | 157715 | LP7 | 2939.2 | 3.9 |
| Anti Her2-LP8 | 156047 | LP8 | 2523.8 | 3.9 |
| Anti Her2-LP10 | 157040 | LP10 | 2771.1 | 4 |
| Anti Her2-LP11 | 156602 | LP11 | 2660.0 | 4 |
| Anti Her2-LP12 | 157212 | LP12 | 2818.1 | 4 |
| Anti Her2-LP14 | 151827 | LP14 | 1469.6 | 4 |
| Anti PRLR mAb | 144579 | | | |
| Anti PRLR-PEG$_3$-N$_3$ | 145373 | NH$_2$-PEG$_3$-N$_3$ | 218.26 | 4 |
| Anti PRLR-LP5 | 149368 | LP5 | 990.0 | 4 |
| Anti PRLR-LP6 | 157589 | LP6 | 3050.3 | 4 |
| Anti PRLR-LP7 | 157169 | LP7 | 2939.2 | 3.9 |
| Anti PRLR-LP8 | 155484 | LP8 | 2523.8 | 4 |
| Anti PRLR-LP10 | 156474 | LP10 | 2771.1 | 4 |
| Anti PRLR-LP11 | 156052 | LP11 | 2660.0 | 4 |
| Anti PRLR-LP14 | 151283 | LP14 | 1469.6 | 4 |
| isotype control mAb | 145430 | | | |
| isotype control-PEG$_3$-N$_3$ | 146235 | NH$_2$-PEG$_3$-N$_3$ | 218.26 | 4 |
| isotype control-LP2 | 151176 | LP2 | 1232.7 | 4 |
| isotype control-LP3 | 152120 | LP3 | 1467.8 | 4 |
| isotype control-LP4 | 152472 | LP4 | 1554.8 | 4 |
| isotype control-LP5 | 150218 | LP5 | 990.0 | 4 |
| isotype control-LP8 | 156355 | LP8 | 2523.8 | 4 |
| isotype control-LP10 | 157340 | LP10 | 2771.1 | 4 |
| isotype control-LP11 | 156893 | LP11 | 2660.0 | 3.4 |
| isotype control-LP12 | 157514 | LP12 | 2818.1 | 3.9 |

Example 64

This example demonstrates methods for characterizing antibody and non-cytotoxic antibody drug conjugates (ncADC).

The antibody and ncADC were characterized by SDS-PAGE, SEC, and MS (ESI). The anti-Her2-LP8 conjugate in Table 6 generated from the anti-Her2 antibody via its azido-functionalized antibody (anti-Her2-PEG$_3$-N$_3$) was characterized by SDS-PAGE performed under non-reducing and reducing conditions (FIG. 11), SEC (FIG. 12), and ESI-MS (FIG. 13), and demonstrated completion of the ncADC formation.

SDS-PAGE was used to analyze the integrity and purity of the ADCs.

In one method, SDS-PAGE conditions included non-reduced and reduced samples (2-4 µg) along with Bench-Mark Pre-Stained Protein Ladder (Invitrogen, cat #10748-010; L #1671922.) were loaded per lane in (1.0 mm×10 well) Novex 4-20% Tris-Glycine Gel and were ran at 180 V, 300 mA, for 80 min. An analytic sample was prepared using Novex Tris-Glycine SDS buffer (2×) (Invitrogen, Cat # LC2676) and the reducing sample was prepared with SDS sample buffer (2×) containing 10% 2-mecaptoethanol.

Figure 11:
FIG. 11 shows Coomassie-stained SDS-PAGE Gel of anti-Her2 antibody, anti-Her2-PEG₃-N₃, and anti-Her2-LP8.

In FIG. 11 are shown a representative gel, indicating the shift of the molecular weights of the antibodies and ncADCs on SDS-PAGE performed under non-reducing and reducing conditions. The masses of the heavy chains were increased from the naked antibodies to the ncADC conjugate. There was no detectable cross-linked material.

As shown in FIG. 11, the SDS-PAGE lanes included the following species based on the following lane labels in Table 7.

TABLE 7

| Lane | Sample |
|---|---|
| 1 | Standards (Bench Mark 10 µL) |
| 2 | Anti Her2 mAb |
| 3 | Anti Her2 mAb-NH-PEG$_3$-N$_3$ |
| 4 | Anti Her2 mAb-LP8 |
| 7 | Anti Her2 mAb (reduced) |
| 8 | Anti Her2 mAb-NH-PEG$_3$-N$_3$ (reduced) |
| 9 | Anti Her2 mAb-LP8 (reduced) |

~2 µg of non-reduced/reduced sample/lane. Novex 4-20% Tris-Glycine Gel;
1.0 mm × 10 well; 180 V, 300 mA, 80 min. BenchMark Pre-Stained Protein Ladder, Invitrogen, cat #10748-010; L #1671922.

ADCs were analyzed for purity by SEC.

To determine the purity of antibody drug conjugates, SEC was performed. Analytical SEC experiments were run using a Waters 600 instrument, on a Superdex 200 (1.0×30 cm) HR column, at flow rate of 0.80 mL/min using PBS pH 7.4, and monitored at λ=280 nm using a Waters 2998 PDA. An analytic sample was composed of 200 µL PBS (pH 7.4) with 30-100 µL of test sample. Preparative SEC purifications were performed using an AKTA instrument from GE Healthcare, on Superdex 200 PG (2.6×60 cm) column, at a flow rate 2 mL/min eluting with PBS pH 7.4, and monitored at λ=280 nm. The SEC results in FIG. 12 indicated typical retention times for monomeric mAb and its conjugates and there was no detectable aggregation or degradation.

Antibody and ADC were analyzed by intact mass analysis by LC-ESI-MS.

Measurement of intact mass for the ncADC samples by LC-ESI-MS was performed to determine drug-payload distribution profile and to calculate the average DAR of intact ADC forms. Each testing sample (20-50 ng, 5 µL) was loaded onto an Acquity UPLC Protein BEH C4 column (10K psi, 300 Å, 1.7 µm, 75 µm×100 mm; Cat No. 186003810). After 3 min desalting, the protein was eluted and mass spectra were acquired by a Waters Synapt G2-Si mass spectrometer.

The deconvoluted mass spectra exhibited a predominant peak for the aglycosylated anti-HER2 antibody with a molecular weight of 145132 Da, and a predominant peak for its azido functionalized anti-PRLR antibody with a molecular weight of 145930 Da, indicating a 798 Da increase compared to its aglycosylated parent antibody (i.e., corresponding to 4 amino-$PEG_3$-azide conjugations to each aglycosylated antibody). Also, the predominant peak for anti-HER2-LP8 conjugate had a molecular weight of 156047 Da, indicating a 10931 Da increase compared to its aglycosylated parent antibody (i.e., corresponding to 4 LP8 conjugations to each aglycosylated antibody). As summarized in Table 6, most site-specific ADCs in this document have 4DAR.

For non-site specific antibody drug conjugates, the DAR values were determined based on the ESI Q-TOF mass analysis. The ESI Q-TOF mass spectra were deconvoluted to zero charge mass spectra using a Maximum Entropy algorithm (MassLynx). The resulting mass spectra demonstrated the distribution of each drug conjugated antibody. The area percentage of a peak represents the relative distribution of the particular drug-loaded antibody species. The average DAR was calculated using the percentage peak area information and the drug load numbers on the antibody.

For non-site specific antibody drug conjugates, the DAR values were determined based on the ESI Q-TOF mass analysis. The ESI Q-TOF mass spectra were deconvoluted to zero charge mass spectra using a Maximum Entropy algorithm (MassLynx). The resulting mass spectra demonstrated the distribution of each drug conjugated antibody. The area percentage of a peak represents the relative distribution of the particular drug-loaded antibody species. The average DAR was calculated using the percentage peak area information and the drug load numbers on the antibody.

Example 65

This example demonstrates methods for LanthaScreen TR-FRET GR Competitive Binding Assay.

To evaluate the ability of novel LXR agonists to bind to the LXR alpha and beta receptor, a cell-free binding assay was performed using a LanthaScreen TR-FRET LXR alpha Coactivator Assay Kit (ThermoFisher, Cat # PV4655) and LXR beta Coactivator Assay Kit (ThermoFisher, Cat # PV4658). The assay was performed according to the manufacturer's instructions. Briefly, a 3-fold serial dilution of LXR agonists were prepared in 100% DMSO starting at 100 µM (100× of final). Serial dilutions were further diluted 50-fold in nuclear receptor buffer F with 5 mM DTT, and transferred to a 384-well assay plate. Next, Fluorescein-D22, LXR alpha or beta LBD-GST, and Tb anti-GST antibody was sequentially added to 384-well assay plate. The plate was then incubated at rt for 2.5 hours while being protected from light. The plate was analyzed on an Envision Multilabel Plate Reader (PerkinElmer) with excitation set at 340 nm and emission filters at 520 nm and 486 nm. The FRET ratio was calculated as 520 nm/486 nm. The $IC_{50}$ values were determined using a four-parameter logistic equation over a 12-point response curve (GraphPad Prism).

As shown in Table 8, LXR agonists of the invention bound in the LXR assay to LXRa with $IC_{50}$ values from below 1 nM to greater than 100 nM and to LXRb with $IC_{50}$ values between from below 1 nM to greater than 100 nM. The reference compounds bound in the LXR assay to LXRa with $IC_{50}$ values less than or equal to 10 nM and to LXRb with $IC_{50}$ values between 1 nM and 10 nM. Under these assay conditions, several of the LXR agonists provided herein displayed a similar or better $IC_{50}$ for binding to LXR than reference compounds.

The cell free binding and cell based functional activity of the compounds in Table 1 are summarized in Table 8. The fold activation in the cell-based assays (as described in Example 68, below) was defined based on the maximum activation of the free payload 9d. Compounds that demonstrated greater than 75% of the activation of the free payload are termed "full activation". Compounds that demonstrated from 25% maximal activation to 75% maximal activation of the free payload are termed "partial activation". Compounds that demonstrated less than 25% of the activation of the free payload are termed "no activation".

TABLE 8

Cell free binding and cell based functional activity at 48 hours

| | Cell free binding | | Activation of THP1/LXR-Luc cells | |
|---|---|---|---|---|
| Cpd # | LXRα $IC_{50}$ | LXRβ $IC_{50}$ | Fold of activation | $EC_{50}$ (nM) |
| 9a | +++ | +++ | Full activation | +++ |
| 9b | +++ | +++ | Full activation | +++ |
| 9c | ++ | +++ | Full activation | ++ |
| 9d | +++ | +++ | Full activation | ++++ |
| 9e | +++ | +++ | Full activation | +++ |
| 9f | +++ | +++ | Full activation | +++ |
| 9h | ++++ | ++++ | Full activation | ++++ |
| 9i | +++ | +++ | Partial activation | ++ |
| 9j | +++ | +++ | Full activation | ++++ |
| 9k | ++ | +++ | Full activation | +++ |
| 9l | ++ | ++ | Full activation | +++ |
| 9m | ++ | +++ | Full activation | +++ |
| 9n | ++ | +++ | Full activation | ++++ |
| 9o | ++ | +++ | Full activation | ++++ |
| 9p | ++ | +++ | Full activation | +++ |
| 9q | +++ | +++ | Full activation | ++ |
| 9r | +++ | +++ | Full activation | ++ |
| 9t | + | + | Partial activation | ++ |
| 9u | ++ | ++ | Partial activation | +++ |
| 17b | ++ | +++ | Full activation | ++ |
| 17c | + | +++ | Full activation | ++++ |
| 31 | +++ | +++ | Partial activation | ++ |
| GW3965 | +++ | +++ | Full activation | + |
| T0901317 | ++++ | +++ | Full activation | ++ |

$IC_{50}$: ++++: ≥1 nM;
+++: ≥10 nM > nM;
++: ≥100 nM >10 nM;
+>100 nM. NT: not tested.
$EC_{50}$: ++++: ≥1 nM;
+++: ≥10 nM >1 nM;
++: ≥100 nM >10 nM;
+: >100 nM. NT: not tested.

Example 66

To determine the ability of LXR agonists to activate ABCA1 and ABCG1 genes, the mRNA levels of these two genes in differentiated macrophages was measured. For the assay, THP-1 human cell line cells were seeded onto 48-well plates at 500,000 cells/well in RPMI 1640 media (Irvine Scientific, #9160) containing 1000 FBS (Gibco, Cat #1043010), 10 µg/mL penicillin-streptomycin (Gibco, Cat #15140122) in 5% $CO_2$ at 37° C. Cells were differentiated into macrophages by treatment with 100 nM Phorbol-12 myristate 13-acetate (Sigma, # P8139), which was added to the media described above, for 72 hours. Differentiated macrophages were treated with a serial dilution of LXR agonist compounds and reference compound T0901317 for a 24-hour period, with a concentration range between $5\times10^{-7}$ M to $5\times10^{-17}$ M. Media from the cells was aspirated and 0.75 mL of TRIzol reagent (Invitrogen, Cat #15596018) was added to lysate the cells. Chloroform was then used for phase separation. The aqueous phase, containing total RNA, was purified using MagMAX™-96 for Microarrays Total RNA Isolation Kit (Ambion, Cat # AM1830) and reverse-transcribed into cDNA using SuperScript® VILO™ Master Mix (Invitrogen, Cat #11755050) as per the manufacturer's instructions. TaqMan® was performed using Gene Expression Master Mix, the ABI 7900HT Sequence Detection System (Applied Biosystems) and the primers and probes indicated below in Table 9. The GAPDH gene was used as the internal control gene to normalize any cDNA input differences.

TABLE 9

Taqman probes and primers

| Gene | Probe Sequence | Forward Primer | Reverse Primer |
|---|---|---|---|
| ABCA1 | CTGACCAATGTGAACAGCTCCAGC | ACATGCGACAGGAGGTGATG | ATGCCCGCAGACAATACGA |
| ABCG1 | AGATAATAACCTCACGGAAGCCCAGCG | GGACCTGCTGAATGGACATC | CCGAGGCAAGGAGGAGAA |
| GADPH | TCAACAGCGACACCCACTCCTC | CCAGGTGGTCTCCTCTGACT | GCTTGACAAAGTGGTCGTTGA |

Figure 14:
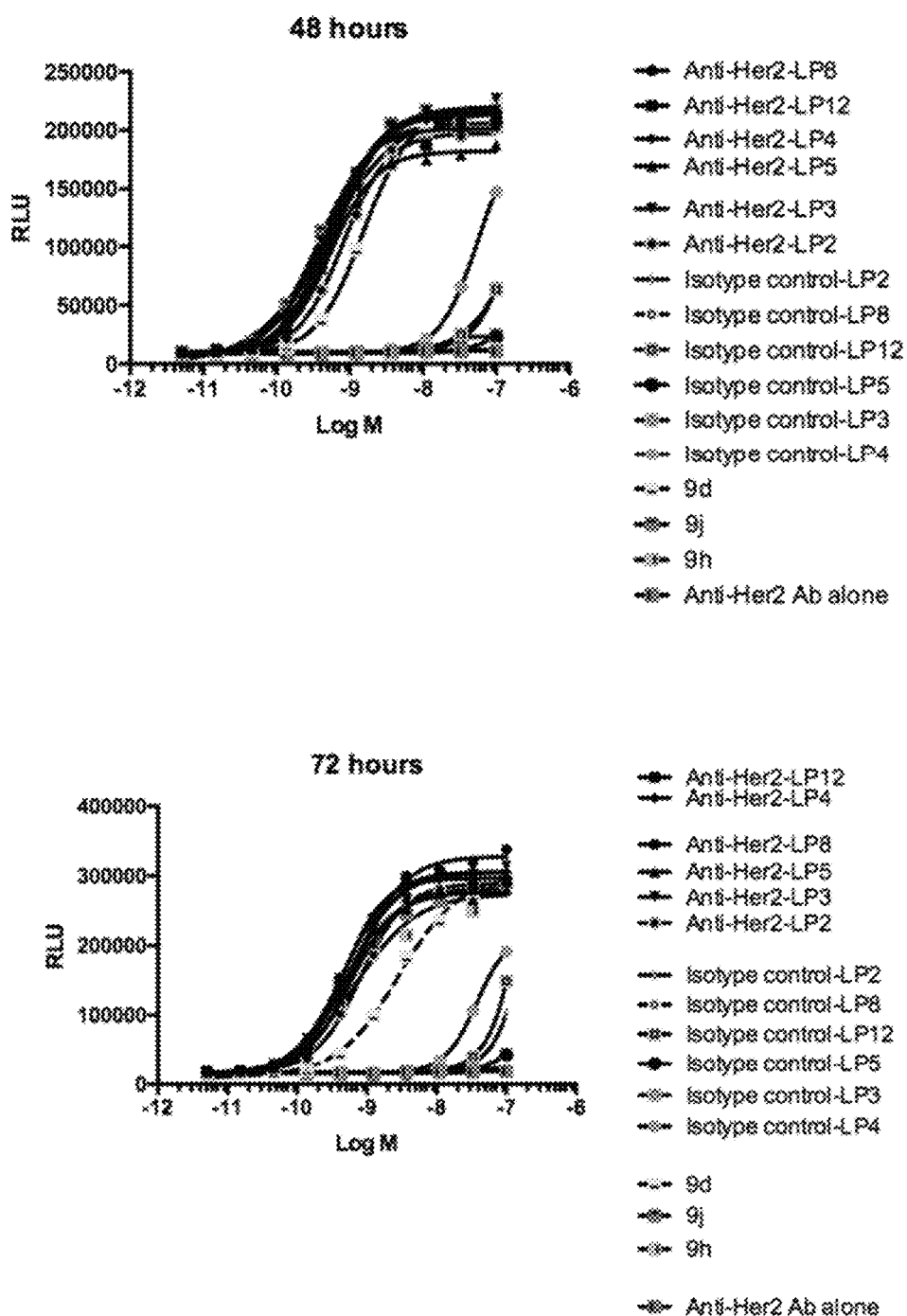
FIG. 14 shows $EC_{50}$ values using a four-parameter logistic equation over a 10-point dose response curve.

All compounds demonstrated induction of LXR endogenous effector target genes ABCA1 and ABCG1 in human THP1 macrophages (FIG. 14). Compounds 9d and 9h showed the highest potency, with ABCA1 induction $EC_{50}$ values that were sub-picomolar, and with ABCG1 induction $EC_{50}$ values that were sub-picomolar. The other compounds tested showed similar levels of ABCA1 and ABCG1 gene activation compared to 9d and 9h, but they activated with nano-molar $EC_{50}$ values.

Example 67

This example demonstrates the generation of bioassay cell lines for evaluation of the LXR-agonists and their antibody conjugates.

A bioassay was developed to assess the activity of LXR agonists after internalization of an agonist or of a ncADC into cells and binding to LXR, a nuclear receptor, using a commercially available LXR reporter (referred to as LXR-Luc) that contains the firefly luciferase gene under control by minimal CMV promoter and tandem repeats of the LXR transcriptional response element. For this assay, a THP1 cell line, which is a human monocytic leukaemia line, was engineered to express full length human Her2 (expressing amino acids M1 through V1255 of accession number NP_004439.2). The subsequent stable cell line was further transduced with a Cignal LXR Luc Reporter (Qiagen, Cat # CLS-7041L). The resulting stable cell line is referred to herein as THP1/Her2/LXR-Luc. The Her2 cell surface expression on THP1/Her2/LXR-Luc cell line was confirmed by FACS (data not shown).

Additionally, a THP1 cell line was transduced with a Cignal LXR Luc Reporter (Qiagen, Cat # CLS-7041L) without the addition of Her2. The resulting stable cell line is referred to herein as THP1/LXR-Luc. All of the antibodies used in in the subsequent bioassays were assessed for their ability to internalize and release a payload on the bioassay cell line used.

Example 68

Figure 15:
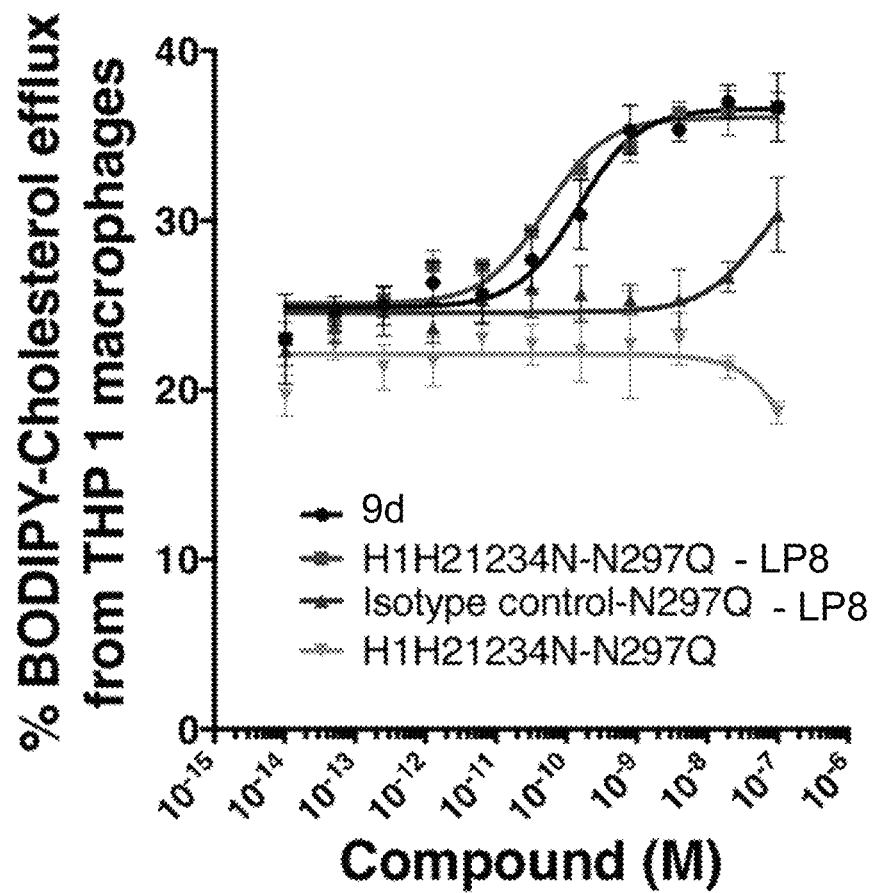
FIG. 15 is a graph illustrating percentage of dose-dependent cholesterol efflux in THP-1 macrophages for an exemplary MSR1 antibody-LXR conjugate, its unconjugated counterpart, an isotype control-LXR conjugate, and the corresponding free payload.

This example assessed the ability of the LXR agonists provided herein, reference compounds, and anti-Her2 antibody-LXR ncADC to activate LXR. The samples were tested in the THP1/LXR-Luc/Her2 bioassay. For the assay, either THP1/LXR-Luc cells or THP1/LXR-Luc/Her2 cells were seeded onto white 96 well plates at 30,000 cells/well in media containing RPMI supplemented with 10% FBS and pencillin/streptomycin (complete media). Subsequently 3-fold serial dilutions of antibody drug conjugates, unconjugated antibodies, or free payloads were added to the cells at final concentration ranging from 100 nM to 0.01 nM. After 48-hour or 72-hour incubation, luciferase activity was determined after the addition of One-Glo™ reagent (Promega, Cat # E6130) to each well of cells. Relative light units (RLUs) were measured on a Victor luminometer (PerkinElmer) and the $EC_{50}$ values were determined using a four-parameter logistic equation over a 10-point dose response curve (GraphPad Prism) (FIG. 15). The $EC_{50}$ values of LXR agonists of the invention and reference compounds are shown in the Table 3. The $EC_{50}$ values of the ncADCs and simultaneously tested LXR agonists are shown in Table 10. The fold activation is calculated based on the maximum activation of the free payload 9d. Molecules tested that demonstrated greater than 75% of the activation of the free payload 9d are termed "full activation". Molecules tested that demonstrated from 25% maximal activation to 75% maximal activation of the free payload 9d are termed "partial activation". Molecules tested that demonstrated less than 25% of the activation of the free payload 9d are termed "no activation".

As shown in Table 10, at 48-hour time point, the free payload, 9d, induced a full activation of THP1/LXR-Luc/Her2 cells with an $EC_{50}$ value of 1.6 nM. Anti-Her2 antibody site-specifically conjugated with linker payloads containing 9d stimulated activation of THP1/LXR-Luc/Her2 cells with $EC_{50}$ values ranging from 0.51 nM to 0.83 nM (Anti-Her2-LP2, LP3, LP5, and LP8). Negative isotype control antibodies conjugated with linker payloads containing 9d did not demonstrate significant activation, except for the control with LP2, which demonstrated slight activation at the highest concentrations tested. The free payload, 9j, induced a full activation of THP1/LXR-Luc/Her2 cells with an $EC_{50}$ value of 0.39 nM. An anti-Her2 antibody site-specifically conjugated with a linker payload containing 9j (Anti-Her2-LP4) stimulated activation of THP1/LXR-Luc/Her2 cells with an $EC_{50}$ value of 0.60 nM. A negative isotype control antibody conjugated with a linker payload containing 9j demonstrated slight activation at the highest concentrations tested. The free payload, 9h, induced a full activation of THP1/LXR-Luc/Her2 cells with an $EC_{50}$ value of 0.50 nM. An anti-Her2 antibody site-specifically conjugated with a linker payload containing 9h (Anti-Her2-LP12) stimulated activation of THP1/LXR-Luc/Her2 cells with an $EC_{50}$ value of 0.47 nM. A negative isotype control antibody with a linker payload containing 9h demonstrated slight activation at the highest concentrations tested.

As shown in Table 10, at 72-hour time point, the free payload, 9d, induced a full activation of THP1/LXR-Luc/Her2 cells with an $EC_{50}$ value of 2.8 nM. Anti-Her2 antibody site-specifically conjugated with linker payloads containing 9d stimulated activation of THP1/LXR-Luc/Her2 cells with $EC_{50}$ values ranging from 0.46 nM to 0.80 nM (Anti-Her2-LP2, LP3, LP5, and LP8). Negative isotype control antibodies conjugated with linker payloads containing 9d did not demonstrate significant activation, except for the control with LP2, which demonstrated slight activation at the highest concentrations tested. The free payload, 9j, induced a full activation of THP1/LXR-Luc/Her2 cells with an $EC_{50}$ value of 0.47 pM. An anti-Her2 antibody site-specifically conjugated with a linker payload containing 9j (Anti-Her2-LP4) stimulated activation of THP1/LXR-Luc/Her2 cells with an $EC_{50}$ value of 0.55 pM. A negative isotype control antibody conjugated with a linker payload containing 9j demonstrated slight activation at the highest concentrations tested. The free payload, 9h, induced a full activation of THP1/LXR-Luc/Her2 cells with an $EC_{50}$ value of 0.65 nM. An anti-Her2 antibody site-specifically conjugated with a linker payload containing 9h (Anti-Her2-LP12) stimulated activation of THP1/LXR-Luc/Her2 cells with an $EC_{50}$ value of 0.45 nM. A negative isotype control antibody conjugated with a linker payload containing 9h demonstrated slight activation at the highest concentrations tested.

Generated anti-MSR1 antibodies were mutated (N297Q) to incorporate a transglutaminase site for conjugation with a therapeutic payload. The site-specific aglycosylated antibodies containing an N297Q mutation were conjugated with amine-$PEG_3$-$N_3$ to generate the azido-functionalized antibody conjugates (mAb-$N_3$), including anti MSR1 Ab-$PEG_3$-$N_3$.

The present example demonstrates a method for making the conjugates. Aglycosylated antibody with a human IgG1 isotype in BupH™ (pH 7-8) was mixed with ≥200 molar equivalents of azido-$dPEG_3$-amine (MW. 218.26 g/mol). The resulting solution was mixed with transglutaminase (25 U/mL; 5U MTG per mg of antibody) resulting in a final concentration of the antibody at 0.5-10 mg/mL, and the solution was then incubated at 37° C. for 4-24 hours while gently shaking. The reaction was monitored by SDS-PAGE or ESI-MS. Upon the completion, the excess amine and MTG were removed by Size Exclusion Chromatography (SEC) to generate the azido-functionalized antibody (mAb-N3). This product was analyzed on SDS-PAGE and ESI-MS. The azido-$dPEG_3$-amine added to two sites—Q295 and Q297- of the antibody resulting in an 804 Da increase for the 4DAR aglycosylated antibody-$PEG_3$-azide conjugate. The conjugation sites were identified and confirmed at $EEQ^{Linker}YQ^{Linker}STYR$ for the 4DAR azido-functionalized antibody via peptide sequence mapping of trypsin digested heavy chains.

The site-specific aglycosylated antibody drug conjugates (ADCs) with a human IgG1 or IgG4 containing an N297Q mutation were prepared by a [2+3] click reaction between the azido-functionalized antibody (mAb-$N_3$) with an alkyne containing linker-payload (LP).

A site-specific antibody conjugate with linker-payload (LP) was prepared by incubating mAb-$PEG_3$-$N_3$ (1-12 mg/mL) in an aqueous medium (e.g., PBS, PBS containing 5% glycerol, HBS) with ≥6 molar equivalents of an LP dissolved in a suitable organic solvent, such as DMSO, DMF

TABLE 10

Activation in THP1/LXR-Luc/Her2 Assay by LXR agonists and ncADCs

| Molecule | 48 hours | | 72 hours | |
|---|---|---|---|---|
| | Level of activation | $EC_{50}$ | Level of activation | $EC_{50}$ (nM) |
| Anti Her2-LP2 | Full activation | 8.3E−10 | Full activation | 8.0E−10 |
| Isotype control-LP2 | Partial activation | NA | Partial activation | NA |
| Anti Her2-LP3 | Full activation | 5.1E−10 | Full activation | 4.6E−10 |
| Isotype control-LP3 | No activation | NA | No activation | NA |
| Anti Her2-LP4 | Full activation | 6.0E−10 | Full activation | 5.5E−10 |
| Isotype control-LP4 | Partial activation | 5.7E−08 | Partial activation | 3.8E−08 |
| Anti Her2-LP5 | Full activation | 5.5E−10 | Full activation | 5.7E−10 |
| Isotype control-LP5 | No activation | NA | No activation | NA |
| Anti Her2-LP8 | Full activation | 6.5E−10 | Full activation | 7.0E−10 |
| Isotype control-LP8 | No activation | NA | No activation | NA |
| Anti Her2-LP12 | Full activation | 4.7E−10 | Full activation | 4.5E−10 |
| Isotype control-LP12 | Partial activation | NA | Partial activation | NA |
| 9d, payload of LP2, 3, 5, & 8 | Full activation | 1.6E−09 | Full activation | 2.8E−09 |
| 9h, payload of LP12 | Full activation | 5.0E−10 | Full activation | 6.5E−10 |
| 9j, payload of LP4 | Full activation | 3.9E−10 | Full activation | 4.7E−10 |
| Anti Her2 antibody alone | No activation | NA | No activation | NA |

NA: not applicable.

Example 69

ADC Conjugation

This example demonstrates another method for site-specific conjugation, generally, of a payload to an antibody or antigen-binding fragment thereof.

or DMA (i.e., the reaction mixture contains 5-20% organic solvent, v/v) at 24° C. to 37° C. for 30 min to 24 hr. The progress of the reaction was monitored by ESI-MS and the absence of mAb-PEG3-N3 indicated the completion of the conjugation. The excess amount of the LP and organic solvent were removed by SEC via elution with PBS, or via protein A column chromatography via elution with acidic buffer followed by neutralization with Tris (pH 8.0). The purified conjugates were analyzed by SEC, SDS-PAGE, and ESI-MS.

In a specific example, the azido-functionalized antibody (1 mg) in 0.800 mL PBSg (PBS, 5% glycerol, pH 7.4) was treated with six molar equivalents of DIBAC-PEG$_4$-D-Lys (COT-α-CD)-VC-PABC-payload (conc. 10 mg/mL in DMSO) for 2 hours at rt and the excess linker payload (LP) was removed by size exclusion chromatography (SEC, Superdex 200 HR, GE Healthcare). The final product was concentrated by ultra-centrifugation and characterized by UV, SEC, SDS-PAGE and ESI-MS.

Example 70

Characterization of ADCs by LC-ESI-MS

Measurement of intact mass for the ADC samples by LC-ESI-MS was performed to determine the drug-payload distribution profile and to calculate the average DAR. Each testing sample (20-50 ng, 5 uL) was loaded onto an Acquity UPLC Protein BEH C4 column (10K psi, 300 Å, 1.7 μm, 75 μm×100 mm; Cat No. 186003810). After 3 min. desalting, the protein was eluted and mass spectra were acquired by a Waters Synapt G2-Si mass spectrometer. As summarized in Table 12, most site-specific ADCs have 3.9-4 DAR for the site specific conjugates.

TABLE 11

Linker-Payload Properties

| LP | cLogP | MF | MW | HPLC purity (%) | HPLC R$_t$ (min) | MS (m/z) 100% | Highest m/z peak |
|---|---|---|---|---|---|---|---|
| LP8 | −0.38 | $C_{124}H_{175}N_{11}O_{44}$ | 2523.76 | 98 | 6.45, 6.55 (B) | 841.8 [M/3 + H] | 1262.4 [M/2 + H] (30%) |
| LP32 | −3.92 | $C_{136}H_{195}N_{11}O_{54}$ | 2848.04 | 96 | 7.48 (B) | 955.0 [(M +18)/3] 949.5 (M/3 + H) | 1424.2 (M/2 + H) (30%) |
| LP15 | 7.53 | $C_{72}H_{100}N_{10}O_{13}$ | 1313.62 | 96 | 8.16 (B) | 657.5 (M/2 + H) (5%) | 1313.6 (M + H) |
| LP13 | −1.48 | $C_{138}H_{193}N_{15}O_{49}$ | 2846.08 | 100 | 6.11, 6.21 (B) | 949.0 (M/3 + H) | 1423.3 (M/2 + H) (5%) |
| LP36 | 6.59 | $C_{115}H_{160}N_{16}O_{28}S$ | 2246.66 | 100 | 7.24 (B) | 749.5 (M/3 + H) | 1123.8 (M/2 + H) (5%) |
| LP39 | 8.70 | $C_{88}H_{112}N_{10}O_{18}$ | 1597.89 | 95 | 5.67 (B) | 799.0 (M/2 + H) | 799.0 (M/2 + H) |
| LP311 | 8.17 | $C_{89}H_{117}N_{11}O_{16}$ | 1596.95 | 95 | 8.51 (B) | 798.5 (M/2 + H) | 798.5 (M/2 + H) |
| LP18 | 6.49 | $C_{101}H_{142}N_{12}O_{23}S$ | 1924.34 | 97 | 7.57 (B) | 642.2 (M/3 + H) | 962.5 (M/2 + H) (70%) |

TABLE 12

ADC Properties

| LP # | MW (LP) | Ab, Ab-N$_3$, or ncADC | MS m/z (ncADC) | DAR (ESI-MS) |
|---|---|---|---|---|
| 8 | 2523.8 | H1H27729P<br>H1H27729P-N$_3$<br>H1H27729P-LP8 | 144166 | 4 |
| 8 | 2523.8 | H1H27731P<br>H1H27731P-N$_3$<br>H1H27731P-LP8 | 144620 | 4 |
| 8 | 2523.8 | H1H27732P<br>H1H27732P-N$_3$<br>H1H27732P-LP8 | 144176 | 5.7 |
| 8 | 2523.8 | H1H27734P<br>H1H27734P-N$_3$<br>H1H27734P-LP8 | 145110 | 4.4 |
| 8 | 2523.8 | H1H27736P<br>H1H27736P-N$_3$<br>H1H27736P-LP8 | 145940 | 4 |
| 8 | 2523.8 | H1H27739P<br>H1H27739P-N$_3$<br>H1H27739P-LP8 | 145251 | 4 |
| 8 | 2523.8 | H1H27747P<br>H1H27747P-N$_3$<br>H1H27747P-LP8 | 145214 | 5.3 |
| | | H1H27749P<br>H1H27749P-N$_3$ | 143441 | 4 |

TABLE 12-continued

| | | ADC Properties | | |
|---|---|---|---|---|
| LP # | MW (LP) | Ab, Ab-N$_3$, or ncADC | MS m/z (ncADC) | DAR (ESI-MS) |
| | | H1H27749P-LP8 | | |
| | | H1H17751P | 146092 | 3.8 |
| | | H1H17751P-N$_3$ | | |
| 8 | 2523.8 | H1H17751P-LP8 | | |
| | | H1H27754P | 145477 | 4.2 |
| | | H1H27754P-N$_3$ | | |
| 8 | 2523.8 | H1H27754P-LP8 | | |
| | | H1H27756P | 145503 | |
| | | H1H27756P-N$_3$ | 146310 | 4 |
| 8 | 2523.8 | H1H27756P-LP8 | 156424 | 4 |
| | | H1H17759P2 | 145126 | |
| | | H1H17759P2-N$_3$ | 145930 | 4 |
| 8 | 2523.8 | H1H17759P2-LP8 | 156046 | 4 |
| | | H1H17760P2 | 145611 | |
| | | H1H17760P2-N$_3$ | 146431 | 4 |
| 8 | 2523.8 | H1H17760P-LP8 | 156533 | 4 |
| | | H1H17761P2 | 145508 | |
| | | H1H17761P2-N$_3$ | 146717 | 6 |
| 8 | 2523.8 | H1H17761P2-LP8 | 161884 159158 | 5.34 |
| | | H1H27762P2 | 144371 | |
| | | H1H27762P2-N$_3$ | 145177 | 4 |
| 8 | 2523.8 | H1H27762P2-LP8 | 155294 | 4 |
| | | H1H27766P2 | 146314 | |
| | | H1H27766P2-N$_3$ | 147121 | 4 |
| 8 | 2523.8 | H1H27766P2-LP8 | 157236 | 4 |
| | | H1H27771P2 | 145966 | |
| | | H1H27771P2-N$_3$ | 146774 | 4 |
| 8 | 2523.8 | H1H27771P2-LP8 | 156890 | 4 |
| | | H1H27773P2 | 145533 | |
| | | H1H27773P2-N$_3$ | 146337 | 4 |
| 8 | 2523.8 | H1H27773P2-LP8 | 156453 | 4 |
| | | H1H27778P2 | 145310 | |
| | | H1H27778P2-N$_3$ | 146115 | 4 |
| 8 | 2523.8 | H1H27778P2-LP8 | 156227 | 4 |
| | | H1H21231N | | |
| | | H1H21231N-N$_3$ | Lot2 | 2 |
| 8 | 2523.8 | H1H21231N-LP8 | Lot4 | 1.9 |
| | | H1H21227N | | |
| | | H1H21227N-N$_3$ | Lot2 | 4 |
| 8 | 2523.8 | H1H21227N-LP8 | Lot3 | 3.7 |
| | | H1H21231N | | |
| | | H1H21231N-N$_3$ | Lot2 | 6 |
| 8 | 2523.8 | H1H21231N-LP8 | Lot3 | 5.9 |
| | | H1H21235N | 145487 | |
| | | H1H21235N-N$_3$ | 146288 | 4 |
| 8 | 2523.8 | H1H21235N-LP8 | 156390 | 4.1 |
| | | H1H25700N | 145484 | |
| | | H1H25700N-N$_3$ | 146688 | 6 |
| 8 | 2523.8 | H1H25700N-LP8 | 161873 | 6 |
| | | H1H25690N | 145157 | |
| | | H1H25690N-N$_3$ | 145969 | 4 |
| 8 | 2523.8 | H1H25690N-LP8 | 156060 | 4.1 |
| | | H1H25695N | 145736 | |
| | | H1H25695N-N$_3$ | 146537 | 4 |
| 8 | 2523.8 | H1H25695N-LP8 | 156637 | 3.9 |
| | | H1H25685N | 145380 | |
| | | H1H25685N-N$_3$ | 146582 | 6 |
| 8 | 2523.8 | H1H25685N-LP8 | 161767 | 5.8 |
| | | H1H21228N | 144830 | |
| | | H1H21228N-N$_3$ | 145631 | 4 |
| 8 | 2523.8 | H1H21228N-LP8 | 155732 | 4.2 |
| | | H1H21234N | 145790 | |
| | | H1H21234N-N$_3$ | 146583 | 4 |
| 8 | 2523.8 | H1H21234N-LP8 | 156691 | 4 |
| 32 | 2848.1 | H1H21234N-LP32 | 157983 | 3.9 |
| 15 | 1313.7 | H1H21234N-LP15 | 151841 | 3.9 |
| 13 | 2846.2 | H1H21234N-LP13 | 157963 | 3.9 |
| 36 | 2246.7 | H1H21234N-LP36 | 155570 | 3.9 |
| 39 | 1597.9 | H1H21234N-LP39 | 152975 | 3.9 |
| 311 | 1597.0 | H1H21234N-LP311 | 152979 | 3.9 |
| Fel D1 | | isotype control-N297Q | | |
| | | isotype control-N297Q-N$_3$ | 146251 | 4 |
| 8 | 2523.8 | isotype control-N297Q-LP8 | 156352 | 3.9 |

Example 71

Biacore Surface Plasmon Resonance Derived Binding Kinetics of Anti-MSR1 Antibody-Drug Conjugates The MSR1 antibodies disclosed herein were conjugated to various liver X receptor (LXR) payloads. This example describes how equilibrium dissociation constant ($K_D$) values for human MSR1 reagents binding to human anti-MSR1 antibody-drug conjugates and their corresponding unconjugated parental antibodies were determined using a real-time surface plasmon resonance-based Biacore T200 biosensor.

All binding studies were performed in 10 mM HEPES, 300 mM NaCl, 3 mM EDTA, and 0.05% v/v Surfactant Tween-20, pH 7.4 (HBS-ET) running buffer at 25° C. The Biacore CM4 sensor chip surface was first derivatized by amine coupling with the goat anti-human Fcγ specific polyclonal antibody (Jackson ImmunoResearch Laboratories, Cat # BR-1008-39) to capture anti-MSR1 monoclonal antibodies. Binding studies were performed on human MSR1 extracellular domain expressed with a N-terminal nonahistidine tag (His9-hMSR1; R&D Systems, Cat #2708-MS). Different concentrations of His9-hMSR1 (100 nM–3.7 nM or 30 nM–3.33 nM; 3-fold serial dilution) were first prepared in HBS-ET running buffer and were injected over anti-human Fcγ captured anti-MSR1 monoclonal antibody surface for 3 minutes at a flow rate of 50 μL/minute, while the dissociation of monoclonal antibody bound MSR1 reagent was monitored for about 8-10 minutes in HBS-ET running buffer.

The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\min) = \frac{\ln(2)}{60 * kd}$$

Binding kinetics parameters for His9-hMSR1 binding to different anti-MSR1 antibody-LXR ADCs and their unconjugated parental antibodies at 25° C. are shown in Table 13. "LP1" represents a linker-payload for which the payload structure is provided in Example 111a.

TABLE 13

Binding kinetics of His-hMSR1 binding to MSR1 Antibody-LXR ADCs and Corresponding Unconjugated Antibodies at 25° C.

| Antibody Captured | ka (M$^{-1}$ s$^{-1}$) | kd (s$^{-1}$) | $K_D$ (Molar) | t1/2 (min) |
|---|---|---|---|---|
| H1H27729P-N297Q | 1.05E+05 | 9.06E−04 | 8.67E−09 | 12.8 |
| H1H27729P-N297Q-LP8 | 5.47E+04 | 7.18E−04 | 1.31E−08 | 16.1 |
| H1H27731P-N297Q | 1.17E+05 | 1.00E−05 | 8.55E−11 | 1155.2 |
| H1H27731P-N297Q-LP8 | 1.28E+05 | 1.00E−05* | 7.80E−11 | 1155.2 |
| H1H27732P-N297Q | 2.20E+05 | 1.00E−05* | 4.50E−11 | 1155.2 |
| H1H27732P-N297Q-LP8 | 1.50E+05 | 1.00E−05* | 6.60E−11 | 1155.2 |
| H1H27734P-N297Q | 7.72E+04 | 5.96E−04 | 7.72E−09 | 19.4 |
| H1H27734P-N297Q-LP8 | 6.93E+04 | 4.49E−04 | 6.49E−09 | 25.7 |
| H1H27736P-N297Q | 1.14E+05 | 1.47E−04 | 1.29E−09 | 78.7 |
| H1H27736P-N297Q-LP8 | 9.59E+04 | 1.21E−04 | 1.26E−09 | 95.5 |
| H1H27739P-N297Q | 1.19E+05 | 5.55E−04 | 4.68E−09 | 20.8 |
| H1H27739P-N297Q-LP8 | 8.88E+04 | 7.22E−04 | 8.14E−09 | 16.0 |
| H1H27747P-N297Q | 1.17E+05 | 2.62E−04 | 2.24E−09 | 44.1 |
| H1H27747P-N297Q-LP8 | 1.36E+05 | 2.03E−04 | 1.49E−09 | 56.9 |
| H1H27749P-N297Q | 1.43E+05 | 1.00E−05* | 6.99E−11 | 1155.2 |
| H1H27749P-N297Q-LP8 | 1.40E+05 | 1.00E−05* | 7.16E−11 | 1155.2 |
| H1H27751P-N297Q | 2.10E+05 | 1.75E−04 | 8.33E−10 | 66.1 |
| H1H27751P-N297Q-LP8 | 2.29E+05 | 1.52E−04 | 6.64E−10 | 76.1 |
| H1H27754P-N297Q | 2.00E+05 | 1.00E−05* | 4.99E−11 | 1155.2 |
| H1H27754P-N297Q-LP8 | 1.77E+05 | 1.00E−05* | 5.64E−11 | 1155.2 |
| H1H27756P-N297Q | 7.21E+04 | 1.19E−04 | 1.65E−09 | 97.4 |
| H1H27756P-N297Q-LP8 | 6.27E+04 | 1.10E−04 | 1.76E−09 | 104.7 |
| H1H27759P-N297Q | 1.03E+05 | 4.35E−04 | 4.23E−09 | 26.6 |
| H1H27759P-N297Q-LP8 | 1.30E+05 | 5.95E−04 | 4.57E−09 | 19.4 |
| H1H27760P-N297Q | 2.31E+05 | 3.83E−04 | 1.66E−09 | 30.2 |
| H1H27760P-N297Q-LP8 | 2.59E+05 | 4.34E−04 | 1.67E−09 | 26.6 |
| H1H27761P-N297Q | 5.95E+05 | 3.62E−04 | 6.09E−10 | 31.9 |
| H1H27761P-N297Q-LP8 | 2.53E+05 | 5.11E−04 | 2.02E−09 | 22.6 |
| H1H27762P-N297Q | 4.05E+05 | 5.60E−04 | 1.38E−09 | 20.6 |
| H1H27762P-N297Q-LP8 | 4.83E+05 | 6.23E−04 | 1.29E−09 | 18.5 |
| H1H27766P-N297Q | 1.72E+05 | 1.00E−05* | 5.83E−11 | 1155.2 |
| H1H27766P-N297Q-LP8 | 4.16E+05 | 2.70E−05 | 6.49E−11 | 427.4 |
| H1H27771P-N297Q | 3.83E+05 | 3.55E−04 | 9.26E−10 | 32.6 |
| H1H27771P-N297Q-LP8 | 3.38E+05 | 4.42E−04 | 1.31E−09 | 26.1 |
| H1H27773P-N297Q | 5.49E+04 | 7.52E−04 | 1.37E−08 | 15.4 |
| H1H27773P-N297Q-LP8 | 2.72E+04 | 9.47E−04 | 3.48E−08 | 12.2 |
| H1H27778P-N297Q | 1.66E+05 | 2.71E−04 | 1.63E−09 | 42.6 |
| H1H27778P-N297Q-LP8 | 2.85E+05 | 2.76E−04 | 9.70E−10 | 41.8 |
| H1H21234N-N297Q | 2.20E+05 | 1.00E−05* | 4.54E−11 | 1155.2 |
| H1H21234N-N297Q-LP8 | 4.90E+05 | 1.00E−05* | 2.04E−11 | 1155.2 |
| H1xH29273P2 | 8.20E+04 | 7.63E−03 | 9.30E−08 | 1.5 |

TABLE 13-continued

Binding kinetics of His-hMSR1 binding to MSR1 Antibody-LXR ADCs and Corresponding Unconjugated Antibodies at 25° C.

| Antibody Captured | ka ($M^{-1}\ s^{-1}$) | kd ($s^{-1}$) | $K_D$ (Molar) | t1/2 (min) |
|---|---|---|---|---|
| H1xH29282P2 | 8.28E+04 | 3.62E−03 | 4.37E−08 | 3.2 |
| H1xH29283P2 | 1.39E+05 | 1.85E−03 | 1.34E−08 | 6.2 |

*indicates that no dissociation of His9-hMSR1 was observed under the current experimental conditions and the $k_d$ value was manually fixed at 1.00E−05 while fitting the data
§indicates that no binding was observed under the current experimental conditions.

At 25° C., different anti-MSR1 antibody-LXR conjugates bound to 9×His-hMSR1 with $K_D$ values ranging from less than or equal to 0.6 pM to 34.8 nM, while the unconjugated parental antibodies bound to 9×His-hMSR1 with $K_D$ values ranging from less than or equal to 0.6 pM to 13.7 nM as shown in Table 13.

Example 72

Anti-MSR1 Antibody-LXR Conjugates Activate Agonist Binding in a LXR-Luciferase Reporter Bioassay
Generation of Assay Cell Line.

To test the efficacy of anti-MSR1 antibody-LXR conjugates in vitro, a cell-based LXR responsive luciferase reporter assay was developed. To generate the assay cell line, a LXR regulated luciferase reporter gene [Cignal Lenti LXR Reporter (luc) kit (Qiagen, Cat # CLS-001L)] was transduced into THP1 cells, and cells were selected for two weeks in puromycin. The lentivirus expresses the firefly luciferase gene under the control of a minimal CMV promoter and tandem repeats of the LXR transcriptional response element. The resulting cell line is referred to as THP1/LXR-Luc cells.

Assay Protocol.

THP1/LXR-Luc cells were seeded onto 96 well plates at 40,000 cells/well in media containing RPMI supplemented with 10% FBS and pencillin/streptomycin and subsequently differentiated with 200 nM Phorbol Myristate Acetate (PMA) for 3 days. After the 3-day differentiation period, three-fold serial dilutions of antibody drug conjugates, unconjugated antibodies, or free payloads in fresh media were added to the cells at final concentration ranging from 100 nM to 0.01 nM. Media alone served as a blank control. Forty-eight hours later, luciferase activity was determined after the addition of One-Glo™ reagent (Promega, Cat # E6130) to each well. Relative light units (RLUs) were measured on a Victor luminometer (PerkinElmer) and $EC_{50}$ values were determined using a four-parameter logistic equation over a 10-point dose response curve (GraphPad Prism). The $EC_{50}$ value of each reagent tested is shown in Table 14. The signal to noise (S/N) was determined by calculating the ratio of RLU of standard one over RLU of standard eight for each of the unconjugated anti-MSR1 antibodies or free payloads. "LP #" represents a linker-payload for which the corresponding structures are provided elsewhere herein, and "P #" represents a payload for which the corresponding structures are provided elsewhere herein.

TABLE 14

Agonist Activity of Anti-MSR1 Antibody-LXR Conjugates, Payloads, and Unconjugated Antibodies

| Molecule tested | $EC_{50}$ (M) | S/N |
|---|---|---|
| H1H21231N-N297Q-LP8 | 8.6E−10 | 14.5 |
| H1H21227N-N297Q-LP8 | 8.9E−10 | 31.0 |

TABLE 14-continued

Agonist Activity of Anti-MSR1 Antibody-LXR Conjugates, Payloads, and Unconjugated Antibodies

| Molecule tested | $EC_{50}$ (M) | S/N |
|---|---|---|
| H1H21231N-N297Q-LP8 | 1.73E−09 | 38.6 |
| H1H21234N-N297Q-LP8 | 3.65E−09 | 18.4 |
| H1H21234N-N297Q-LP15 | 6.3E−10 | 9.0 |
| H1H21234N-N297Q-LP13 | 9.8E−10 | 9.6 |
| H1H21234N-N297Q-LP36 | 1.02E−09 | 9.2 |
| H1H21234N-N297Q-LP39 | 1.12E−09 | 8.3 |
| H1H21234N-N297Q-LP311 | 8.1E−10 | 10.0 |
| H1H21234N-N297Q-LP32 | 8.7E−10 | 9.1 |
| H1H27729N-N297Q-LP8 | 1.64E−09 | 14.5 |
| H1H27731N-N297Q-LP8 | 1.46E−09 | 15.5 |
| H1H27732N-N297Q-LP8 | 8.2E−10 | 19.1 |
| H1H27734N-N297Q-LP8 | 5.19E−09 | 17.8 |
| H1H27736N-N297Q-LP8 | 1.01E−09 | 16.4 |
| H1H27739N-N297Q-LP8 | 1.60E−09 | 21.0 |
| H1H27747N-N297Q-LP8 | 4.77E−09 | 20.6 |
| H1H27749N-N297Q-LP8 | 1.46E−09 | 13.1 |
| H1H27751N-N297Q-LP8 | 1.54E−09 | 17.9 |
| H1H27754N-N297Q-LP8 | 1.30E−09 | 17.3 |
| H1H27756N-N297Q-LP8 | 1.61E−09 | 18.6 |
| H1H27759N-N297Q-LP8 | 5.94E−09 | 18.9 |
| H1H27760N-N297Q-LP8 | 6.34E−09 | 21.5 |
| H1H27761N-N297Q-LP8 | 5.72E−09 | 20.7 |
| H1H27762N-N297Q-LP8 | 7.02E−09 | 16.4 |
| H1H27766N-N297Q-LP8 | 1.277E−08 | 11.3 |
| H1H27771N-N297Q-LP8 | 2.41E−09 | 17.3 |
| H1H27773N-N297Q-LP8 | >4.05E−08 | 12.9 |
| H1H27778N-N297Q-LP8 | 1.51E−09 | 16.1 |
| H1H21235N-N297Q-LP8 | 8.3E−10 | 8.2 |
| H1H25700N-N297Q-LP8 | 1.13E−09 | 7.4 |
| H1H25690N-N297Q-LP8 | 2.5E−10 | 8.0 |
| H1H25695N-N297Q-LP8 | 1.87E−09 | 9.8 |
| H1H25685N-N297Q-LP8 | 7.8E−10 | 8.3 |
| Isotype Control-N297Q-LP8 | >6.6E−08 | 2.7 |
| H1H21234N-N297Q | No activation | No activation |
| 9d | 1.14E−09 | 15.9 |
| 9j | 4.6E−10 | 5.7 |
| 9l | 2.09E−09 | 8.9 |
| 9o | 3.7E−10 | 8.3 |

As shown in Table 14, at the 48-hour time point, all of the anti-MSR1 antibodies conjugated with LP 8 demonstrated stimulation of the THP1/Luc cells with $EC_{50}$ values ranging from 0.2 nM to greater than 140.5 nM with S/N values ranging from 7.4 to 38.6. One exemplary anti-MSR1 antibody-LXR conjugate (H1H21234N-N297Q-LP 8) demonstrated stimulation of the THP1/Luc cells with an $EC_{50}$ value of 3.7 nM and S/N of 18.4. The free payload, 9d, demonstrated stimulation of the THP1/Luc cells with an average $EC_{50}$ of 15.9 nM. The isotype control antibody conjugated with LP 8 (Isotype control-LP 8) had an average $EC_{50}$ value of >66 nM and S/N of 2.7. Additionally, H1H21234N-N297Q conjugated with additional LXR agonist linker-payloads (H1H21234N-N297Q-LP 15, H1H21234N-N297Q-LP 13, H1H21234N-N297Q-LP 36, H1H21234N-N297Q-LP 39, H1H21234N-N297Q-LP 311, and H1H21234N-N297Q-LP 32) tested demonstrated stimulation of the THP1/Luc cells with $EC_{50}$ values ranging from 0.63 nM to greater than 73 nM and S/N ranging from 1.4 to 10. Additional LXR agonist payloads tested (9j, 9l, and 9o) demonstrated stimulation of the THP1/Luc cells with $EC_{50}$ values ranging from 0.37 nM to 2.09 nM and S/N ranging from 5.7 to 8.9. One unconjugated anti-MSR1 antibody (H1H21234N) alone did not have any impact on stimulation of the THP/Luc cells.

Example 73

Anti-MSR1 Antibody-LXR Conjugates Activate Cholesterol Efflux in THP-1 Cells

The ability of anti-MSR1 antibody-LXR conjugates to activate cholesterol efflux in a human macrophage cell line (THP-1; ATCC Catalog # TIB-202), was assessed using a fluorescent cholesterol analog.

Briefly, THP-1 cells were seeded onto 96-well poly-lysine coated plates (Corning, Catalog #354640) at 100,000 cells/well in RPMI 1640 media (Irvine Scientific, Catalog #9160) containing 10% FBS (Gibco, Catalog #1043010), 10 µg/mL penicillin-streptomycin (Gibco, Catalog #15140122) and incubated at 5% $CO_2$ at 37° C. Cells were differentiated into macrophages by addition of 100 nM Phorbol-12 myristate 13-acetate (Sigma, Catalog #P 8139) to the media and subjected to further incubation for 96 hours. Differentiated macrophages were then incubated in phenol red free RPMI 1640 media (Gibco, Catalog #32404-014) containing 25 pM BODIPY-cholesterol (Avanti Polar Lipids, Catalog #810255P), 0.2% bovine serum albumin (BSA; Sigma Catalog # A7211), and 10 µg/mL penicillin-streptomycin for 24 hours, followed by a 24-hour treatment with serial dilutions of ranging from $1 \times 10^7$ M to $5 \times 10^{-14}$ M of either free payload, anti-MSR1 antibody-LXR conjugate (H1H21234N-N297Q-LP 8), Isotype control-LXR conjugate (Isotype control-N297Q-LP 8), and unconjugated anti-MSR1 antibody (H1H21234N) in phenol red free RPMI 1640 media containing 0.2% BSA. Cells were washed with phenol red free RPMI 1640 media and incubated with 100 µL of acceptor media containing 50 µg/mL high density lipoprotein (Millipore Catalog #437641), 10 µg/mL apolipoprotein A1 (Millipore, Catalog #ALP10) in phenol red free RPMI 1640 media for 5 hours, after which, the acceptor media was collected and cells were lysed in 100 µL of RIPA buffer (Millipore, Catalog #20-188) for 2 hours with gentle agitation at room temperature. Fluorescence was measured in these fractions at excitation 482 nm, emission 515 nm in SpectraMax i3 plate reader (Molecular Devices).

Percentage of BODIPY-cholesterol efflux was calculated using the following formula: [fluorescence in acceptor media/(fluorescence in acceptor media+fluorescence in cell lysate)]×100. Table 15 provides activated cholesterol efflux for the tested articles, and FIG. 15 illustrates the data in graph form.

TABLE 15

Activation of cholesterol efflux by antibody-LXR conjugates and comparators

| Molecule tested | Cholesterol Efflux activation $EC_{50}$ (M) | Maximum efflux (%) |
| --- | --- | --- |
| 9d | 1.5E−10 | 36.7 |
| H1H21234N-N297Q-LP8 | 5.0E−11 | 36.7 |
| Isotype control-N297Q-LP8 | >6.4E−8 | 30.3 |
| H1H21234N-N297Q | N/A | 18.7 |

As shown in Table 15, after 24 hours, H1H21234N-N297Q-LP 8 conjugate demonstrated the largest amount of cholesterol efflux with a maximum percent efflux of 36.6% and an $EC_{50}$ value of 50 pM. The free payload 9d demonstrated the second largest amount of cholesterol efflux with a maximum percent efflux of 36.6% and an $EC_{50}$ value of 150 pM. The Isotype control-N297Q-LP 8 conjugate demonstrated a minimal amount of cholesterol efflux with a maximum percent efflux of 30.3%. The unconjugated antibody, H1H21234N-N297Q, did not demonstrated any measurable cholesterol efflux.

Example 74

In Vivo Effect of Anti-MSR1 Antibody-LXR Conjugates on Atherosclerosis in a Mouse Model The effect of an anti-MSR1 antibody-LXR agonist conjugate, H1H21234N-N297Q-LP 8, on atherosclerosis development was evaluated in vivo in mice homozygous for the expression of human MSR1 extracellular domain in place of the mouse MSR1 extracellular domain and homozygous for deletion of the apoE gene (referred to herein as $Msr1^{hu/hu}$ $ApoE^{-/-}$ mice).

The $Msr1^{hu/hu}$ $ApoE^{-/-}$ mice were pre-bled 6 days before the start of the experiment after 4-hour fast and were then placed on an atherogenic western diet (Research Diets, Cat #106452). The mice were sorted into groups (n=7-9 each) based on their baseline triglycerides (TG) and low-density lipoprotein cholesterol (LDL-C) values. An MSR1 antibody (H1H21234N-N297Q) or MSR1 antibody-LXR agonist conjugate (H1H21234N-N297Q-LP 8) were administered by weekly subcutaneous injections at 25 mg/kg dose (based on the antibody concentration) starting on day 0 for 16 weeks. Serum was collected at 4, 8, and 16 weeks of the study after 4-hour fast to evaluate serum lipids using Advi-aXPT Chemistry System (Siemens). Average serum lipid values were calculated for each time point. Results, expressed as (mean±SEM) are shown in FIG. 16. FIG. 16 illustrates that administration of the MSR1 antibody-LXR agonist conjugate H1H21234N-N297Q-LP 8 did not have an effect on serum lipid levels.

Mice were sacrificed at the end of the study under nonfasted conditions 6 days after the last injection anti-MSR1 antibody or MSR1 antibody-LXR agonist ncADC, and their heart and liver were collected. Hearts were imbedded in Optimal cutting temperature compound (OCT), and sectioned perpendicular to the axis of the aorta, starting within the heart and working in the direction of the aortic arch. Once the aortic root was identified by the appearance of aortic valve leaflets, serial cross sections (12 µm thick) were taken and mounted on consecutive slides (VWR International, Cat #16004-406). These sections were stained with hematoxylin and eosin stain (H&E stain), Oil Red O lipid stain, and rat-anti-CD68 antibody, (Abcam, Cat # ab201844) to label macrophages for analysis. An Aperio AT2 slide scanner (Leica Biosystems, Illinois) was used to scan the slides and to generate images. For each mouse, the lipid area was measured using HALO software (Indica Labs, New Mexico) in 7 subsequent cross sections based on Oil Red O staining, and subsequently the average of total lesion lipid area per mouse was calculated using these measurements. All measurements were conducted by an analyst who was blinded to the treatment groups. Results, expressed as (mean±SEM) are shown in FIG. 17A. FIG. 17A illustrates that administration of the MSR1 antibody-LXR agonist conjugate H1H21234N-N297Q-LP 8 led to reduction in atherosclerotic lesion area.

In addition, H&E stained slides were used to calculate Intima/Media ratio, which represents the normalized value of plaque size. The internal and external elastic laminas of arterial media and lumen areas were measured in 7 subsequent cross sections for each mouse using the H&E stained sections and the average values were calculated per mouse. Intima/media ratio were calculated using the equation:

Intima/media ratio=(Internal elastic lamina area−Lumen area)/(External elastic lamina area−Internal elastic lamina area)

Results, expressed as (mean±SEM) are shown in FIG. 17B.

The macrophage content in the sections was measured using slides stained with rat anti-CD68 antibody. For each mouse, macrophage positive area was measured using HALO software in at least 5 subsequent cross sections, and the average of total macrophage content per mouse was calculated using these measurements. Results, expressed as (mean±SEM) are shown in FIG. 17C. FIG. 17C illustrates that administration of the MSR1 antibody-LXR agonist conjugate H1H21234N-N297Q-LP 8 led to reduction in macrophage content.

Livers collected at sacrifice were used for qRT-PCR and lipid extraction. One piece of liver from each mouse was placed in RNAlader (Invitrogen, Cat #AM7023) for RNA extraction and then the expression of lipogenic genes (Srebf1, Acc, Fasn) to evaluated de novo lipogenesis was evaluated by qRT-PCR using standard methods. Results, expressed as (mean±SEM) are shown in FIG. 18. FIG. 18 illustrates that administration of the MSR1 antibody-LXR agonist conjugate H1H21234N-N297Q-LP 8 has no effect on hepatic triglyceride or cholesterol level.

Lipids were extracted from the second piece of liver from each mouse by Folch's method and solubilized by Carr's method. The levels of TG, total and free cholesterol were measured using enzymatic assays for detection (Teco Diagnostics, Cat # T532-480 (TG); Thermo Fisher Scientific, Cat #TR13421 (total cholesterol); Waco Diagnostics, Cat #993-02501 (free cholesterol)) and normalized to wet tissue weight. Results, expressed as (mean SEM) are shown in FIG. 19. FIG. 19 illustrates that administration of the MSR1 antibody-LXR agonist conjugate H1H21234N-N297Q-LP 8 has no effect on hepatic de novo lipogenesis.

What is claimed is:

1. A compound of Formula A

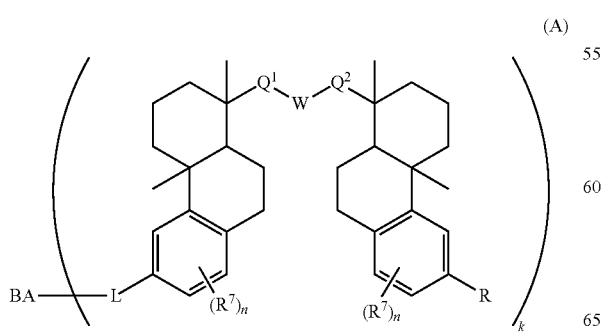

(A)

or a pharmaceutically acceptable salt, or stereoisomeric form thereof, wherein

L is a linker or X—Y—Z, wherein

X is —NH— or —O—;

Y is an enzymatically cleavable moiety; a self-immolative group; an acid-labile moiety comprising an alkoxamine, ketoxamine, carbonate, or phosphonate; $PEG_n$; a sugar moiety comprising a glucuronide; and/or an enhancement group comprising a cyclodextrin and/or an alkyl, heteroalkyl, alkylenyl, or heteroalkylenyl sulfonic acid; and Z is a binding agent linker (BL) wherein Z is covalently bound to BA;

BA is an antibody or antigen binding fragment thereof;

k ranges from about one to about eight, representing an average number of units of a payload conjugated to BA;

each of $Q^1$ and $Q^2$ is independently —$CH_2$, C(O)—, —C(H)(OH)—, or —C(OH)$_2$—;

W is —CH$_2$—, —N(H)—, or —O—;

R is independently hydrogen, —OH, C$_{1-6}$ alkyl, or —OP(O)(OR$^6$)(OH); and each R$^6$ is, independently in each instance, hydrogen, an amino acid residue, a peptide, or alkyl; and each R$^7$ is independently halo, C$_{1-6}$ alkyl, C$_{1-6}$ alkoxy, —CN, O-glucose, O-amino acid residue, or O-PEG$_n$, wherein each n is an integer from zero to three.

2. The compound of claim 1, comprising BA linked via a linker L to a compound selected from the group consisting of

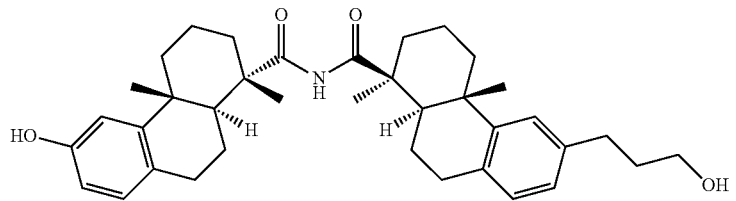

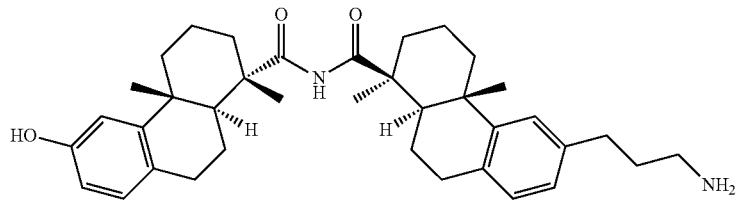

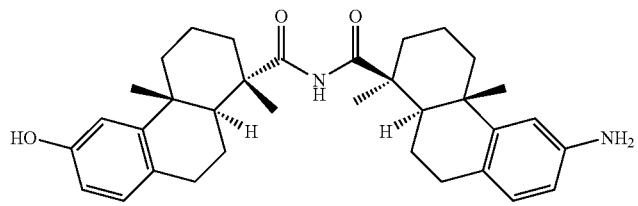

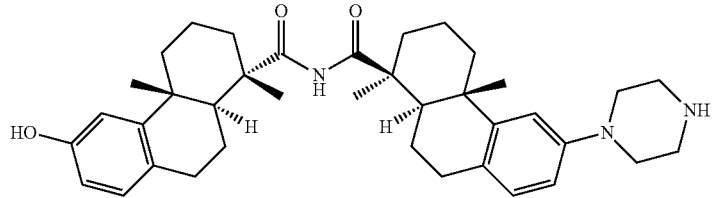

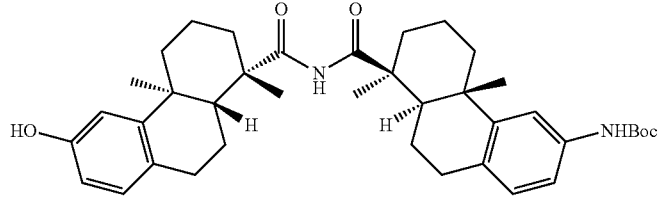

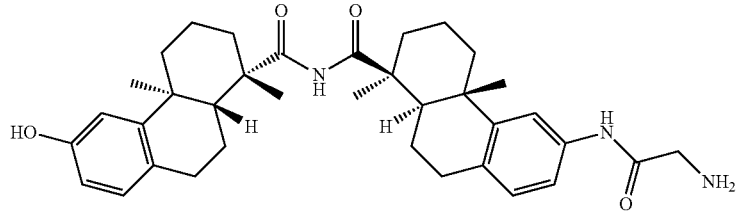

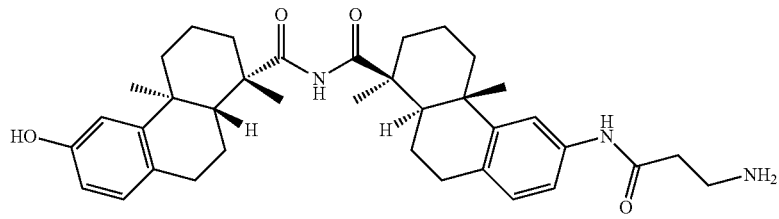

-continued
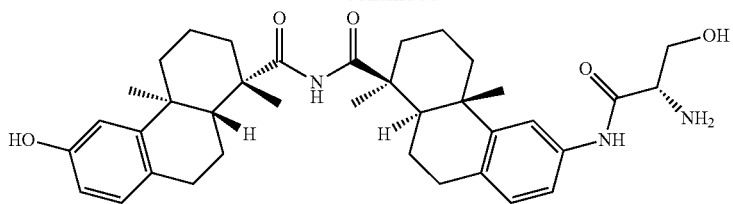
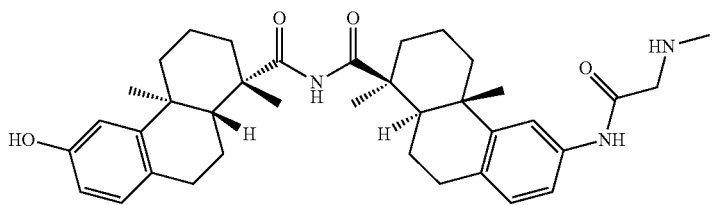
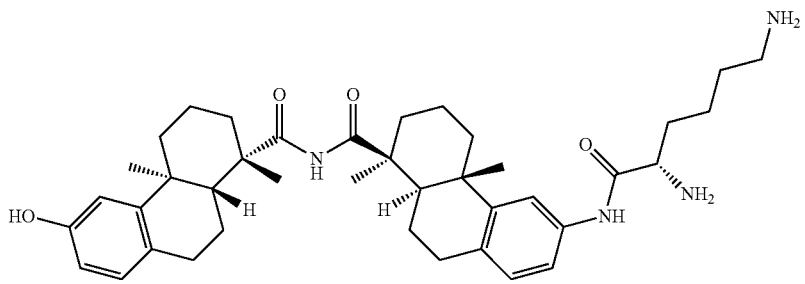
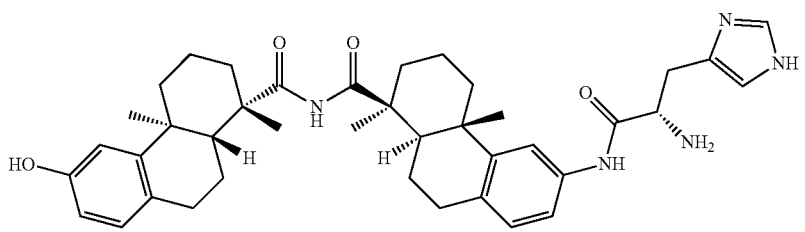
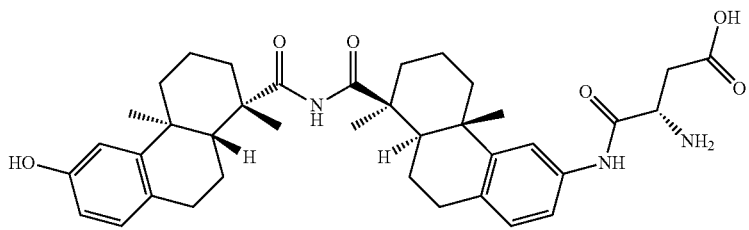
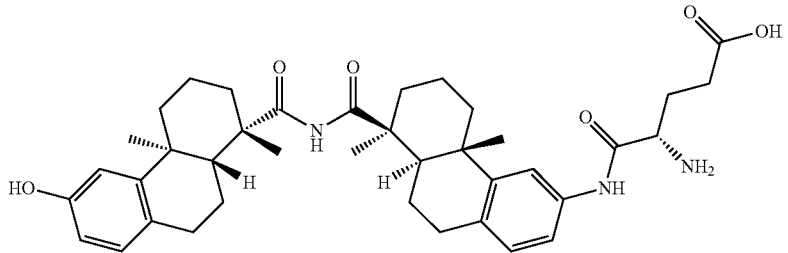
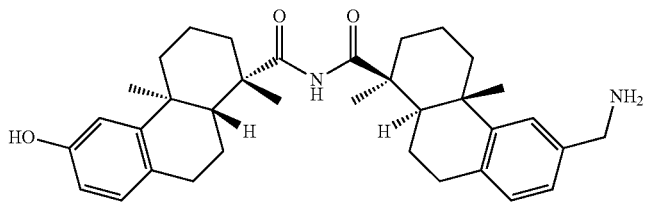

-continued
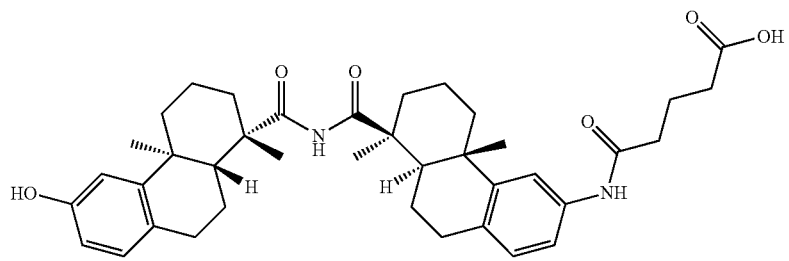
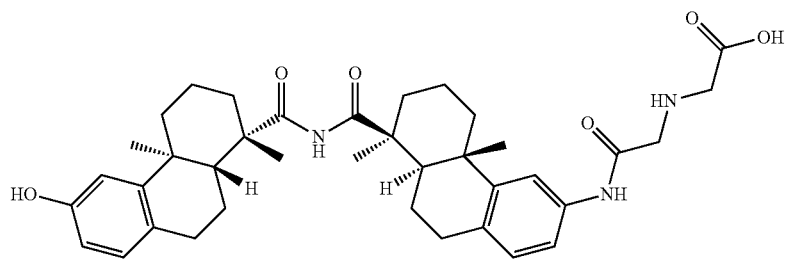
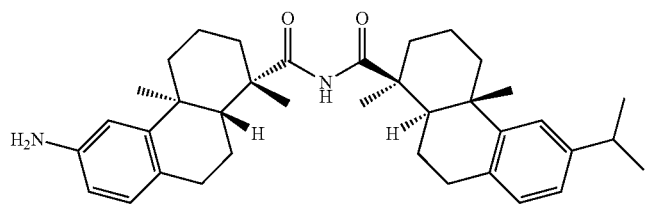
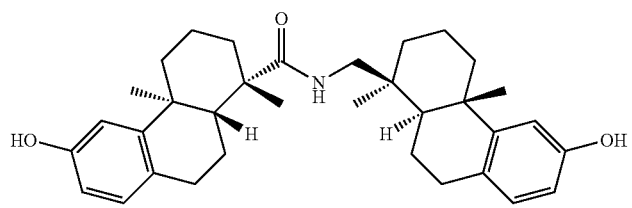
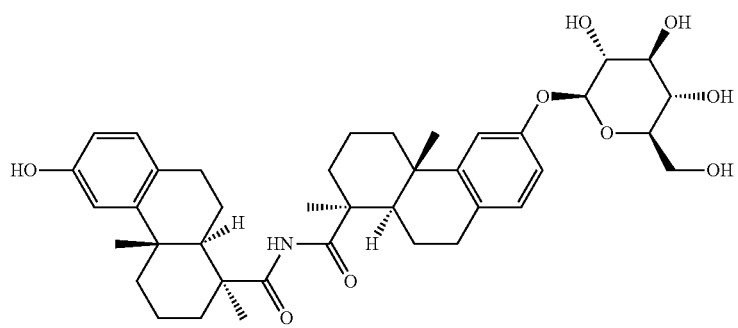
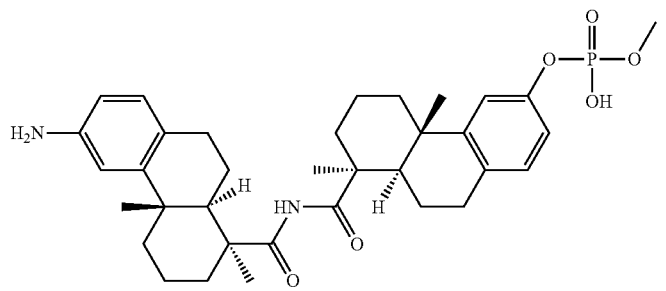
and

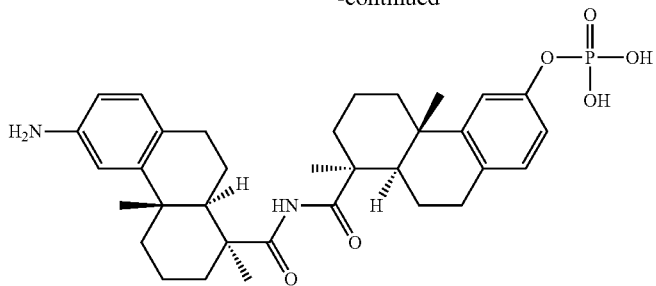
or a regioisomer, stereoisomeric form, pharmaceutically acceptable salt, or solvate thereof; wherein k ranges from about one to about four, representing an average number of units of a payload conjugated to BA.
3. The compound of claim 1, comprising BA linked to a compound selected from the group consisting of
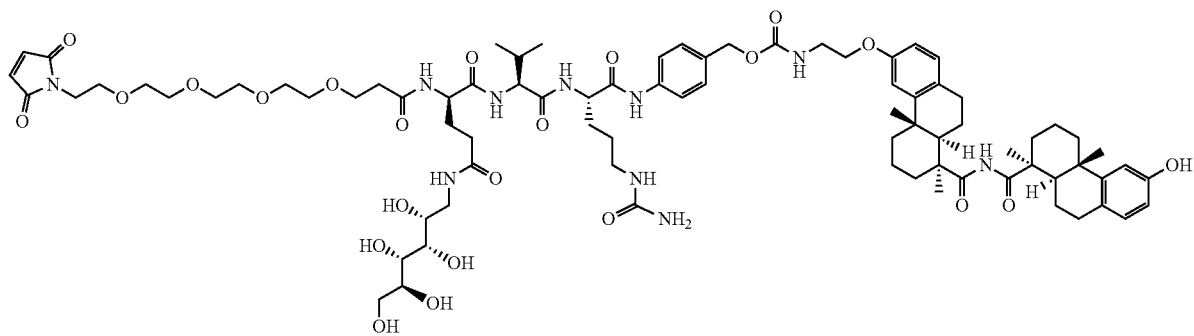
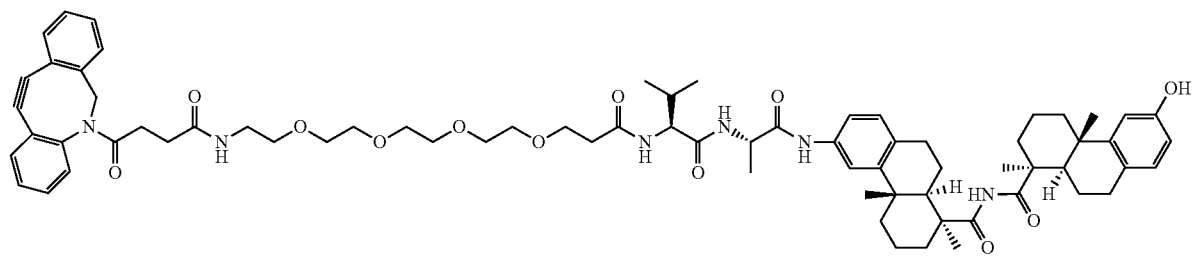
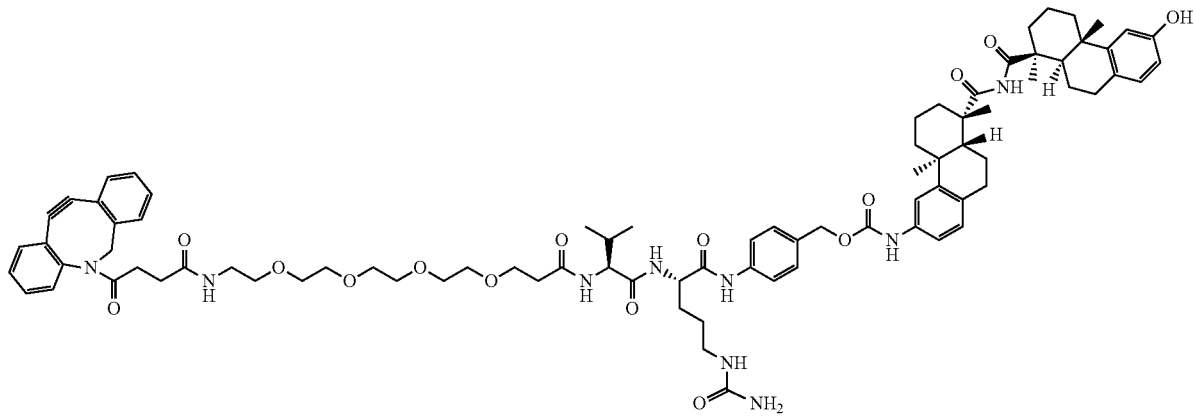

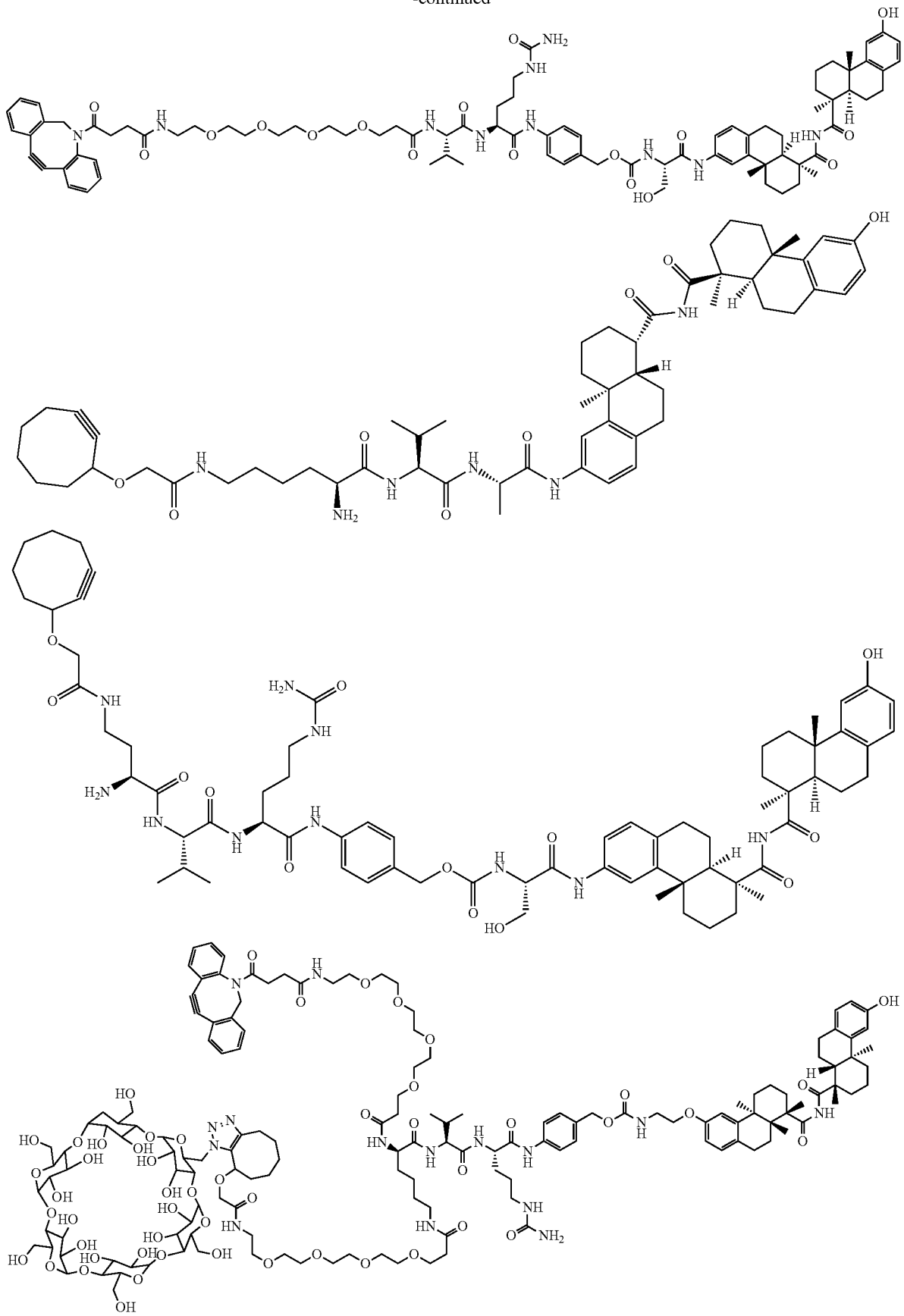

439
440
-continued
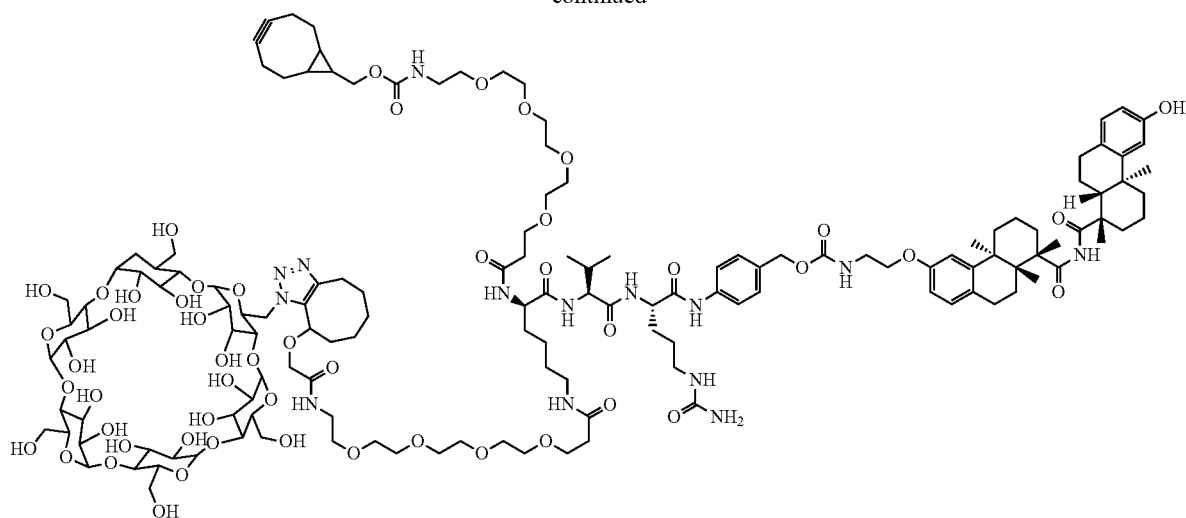
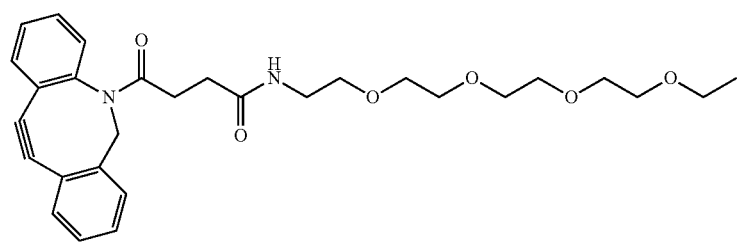
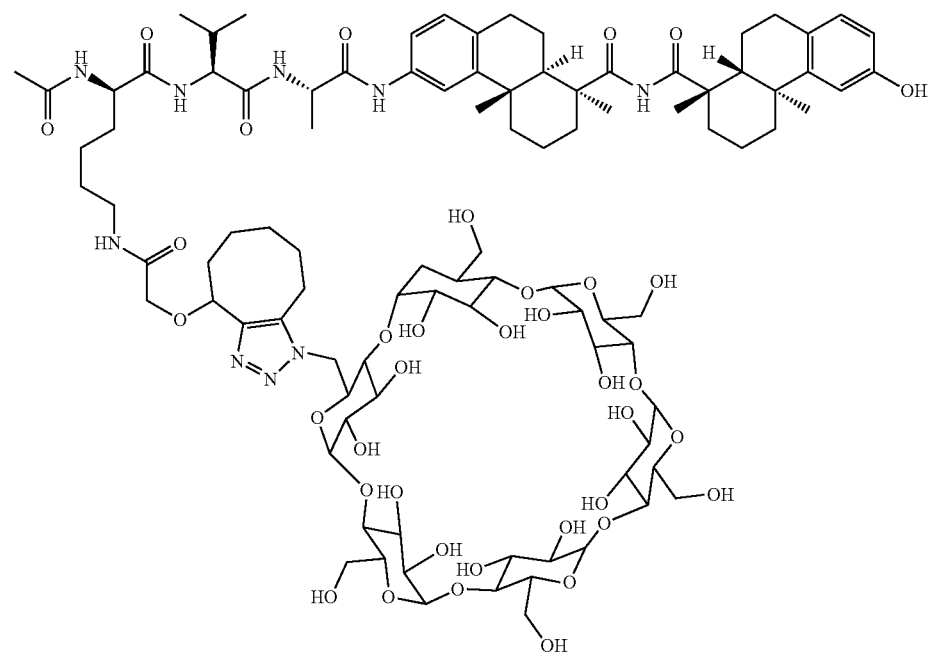

441
442
-continued
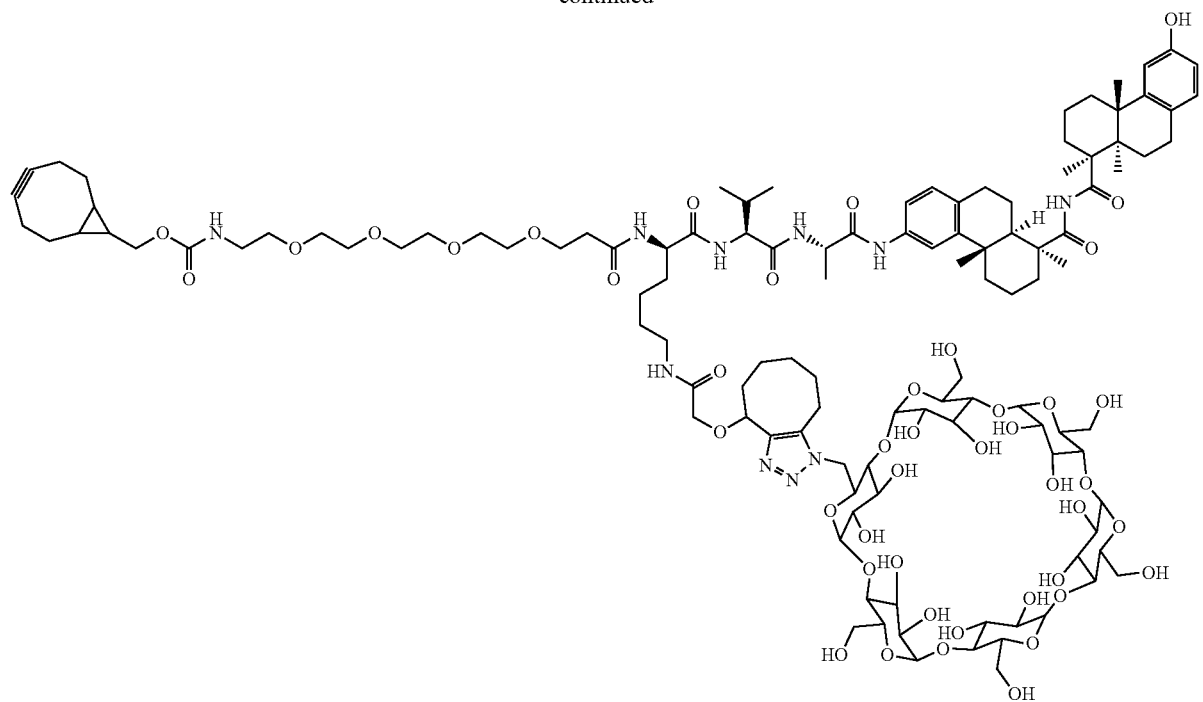
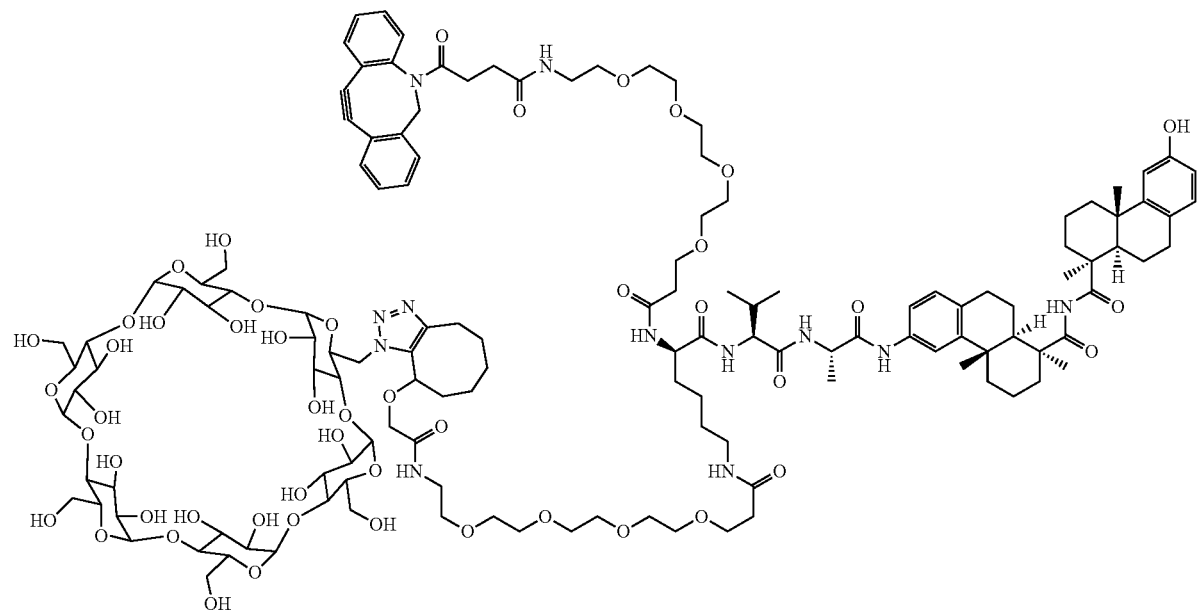

443
444
-continued
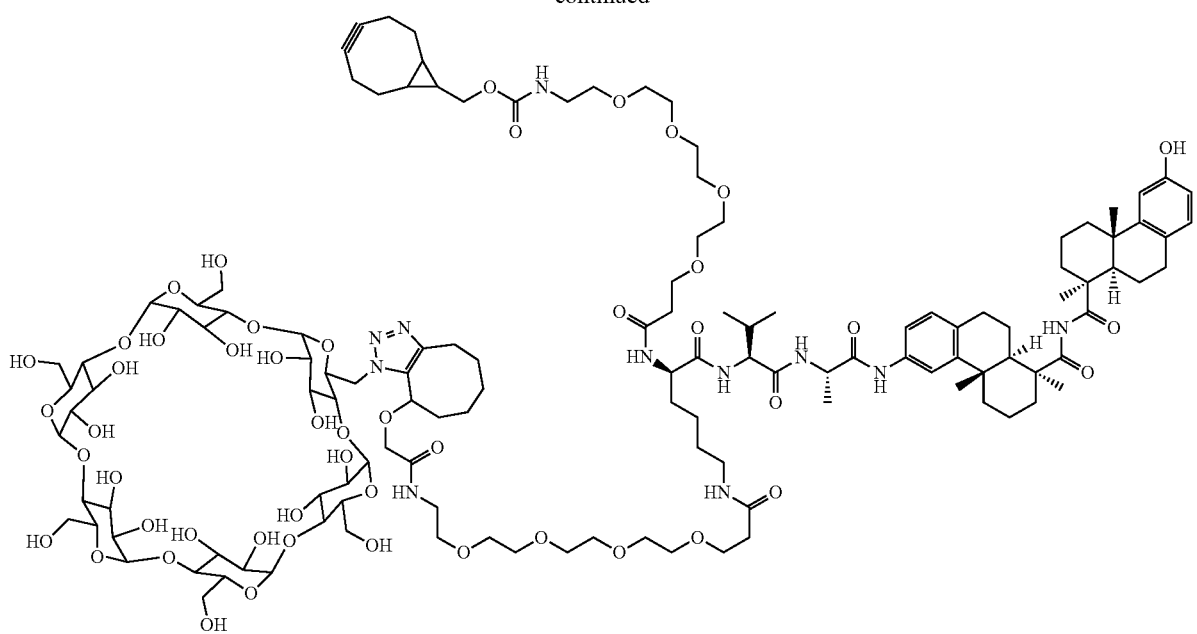
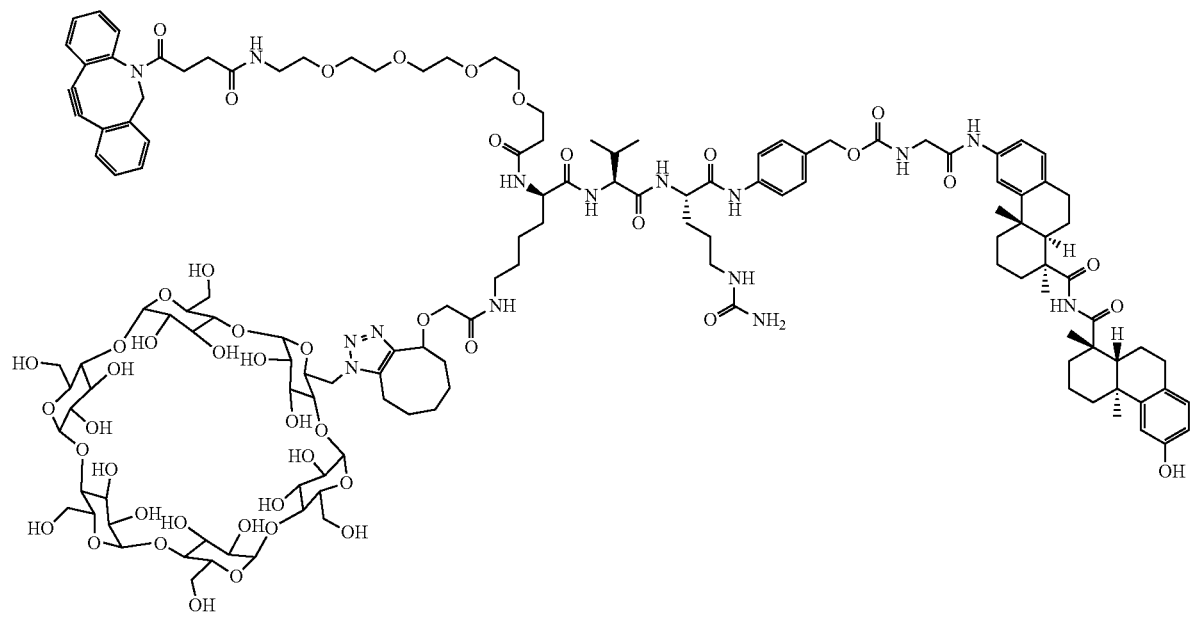

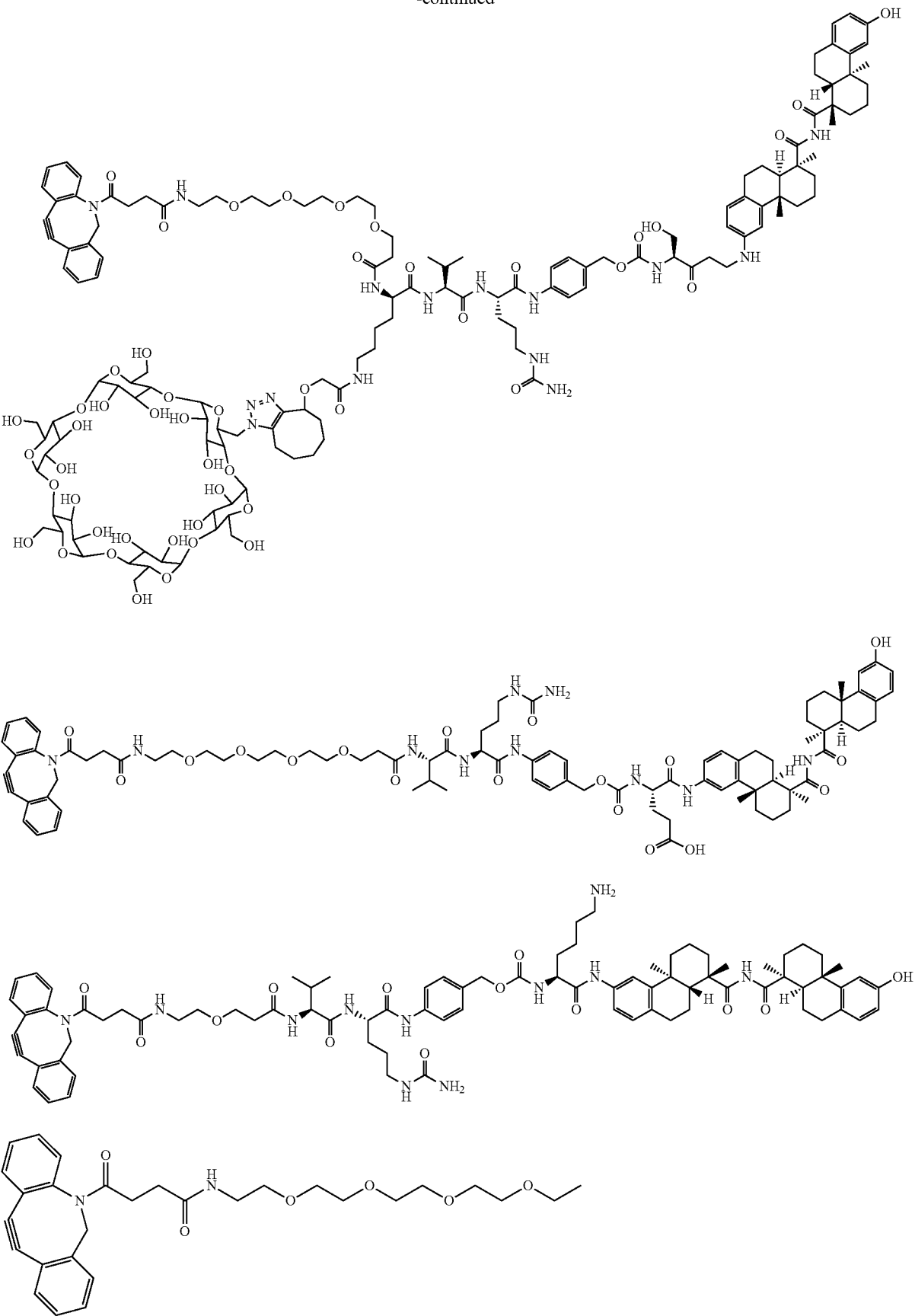

-continued
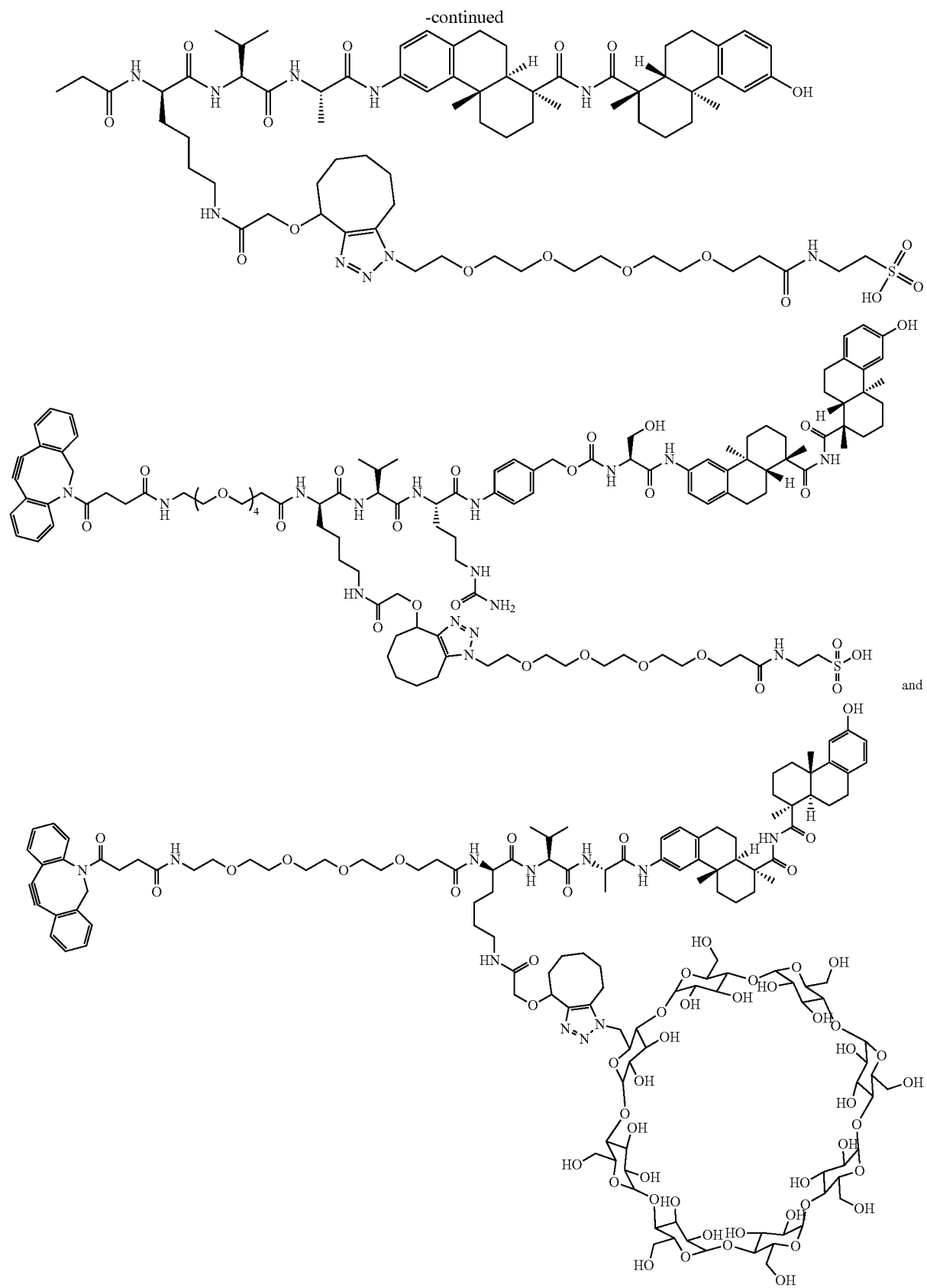
or a regioisomer, stereoisomeric form, pharmaceutically acceptable salt, or solvate thereof; wherein k ranges from about one to about four, representing an average number of units of a payload conjugated to BA.

4. The compound of claim 1, selected from the group consisting of
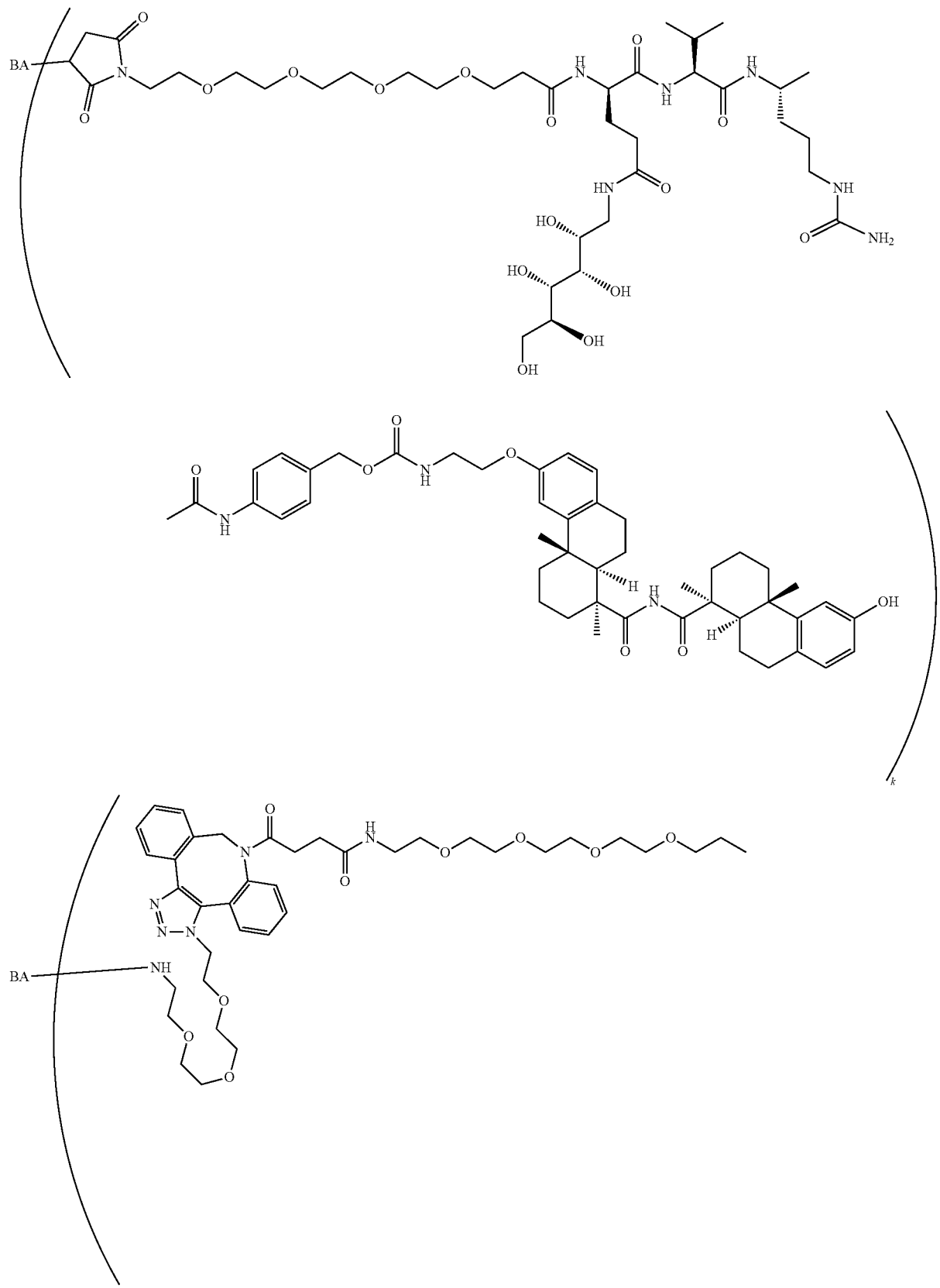

451
-continued
452
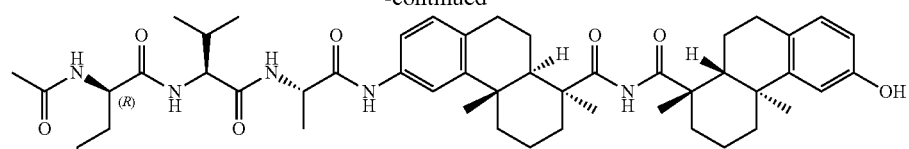
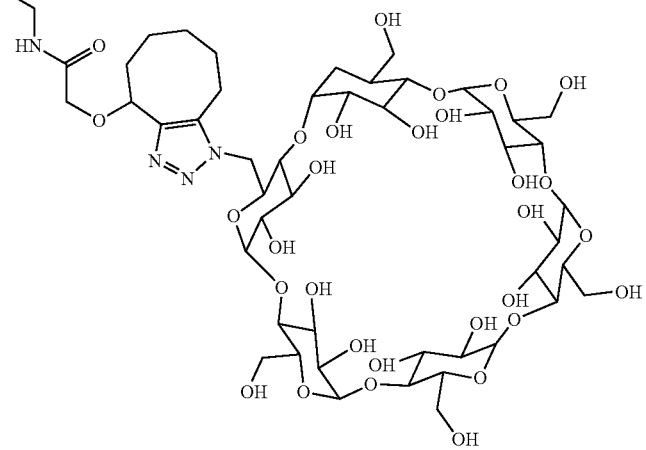
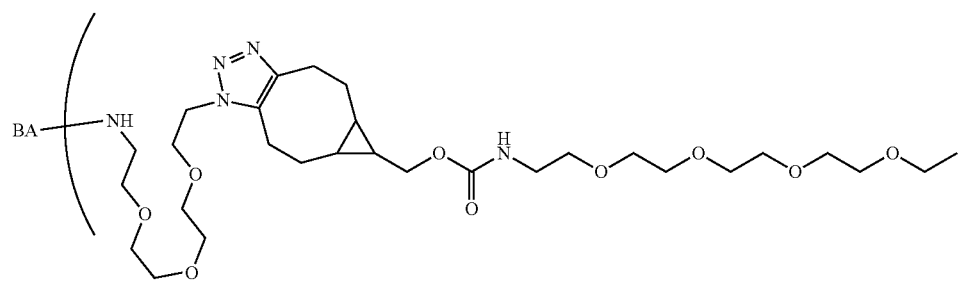
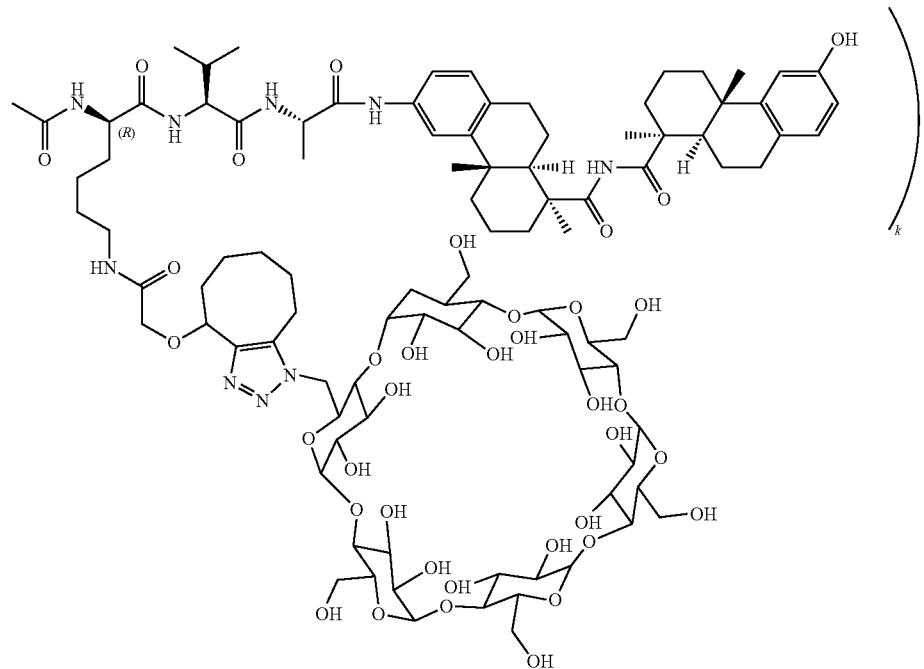

453
454
-continued
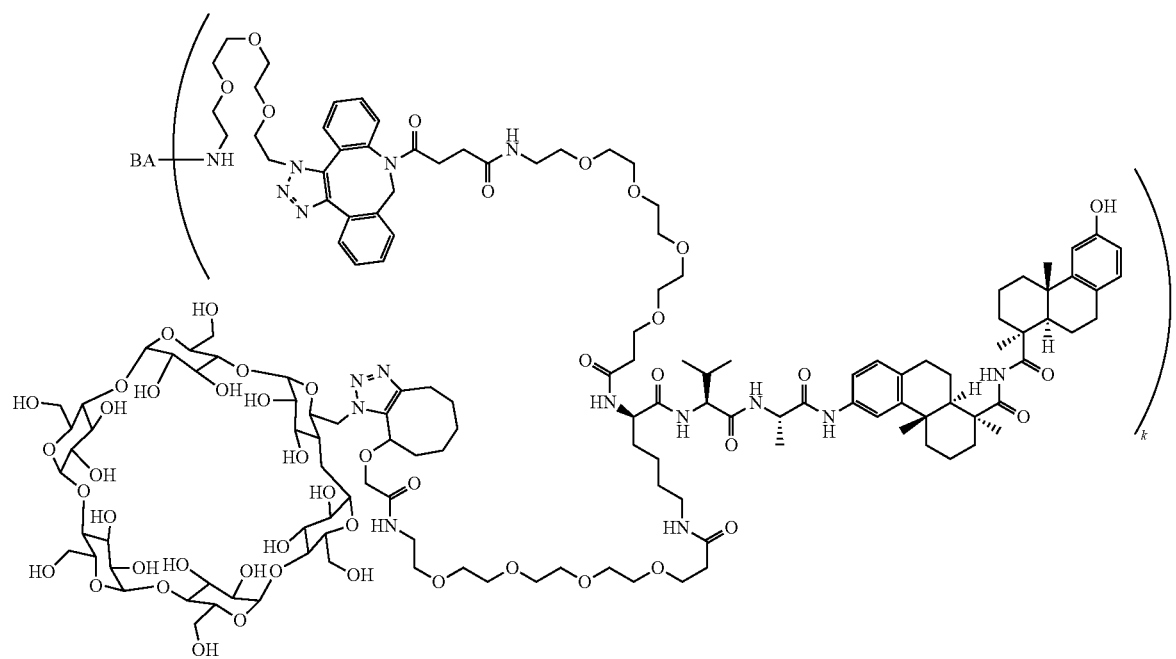
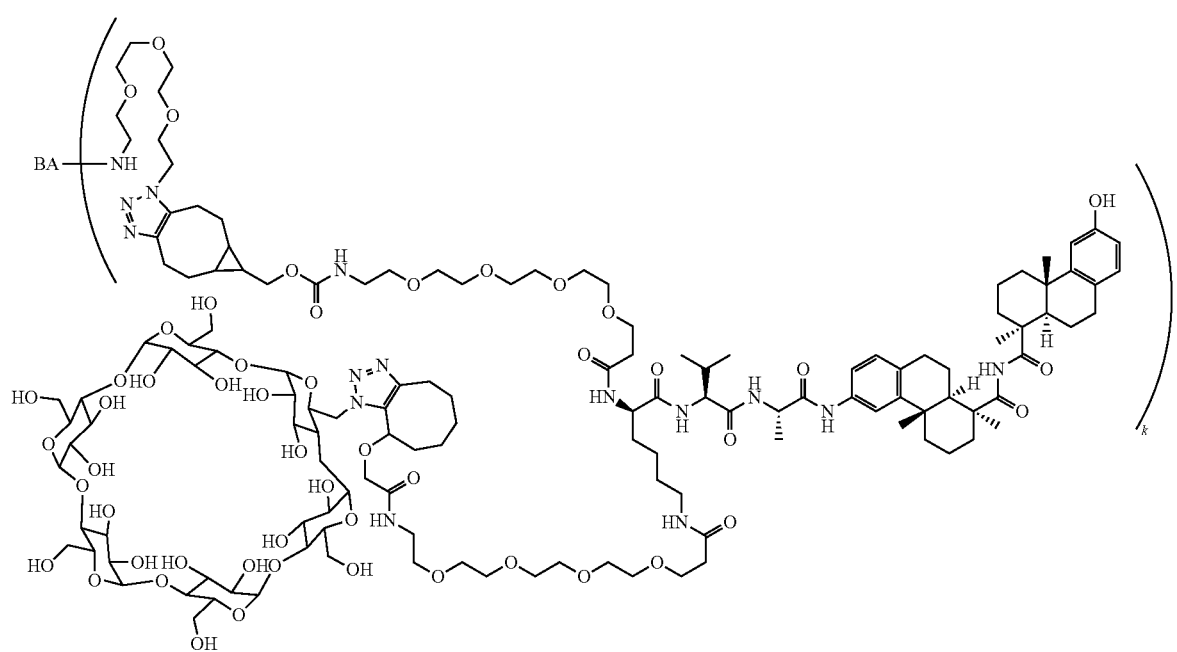

455
-continued
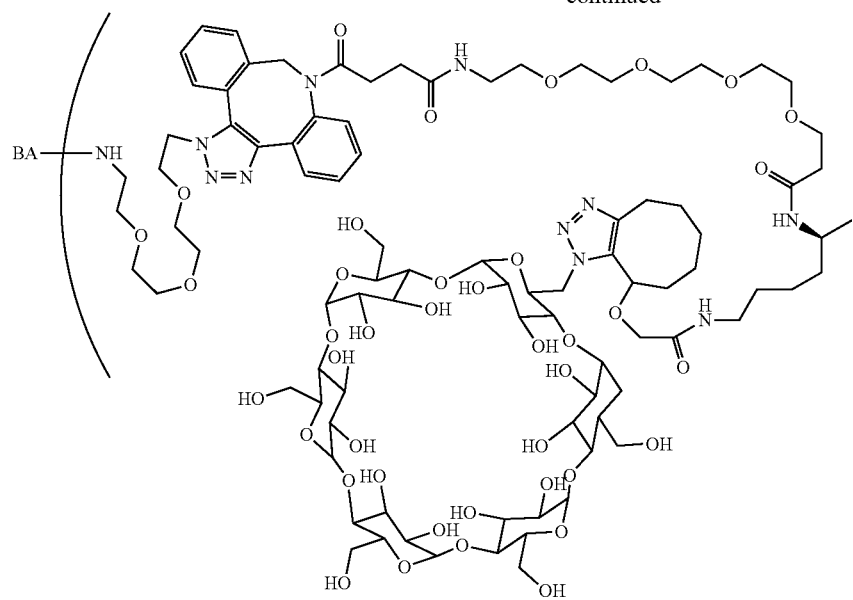
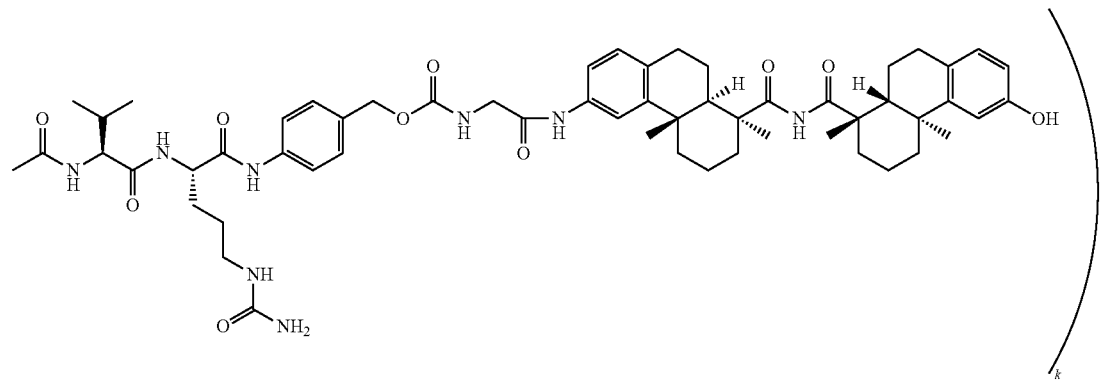
456
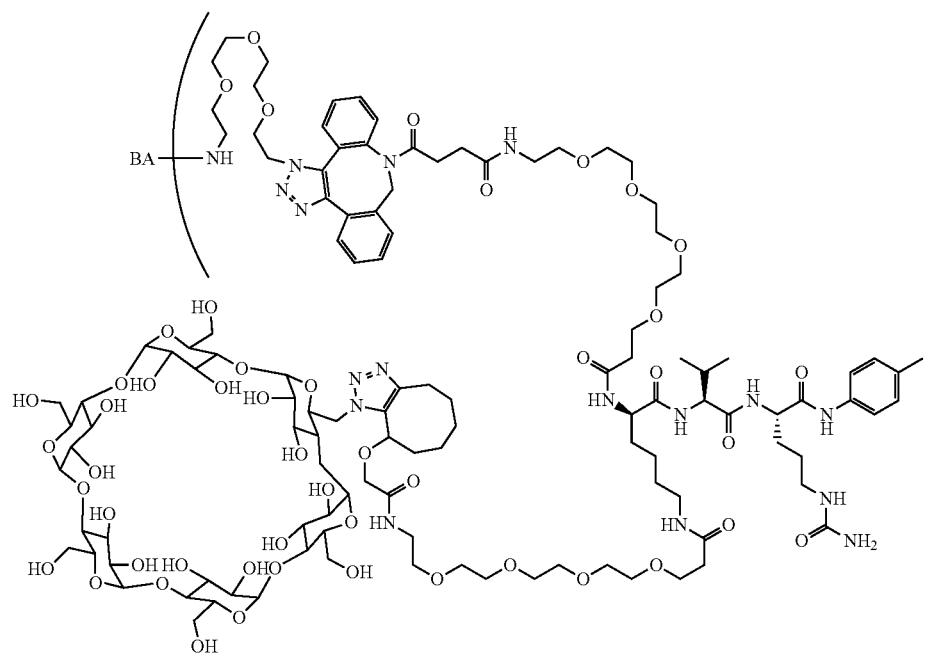

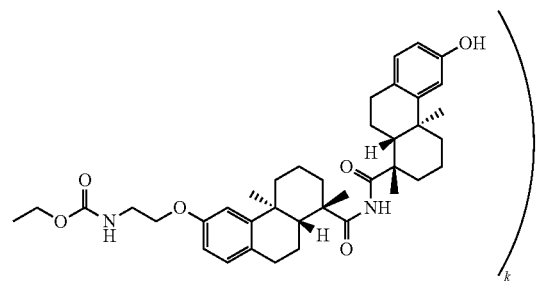
-continued
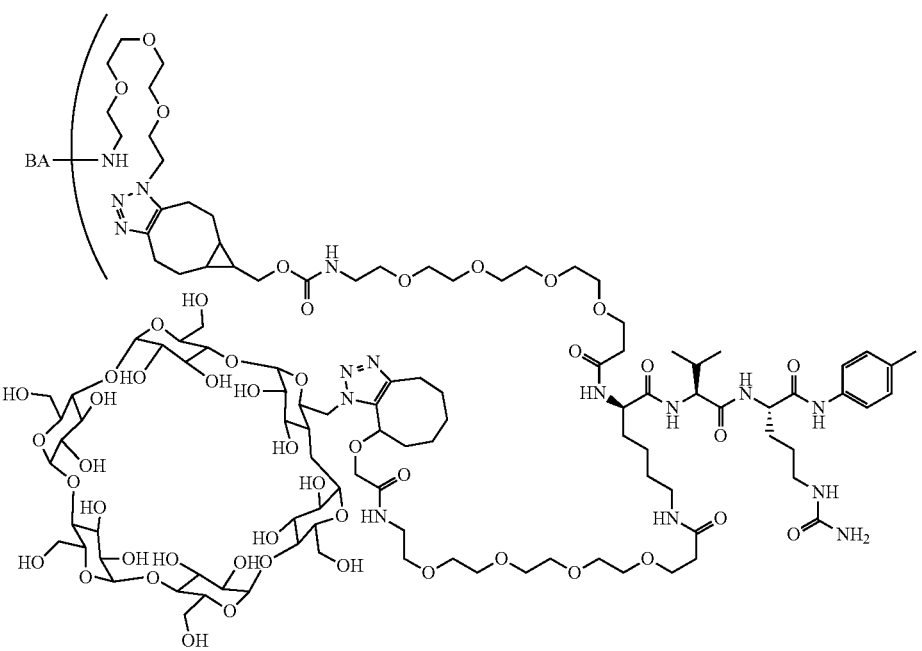
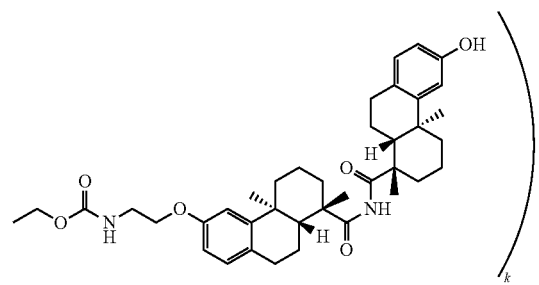

-continued
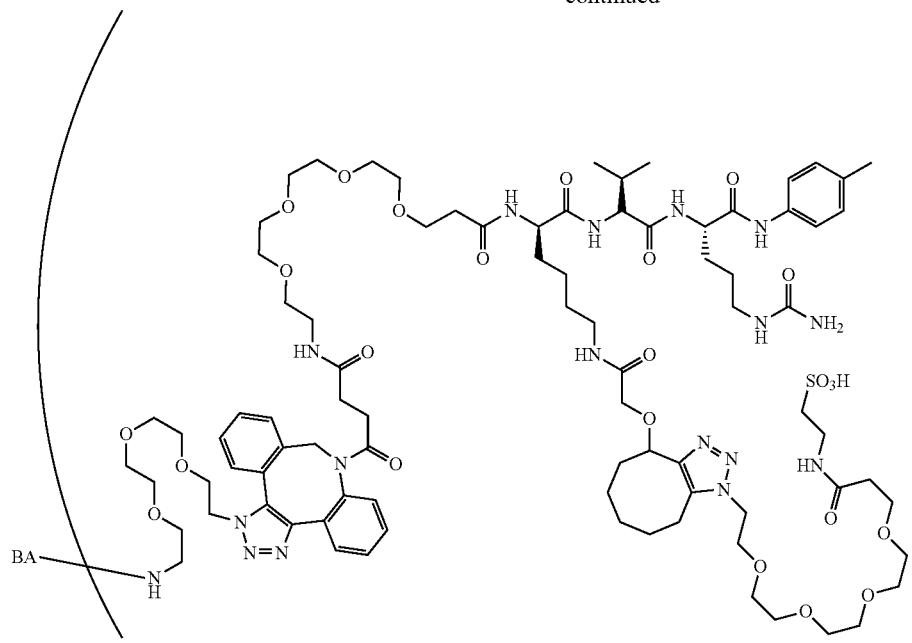
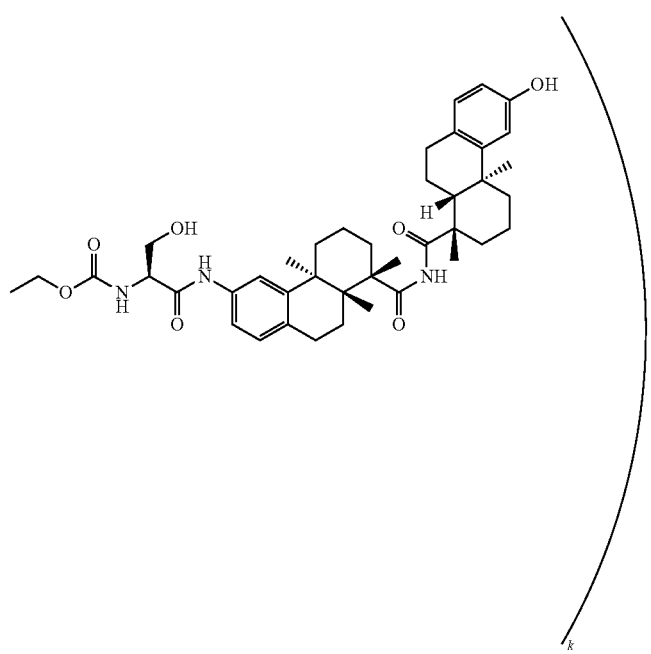

461  462
-continued
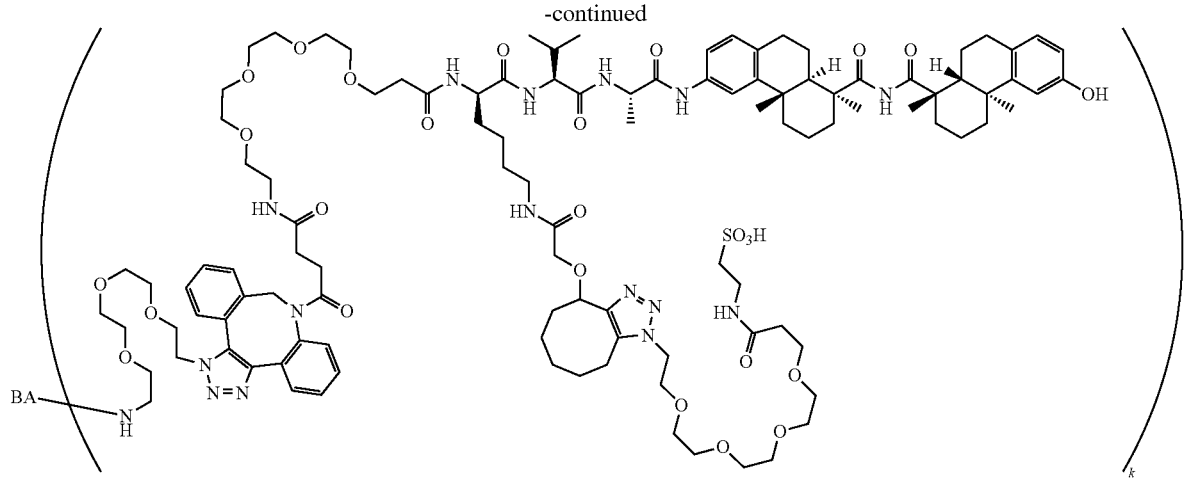
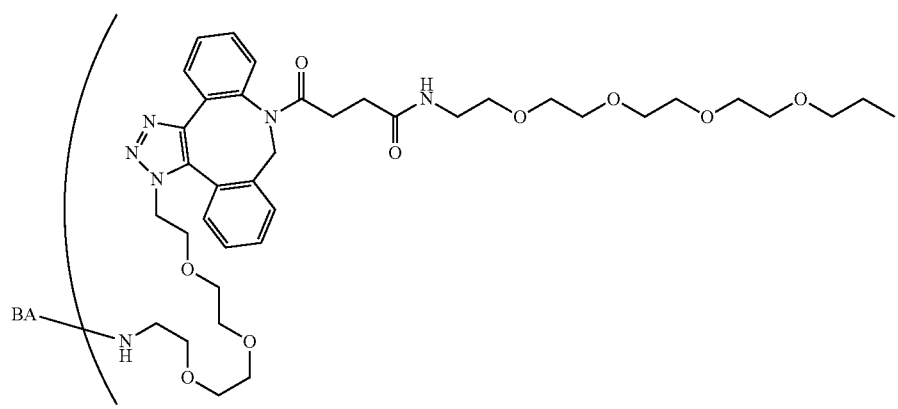
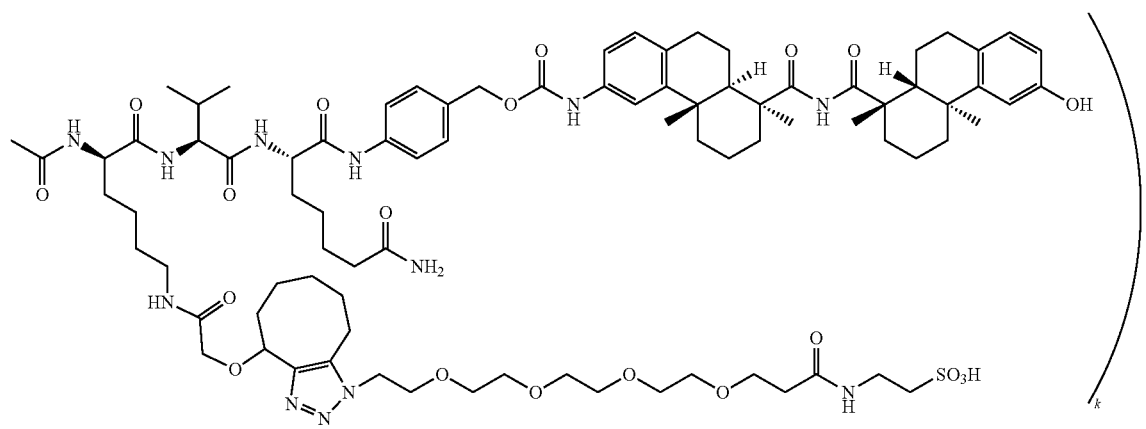

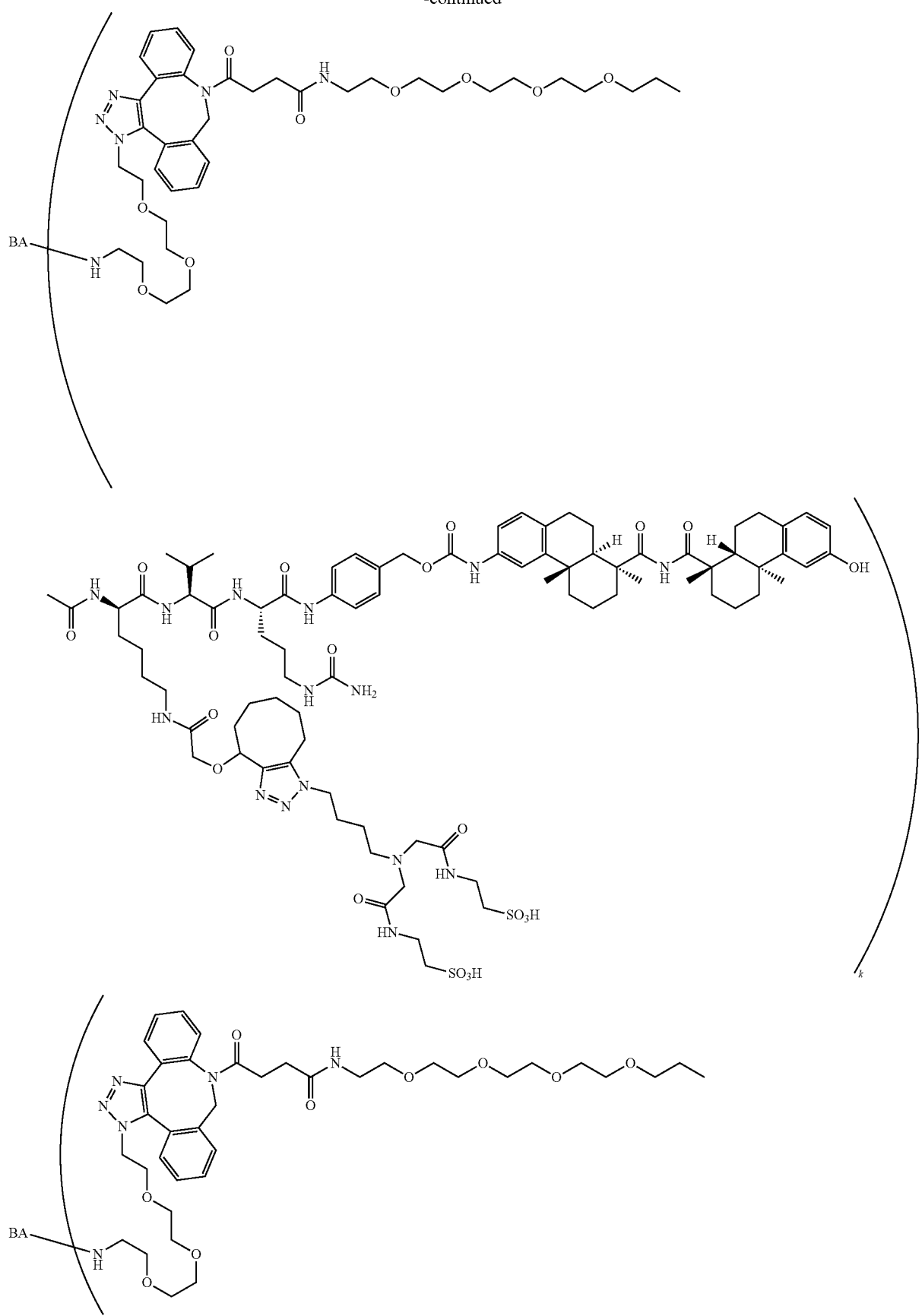

465 466
-continued
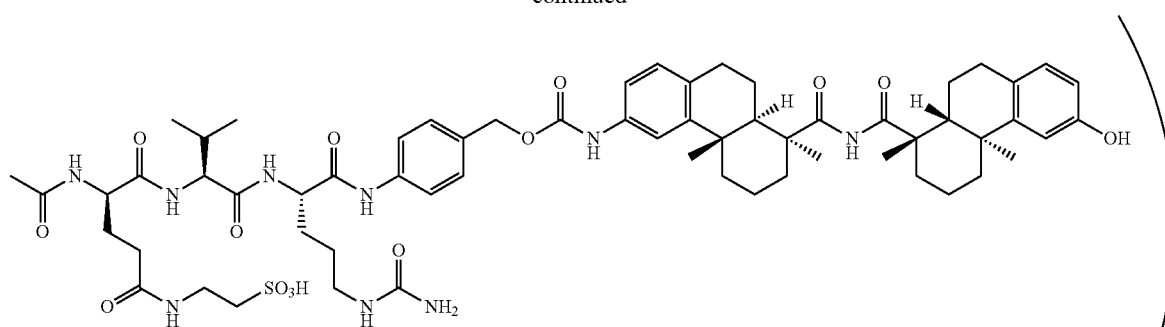
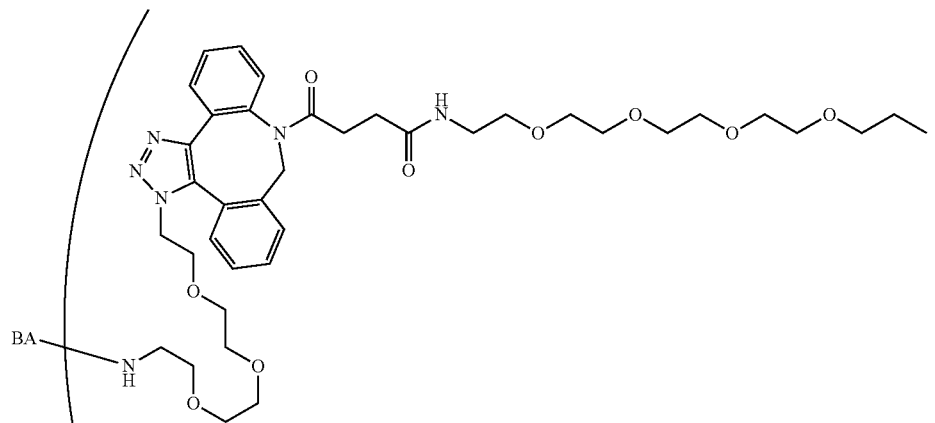
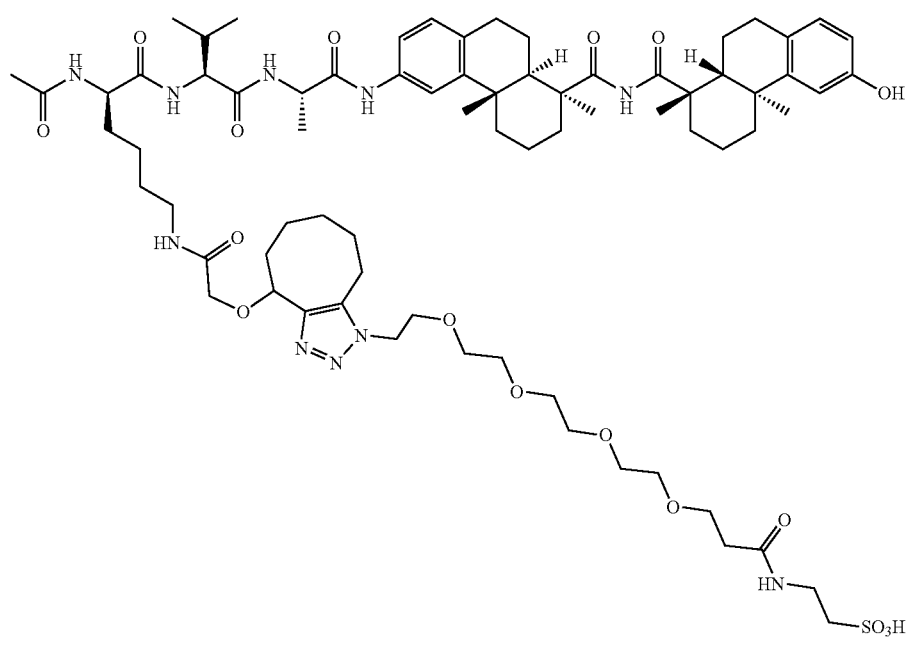

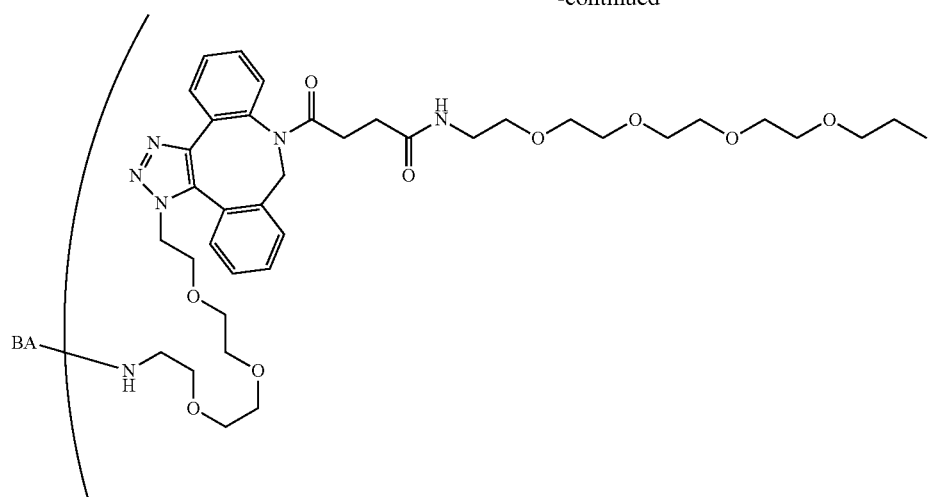
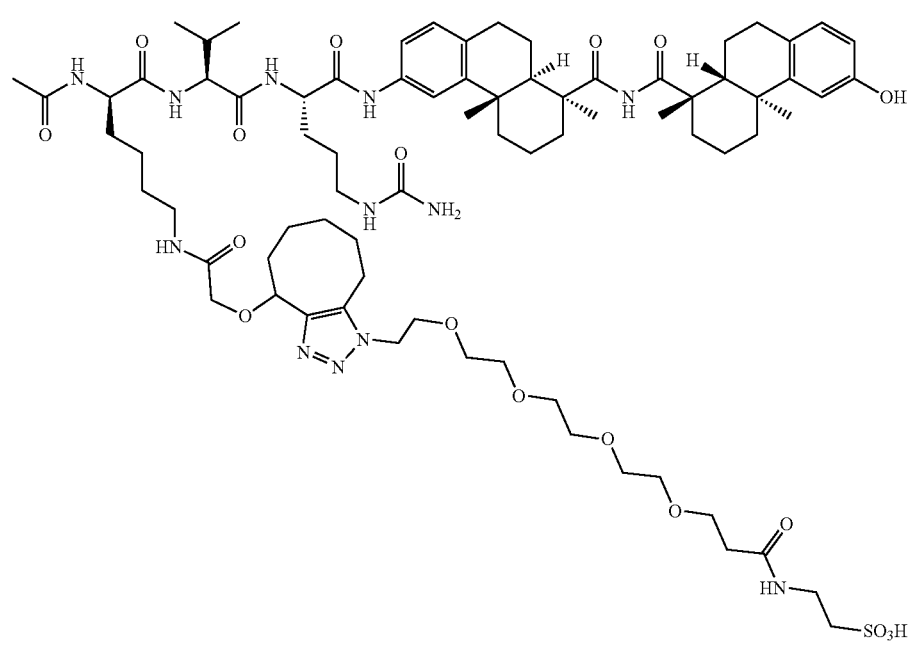

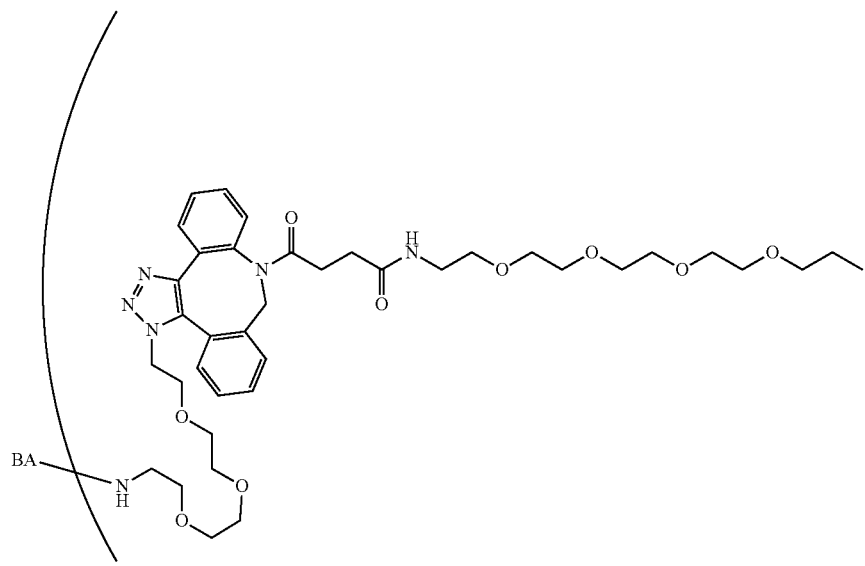
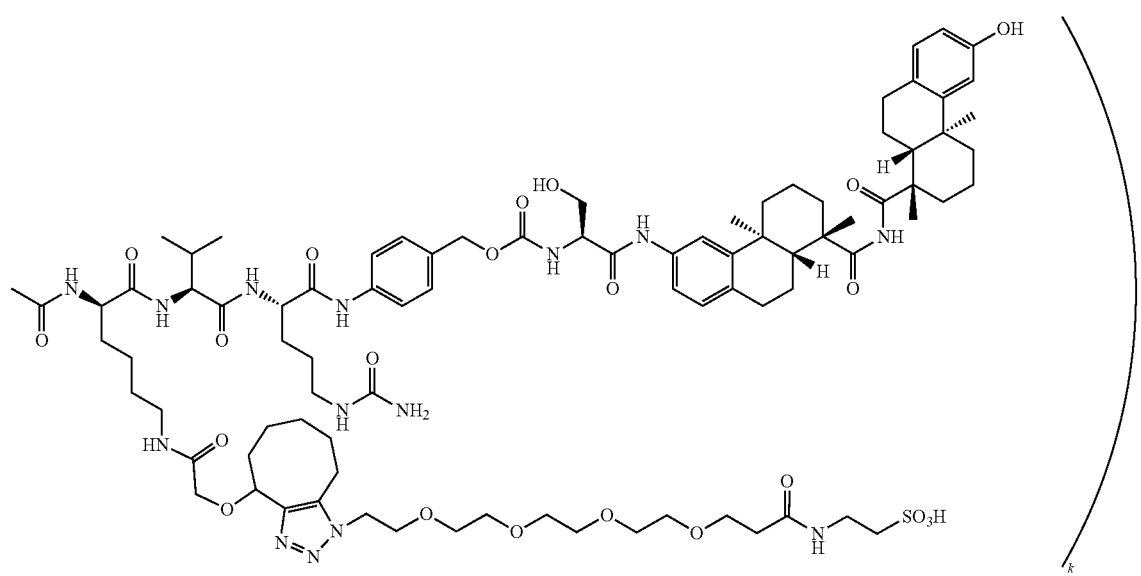

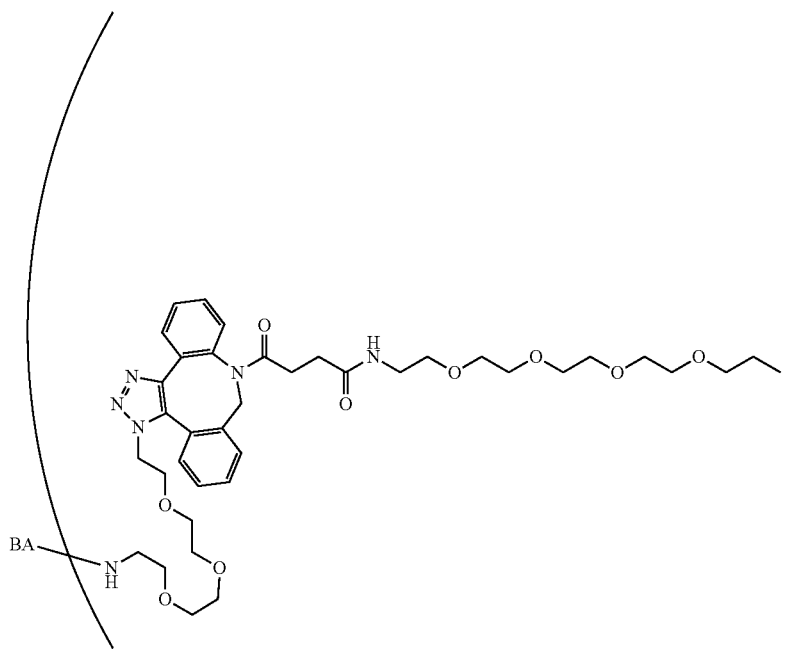
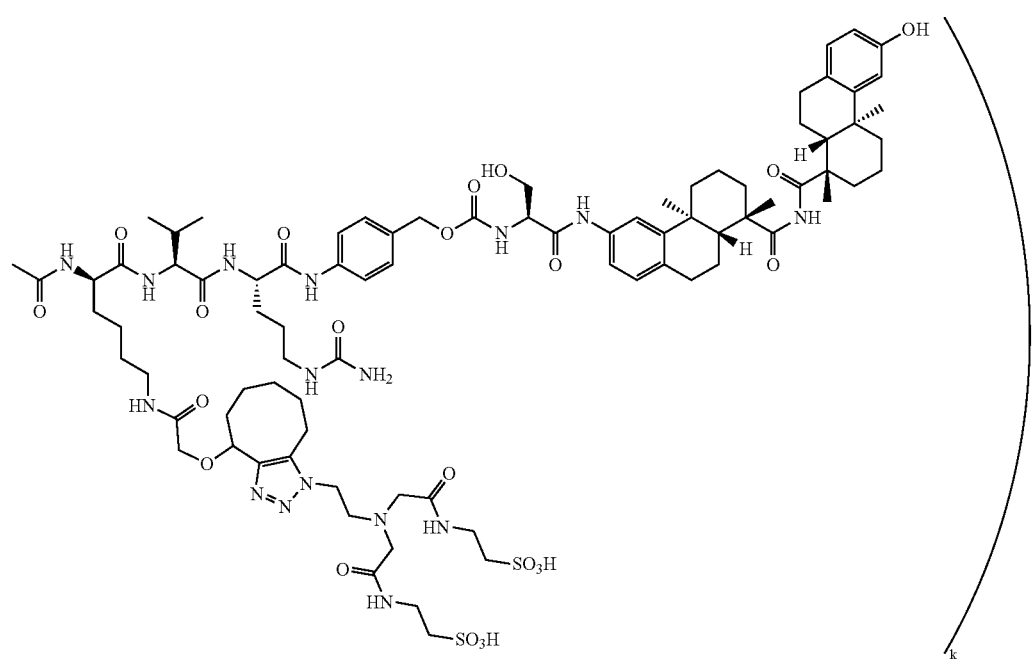

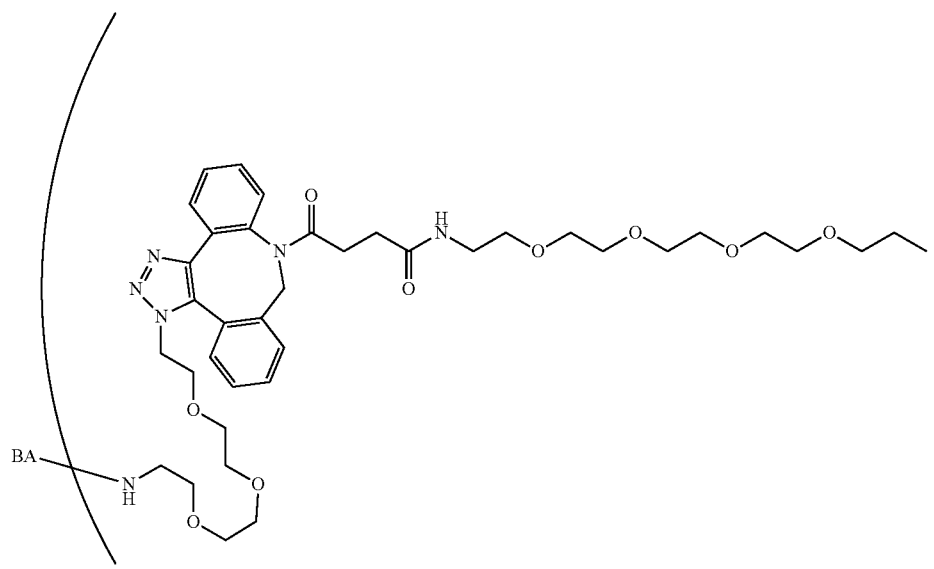
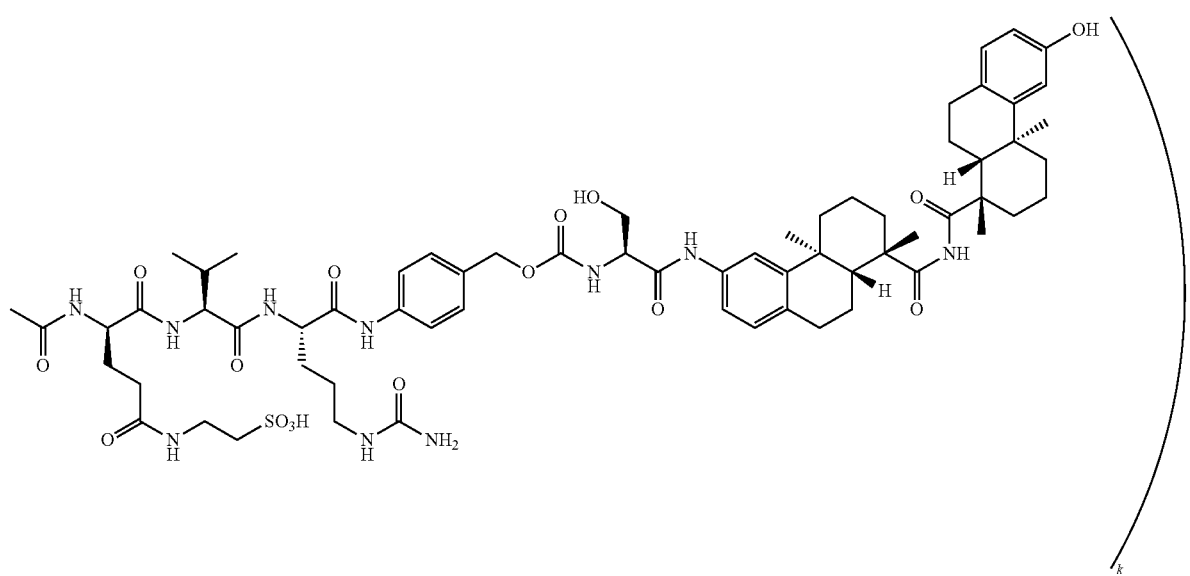

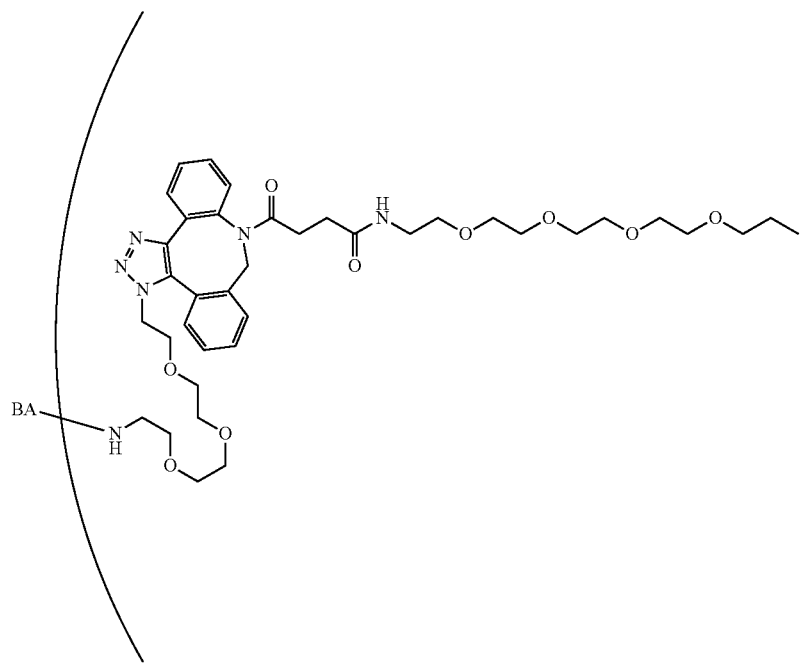
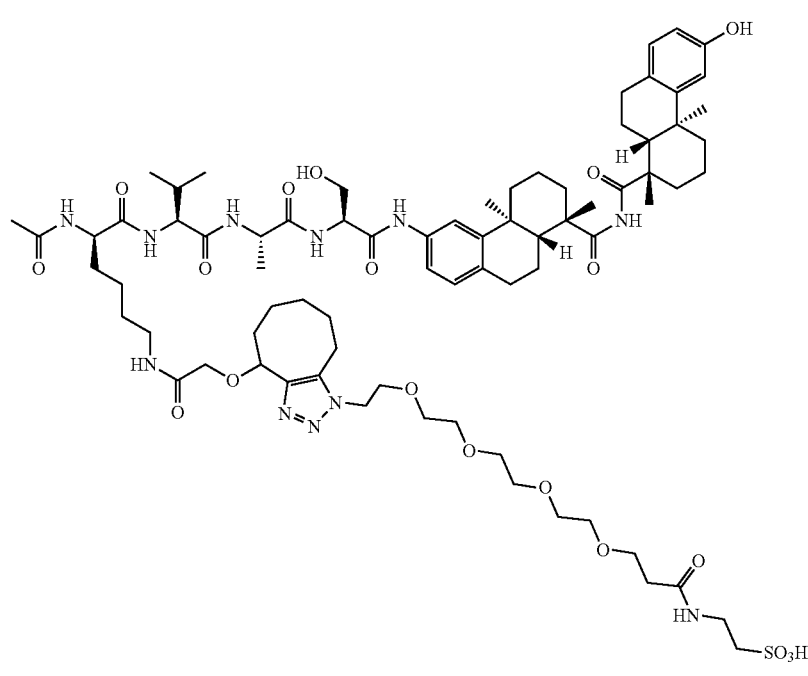

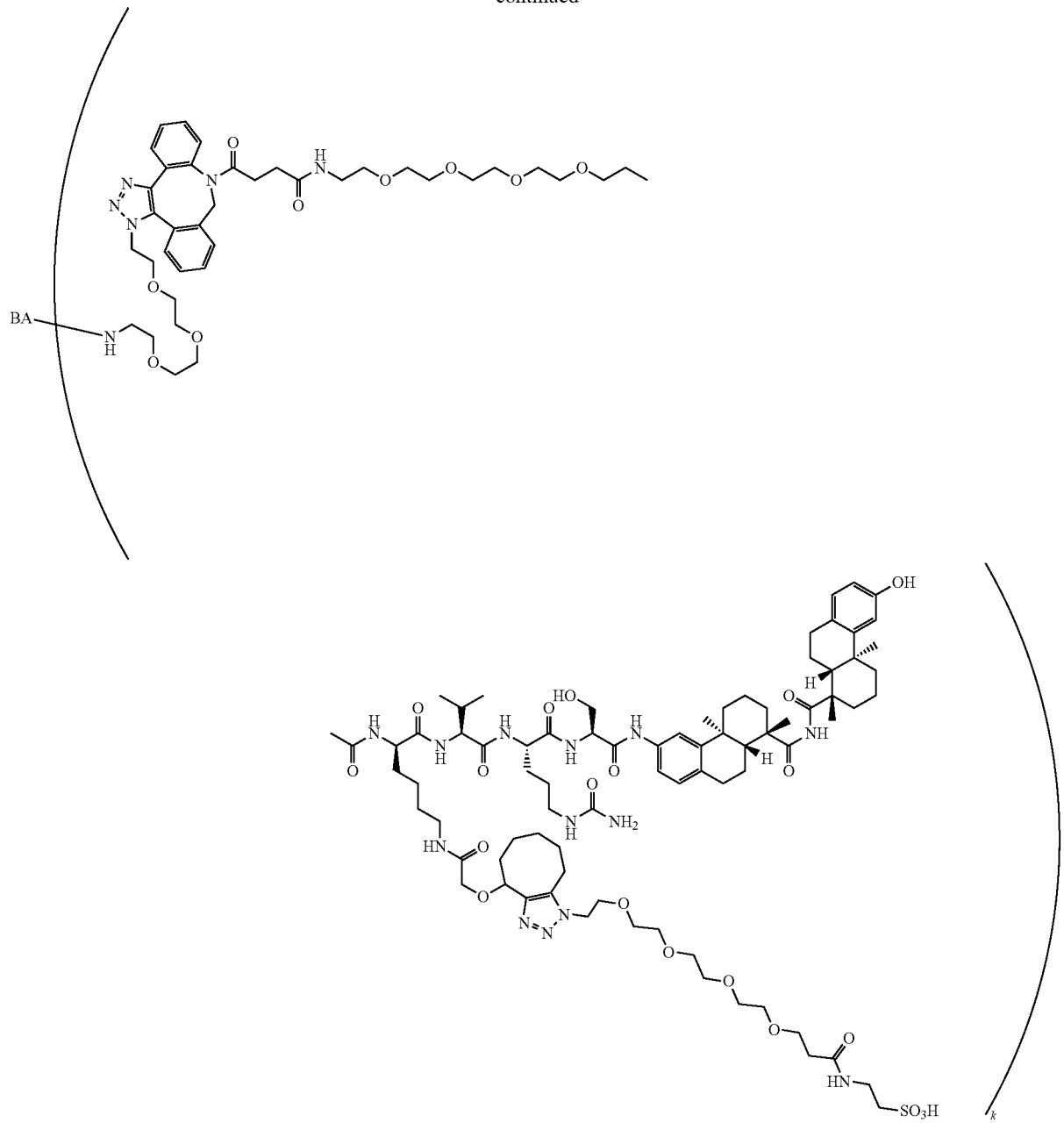

or a regioisomer, stereoisomeric form, pharmaceutically acceptable salt, or solvate thereof; wherein k ranges from about one to about four, representing an average number of units of a payload conjugated to BA.

5. The compound of claim 4, wherein k is about two.

6. The compound of claim 4, wherein k is about four.

7. The compound of claim 4, wherein BA is an antibody or antigen binding fragment thereof having binding specificity for an antigen selected from the group consisting of class A-J scavenger receptors.

8. The compound of claim 4, wherein BA is an antibody or antigen binding fragment thereof having binding specificity for an antigen selected from the group consisting of MSR1, MARCO, SRCL, SCARA5, COLEC12, CD36, LIMPII, SRBI, SRBII, CD68, LAMP, LOX-1, Dectin-1, SREC-I, SREC-II, MEGF, CXCL16, Fasciclin, FEEL-1, FEEL-2, CD163, RAGE, C-type lectin superfamily members, DEC205, CD206, Dectin-2, Mincle, DC-SIGN, DNGR-1, VSIG4, CSFIR, ASGPR, and APLP-2.

9. The compound of claim 4, wherein BA is an antibody or antigen binding fragment thereof having binding specificity for Her2 or PRLR.

10. The compound of claim 4, wherein BA is an antibody or antigen binding fragment thereof having binding specificity for MSR1.

11. The compound of claim 4, wherein BA is an antibody or antigen binding fragment thereof linked through one or more N295 residues.

12. The compound of claim 4, wherein BA is an antibody or antigen binding fragment thereof linked through one or more N295 and N297Q residues.

13. The compound of claim 1, having the structure
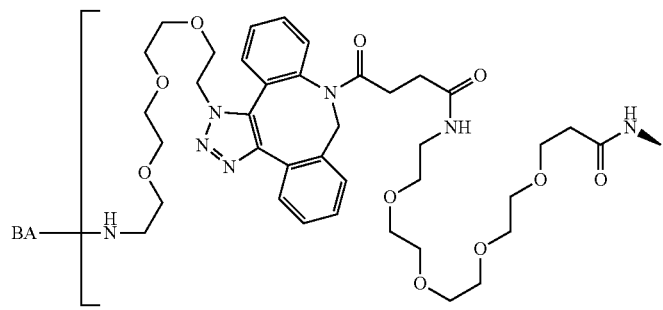
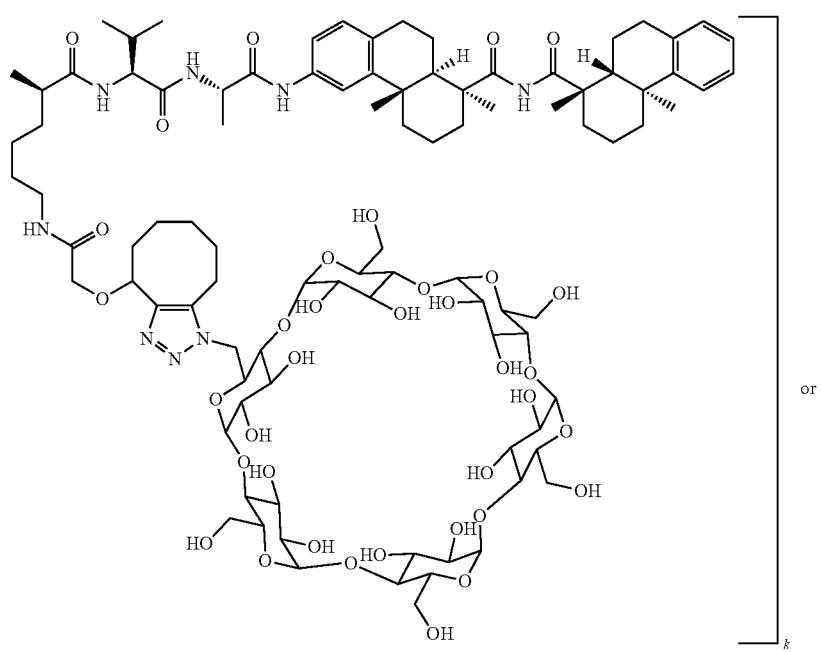
or
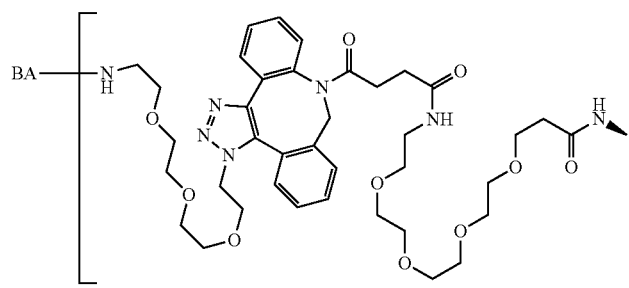

-continued
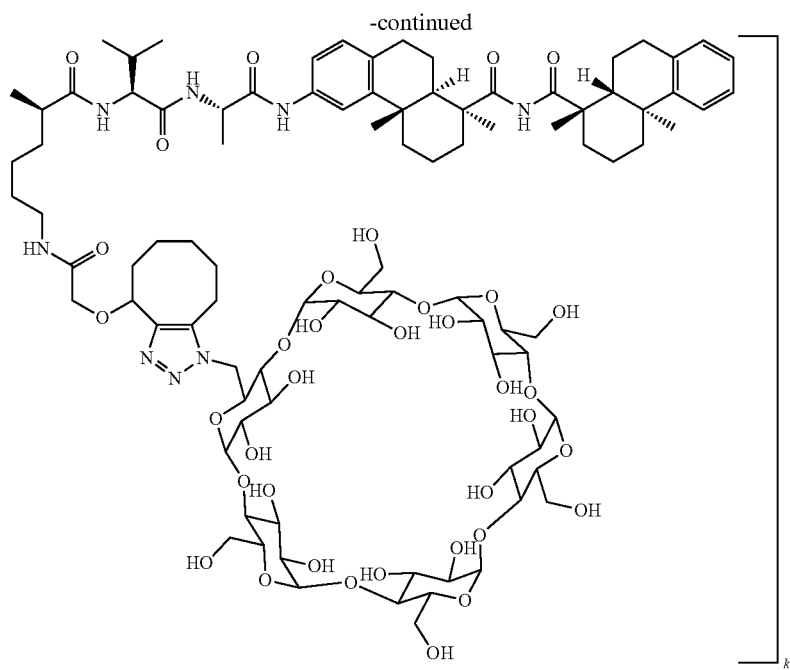
wherein BA is a binding agent; and k ranges from about one to about four, representing an average number of units of a payload conjugated to BA.
14. The compound of claim 1, having the structure
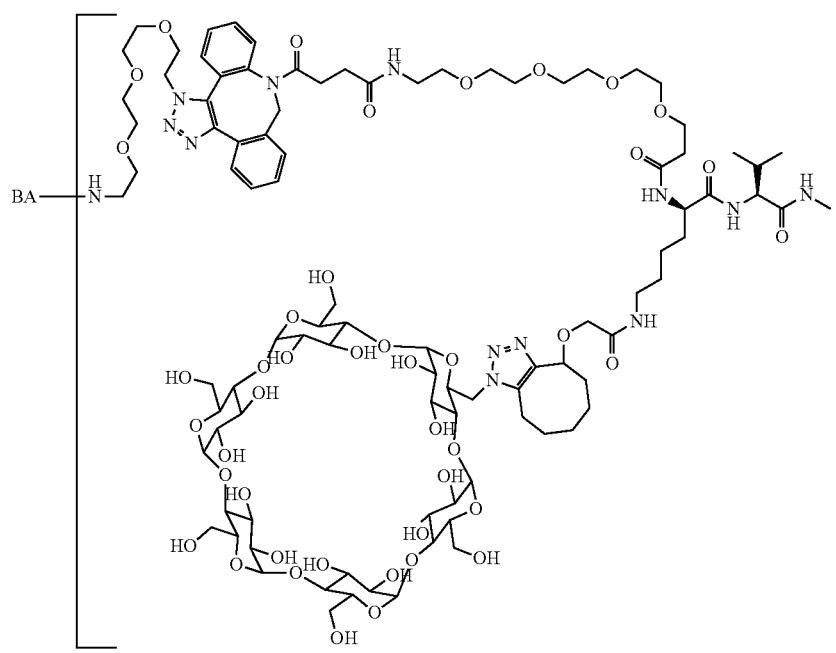

-continued
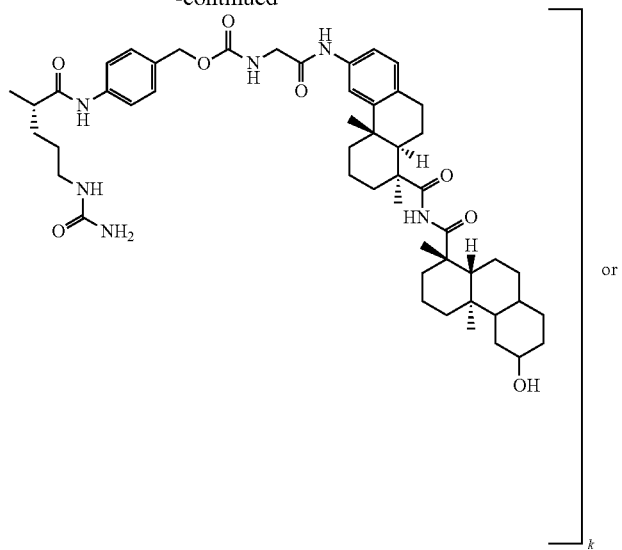
or
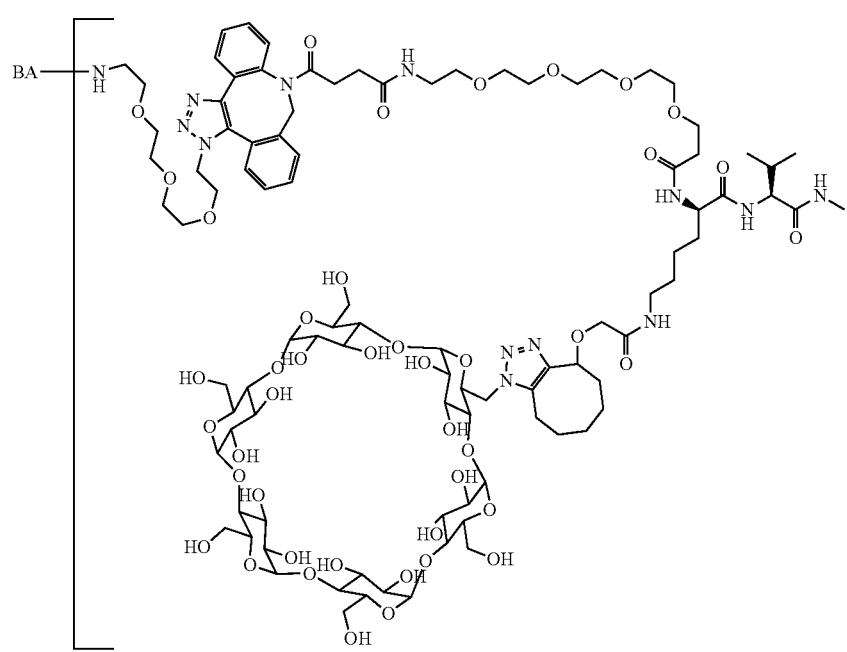

-continued
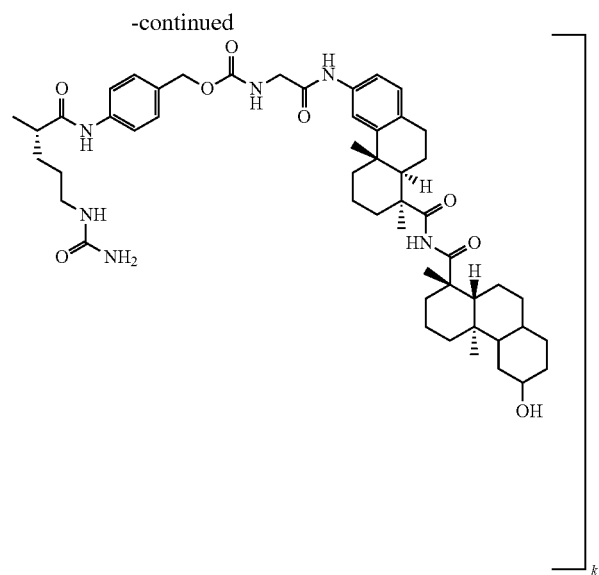
wherein BA is a binding agent; and k ranges from about one to about eight, representing an average number of units of a payload conjugated to BA.
15. The compound of claim 1, having the structure
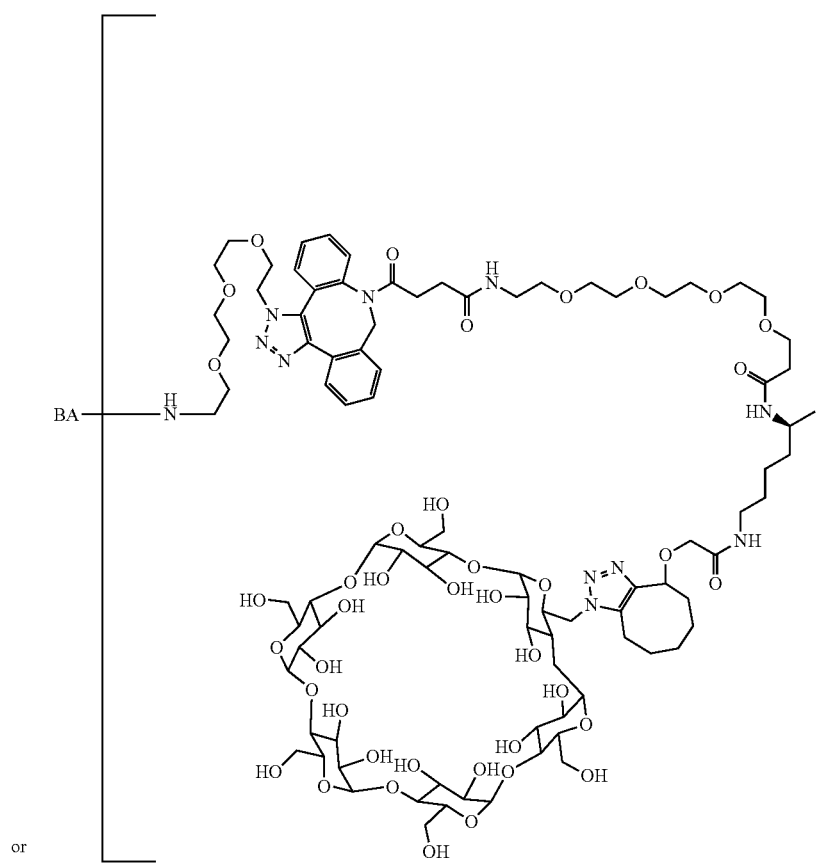
or

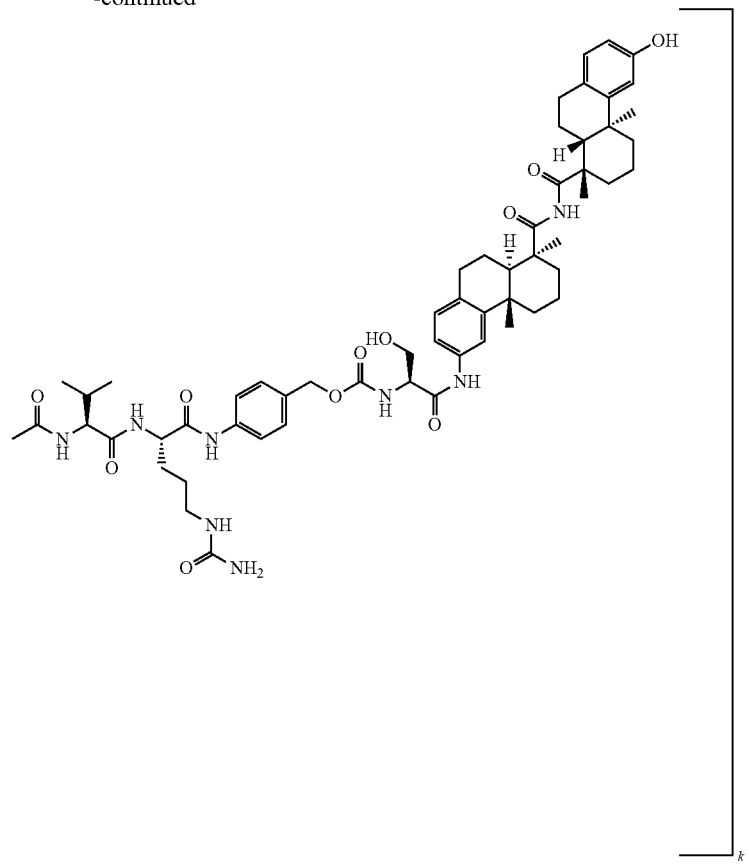
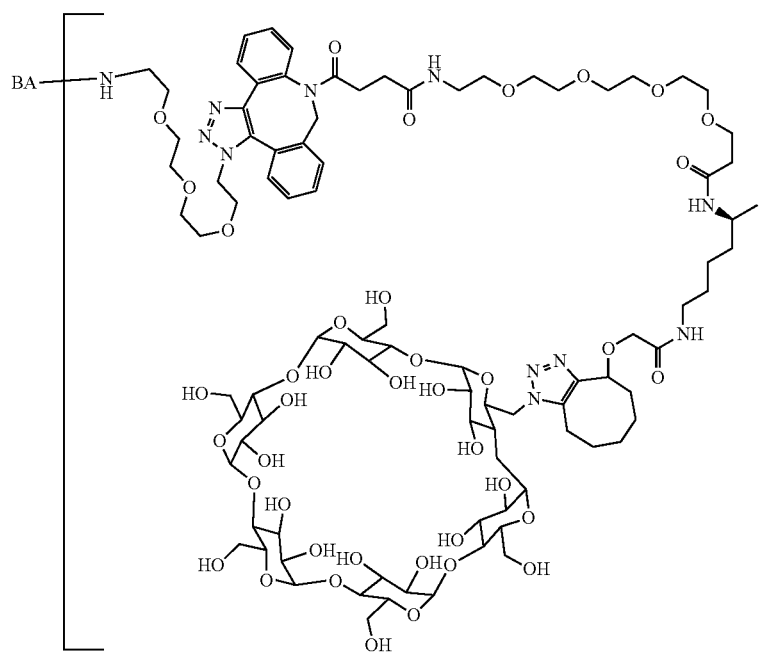

-continued
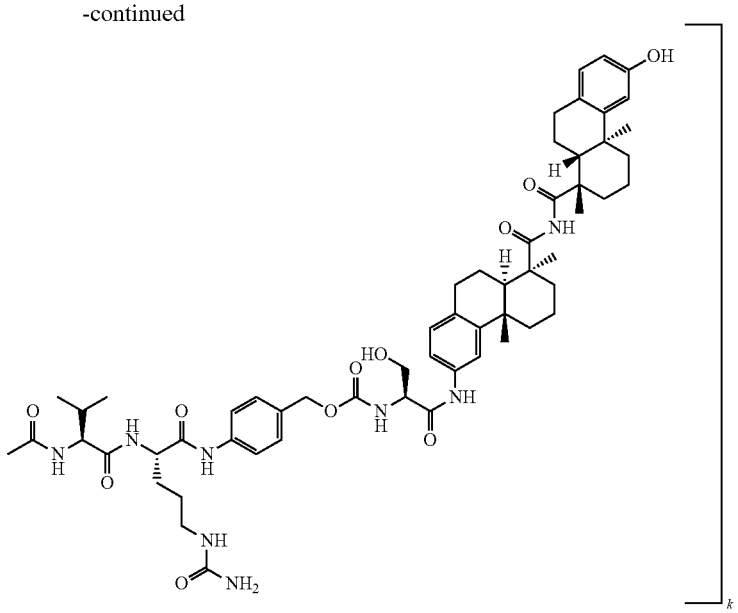
wherein BA is a binding agent; and k ranges from about one to about eight, representing an average number of units of a payload conjugated to BA.
16. The compound of claim 1, having the structure
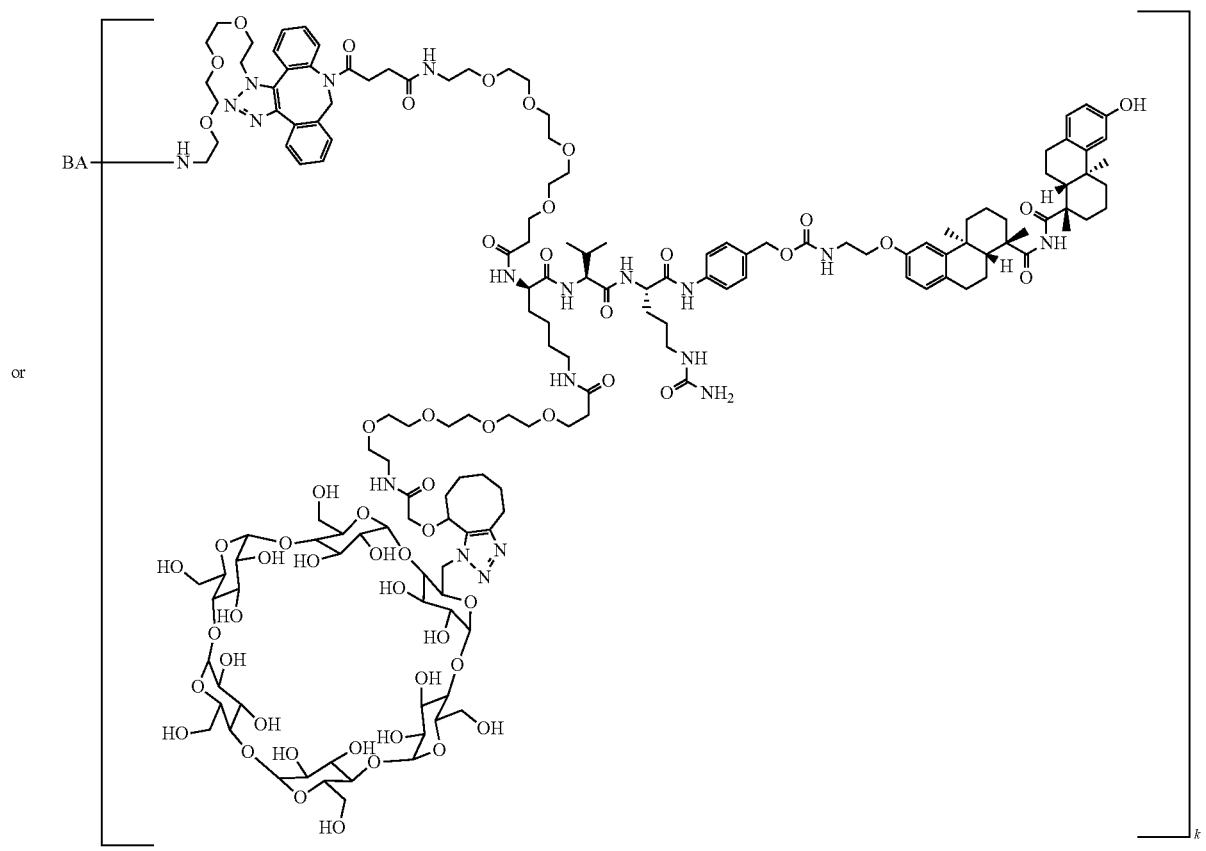
or

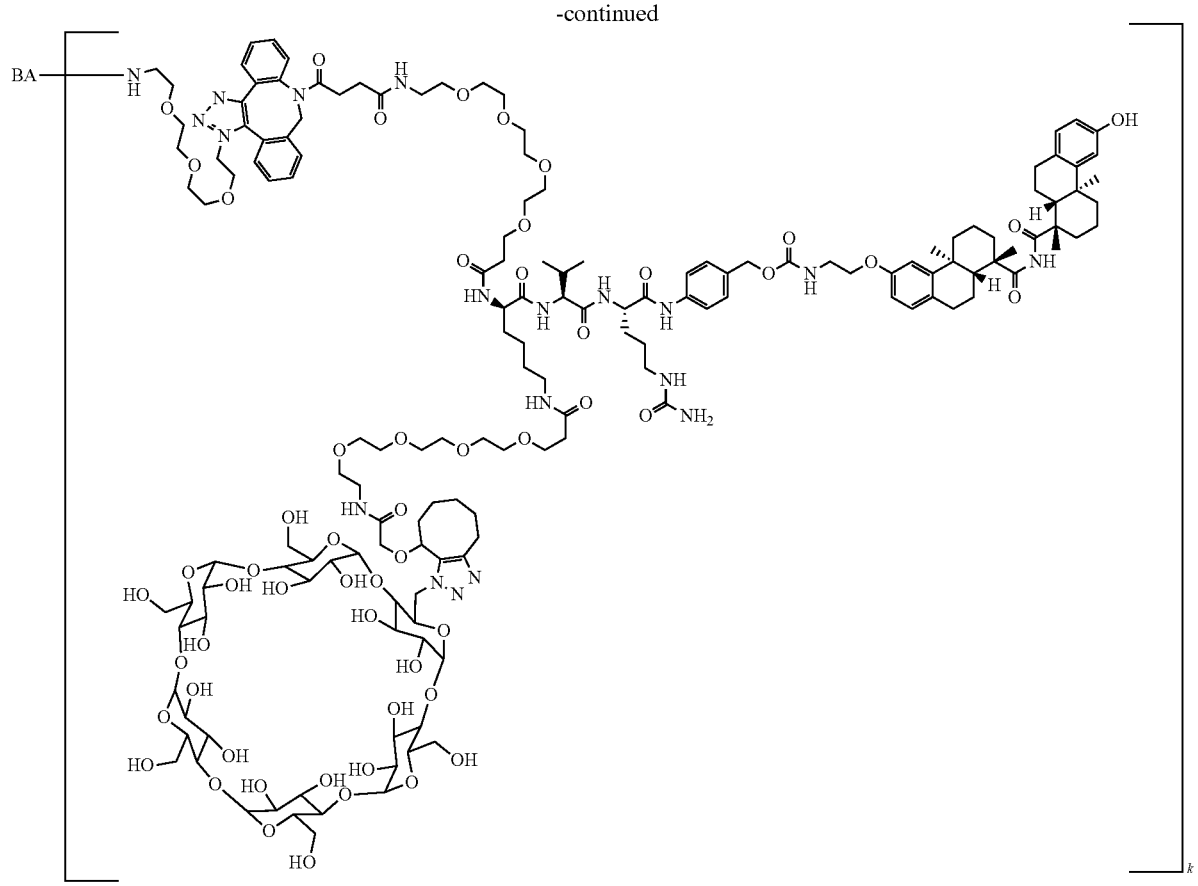
wherein BA is a binding agent; and k ranges from about one to about eight, representing an average number of units of a payload conjugated to BA.
17. The compound of claim 1, selected from the group consisting of
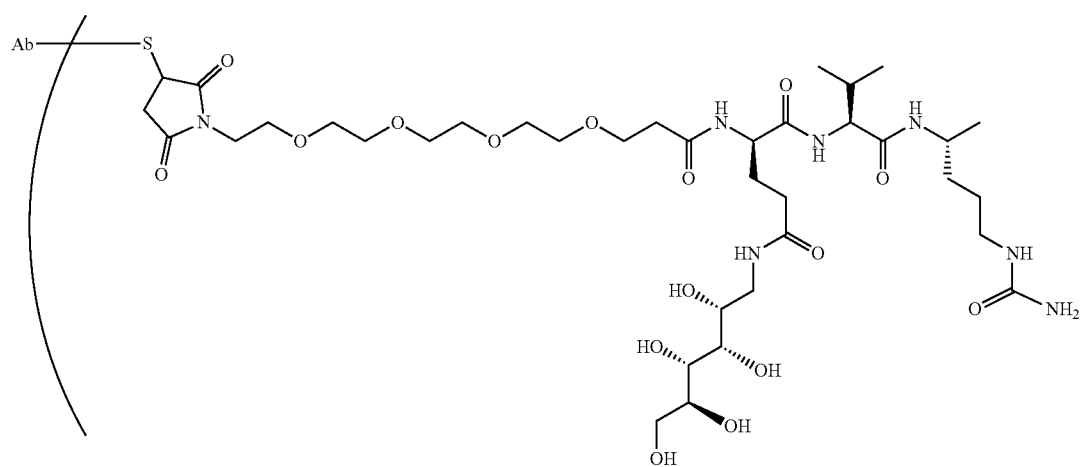

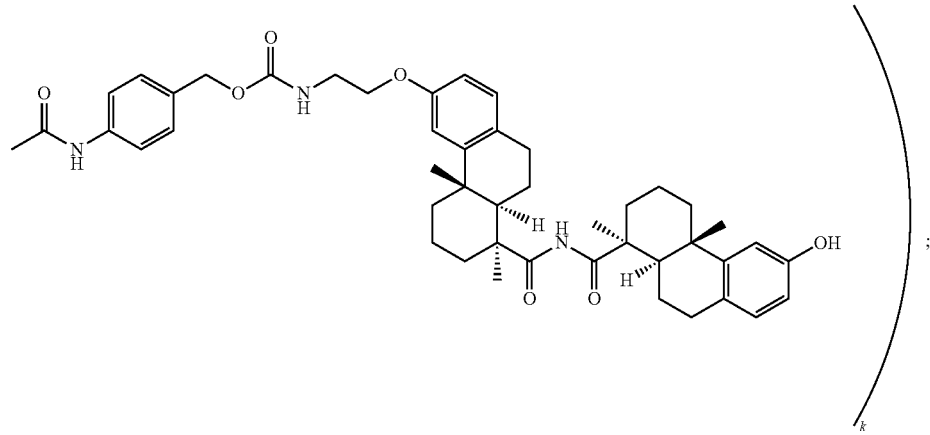
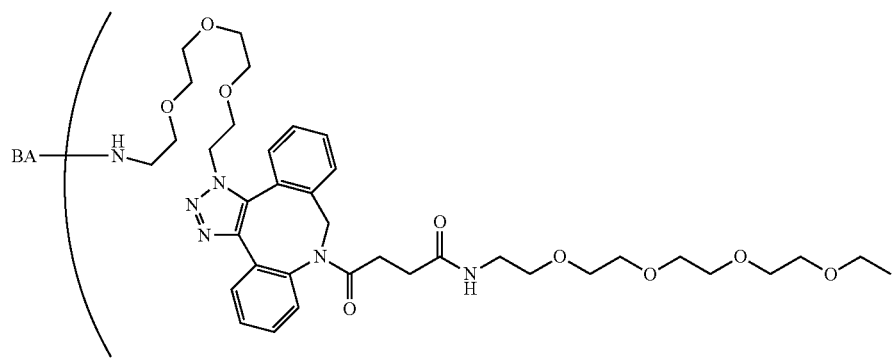
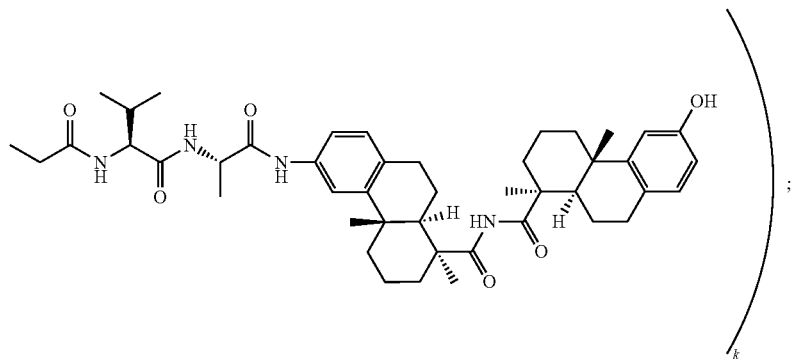
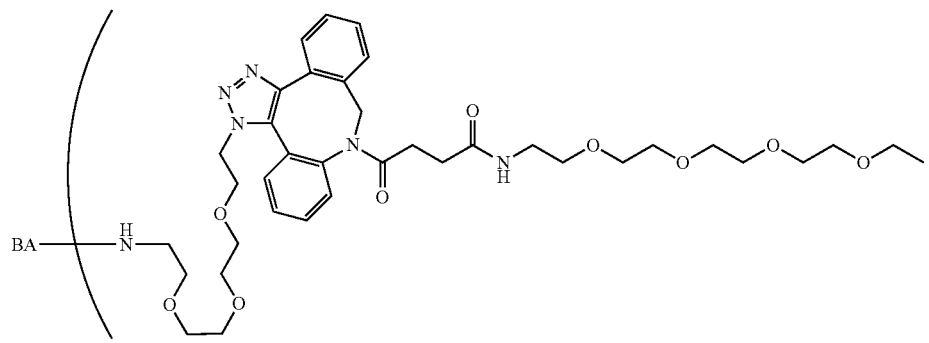

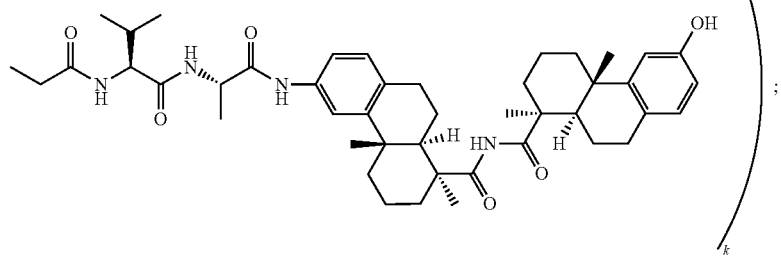
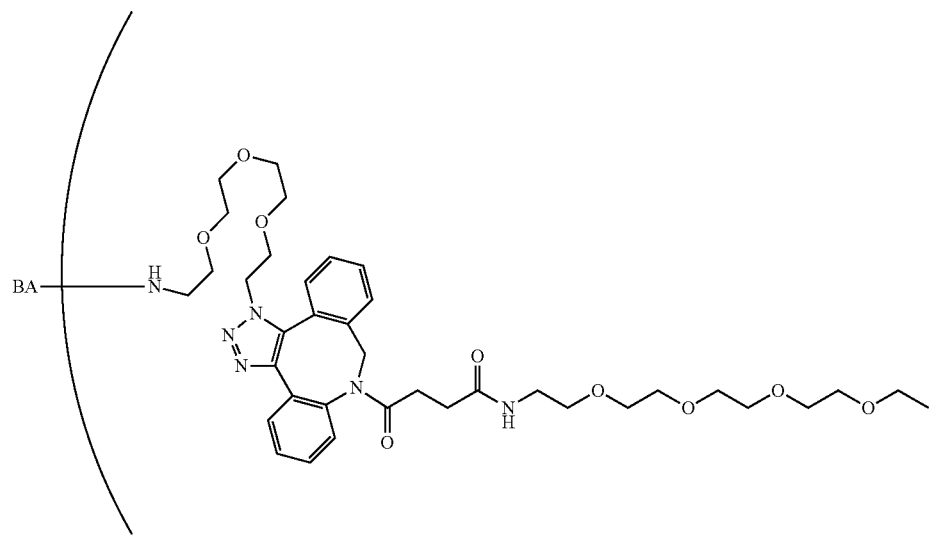
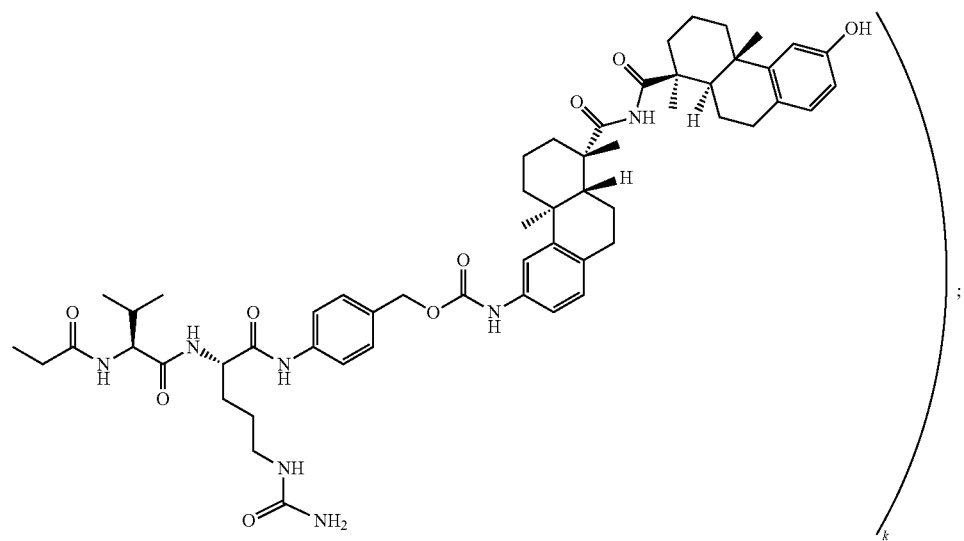

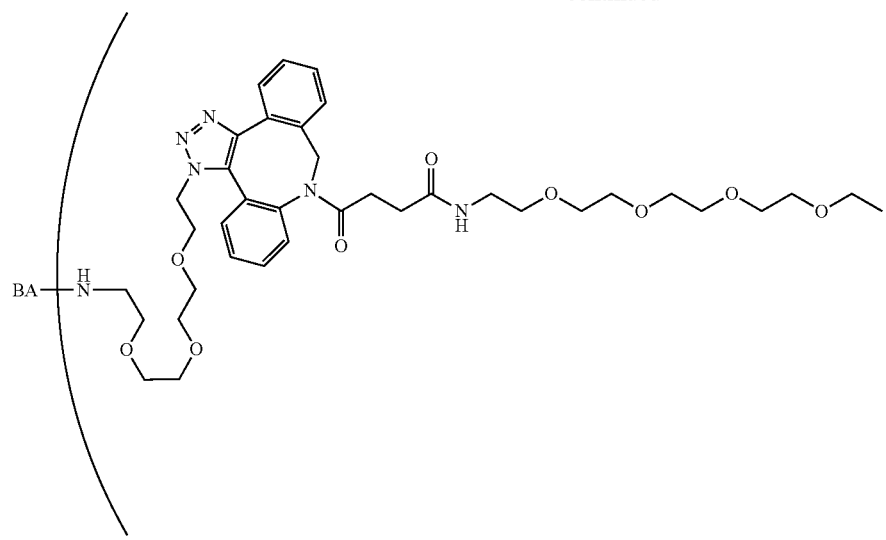
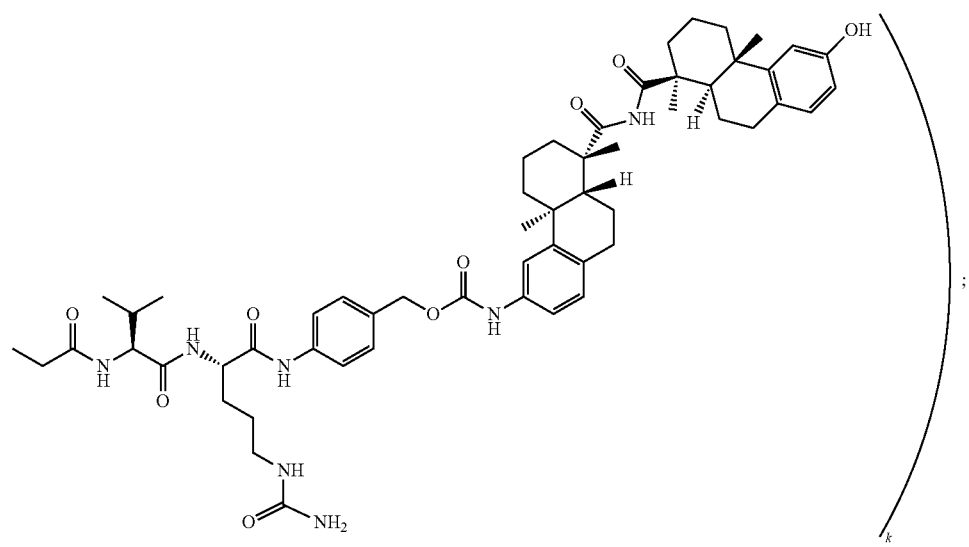
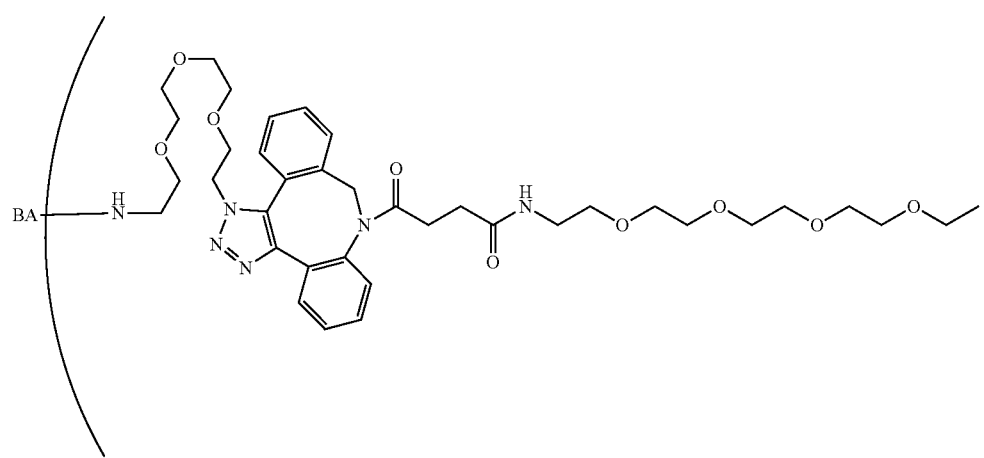

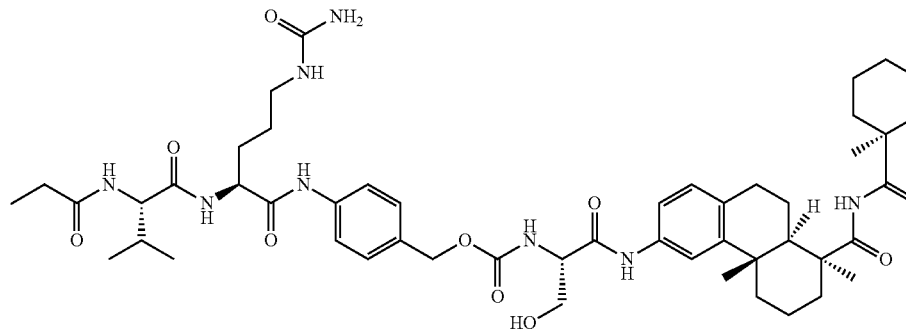
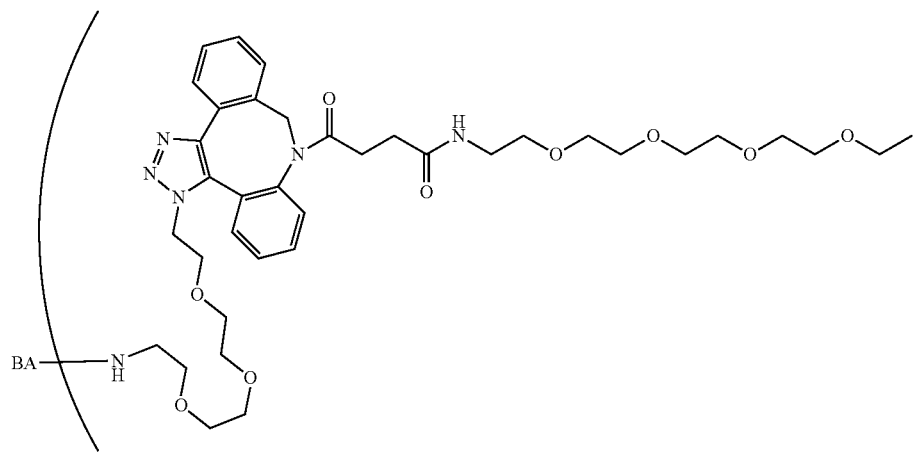
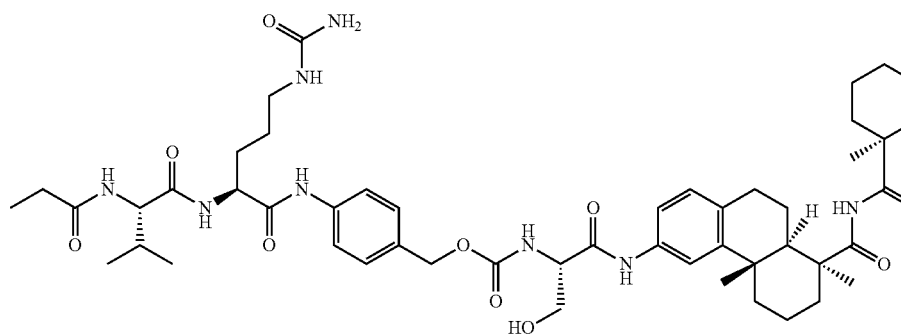

501 502
-continued
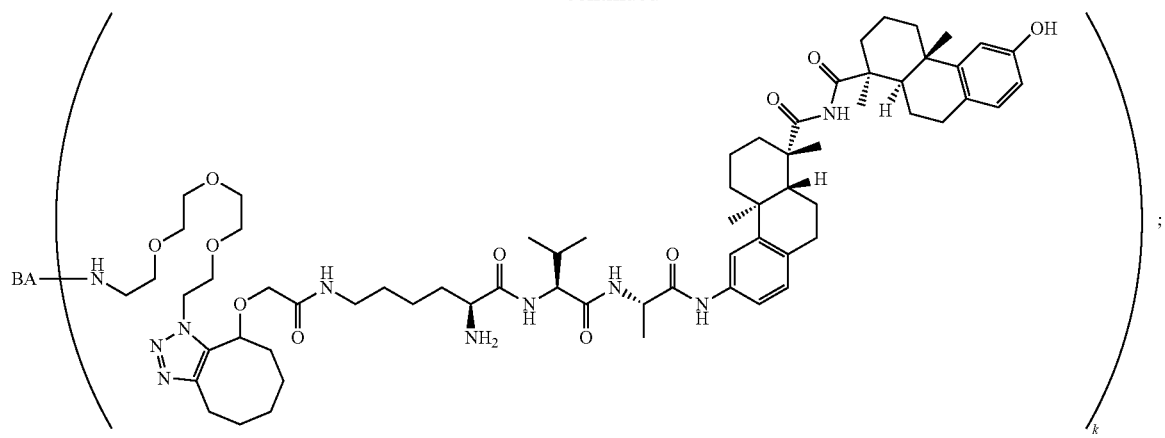
;
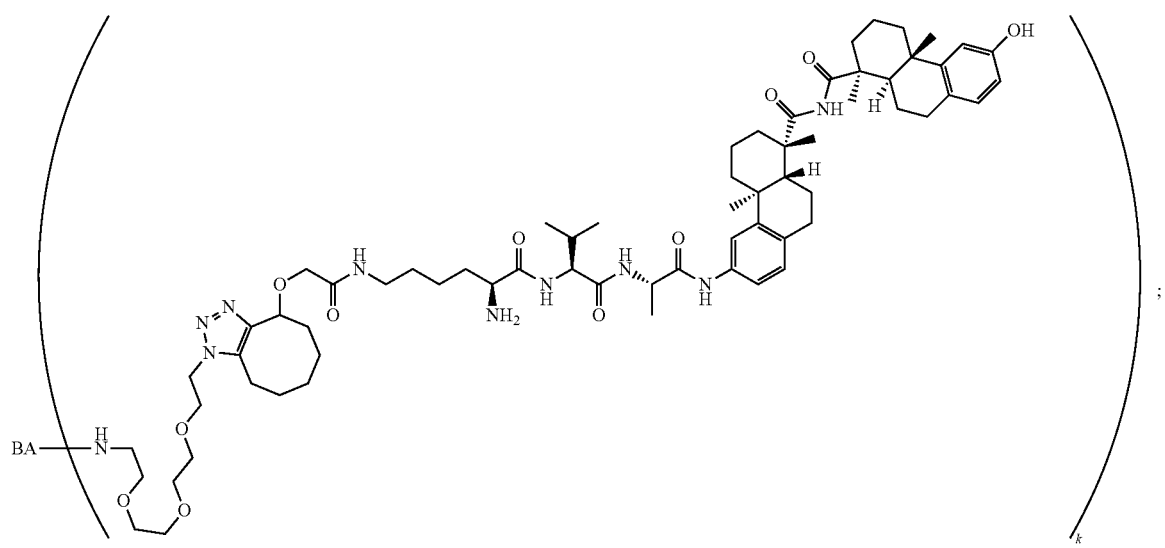
;
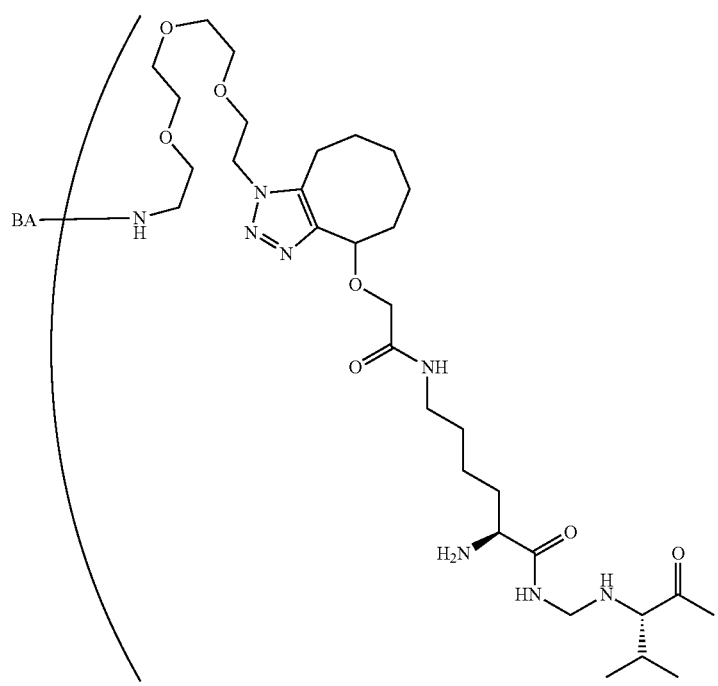

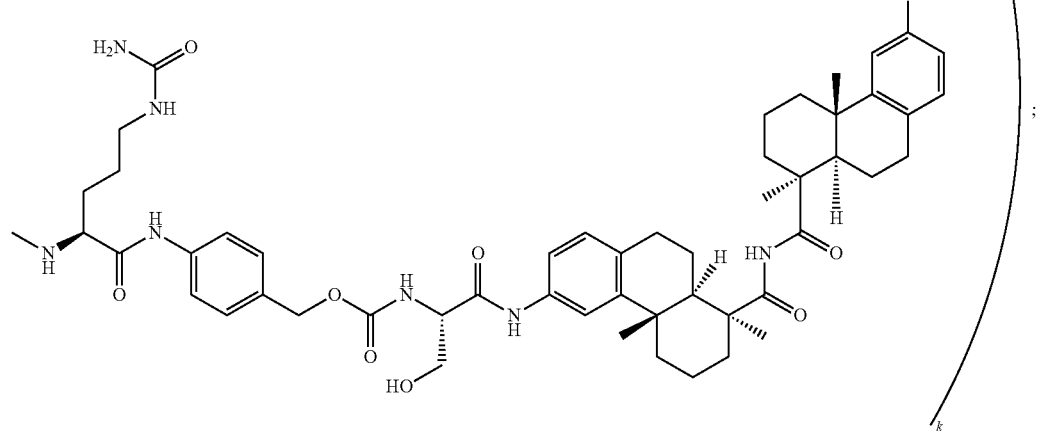
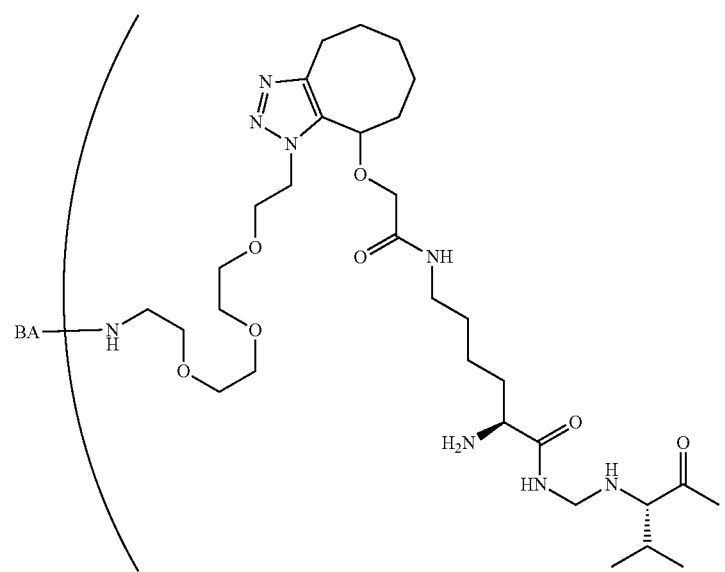

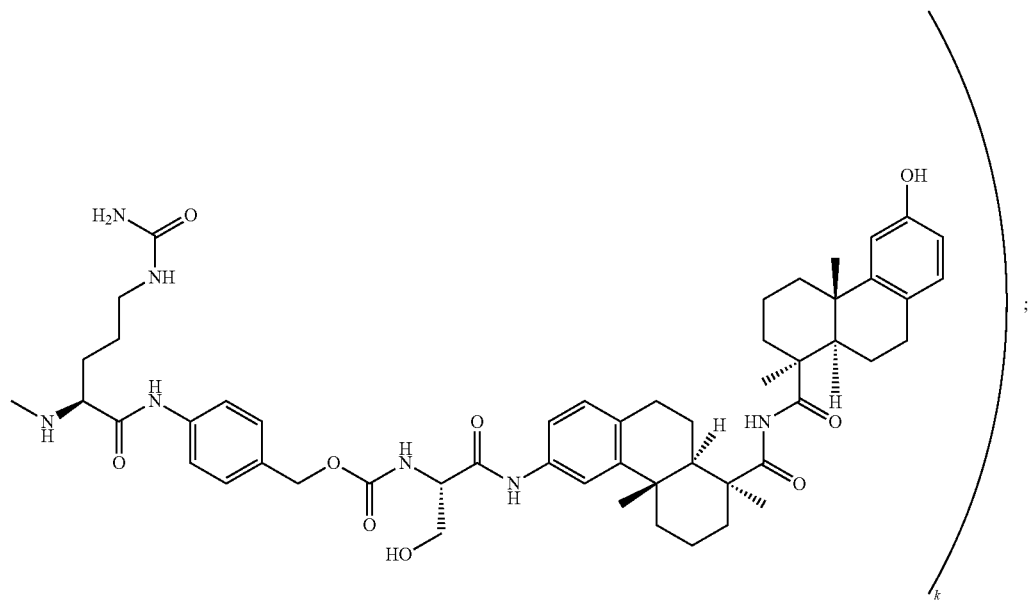
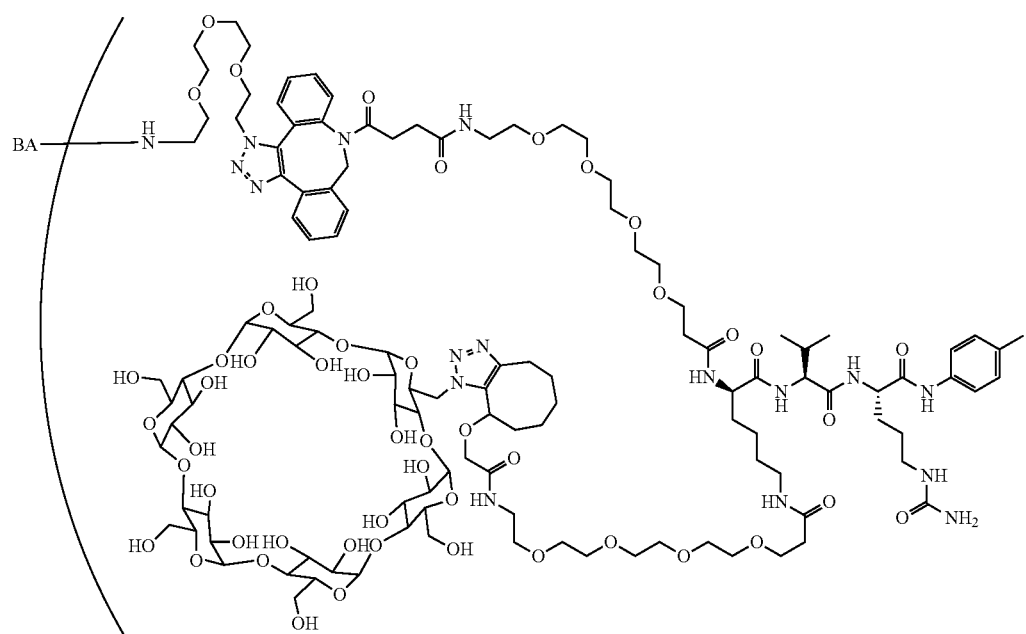

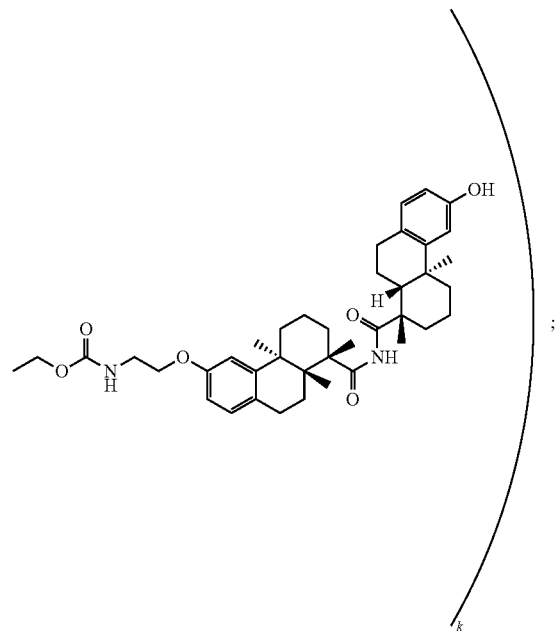
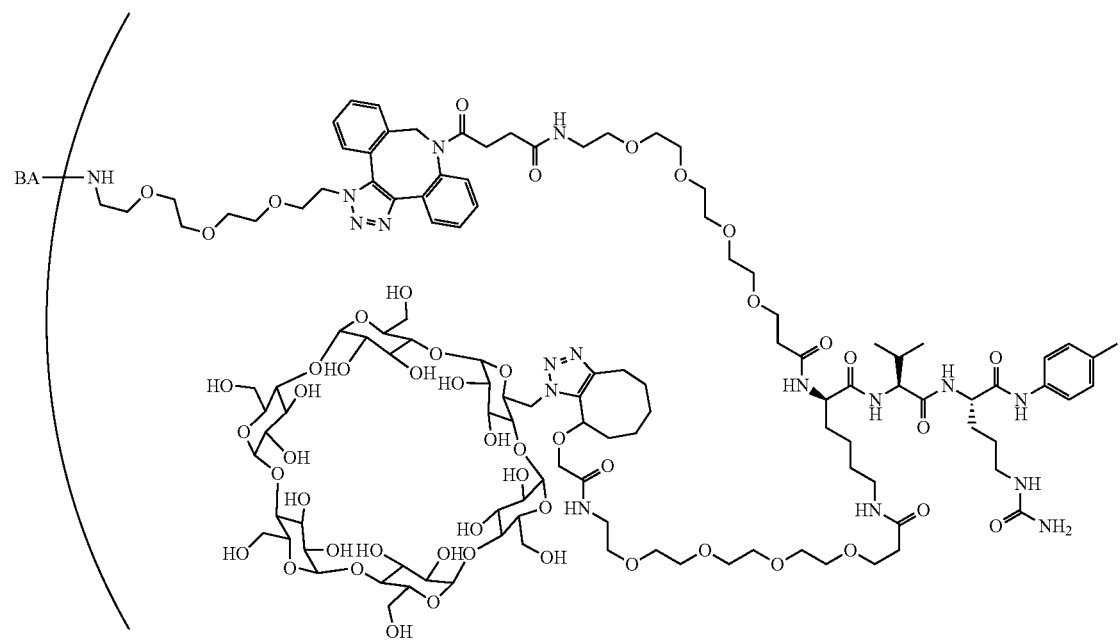

-continued
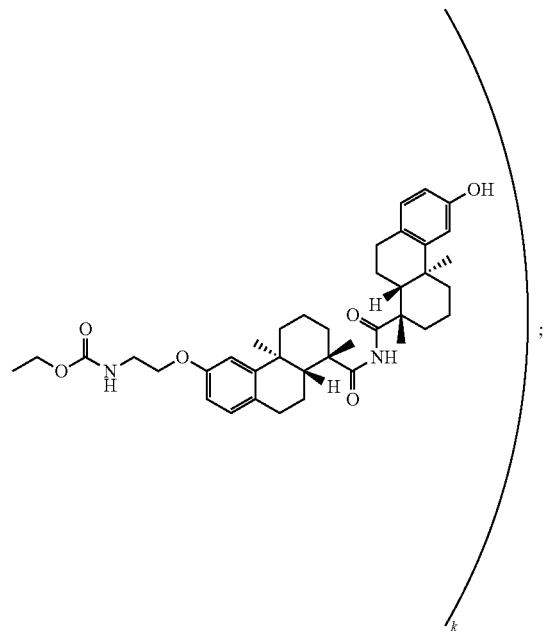
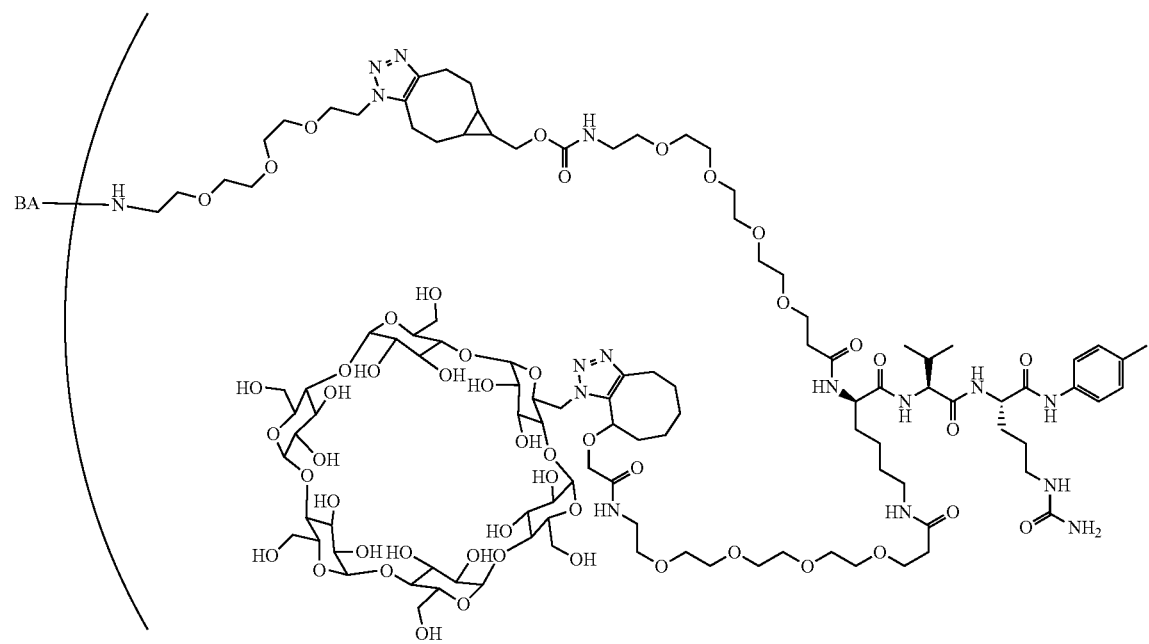

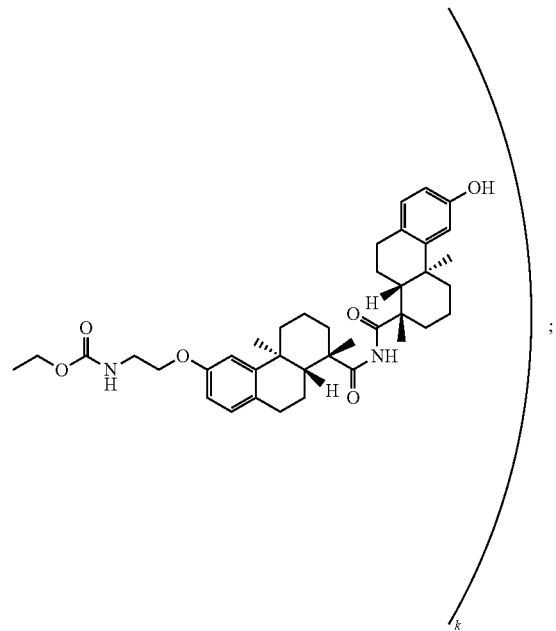
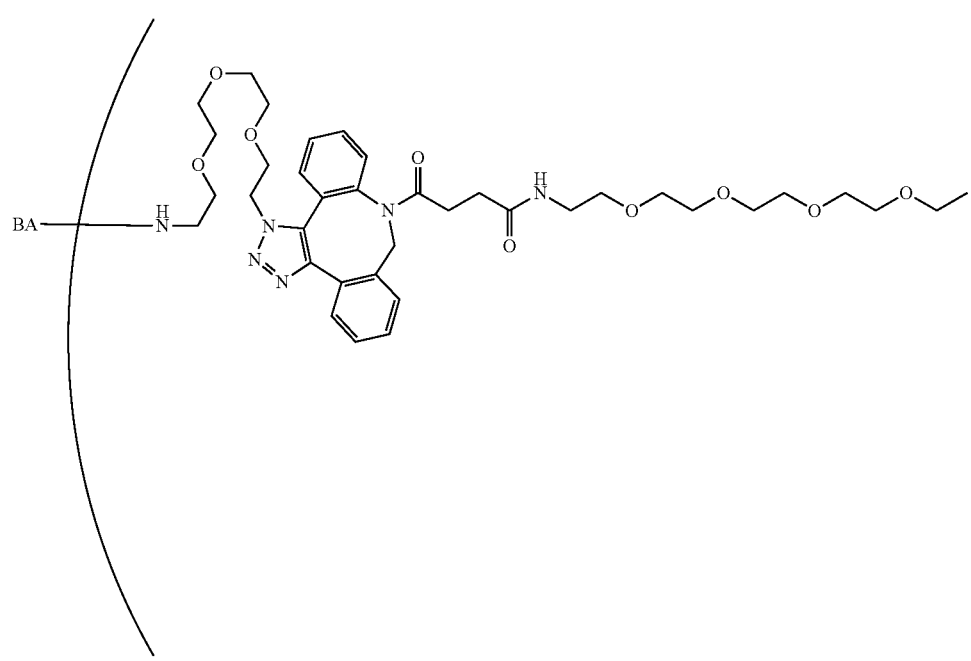

513
514
-continued
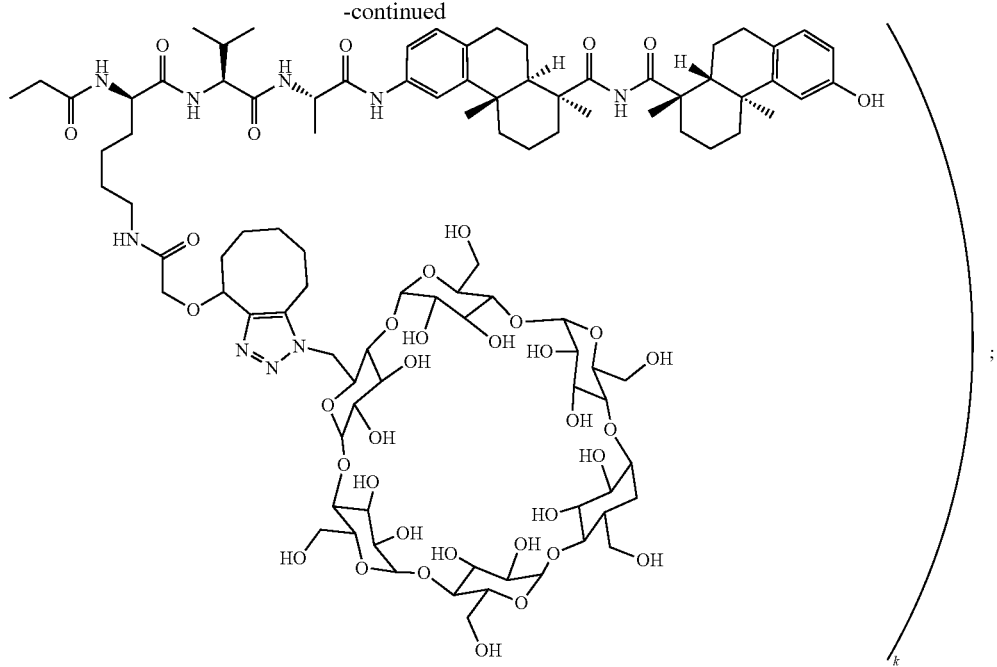
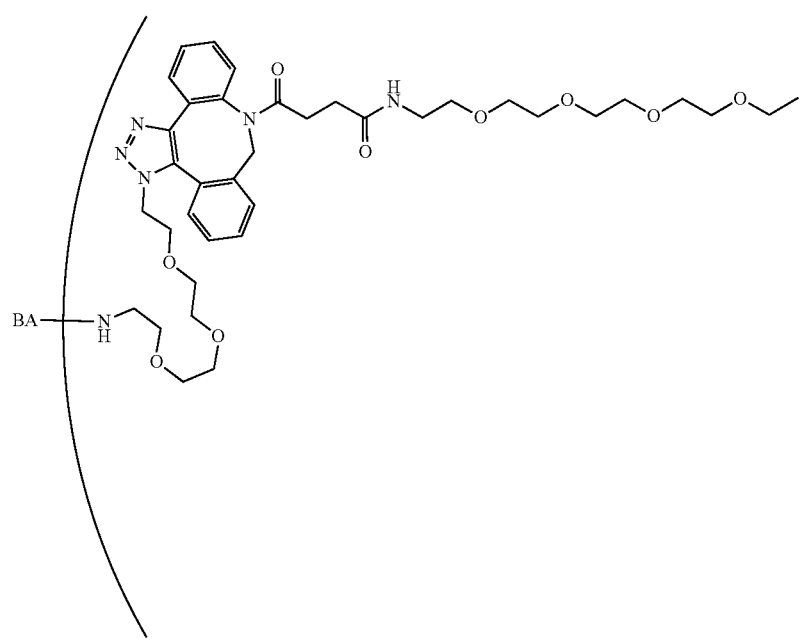

515 516
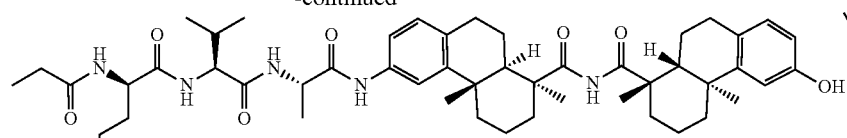
-continued
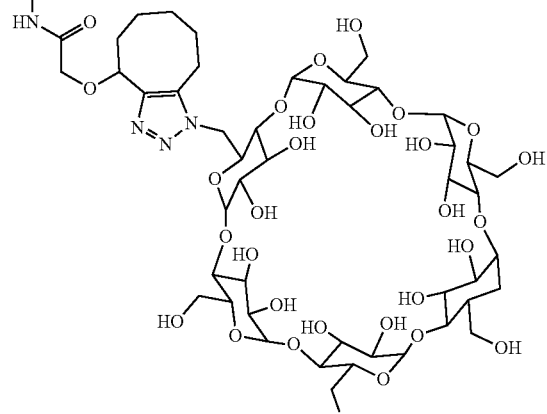
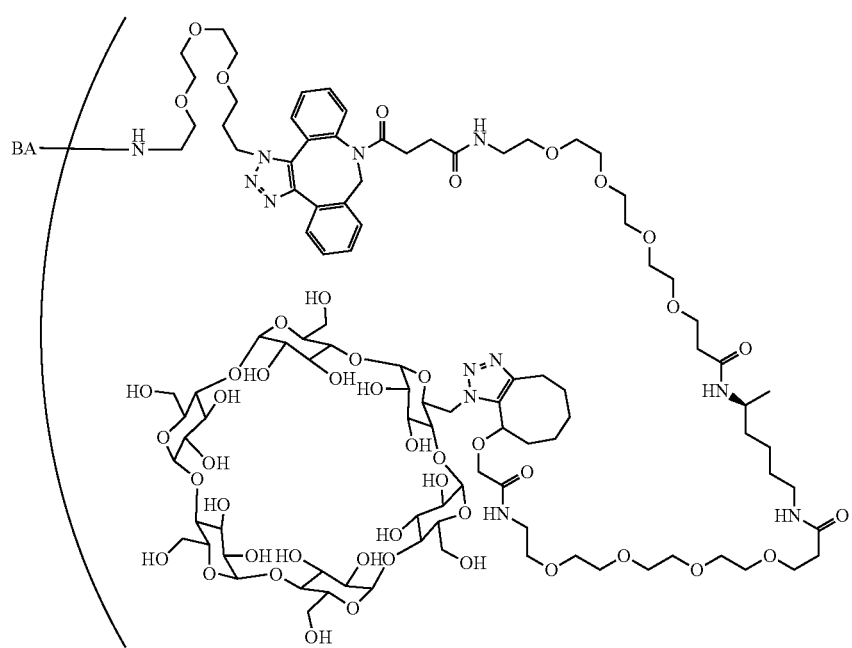

-continued
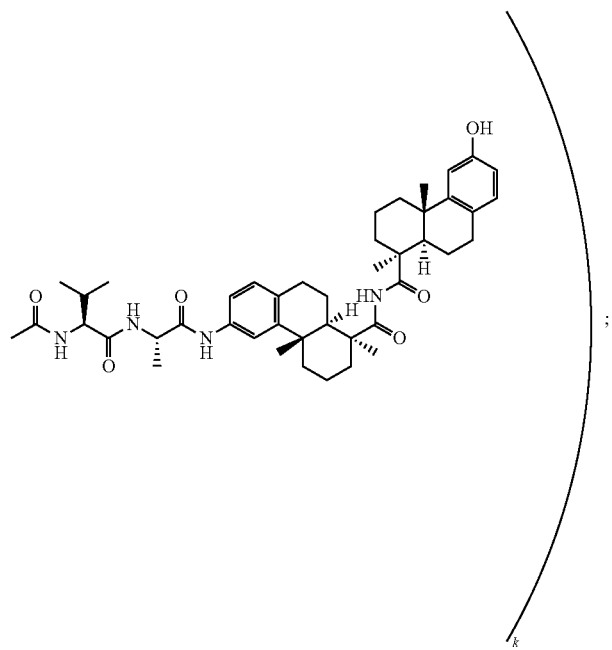
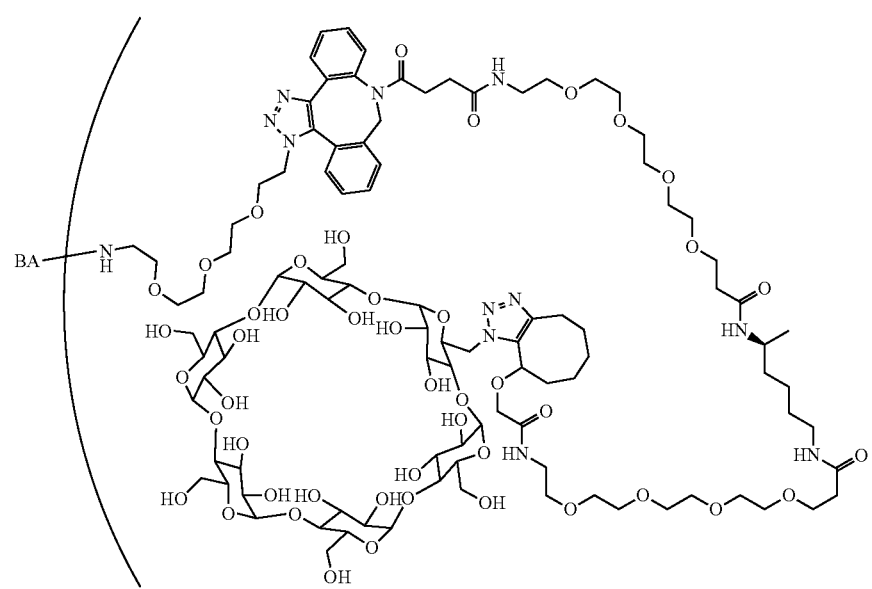

-continued
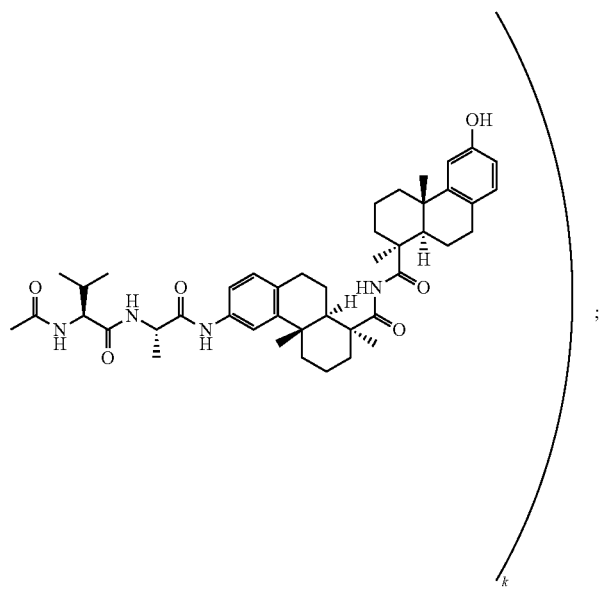
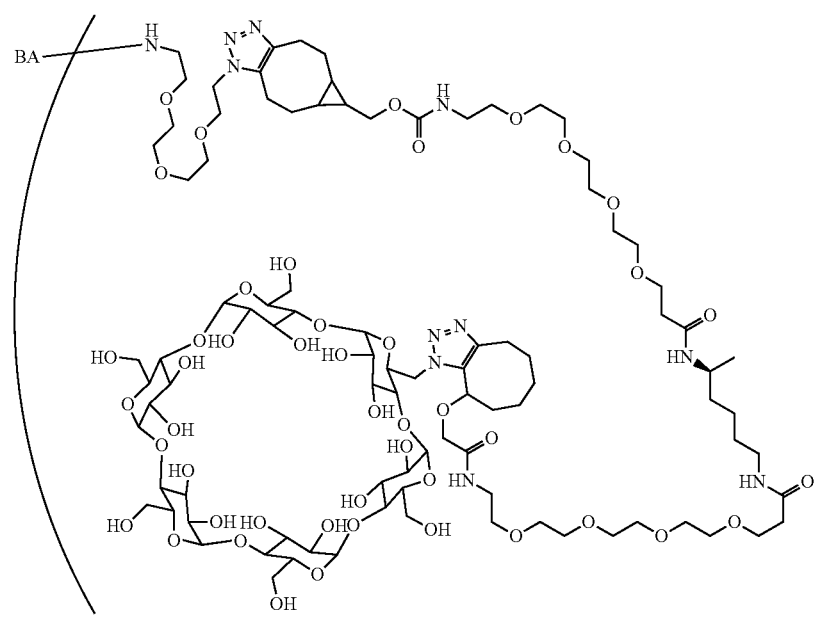

-continued
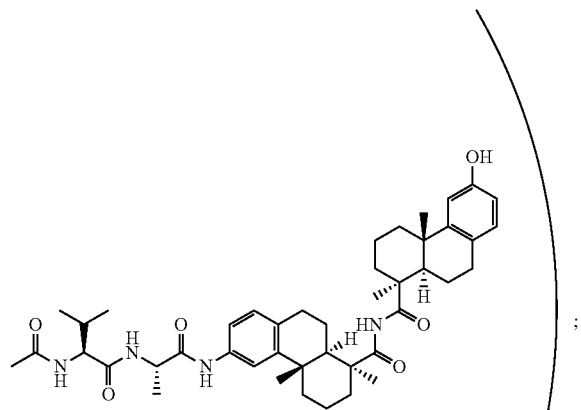
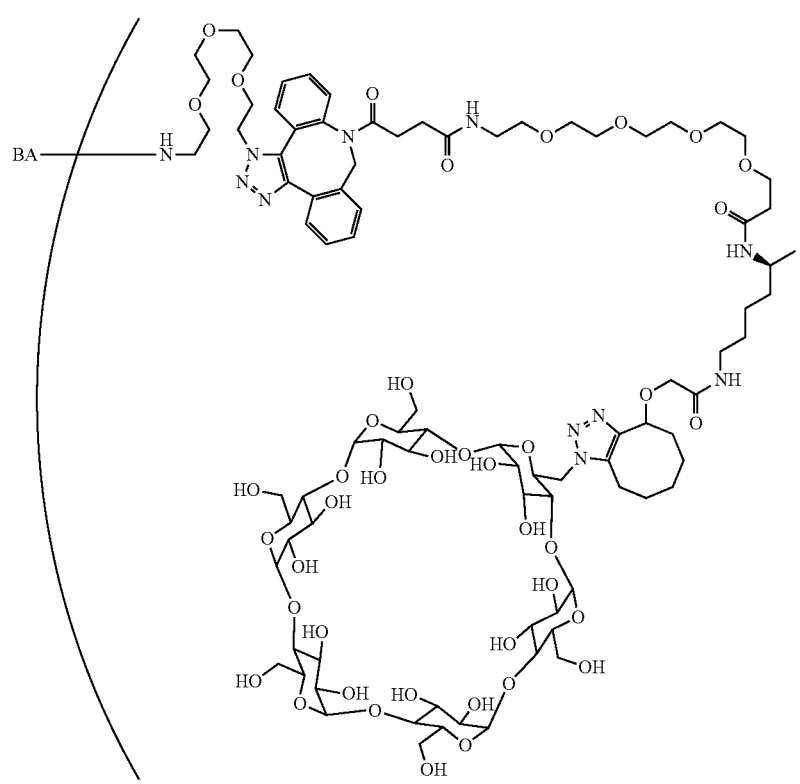

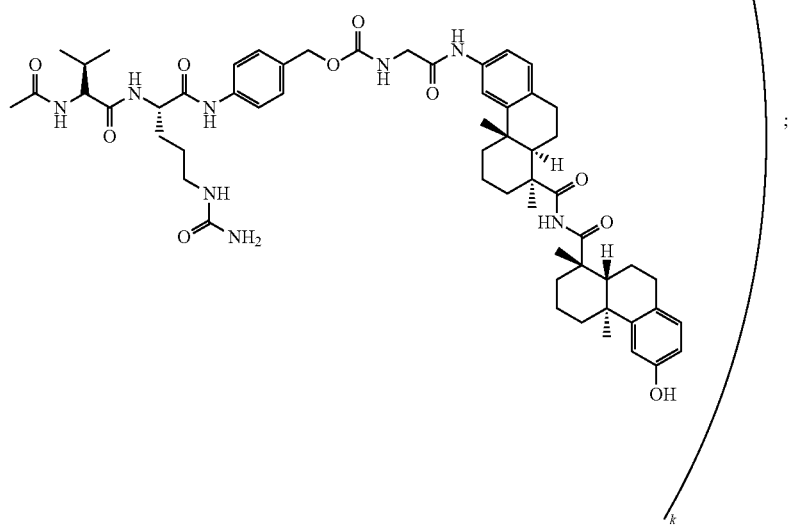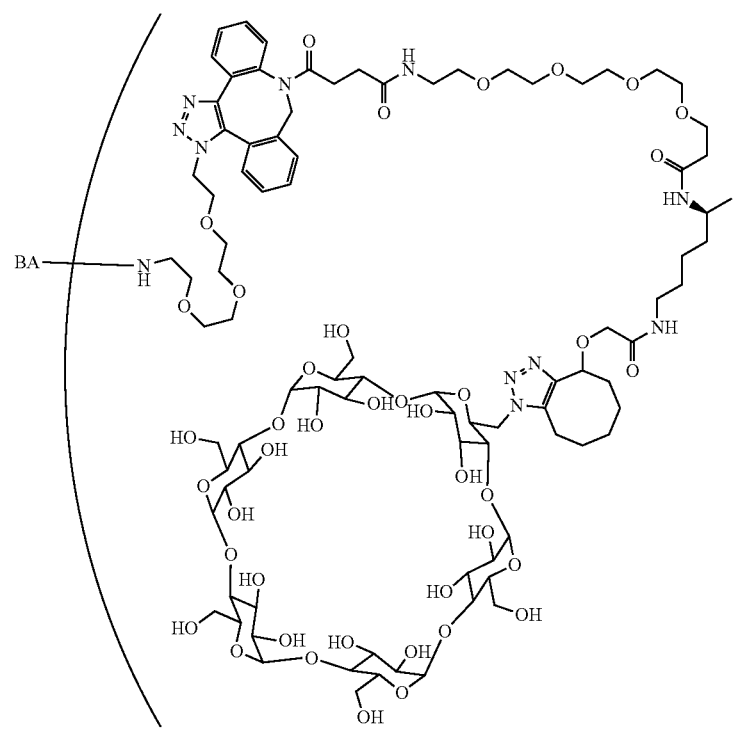

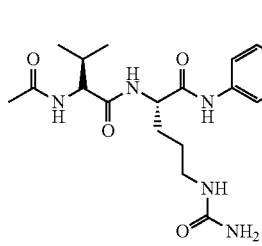
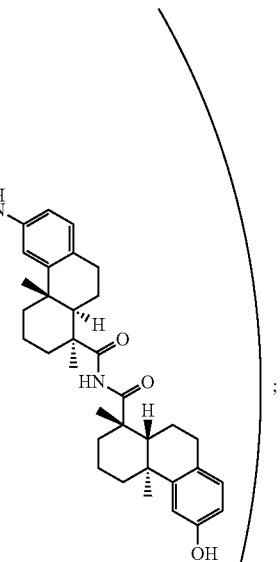
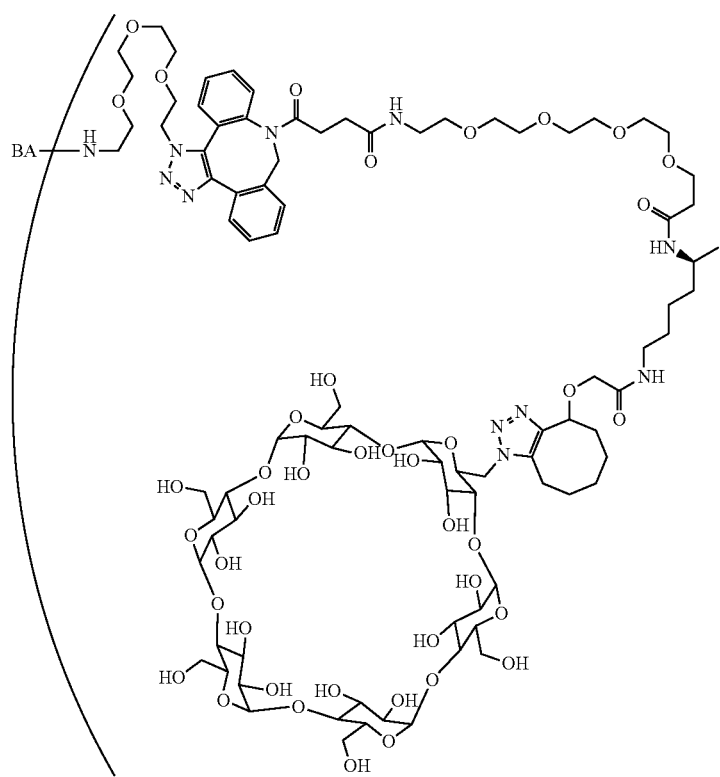

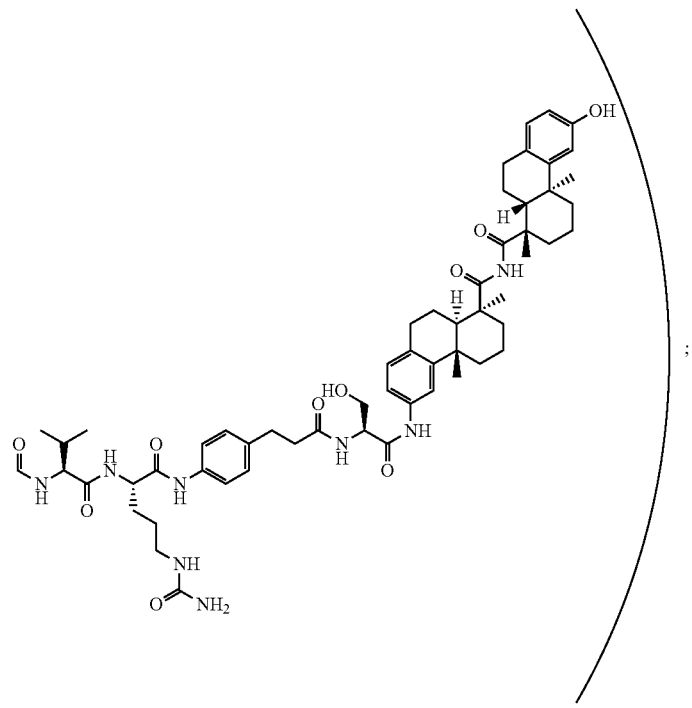
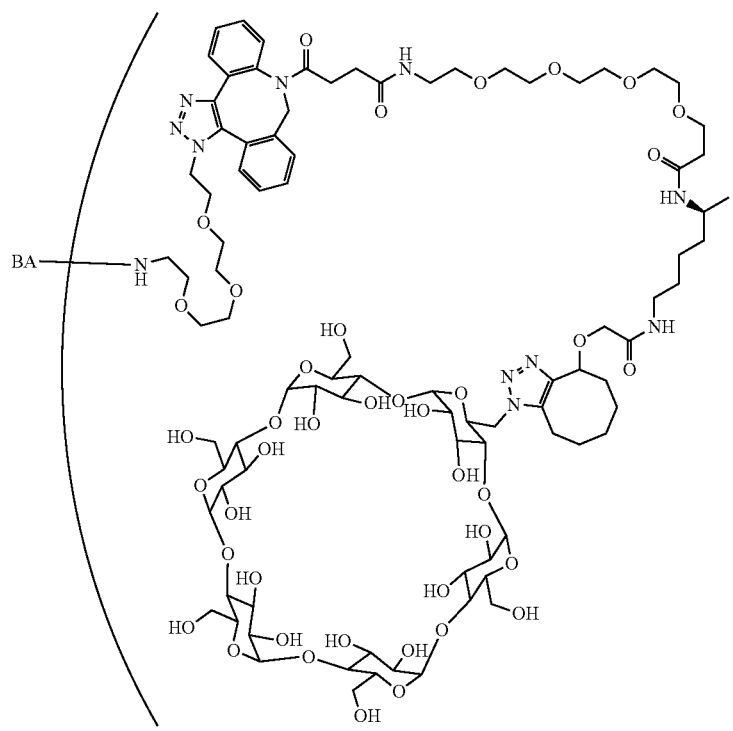

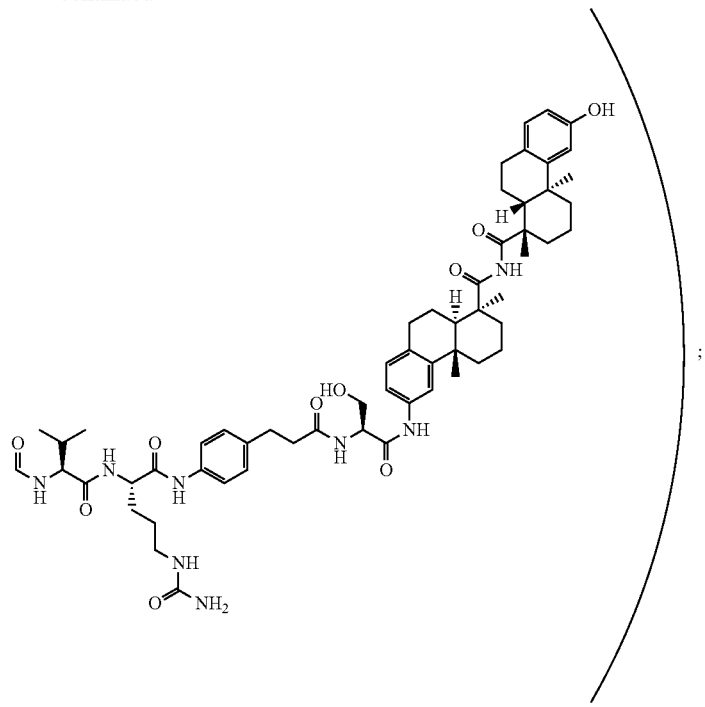
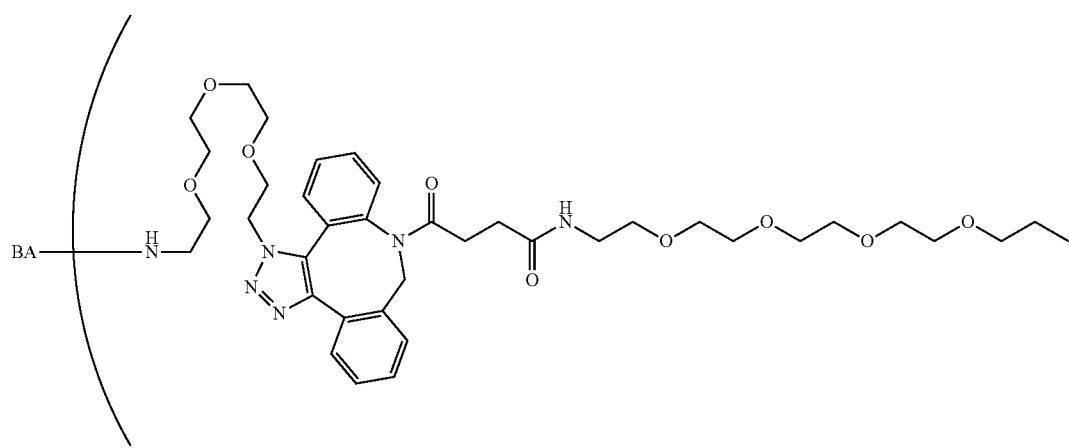
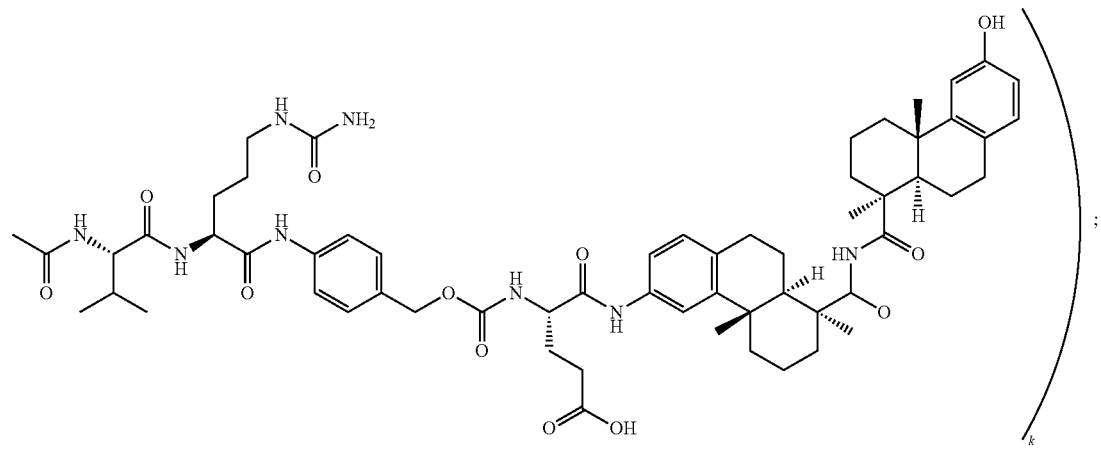

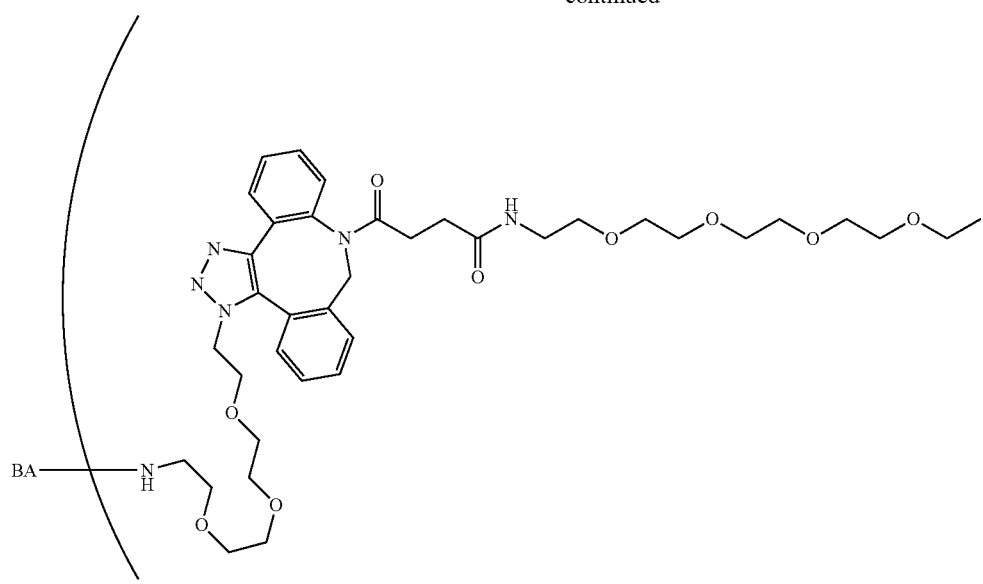
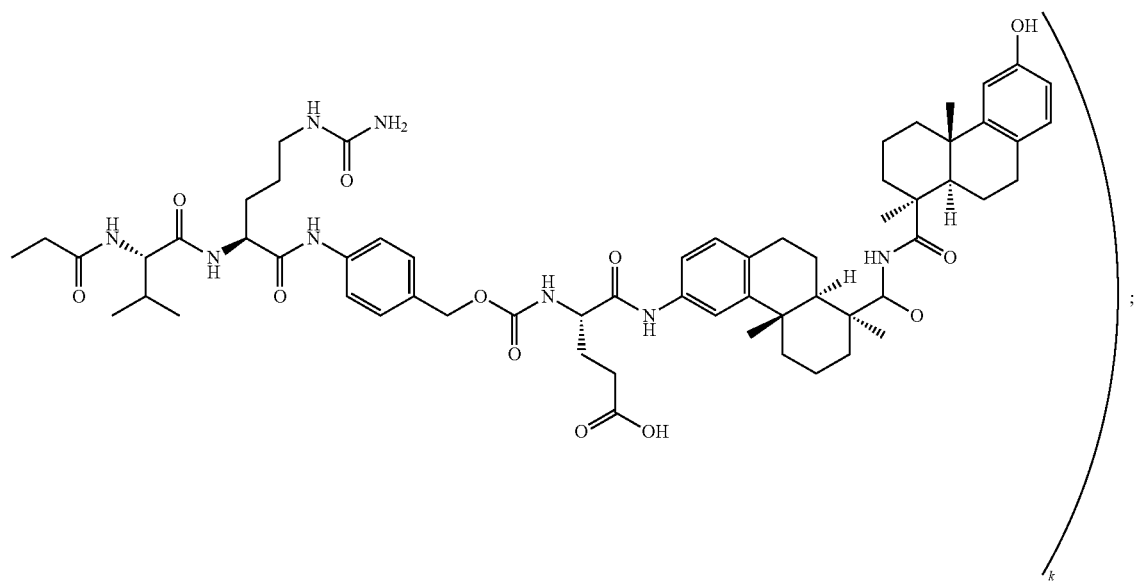
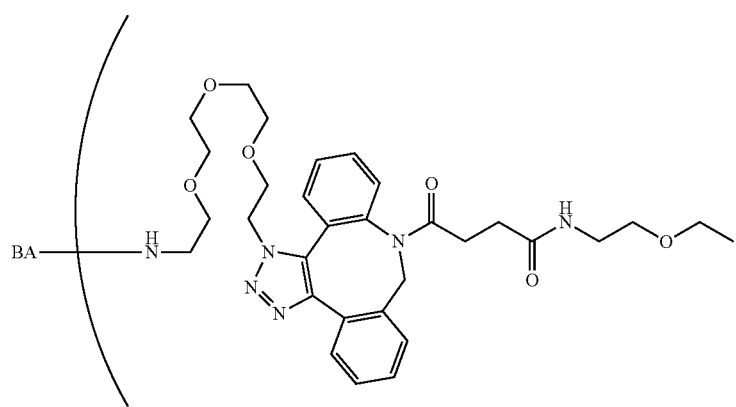

533 534
-continued
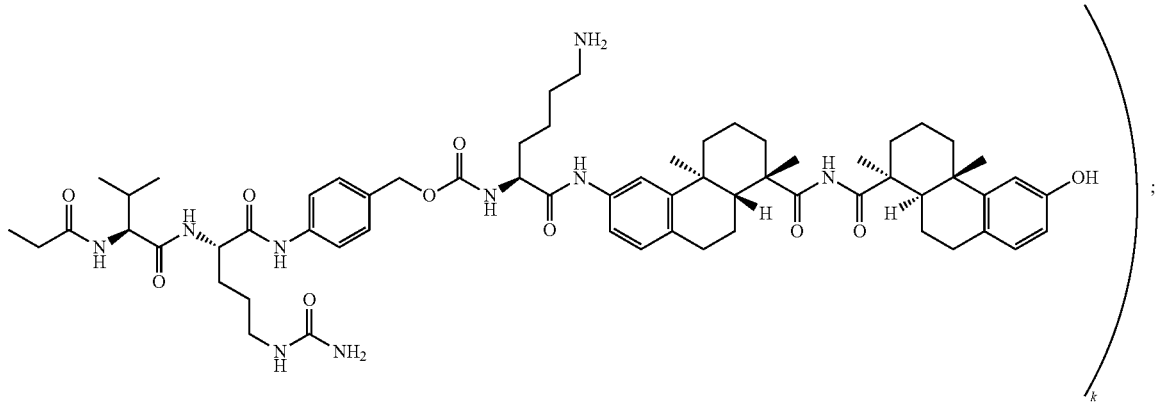
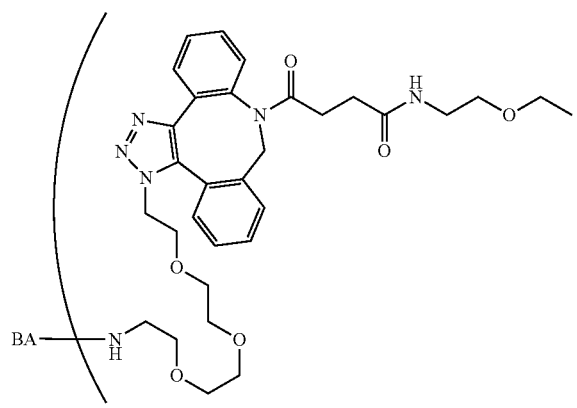
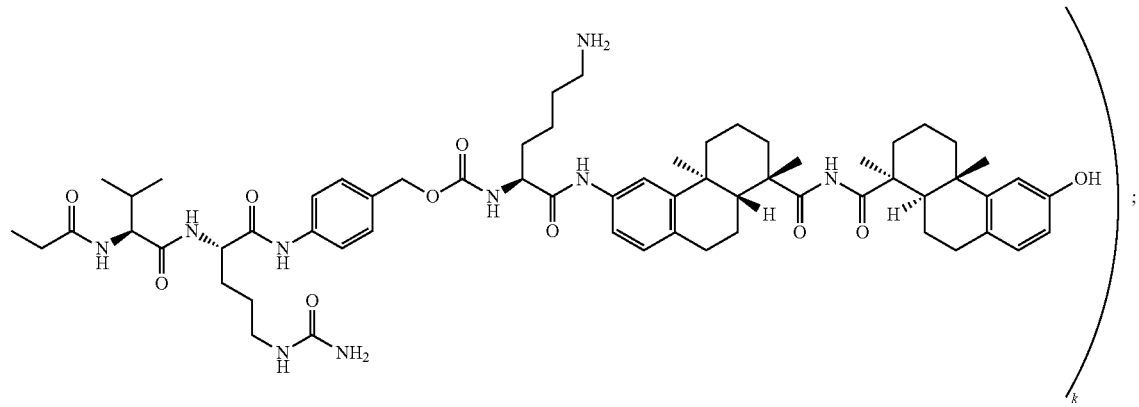

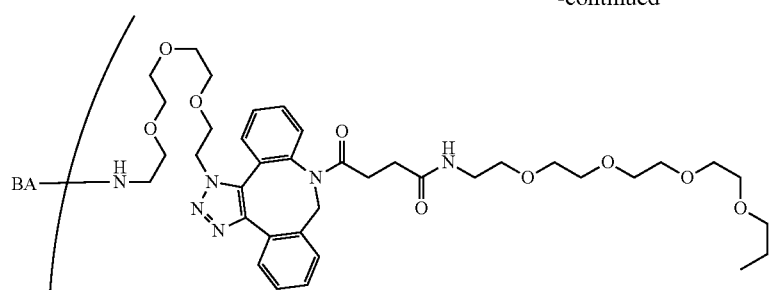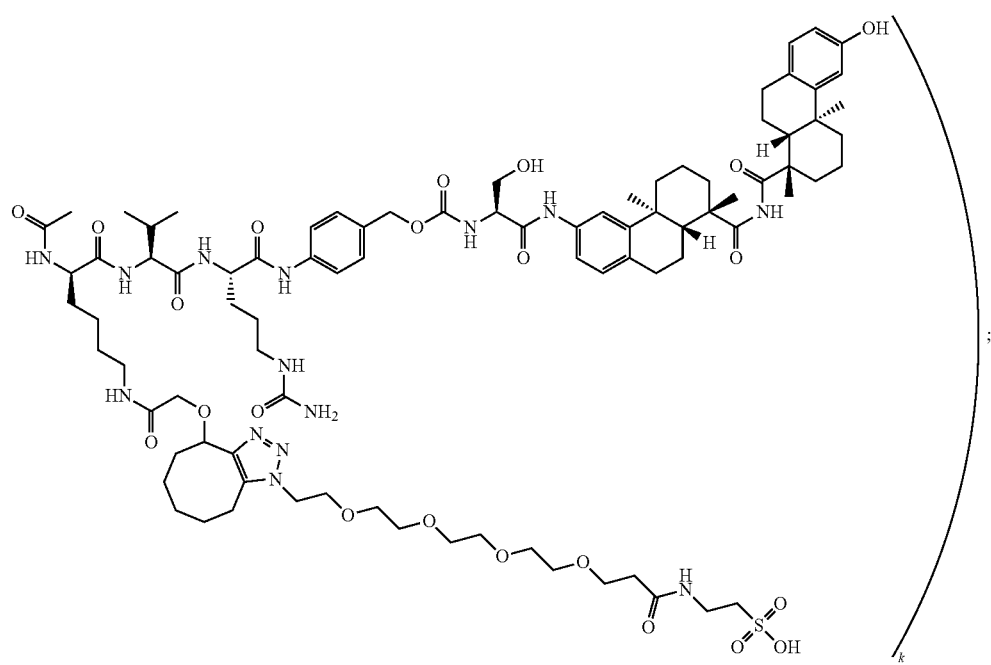

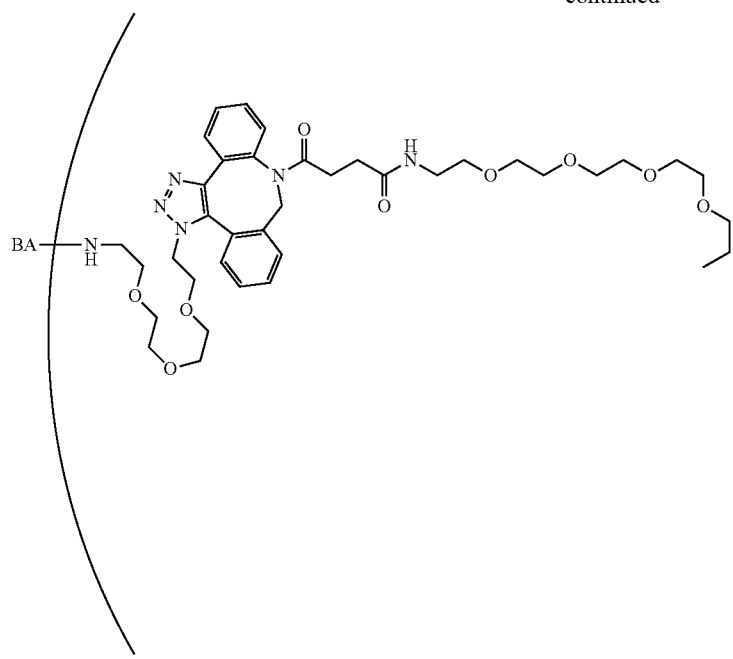
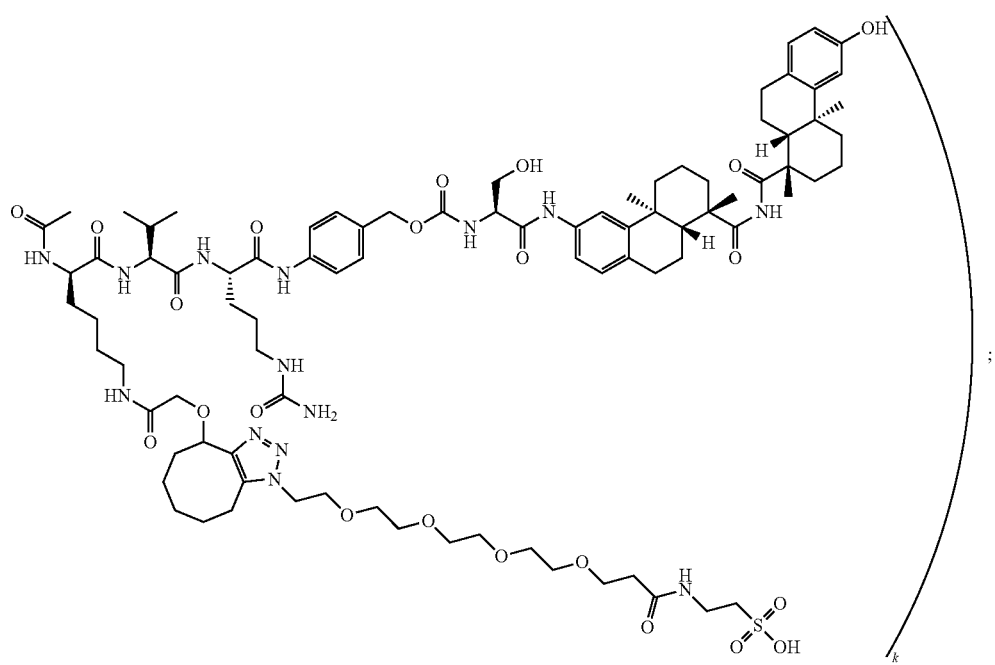

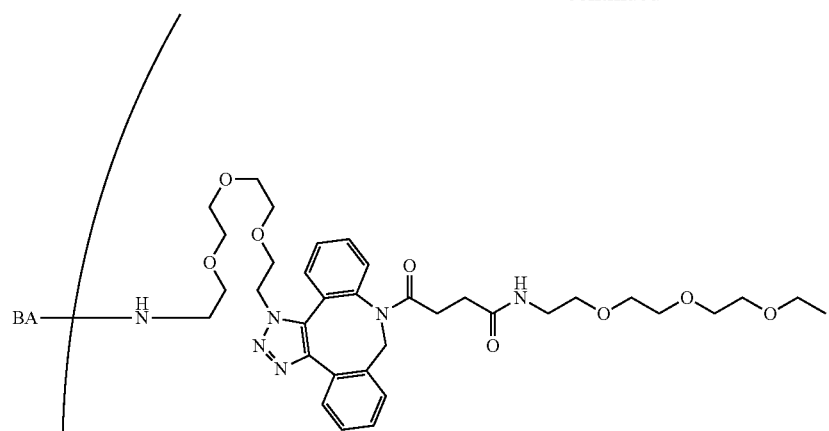
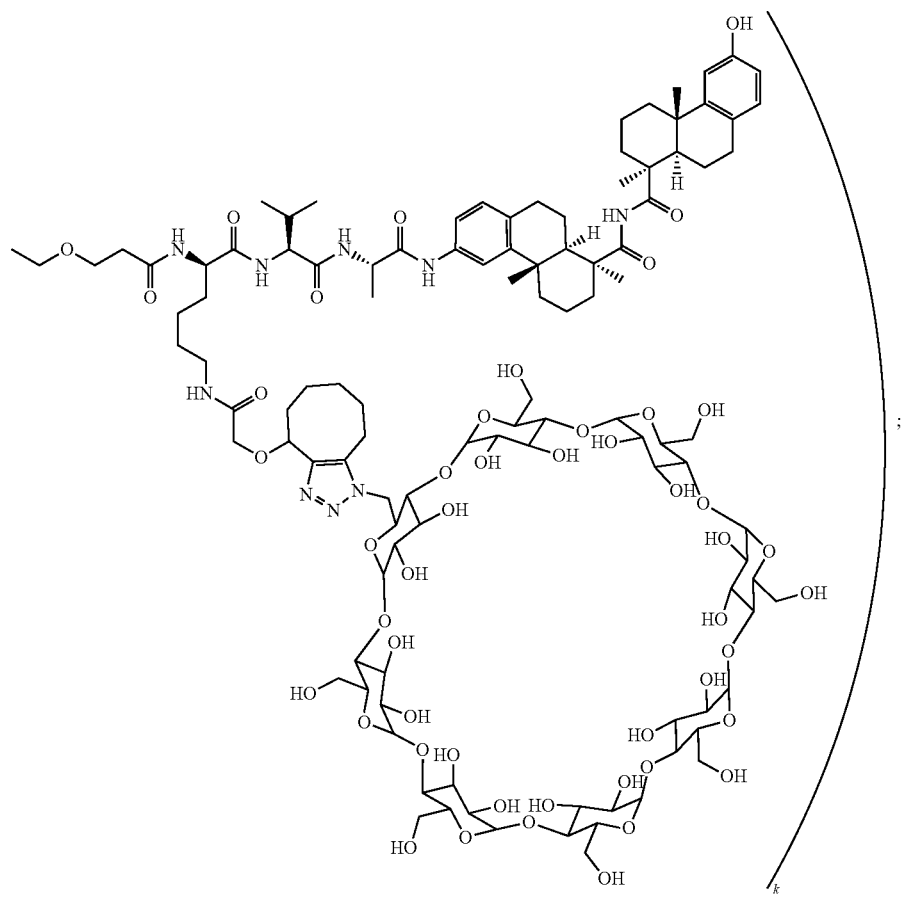

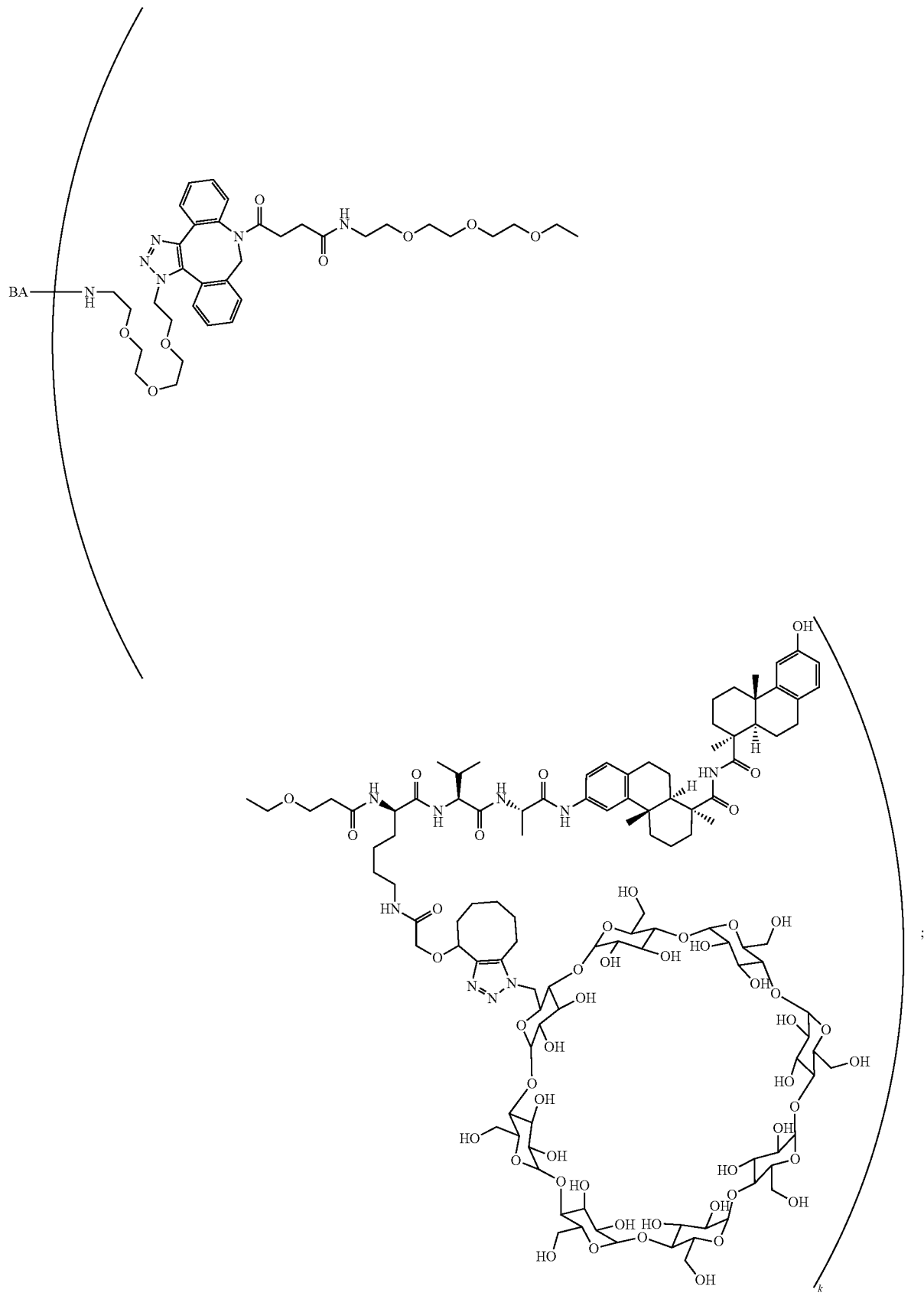

or a regioisomer, stereoisomeric form, pharmaceutically acceptable salt, or solvate thereof, wherein k ranges from about one to about four, representing an average number of units of a payload conjugated to BA.

18. The compound of claim 1, comprising BA linked via a linker to a compound as depicted in the following formula

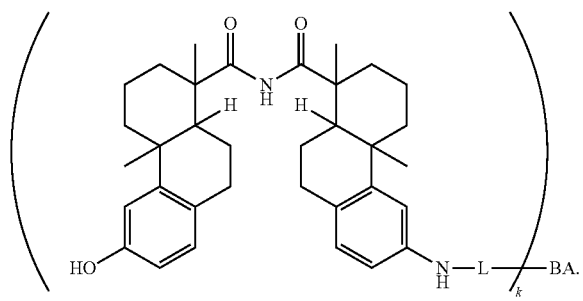

19. The compound of claim 3, wherein BA is an antibody or antigen binding fragment thereof conjugated to a primary amine compound at a glutamine residue, and L is bonded to BA through the primary amine compound.

20. The compound of claim 19, wherein the primary amine compound comprises a divalent PEG group.

21. A pharmaceutical composition comprising the compound of claim 1 and a pharmaceutically acceptable excipient, carrier, or diluent.

22. A method for the treatment of dyslipidemia in a subject comprising the administration to the subject an effective treatment amount of the compound of claim 1.

23. A method for the treatment of dyslipidemia in a subject comprising the administration to the subject an effective treatment amount of the pharmaceutical composition of claim 21.

* * * * *